(12) United States Patent
Burton et al.

(10) Patent No.: US 11,130,802 B2
(45) Date of Patent: Sep. 28, 2021

(54) ANTI-LAP ANTIBODY VARIANTS

(71) Applicants: Tilos Therapeutics, Inc., Rahway, NJ (US); Merck Sharp & Dohme Corp., Rahway, NJ (US)

(72) Inventors: Randall Burton, Billerica, MA (US); Jessie M. English, Cambridge, MA (US); Barbara S. Fox, Wayland, MA (US); Stavros Kopsiaftis, West Roxbury, MA (US); Renee Moore, Medway, MA (US); Patricia Rao, Acton, MA (US); Kenneth J. Simon, Milton, MA (US)

(73) Assignees: Tilos Therapeutics, Inc., Rahway, NJ (US); Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/597,593

(22) Filed: Oct. 9, 2019

(65) Prior Publication Data

US 2020/0140530 A1    May 7, 2020

Related U.S. Application Data

(60) Provisional application No. 62/757,519, filed on Nov. 8, 2018, provisional application No. 62/750,065, filed on Oct. 24, 2018, provisional application No. 62/744,045, filed on Oct. 10, 2018.

(51) Int. Cl.
| | |
|---|---|
| C07K 16/18 | (2006.01) |
| A61P 35/04 | (2006.01) |
| A61P 35/00 | (2006.01) |
| A61K 39/00 | (2006.01) |
| G01N 33/574 | (2006.01) |
| G01N 33/68 | (2006.01) |

(52) U.S. Cl.
CPC .............. *C07K 16/18* (2013.01); *A61P 35/00* (2018.01); *A61P 35/04* (2018.01); *G01N 33/574* (2013.01); *G01N 33/68* (2013.01); *A61K 2039/507* (2013.01); *C07K 2317/24* (2013.01); *C07K 2317/31* (2013.01); *C07K 2317/52* (2013.01); *C07K 2317/565* (2013.01); *C07K 2317/70* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,439,196 A | 3/1984 | Higuchi |
| 4,444,887 A | 4/1984 | Hoffmann |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,596,556 A | 6/1986 | Morrow et al. |
| 4,716,111 A | 12/1987 | Osband et al. |
| 4,790,824 A | 12/1988 | Morrow et al. |
| 4,816,567 A | 3/1989 | Cabilly et al. |
| 4,881,175 A | 11/1989 | Ladner |
| 4,941,880 A | 7/1990 | Burns |
| 4,946,778 A | 8/1990 | Ladner et al. |
| 5,013,653 A | 5/1991 | Huston et al. |
| 5,064,413 A | 11/1991 | McKinnon et al. |
| 5,091,513 A | 2/1992 | Huston et al. |
| 5,132,405 A | 7/1992 | Huston et al. |
| 5,225,539 A | 7/1993 | Winter |
| 5,229,275 A | 7/1993 | Goroff |
| 5,258,498 A | 11/1993 | Huston et al. |
| 5,260,203 A | 11/1993 | Ladner et al. |
| 5,312,335 A | 5/1994 | McKinnon et al. |
| 5,374,548 A | 12/1994 | Caras et al. |
| 5,383,851 A | 1/1995 | McKinnon, Jr. et al. |
| 5,399,163 A | 3/1995 | Peterson et al. |
| 5,399,331 A | 3/1995 | Loughrey et al. |
| 5,416,016 A | 5/1995 | Low et al. |
| 5,455,030 A | 10/1995 | Ladner et al. |
| 5,476,786 A | 12/1995 | Huston |
| 5,482,858 A | 1/1996 | Huston et al. |
| 5,530,101 A | 6/1996 | Queen et al. |

(Continued)

FOREIGN PATENT DOCUMENTS

| | | |
|---|---|---|
| EP | 0154316 A2 | 9/1985 |
| EP | 0401384 A1 | 12/1990 |

(Continued)

OTHER PUBLICATIONS

Sequence alignment COBALT, Jan. 23, 2021 (Year: 2021).*

(Continued)

*Primary Examiner* — Elly-Gerald Stoica
(74) *Attorney, Agent, or Firm* — Letitia Walker; Anna Cocuzzo

(57) ABSTRACT

Provided herein are anti-LAP antibodies (e.g., recombinant humanized, chimeric, and human anti-LAP antibodies) or antigen binding fragments thereof which have therapeutically beneficial properties, such as binding specifically to LAP-TGFβ1 on cells but not to LAP-TGFβ1 in extracellular matrix, as well as compositions including the same. Also provided are uses of these antibodies or antigen binding fragments in therapeutic applications, such as in the treatment of cancer, and diagnostic applications.

18 Claims, 73 Drawing Sheets

Specification includes a Sequence Listing.

(56) References Cited

U.S. PATENT DOCUMENTS

| | | |
|---|---|---|
| 5,565,332 A | 10/1996 | Hoogenboom et al. |
| 5,567,610 A | 10/1996 | Borrebaeck et al. |
| 5,585,089 A | 12/1996 | Queen et al. |
| 5,624,821 A | 4/1997 | Winter et al. |
| 5,648,260 A | 7/1997 | Winter et al. |
| 5,677,425 A | 10/1997 | Bodmer et al. |
| 5,693,762 A | 12/1997 | Queen et al. |
| 5,714,350 A | 2/1998 | Co et al. |
| 5,714,352 A | 2/1998 | Jakobobits |
| 5,723,323 A | 3/1998 | Kauffman et al. |
| 5,763,192 A | 6/1998 | Kauffman et al. |
| 5,766,886 A | 6/1998 | Studnicka et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,869,046 A | 2/1999 | Presta et al. |
| 5,976,862 A | 11/1999 | Kauffman et al. |
| 6,005,079 A | 12/1999 | Casterman et al. |
| 6,121,022 A | 9/2000 | Presta et al. |
| 6,165,745 A | 12/2000 | Ward et al. |
| 6,180,370 B1 | 1/2001 | Queen et al. |
| 6,194,551 B1 | 2/2001 | Idusogie et al. |
| 6,204,023 B1 | 3/2001 | Robinson et al. |
| 6,207,156 B1 | 3/2001 | Kuchroo et al. |
| 6,277,375 B1 | 8/2001 | Ward |
| 6,350,861 B1 | 2/2002 | Co et al. |
| 6,737,056 B1 | 5/2004 | Presta |
| 6,946,292 B2 | 9/2005 | Kanda et al. |
| 6,989,452 B2 | 1/2006 | Ng et al. |
| 7,029,872 B2 | 4/2006 | Gerngross |
| 7,087,600 B2 | 8/2006 | Ng et al. |
| 7,125,689 B2 | 10/2006 | Carr et al. |
| 7,129,261 B2 | 10/2006 | Ng et al. |
| 7,132,255 B2 | 11/2006 | Blumberg |
| 7,214,775 B2 | 5/2007 | Hanai et al. |
| 7,317,091 B2 | 1/2008 | Lazar et al. |
| 7,388,088 B2 | 6/2008 | Marks et al. |
| 7,449,308 B2 | 11/2008 | Gerngross et al. |
| 7,635,757 B2 | 12/2009 | Freeman et al. |
| 7,803,553 B2 | 9/2010 | Kojima et al. |
| 8,101,720 B2 | 1/2012 | Lazar et al. |
| 8,198,412 B2 | 6/2012 | Kojima et al. |
| 8,217,149 B2 | 7/2012 | Irving et al. |
| 8,951,521 B2 | 2/2015 | Kojima et al. |
| 9,573,995 B2 | 2/2017 | Schurpf et al. |
| 9,580,500 B2 | 2/2017 | Schurpf et al. |
| 10,017,567 B2 | 7/2018 | Weiner et al. |
| 10,233,247 B2 | 3/2019 | Hanai et al. |
| 2003/0068661 A1 | 4/2003 | Hockfield et al. |
| 2005/0276802 A1 | 12/2005 | Adams et al. |
| 2005/0276812 A1 | 12/2005 | Ebens et al. |
| 2006/0004081 A1 | 1/2006 | Chen et al. |
| 2006/0024317 A1 | 2/2006 | Boyd et al. |
| 2006/0247295 A1 | 11/2006 | Gangwar et al. |
| 2008/0038748 A1 | 2/2008 | Kojima et al. |
| 2008/0206219 A1 | 8/2008 | Coussens et al. |
| 2008/0227704 A1 | 9/2008 | Kamens et al. |
| 2008/0280827 A1 | 11/2008 | Kojima et al. |
| 2009/0317368 A1 | 12/2009 | Chen |
| 2011/0064653 A1 | 3/2011 | Hansen et al. |
| 2011/0070163 A1 | 3/2011 | Gonda et al. |
| 2011/0070238 A1 | 3/2011 | Triebel et al. |
| 2011/0150892 A1 | 6/2011 | Thudium et al. |
| 2013/0028915 A1 | 1/2013 | Palucka et al. |
| 2013/0071403 A1 | 3/2013 | Rolland et al. |
| 2014/0328860 A1 | 11/2014 | Scandura et al. |
| 2015/0033703 A1 | 2/2015 | Hyde et al. |
| 2015/0273056 A1 | 10/2015 | Blumberg et al. |
| 2015/0284455 A1 | 10/2015 | Springer et al. |
| 2015/0337034 A1 | 11/2015 | Schurpf |
| 2016/0289315 A1 | 10/2016 | Mirza et al. |
| 2017/0073406 A1 | 3/2017 | Schurpf et al. |
| 2017/0190767 A1 | 7/2017 | Schurpf et al. |
| 2017/0210798 A1 | 7/2017 | Schurpf et al. |
| 2018/0009886 A1 | 1/2018 | Weiner et al. |
| 2018/0030128 A1 | 2/2018 | Weiner et al. |
| 2018/0207267 A1 | 7/2018 | Schurpf et al. |
| 2019/0071493 A1 | 3/2019 | Schurpf et al. |

FOREIGN PATENT DOCUMENTS

| | | |
|---|---|---|
| EP | 404097 B1 | 12/1990 |
| EP | 0239400 B1 | 8/1994 |
| EP | 1176195 A1 | 4/2000 |
| EP | 1229125 A1 | 8/2002 |
| EP | 0592106 B1 | 11/2004 |
| EP | 0519596 B1 | 2/2005 |
| EP | 1674480 A1 | 6/2006 |
| EP | 2878308 A1 | 6/2015 |
| JP | 2006523179 A | 10/2006 |
| JP | 2008247900 A | 10/2008 |
| JP | 2008289478 A | 12/2008 |
| WO | 1990014424 A1 | 11/1990 |
| WO | 1990014430 A1 | 11/1990 |
| WO | 1990014443 A1 | 11/1990 |
| WO | 1991009967 A1 | 7/1991 |
| WO | 1991010741 A1 | 7/1991 |
| WO | 1992001047 A1 | 1/1992 |
| WO | 1992003461 A1 | 3/1992 |
| WO | 1992011272 A1 | 7/1992 |
| WO | 1993006213 A1 | 4/1993 |
| WO | WO199311161 A1 | 6/1993 |
| WO | WO1994404678 A1 | 3/1994 |
| WO | 1994011026 A2 | 5/1994 |
| WO | 1994018219 A1 | 8/1994 |
| WO | 9425591 A1 | 11/1994 |
| WO | 199429351 A2 | 12/1994 |
| WO | 1995017886 A1 | 7/1995 |
| WO | 1996032478 A1 | 10/1996 |
| WO | 1996033735 A1 | 10/1996 |
| WO | 1996034096 A1 | 10/1996 |
| WO | 1997020032 A1 | 6/1997 |
| WO | 199734631 A1 | 9/1997 |
| WO | 1998016654 A1 | 4/1998 |
| WO | 1998024893 A2 | 6/1998 |
| WO | 1998042752 A1 | 10/1998 |
| WO | 1998046645 A2 | 10/1998 |
| WO | 1998050433 A2 | 11/1998 |
| WO | 1999006834 A2 | 2/1999 |
| WO | 199954342 A1 | 10/1999 |
| WO | 2000031246 A2 | 6/2000 |
| WO | WO0037504 A2 | 6/2000 |
| WO | 200042072 A2 | 7/2000 |
| WO | 2000061739 A1 | 10/2000 |
| WO | 2001058957 A2 | 8/2001 |
| WO | 2002006919 A2 | 1/2002 |
| WO | 2002031240 A2 | 4/2002 |
| WO | 2002085306 A2 | 10/2002 |
| WO | 2002096910 A1 | 12/2002 |
| WO | WO03011878 A2 | 2/2003 |
| WO | 2003035835 A2 | 5/2003 |
| WO | 2003086310 A2 | 10/2003 |
| WO | 2003099196 A2 | 12/2003 |
| WO | 2004016750 A2 | 2/2004 |
| WO | 2004029207 A2 | 4/2004 |
| WO | 2004035752 A2 | 4/2004 |
| WO | 2004063351 A2 | 7/2004 |
| WO | 2004074455 A2 | 9/2004 |
| WO | 2004099249 A2 | 11/2004 |
| WO | 2005023870 A1 | 3/2005 |
| WO | 2005040217 A2 | 5/2005 |
| WO | 2005070963 A1 | 8/2005 |
| WO | 2005092925 A2 | 10/2005 |
| WO | 2005117973 A2 | 12/2005 |
| WO | 2005120571 A2 | 12/2005 |
| WO | 2006020114 A2 | 2/2006 |
| WO | WO2006014679 A1 | 2/2006 |
| WO | 2006057702 A2 | 6/2006 |
| WO | 2006086469 A2 | 8/2006 |
| WO | 2006091209 A2 | 8/2006 |
| WO | 2006116002 A2 | 11/2006 |
| WO | 2006122150 A1 | 11/2006 |
| WO | 2007038658 A2 | 4/2007 |
| WO | 2007051081 A1 | 5/2007 |

(56) References Cited

FOREIGN PATENT DOCUMENTS

| WO | 2007059404 A2 | 5/2007 |
|---|---|---|
| WO | 2007075598 A2 | 7/2007 |
| WO | 2008036642 A2 | 3/2008 |
| WO | 2008036653 A2 | 3/2008 |
| WO | 2008083312 A2 | 7/2008 |
| WO | 2008103693 A2 | 8/2008 |
| WO | WO2008132601 A1 | 11/2008 |
| WO | 2009014708 A2 | 1/2009 |
| WO | 2009044273 A2 | 4/2009 |
| WO | 2009059278 A1 | 5/2009 |
| WO | 2009073620 A2 | 6/2009 |
| WO | 2009114335 A2 | 9/2009 |
| WO | 2009119455 A1 | 10/2009 |
| WO | 2010019570 A2 | 2/2010 |
| WO | 2010124276 A2 | 10/2010 |
| WO | 2011056652 A1 | 5/2011 |
| WO | 2011066389 A1 | 6/2011 |
| WO | 2011070024 A1 | 6/2011 |
| WO | 2011102483 A1 | 8/2011 |
| WO | 2011107553 A1 | 9/2011 |
| WO | 2011109400 A2 | 9/2011 |
| WO | 2011131407 A1 | 10/2011 |
| WO | 2011140249 A2 | 11/2011 |
| WO | 2011161699 A2 | 12/2011 |
| WO | 2012029792 A1 | 3/2012 |
| WO | 2012032433 A1 | 3/2012 |
| WO | 2012142237 A1 | 10/2012 |
| WO | 2012145493 A1 | 10/2012 |
| WO | 2013/079174 A1 | 6/2013 |
| WO | 2013087699 A1 | 6/2013 |
| WO | 2013119716 A1 | 8/2013 |
| WO | 2013132044 A1 | 9/2013 |
| WO | 2013134365 A1 | 9/2013 |
| WO | 2013169264 A1 | 11/2013 |
| WO | 2013173223 A1 | 11/2013 |
| WO | 2014008218 A1 | 1/2014 |
| WO | 2014036357 A1 | 3/2014 |
| WO | 2014059251 A1 | 4/2014 |
| WO | 2014074532 A2 | 5/2014 |
| WO | 2014182676 A2 | 11/2014 |
| WO | 2015171691 A2 | 11/2015 |
| WO | 2016115345 A1 | 7/2016 |
| WO | 2016161410 A2 | 10/2016 |
| WO | 2017156500 A1 | 9/2017 |
| WO | 2018013939 A1 | 1/2018 |
| WO | 2018043734 A1 | 3/2018 |
| WO | 2018129329 A1 | 7/2018 |
| WO | 2018208888 A1 | 11/2018 |
| WO | 2019023661 A1 | 1/2019 |
| WO | 2019075090 A1 | 4/2019 |

OTHER PUBLICATIONS

Afonine, Pavel V. et al., Real-space refinement in PHENIX for cryo-EM and crystallography, Acta Cryst., 2018, 531-544, 74.

Alexander, Anthony J. et al., Monitoring of IgG Antibody Thermal Stability by Micellar Electrokinetic Capillary Chromatography and Matrix-Assisted Laser Desorption/Ionization Mass Spectrometry, Anal. Chem., 1995, 3626-3632, 67.

Ali, Naeem A. et al., Latency Associated Peptide Has In Vitro and In Vivo Immune Effects Independent of TGF-beta1, PLOS One, 2008, 1-9, 3(4):e1914.

Almagro, Juan C. et al., Humanization of antibodies, Frontiers in Bioscience, 2008, 1619-1633, 13.

Altschul S.F. et al, Gapped BLAST and PSI-BLAST: a new generation of protein database search programs, Nucleic Acids Research, 1997, 3389-3402, 25-17, Oxford University Press.

Altschul, Stephen F. et al., Basic Local Alignment Search Tool, J. Mol. Biol., 1990, 403-410, 215.

Andersson, John et al., CD4 + FoxP3 + regulatory T cells confer infectious tolerance in a TGF-beta-dependent manner, J. Exp. Med., 2008, 1975-1981, 205(9).

Annes, Justin P. et al., Integrin alpha v beta6-mediated activation of latent TGF-beta requires the latent TGF-beta binding protein-1, The Journal of Cell Biology, 2004, 723-734, 165.

Arnon, Ruth et al., Monoclonal Antibodies for Immunotargeting of Drugs in Cancer Therapy, Monoclonal Antibodies and Cancer Therapy, 1985, 243-256, N/A.

Basile, J. I. et al., Mycobacterium tuberculosis multi-drug-resistant strain M induces IL-17+ IFNγ—CD4+ T cell expansion through an IL-23 and TGF-b-dependent mechanism in patients with MDR-TB tuberculosis, Clinical and Experimental Immunology, 2016, 160-173, 187.

Berge, S.M., et al.,, "Pharmaceutical Salts", J. Pharm. Sci, 1977, pp. 1-19, vol. 66, No. 1.

Biernacka, Anna et al., TGF-β signaling in fibrosis, Growth Factors, 2011, 196-202, 29(5).

Biolegend, Leaf™ Purified anti-human/mouse Latent TGF-beta Antibody, BioLegend Enabling Legendary Discovery, 2014, 1-3, Version 1.

Biolegend, Ultra-Leaf™ Purified anti-mouse/human LAP (TGF-beta1) Antibody, Biolegend Enabaling Legendary Discovery, 2014, 1-2, Version 2.

Bird, Robert E. et al., Single-Chain Antigen-Binding Proteins, Science, 1988, 423-426, 242.

Bird, Thomas G et al., TGFβ inhibition restores a regenerative response in acute liver injury by suppressing paracrine senescence, Sci Transl Med., 2018, 1-30, 10:aan1230.

Bischoff, Rainer et al., Deamidation of asparagine and glutamine residues in proteins and peptides: structural determinants and analytical methodology, Journal of Chromatography B., 1994, 261-278, 662.

Bloemen, P.G.M. et al., Adhesion molecules: a new target for immunoliposome-mediated drug delivery, FEBS Letters, 1995, 140-144, 357.

Bordusa, Frank, Protease-catalyzed Formation of C—N Bonds, Highlights in Bioorganic Chemistry, 2004, 389-403, Chapter 5.

Broderick, Lori, Membrane-Associated TGF-beta1 Inhibits Human Memory T Cell Signaling in Malignant and Nonmalignant Inflammatory Microenvironments, The Journal of Immunology, 2006, 3082-3088, 177(5).

Brubaker, Marcus A. et al, Building Proteins in a Day: Efficient 3D Molecular Structure Estimation with Electron Cryomicroscopy, IEEE Trans Pattern Anal Mach Intell, 2017, 706-718, 39.

Brummell, David A. et al., Probing the Combining Site of an anti-Carbohydrate Antibody by Saturation-Mutagenesis: role of the Heavy-Chain CDR3 Residues, Biochemistry, 1993, 1180-1187, 32.

Burks, Elizabeth A. et al., In vitro scanning saturation mutagenesis of an antibody binding pocket, Proc. Natl. Acad. Sci. USA, 1997, 412-417, 94.

C. Lloyd et al., Modelling the human immune response: performance of a 10" human antibody repertoire against a broad panel of therapeutically relevant antigens, Protein Engineering Design & Selection, 2009, 159-168, 22-3.

Camacho, L. H. et al., Phase 1 clinical trial of anti-CTLA4 human monoclonal antibody CP-675,206 in patients (pts) with advanced solid malignancies, J. Clin. Oncology, 2004, 1-3, 22(145): Abstract 2505.

Cao, Xuefang et al., Granzyme B and Perforin Are Important for Regulatory T Cell-Mediated Suppression of Tumor Clearance, Immunity, 2007, 635-646, 27(4).

Carambia, Antonella et al, TGF-beta-dependent induction of CD4+ CD25+Foxp3+ Tregs by liver sinusoidal endothelial cells, Journal of Hepatology, 2014, 594-599, 61(3).

Cardone, Giovanni et al., One number does not fit all: mapping local variations in resolution in cryo-EM reconstructions, J Struct Biol, 2013, 226-236, 184.

Carrillo-Galves, Ana Belen et al., Mesenchymal Stromal Cells Express GARP/LRRC32 on Their Surface: Effects on Their Biology and Immunomodulatory Capacity, Stem Cells, 2015, 183-195, 33(1).

Carter, Paul et al., Humanization of an anti-p185HER2 antibody for human cancer therapy, Proc. Natl. Acad. Sci. USA, 1992, 4285-4289, 89.

Ceska, Tom et al., Cryo-EM in drug discovery, Biochemical Society Transactions, 2019, 281-293, 47.

(56) References Cited

OTHER PUBLICATIONS

Champe, Mark et al., Monoclonal Antibodies That Block the Activity of Leukocyte Function-associated Antigen 1 Recognize Three Discrete Epitopes in the Inserted Domain of CD11a, J. Biol. Chem., 1995, 1388-1394, 270.
Chappel, M. Suzanne et al., Identification of a Secondary Fc-yRI Binding Site within a Genetically Engineered Human IgG Antibody, J. Biol. Chem., 1993, 25124-25131, 268.
Chen, et al., Influence of histidine on the stability and physical properties of a fully human antibody in aqueous and solid forms, 2003, 1952-1960, 20(12), Pharm Res.
Chen, Mei-Ling et al., Latency-Associated Peptide Identifies a Novel CD4CD25 Regulatory T Cell Subset with TGFbeta-Mediated Function and Enhanced Suppression of Experimental Autoimmune Encephalomyelitis, The Journal of Immunology, 2008, 7327-7337, 180(11).
Chen, Xianghong et al., Induction of myelodysplasia by myeloid-derived suppressor cells, The Journal of Clinical Investigation, 2013, 4595-4611, 123.
Cheung et al., Epitope-specific antibody response to the surface antigen of duck hepatitis B virus in infected ducks, Virology, 1990, pp. 546-552, 176.
Cheung, Ka-Wai et al., alpha4beta7+ CD4+ Effector/Effector Memory T Cells Differentiate into Productively and Latently Infected Central Memory T Cells by Transforming Growth Factor beta1 during HIV-1 Infection, Journal of Virology, 2018, 1-18, 92(8):e01510-17.
Choi et al., PNAS, PNAS, 2003, pp. 5022-5027, 100.
Chothia et al, Canonical Structures for the Hypervariable Regions of Immunoglobins, J. Mol. Biol., 1987, 901-917, 196.
Chothia, Cyrus et al., Conformations of immunoglobulin hypervariable regions, Nature, 1989, 878-883, 342.
Clackson et al., Making Antibody Fragments Using Phage Display Libraries, Nature, 1991, pp. 624-628, vol. 352.
Cohn, Allen et al., A phase I dose-escalation study to a predefined dose of a transforming growth factor-β1 monoclonal antibody (TβM1) in patients with metastatic cancer, International Journal of Oncology, 2014, 2221-2231, 45.
Cunningham et al., High resolution Epitope mapping of hgH-receptor interactions by alanine-scanning mutagenesis, Science, 1985, pp. 1081-1085, 244.
Curran et al., PD1 and CTLA4 combination blockade expands infiltrating T cells and reduces regulatory T adn myeloid cells within B16 melanoma tumors, PNAS, 2010, pp. 4275-4280, vol. 107.
D'Ambrosio, Antonella et al., Lamina Propria CD4+LAP+ Regulatory T Cells Are Increased in Active Ulcerative Colitis but Show Increased IL-17 Expression and Reduced Suppressor Activity, Journal of Crohn's and Colitis, 2016, 346-353, 10(3).
Dacunha, Andrew R et al., In vivo anti-LAP mAb enhances IL-17/IFN-γ responses and abrogates anti-CD3-induced oral tolerance, International Immunology, 2014, 73-82, 27(2).
Dall'Acqua, William F. et al., Properties of Human IgG1s Engineered for Enhanced Binding to the Neonatal Fc Receptor (FcRn), Journal of Biological Chemistry, 2006, 23514-23524, 281(33).
Dall'Acqua, William F. et al., Increasing the Affinity of a Human IgG1 for the Neonatal Fc Receptor: Biological Consequences, Journal of Immunology, 2002, 5171-5180, 169.
Database accession No. EMB-623504224; Database Embase [Online]Elsevier Science Publishers, I Amsterdam, NL, Jul. 1, 2018, Kopsiaftis S. et al. Radiation induces LAP, latency-associated peptide of TGF-beta, on the surface of lymphoid cells in the tumor microenvironment, XP002788173, abstract, 2 pages.
De Graaf, Albert J. et al., Nonnatural Amino Acids for Site-Specific Protein Conjugation, Bioconjug. Chem., 2009, 1281-1295, 20.
Dranoff, Glenn et al., Vaccination with irradiated tumor cells engineered to secrete murine granulocyte-macrophage colony-stimulating factor stimulates potent, specific, and long-lasting anti-tumor immunity, Proc. Natl. Acad. Sci. USA, 1993, 3539-3543, 90.
Duan, Wei et al., Inducible CD4+LAP+Foxp3—Regulatory T Cells Suppress Allergic Inflammation, Journal of Immunology, 2011, 6499-6507, 187(12).

Dussiot, Michael et al., An activin receptor IIA ligand trap corrects ineffective erythropoiesis in β-thalassemia, Nature Medicine, 2014, 398-407, 20.
Edwards, Justin P. et al, The GARP/Latent TGF-β1 complex on Treg cells modulates the induction of peripherally derived Treg cells during oral tolerance, Eur J Immunol, 2016, 1480-1489, 46.
Elkord, Eyad et al., Helios, and not FoxP3, is the marker of activated Tregs expressing GARP/LAP, Oncotarget, 2015, 20026-20036, 6(24).
Emsley et al., Features and development of Coot, Biological Crystallography, 2010, pp. 486-501, D66.
English Language Translation of International Preliminary Report on Patentability for PCT/JP2011/053559 dated Sep. 18, 2012, 6 pages.
Extended European Search Report for EP 16737879.3, dated May 29, 2018, 12 pages.
Fernandez, Isis E. et al., Peripheral blood myeloid-derived suppressor cells reflect disease status in idiopathic pulmonary fibrosis, Eur Respir J, 2016, 1171-1183, 48.
Foote et al., Antibody Framework Residues Affecting the Conformation of the Hypervariable Loops, J. Mol. Biol., 1992, pp. 487-499, vol. 224.
Frank, S. et al., Specificity and Cross-Reactivity, Immunology and Evolution of Infectious Disease, 2002, 1-33, Chapter 4.
Frese, Marc-Andre et al., Formylglycine Aldehyde Tag—Protein Engineering through a Novel Post-translational Modification, ChemBioChem, 2009, 425-427, 10.
Fridrich, Sven et al., How Soluble GARP Enhances TGFβ Activation, PLOS One, 2016, 1-16, 11(4):e0153290.
Gabriely, Galina, Targeting latency-associated peptide promotes antitumor immunity, Sci Immunol., 2017, 1-13, 2 (11).
Gala, Françoise A. et al., V Region Carbohydrate and Antibody Expression, The Journal of Immunology, 2004, 5489-5494, 172.
Gandhi, Roopali et al., Cutting Edge: Human Latency-.Associated Peptide + T Cells: A Novel Regulatory T Cell Subset, Journal of Immunology, 2010, 4620-4624, 184(9).
Gandhi, Roopali et al., Cutting Edge: Immature Human Dendritic Cells Express Latency-Associated Peptide and Inhibit T Cell Activation in a TGF-beta-Dependent Manner, Journal of Immunology, 2007, 4017-4021, 178(7).
Gautier, Arnaud et al., An Engineered Protein Tag for Multiprotein Labeling in Living Cells, Chemistry & Biology, 2008, 128-136, 15.
Gerlach, J. Tilman et al., Recurrence of Hepatitis C Virus After loss of Virus-Specific CD4 + T-Cell Response in Acute Hepatitis C, Gastroenterology, 1999, 933-941, 117(4).
Geyh, Stefanie et al., Transforming growth factor β1-mediated functional inhibition of mesenchymal stromal cells in myelodysplastic syndromes and acute myeloid leukemia, Haematologica, 2018, 1462-1471, 103.
Ghirlando, Rodolfo et al., Glycosylation of human IgG-Fc: influences on structure revealed by differential scanning microcalorimetry, Immunology Letters, 1999, 47-52, 68.
Gray et al., Optimising anti-tumor CD8 T-cell responses using combinations of ummunnomodulatory antibodies, Eur. J. Immunol., 2008, pp. 2499-2511, vol. 38.
Greenberg, Philip D. et al., Deficient Cellular Immunity—Finding and Fixing the Defects, Science, 1999, 546-551, 285.
Hackenberger, Christian P. R. et al., Chemoselective Ligation and Modification Strategies for Peptides and Proteins, Angew. Chem. Int. Ed., 2008, 10030-10074, 47.
Hamilton, Stephen R. et al., Glycosylation engineering in yeast: the advent of fully humanized yeast, Current Opinion in Biotechnology, 2007, 387-392, 18.
Hamilton, Stephen R. et al., Humanization of Yeast to Produce Complex Terminally Sialylated Glycoproteins, Science, 2006, 1441-1443, 313.
Hamilton, Stephen R. et al., Production of Complex Human Glycoproteins in Yeast, Science, 2003, 1244-1246, 301.
Hammerling, Gunter J., Monoclonal Antibodies and T-Cell Hybridomas, Elsevier, N.Y., 1981, 563-587, N/A.
Hanada, Tetsuro et al., Suppressive regulatory T cells and latent transforming growth factor-β-expressing macrophages are altered in the peritoneal fluid of patients with endometriosis, Reproductive Biology and Endocrinology, 2018, 1-8, 16:9.

(56) References Cited

OTHER PUBLICATIONS

Harlow, Ed, Antibodies, A Laboratory Manual, 1988, 139-243, Chapter 6.
He, Yu-Fei et al., Blocking Programmed Death-1 Ligand-PD-1 Interactions by Local Gene Therapy Results in Enhancement of Antitumor Effect of Secondary Lymphoid Tissue Chemokine, J. Immunol., 2004, 4919-4928, 173.
Hinton, Paul R. et al., An Engineered Human IgG1 Antibody with Longer Serum Half-Life, Journal of Immunology, 2006, 346-356, 176.
Hinton, Paul R. et al., Engineered Human IgG Antibodies with Longer Serum Half-lives in Primates, The Journal of Biological Chemistry, 2004, 6213-6216, 279(8).
Holliger et al., Diabodies, Proc. Natl. Acad. Sci. USA, 1993, No. 14, pp. 6444-6448, 90.
Holliger et al., Engineered antibody fragments and the rise of single domains, Nat. Biotechnol., 2005, pp. 1126-1136, 23.
Hurwitz, Arthur A. et al., CTLA-4 blockade synergizes with tumor-derived granulocyte-macrophage colony-stimulating factor for treatment of an experimental mammary carcinoma, Proc. Natl. Acad. Sci. USA, 1998, 10067-10071, 95(17).
Huston, James S. et al., Protein engineering of antibody binding sites: Recovery of specific activity in an anti-digoxin single-chain Fv analogue produced in Escherichia coli, Proc. Natl. Acad. Sci. USA, 1988, 5879-5883, 85.
International Preliminary Report on Patentability for PCT/US2013/064506, dated Apr. 14, 2015, 11 pages.
International Preliminary Report on Patentability for PCT/US2016/013408, dated Jul. 27, 2017, 20 pages.
International Search Report and Written Opinion for PCT/US2013/064506, dated Jan. 30, 2014, 18 pages.
International Search Report and Written Opinion for PCT/US2016/013408, dated May 2, 2016, 24 pages.
International Search Report and Written Opinion, PCT/US2018/055253, dated Feb. 26, 2019, 17 pages.
Jespers, Guiding the selection of human antibodies from phage display repertoires to a single epitope of an antigen, Bio Technology, 1994, pp. 899-903, 12.
Jie, H-B et al., Intratumoral regulatory T cells upregulate immunosuppressive molecules in head and neck cancer patients, British Journal of Cancer, 2013, 2629-2635, 109(10).
Jones, Peter T. et al., Replacing the complementarity-determining regions in a human antibody with those from a mouse, Nature, 1986, 522-525, 321.
Kabat, The Structural Basis of Antibody Complementarity, Adv. Prot. Chem., 1978, 1-75, 32.
Kabat, Unusual Distributions of Amino Acids in Complementarity-determining (Hypervriable) Segment of Heavy and Light Chains of Immunoglobulins and Their Possible Roles in Specificity of Antibody-combining Sites, J. Biol. Chem., 1977, 6609-6616, 252.
Keinanen, Kari et al., Biosynthetic lipid-tagging of antibodies, FEBS Letters, 1994, 123-126, 346.
Killion, Jerald J. et al., Systemic Targeting of Liposome-Encapsulated Immunomodulators to Macrophages for Treatment of Cancer Metastasis, Immunomethods, 1994, 273-279, 4.
Kirkland et al., Analysis of the tine specificity and cross-reactivity of monoclonal anti-lipid A antibodies, J. Immunol., 1986, pp. 3614-3619, 137.
Kobayashi, Hiroyski et al., Tryptophan H33 plays an important role in pyrimidine (6-4) pyrimidone photoproduct binding by a high-affinity antibody, Protein Eng., 1999, 879-884, 12(10).
Kohler et al., Continuous Cultures of Fused Cells Secreting Antibody of Predefined Specificity, Nature, 1975, pp. 495-497, vol. 256.
Kohrt, Holbrook E. et al., CD137 stimulation enhances the antilymphoma activity of anti-CD20 antibodies, Blood, 2011, 2423-2432, 117.
Kopsiaftis, Stavros et al., Abstract 72: Radiation induces LAP, latency-associated peptide of TGF-beta, on the surface of lymphoid cells in the tumor microenvironment, American Association for Cancer Research, 2018, 1-2, 78(13 Suppl): Abstract No. 72.
Kostelny et al., Formation of a bispecific antibody by the use of leucine zippers, J. Immunol., 1992, pp. 1547-1553, 148.
Krishnamurthy, Rajesh et al., The Stability Factor: Importance in Formulation Development, Current Pharmaceutical Biotechnology, 2002, 361-371, 3.
Krissinel, Evgeny et al., Inference of Macromolecular Assemblies from Crystalline State, J Mol Biol, 2007, 774-797, 372.
Kugler, Alexander et al., Regression of human metastatic renal cell carcinoma after vaccination with tumor cell-dendritic cell hybrids, Nature Medicine, 2000, 332-336, 6.
Lazar, Greg A. et al., Engineered antibody Fc variants with enhanced effector function, Proc Natl Acad Sci USA, 2006, 4005-4010, 103(11).
Lee, Robert J. et al., Folate-mediated tumor cell targeting of liposome-entrapped doxorubicin in vitro, Biochimica et Biophysica Acta, 1995, 134-144, 1233.
Leger, Olivier et al., Humanization of Antibodies, Molecular Medicine and Medicinal Chemistry, 2011, 1-23, Chapter 1.
Li, Huijuan et al., Optimization of humanized IgGs in glycoengineered Pichia pastoris, Nature Biotechnology, 2006, 210-215, 24(2).
Liénart, Stéphanie et al., Structural basis of latent TGF-beta1 presentation and activation by GARP on human regulatory T cells, Science, 2018, 952-956, 362.
Lonberg, Nils et al., Human Antibodies from Transgenic Mice, Intern. Rev. Immunol., 1995, 65-93, 13.
Lonning, Scott et al., Antibody Targeting of TGF-beta in Cancer Patients, Current Pharmaceutical Biotechnology, 2011, 2176-2189, 12.
Mahalingam, Jayashri et al., CD4+ T Cells Expressing Latency-Associated Peptide and Foxp3 Are an Activated Subgroup of Regulatory T Cells Enriched in Patients with Colorectal Cancer, PLoS One, 2014, 1-9, 9(9): e108554.
Mahalingam, Jayashri et al., Lap+CD4' T Cells Are Suppressors Accumulated in the Tumor Sites and Associated with the Progression of Colorectal Cancer, Clinical Cancer Research, 2012, 5224-5233, 18(19).
Marks et al., by passing Immunization, J. Mol. Biol., 1991, pp. 581-597, 222.
Marks et al., By-Passing Immunization: Building High Affinity Human Antibodies by Chain Shuffling, Bio/Technology, 1992, Issue No. 7, pp. 779-783, 10.
Marshall, R. D., Glycoproteins, Ann. Rev. Biochem., 1972, 673-702, 41.
Mascarenhas, John et al., Anti-transforming growth factor-b therapy in patients with myelofibrosis, Leukemia & Lymphoma, 2014, 450-452, 55.
Maynard, Jennifer et al., Antibody Engineering, Annu. Rev. Biomed. Eng., 2000, 339-376, 2.
McCafferty, John et al., Phage antibodies: filamentous phage displaying antibody variable domains, Nature, 1990, 552-554, 348.
Melero, Ignacio et al., Immunostimulatory monoclonal antibodies for cancer therapy, Nature Reviews, 2007, 95-106, 7.
Metelli, Alessandra et al., Immunoregulatory functions and the therapeutic implications of GARP-TGF-β in Inflammation and cancer, Journal of Hematology & Oncology, 2018, 1-11, 11:24.
Mies, Anna et al., Activin Receptor II Ligand Traps and Their Therapeutic Potential in Myelodysplastic Syndromes with Ring Sideroblasts, Curr Hematol Malig Rep, 2016, 416-424, 11.
Mimura, Y. et al., The influence of glycosylation on the thermal stability and effector function expression of human IgG1-Fc: properties of a series of truncated glycoforms, Molecular Immunology, 2000, 697-706, 37.
Mokyr, Margalit B. et al., Realization of the Therapeutic Potential of CTLA-4 Blockade in Low-Dose Chemotherapy-treated Tumor-bearing Mice, Cancer Research, 1998, 5301-5304, 58.
Moldenhauer et al., Identity of HML-1 Antigen on Intestinal Intra Epithelial T Cells and of B-1y7 Antigen on Hairy Cell Leukemia, Scan. J. Immunol., 1990, pp. 77-82, 32.
Morel et al., Monoclonal Antibodies to Bovine Serum Albumin: Affinity and Specificity Determinations, Mol. Immunol., 1988, Issue No. 1, pp. 7-15, 25.

(56) References Cited

OTHER PUBLICATIONS

Morrison, Sherie L. et al., Chimeric human antibody molecules: Mouse antigen-binding domains with human constant region domains, Proc. Natl. Acad. Sci. USA, 1984, 6851-6855, 81.

Murray, A. et al., Epitope Affinity Chromatography and Biophysical Studies of Monoclonal Antibodies and Recombinant Antibody Fragments, Journal of Chromatographic Science, 2002, 343-349, 40.

Muyldermans, Recognition of antigens by single-domain antibody fragments: the superfluous luxury of paired domains, Trends Biochem. Sci., 2001, 230-235, 26.

Myers, Eugene W. et al., Optimal alignments in linear space, Comput. Appl. Biosci., 1988, 11-17, 4(1).

Nakamura, Kazuhiko et al., TGF-beta 1 Plays an Important Role in the Mechanism of CD4+CD25+ Regulatory T Cell Activity in Both Humans and Mice, Journal of Immunology, 2004, 834-842, 172(2).

Needleman, Saul. B. et al., A General Method Applicable to the Search for Similarities in the Amino Acid Sequence of Two Proteins, J. Mol. Biol., 1970, 443-453, 48.

Nestle, Frank O. et al., Vaccination of melanoma patients with peptide- or tumor lysate-pulsed dendritic cells, Nature Medicine, 1998, 328-332, 4.

Nett, Juergen H. et al., A combinatorial genetic library approach to target heterologous glycosylation enzymes to the endoplasmic reticulum or the Golgi apparatus of Pichia pastoris, Yeast, 2011, 237-252, 28.

Nicolaou, K. C. et al., Calicheamicin 01: A Rationally Designed Molecule with Extremely Potent and Selective DNA Cleaving Properties and Apoptosis Inducing Activity, Angew. Chem. Int. Ed. Engl., 1994, 183-186, 33.

Nordstrom, Jeffrey L. et al., Anti-tumor activity and toxicokinetics analysis of MGAH22, an anti-HER2 monoclonal antibody with enhanced Fcgamma receptor binding properties, Breast Cancer Research, 2011, 1-14, 13.

Oida, Takatoku et al., CD4+CD25—T Cells That Express Latency-Associated Peptide on the Surface Suppress CD4+CD45RBhigh-Induced Colitis by a TGF-Beta-Dependent Mechanism, Journal of Immunology, 2003, 2516-2522, 170(5).

Oida, Takatoku et al., Depletion of TGF-Beta from fetal bovine serum, J. Immunol. Methods, 2010, 195-198, 362 (1-2).

Oida, Takatoku et al., Overexpression of TGF-Beta 1 Gene Induces Cell Surface Localized Glucose-Regulated Protein 78-Associated Latency-Associated Peptide/TGF-Beta, Journal of Immunology, 2010, 3529-3535, 185(6).

Oida, Takatoku et al., TGF-beta Induces Surface LAP Expression on Murine CD4 T Cells Independent of Foxp3 Induction, PLOS ONE, 2010, 1-8, 5(11): e15523.

Owais, Mohammad et al., Chloroquine Encapsulated in Malaria-Infected Erythrocyte-Specific Antibody-Bearing Liposomes Effectively Controls Chloroquine-Resistant Plasmodium berghei Infections in Mice, Antimicrobial Agents and Chemotherapy, 1995, 180-184, 39.

Padlan, Eduardo A., A Possible Procedure for Reducing the Immunogenicity of Antibody Variable Domains While Preserving Their Ligand-Binding Properties, Molecular Immunology, 1991, 489-498, 28(4/5).

Parekh, R. B. et al., Association of rheumatoid arthritis and primary osteoarthritis with changes in the glycosylation pattern of total serum IgG, Nature, 1985, 452-457, 316.

Pluckthun, A. et al., Antibodies from *Escherichia coli*, The Pharmacology of Monoclonal Antibodies, 1994, 269-315, Chapter 11.

Presta, L G et al., Humanization of an antibody directed against IgE, The Journal of Immunology, 1993, 2623-2632, 151.

Presta, Leonard G. et al., Antibody engineering, Curr. Op. Struct. Biol., 1992, 593-596, 2.

Presta, Leonard G. et al., Selection, design, and engineering of therapeutic antibodies, J. Allergy Clin. Immunol., 2005, 731-736, 116(4).

Presta, Leonard G., Engineering of therapeutic antibodies to minimize immunogenicity and optimize function, Advanced Drug Delivery Reviews, 2006, 640-656, 58.

Punjani, Ali et al., cryoSPARC: algorithms for rapid unsupervised cryo-EM structure determination, Nature Methods, 2017, 290-296, 14.

Qin, Yan et al, A Milieu Molecule for TGF-beta Required for Microglia Function in the Nervous System, Cell, 2018, 1-16, 174.

Raghunathan, Gopalan et al., Antigen-binding site anatomy and somatic mutations in antibodies that recognize different types of antigens, J. Mol. Recognit., 2012, 103-113, 25.

Ranade, Vasant V., Drug Delivery Systems. 1. Site-Specific Drug Delivery Using Liposomes as Carriers, J. Clin. Pharmacol., 1989, 685-694, 29.

Reichmann, Single domain antibodies: comparison of camel VH and camelised human VH domains, J. Immunol. Methods, 1999, 25-38, 231.

Reissner, K J. et al., Deamidation and isoaspartate formation in proteins: unwanted alterations or surreptitious signals?, Cell. Mol. Life Sci., 2003, 1281-1295, 60.

Ren, Hongjun et al., A Biocompatible Condensation Reaction for the Labeling of Terminal Cysteine Residues on Proteins, Angew. Chem. Int. Ed., 2009, 9658-9662, 48.

Renaud, Jean-Paul et al., Cryo-EM in drug discovery: achievements, limitations and prospects, Nature Reviews / Drug Discovery, 2018, 471-492, 17.

Restifo, N. et al., Cancer Vaccines, Cancer: Principles & Practice of Oncology, Fifth Edition, 1997, 3023-3043, Chapter 61.

Riechmann, Lutz et al., Reshaping human antibodies for therapy, Nature, 1988, 323-329, 332.

Rifkin, Daniel B. et al., LTBPs in Biology and Medicine; LTBP Diseases, Matrix Biol., 2018, 90-99, 71-72.

Robertson, Ian B. et al., Unchaining the beast; insights from structural and evolutionary studies on TGFbeta secretion, sequestration, and activation, Cytokine Growth Factor Rev., 2013, 355-372, 24.

Roguska, Michael A. et al., Humanization of murine monoclonal antibodies through variable domain resurfacing, Proc. Natl. Acad Sci. USA, 1994, 969-973, 91.

Samid, May Abd Al et al., Combining FoxP3 and Helios with GARP/LAP markers can identify expanded Treg subsets in cancer patients, Oncotarget, 2016, 14083-14094, 7(12).

Santegoets, Saskia J.A.M. et al., Monitoring regulatory T cells in clinical samples: consensus on an essential marker set and gating strategy for regulatory T cell analysis by flow cytometry, Cancer Immunol Immunother, 2015, 1271-1286, 64(10).

Sarmay, Gabriella et al., Mapping and Comparison of the Interaction Sites on the Fc Region of IgG Responsible for Triggering Antibody Dependent Cellular Cytotoxicity (ADCC) Through Different Types of Human Fcγ Receptor, Molec. Immunol., 1992, 633-639, 29(5).

Scapin, Giovanna et al., Cryo-EM for Small Molecules Discovery, Design, Understanding, and Application, Cell Chemical Biology, 2018, 1318-1325, 25.

Schreier, Hans et al., Targeting of Liposomes to Cells Expressing CD4 Using Glycosylphosphatidylinositol-anchored gp120, Journal of Biological Chemistry, 1994, 9090-9098, 269.

Scurr, M. et al., Highly prevalent colorectal cancer-infiltrating LAP + Foxp3—T cells exhibit more potent immunosuppressive activity than Foxp3 + regulatory T cells, Mucosal Immunol., 2014, 428-439, 7(2).

Senter, Peter D, Potent antibody drug conjugates for cancer therapy, Curr. Opin. Chem. Biol., 2009, 235-244, 13.

Shah, Mamta et al., Neutralisation of TGF-Beta1 and TGF-Beta2 or exogenous addition of TGF-Beta3 to cutaneous rat wounds reduces scarring, Journal of Cell Science, 1995, 985-1002, 108.

Shields et al., Lack of fucose on human IgG1 N linked oligosaccharide improves binding to human Fc gamma RIII and antibody dependent cellular toxicity, J. Biol. Chem., 2002, pp. 26733-26740, 277.

Shields, Robert L. et al., High Resolution Mapping of the Bidning Site on Human IgG1 for FcγRI, FcγRII, FcγRIII, and ReRn and

(56) References Cited

OTHER PUBLICATIONS

Design of IgG1 Variants with Improved Binding to the FcγR*, The Journal of Biological Chemistry, 2001, 6591-6604, 276(9).

Sims, M J et al., A humanized CD18 antibody can block function without cell destruction, The Journal of Immunology, 1993, 2296-2308, 151.

Songsivilai et al., Bispecific antibody: a tool for diagnosis and treatment of disease, Clin. Exp. Immunol., 1990, pp. 315-321, 79.

Spiro et al., Protein Glycosylation, Glycobiol., 2002, pp. 43R-56R, 12.

Stahli et al., Distinction of Epitopes by monoclonal antibodies, Methods in Enzymology, 1983, pp. 242-253, 9.

Stavenhagen, Jeffrey B. et al., Fc Optimization of Therapeutic Antibodies Enhances Their Ability to Kill Tumor Cells In vitro and Controls Tumor Expansion In vivo via Low-Affinity Activating Fcgamma Receptors, Cancer Research, 2007, 8882-8890, 67.

Strohl, William R., Optimization of Fc-mediated effector functions of monoclonal antibodies, Current Opinion in Biotechnology, 2009, 685-691, 20.

Studnicka, Gary M. et al., Human-engineered monoclonal antibodies retain full specific binding activity by preserving non-CDR complementaritymodulating residues, Protein Engineering, 1994, 805-814, 7(6).

Sun, Jinging et al., Identification of Human Regulatory T Cells in the Setting of T-Cell Activation and Anti-CTLA-4 Immunotherapy on the Basis of Expression of Latency-Associated Peptide, Cancer Discovery, 2011, 122-130, 2(2).

Sunbul, Murat et al., Site specific protein labeling by enzymatic posttranslational modification, Organic & Biomolecular Chemistry, 2009, 3361-3371, 7.

Taki, Masumi et al., Transglutaminase-mediated N- and C-terminal fluorescein labeling of a protein can support the native activity of the modified protein, Protein Engineering, Design & Selection, 2004, 119-126, 17(2).

Tansey, Malu G. et al., The TNF superfamily in 2009: new pathways, new indications, and new drugs, Drug Discovery Today, 2009, 1082-1088, 14.

Taylor, E. Vogel et al., Native Chemical Ligation: SemiSynthesis of Post-translationally Modified Proteins and Biological Probes, Nucleic Acids and Molecular Biology, 2009, 65-96, 22.

Tran, Dat Q. et al., GARP (LRRC32) is essential for the surface expression of latent TGF-Beta on platelets and activated FOXP3+ regulatory T cells, PNAS, 2009, 13445-13450, 106(32).

Tsumura, Haruhiko et al., Generation of Recombinant Human Large Latent Transforming Growth Factor-Beta1 and Monoclonal Antibodies to It, Bioscience, Biotechnology, and Biochemistry, 2000, 17-23, 64(1).

Umana et al., Engineered glycoforms of an antineuroblastoma IgG1 with optimized antibody dependent cellular cytotoxic activity, Nature Biotechnology, 1999, pp. 176-180, 17.

Umezawa, F. et al., Liposome Targeting to Mouse Brain: Mannose As a Recognition Marker, Biochemical and Biophysical Research Communications, 1988, 1038-1044, 153.

Van Regenmortel, M.H.V., From absolute to exquisite specificity. Reflections on the fuzzy nature of species, specificity and antigenic sites, Journal of Immunological Methods, 1998, 37-48, 216(1-2).

Verhoeyen, Martine et al., Reshaping Human Antibodies: Grafting an Antilysozyme Activity, Science, 1988, 1534-1537, 239.

Wallace, Caroline H. et al., B lymphocytes confer immune tolerance via cell surface GARP-TGF-β complex, JCI Insight, 2018, 1-18, 3:e99863.

Wallick, Susan C. et al., Glycosylation of a VH Residue of a Monoclonal Antibody Against a (I-6) Dextran Increases Its Affinity for Antigen, J. Exp. Med., 1988, 1099-1109, 168.

Ward, E. Sally et al., Binding activities of a repertoire of single immunoglobulin variable domains secreted from *Escherichia coli*, Nature, 1989, 544-546, 341.

Waterhouse, Peter et al., Combinatorial infection and in vivo recombination: a strategy for making large phage antibody repertoires, Nuc. Acids. Res., 1993, 2265-2266, 21.

Xu, Xin et al., Transforming growth factor-β in stem cells and tissue homeostasis, Bone Research, 2018, 1-31, 6(2).

Yeung, Yik Andy et al., Engineering Human IgG1 Affinity to Human Neonatal Fc Receptor: Impact of Affinity Improvement on Pharmacokinetics in Primates, J. Immunol., 2009, 7663-7671, 182.

Zhang, Congcong et al., Chimeric Antigen Receptor-Engineered NK-92 Cells: An Off-the-Shelf Cellular Therapeutic for Targeted Elimination of Cancer Cells and Induction of Protective Antitumor Immunity, Frontiers in Immunology, 2017, 1-17, 8.

Zhang, Hongru et al., Critical Role of Myeloid-Derived Suppressor Cells in mer-Induced Liver Immune Suppression through Inhibition of NKT Cell Function, Frontiers in Immunology, 2017, 1-15, vol. 8: Article 129.

Zhang, Shuai et al., Tumor-associated macrophages promote tumor metastasis via the TGF-β/SOX9 axis in non-small cell lung cancer, Oncotarget, 2017, 99801-99815, 8(59).

Zhang, Yu et al, Mammary-tumor-educated B cells acquire LAP/TGF-beta and PD-L1 expression and suppress anti-tumor immune responses, International Immunology, 2016, 423-433, 28(9).

Zheng, Liwei et al., Aberrant activation of latent transforming growth factor-β initiates the onset of temporomandibular joint osteoarthritis, Bone Research, 2018, 1-10, 6:26.

Zhong, Wu et al., Role of LAP+CD4+ T cells in the tumor microenvironment of colorectal cancer, World Journal of Gastroenterology, 2017, 455-463, 23(3).

\* cited by examiner

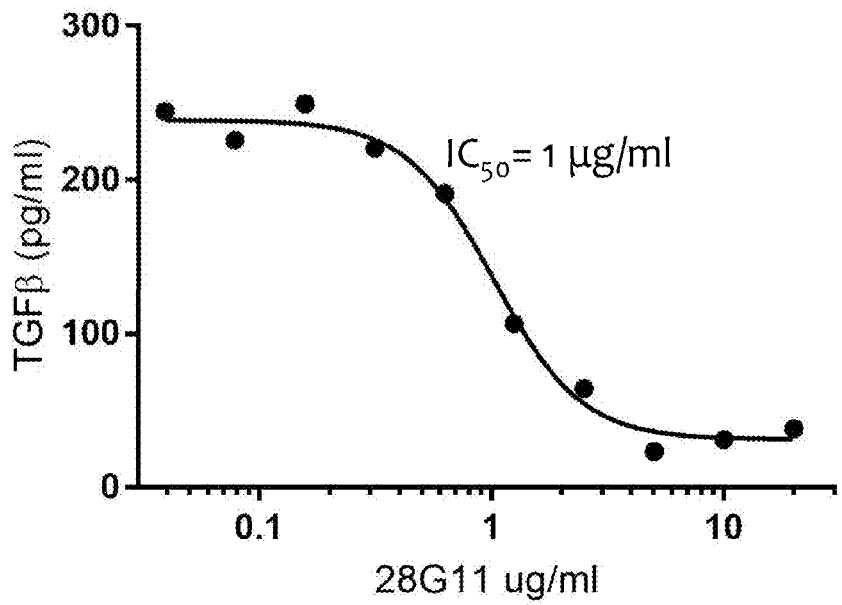
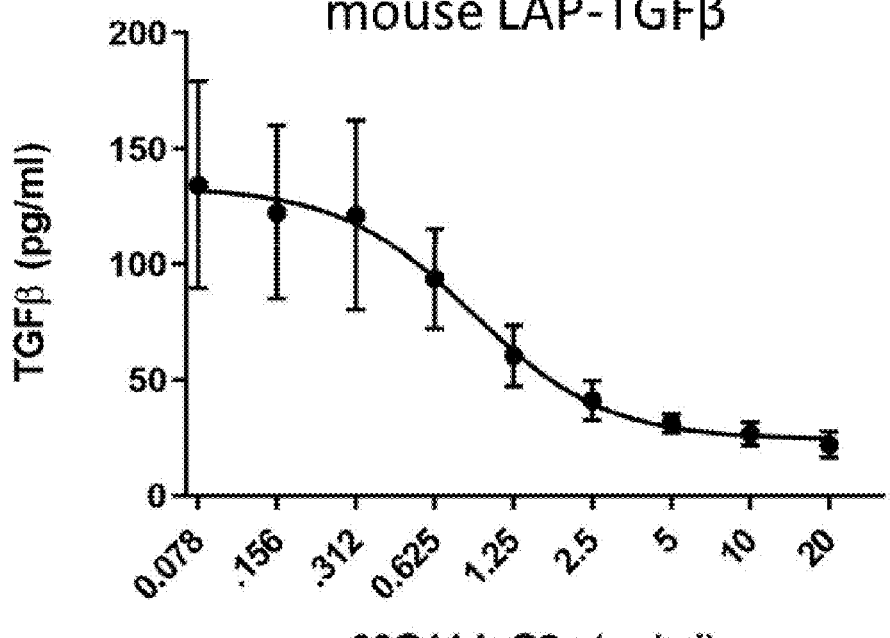
FIG. 5B

17G8

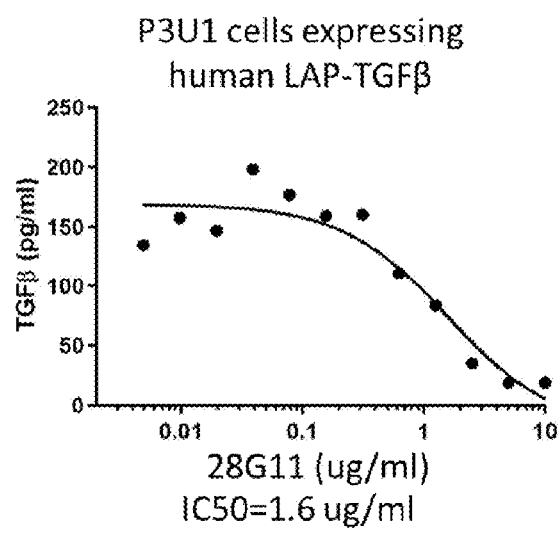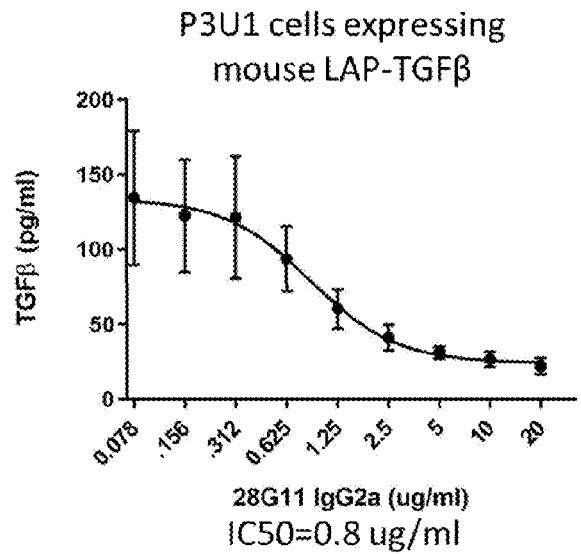
FIG. 6G
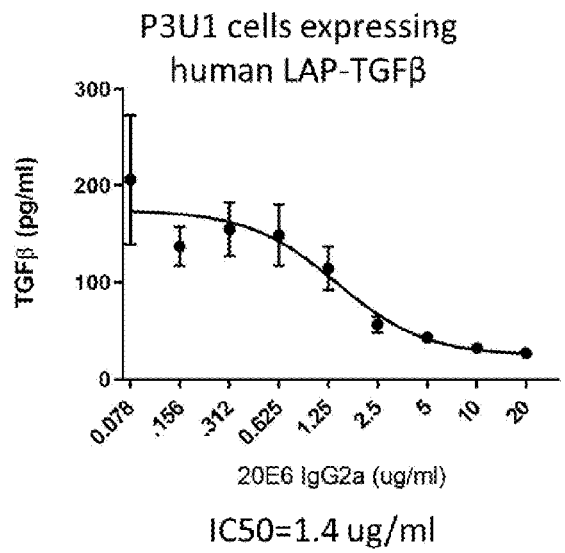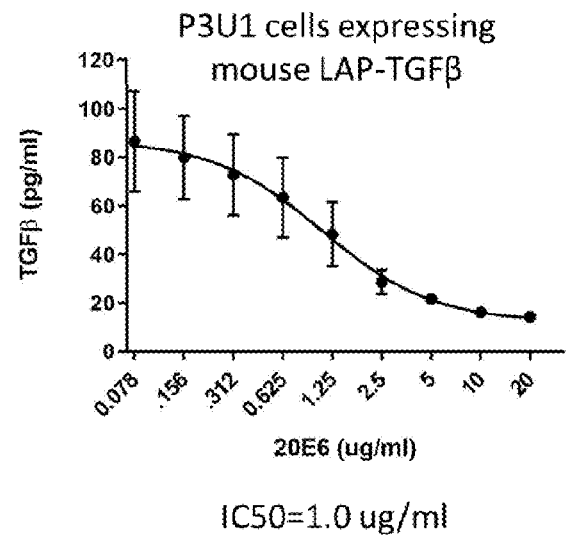
FIG. 6H

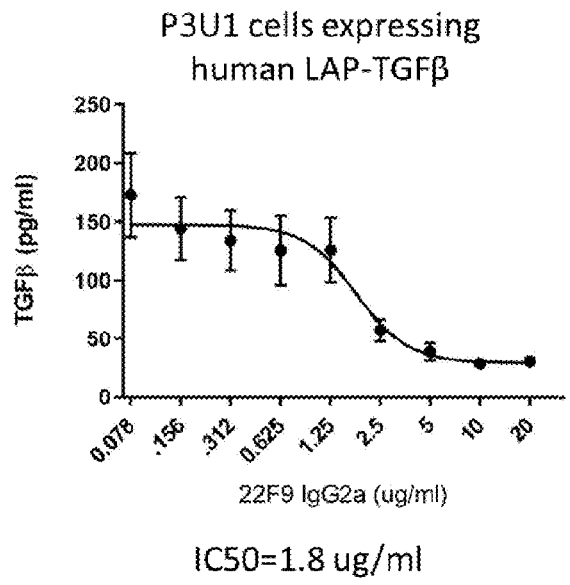
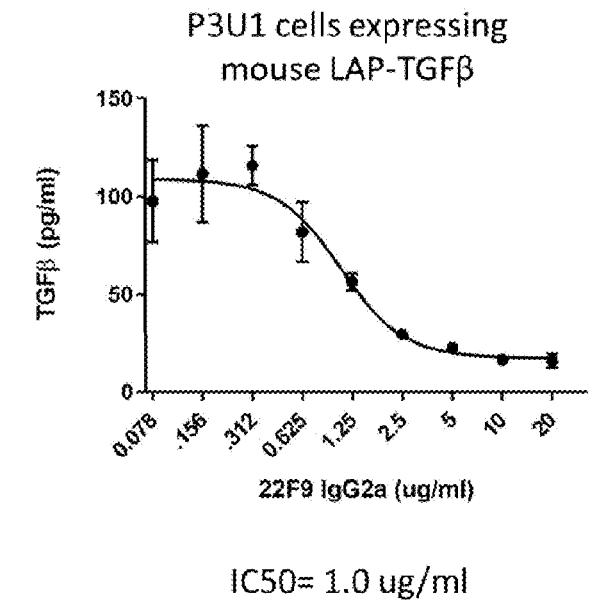
FIG. 6I
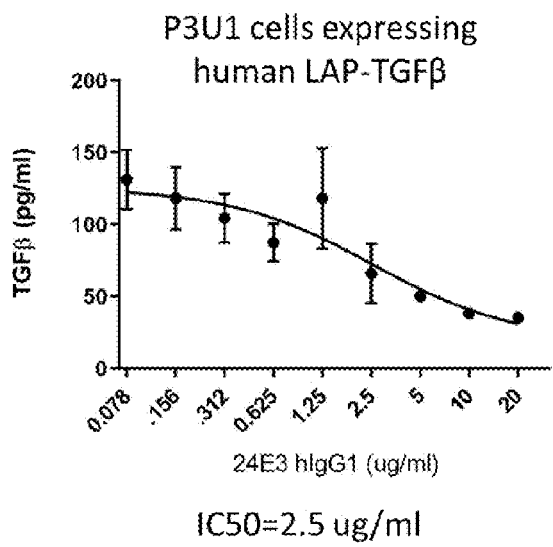
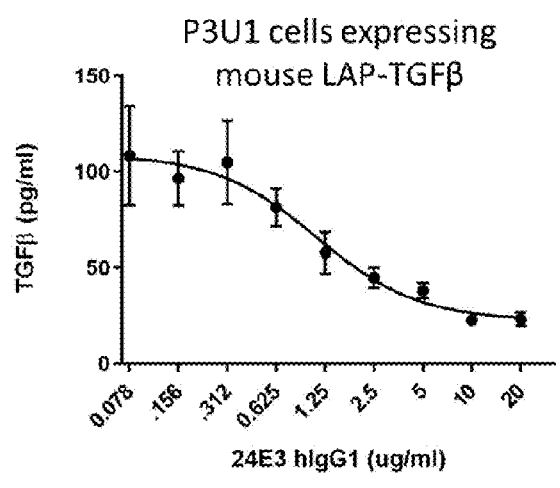
FIG. 6J

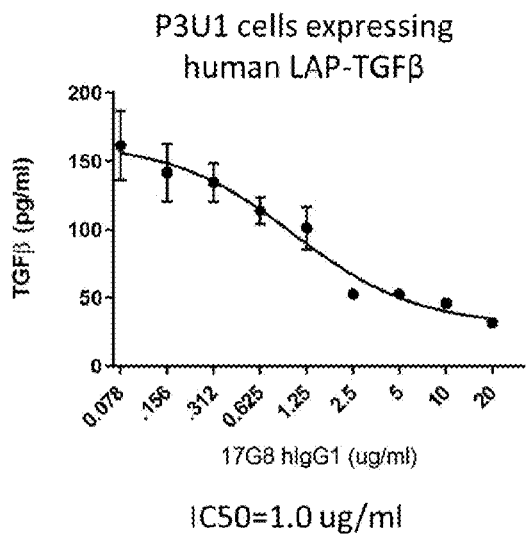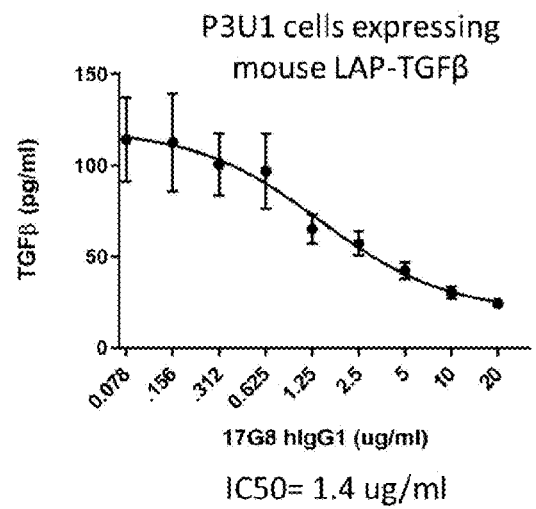
FIG. 6K
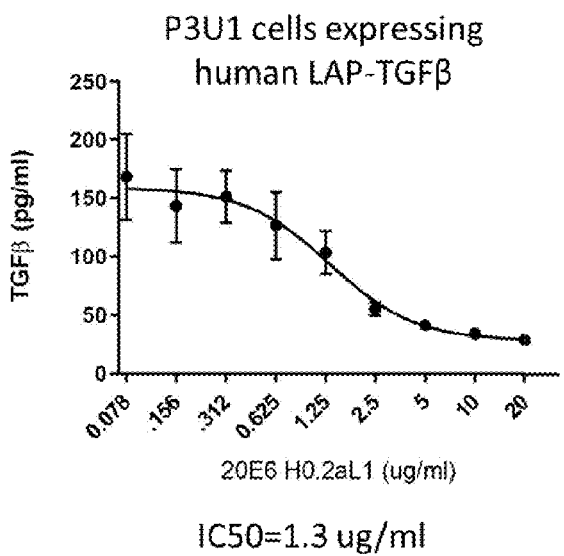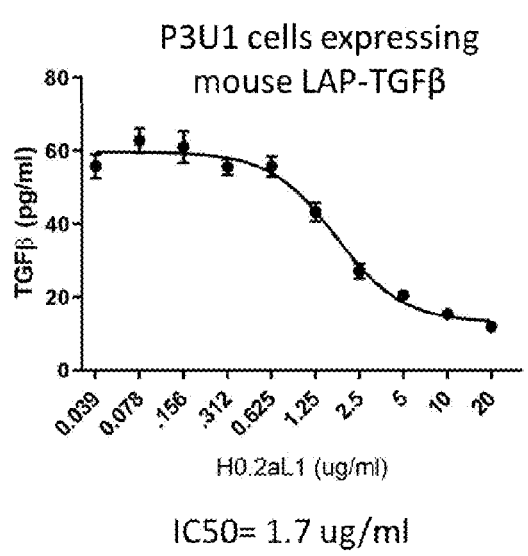
FIG. 6L

5 μg competitor, 0.31 μg biotin-28G11

```
              Region 1           Region 2

Human   1    LSTCKTIDMELVKRKRIEAIRGQILSKLRLASPPSQGEVPPGPLPEAVLALYNSTRDRVA    60
Mouse   1    LSTCKTIDMELVKRKRIEAIRGQILSKLRLASPPSQGEVPPGPLPEAVLALYNSTRDRVA    60

Human  61    GESAEPEPEPEADYYAKEVTRVLMVETHNEIYDKFKQSTHSIYMFFNTSELREAVPEPVL   120
Mouse  61    GESA+PEPEPEADYYAKEVTRVLMV+ +N IY+K   +HSIYMFFNTS++REAVPEP L
             GESADPEPEPEADYYAKEVTRVLMVDRNNAIYEKTKDISHSIYMFFNTSDIREAVPEPPL   120

Human 121    LSRAELRLLRLLKLKVEQHVELYQKYSNNSWRYLSNRLLAPSDSPEWLSFDVTGVVRQWLS   180
Mouse 121    LSRAELRL RLK  VEQHVELYQKYSNNSWRYL NRLL P+D+PEWLSFDVTGVVRQWL+
             LSRAELRLQRLKSSVEQHVELYQKYSNNSWRYLGNRLLTPTDTPEWLSFDVTGVVRQWLN   180

Human 181    RGGEIEGFRLSAHCSCDSRDNTLQVDINAGFTTGRRGDLATIHGMNRPFLLLMATPLERA   240
Mouse 181    +G  I+GFR  SAHCSCDS+DN L  V+IN G +   RRGDL  TIH MNRPFLLLMATPLERA
             QGDGIQGFRFSAHCSCDSKDNKLHVEIN-GISPKRRGDLGTIHDMNRPFLLLMATPLERA   239

Region 3
Human 241    QHLQSSRHRRALDTNYCFSSTEKNCCVRQLYIDFRKDLGWKWIHEPKGYHANFCLGPCPY   300
Mouse 240    QHL SSRHRRALDTNYCFSSTEKNCCVRQLYIDFRKDLGWKWIHEPKGYHANFCLGPCPY
             QHLHSSRHRRALDTNYCFSSTEKNCCVRQLYIDFRKDLGWKWIHEPKGYHANFCLGPCPY   299

Region 4
Human 301    IWSLDTQYSKVLALYNQHNPGASAAPCCVPQALEPLPIVYYVGRKPKVEQLSNMIVRSCK   360
Mouse 300    IWSLDTQYSKVLALYNQHNPGASA+PCCVPQALEPLPIVYYVGRKPKVEQLSNMIVRSCK
             IWSLDTQYSKVLALYNQHNPGASASPCCVPQALEPLPIVYYVGRKPKVEQLSNMIVRSCK   359

Human 361    CS    362    (SEQ ID NO: 257)
Mouse 360    CS
             CS    361    (SEQ ID NO: 7)
```

FIG. 34

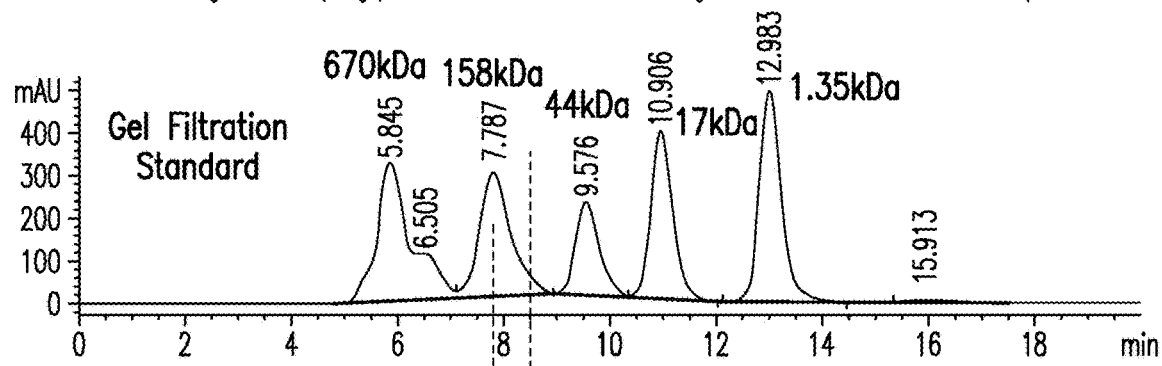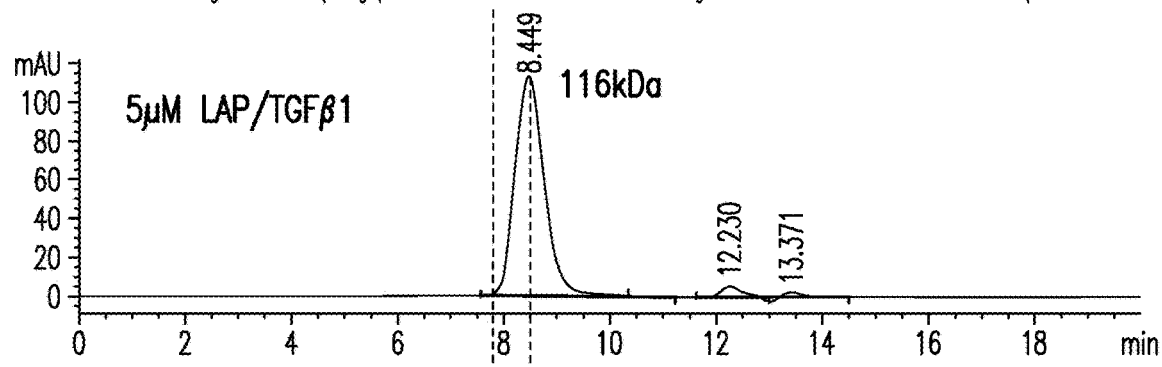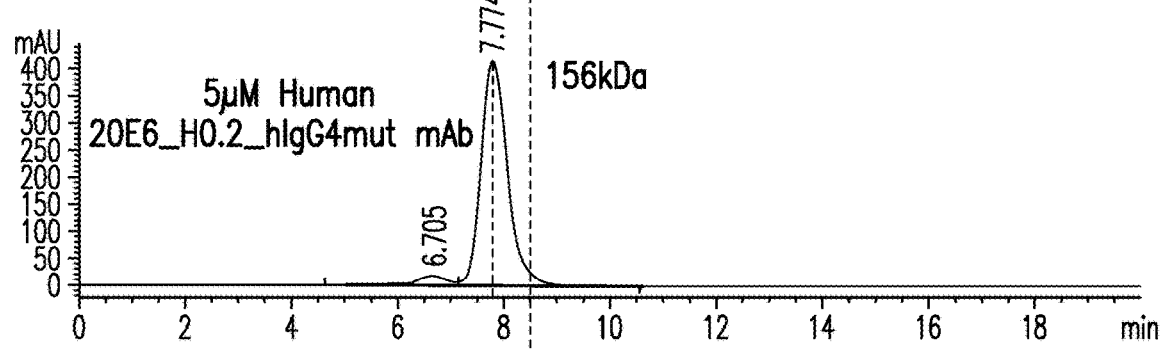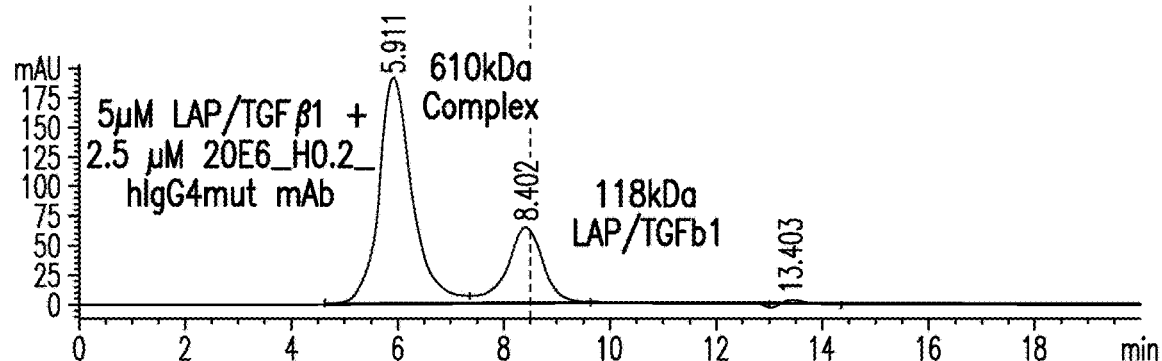
FIG.35A

Isotype control

PD-1 alone

16B4 alone

16B4 + PD-1

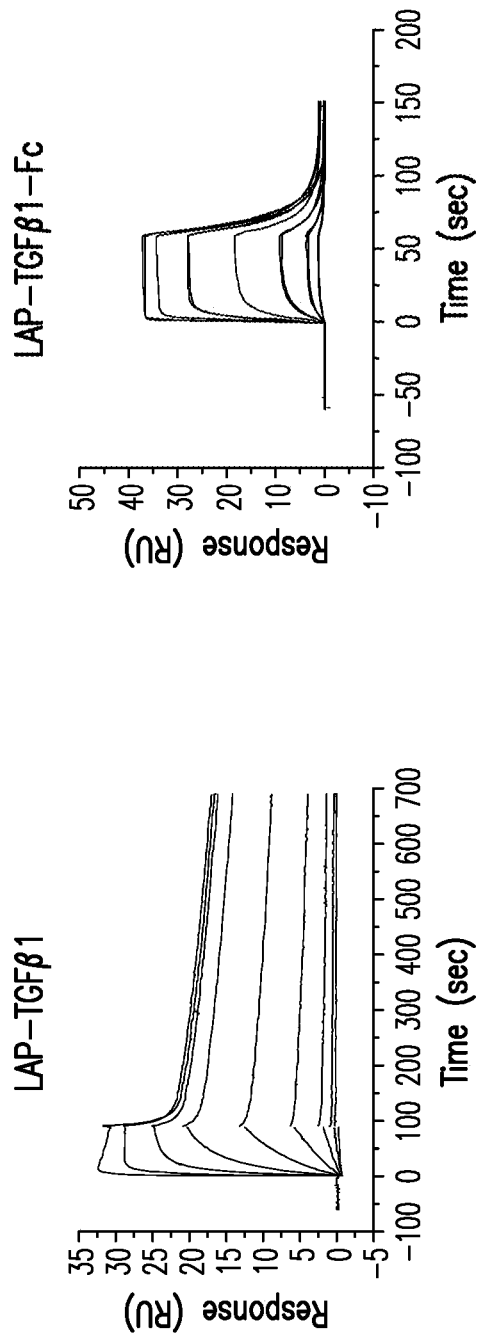
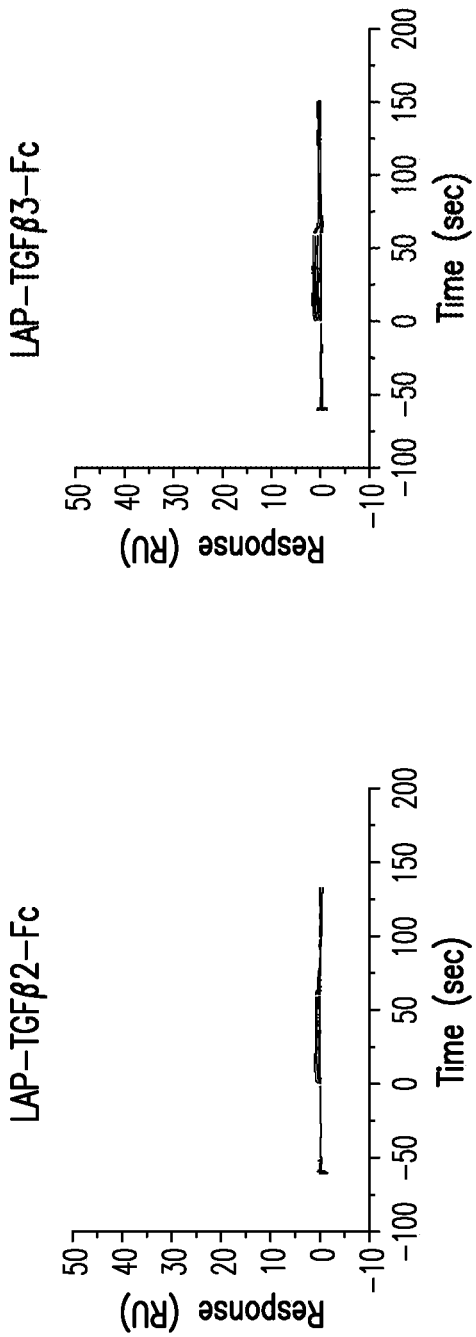
FIG. 44A  FIG. 44B  FIG. 44C  FIG. 44D

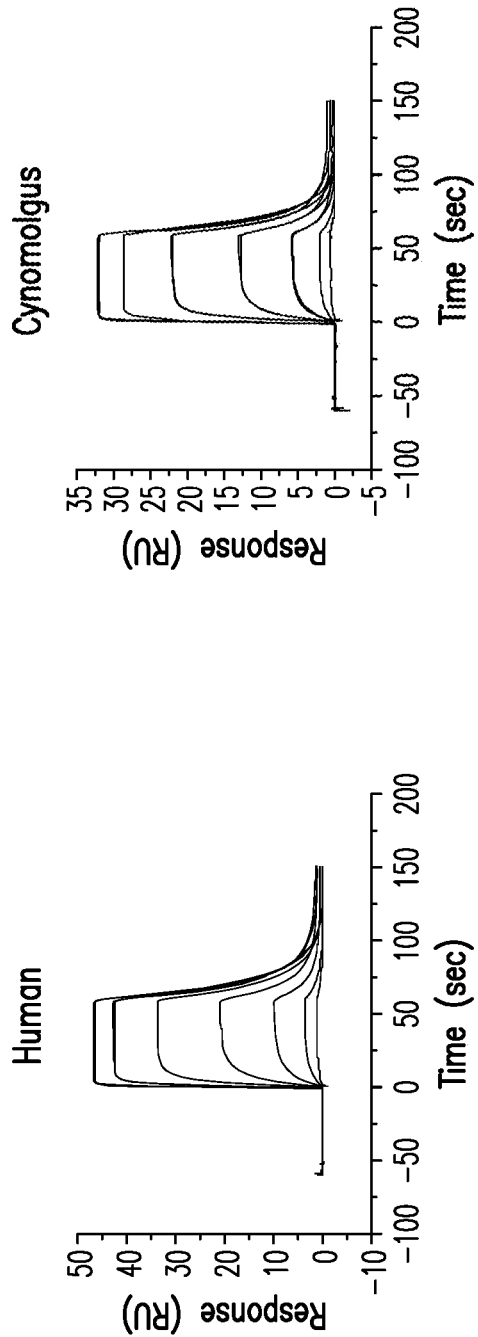
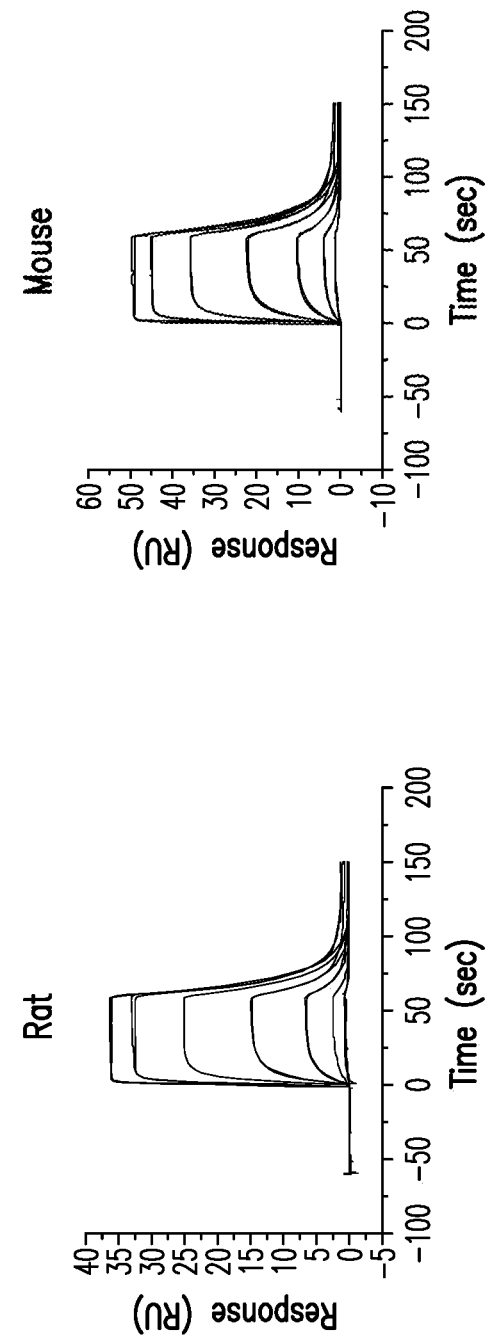
FIG. 45A  FIG. 45B  FIG. 45C  FIG. 45D

ANTI-LAP ANTIBODY VARIANTS

RELATED APPLICATIONS

This application claims the benefit of U.S. Provisional Patent Application No. 62/744,045, filed Oct. 10, 2018, U.S. Provisional Patent Application No. 62/750,065, filed Oct. 24, 2018, and U.S. Provisional Patent Application No. 62/757,519, filed Nov. 8, 2018, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Oct. 9, 2019, is named TTJ_003_Sequence_Listing.txt and is 457,042 bytes in size.

FIELD OF THE INVENTION

The present invention relates to anti-LAP antibodies or antigen binding fragments thereof. Another aspect of the invention relates to compositions and kits comprising the anti-LAP antibodies or antigen binding fragments. Another aspect of the invention relates to methods for treating diseases, for example cancer, by administering the antibodies or antigen binding fragments.

BACKGROUND

Transforming growth factor beta 1 (TGFβ1) is synthesized as a pro-protein complex, in which the mature cytokine is caged within LAP (latency associated peptide), which is the latency associated peptide of TGFβ1. The LAP-TGFβ1 complex is disulfide bonded to one of five currently known anchor proteins: Glycoprotein A repetitions predominant (GARP), Leucine-rich repeat-containing protein 33 (LRRC33), Latent-transforming growth factor beta-binding protein 1 (LTBP1), Latent-transforming growth factor beta-binding protein 3 (LTBP3), and Latent-transforming growth factor beta-binding protein 4 (LTBP4). These anchor proteins localize latent TGFβ1 in particular sites and on particular cells within the body.

GARP, also referred to as leucine-rich repeat protein 32 or LRRC32, is a transmembrane protein that anchors LAP-TGFβ1 to the surface of lymphocytes, most notably regulatory T cells. GARP is also expressed on platelets, B cells, NK cells, fibroblasts, mesenchymal stromal cells, mesenchymal stem cells, and endothelial cells and also governs LAP-TGFβ1 expression on those cell types. LRRC33 is a transmembrane protein that is reported to anchor LAP-TGFβ1 to the surface of myeloid cells, most notably macrophages, dendritic cells, and myeloid derived suppressor cells (MDSCs). LTBP1, LTBP3, and LTBP4 are secreted molecules that anchor LAP-TGFβ1 into the extracellular matrix (ECM).

Although LAP binding agents have been used in the art as tools to identify certain cell populations, little is known about LAP's relevance in disease states.

The location of the LAP-TGFβ1 complex is of critical biological and clinical importance because, once the mature TGFβ1 cytokine, which has a short half-life in solution, is released, it acts locally, either in an autocrine or near paracrine fashion. Therefore, the anchor proteins are a principal mechanism whereby latent TGFβ1 is staged in a specific location, awaiting the release of the potent mature cytokine to act on the local tissue.

LAP-TGFβ1 has different functions when expressed in different locations. For example, LAP-TGFβ1 anchored by LTBPs in the extracellular matrix is of primary importance for tissue homeostasis. In this regard, Xu et al. (*Bone Research* 2018; 6:2) noted that "the TGF-β complex is more like a molecular sensor that responds instantly to ECM perturbations through the release of an active ligand that exerts physiological effects at a cellular level, thus ensuring normal tissue homeostasis."

Alterations in LAP-TGFβ1 incorporation into the extracellular matrix are known to result in human disease. For example, deletion of LTBP-3 in both mice and humans results in similar defects in both bone and dental formation. LTBP-3 defects are also associated with the aortic dilation seen in Marfan syndrome (Rifkin et al., Matrix Biol 2018; 71-72:90-99). These effects are believed to be due to aberrant direct effects of TGFβ1 in the local extracellular matrix (Xu et al, Bone Research 2018; 6:2).

In contrast to anchor proteins that localize LAP-TGFβ1 to the extracellular matrix, LAP-TGFβ1 anchored by GARP is of primary importance for the immunosuppressive function of regulatory T cells (Edwards et al, *Eur J Immunol* 2016; 46:1480-9) and of suppressive B cell subpopulations (Wallace et al, JCI Insight 2018; 3:e99863). Some tumors have also been shown to express GARP, allowing them to locally express TGFβ and directly suppress the immune system in the tumor microenvironment and support their own growth (Metelli et al, Journal of Hematology & Oncology 2018; 11:24).

LAP-TGFβ1 anchored to myeloid cells is of primary importance for the immunosuppressive function of MDSCs (Zhang H et al., *Frontiers in Immunology* 2017; 8:1-15) and of M2 macrophages (Zhang et al., Oncotarget 2017; 8:99801-15). According to a recent study, myeloid cells have been shown to use the anchor protein LRRC33 to anchor latent TGFβ to the cell surface (Qin et al., *Cell* 2018; 174:1-16).

Recent developments in cancer therapy have focused on harnessing a patient's immune system by, e.g., activation of exhausted immune cell populations, vaccination, and removal of immunosuppressive cell populations. Given the ongoing need for improved strategies for targeting (and diagnosing) diseases such as cancer, novel agents and methods that are useful for these purposes are desired.

SUMMARY

An aspect of the invention provided herein is a construct (e.g., polynucleotide, expression vector and host cell), protein or peptide comprising any of the sequences described herein, for example, the amino acid sequences found in tables such as Table 34. Provided herein are antibodies and antigen binding fragments thereof that bind LAP comprising the structural and functional features specified below (e.g., any one of the amino acid sequences of SEQ ID NOs: 16-197, 214, 216-240, 242-245, 248, 249 and 255 in Table 34). For example, the antibodies and antigen binding fragments comprise the amino acid sequences described in the tables herein, e.g., SEQ ID NOs: 16-197, 214, and 216-255. In various embodiments, the LAP comprises a complex and/or an epitope comprising LAP and a TGFβ (e.g., TGFβ1). In various embodiments, the epitope is described in examples herein, e.g., Examples 19-23.

An aspect of the invention provides isolated monoclonal antibodies (e.g., recombinant humanized, chimeric, and human antibodies) which exhibit therapeutically advantageous patterns of binding to LAP-TGFβ1 (e.g., human LAP-TGFβ1) and functional properties compared to prior anti-LAP antibodies. In one embodiment, the anti-LAP antibodies selectively bind to LAP-TGFβ1 on cells (e.g., immune cells and other immunosuppressive cells) but not to LAP-TGFβ1 in the extracellular matrix, and thus are able to target a broad range of clinically relevant cell types while sparing the natural function/activation of LAP-TGFβ1 in the extracellular matrix. Because TGFβ acts in an autocrine or near-paracrine manner, selective binding to specific cell populations will result in inhibition of the production of mature TGFβ in the immediate proximity of the indicated cell population. Accordingly, the antibodies described herein provide the clinical benefit of inhibiting TGFβ activation and release of the mature cytokine in a highly selective, cell-specific manner. In some embodiments, the anti-LAP antibodies are of an isotype with active effector function and enhanced binding of a specific anti-LAP antibody to a given cell population will result in increased depletion of that cell population by ADCC or CDC. Accordingly, anti-LAP antibodies disclosed herein are ideal for treating a broad variety of diseases, including cancers and other diseases involving immunosuppressive cells, both in monotherapy and combination with other immunomodulatory or therapeutic agents (e.g., immune checkpoint inhibitors).

In another aspect of the invention, provided herein is an antibody (e.g., recombinant humanized, chimeric, domain, or human antibody) or antigen binding fragment thereof which specifically binds to LAP comprising:

(a) a heavy chain variable region comprising complementarity determining region (CDR) 1, CDR2, and CDR3 regions comprising the amino acid sequences of SEQ ID NOs: 16, 26, and 18, respectively, and a light chain variable region comprising CDR1, CDR2, and CDR3 regions comprising the amino acid sequences of SEQ ID NOs: 19, 20, and 21, respectively;

(b) a heavy chain variable region comprising CDR1, CDR2, and CDR3 regions comprising the amino acid sequences of SEQ ID NOs: 54, 55, and 56, respectively, and a light chain variable region comprising CDR1, CDR2, and CDR3 regions comprising the amino acid sequences of SEQ ID NOs: 57, 58, and 59, respectively;

(c) a heavy chain variable region comprising CDR1, CDR2, and CDR3 regions comprising the amino acid sequences of SEQ ID NOs: 54, 66, and 56, respectively, and a light chain variable region comprising CDR1, CDR2, and CDR3 regions comprising the amino acid sequences of SEQ ID NOs: 57, 58, and 59, respectively;

(d) a heavy chain variable region comprising CDR1, CDR2, and CDR3 regions comprising the amino acid sequences of SEQ ID NOs: 54, 55, and 68, respectively, and a light chain variable region comprising CDR1, CDR2, and CDR3 regions comprising the amino acid sequences of SEQ ID NOs: 57, 58, and 59, respectively;

(e) a heavy chain variable region comprising CDR1, CDR2, and CDR3 regions comprising the amino acid sequences of SEQ ID NOs: 54, 66, and 68, respectively, and a light chain variable region comprising CDR1, CDR2, and CDR3 regions comprising the amino acid sequences of SEQ ID NOs: 57, 58, and 59, respectively;

(f) a heavy chain variable region comprising CDR1, CDR2, and CDR3 regions comprising the amino acid sequences of SEQ ID NOs: 110, 111, and 112, respectively, and a light chain variable region comprising CDR1, CDR2, and CDR3 regions comprising the amino acid sequences of SEQ ID NOs: 113, 114, and 115, respectively; or (g) a heavy chain variable region comprising CDR1, CDR2, and CDR3 regions comprising the amino acid sequences of SEQ ID NOs: 110, 120, and 112, respectively, and a light chain variable region comprising CDR1, CDR2, and CDR3 regions comprising the amino acid sequences of SEQ ID NOs: 113, 114, and 115, respectively.

In various embodiments, the antibody is a humanized antibody, chimeric antibody, or human antibody.

In various embodiments, the administering step (e.g., in a method of treating or diagnosing a subject) is performed with the antibody. In various embodiments, the antibody is a humanized antibody, chimeric antibody or human antibody. In various embodiments, the LAP is human LAP, cynomolgus monkey (cyno) LAP, rat LAP, and/or mouse LAP. In various embodiments, the administering step (e.g., in a method of treating or diagnosing a subject) is performed with the antigen binding fragment.

In various embodiments, the constant region of the antibody is a human IgG1 constant region. For example, the IgG1 constant region comprises the amino acid sequence set forth in a table disclosed herein, (e.g., Table 34). For example, the IgG1 constant region comprises the amino acid sequence set forth in SEQ ID NOs: 196, 244, or 245. In various embodiments, the constant region of the antibody is a human IgG4 constant region. For example, the human IgG4 constant region comprises the amino acid sequence set forth in SEQ ID NO: 197.

In another aspect of the invention, provided herein is an isolated antibody or antigen binding fragment which specifically binds to human LAP and comprises heavy and light chain variable region sequences which are at least 80%, 85%, 90%, 95%, 98%, 99%, or 100% identical to the amino acid sequences selected from the group consisting of: (a) SEQ ID NOs: 42 and 52, respectively; (b) SEQ ID NOs: 101 and 104, respectively; (c) SEQ ID NOs: 98 and 104, respectively; (d) SEQ ID NOs: 133 and 154, respectively; and (e) SEQ ID NOs: 218 and 154, respectively.

In another aspect of the invention, provided herein is an isolated antibody or antigen binding fragment which specifically binds to human LAP and comprises a heavy chain variable region comprising the amino acid sequence of SEQ ID NO: 218 or a heavy chain variable region comprising the amino acid sequence of SEQ ID NO: 218 with 1, 2, or 3 amino acid substitutions; and a light chain variable region comprising the amino acid sequence of SEQ ID NO: 154 or a light chain variable region comprising the amino acid sequence of SEQ ID NO: 154 with 1, 2, or 3 amino acid substitutions. In various embodiments, at least one substitution is located within a CDR. In various embodiments, at least one substitution is located within a framework region. In various embodiments, at least one substitution is located within at least one CDR and at least one the framework region. In various embodiments, any and/or all of the at least one substitution is located and/or found within the framework region(s). In various embodiments, the antibody is a humanized antibody, chimeric antibody, or human antibody. Another aspect of the invention provided herein is an isolated antibody or antigen binding fragment which specifically binds to human LAP and comprises a heavy chain variable region comprising the amino acid sequence of SEQ ID NO: 218 or a heavy chain variable region comprising the amino acid sequence of SEQ ID NO: 218 with 1-5, 5-10, 10-15, 15-20, or 20-25 amino acid substitutions; and a light chain variable region comprising the amino acid sequence of SEQ ID NO: 154 or a light chain variable region comprising the amino acid sequence of SEQ ID NO: 154 with 1-5, 5-10, 10-15, 15-20, or 20-25 amino acid substitutions. For example, at least one substitution is located in at least one CDR region. In various embodiments, the at least one substitution is located within multiple CDRs. In various embodiments, the at least one substitution is located within at least one framework region. In various embodiments, the at least one substitution is located within at least one CDR and in at least one framework region. In various embodiments, any and/or all of the at least one substitution is located and/or found within the framework region(s). In various embodiments, the antibody is a humanized antibody, chimeric antibody, or human antibody.

Another aspect of the invention provided herein is an isolated antibody or antigen binding fragment which specifically binds to human LAP, wherein the antibody or antigen binding fragment comprises a heavy chain variable region comprising the amino acid sequence of SEQ ID NO: 218, wherein the antibody or antigen binding fragment comprises a light chain variable region comprising the amino acid sequence of SEQ ID NO: 154. In various embodiments, the antibody is a humanized antibody, chimeric antibody, or human antibody.

Another aspect of the invention provided herein is an isolated antibody or antigen binding fragment which specifically binds to human LAP, wherein the antibody or antigen binding fragment comprises a heavy chain variable region consisting of the amino acid sequence of SEQ ID NO: 218, wherein the antibody or antigen binding fragment comprises a light chain variable region consisting of the amino acid sequence of SEQ ID NO: 154. In various embodiments, the antibody is a humanized antibody, chimeric antibody, or human antibody.

Another aspect of the invention provided herein is an isolated antibody or antigen binding fragment which specifically binds to human LAP, wherein the antibody or antigen binding fragment comprises a heavy chain comprising the amino acid sequence of SEQ ID NO: 219, wherein the antibody or antigen binding fragment comprises a light chain comprising the amino acid sequence of SEQ ID NO: 155. In various embodiments, the antibody is a humanized antibody, chimeric antibody, or human antibody.

Another aspect of the invention provided herein is an isolated antibody or antigen binding fragment which specifically binds to human LAP, wherein the antibody or antigen binding fragment comprises a heavy chain consisting of the amino acid sequence of SEQ ID NO: 219, wherein the antibody or antigen binding fragment comprises a light chain consisting of the amino acid sequence of SEQ ID NO: 155. In various embodiments, the antibody is a humanized antibody, chimeric antibody, or human antibody. In another aspect of the invention, provided herein is an isolated antibody or antigen binding fragment which specifically binds to human LAP and comprises heavy and light chain sequences which are at least 80%, 85%, 90%, 95%, 98%, 99%, or 100% identical to the amino acid sequences selected from the group consisting of: (a) SEQ ID NOs: 43 and 53, respectively; (b) SEQ ID NOs: 45 and 53, respectively; (c) SEQ ID NOs: 102 and 105, respectively; (d) SEQ ID NOs: 103 and 105, respectively; (e) SEQ ID NOs: 99 and 105, respectively; (f) SEQ ID NOs: 100 and 105, respectively; (g) SEQ ID NOs: 134 and 155, respectively; (h) SEQ ID NOs: 135 and 155, respectively; (i) SEQ ID NOs: 219 and 155, respectively; and (j) SEQ ID NOs: 220 and 155, respectively. For example, at least one substitution is located in at least one CDR region. In various embodiments, the at least one substitution is located within multiple CDRs. In various embodiments, the at least one substitution is located within at least one framework region. In various embodiments, the at least one substitution is located within at least one CDR and in at least one framework region. In various embodiments, any and/or all of the at least one substitution is located and/or found within the framework region(s). In various embodiments, the antibody is a humanized antibody, chimeric antibody, or human antibody.

In another aspect of the invention, provided herein is an isolated antibody or antigen binding fragment which binds to human LAP and comprises a heavy chain variable region comprising CDR1, CDR2, and CDR3 regions comprising the amino acid sequences of SEQ ID NOs: 110, 120, and 112, respectively, and a light chain variable region comprising CDR1, CDR2, and CDR3 regions comprising the amino acid sequences of SEQ ID NOs: 113, 114, and 115, respectively, wherein the antibody further comprises a human IgG1 constant region. In various embodiments, the antibody is a humanized antibody, chimeric antibody, or human antibody.

In another aspect of the invention, provided herein is an isolated antibody or antigen binding fragment which binds to human LAP and comprises a heavy chain variable region comprising CDR1, CDR2, and CDR3 regions comprising amino acid sequences that are at least 80%, 85%, 90%, 95%, 98%, 99%, or 100% identical to the amino acid sequences SEQ ID NOs: 110, 120, and 112, respectively, and a light chain variable region comprising CDR1, CDR2, and CDR3 regions comprising amino acid sequences that are at least 80%, 85%, 90%, 95%, 98%, 99%, or 100% identical to the amino acid sequences of SEQ ID NOs: 113, 114, and 115, respectively, wherein the antibody further comprises a human IgG1 constant region. In various embodiments, the antibody is a humanized antibody, chimeric antibody, or human antibody.

In another aspect of the invention, provided herein is an isolated antibody or antigen binding fragment which binds to human LAP and comprises a heavy chain variable region comprising CDR1, CDR2, and CDR3 regions comprising the amino acid sequences of SEQ ID NOs: 110, 120, and 112, respectively, and a light chain variable region comprising CDR1, CDR2, and CDR3 regions comprising the amino acid sequences of SEQ ID NOs: 113, 114, and 115, respectively, wherein the antibody further comprises a mutant human IgG4 constant region comprising the amino acid sequence of SEQ ID NO: 197. In various embodiments, the antibody is a humanized antibody, chimeric antibody, or human antibody.

An aspect of the invention provides an anti-LAP antibody or antigen-binding fragment thereof described herein (e.g., 20E6 and humanized versions thereof described in Table 34) is in association with an isolated antibody comprising an immunoglobulin heavy chain comprising the amino acid sequence of SEQ ID NO: 240 and an immunoglobulin light chain comprising the amino acid sequence of SEQ ID NO: 241.

An aspect of the invention provides anti-LAP antibody or antigen-binding fragment thereof described herein (e.g., 20E6 and humanized versions thereof described in Table 34) is in association with an isolated antibody comprising an immunoglobulin heavy chain comprising the amino acid sequence of SEQ ID NO: 246 and an immunoglobulin light chain comprising the amino acid sequence of SEQ ID NO: 247.

In another aspect of the invention provided herein is an isolated antibody or antigen binding fragment which binds to the same epitope on LAP as the anti-LAP antibodies or antigen binding fragments described herein. In another aspect provided herein is an isolated antibody or antigen binding fragment which binds to the same amino acids or groups of amino acids on LAP as the anti-LAP antibodies or antigen binding fragments described herein. For example, the epitope (e.g., LAP and a LAP complex comprising LAP and TBFβ1), antibody, or antigen binding fragment has the characteristics described herein, such as Tables 25, 26, 27, 28, 29, and/or 30. In some embodiments, the anti-LAP antibody binds to specific amino acids of human LAP, for example amino acids 31-40, 274-280, and 340-343 of human LAP-TGFβ1 (SEQ ID NO: 1), e.g., as assessed by at least one structural analytical method such as crystallography and/or cryo-EM. In some embodiments, the anti-LAP antigen binding fragment binds to specific amino acids of human LAP, for example amino acids 31-40, 274-280, and 340-343 of human LAP-TGFβ1 (SEQ ID NO: 1), e.g., as assessed by at least one structural analytical method such as crystallography and/or cryo-EM. In various embodiments, the antibody or the antigen binding fragment binds to one or more amino acids within the recited amino acids, i.e., one or more amino acids within amino acids 31-40, 274-280, and 340-343 of human LAP-TGFβ1 (SEQ ID NO: 1). In some embodiments, the isolated antibody or antigen binding fragment binds to one or more residues of residues 31-40, 274-280, and 340-343 of human LAP-TGFβ1 (SEQ ID NO: 1), or binds to one or more residues of residues 31-43, 272-283, and 340-344 of human LAP-TGFβ1 (SEQ ID NO: 1). In some embodiments, the anti-LAP antibody or antigen binding fragment thereof binds to a specific region or regions of LAP-TGFβ1, for example, Region 1, Region 2, Region 3, and/or Region 4 as shown in FIG. 34, e.g., as assessed by at least one structural analytical method such as HDX-MS.

In some embodiments, the antibody or antigen binding fragment binds to human LAP (e.g., with a $K_D$ of about 11 nm, with a $K_D$ of 11 nM or less, or with a $K_D$ of 10 nM or less). In various embodiments, the antibody or antigen binding fragment binds to LAP (e.g., human, cyno, rat or mouse) with a $K_D$ of 60 nM or less, 50 nM or less, 40 nM or less, 30 nM or less, 20 nM or less, or 10 nM or less. In some embodiments, the antibody or antigen binding fragment binds to human LAP (e.g., with a $K_D$ of less than 60 nM, 50 nM, 40 nM, 30 nM, 20 nM, or 10 nM). In some embodiments, the antibody or antigen binding fragment binds to human LAP with a $K_D$ of about 40-60 nM, or about 50-60 nM. In various embodiments, the $K_D$ is determined by Octet binding analysis. In various embodiments, the $K_D$ is determined by BIACORE® surface plasmon resonance (referred to interchangeably as "BiaCore" and "BIACore") binding analysis. In various embodiments, the antibody or antigen binding fragment has a binding affinity described herein, e.g., Tables 31-32. In some embodiments, the antibody or antigen binding fragment inhibits TGFβ1 activation. In various embodiments, the antibody or antigen binding fragment inhibits integrin activation of TGFβ and/or release of human LAP from the LAP-TGFβ1 complex. In some embodiments, the antibody or antigen binding fragment binds to both human and murine LAP. In some embodiments, the antibody or antigen binding fragment binds to human LAP in the absence of an anchor protein. In some embodiments, the antibody or antigen binding fragment binds or is determined to bind to LAP-TGFβ1 complexed with an anchor protein (e.g., GARP, LRRC33) on immunosuppressive cells, but does not bind to the anchor protein or to an epitope composed of residues of both LAP-TGFβ and the anchor protein. Immunosuppressive cells include, for example, suppressive T cells (e.g., regulatory T cells, activated T cells), cancer-associated fibroblasts, M2 macrophages, cancer cells expressing LAP-TGFβ1, and/or monocytic myeloid-derived suppressor cells. In some embodiments, the antibody or antigen binding fragment does not bind free TGFβ1 or empty LAP. In some embodiments, the antibody or antigen binding fragment does not bind to LAP in extracellular matrix. In some embodiments, the antibody or antigen binding fragment does not bind or is determined to not to bind to LAP complexed with LTBP1, LTBP3 and/or LTBP4. In some embodiments, the antibody or antigen binding fragment binds or is determined to bind to human LAP-TGFβ1 comprising K27C and Y75C mutations and/or all or a portion of (e.g., within) residues 82-130 of human LAP-TGFβ1 (SEQ ID NO: 1), but not human LAP-TGFβ1 comprising the Y74T mutation.

In some embodiments, the antibody or antigen binding fragment binds or is determined to bind to both GARP-positive immunosuppressive cells and GARP-negative immunosuppressive cells. In some embodiments, the antibody or antigen binding fragment binds or is determined to bind to platelets, but does not cause platelet aggregation or platelet degranulation.

In some embodiments, the antibody is an IgG1, IgG2, IgG3, IgG4, IgD, IgA, IgE, or IgM antibody, or variant thereof. In some embodiments, the antibody is a chimeric, domain, humanized, or human antibody.

In any of the above-mentioned embodiments, the antibody or antigen binding fragment thereof can comprise any of the variable light chains described herein and light chain constant domain described herein (e.g., a human light chain constant domain). For example, the light chain constant domain is recited in Table 34. In one embodiment, the antibody or antigen binding fragment thereof comprises a human kappa light chain constant domain or a variant thereof. In various embodiments, the variant comprises up to 1-25 modified amino acid substitutions (e.g., 20 substitutions). In another embodiment, the antibody or antigen binding fragment thereof comprises a human lambda light chain constant domain or a variant thereof. In various embodiments, the variant comprises up to 1-25 modified amino acid substitutions (e.g., 20 substitutions). In one embodiment, the antibody or antigen binding fragment thereof comprises a human kappa light chain constant domain comprising the amino acid sequence of SEQ ID NO: 256.

In another aspect of the invention, provided herein is a bispecific antibody comprising a first binding region with a specificity for LAP of an anti-LAP antibody described herein, and a second binding region or therapeutic agent which binds to another antigen, e.g., a tumor-associated antigen, CD4, CD8, CD45, CD56, CD14, CD16, CD19, CD11b, CD25, CD20, CD22, CD30, CD38, CD114, CD23, CD73, CD163, CD206, CD203, CD200R or CD39. In various embodiments, the second binding region or therapeutic agent which binds to a receptor protein.

In another aspect of the invention, provided herein is an immunoconjugate comprising an anti-LAP antibody or antigen binding fragment described herein linked to a detectable moiety, a binding moiety, a labeling moiety, and/or a biologically active moiety, e.g., a bispecific molecule and/or a bifunctional molecule. For example, the biologically active moiety comprises a receptor trap construct.

In another aspect of the invention, provided herein is a nucleic acid (one or more nucleic acids) comprising a nucleotide sequence that encodes the heavy and/or light chain variable region of an anti-LAP antibody or antigen binding fragment described herein, as well as expression vector(s) comprising the same, and cells transformed with the expression vector(s). In another aspect, provided herein is a nucleic acid (one or more nucleic acids) comprising a nucleotide sequence that encodes the heavy chain and/or light chain of an anti-LAP antibody or antigen binding fragment described herein, as well as expression vector(s) comprising the same, and cells transformed with the expression vector(s).

In another aspect of the invention, provided herein is a pharmaceutical composition comprising an anti-LAP antibody or antigen binding fragment described herein and a pharmaceutically acceptable carrier. In some embodiments, the composition comprises one or more additional therapeutic agents, such as an anti-cancer agent, a chemotherapeutic agent, an immunomodulatory agent (e.g., an immunostimulatory agent or immunosuppressive agent), an anti-inflammatory agent, and/or an immune checkpoint blocker (e.g., an anti-PD-1 antibody, an anti-PD-L1 antibody, an anti-LAG-3 antibody, an anti-CTLA-4 antibody, an anti-TIGIT antibody, and an anti-TIM3 antibody). For example, the PD-1 antibody is pembrolizumab.

In an embodiment, an anti-LAP antibody or antigen-binding fragment thereof described herein (e.g., 20E6 and humanized versions thereof described in Table 34) is in association with an isolated antibody comprising an immunoglobulin heavy chain comprising the amino acid sequence of SEQ ID NO: 240 and an immunoglobulin light chain comprising the amino acid sequence of SEQ ID NO: 241. SEQ ID NOs: 240 and 241 correspond to the heavy chain and light chain sequences of pembrolizumab.

In an embodiment, an anti-LAP antibody or antigen-binding fragment thereof described herein (e.g., 20E6 and humanized versions thereof described in Table 34) is in association with an isolated antibody comprising an immunoglobulin heavy chain comprising the amino acid sequence of SEQ ID NO: 246 and an immunoglobulin light chain comprising the amino acid sequence of SEQ ID NO: 247. SEQ ID NOs: 246 and 247 correspond to the heavy and light chain sequences of pembrolizumab.

In another aspect of the invention, provided herein are kits comprising an anti-LAP antibody or antigen binding fragment described herein and instructions for use.

In another aspect of the invention, provided herein is a method of making an antibody that specifically binds to LAP comprising: (a) immunizing an animal with a polypeptide comprising an epitope on human LAP recognized by 28G11, (b) selecting from the immunized animal an antibody that binds to the same epitope as 28G11, and (c) isolating the antibody selected from step (b). In some embodiments, the antibody binds to a human LAP complex comprising TGFβ1. In some embodiments, the antibody binds to all or a portion (e.g., within) residues 82-130 of human LAP.

In another aspect of the invention, provided herein is a method of selectively inhibiting TGFβ1 activation on cells (e.g., immunosuppressive cells such as suppressive T cells (e.g., regulatory T cells, activated T cells), M2 macrophages, cancer cells expressing LAP-TGFβ1, cancer-associated fibroblasts, mesenchymal stromal cells mesenchymal stem cells, and/or monocytic myeloid-derived suppressor cells), but not TGFβ1 activation on extracellular matrix, comprising administering to the subject any anti-LAP antibody or antigen binding fragment, bispecific molecule, immunoconjugate, and/or pharmaceutical composition described herein.

In another aspect of the invention, provided herein is a method of treating cancer comprising administering to a subject in need thereof a therapeutically effective amount of any anti-LAP antibody or antigen binding fragment, bispecific molecule, immunoconjugate, and/or pharmaceutical composition described herein.

In some embodiments, the cancer is characterized by abnormal TGFβ activity. In some embodiments, the cancer is associated with infiltration of cluster of differentiation 4 (CD4)+ regulatory T cells, cluster of differentiation 8 (CD8)+ regulatory T cells, regulatory B cells, myeloid-derived suppressor cells, tumor-associated macrophages, cancer-associated fibroblasts, and/or innate lymphoid cells.

In some embodiments, the cancer is breast cancer, bladder cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, or myelodysplastic syndromes.

In some embodiments of the methods described above, one or more additional therapies is administered, for example, radiation therapy, chemotherapy, an immune checkpoint inhibitor (e.g., an anti-PD-1 antibody, an anti-PD-L1 antibody, an anti-LAG-3 antibody, an anti-CTLA-4 antibody, an anti-TIGIT antibody, and an anti-TIM3 antibody), immunostimulatory therapy, immunosuppressive therapy, cell therapy, and a therapeutic agent (e.g., anti-cancer agent, a chemotherapeutic agent, an immunosuppressive agent, an immunomodulatory agent, and an anti-inflammatory agent).

In another aspect of the invention, provided herein is a method of detecting LAP comprising contacting a sample (e.g., a biological sample) with any anti-LAP antibody or antigen binding fragment, bispecific molecule, immunoconjugate, and/or pharmaceutical composition described herein, and detecting the complex.

In another aspect of the invention, provided herein is a method of diagnosing a cancer associated with regulatory T cell infiltration comprising contacting a biological sample from a patient afflicted with the cancer with any anti-LAP antibody or antigen binding fragment, bispecific molecule, immunoconjugate, and/or pharmaceutical composition described herein, wherein positive staining with the antibody or antigen binding fragment, bispecific molecule, immunoconjugate, and/or pharmaceutical composition indicates the cancer is associated with regulatory T cell infiltration.

In another aspect of the invention, provided herein is a method of diagnosing a cancer associated with GARP-negative suppressive cells comprising contacting a biological sample from a patient afflicted with the cancer with any anti-LAP antibody or antigen binding fragment, bispecific molecule, immunoconjugate, and/or pharmaceutical composition described herein which binds to GARP-negative suppressive cells, wherein positive staining with the antibody or antigen binding fragment, bispecific molecule, immunoconjugate, and/or pharmaceutical composition and negative staining with an anti-GARP antibody indicates the cancer is associated with GARP-negative suppressive cells.

In another aspect of the invention, provided herein is a method of selecting a patient afflicted with cancer for treatment with an anti-LAP antibody or antigen binding fragment, bispecific molecule, immunoconjugate, and/or pharmaceutical composition described herein comprising contacting a biological sample from the patient with the antibody or antigen binding fragment, bispecific molecule, immunoconjugate, and/or pharmaceutical composition, wherein positive staining with the antibody or antigen binding fragment indicates the cancer is amenable to treatment with the antibody.

In another aspect of the invention, provided herein is a method of determining the response of a patient afflicted with cancer to treatment with an anti-LAP antibody or antigen binding fragment described herein comprising contacting a biological sample from the patient with the antibody or antigen binding fragment, wherein reduced staining with the antibody or antigen binding fragment, bispecific molecule, immunoconjugate, and/or pharmaceutical composition indicates the cancer is responding to treatment with the antibody.

In another aspect of the invention, provided herein is a method of making an antibody that specifically binds to the same epitope on human LAP recognized by 28G11 comprising immunizing an animal with an immunogen comprising a peptide, wherein the peptide comprises the epitope recognized by 28G11, selecting from the immunized animal an antibody that binds to the same epitope as 28G11, and obtaining an antibody that binds to the same epitope as 28G11. In various embodiments, the human LAP comprises a complex comprising human LAP and TGFβ1.

Another aspect of the invention are uses of any of the anti-LAP antibodies or antigen binding fragments, bispecific molecules, immunoconjugates, and/or pharmaceutical compositions described herein for selectively inhibiting TGFβ1 activation on immunosuppressive cells, but not TGFβ1 activation on extracellular matrix; treating cancer; diagnosing a cancer (e.g., a cancer associated with regulatory T cell infiltration or GARP-negative suppressive cells); selecting a patient afflicted with cancer; and determining the response of a patient afflicted with cancer to treatment with the anti-LAP antibodies described herein. Also provided are uses of any of the anti-LAP antibodies or antigen binding fragments, bispecific molecules, immunoconjugates, and/or pharmaceutical compositions described herein for preparing a medicament to selectively inhibit TGFβ1 activation on immunosuppressive cells, but not TGFβ1 activation on extracellular matrix, and to treat cancer.

BRIEF DESCRIPTION OF THE FIGURES

FIGS. 5A and 5B are sets of graphs showing the effects of 28G11 on TGFβ1 activation in P3U1 cells expressing human LAP-TGFβ1 (FIG. 5A) and murine LAP-TGFβ1 (FIG. 5B).

FIGS. 6G-6L are graphs showing the effects of 28G11_IgG2a (FIG. 6G), 20E6_IgG2a (FIG. 6H), 22F9_IgG2a (FIG. 6I), 24E3_hIgG1 (FIG. 6J), 17G8_hIgG1 (FIG. 6K), and 20E6_H0.2aL1_hIgG1 (FIG. 6L) on TGFβ1 activation in P3U1 cells expressing human or mouse LAP-TGFβ1.

FIG. 34 is a sequence alignment between human LAP-TGFβ1 and mouse LAP-TGFβ1. Epitopes identified are all in regions that are homologous between human and mouse LAP-TGFβ1. The human LAP-TGFβ1 sequence in the figure corresponds to SEQ ID NO: 257. The mouse LAP-TGFβ1 sequence in the figure corresponds to SEQ ID NO: 7.

FIGS. 35A and 35B are size-exclusion chromatograms for human LAP-TGFβ1, GARP-LAP-TGFβ1, humanized 20E6, and complexes. The elution time for each sample is consistent with the gel filtration standard. Molecular weight reported was determined from the light scattering detector.

FIG. 36A (anti-PD-1 antibody alone), FIG. 36B (28G11_IgG2a+anti-PD-1 antibody), FIG. 36C (IgG2a isotype control), FIG. 36D (anti-PD-1 antibody alone), FIG. 36E (16B4_IgG2a alone), and FIG. 36F (16B4_IgG2a+anti-PD-1 antibody). The anti-PD-1 antibody was a rat anti-PD-1 (clone RMP1-14)-IgG2a antibody.

FIG. 43A is a graph summary of efficacy of 28G11-mIgG2a and FIG. 43B is a graph summary of efficacy of 20E6-mIgG2a. Also shown is a tumor volume data for control antibodies (FIG. 43C), antibody 20E6-mIgG2a (FIG. 43D), antibody 28G11-mIgG2a (FIG. 43E), anti-PD-1 antibody (FIG. 43F), a combination of antibody 20E6-mIgG2a and anti-PD-1 antibody (FIG. 43G), and antibody 28G11-mIgG2a and anti-PD-1 antibody (FIG. 43H).

FIGS. 44A-44D are a series of Biacore graphs showing binding of anti-LAP F(ab') to human LAP-TGFβ isoforms 1, 2, and 3.

FIGS. 45A-45D are a series of Biacore graphs showing binding of anti-LAP F(ab') to human, cynomolgus monkey, rat, and mouse LAP-TGFβ1.

DETAILED DESCRIPTION

Definitions

Figure 1A:
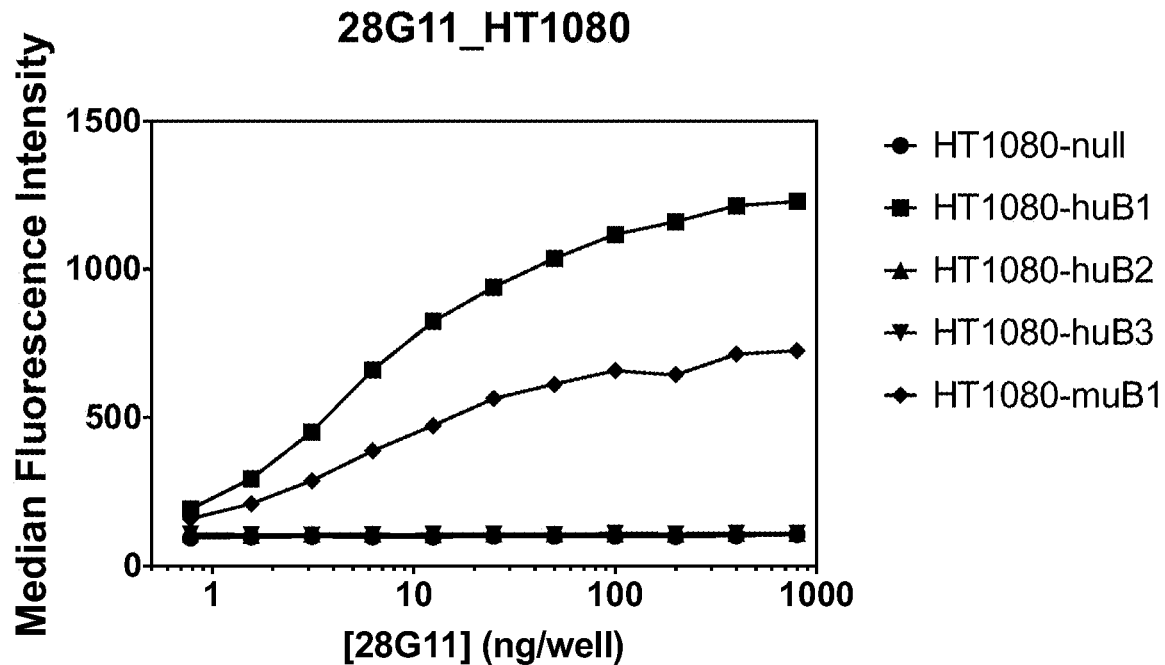
FIGS. 1A-1F are graphs showing the binding of antibodies 28G11_hIgG1, 22F9_hIgG1, 20E6_hIgG1, 17G8_hIgG1, 24E3_hIgG1, and 2C9_(hyb) on non-transfected HT1080 cells (HT 1080-null) and HT1080 cells overexpressing human LAP-TGFβ1 (HT1080-huB1), human LAP-TGFβ2 (HT1080-huB2), human LAP-TGFβ3 (HT1080-huB3), and murine LAP-TGFβ1 (HT1080-muB1). [TGFβ2=transforming growth factor beta-2; TGFβ3=transforming growth factor beta-3]
Figure 1B:
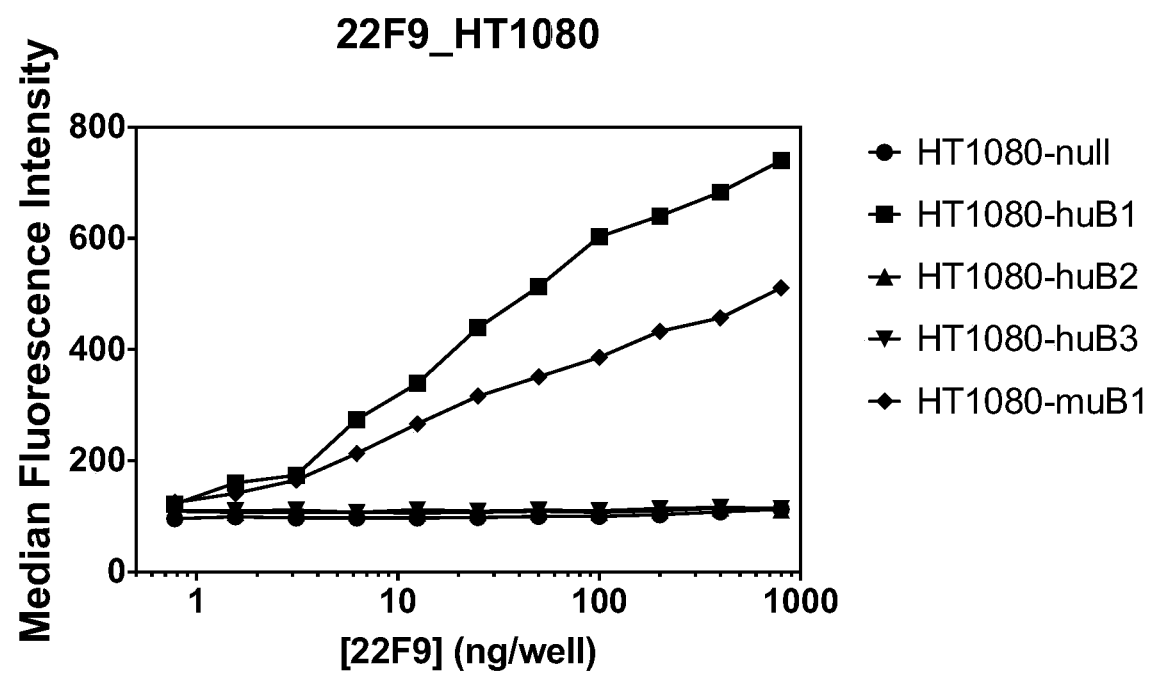
Figure 1C:
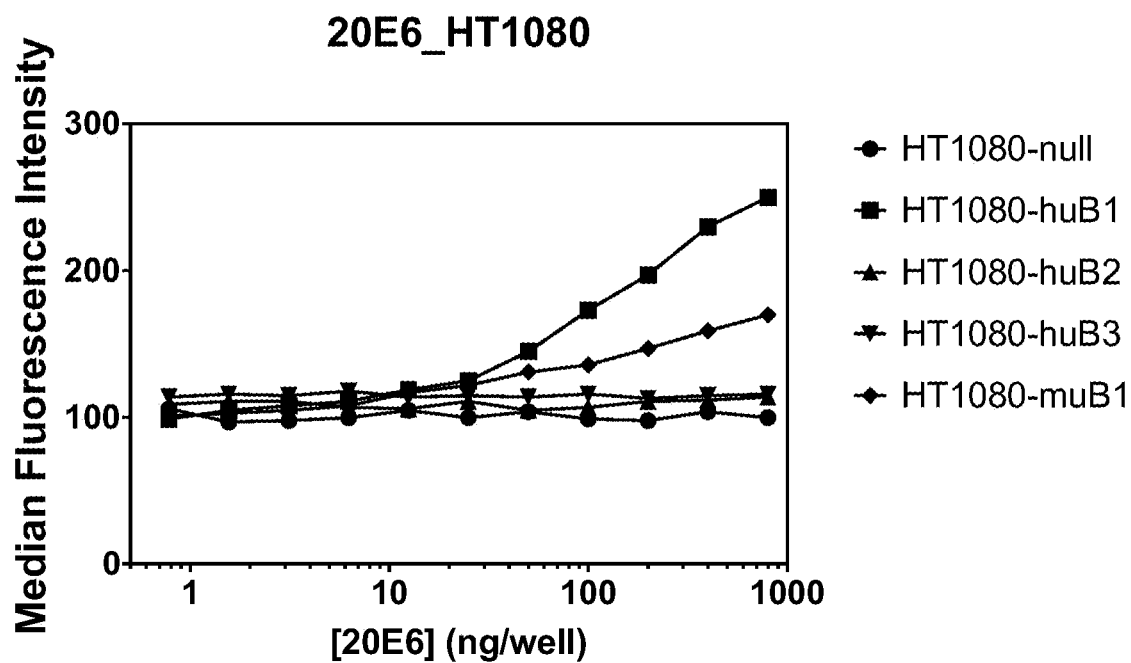
Figure 1D:
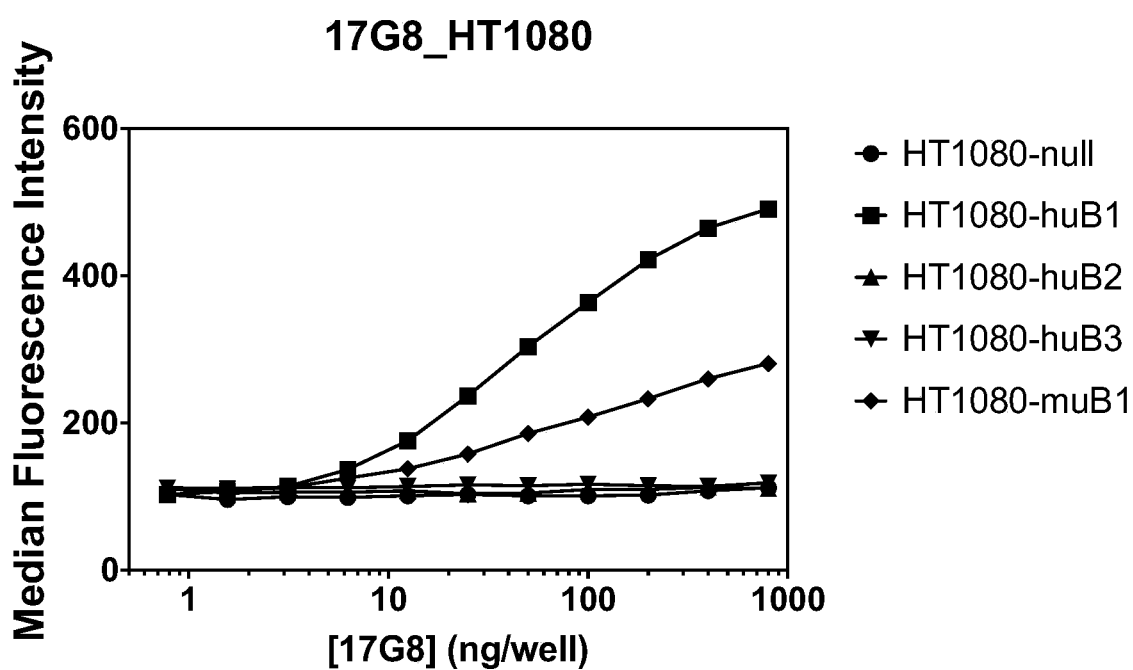
Figure 1E:
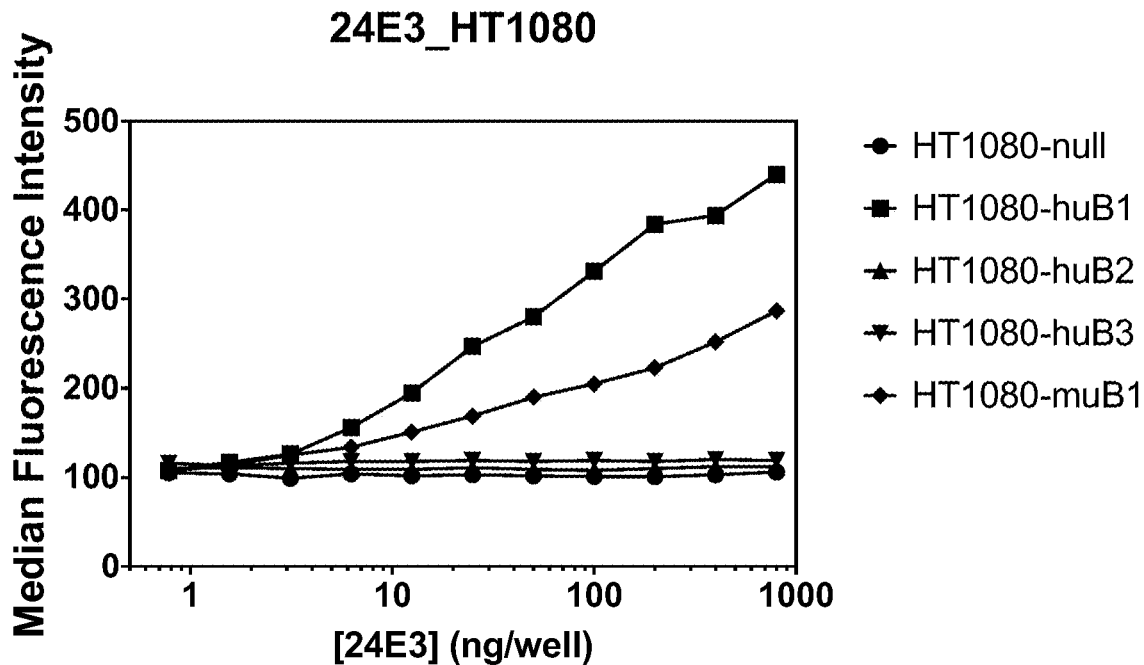
Figure 1F:
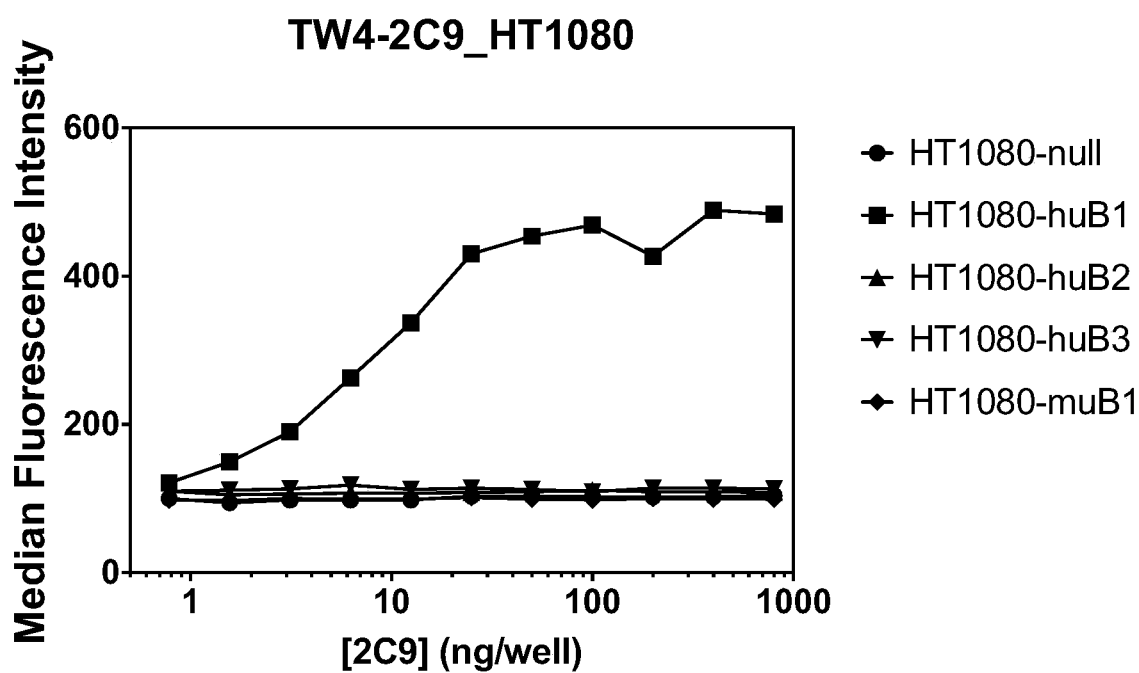
Figure 2A:
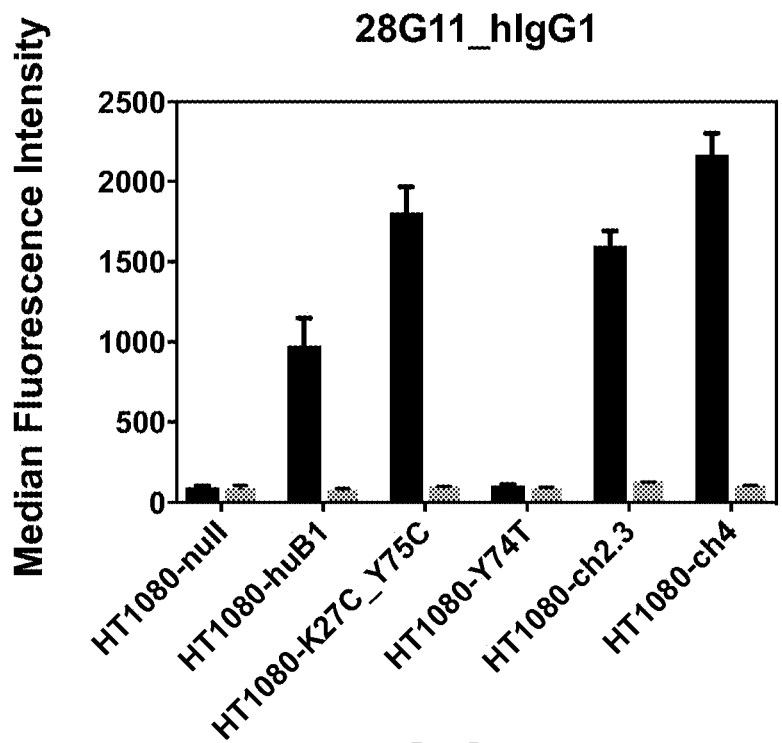
FIGS. 2A-2F are graphs showing the binding of antibodies 28G11_hIgG1, 22F9_hIgG1, 20E6_hIgG1, 17G8_hIgG1, 24E3_hIgG1, and 2C9_(hyb) to the indicated LAP-TGFβ variants. Black bars correspond to the indicated antibody binding to HT1080 cells over-expressing human LAP-TGFβ1. Gray bars correspond to negative controls samples where no anti-LAP antibody was added. HT1080-huB1: HT1080 cells overexpressing LAP-TGFβ1, HT1080-K27C_Y75C: HT1080 cells overexpressing LAP-TGFβ1 with K27C and Y75C mutations (mutations that prevent TGFβ1 activation by integrins; "closed" conformation"), HT1080-Y74T: HT1080 cells overexpressing LAP-TGFβ1 with a Y74T mutation (mutation that favors spontaneous release of TGFβ1 ("open conformation"); HT1080-ch2.3: HT1080 cells overexpressing chimeric LAP-TGFβ1 in which exon 2.3 (residues 131-164) of human LAP-TGFβ1 have been replaced with corresponding residues from chicken LAP-TGFβ1 (UniProt accession # H9CX01); HT1080-ch4: HT1080 cells overexpressing chimeric LAP-TGFβ1 in which exon 4 (residues 183-208) of human LAP-TGFβ1 has been replaced with exon 4 from chicken LAP-TGFβ1.
Figure 2B:
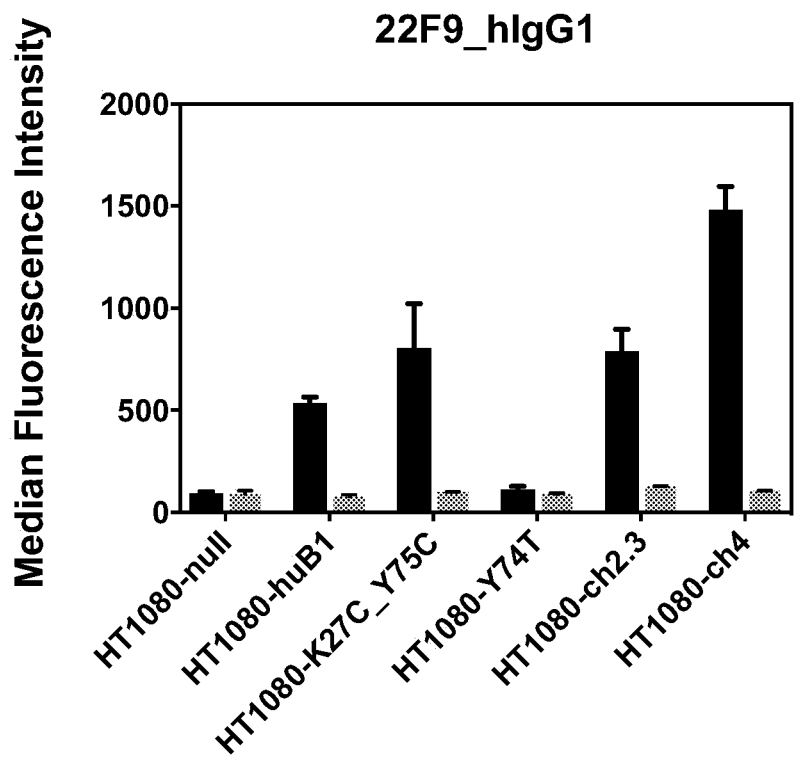
Figure 2C:
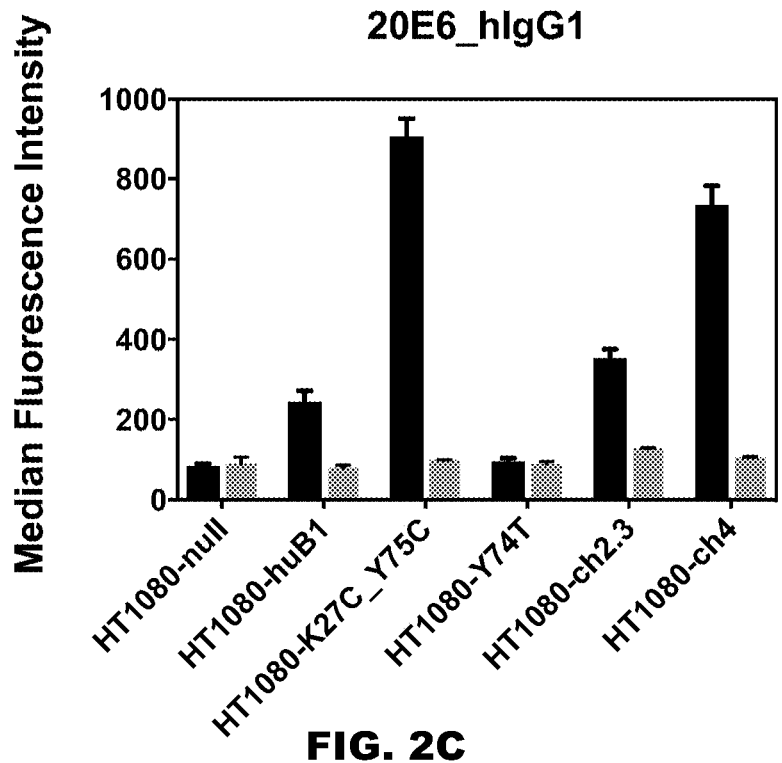
Figure 2D:
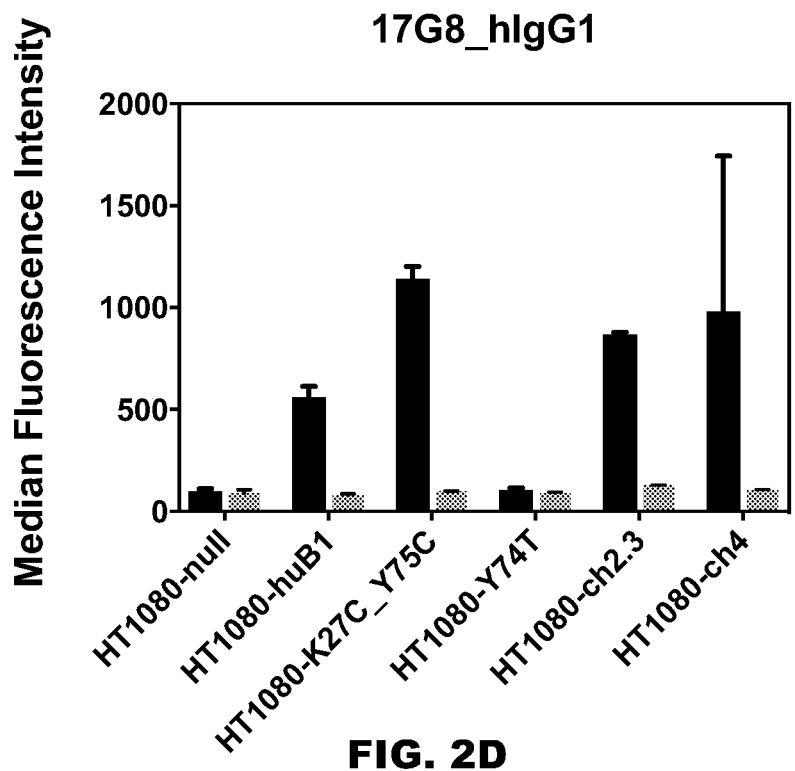
Figure 2E:
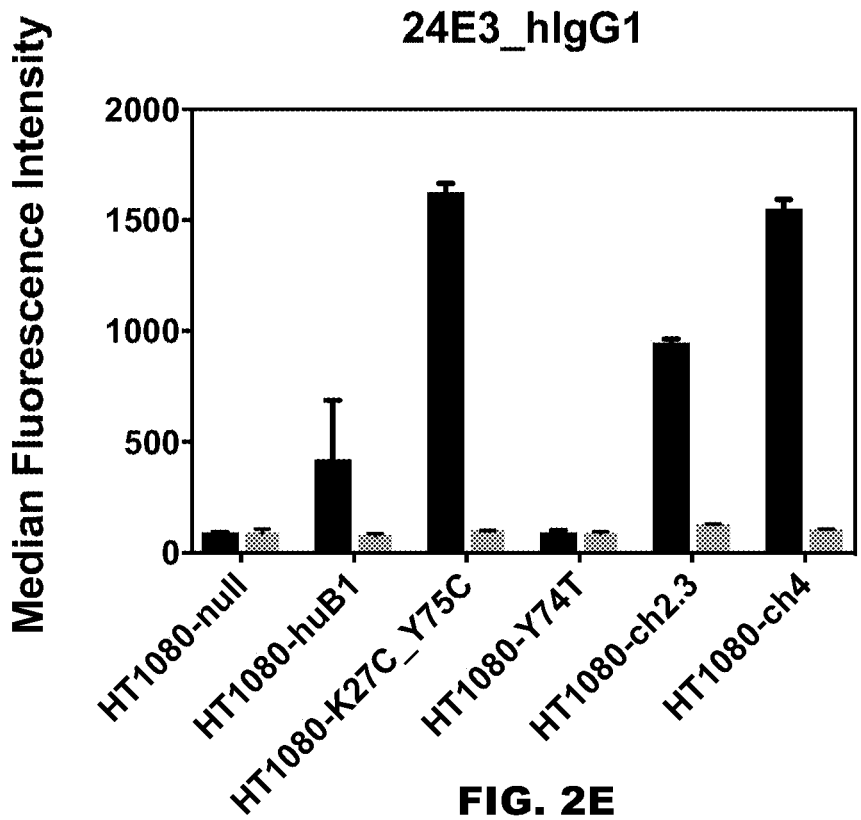
Figure 2F:
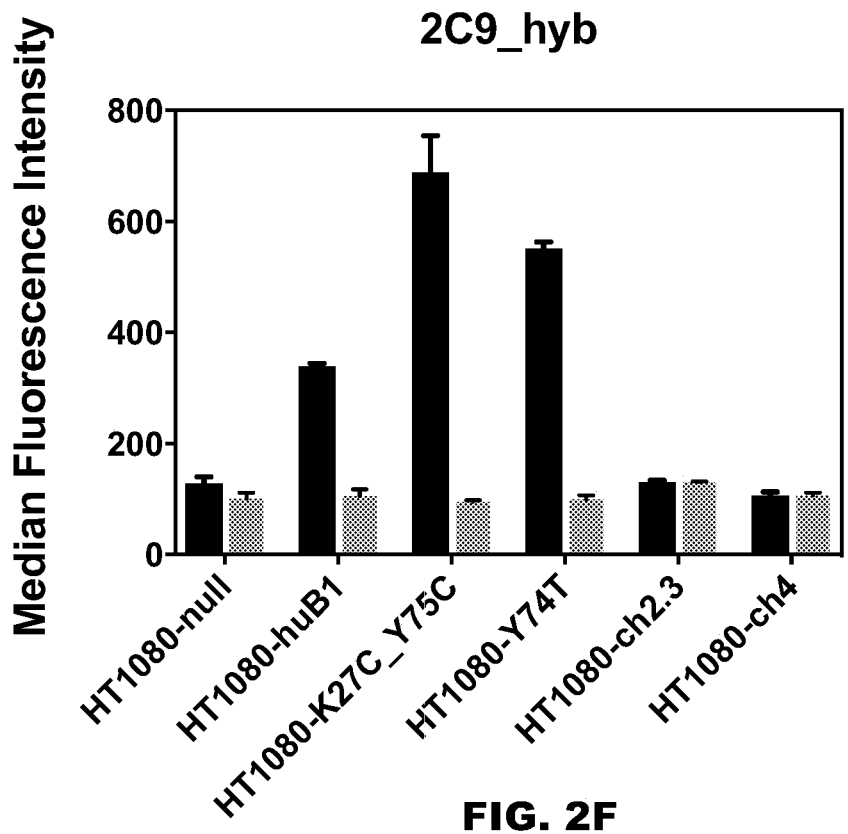
Figure 3A:
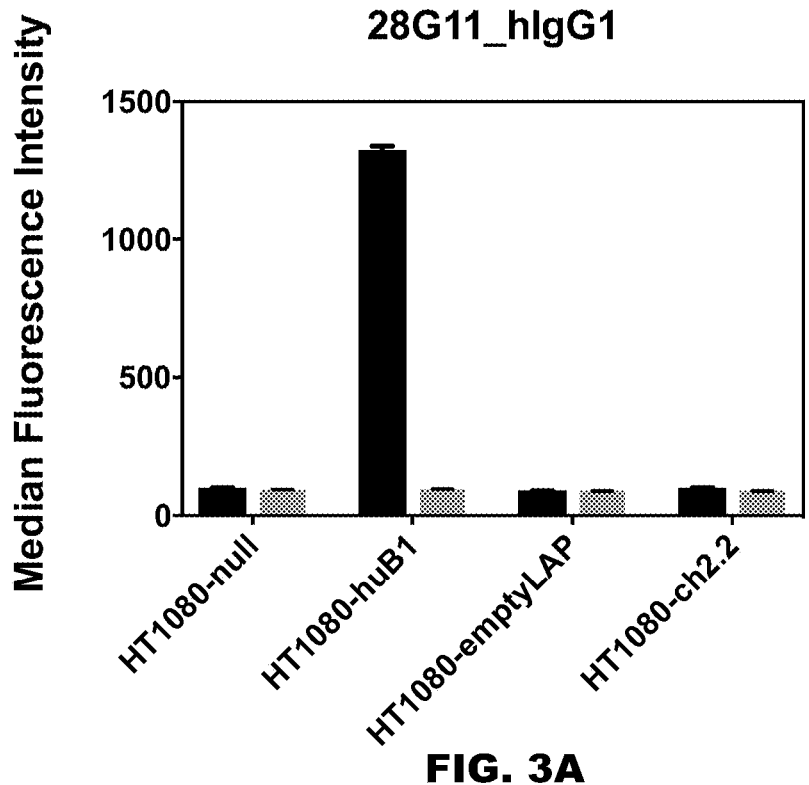
FIGS. 3A-3F are graphs showing the binding of antibodies 28G11_hIgG1, 22F9_hIgG1, 20E6_hIgG1, 17G8_hIgG1, 24E3_hIgG1, and 2C9_(hyb) to the indicated LAP-TGFβ variants. Black bars correspond to the indicated antibody binding to HT1080 cells over-expressing human LAP-TGFβ1. Gray bars correspond to negative controls samples where no anti-LAP antibody was added. HT1080-huB1: HT1080 cells overexpressing LAP-TGFβ1, HT1080-emptyLAP: HT1080 cells overexpressing LAP which does not include the mature TGFβ1 cytokine, HT1080-ch2.2: HT1080 cells overexpressing chimeric LAP-TGFβ1 in which exon 2.2 (residues 108-130) of human LAP-TGFβ1 has been replaced with exon 2.2 from chicken LAP-TGFβ1.
Figure 3B:
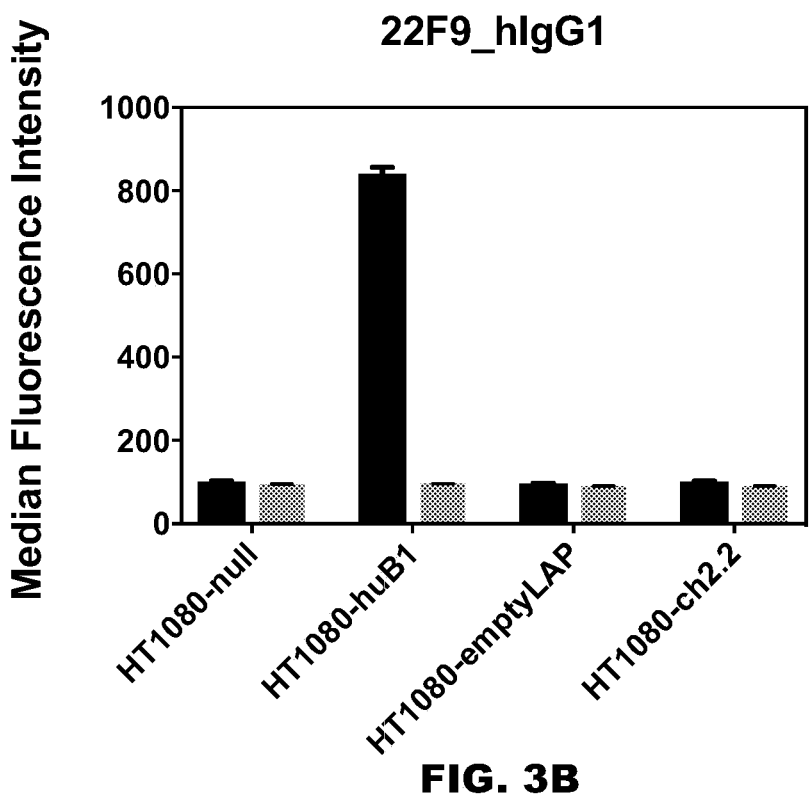
Figure 3C:
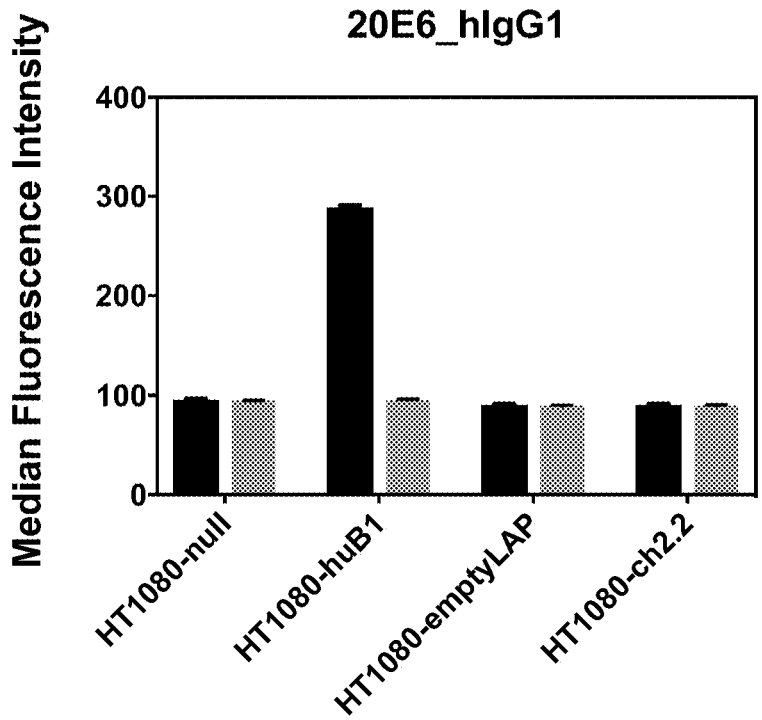
Figure 3D:
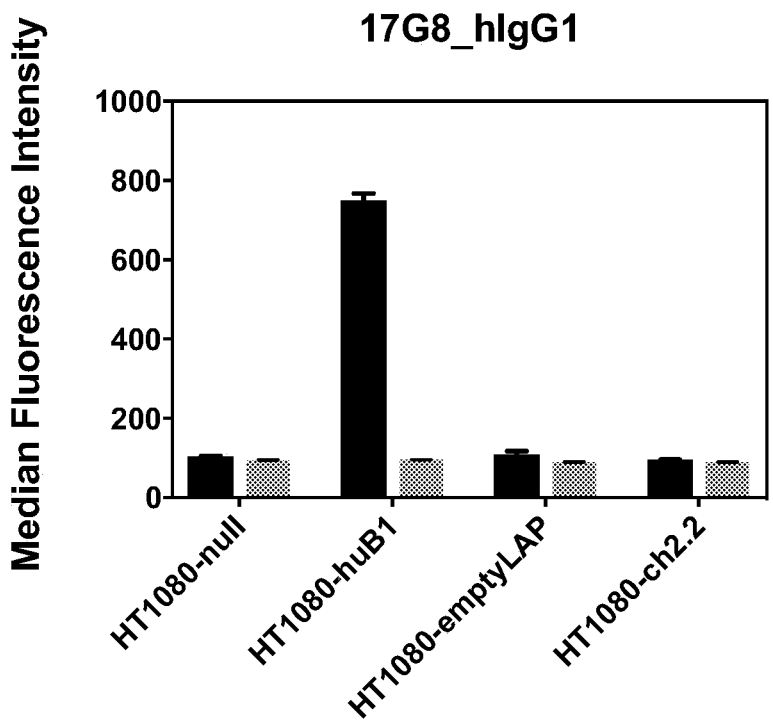
Figure 3E:
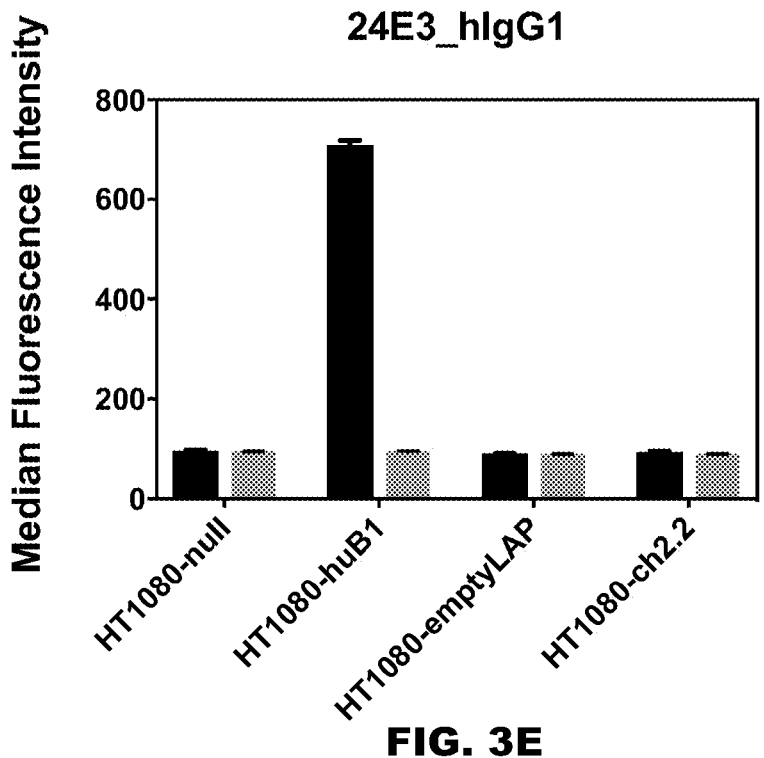
Figure 3F:
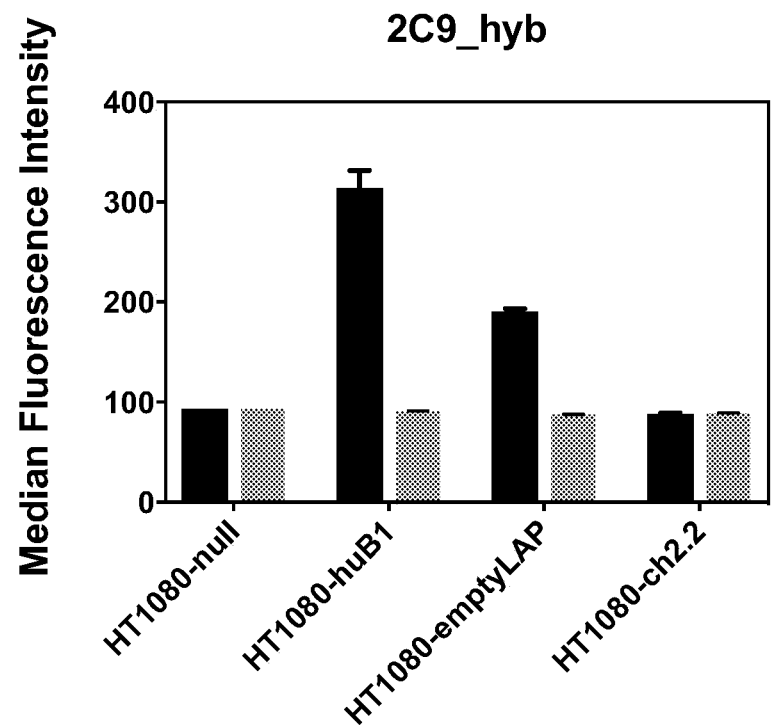

In order for the following detailed description to be readily understood, certain terms are first defined. Additional definitions are provided throughout.

"Abnormal" in the context of the activity, level or expression of a molecule means that the activity, level or expression is outside of the normal activity, level or expression for that molecule. "Normal" in the context of activity, level or expression refers to the range of activity, level or expression of the protein found in a population of healthy, gender- and age-matched subjects. The minimal size of this healthy population may be determined using standard statistical measures, e.g., the practitioner could take into account the incidence of the disease in the general population and the level of statistical certainty desired in the results. Preferably, the normal range for activity, level or expression of a biomarker is determined from a population of subjects (e.g., at least five, ten or twenty subjects), more preferably from a population of at least forty or eighty subjects, and even more preferably from more than 100 subjects.

As used herein, "Latency associated peptide" or "LAP" refers to the amino-terminal domain of the human TGFβ1 precursor peptide and has the amino acid sequence set forth in SEQ ID NO: 2. "LAP-TGFβ1" and "LAP/TGFβ1" are used interchangeably herein to refer to the human TGFβ1 precursor peptide (which includes the TGFβ1 cytokine) and includes the amino acid sequence of SEQ ID NO: 1 (Uniprot spIP011371TGFB1_HUMAN with signal sequence removed).

LAP can also refer to the amino-terminal domains of the human TGFβ2 precursor peptide (LAP region: SEQ ID NO: 4, LAP-TGFβ2: SEQ ID NO: 3) and human TGFβ3 precursor peptide (LAP region: SEQ ID NO: 6, LAP-TGFβ2: SEQ ID NO: 5), as well as their counterparts from other species (e.g., mouse TGFβ1 precursor peptide (mouse LAP region: SEQ ID NO: 8; mouse LAP-TGFβ1: SEQ ID NO: 7), mouse TGFβ2 precursor peptide (mouse LAP region: SEQ ID NO: 10; mouse LAP-TGFβ2: SEQ ID NO: 9), and mouse TGFβ3 precursor peptide (mouse LAP region: SEQ ID NO: 12; mouse LAP-TGFβ3: SEQ ID NO: 11)) and other naturally occurring allelic, splice variants, and processed forms thereof. LAP is synthesized as a complex with TGFβ. LAP in the absence of mature TGFβ is referred to as "empty LAP." Unless otherwise specified, "empty LAP" as used herein refers to LAP originating from the N-terminal domain of human TGFβ1. In addition to residues on LAP, the anti-LAP antibodies described herein may also bind to residues of mature TGFβ within the LAP-TGFβ1 complex. Notwithstanding, in all cases, the antibody at least binds to residues in the LAP portion of the complex.

As used herein "free TGFβ1" refers to the mature TGFβ1 cytokine, i.e., TGFβ1 that is not complexed with LAP.

As used herein, "anchor protein" refers to a protein that anchors LAP-TGFβ to a cell surface or to the extracellular matrix. Exemplary anchor proteins include GARP, LRRC33, LTBP1, LTBP3, and LTBP4. GARP and LRRC33 are proteins that anchor LAP-TGFβ to the surface of cells, and LTBP1, LTBP3, and LTBP4 are proteins that anchor LAP-TGFβ to the extracellular matrix.

The term "antibody" as used herein includes whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen binding portion thereof. Each heavy chain is comprised of a heavy chain variable region (abbreviated herein as $V_H$) and a heavy chain constant region. In certain naturally occurring antibodies, the heavy chain constant region is comprised of three domains, CH1, CH2, and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5 \times 10^{-9}$ M or less, and most preferably between $10^{-8}$ M and $10^{-10}$ M or less, but does not bind with high affinity to unrelated antigens.

The phrase "antigen-binding portion" of an antibody, as used herein, refers to one or more fragments of an antibody that retain the ability to specifically bind to an antigen (e.g., human and/or mouse LAP). It has been shown that the antigen-binding function of an antibody can be performed by fragments of a full-length antibody. Examples of binding fragments of an antibody include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

Antibody fragments within the scope of the present invention also include F(ab')2 fragments which may be produced by enzymatic cleavage of an IgG by, for example, pepsin. Fab fragments may be produced by, for example, reduction of F(ab')2 with dithiothreitol or mercaptoethylamine. A Fab fragment is a VL-CL chain appended to a VH-CH1 chain by a disulfide bridge. A F(ab')2 fragment is two Fab fragments which, in turn, are appended by two disulfide bridges. The Fab portion of an F(ab')2 molecule includes a portion of the Fc region between which disulfide bridges are located.

The term "acceptor human framework" refers to a framework comprising the amino acid sequence of a light chain variable domain ($V_L$) framework or a heavy chain variable domain ($V_H$) framework derived from a human immunoglobulin framework or a human consensus framework. An acceptor human framework "derived from" a human immunoglobulin framework or a human consensus framework may have the same amino acid sequence as the naturally-occurring human immunoglobulin framework or human consensus framework, or it may have amino acid sequence changes compared to wild-type naturally-occurring human immunoglobulin framework or human consensus framework. In some embodiments, the number of amino acid changes are 10, 9, 8, 7, 6, 5, 4, 3, or 2, or 1. In some embodiments, the $V_L$ acceptor human framework is identical in sequence to the $V_L$ human immunoglobulin framework sequence or human consensus framework sequence.

A "multispecific antibody" is an antibody (e.g., bispecific antibodies, tri-specific antibodies) that recognizes two or more different antigens or epitopes.

The term "binding protein" as used herein also refers to a non-naturally occurring (or recombinant) protein that specifically binds to at least one target antigen.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, Clin. Exp. Immunol. 79:315-321 (1990); Kostelny et al., J. Immunol. 148, 1547-1553 (1992). Bifunctional antibodies include, for example, heterodimeric antibody conjugates (e.g., two antibodies or antibody fragments joined together with each having different specificities), antibody/cell surface-binding molecule conjugates (e.g., an antibody conjugated to a non-antibody molecule such as a receptor), and hybrid antibodies (e.g., an antibody having binding sites for two different antigens).

The term "recombinant antibody," refers to antibodies that are prepared, expressed, created or isolated by recombinant means, such as (a) antibodies isolated from an animal (e.g., a mouse) that is transgenic or transchromosomal for immunoglobulin genes (e.g., human immunoglobulin genes) or a hybridoma prepared therefrom, (b) antibodies isolated from a host cell transformed to express the antibody, e.g., from a transfectoma, (c) antibodies isolated from a recombinant, combinatorial antibody library (e.g., containing human antibody sequences) using phage display, and (d) antibodies prepared, expressed, created or isolated by any other means that involve splicing of immunoglobulin gene sequences (e.g., human immunoglobulin genes) to other DNA sequences. Such recombinant antibodies may have variable and constant regions derived from human germline immunoglobulin sequences. In certain embodiments, however, such recombinant human antibodies can be subjected to in vitro mutagenesis and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

A "human" antibody refers to an antibody having variable regions in which both the framework and CDR regions are derived from human germline immunoglobulin sequences. Furthermore, if the antibody contains a constant region, the constant region also is derived from human germline immunoglobulin sequences. Also encompassed are antibodies derived from human germline immunoglobulin sequences that include normal somatic hypermutations which alter the germline immunoglobulin sequences relative to the wild-type germline immunoglobulin sequences.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Any additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one or more species and the constant regions are derived from another species, such as an antibody in which the variable regions are derived from a mouse antibody and the constant regions are derived from a human antibody. See U.S. Pat. No. 4,816,567; and Morrison et al., (1984) *Proc. Natl. Acad Sci. USA* 81: 6851-6855.

As used herein, the term "monoclonal antibody" refers to an antibody obtained from a population of substantially homogeneous antibodies, i.e., the individual antibodies in the population are substantially similar and bind the same epitope(s) (e.g., the antibodies display a single binding specificity and affinity), except for possible variants that may arise during production of the monoclonal antibody, such variants generally being present in minor amounts.

"Monoclonal" indicates the character of the antibody as having been obtained from a substantially homogenous population of antibodies, and does not require production of the antibody by any particular method.

The term "monoclonal antibody," as used herein, refers to an antibody that displays a single binding specificity and affinity for a particular epitope or a composition of antibodies in which all antibodies display a single binding specificity and affinity for a particular epitope. For example, the monoclonal antibodies to be used in accordance with the present invention may be made by the hybridoma method first described by Kohler et al., (1975) *Nature* 256: 495, or may be made by recombinant DNA methods (see, e.g., U.S. Pat. No. 4,816,567). The "monoclonal antibodies" may also be isolated from phage antibody libraries using the techniques described in Clackson et al., (1991) *Nature* 352: 624-628 and Marks et al., (1991) *J. Mol. Biol.* 222: 581-597.

Antigen binding fragments (including scFvs) of such immunoglobulins are also encompassed by the term "monoclonal antibody" as used herein. Monoclonal antibodies are highly specific, being directed against a single antigenic site. Furthermore, in contrast to conventional (polyclonal) antibody preparations, which typically include different antibodies directed against different epitopes on the antigen, each monoclonal antibody is directed against a single epitope. Monoclonal antibodies can be prepared using any art recognized technique and those described herein such as, for example, a hybridoma method, a transgenic animal, recombinant DNA methods (see, e.g., U.S. Pat. No. 4,816,567), or using phage antibody libraries using the techniques described in, for example, U.S. Pat. No. 7,388,088 and PCT Pub. No. WO 00/31246). Monoclonal antibodies include chimeric antibodies, human antibodies, and humanized antibodies and may occur naturally or be produced recombinantly.

A "domain antibody" is an immunologically functional immunoglobulin fragment containing only the variable region of a heavy chain or the variable region of a light chain. In some instances, two or more $V_H$ regions are covalently joined with a peptide linker to create a bivalent domain antibody. The two $V_H$ regions of a bivalent domain antibody may target the same or different antigens.

A "bivalent antibody" comprises two antigen binding sites. In some instances, the two binding sites have the same antigen specificities. However, bivalent antibodies may be bispecific (see below).

As used herein, the term "single-chain Fv" or "scFv" antibody refers to antibody fragments comprising the $V_H$ and $V_L$ domains of antibody, wherein these domains are present in a single polypeptide chain. Generally, the Fv polypeptide further comprises a polypeptide linker. For a review of sFv, see Pluckthun (1994) THE PHARMACOLOGY OF MONOCLONAL ANTIBODIES, vol. 113, Rosenburg and Moore eds. Springer-Verlag, New York, pp. 269-315.

The monoclonal antibodies herein also include camelized single domain antibodies. See, e.g., Muyldermans et al. (2001) *Trends Biochem. Sci.* 26:230; Reichmann et al. (1999) *J. Immunol. Methods* 231:25; WO 94/04678; WO 94/25591; U.S. Pat. No. 6,005,079, which are hereby incorporated by reference in their entireties). In one embodiment, the present invention provides single domain antibodies comprising two $V_H$ domains with modifications such that single domain antibodies are formed.

As used herein, the term "diabodies" refers to small antibody fragments with two antigen-binding sites, which fragments comprise a heavy chain variable domain ($V_H$) connected to a light chain variable domain ($V_L$) in the same polypeptide chain ($V_H$—$V_L$ or $V_L$—$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

The antibodies of the present invention also include antibodies with modified (or blocked) Fc regions to provide altered effector functions. See, e.g., U.S. Pat. No. 5,624,821;

WO2003/086310; WO2005/120571; WO2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes, such as substitutions, deletions and insertions, glycosylation or deglycosylation, and adding multiple Fc. Changes to the Fc may be utilized to alter the half-life of antibodies in therapeutic antibodies, and a longer half-life would result in less frequent dosing, with the concomitant increased convenience and decreased use of material. See Presta (2005) *J. Allergy Clin. Immunol.* 116: 731 at 734-35.

The term "fully human antibody" refers to an antibody that comprises human immunoglobulin protein sequences only. A fully human antibody may contain murine carbohydrate chains if produced in a mouse, in a mouse cell, or in a hybridoma derived from a mouse cell. Similarly, "mouse antibody" refers to an antibody which comprises mouse immunoglobulin sequences only.

As used herein, the term "hypervariable region" (sometimes referred to as the "variable region") refers to the amino acid residues of an antibody that are responsible for antigen-binding. The hypervariable region comprises amino acid residues from a "complementarity determining region" or "CDR" (e.g. residues 24-34 (CDRL1), 50-56 (CDRL2) and 89-97 (CDRL3) in the light chain variable domain and residues 31-35 (CDRH1), 50-65 (CDRH2) and 95-102 (CDRH3) in the heavy chain variable domain; Kabat et al., (1991) Sequences of Proteins of Immunological Interest, 5th Ed. Public Health Service, National Institutes of Health, Bethesda, Md.) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, (1987) *J. Mol. Biol.* 196: 901-917).

As used herein, the term "framework" or "FR" residues refers to those variable domain residues other than the hypervariable region residues defined herein as CDR residues. The residue numbering above relates to the Kabat numbering system and does not necessarily correspond in detail to the sequence numbering in the accompanying Sequence Listing. Amino acid residues in antibodies can also be defined using other numbering systems, such as Chothia, enhanced Chothia, IMGT, Kabat/Chothia composite, Honegger (AHo), Contact, or any other conventional antibody numbering scheme.

An "isolated antibody," as used herein, is intended to refer to an antibody which is substantially free of other antibodies having different antigenic specificities. As used herein, "isotype" refers to the antibody class (e.g., IgG (including IgG1, IgG2, IgG3, and IgG4), IgM, IgA (including IgA1 and IgA2), IgD, and IgE antibody) that is encoded by the heavy chain constant region genes of the antibody.

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain).

An "Fc region," "Fc domain," or "Fc" refers to the C-terminal region of the heavy chain of an antibody. Thus, an Fc region comprises the constant region of an antibody excluding the first constant region immunoglobulin domain (e.g., CH1 or CL).

The term "epitope" or "antigenic determinant" refers to a site on an antigen (e.g., human LAP-TGFβ1) to which an immunoglobulin or antibody specifically binds. Epitopes can be formed both from contiguous amino acids (usually a linear epitope) or noncontiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14, 15, 16, 17, 18, 19, 20, 21, or 22 amino acids in a unique spatial conformation.

The term "epitope mapping" refers to the process of identifying the molecular determinants on the antigen involved in antibody-antigen recognition. Methods for determining what epitopes are bound by a given antibody are well known in the art and include, for example, immunoblotting and immunoprecipitation assays, wherein overlapping or contiguous peptides from, e.g., LAP-TGFβ1 are tested for reactivity with a given antibody (e.g., anti-LAP antibody); x-ray crystallography; antigen mutational analysis, two-dimensional nuclear magnetic resonance; yeast display; and hydrogen/deuterium exchange-mass spectrometry (HDX-MS) (see, e.g., *Epitope Mapping Protocols in Methods in Molecular Biology*, Vol. 66, G. E. Morris, Ed. (1996)). See also Champe et al. (1995) *J. Biol. Chem.* 270:1388-1394.

The term "binds to the same epitope" with reference to two or more antibodies means that the antibodies bind to the same segment or same segments of amino acid residues, as determined by a given method. Techniques for determining whether antibodies bind to the "same epitope on LAP-TGFβ1" with the antibodies described herein include, for example, epitope mapping methods, such as x-ray analyses of crystals of antigen:antibody complexes, which provides atomic resolution of the epitope, and HDX-MS. Other methods monitor the binding of the antibody to antigen fragments (e.g. proteolytic fragments) or to mutated variations of the antigen where loss of binding due to a modification of an amino acid residue within the antigen sequence is often considered an indication of an epitope component, such as alanine scanning mutagenesis (Cunningham & Wells (1985) *Science* 244:1081), yeast display of mutant target sequence variants, or analysis of chimeras (e.g., as described in Examples 2 and 3). In addition, computational combinatorial methods for epitope mapping can also be used. These methods rely on the ability of the antibody of interest to affinity isolate specific short peptides from combinatorial phage display peptide libraries. Antibodies having the same $V_H$ and $V_L$ or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known binding competition experiments, e.g., BIACORE® surface plasmon resonance (SPR) analysis. In certain embodiments, an antibody competes with, and inhibits binding of another antibody to a target by at least 50%, 60%, 70%, 80%, 90% or 100%. The level of inhibition or competition may be different depending on which antibody is the "blocking antibody" (i.e., the antibody that when combined with an antigen blocks another immunologic reaction with the antigen). Competition assays can be conducted as described, for example, in Ed Harlow and David Lane, Cold Spring Harb. Protoc. 2006; doi:10.1101/pdb-.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope, or to adjacent epitopes (e.g., as evidenced by steric hindrance). Two antibodies "cross-compete" if antibodies block each other both ways by at least 50%, i.e., regardless of whether one or the other antibody is contacted first with the antigen in the competition experiment.

Competitive binding assays for determining whether two antibodies compete or cross-compete for binding include competition for binding to cells expressing LAP-TGFβ1, e.g., by flow cytometry. Other methods include: surface plasmon resonance (SPR) (e.g., BIACORE®), solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) using a predetermined antigen as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Any $K_D$ greater than about $10^{-4}$ M is generally considered to indicate nonspecific binding.

The term "$k_{assoc}$" or "$k_a$", as used herein, refers to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system or flow cytometry and Scatchard analysis, or bio-layer interferometry.

The term "EC50" in the context of an in vitro or in vivo assay using an antibody refers to the concentration of an antibody that induces a response that is 50% of the maximal response, i.e., halfway between the maximal response and the baseline.

The term "cross-reacts," as used herein, refers to the ability of an antibody described herein to bind to LAP-TGFβ1 from a different species. For example, an antibody described herein that binds human LAP-TGFβ1 may also bind another species of LAP-TGFβ1 (e.g., murine LAP-TGFβ1, rat LAP-TGFβ1, or cynomolgus monkey LAP-TGFβ1). Cross-reactivity may be measured by detecting a specific reactivity with purified antigen in binding assays (e.g., SPR, ELISA, bio-layer interferometry) or binding to, or otherwise functionally interacting with, cells physiologically expressing LAP-TGFβ1 (e.g., HT1080 cells overexpressing LAP-TGFβ1). Methods for determining cross-reactivity include standard binding assays as described herein, for example, by bio-layer interferometry or flow cytometric techniques.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody fragments (e.g., $V_H$, $V_L$, CDR3), is intended to refer to a nucleic acid molecule in which the nucleotide sequences are essentially free of other genomic nucleotide sequences, e.g., those encoding antibodies that bind antigens other than LAP, which other sequences may naturally flank the nucleic acid in human genomic DNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

Also provided are "conservative sequence modifications" of the sequences set forth herein, i.e., amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into a sequence in a table herein (e.g., Table 34) by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-LAP antibody is preferably replaced with another amino acid residue from the same side chain family. Methods of identifying nucleotide and amino acid conservative substitutions which do not eliminate antigen binding are well-known in the art (see, e.g., Brummell et al., *Biochem.* 32:1180-1187 (1993); Kobayashi et al. *Protein Eng.* 12(10):879-884 (1999); and Burks et al. *Proc. Natl. Acad. Sci. USA* 94:412-417 (1997)). Alternatively, in another embodiment, mutations can be introduced randomly along all or part of an anti-LAP antibody coding sequence, such as by saturation mutagenesis, and the resulting modified anti-LAP antibodies can be screened for binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 80% to 85%, 85% to 90% or 90% to 95%, and more preferably at least about 98% to 99.5% of the nucleotides. Alternatively, substantial homology exists when the segments will hybridize under selective hybridization conditions, to the complement of the strand. For polypeptides, the term "substantial homology" indicates that two polypeptides, or designated sequences thereof, when optimally aligned and compared, are identical, with appropriate amino acid insertions or deletions, in at least about 80% of the amino acids, usually at least about 80% to 85%, 85% to 90%, 90% to 95%, and more preferably at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below. The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or two amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See www.ncbi.nlm.nih.gov.

The term "recombinant host cell" (or simply "host cell"), as used herein, is intended to refer to a cell that comprises a nucleic acid that is not naturally present in the cell, and may be a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "inhibition" as used herein, refers to any statistically significant decrease in biological activity, including partial and full blocking of the activity. For example, "inhibition" can refer to a statistically significant decrease of about 10%, 20%, 30%, 40%, 50%, 60%, 70%, 80%, 90%, 95%, 96%, 97%, 98%, 99%, or 100% in biological activity.

As used herein, "TGFβ1 activation" refers to the release of the mature cytokine TGFβ1 from the latent complex made up of LAP and TGFβ1. There are many mechanisms known to induce TGFβ1 activation (see Robertson I B, Rifkin D B. Unchaining the beast; insights from structural and evolutionary studies on TGFβ1 secretion, sequestration, and activation. Cytokine Growth Factor Rev. 2013 August; 24(4): 355-72). The mature cytokine can be detected using a specific ELISA or similar detection methodology or through the use of a reporter cell line that expresses a TGFβ receptor.

For example, as used herein, the term "inhibits TGFβ1 activation" includes any measurable decrease in TGFβ1 activation, e.g., an inhibition of TGFβ1 activation by at least about 10%, for example, at least about 20%, at least about 30%, at least about 40%, at least about 50%, at least about 60%, at least about 70%, at least about 80%, at least about 90%, at least about 99%, or about 100%, relative to a control (e.g., a control antibody). The inhibition may be specific to a single mechanism of TGFβ1 activation or may be generalizable to all mechanisms of TGFβ1 activation. As used herein, the term "inhibits TGFβ1 activation" includes inhibition of at least one activation mechanism.

The terms "treat," "treating," and "treatment," as used herein, refer to therapeutic or preventative measures described herein. The methods of "treatment" employ administration to a subject with a tumor or cancer or a subject who is predisposed to having such a disease or disorder, an anti-LAP antibody (e.g., anti-human LAP antibody) described herein, in order to prevent, cure, delay, reduce the severity of, or ameliorate one or more symptoms of the disease or disorder or recurring disease or disorder, or in order to prolong the survival of a subject beyond that expected in the absence of such treatment.

"Immunotherapy" refers to the treatment of a subject afflicted with, or at risk of contracting or suffering a recurrence of, a disease by a method comprising inducing, enhancing, suppressing or otherwise modifying an immune response.

"Immunostimulating therapy" or "immunostimulatory therapy" refers to a therapy that results in increasing (inducing or enhancing) an immune response in a subject for, e.g., treating cancer.

As used herein, "immune cell" refers to the subset of blood cells known as white blood cells, which include mononuclear cells such as lymphocytes, monocytes, macrophages, and granulocytes.

As used herein, "immunosuppressive cell" refers to a cell that contributes to or promotes an immunosuppressive tumor microenvironment. The presence of a population of immunosuppressive cells in a tumor microenvironment increases the tumor's resistance to an immune response, resulting in tumor protection, tumor escape, and/or tumor metastasis. Unless countered in some manner, these immunosuppressive cells can decrease the efficacy of immune-mediated anti-cancer treatments. Exemplary immunosuppressive cells include cancer-associated fibroblasts, myeloid-derived suppressor cells, regulatory T cells (Tregs), tumor cells expressing LAP, and immunosuppressive macrophages. These cell types can be identified by one skilled in the art using, e.g., flow cytometry to identify markers of Tregs (e.g., CD4, FoxP3, CD127, and CD25), macrophages (e.g., CSF-IR, CD203, CD206, CD163, IL-10, and TGFβ), cancer associated fibroblasts (e.g., alpha smooth muscle actin, fibroblast activation protein, tenascin-C, periostin, NG2, vimentin, desmin, PDGFR alpha and beta, FSP-1, ASPN, and STC1), and myeloid-derived suppressor cells (e.g., CD11b, CD33, CD14, or CD15, and low levels of HLA DR). It is understood that immunosuppressive cells may also be important in suppressing the immune system in other disease states.

As used herein, "suppressive T cells" refer to T cells that contribute to or promote an immunosuppressive microenvironment. Exemplary suppressive T cells include CD4+ regulatory T cells and CD8+ regulatory T cells. Such cells can be identified by one skilled in the art using, e.g., flow cytometry to identify markers such as FoxP3, LAP or Helios.

As used herein, "regulatory T cells" or "Tregs" refer to immunosuppressive cells that generally suppress or downregulate induction and proliferation of effector T cells. Tregs generally express the biomarkers CD4, FOXP3, and CD25 and are thought to be derived from the same lineage as naïve CD4 cells.

"T effector" ("$T_{eff}$") cells refers to T cells (e.g., CD4+ and CD8+ T cells) with cytolytic activities as well as T helper (Th) cells, which secrete inflammatory cytokines and activate and direct other immune cells, but does not include regulatory T cells (Treg cells).

As used herein, "administering" refers to the physical introduction of a molecule (e.g., an antibody or antigen binding fragment that binds LAP) or of a composition comprising a therapeutic agent (e.g., an anti-LAP antibody or antigen binding fragment) to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, "cancer" refers to a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

As used herein, "autoimmune disease" describes a disease state or syndrome whereby a subject's body produces a dysfunctional immune response against the subject's own body components, with adverse effects.

As used herein, "fibrosis" refers to disorders or disease states that are caused by or accompanied by the abnormal deposition of extracellular matrix (i.e., not formation of fibrous tissue in normal organ and tissue). Fibrosis is characterized by excessive accumulation of extracellular matrix in the affected tissue that often results in destruction of its normal architecture and causes significant organ dysfunction. Although fibrotic conditions in various organs have diverse etiologies, fibrosis typically results from chronic persistent inflammation induced by a variety of stimuli, such as chronic infections, ischemia, allergic and autoimmune reactions, chemical insults or radiation injury (from Biernacka, 2011 Growth Factors. 2011 October; 29(5):196-202. doi: 10.3109/08977194.2011.595714. Epub 2011 Jul. 11). Fibrosis may affect the heart, liver, kidney, lung and skin and is also a central feature in many cancers. As used herein, "cell therapy" refers to a method of treatment involving the administration of live cells (e.g., CAR T cells, and NK cells).

The terms "treat," "treating," and "treatment," as used herein, refer to any type of intervention or process performed on, or administering an active agent (e.g., an anti-LAP antibody or antigen binding fragment) to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

As used herein, "adjunctive" or "combined" administration (co-administration) includes simultaneous administration of the agents and/or compounds in the same or different dosage form, or separate administration of the compounds (e.g., sequential administration). For example at least one agent comprises an anti-LAP antibody or antigen binding fragment. Thus, a first antibody or antigen binding fragment, e.g., an anti-LAP antibody or antigen binding fragment, and a second, third, or more antibodies or antigen binding fragments can be simultaneously administered in a single formulation. Alternatively, the first and second (or more) antibodies or antigen binding fragments can be formulated for separate administration and are administered concurrently or sequentially.

"Combination" therapy, as used herein, means administration of two or more therapeutic agents in a coordinated fashion, and includes, but is not limited to, concurrent dosing. Specifically, combination therapy encompasses both co-administration (e.g. administration of a co-formulation or simultaneous administration of separate therapeutic compositions) and serial or sequential administration, provided that administration of one therapeutic agent is conditioned in some way on administration of another therapeutic agent. For example, one therapeutic agent may be administered only after a different therapeutic agent has been administered and allowed to act for a prescribed period of time. (See, e.g., Kohrt et al. (2011) Blood 117:2423). For example, the anti-LAP antibody can be administered first followed by (e.g., immediately followed by) the administration of a second antibody (e.g., an anti-PD-1 antibody) or antigen binding fragment, or vice versa. In one embodiment, the anti-LAP antibody or antigen binding fragment is administered prior to administration of the second antibody or antigen binding fragment. In another embodiment, the anti-LAP antibody or antigen binding fragment is administered, for example, a few minutes (e.g., within about 30 minutes) or at least one hour of the second antibody or antigen binding fragment. Such concurrent or sequential administration preferably results in both antibodies or antigen binding fragments being simultaneously present in treated patients.

The term "effective dose" or "effective dosage" is defined as an amount sufficient to achieve or at least partially achieve a desired effect. A "therapeutically effective amount" or "therapeutically effective dosage" of a drug (e.g., anti-LAP antibody or antigen binding fragment) is any amount of the drug or therapeutic agent that, when used alone or in combination with another therapeutic agent, promotes disease regression evidenced by a decrease in severity of disease symptoms, an increase or therapeutic agent in frequency and duration of disease symptom-free periods, or a prevention of impairment or disability due to the disease affliction. A therapeutically effective amount or dosage of a drug or therapeutic agent includes a "prophylactically effective amount" or a "prophylactically effective dosage", which is any amount of the drug or therapeutic agent that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

The administration of effective amounts of the anti-LAP antibody or antigen binding fragment alone, or anti-LAP antibody or antigen binding fragment combined with another compound or agent (e.g., an immune checkpoint blocker such as an anti-PD-1 antibody), according to any of the methods provided herein, can result in at least one therapeutic effect, including, for example, reduced tumor growth or size, reduced number of indicia of cancer (e.g., metastatic lesions) appearing over time, complete remission, partial remission, or stable disease. For example, the methods of treatment produce a comparable clinical benefit rate (CBR=complete remission (CR)+ partial remission (PR)+ stable disease (SD) lasting ≥6 months) better than that achieved without administration of the anti-LAP antibody or antigen binding fragment, or than that achieved with administration of any one of the combined antibodies, e.g., the improvement of clinical benefit rate is about 20% 20%, 30%, 40%, 50%, 60%, 70%, 80% or more.

By way of example, for the treatment of tumors, a therapeutically effective amount or dosage of the drug or therapeutic agent (e.g., anti-LAP antibody or antigen binding fragment) inhibits tumor cell growth by at least about 20%, by at least about 30% by at least about 40%, by at least about 50%, by at least about 60%, by at least above 70%, by at least about 80%, or by at least about 90% relative to untreated subjects. In some embodiments, a therapeutically effective amount or dosage of the drug or therapeutic agent completely inhibits cell growth or tumor growth, i.e., inhibits cell growth or tumor growth by 100%. The ability of a compound or therapeutic agent, including an antibody, to inhibit tumor growth can be evaluated using the assays described herein. Alternatively, this property of a composition comprising the compound or therapeutic agent can be evaluated by examining the ability of the composition to inhibit cell growth; such inhibition can be measured in vitro by assays known to the skilled practitioner.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, cats, dogs, cows, chickens, amphibians, reptiles, etc.

The term "sample" refers to tissue, bodily fluid, or a cell (or a fraction of any of the foregoing) taken from a patient or a subject. Normally, the tissue or cell will be removed from the patient, but in vivo diagnosis is also contemplated. In the case of a solid tumor, a tissue sample can be taken from a surgically removed tumor and prepared for testing by conventional techniques. In the case of lymphomas and leukemias, lymphocytes, leukemic cells, or lymph tissues can be obtained (e.g., leukemic cells from blood) and appropriately prepared. Other samples, including urine, tears, serum, plasma, cerebrospinal fluid, feces, sputum, cell extracts etc. can also be useful for particular cancers.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising," "consisting essentially of," and "consisting of" may be optionally replaced with either of the other two terms, thus describing alternative aspects of the scope of the subject matter. The invention illustratively described herein suitably may be practiced in the absence of any element or elements, limitation or limitations which is not specifically disclosed herein.

As used herein, the singular forms "a," "an," and "the" include plural referents unless the context clearly dictates otherwise. The use of "or" or "and" means "and/or" unless stated otherwise. Furthermore, use of the term "including" as well as other forms, such as "include," "includes," and "included," is not limiting.

The term "about" as used herein when referring to a measurable value such as an amount, a temporal duration and the like, encompasses variations of up to ±10% from the specified value. Unless otherwise indicated, all numbers expressing quantities of ingredients, properties such as molecular weight, reaction conditions, etc., used herein are to be understood as being modified by the term "about".

As used herein, "and/or" is to be taken as specific disclosure of each of the two specified features or components with or without the other. Thus, the term "and/or" as used in a phrase such as "A and/or B" includes "A and B," "A or B," "A" alone, and "B" alone. Likewise, the term "and/or" as used in a phrase such as "A, B, and/or C" encompasses each of the following: A, B, and C; A, B, or C; A or C; A or B; B or C; A and C; A and B; B and C; A alone; B alone; and C alone.

As used herein, the terms "ug" and "uM" are used interchangeably with "µg" and "µM," respectively.

Various aspects described herein are described in further detail in the following subsections.

I. Anti-LAP Antibodies

In one aspect, provided herein is an isolated anti-LAP antibody (i.e., an antibody that binds LAP) or antigen binding fragment thereof.

In one aspect, provided herein is an isolated anti-LAP antibody (e.g., recombinant humanized, chimeric, or human antibody) or antigen binding fragment thereof which comprises:

(a) a heavy chain variable region comprising CDR1, CDR2, and CDR3 regions comprising the amino acid sequences of SEQ ID NOs: 16, 26, and 18, respectively, and a light chain variable region comprising CDR1, CDR2, and CDR3 regions comprising the amino acid sequences of SEQ ID NOs: 19, 20, and 21, respectively;

(b) a heavy chain variable region comprising CDR1, CDR2, and CDR3 regions comprising the amino acid sequences of SEQ ID NOs: 16, 27, and 18, respectively, and a light chain variable region comprising CDR1, CDR2, and CDR3 regions comprising the amino acid sequences of SEQ ID NOs: 19, 20, and 21, respectively;

(c) a heavy chain variable region comprising CDR1, CDR2, and CDR3 regions comprising the amino acid sequences of SEQ ID NOs: 16, 28, and 18, respectively, and a light chain variable region comprising CDR1, CDR2, and CDR3 regions comprising the amino acid sequences of SEQ ID NOs: 19, 20, and 21, respectively;

(d) a heavy chain variable region comprising CDR1, CDR2, and CDR3 regions comprising the amino acid sequences of SEQ ID NOs: 16, 29, and 18, respectively, and a light chain variable region comprising CDR1, CDR2, and CDR3 regions comprising the amino acid sequences of SEQ ID NOs: 19, 20, and 21, respectively;

(e) a heavy chain variable region comprising CDR1, CDR2, and CDR3 regions comprising the amino acid sequences of SEQ ID NOs: 16, 30, and 18, respectively, and a light chain variable region comprising CDR1, CDR2, and CDR3 regions comprising the amino acid sequences of SEQ ID NOs: 19, 20, and 21, respectively;

(f) a heavy chain variable region comprising CDR1, CDR2, and CDR3 regions comprising the amino acid sequences of SEQ ID NOs: 54, 55, and 56, respectively, and a light chain variable region comprising CDR1, CDR2, and CDR3 regions comprising the amino acid sequences of SEQ ID NOs: 57, 58, and 59, respectively;

(g) a heavy chain variable region comprising CDR1, CDR2, and CDR3 regions comprising the amino acid sequences of SEQ ID NOs: 54, 64, and 56, respectively, and a light chain variable region comprising CDR1, CDR2, and CDR3 regions comprising the amino acid sequences of SEQ ID NOs: 57, 58, and 59, respectively;

(h) a heavy chain variable region comprising CDR1, CDR2, and CDR3 regions comprising the amino acid sequences of SEQ ID NOs: 54, 65, and 56, respectively, and a light chain variable region comprising CDR1, CDR2, and CDR3 regions comprising the amino acid sequences of SEQ ID NOs: 57, 58, and 59, respectively;

(i) a heavy chain variable region comprising CDR1, CDR2, and CDR3 regions comprising the amino acid sequences of SEQ ID NOs: 54, 66, and 56, respectively, and a light chain variable region comprising CDR1, CDR2, and CDR3 regions comprising the amino acid sequences of SEQ ID NOs: 57, 58, and 59, respectively;

(j) a heavy chain variable region comprising CDR1, CDR2, and CDR3 regions comprising the amino acid sequences of SEQ ID NOs: 54, 67, and 56, respectively, and a light chain variable region comprising CDR1, CDR2, and CDR3 regions comprising the amino acid sequences of SEQ ID NOs: 57, 58, and 59, respectively;

(k) a heavy chain variable region comprising CDR1, CDR2, and CDR3 regions comprising the amino acid sequences of SEQ ID NOs: 54, 55, and 68, respectively, and a light chain variable region comprising CDR1, CDR2, and CDR3 regions comprising the amino acid sequences of SEQ ID NOs: 57, 58, and 59, respectively;

(l) a heavy chain variable region comprising CDR1, CDR2, and CDR3 regions comprising the amino acid sequences of SEQ ID NOs: 54, 55, and 69, respectively, and a light chain variable region comprising CDR1, CDR2, and CDR3 regions comprising the amino acid sequences of SEQ ID NOs: 57, 58, and 59, respectively;

(m) a heavy chain variable region comprising CDR1, CDR2, and CDR3 regions comprising the amino acid sequences of SEQ ID NOs: 54, 55, and 70, respectively, and a light chain variable region comprising CDR1, CDR2, and CDR3 regions comprising the amino acid sequences of SEQ ID NOs: 57, 58, and 59, respectively;

(n) a heavy chain variable region comprising CDR1, CDR2, and CDR3 regions comprising the amino acid sequences of SEQ ID NOs: 54, 66, and 68, respectively, and a light chain variable region comprising CDR1, CDR2, and CDR3 regions comprising the amino acid sequences of SEQ ID NOs: 57, 58, and 59, respectively;

(o) a heavy chain variable region comprising CDR1, CDR2, and CDR3 regions comprising the amino acid sequences of SEQ ID NOs: 110, 111, and 112, respectively, and a light chain variable region comprising CDR1, CDR2, and CDR3 regions comprising the amino acid sequences of SEQ ID NOs: 113, 114, and 115, respectively;

(p) a heavy chain variable region comprising CDR1, CDR2, and CDR3 regions comprising the amino acid sequences of SEQ ID NOs: 110, 120, and 112, respectively, and a light chain variable region comprising CDR1, CDR2, and CDR3 regions comprising the amino acid sequences of SEQ ID NOs: 113, 114, and 115, respectively;

(q) a heavy chain variable region comprising CDR1, CDR2, and CDR3 regions comprising the amino acid sequences of SEQ ID NOs: 110, 121, and 112, respectively, and a light chain variable region comprising CDR1, CDR2, and CDR3 regions comprising the amino acid sequences of SEQ ID NOs: 113, 114, and 115, respectively;

(r) a heavy chain variable region comprising CDR1, CDR2, and CDR3 regions comprising the amino acid sequences of SEQ ID NOs: 110, 122, and 112, respectively, and a light chain variable region comprising CDR1, CDR2, and CDR3 regions comprising the amino acid sequences of SEQ ID NOs: 113, 114, and 115, respectively;

(s) a heavy chain variable region comprising CDR1, CDR2, and CDR3 regions comprising the amino acid sequences of SEQ ID NOs: 110, 123, and 112, respectively, and a light chain variable region comprising CDR1, CDR2, and CDR3 regions comprising the amino acid sequences of SEQ ID NOs: 113, 114, and 115, respectively;

(t) a heavy chain variable region comprising CDR1, CDR2, and CDR3 regions comprising the amino acid sequences of SEQ ID NOs: 110, 124, and 112, respectively, and a light chain variable region comprising CDR1, CDR2, and CDR3 regions comprising the amino acid sequences of SEQ ID NOs: 113, 114, and 115, respectively;

(u) a heavy chain variable region comprising CDR1, CDR2, and CDR3 regions comprising the amino acid sequences of SEQ ID NOs: 110, 125, and 112, respectively, and a light chain variable region comprising CDR1, CDR2, and CDR3 regions comprising the amino acid sequences of SEQ ID NOs: 113, 114, and 115, respectively;

(v) a heavy chain variable region comprising CDR1, CDR2, and CDR3 regions comprising the amino acid sequences of SEQ ID NOs: 110, 126, and 112, respectively, and a light chain variable region comprising CDR1, CDR2, and CDR3 regions comprising the amino acid sequences of SEQ ID NOs: 113, 114, and 115, respectively;

(w) a heavy chain variable region comprising CDR1, CDR2, and CDR3 regions comprising the amino acid sequences of SEQ ID NOs: 162, 163, and 164, respectively, and a light chain variable region comprising CDR1, CDR2, and CDR3 regions comprising the amino acid sequences of SEQ ID NOs: 165, 166, and 167, respectively;

(x) a heavy chain variable region comprising CDR1, CDR2, and CDR3 regions comprising the amino acid sequences of SEQ ID NOs: 162, 172, and 164, respectively, and a light chain variable region comprising CDR1, CDR2, and CDR3 regions comprising the amino acid sequences of SEQ ID NOs: 165, 166, and 167, respectively;

(y) a heavy chain variable region comprising CDR1, CDR2, and CDR3 regions comprising the amino acid sequences of SEQ ID NOs: 162, 173, and 164, respectively, and a light chain variable region comprising CDR1, CDR2, and CDR3 regions comprising the amino acid sequences of SEQ ID NOs: 165, 166, and 167, respectively;

(z) a heavy chain variable region comprising CDR1, CDR2, and CDR3 regions comprising the amino acid sequences of SEQ ID NOs: 162, 174, and 164, respectively, and a light chain variable region comprising CDR1, CDR2, and CDR3 regions comprising the amino acid sequences of SEQ ID NOs: 165, 166, and 167, respectively;

(aa) a heavy chain variable region comprising CDR1, CDR2, and CDR3 regions comprising the amino acid sequences of SEQ ID NOs: 162, 174, and 164, respectively, and a light chain variable region comprising CDR1, CDR2, and CDR3 regions comprising the amino acid sequences of SEQ ID NOs: 165, 166, and 167, respectively;

(ab) a heavy chain variable region comprising CDR1, CDR2, and CDR3 regions comprising the amino acid sequences of SEQ ID NOs: 162, 176, and 164, respectively, and a light chain variable region comprising CDR1, CDR2, and CDR3 regions comprising the amino acid sequences of SEQ ID NOs: 165, 166, and 167, respectively;

(ac) a heavy chain variable region comprising CDR1, CDR2, and CDR3 regions comprising the amino acid sequences of SEQ ID NOs: 162, 177, and 164, respectively, and a light chain variable region comprising CDR1, CDR2, and CDR3 regions comprising the amino acid sequences of SEQ ID NOs: 165, 166, and 167, respectively;

(ad) a heavy chain variable region comprising CDR1, CDR2, and CDR3 regions comprising the amino acid sequences of SEQ ID NOs: 162, 178, and 164, respectively, and a light chain variable region comprising CDR1, CDR2, and CDR3 regions comprising the amino acid sequences of SEQ ID NOs: 165, 166, and 167, respectively;

(ae) a heavy chain variable region comprising CDR1, CDR2, and CDR3 regions comprising the amino acid sequences of SEQ ID NOs: 179, 180, and 181, respectively, and a light chain variable region comprising CDR1, CDR2, and CDR3 regions comprising the amino acid sequences of SEQ ID NOs: 182, 183, and 184, respectively; or (af) a heavy chain variable region comprising CDR1, CDR2, and CDR3 regions comprising the amino acid sequences of SEQ ID NOs: 179, 189, and 181, respectively, and a light chain variable region comprising CDR1, CDR2, and CDR3 regions comprising the amino acid sequences of SEQ ID NOs: 182, 183, and 184, respectively;

(ag) a heavy chain variable region comprising CDR1, CDR2, and CDR3 regions comprising the amino acid sequences of SEQ ID NOs: 179, 190, and 181, respectively, and a light chain variable region comprising CDR1, CDR2, and CDR3 regions comprising the amino acid sequences of SEQ ID NOs: 182, 183, and 184, respectively;

(ah) a heavy chain variable region comprising CDR1, CDR2, and CDR3 regions comprising the amino acid sequences of SEQ ID NOs: 179, 191, and 181, respectively, and a light chain variable region comprising CDR1, CDR2, and CDR3 regions comprising the amino acid sequences of SEQ ID NOs: 182, 183, and 184, respectively;

(ai) a heavy chain variable region comprising CDR1, CDR2, and CDR3 regions comprising the amino acid sequences of SEQ ID NOs: 179, 192, and 181, respectively, and a light chain variable region comprising CDR1, CDR2, and CDR3 regions comprising the amino acid sequences of SEQ ID NOs: 182, 183, and 184, respectively;

(aj) a heavy chain variable region comprising CDR1, CDR2, and CDR3 regions comprising the amino acid sequences of SEQ ID NOs: 179, 193, and 181, respectively, and a light chain variable region comprising CDR1, CDR2, and CDR3 regions comprising the amino acid sequences of SEQ ID NOs: 182, 183, and 184, respectively;

(ak) a heavy chain variable region comprising CDR1, CDR2, and CDR3 regions comprising the amino acid sequences of SEQ ID NOs: 179, 194, and 181, respectively, and a light chain variable region comprising CDR1, CDR2, and CDR3 regions comprising the amino acid sequences of SEQ ID NOs: 182, 183, and 184, respectively;

(al) a heavy chain variable region comprising CDR1, CDR2, and CDR3 regions comprising the amino acid sequences of SEQ ID NOs: 179, 195, and 181, respectively, and a light chain variable region comprising CDR1, CDR2, and CDR3 regions comprising the amino acid sequences of SEQ ID NOs: 182, 183, and 184, respectively;

(am) a heavy chain variable region comprising CDR1, CDR2, and CDR3 regions comprising the amino acid sequences of SEQ ID NOs: 225, 226, and 227, respectively, and a light chain variable region comprising CDR1, CDR2, and CDR3 regions comprising the amino acid sequences of SEQ ID NOs: 228, 229, and 230, respectively;

(an) a heavy chain variable region comprising CDR1, CDR2, and CDR3 regions comprising the amino acid sequences of SEQ ID NOs: 225, 231, and 227, respectively, and a light chain variable region comprising CDR1, CDR2, and CDR3 regions comprising the amino acid sequences of SEQ ID NOs: 228, 229, and 230, respectively;

(ao) a heavy chain variable region comprising CDR1, CDR2, and CDR3 regions comprising the amino acid sequences of SEQ ID NOs: 225, 232, and 227, respectively, and a light chain variable region comprising CDR1, CDR2, and CDR3 regions comprising the amino acid sequences of SEQ ID NOs: 228, 229, and 230, respectively; or (ap) a heavy chain variable region comprising CDR1, CDR2, and CDR3 regions comprising the amino acid sequences of SEQ ID NOs: 225, 233, and 227, respectively, and a light chain variable region comprising CDR1, CDR2, and CDR3 regions comprising the amino acid sequences of SEQ ID NOs: 228, 229, and 230, respectively.

In some embodiments, the anti-LAP antibody (e.g., recombinant humanized, chimeric, or human antibody) or antigen binding fragment comprises a heavy chain variable region comprising CDR1, CDR2, and CDR3 regions comprising the amino acid sequences of SEQ ID NOs: 16, 17, and 18, respectively, and a light chain variable region comprising CDR1, CDR2, and CDR3 regions comprising the amino acid sequences of SEQ ID NOs: 19, 20, and 21, respectively, except wherein position 56 of the heavy chain variable region (corresponding to position 7 of SEQ ID NO: 17) is an amino acid other than N (e.g., Q, S, H, L, D)) or is substituted with an amino acid residue other than N (e.g., Q, S, H, L, D).

In some embodiments, the anti-LAP antibody (e.g., recombinant humanized, chimeric, or human antibody) or antigen binding fragment comprises a heavy chain variable region comprising CDR1, CDR2, and CDR3 regions comprising the amino acid sequences of SEQ ID NOs: 54, 55, and 56, respectively, and a light chain variable region comprising CDR1, CDR2, and CDR3 regions comprising the amino acid sequences of SEQ ID NOs: 57, 58, and 59, respectively, except wherein position 54 of the heavy chain variable region (corresponding to position 5 of SEQ ID NO: 55) is an amino acid other than N (e.g., Q, A, H, S) or is substituted with an amino acid residue other than N (e.g., Q, A, H, S).

In some embodiments, the anti-LAP antibody (e.g., recombinant humanized, chimeric, or human antibody) or antigen binding fragment comprises a heavy chain variable region comprising CDR1, CDR2, and CDR3 regions comprising the amino acid sequences of SEQ ID NOs: 54, 55, and 56, respectively, and a light chain variable region comprising CDR1, CDR2, and CDR3 regions comprising the amino acid sequences of SEQ ID NOs: 57, 58, and 59, respectively, except wherein position 102 of the heavy chain variable region (corresponding to position 4 of SEQ ID NO: 56) is an amino acid other than D (e.g., A, E, G)) or is substituted with an amino acid residue other than D (e.g., A, E, G).

In some embodiments, the anti-LAP antibody (e.g., recombinant humanized, chimeric, or human antibody) or antigen binding fragment comprises a heavy chain variable region comprising CDR1, CDR2, and CDR3 regions comprising the amino acid sequences of SEQ ID NOs: 54, 55, and 56, respectively, and a light chain variable region comprising CDR1, CDR2, and CDR3 regions comprising the amino acid sequences of SEQ ID NOs: 57, 58, and 59, respectively, except wherein position 54 of the heavy chain variable region (corresponding to position 5 of SEQ ID NO: 55) is an amino acid other than N (e.g., Q, A, H, S) or is substituted with an amino acid residue other than N (e.g., Q, A, H, S), and wherein position 102 of the heavy chain variable region (corresponding to position 4 of SEQ ID NO: 56) is an amino acid other than D (e.g., A, E, G)) or is substituted with an amino acid residue other than D (e.g., A, E, G).

In some embodiments, the anti-LAP antibody (e.g., recombinant humanized, chimeric, or human antibody) or antigen binding fragment comprises a heavy chain variable region comprising CDR1, CDR2, and CDR3 regions comprising the amino acid sequences of SEQ ID NOs: 110, 111, and 112, respectively, and a light chain variable region comprising CDR1, CDR2, and CDR3 regions comprising the amino acid sequences of SEQ ID NOs: 113, 114, and 115, respectively, except wherein position 54 of the heavy chain variable region (corresponding to position 5 of SEQ ID NO: 111) is an amino acid other than N (e.g., Q, G, A, S, H, L, D)) or is substituted with an amino acid residue other than N (e.g., Q, G, A, S, H, L, D).

In some embodiments, the anti-LAP antibody (e.g., recombinant humanized, chimeric, or human antibody) or antigen binding fragment comprises a heavy chain variable region comprising CDR1, CDR2, and CDR3 regions comprising the amino acid sequences of SEQ ID NOs: 162, 163, and 164, respectively, and a light chain variable region comprising CDR1, CDR2, and CDR3 regions comprising the amino acid sequences of SEQ ID NOs: 165, 166, and 167, respectively, except wherein position 56 of the heavy chain variable region (corresponding to position 7 of SEQ ID NO: 163) is an amino acid other than N (e.g., Q, G, A, S, H, L, D) or is substituted with an amino acid residue other than N (Q, G, A, S, H, L, D).

In some embodiments, the anti-LAP antibody (e.g., recombinant humanized, chimeric, or human antibody) or antigen binding fragment comprises a heavy chain variable region comprising CDR1, CDR2, and CDR3 regions comprising the amino acid sequences of SEQ ID NOs: 179, 180, and 181, respectively, and a light chain variable region comprising CDR1, CDR2, and CDR3 regions comprising the amino acid sequences of SEQ ID NOs: 182, 183, and 184, respectively, except wherein position 55 of the heavy chain variable region (corresponding to position 6 of SEQ ID NO: 180) is an amino acid other than N (e.g., Q, G, A, S, H, L, D) or is substituted with an amino acid residue other than N (e.g., Q, G, A, S, H, L, D).

In some embodiments, the anti-LAP antibody (e.g., recombinant humanized, chimeric, or human antibody) comprises a heavy chain variable region comprising CDR1, CDR2, and CDR3 regions comprising the amino acid sequences of SEQ ID NOs: 225, 226, and 227, respectively, and a light chain variable region comprising CDR1, CDR2, and CDR3 regions comprising the amino acid sequences of SEQ ID NOs: 228, 229, and 230, respectively, except wherein position 55 of the heavy chain variable region (corresponding to position 5 of SEQ ID NO: 226) is an amino acid other than D (e.g., G, A, E) or is substituted with an amino acid residue other than D (e.g., G, A, E).

In some embodiments, the anti-LAP antibody comprises the heavy chain CDR sequences of any of subparts (a)-(ap) above, and a constant region, e.g., a human IgG constant region (e.g., IgG1, IgG2, IgG3, or IgG4, or variants thereof). In some embodiments, the constant region is a human IgG1 constant region comprising the amino acid sequence set forth in SEQ ID NO: 196. In some embodiments, the constant region is a variant human IgG4 constant region comprising the amino acid sequence set forth in SEQ ID NO: 197. In some embodiments, a heavy chain variable region comprising the heavy chain CDR sequences of any of subparts (a)-(ap) above may be linked to a constant domain to form a heavy chain (e.g., a full length heavy chain). Similarly, a light chain variable region comprising the light chain CDR sequences of any of subparts (a)-(ap) above may be linked to a constant region to form a light chain (e.g., a full length light chain). A full length heavy chain (with the exception of the C-terminal lysine (K) or with the exception of the C-terminal glycine and lysine (GK), which may be absent or removed) and full length light chain combine to form a full length antibody.

In another aspect, provided herein are isolated anti-LAP antibodies comprising:
(a) heavy and light chain variable region sequences comprising SEQ ID NOs: 42 and 52, respectively;
(b) heavy and light chain variable region sequences comprising SEQ ID NOs: 40 and 52, respectively;
(c) heavy and light chain variable region sequences comprising SEQ ID NOs: 35 and 46, respectively;
(d) heavy and light chain variable region sequences comprising SEQ ID NOs: 35 and 50, respectively;
(e) heavy and light chain variable region sequences comprising SEQ ID NOs: 101 and 104, respectively;
(f) heavy and light chain variable region sequences comprising SEQ ID NOs: 98 and 104, respectively;
(g) heavy and light chain variable region sequences comprising SEQ ID NOs: 92 and 104, respectively;
(h) heavy and light chain variable region sequences comprising SEQ ID NOs: 92 and 106, respectively;
(i) heavy and light chain variable region sequences comprising SEQ ID NOs: 95 and 104, respectively;
(j) heavy and light chain variable region sequences comprising SEQ ID NOs: 77 and 104, respectively;
(k) heavy and light chain variable region sequences comprising SEQ ID NOs: 82 and 104, respectively;
(l) heavy and light chain variable region sequences comprising SEQ ID NOs: 87 and 104, respectively;
(m) heavy and light chain variable region sequences comprising SEQ ID NOs: 133 and 154, respectively;
(n) heavy and light chain variable region sequences comprising SEQ ID NOs: 130 and 154, respectively;
(o) heavy and light chain variable region sequences comprising SEQ ID NOs: 127 and 154, respectively;
(p) heavy and light chain variable region sequences comprising SEQ ID NOs: 144 and 154, respectively;
(q) heavy and light chain variable region sequences comprising SEQ ID NOs: 146 and 154, respectively;
(r) heavy and light chain variable region sequences comprising SEQ ID NOs: 148 and 154, respectively;
(s) heavy and light chain variable region sequences comprising SEQ ID NOs: 150 and 154, respectively; or
(t) heavy and light chain variable region sequences comprising SEQ ID NOs: 218 and 154, respectively.

In some embodiments, the anti-LAP antibody has variable region sequences with potential liability sites, e.g., deamidation sites and/or isomerization sites) removed.

Accordingly, in some embodiments, the anti-LAP antibody comprises heavy and light chain variable region sequences of any of subparts (a)-(d) above, except wherein position 56 of the heavy chain variable region is an amino acid other than N (e.g., Q, S, H, L, D)) or is substituted with an amino acid residue other than N (e.g., Q, S, H, L, D).

In some embodiments, the anti-LAP antibody comprises heavy and light chain variable region sequences of any of subparts (e)-(l) above, except wherein position 54 of the heavy chain variable region is an amino acid other than N (e.g., Q, A, H, S) or is substituted with an amino acid residue other than N (e.g., Q, A, H, S).

In some embodiments, the anti-LAP antibody comprises heavy and light chain variable region sequences of any of subparts (e)-(l) above, except wherein position 102 of the heavy chain variable region is an amino acid other than D (e.g., A, E, G) or is substituted with an amino acid residue other than D (e.g., A, E, G).

In some embodiments, the anti-LAP antibody comprises heavy and light chain variable region sequences of any of subparts (e)-(l) above, except wherein position 54 of the heavy chain variable region is an amino acid other than N (e.g., Q, A, H, S) or is substituted with an amino acid residue other than N (e.g., Q, A, H, S), and wherein position 102 of the heavy chain variable region is an amino acid other than D (e.g., A, E, G) or is substituted with an amino acid residue other than D (e.g., A, E, G).

In some embodiments, the anti-LAP antibody comprises heavy and light chain variable region sequences of any of subparts (m)-(t) above, except wherein position 54 of the heavy chain variable region is an amino acid other than N (e.g., Q, G, A, S, H, L, D)) or is substituted with an amino acid residue other than N (e.g., Q, G, A, S, H, L, D).

In some embodiments, the anti-LAP antibody comprises a heavy chain and/or light chain variable region sequence that is at least 80%, 85%, 90%, 95%, 96%, 97%, 98%, or 99% identical to the heavy chain and/or light chain variable region sequences of any of subparts (a)-(t) above. In some embodiments, the heavy chain and/or light chain variable region sequences of any of subparts (a)-(t) above has 1, 2, 3, 4, 5, 1-2, 1-3, 1-4, or 1-5 amino acid substitutions (e.g., conservative amino acid substitutions). In some embodiments, the anti-LAP antibody does not have heavy and light chain variable region sequences which are identical to SEQ ID NOs: 22 and 23, respectively; 60 and 61, respectively; 116 and 117, respectively; 168 and 169, respectively; or 185 and 186, respectively. These anti-LAP antibodies can be tested for various properties that are clinically advantageous (e.g., binding to LAP-TGFβ1, inhibiting the activation of TGFβ1, binding to various cell (e.g., immune cell) populations, inhibiting tumor growth in vivo) using the assays and animal models described herein, for example, in the Examples.

In some embodiments, the anti-LAP antibody comprises the heavy chain variable region sequences of any of subparts (a)-(t) above, and a constant region, e.g., a human IgG constant region (e.g., IgG1, IgG2, IgG3, or IgG4, or variants thereof). In some embodiments, the constant region is a human IgG1 constant region comprising the amino acid sequence set forth in SEQ ID NO: 196. In some embodiments, the constant region is a variant human IgG4 constant region comprising the amino acid sequence set forth in SEQ ID NO: 197. In some embodiments, the heavy chain variable region sequences of any of subparts (a)-(t) above may be linked to a constant domain to form a heavy chain (e.g., a full length heavy chain). Similarly, the light chain variable region sequences of any of subparts (a)-(t) above may be linked to a constant region to form a light chain (e.g., a full length light chain). A full length heavy chain (with the exception of the C-terminal lysine (K) or with the exception of the C-terminal glycine and lysine (GK), which may be absent or removed) and full length light chain combine to form a full length antibody.

Accordingly, in some embodiments, provided herein are anti-LAP antibodies comprising (a) heavy chain CDR1-3 sequences comprising SEQ ID NOs: 225, 231, and 227, respectively, and light chain CDR1-3 sequences comprising SEQ ID NOs: 228, 229, and 230, respectively, (b) heavy chain CDR1-3 sequences comprising SEQ ID NOs: 225, 232, and 227, respectively, and light chain CDR1-3 sequences comprising SEQ ID NOs: 228, 229, and 230, respectively, or (c) heavy chain CDR1-3 sequences comprising SEQ ID NOs: 225, 233, and 227, respectively, and light chain CDR1-3 sequences comprising SEQ ID NOs: 228, 229, and 230, respectively.

In some embodiments, provided herein are antibodies comprising heavy and light chain variable region sequences comprising (a) SEQ ID NOs: 234 and 224, respectively, (b) SEQ ID NOs: 235 and 224, respectively, or (c) SEQ ID NOs: 236 and 224, respectively.

In some embodiments, provided herein are anti-LAP antibodies comprising heavy and light chain sequences comprising (a) SEQ ID NOs: 237 and 222, respectively, (b) SEQ ID NOs: 238 and 222, respectively, or (c) SEQ ID NOs: 239 and 222, respectively.

In another aspect, provided herein are isolated anti-LAP antibodies comprising:
(a) heavy and light chain sequences comprising SEQ ID NOs: 43 and 53, respectively;
(b) heavy and light chain sequences comprising SEQ ID NOs: 45 and 53, respectively;
(c) heavy and light chain sequences comprising SEQ ID NOs: 41 and 53, respectively;
(d) heavy and light chain sequences comprising SEQ ID NOs: 36 and 47, respectively;
(e) heavy and light chain sequences comprising SEQ ID NOs: 37 and 47, respectively;
(f) heavy and light chain sequences comprising SEQ ID NOs: 36 and 51, respectively;
(g) heavy and light chain sequences comprising SEQ ID NOs: 37 and 51, respectively;
(h) heavy and light chain sequences comprising SEQ ID NOs: 102 and 105, respectively;
(i) heavy and light chain sequences comprising SEQ ID NOs: 103 and 105, respectively;
(j) heavy and light chain sequences comprising SEQ ID NOs: 99 and 105, respectively;
(k) heavy and light chain sequences comprising SEQ ID NOs: 100 and 105, respectively;
(l) heavy and light chain sequences comprising SEQ ID NOs: 93 and 105, respectively;
(m) heavy and light chain sequences comprising SEQ ID NOs: 94 and 105, respectively;
(n) heavy and light chain sequences comprising SEQ ID NOs: 93 and 107, respectively;
(o) heavy and light chain sequences comprising SEQ ID NOs: 94 and 107, respectively;
(p) heavy and light chain sequences comprising SEQ ID NOs: 96 and 105, respectively;
(q) heavy and light chain sequences comprising SEQ ID NOs: 97 and 105, respectively;
(r) heavy and light chain sequences comprising SEQ ID NOs: 78 and 105, respectively;
(s) heavy and light chain sequences comprising SEQ ID NOs: 79 and 105, respectively;
(t) heavy and light chain sequences comprising SEQ ID NOs: 83 and 105, respectively;
(u) heavy and light chain sequences comprising SEQ ID NOs: 84 and 105, respectively;
(v) heavy and light chain sequences comprising SEQ ID NOs: 88 and 105, respectively;
(w) heavy and light chain sequences comprising SEQ ID NOs: 89 and 105, respectively;
(x) heavy and light chain sequences comprising SEQ ID NOs: 134 and 155, respectively;
(y) heavy and light chain sequences comprising SEQ ID NOs: 135 and 155, respectively;
(z) heavy and light chain sequences comprising SEQ ID NOs: 131 and 155, respectively;
(aa) heavy and light chain sequences comprising SEQ ID NOs: 132 and 155, respectively;
(ab) heavy and light chain sequences comprising SEQ ID NOs: 128 and 155, respectively;
(ac) heavy and light chain sequences comprising SEQ ID NOs: 129 and 155, respectively;
(ad) heavy and light chain sequences comprising SEQ ID NOs: 145 and 155, respectively;
(ae) heavy and light chain sequences comprising SEQ ID NOs: 147 and 155, respectively;
(af) heavy and light chain sequences comprising SEQ ID NOs: 149 and 155, respectively;
(ag) heavy and light chain sequences comprising SEQ ID NOs: 151 and 155, respectively;
(ah) heavy and light chain sequences comprising SEQ ID NOs: 219 and 155, respectively; or
(ai) heavy and light chain sequences comprising SEQ ID NOs: 220 and 155, respectively.

In some embodiments, the full length heavy chain lacks the C-terminal lysine residue (which may be absent or removed).

In some embodiments, the anti-LAP antibody has heavy and light chain sequences with potential liability sites, e.g., deamidation sites and/or isomerization sites) removed. Accordingly, in some embodiments, the anti-LAP antibody comprises heavy and light chain sequences of any of subparts (a)-(g) above, except wherein position 56 of the heavy chain is an amino acid other than N (e.g., Q, S, H, L, D) or is substituted with an amino acid residue other than N (e.g., Q, S, H, L, D).

In some embodiments, the anti-LAP antibody comprises heavy and light chain sequences of any of subparts (h)-(w) above, except wherein position 54 of the heavy chain is an amino acid other than N (e.g., Q, A, H, S) or is substituted with an amino acid residue other than N, H, or S (e.g., Q, A, H, S).

In some embodiments, the anti-LAP antibody comprises heavy and light chain sequences of any of subparts (h)-(w) above, except wherein position 102 of the heavy chain variable region is an amino acid other than D (e.g., A, E, G) or is substituted with an amino acid residue other than D (e.g., A, E, G).

In some embodiments, the anti-LAP antibody comprises heavy and light chain sequences of any of subparts (h)-(w) above, except wherein position 54 of the heavy chain is an amino acid other than N (e.g., Q, A, H, S) or is substituted with an amino acid residue other than N, H, or S (e.g., Q, A, H, S) and position 102 of the heavy chain variable region is an amino acid other than D (e.g., A, E, G) or is substituted with an amino acid residue other than D (e.g., A, E, G).

In some embodiments, the anti-LAP antibody comprises heavy and light chain sequences of any of subparts (x)-(ai) above, except wherein position 54 of the heavy chain variable region is an amino acid other than N (e.g., Q, G, A, S, H, L, D) or is substituted with an amino acid residue other than N (e.g., Q, G, A, S, H, L, D).

In some embodiments, the anti-LAP antibody comprises a heavy chain and/or light chain sequence that is at least 80%, 85%, 90%, 95%, 96%, 97%, 98%, 99%, 99.5%, or 99.7% identical to the heavy chain and/or light chain sequences of any of subparts (a)-(ai) above. In some embodiments, the heavy chain and/or light chain sequences of any of subparts (a)-(ai) above has 1, 2, 3, 4, 5, 1-2, 1-3, 1-4, or 1-5 amino acid substitutions (e.g., conservative amino acid substitutions). In some embodiments, the anti-LAP antibody does not have a heavy and/or light chain variable region sequence which is identical to SEQ ID NOs: 24 and 25, respectively; 62 and 63 respectively; or 118 and 119, respectively. These anti-LAP antibodies can be tested for various properties that are clinically advantageous (e.g., binding to LAP-TGFβ1, inhibiting the activation of TGFβ1, binding to various cell (e.g., immune cell) populations, inhibiting tumor growth in vivo) using the assays and animal models described herein, for example, in the Examples.

In some embodiments, an anti-LAP antibody or antigen binding fragment comprising VHCDR1-3 sequences of SEQ ID NOs: 110, 120, and 113, respectively, and VLCDR1-3 sequences of SEQ ID NOs: 113, 114, and 115, respectively, has one or more amino acid substitutions in the CDRs or variable regions. For example, in some embodiments, no more than 3 amino acids (i.e., 1, 2, or 3 amino acids) are substituted in the six heavy and light chain CDRs (collectively), or two heavy and light chain variable regions (collectively).

In some embodiments, an anti-LAP antibody or antigen binding fragment comprises a VHCDR1 which has 1, 2, 3, 4, 5, 6, 7, 8, 9, or 10 amino acid substitutions, for example, conservative amino acid substitutions, relative to GYTFT-SYWMH (SEQ ID NO: 110).

In some embodiments, an anti-LAP antibody or antigen binding fragment comprises a VHCDR2 which has 1, 2, 3, 4, 5, 6, 7, 8, 9, or 10 amino acid substitutions, for example, conservative amino acid substitutions, relative to RIDPQSGGIK (SEQ ID NO: 120). In some embodiments, the VHCDR2 comprises the sequence: $RX_1X_2X_3X_4XSX_6X_7X_8X_9$, wherein $X_1$-$X_9$ can be any amino acid. In some embodiments, only 1 position among $X_1$-$X_9$ is substituted relative to the amino acid sequence of SEQ ID NO: 120.

In some embodiments, an anti-LAP antibody or antigen binding fragment comprises a VHCDR3 comprising 1, 2, 3, 4, 5, 6, 7, 8, or 9 amino acid substitutions, for example, conservative amino acid substitutions, relative to WDYG-GYFDV (SEQ ID NO: 112). In some embodiments, the VHCDR3 comprises the sequence: $WX_1YGGYFX_2X_3$ (SEQ ID NO: 242), wherein $X_1$-$X_3$ can be any amino acid. In some embodiments, only 1 position among $X_1$-$X_3$ is substituted relative to the amino acid sequence of SEQ ID NO: 112.

In some embodiments, an anti-LAP antibody or antigen binding fragment comprises a VLCDR1 comprising 1, 2, 3, 4, 5, 6, 7, 8, 9, 10, or 11 amino acid substitutions, for example, conservative amino acid substitutions, relative to RASQDITNYLN (SEQ ID NO: 113). In some embodiments, the VLCDR1 may comprise the sequence: $RX_1X_2X_3DIX_4X_5YX_6X_7$, wherein $X_1$-$X_7$ is any amino acid. In some embodiments, only 1 position among $X_1$-$X_7$ is substituted relative to the amino acid sequence of SEQ ID NO: 113.

In some embodiments, an anti-LAP antibody or antigen binding fragment comprises a VLCDR2 comprising 1, 2, 3, 4, 5, 6, or 7 amino acid substitutions, for example, conservative amino acid substitutions, relative to YTSRLHS (SEQ ID NO: 114). In some embodiments, the VLCDR2 comprises the sequence: $YX_1X_2RX_3X_4X_5$, wherein $X_1$-$X_5$ is any amino acid. In some embodiments, only 1 position among $X_1$-$X_5$ is substituted relative to the amino acid sequence of SEQ ID NO: 114.

In some embodiments, an anti-LAP antibody or antigen binding fragment comprises a VLCDR3 comprising 1, 2, 3, 4, 5, 6, 7, 8, or 9 amino acid substitutions, for example, conservative amino acid substitutions, relative to QQGDTLPWT (SEQ ID NO: 115). In some embodiments, the VLCDR3 may comprise the sequence: $QQGDX_1LPWT$ (SEQ ID NO: 243), wherein $X_1$ is any amino acid.

Functional features of the anti-LAP antibodies or antigen binding fragment provided herein are described below in more detail.

In some embodiments, the anti-LAP antibody or antigen binding fragment described herein binds to LAP-TGFβ1 (e.g., human LAP-TGFβ1) in the absence of an anchor protein. For example, the anti-LAP antibody or antigen binding fragment described herein binds to recombinant human LAP-TGFβ1 in an assay that does not include an anchor protein.

In some embodiments, the anti-LAP antibody or antigen binding fragment described herein binds to LAP-TGFβ1 (e.g., soluble LAP-TGFβ1) with a $K_D$ of 100 nM or less, such as 90 nM or less, 80 nM or less, 70 nM or less, 60 nM or less, 50 nM or less, such as 40 nM or less, 30 nM or less, 20 nM or less, 10 nM or less, 5 nM or less, 3 nM or less, 1 nM or less, 0.9 nM or less, 0.8 nM or less, 0.7 nM or less, 0.6 nM or less, 0.5 nM or less, 0.4 nM or less, 0.3 nM or less, 0.2 nM or less, 0.1 nM or less, 10 nM to 0.1 nM, 5 nM to 0.1 nM, 3 nM to 0.1 nM, 1 nM to 0.1 nM, 0.8 nM to 0.1 nM, 0.5 nM to 0.1 nM, 10 nM to 0.5 nM, 10 nM to 0.8 nM, 10 nM to 1 nM, 1 nM to 0.5 nM, or 1 nM to 0.8 nM, as assessed by, e.g., bio-layer interferometry (e.g., as described in Example 1), or as determined by Octet or BIACore. In some embodiments, the anti-LAP antibody or antigen binding fragment described herein binds to LAP-TGFβ1 (e.g., human, cyno, rat and) with a $K_D$ in an Example herein. In various embodiments, the anti-LAP antibody or antigen binding fragment described herein binds to human LAP-TGFβ1, rat LAP-TGFβ1, cyno LAP-TGFβ1, and/or murine LAP-TGFβ1.

In some embodiments, the anti-LAP antibody or antigen binding fragment described herein described herein binds to LAP-TGFβ1 complexed with an anchor protein on immunosuppressive cells, but does not bind to the anchor protein. In some embodiments, the anchor protein is GARP or LRRC33.

In some embodiments, the anti-LAP antibody or antigen binding fragment described herein described herein selectively inhibits TGFβ1 activation on immunosuppressive cells without inhibiting TGFβ1 activation on extracellular matrix.

In some embodiments, the anti-LAP antibody or antigen binding fragment described herein does not bind to LAP complexed with LTBP1, LTBP3, and/or LTBP4.

In some embodiments, the anti-LAP antibody or antigen binding fragment described herein does not bind to LAP-TGFβ2 (e.g., human LAP-TGFβ2) and LAP-TGFβ3 (e.g., human LAP-TGFβ3), as assessed by, e.g., flow cytometry using cells that overexpress TGFβ2 or TGFβ3, or bio-layer interferometry with recombinant LAP-TGFβ2 or LAP-TGFβ3. For example, in some embodiments, the anti-LAP antibody or antigen binding fragment described herein binds to LAP-TGFβ2 or LAP-TGFβ3 with a signal or affinity that is not significantly above the signal seen with a control antibody (e.g., isotype control) or the signal seen in the absence of anti-LAP antibody (e.g., as described in Example 2).

In some embodiments, the anti-LAP antibody or antigen binding fragment described herein inhibits TGFβ1 activation, as assessed by, e.g., ELISA detection of free TGFβ1 in a culture of P3U1 cells overexpressing LAP-TGFβ1. In some embodiments, the anti-LAP antibody or antigen binding fragment described herein inhibits (or is determined to inhibit) TGFβ1 activation by about 50% or more, e.g., by about 60% or more, by about 70% or more, by about 80% or more, or by about 90% or more, as assessed by ELISA, e.g., ELISA detection of free TGFβ1 in a culture of P3U1 cells overexpressing LAP-TGFβ1 (e.g., as described in Example 4).

In some embodiments, the anti-LAP antibody or antigen binding fragment described herein binds to mouse and human LAP-TGFβ1, as assessed by, e.g., flow cytometry of activated immune cell populations.

In some embodiments, the anti-LAP antibody or antigen binding fragment described herein does not bind to free TGFβ1 (i.e., TGFβ1 without LAP), as assessed by, e.g., ELISA. In some embodiments, the anti-LAP antibody or antigen binding fragment described herein does not bind to empty LAP (i.e., LAP that is not complexed with TGFβ1), as assessed by, e.g., bio-layer interferometry. For example, in some embodiments, the anti-LAP antibody or antigen binding fragment described herein binds to free TGFβ1 or empty with a signal or affinity that is not significantly above the signal seen with a control antibody (e.g., isotype control) or the signal seen in the absence of anti-LAP antibody (e.g., as described in Example 2).

In some embodiments, the anti-LAP antibody or antigen binding fragment described herein binds to human LAP-TGFβ1 comprising K27C and Y75C mutations (SEQ ID NO: 12. In another embodiment, the anti-LAP antibody or antigen binding fragment described herein does not bind to (or are determined not to bind to) human LAP-TGFβ1 comprising a Y74T mutation (SEQ ID NO: 13). In another embodiment, the anti-LAP antibody or antigen binding fragment described herein binds to (or is determined to bind to) human LAP-TGFβ1 comprising K27C and Y75C mutations, but not to LAP-TGFβ1 comprising a Y74T mutation.

In some embodiments, the anti-LAP antibodies bind to all or a portion of residues 82-130 of human LAP-TGFβ1 (SEQ ID NO: 1).

In some embodiments, the anti-LAP antibodies bind within residues 82-130 of human LAP-TGFβ1 (SEQ ID NO: 1),In some embodiments, the anti-LAP antibody or antigen binding fragment binds to one or more regions on human LAP-TGFβ1 (SEQ ID NO: 1) comprising or consisting of amino acids 31-40, 274-280, and 340-343. In some embodiments, the anti-LAP antibody or antigen binding fragment binds to amino acids 31-40, 274-280, and 340-343 of human LAP-TGFβ1 (SEQ ID NO: 1). In some embodiments, the epitope is determined by cryo-EM.

In some embodiments, the anti-LAP antibody or antigen binding fragment binds to one or more regions on human an LAP-TGFβ1 (SEQ ID NO: 1) comprising or consisting of amino acids 31-38, 278-281, and 342-344. In some embodiments, the anti-LAP antibodies bind to amino acids 31-38, 278-281, and 342-344 of human LAP-TGFβ1 (SEQ ID NO: 1). In some embodiments, the epitope is determined by cryo-EM. In some embodiments, the anti-LAP antibody or antigen binding fragment binds to one or more regions on human an LAP-TGFβ1 (SEQ ID NO: 1) comprising or consisting of amino acids 35-43, 272-275, 280-283, and 340 (SEQ ID NO: 1). In some embodiments, the anti-LAP antibody or antigen binding fragment binds to amino acids 35-43, 272-275, 280-283, and 340 of human LAP-TGFβ1 (SEQ ID NO: 1). In some embodiments, the epitope is determined by cryo-EM.

As discussed above, the anti-LAP antibody or antigen binding fragment described herein binds to LAP-TGFβ1 on cells, such as immune cells, e.g., immunosuppressive cells. Immunosuppressive cells include, but are not limited to, suppressive T cells (e.g., regulatory T cells, activated T cells, suppressive CD8+ T cells), M1 macrophages, M2 macrophages, dendritic cells, regulatory B cells, granulocytic MDSCs, and/or monocytic MDSCs, as assessed, e.g., by flow cytometry. In some embodiments, the anti-LAP antibody or antigen binding fragment described herein binds to cells other than immune cells, such as tumor cells, fibroblasts (including cancer associated fibroblasts), mesenchymal stromal cells, mesenchymal stem cells, hemopoietic stem cells, non-myelinating Schwann cells, myofibroblasts, endothelial cells, platelets, megakaryocytes, pericytes, and/or hepatic stellate cells. In some embodiments, the anti-LAP antibody or antigen binding fragment described herein binds to LAP-TGFβ1 on both immune cells (e.g., immunosuppressive cells) and non-immune cells.

In some embodiments, the anti-LAP antibody or antigen binding fragment described herein binds to LAP-TGFβ1 on GARP-positive cells (e.g., GARP-positive immunosuppressive cells). In some embodiments, the anti-LAP antibody or antigen binding fragment described herein binds to (or are determined to bind to) LAP-TGFβ1 on GARP-negative cells (e.g., GARP-negative immunosuppressive cells). In some embodiments, the anti-LAP antibody or antigen binding fragment described herein binds to LAP-TGFβ1 on both GARP-positive and GARP-negative cells, as assessed, e.g., by flow cytometry.

In some embodiments, the anti-LAP antibody or antigen binding fragment described herein reduces the endogenous expression of CD73. In some embodiments, the anti-LAP antibody or antigen binding fragment described herein inhibits the increase of CD73 expression caused by a treatment, e.g., radiation. CD73 expression can be determined using standard methods known in the art (e.g., as described in Example 16).

In some embodiments, the anti-LAP antibody or antigen binding fragment described herein binds to LAP-TGFβ1 expressed on cells (e.g., human or mouse LAP-TGFβ1 expressed on, e.g., P3U1 cells) with an EC50 of 1000 ng/ml or less, 500 ng/ml or less, 200 ng/ml or less, 150 ng/ml or less, 100 ng/ml or less, 50 ng/ml or less, 25 ng/ml or less, 10 ng/ml or less, 5 ng/ml or less, 2 ng/ml or less, 1 ng/ml to 200 ng/ml, 1 ng/ml to 150 ng/ml, 1 ng/ml to 100 ng/ml, 1 ng/ml to 50 ng/ml, 1 ng/ml to 25 ng/ml, 1 ng/ml to 10 ng/ml, or 1 ng/ml to 5 ng/ml, as measured by flow cytometry (e.g., as described in Example 2).

The binding of the anti-LAP antibody or antigen binding fragment to LAP-TGFβ1 may also be defined using quantitative immunofluorescence by flow cytometry, which allows the number of antibody molecules bound per cell to be quantified. Accordingly, in some embodiments, the number of anti-LAP antibodies bound to a cell that also expresses GARP may be equal to the number of anti-GARP antibodies bound to that cell, or may be at least 80%, at least 50%, at least 20%, at least 10%, at least 5%, at least 1%, or at least 0.1% of the number of anti-GARP antibodies bound to that cell. In some embodiments, the number of LAP-TGFβ1 molecules expressed per cell may be quantified using quantitative immunofluorescence using an anti-LAP antibody of a group that detects the majority of LAP molecules; examples of such antibodies include 2F8, 2C9, 16B4 and the anti-LAP monoclonal antibody #27232 (R&D Systems). In some embodiments, the number of anti-LAP antibodies bound to the cell may be equal to the number of LAP molecules on the cell, or may be at least 80%, at least 50%, at least 20%, at least 10%, at least 5%, at least 1% or at least 0.1% of the number of LAP molecules expressed on that cell.

In some embodiments, the anti-LAP antibody or antigen binding fragment described herein inhibits TGFβ1 activation by, for example, 10% or more, for example, 20% or more, 30% or more, 40% or more, 50% or more, 60% or more, 70% or more, 80% or more, 90% or more, or 95% or more, relative to a control (e.g., a control antibody), as measured by ELISA (e.g., as described in Example 4).

Preferably, the anti-LAP antibody or antigen binding fragment described herein binds to soluble LAP-TGFβ1 with high affinity, for example, with a $K_D$ of $10^{-7}$ M or less, $10^{-8}$ M or less, 10 M or less, $10^{-10}$ M or less, $10^{-11}$ M or less, $10^{-12}$ M or less, $10^{-12}$ M to $10^{-7}$ M, $10^{-11}$ M to $10^{-7}$ M, $10^{-10}$ M to $10^{-7}$ M, or $10^{-9}$ M to $10^{-7}$ M, as measured by bio-layer interferometry (e.g., as described in Example 1).

In some embodiments, the anti-LAP antibody or antigen binding fragment described herein does not bind to LAP-TGFβ1 in the extracellular matrix. For example, the anti-LAP antibody or antigen binding fragment described herein do not bind to LAP-TGFβ1 in the extracellular matrix, as assessed by ELISA, wherein the O.D. signal for the antibody or antigen binding fragment binding is not significantly above the signal seen in the absence of the anti-LAP antibody or antigen binding fragment described herein or the signal seen with a control antibody (e.g., isotype control) (e.g., as described in Example 5).

In some embodiments, the anti-LAP antibody or antigen binding fragment described herein do not inhibit TGFβ activation in the ECM, as assessed by, e.g., ELISA detection of free TGFβ1 in an assay combining a source of LAP-TGFβ1 in the ECM (e.g., as described in Example 5) with MMP-2, MMP-9, thrombospondin or cells expressing aVβ6 or aVβ8 integrins.

In some embodiments, the anti-LAP antibody or antigen binding fragment described herein binds to LAP-TGFβ1 on platelets. For example, in some embodiments, at least 5%, at least 10%, at least 20% or at least 50% of platelets can be detected by binding of the anti-LAP antibody (e.g. display a signal above that seen with an isotype control antibody) by flow cytometry (e.g., as described in Example 6). In some embodiments, the anti-LAP antibody or antigen binding fragment described herein binds to platelets but do not cause platelet aggregation or platelet degranulation.

In some embodiments, the anti-LAP antibody or antigen binding fragment described herein binds to immune cells, e.g., suppressive T cells (e.g., regulatory T cells), M2 macrophages, monocytic MDSCs, CD11b-positive cells, and/or dendritic cells. For example, in some embodiments, at least 0.5%, at least 1%, at least 2%, at least 5%, at least 7%, at least 10%, at least 20%, or at least 50% of these cell types can be detected by binding of the anti-LAP antibody (e.g. display a signal above that seen with an isotype control antibody) by flow cytometry (e.g., as described in Example 7). In some embodiments, the anti-LAP antibody or antigen binding fragment described herein is considered to bind to these cell types if they bind ≥2 standard deviations above isotype control.

In some embodiments, the anti-LAP antibody or antigen binding fragment described herein binds to GARP-negative leukocytes. For example, in some embodiments, at least 0.5%, at least 1%, at least 2%, at least 5%, at least 7%, at least 10%, at least 20% or at least 50% of GARP-negative leukocytes can be detected by binding of the anti-LAP antibody (e.g. display a signal above that seen with an isotype control antibody) by flow cytometry (e.g., as described in Example 7).

An antibody or antigen binding fragment that exhibits one or more of the functional properties described above (e.g., biochemical, immunochemical, cellular, physiological or other biological activities), as determined using methods known to the art and described herein, will be understood to relate to a statistically significant difference in the particular activity relative to that seen in the absence of the antibody (e.g., or when a control antibody of irrelevant specificity is present). Preferably, the anti-LAP antibody-induced increases in a measured parameter effects a statistically significant increase by at least 10% of the measured parameter, more preferably by at least 20%, 30%, 40%, 50%, 60%, 70%, 80%, 90%, 95%, or 100% (i.e., 2 fold), 3 fold, 5 fold or 10 fold. Conversely, anti-LAP antibody-induced decreases in a measured parameter (e.g., TGFβ1 activation) effects a statistically significant decrease by at least 10%, 20%, 30%, 40%, 50%, 60%, 70%, 80%, 90%, 95%, 97%, 98%, 99%, or 100%.

Also provided herein are anti-LAP antibodies that bind to the same epitope on human LAP-TGFβ1 as any of the anti-LAP antibodies described herein. These antibodies have the ability to cross-compete for binding to human LAP-TGFβ1 with any of the anti-LAP antibodies described herein. In some embodiments, the anti-LAP antibodies bind one or more amino acids within residues 82-130 of human LAP-TGFβ1 (SEQ ID NO: 1).

Antibodies disclosed herein include all known forms of antibodies and other protein scaffolds with antibody-like properties. For example, the antibody can be a human antibody, a humanized antibody, a bispecific antibody, an immunoconjugate, a chimeric antibody, or a protein scaffold with antibody-like properties, such as fibronectin or ankyrin repeats.

In some embodiments, the antibody is a bispecific antibody comprising a first and second binding region, wherein the first binding region comprises the binding specificity (e.g., antigen-binding region) of an anti-LAP antibody described herein, and a second binding region that does not bind to LAP. In some embodiments, the second binding region binds to a protein that is not expressed on platelets.

The antibody also can be a Fab, F(ab')2, scFv, AFFIBODY, avimer, nanobody, single chain antibody, or a domain antibody. The antibody also can have any isotype, including any of the following isotypes: IgG1, IgG2, IgG3, IgG4, IgM, IgA1, IgA2, IgAsec, IgD, and IgE. Full-length antibodies can be prepared from $V_H$ and $V_L$ sequences using standard recombinant DNA techniques and nucleic acid encoding the desired constant region sequences to be operatively linked to the variable region sequences.

In certain embodiments, the antibodies described herein may have effector function or may have reduced or no effector function. In certain embodiments, anti-LAP antibodies comprise an effector-less or mostly effector-less Fc, e.g., IgG2 or IgG4. Generally, variable regions described herein may be linked to an Fc comprising one or more modification, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or be modified to alter its glycosylation, to alter one or more functional properties of the antibody. Each of these embodiments is described in further detail below. The numbering of residues in the Fc region is that of the EU index of Kabat.

In some embodiments, the Fc region is a variant Fc region, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity. For example, modifications can be made in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for Clq and/or (d) has increased or decreased affinity for a Fc receptor relative to the parent Fc. Such Fc region variants will generally comprise at least one amino acid modification in the Fc region. Combining amino acid modifications is thought to be particularly desirable. For example, the variant Fc region may include two, three, four, five, etc. substitutions therein, e.g. of the specific Fc region positions identified herein.

A variant Fc region may also comprise a sequence alteration wherein amino acids involved in disulfide bond formation are removed or replaced with other amino acids. Such removal may avoid reaction with other cysteine-containing proteins present in the host cell used to produce the antibodies described herein. Even when cysteine residues are removed, single chain Fc domains can still form a dimeric Fc domain that is held together non-covalently. In other embodiments, the Fc region may be modified to make it more compatible with a selected host cell. For example, one may remove the PA sequence near the N-terminus of a typical native Fc region, which may be recognized by a digestive enzyme in *E. coli* such as proline iminopeptidase. In other embodiments, one or more glycosylation sites within the Fc domain may be removed. Residues that are typically glycosylated (e.g., asparagine) may confer cytolytic response. Such residues may be deleted or substituted with unglycosylated residues (e.g., alanine). In other embodiments, sites involved in interaction with complement, such as the Clq binding site, may be removed from the Fc region. For example, one may delete or substitute the EKK sequence of human IgG1. In certain embodiments, sites that affect binding to Fc receptors may be removed, preferably sites other than salvage receptor binding sites. In other embodiments, an Fc region may be modified to remove an ADCC site. ADCC sites are known in the art; see, for example, Molec. Immunol. 29 (5): 633-9 (1992) with regard to ADCC sites in IgG1. Specific examples of variant Fc domains are disclosed for example, in PCT Publication numbers WO 97/34631 and WO 96/32478.

In one embodiment, the hinge region of Fc is modified such that the number of cysteine residues in the hinge region is altered, e.g., increased or decreased. This approach is described further in U.S. Pat. No. 5,677,425 by Bodmer et al. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al. In another example, one or more amino acids selected from amino acid residues 329, 331 and 322 can be replaced with a different amino acid residue such that the antibody has altered Clq binding and/or reduced or abolished complement dependent cytotoxicity (CDC). This approach is described in further detail in U.S. Pat. No. 6,194,551 by Idusogie et al. In another example, one or more amino acid residues within amino acid positions 231 and 239 are altered to thereby alter the ability of the antibody to fix complement. This approach is described further in PCT Publication number WO 94/29351 by Bodmer et al.

In yet another example, the Fc region may be modified to increase antibody dependent cellular cytotoxicity (ADCC) and/or to increase the affinity for an Fcγ receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F/324T. Other modifications for enhancing FcγR and complement interactions include but are not limited to substitutions 298A, 333A, 334A, 326A, 2471, 339D, 339Q, 280H, 290S, 298D, 298V, 243L, 292P, 300L, 396L, 3051, and 396L. These and other modifications are reviewed in Strohl, 2009, Current Opinion in Biotechnology 20:685-691.

Fc modifications that increase binding to an Fcγ receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 3338, 340, 360, 373, 376, 379, 382, 388, 389, 398, 414, 416, 419, 430, 434, 435, 437, 438 or 439 of the Fc region, wherein the numbering of the residues in the Fc region is that of the EU index as in Kabat (PCT Patent Publication number WO00/42072).

Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, and 328, wherein numbering is according to the EU index. Exemplary substitutions include but are not limited to 234G, 235G, 236R, 237K, 267R, 269R, 325L, and 328R, wherein numbering is according to the EU index. An Fc variant may comprise 236R/328R. Other modifications for reducing FcγR and complement interactions include substitutions 297A, 234A, 235A, 237A, 318A, 228P, 236E, 268Q, 309L, 330S, 331 S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691. Optionally, the Fc region may comprise a non-naturally occurring amino acid residue at additional and/or alternative positions known to one skilled in the art (see, e.g., U.S. Pat. Nos. 5,624,821; 6,277,375; 6,737,056; 6,194,551; 7,317,091; 8,101,720; PCT Patent Publication numbers WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/020114).

Fc variants that enhance affinity for an inhibitory receptor FcγRllb may also be used. Such variants may provide an Fc fusion protein with immunomodulatory activities related to FcγRllb+ cells, including for example B cells and monocytes. In one embodiment, the Fc variants provide selectively enhanced affinity to FcγRllb relative to one or more activating receptors. Modifications for altering binding to FcγRllb include one or more modifications at a position selected from the group consisting of 234, 235, 236, 237, 239, 266, 267, 268, 325, 326, 327, 328, and 332, according to the EU index. Exemplary substitutions for enhancing FcγRllb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcγRllb include 235Y/267E, 236D/267E, 239D/268D, 239D/267E, 267E/268D, 267E/268E, and 267E/328F.

In certain embodiments, the antibody is modified to increase its biological half-life. Various approaches are possible. For example, this may be done by increasing the binding affinity of the Fc region for FcRn. For example, one or more of more of following residues can be mutated: 252, 254, 256, 433, 435, 436, as described in U.S. Pat. No. 6,277,375. Specific exemplary substitutions include one or more of the following: T252L, T254S, and/or T256F. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 286A, 305A, 307A, 307Q, 311A, 312A, 376A, 378Q, 380A, 382A, 434A (Shields et al, Journal of Biological Chemistry, 2001, 276 (9):6591-6604), 252F, 252T, 252Y, 252W, 254T, 256S, 256R, 256Q, 256E, 256D, 256T, 309P, 311S, 433R, 433S, 4331, 433P, 433Q, 434H, 434F, 434Y, 252Y/254T/256E, 433K/434F/436H, 308T/309P/311S (Dall Acqua et al. Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671. In certain embodiments, hybrid IgG isotypes with particular biological characteristics may be used. For example, an IgG1/IgG3 hybrid variant may be constructed by substituting IgG1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 4221, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed that comprises one or more substitutions, e.g., one or more of the following amino acid substitutions: 233E, 234L, 235L, -236G (referring to an insertion of a glycine at position 236), and 327A.

Moreover, the binding sites on human IgG1 for FcγR1, FcγRII, FcγRIII and FcRn have been mapped and variants with improved binding have been described (see Shields, R. L. et al. (2001) J. Biol. Chem. 276:6591-6604). Specific mutations at positions 256, 290, 298, 333, 334 and 339 were shown to improve binding to FcγRIII Additionally, the following combination mutants were shown to improve FcγRIII binding: T256A/S298A, S298A/E333A, S298A/K224A and S298A/E333A/K334A, which has been shown to exhibit enhanced FcγRIIIa binding and ADCC activity (Shields et al., 2001). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006). In addition, IgG1 mutants containing L235V, F243L, R292P, Y300L and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al., 2007; Nordstrom et al., 2011). Other Fc mutants that may be used include: S298A/E333A/L334A, S239D/I332E, S239D/I332E/A330L, L235V/F243L/R292P/Y300L/P396L, and M428L/N434S.

When using an IgG4 constant domain, it is usually preferable to include the substitution S228P, which mimics the hinge sequence in IgG1 and thereby stabilizes IgG4 molecules.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al. Glycosylation of the constant region on N297 may be prevented by mutating the N297 residue to another residue, e.g., N297A, and/or by mutating an adjacent amino acid, e.g., 298 to thereby reduce glycosylation on N297.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies described herein to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication number WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication number WO 99/54342 by Umana et al. describes cell lines engineered to express glycoprotein-modifying glycosyl transferases (e.g., beta(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17:176-180).

Another modification of the antibodies described herein is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, European patent number EP 0 154 316 by Nishimura et al. and European patent number EP 0 401 384 by Ishikawa et al.

The affinities and binding properties of an Fc region for its ligand may be determined by a variety of in vitro assay methods (biochemical or immunological based assays) known in the art including, but not limited to, equilibrium methods (e.g., enzyme-linked immunosorbent assay (ELISA), or radioimmunoassay (RIA)), or kinetics (e.g., BIACORE analysis), and other methods such as indirect binding assays, competitive inhibition assays, fluorescence resonance energy transfer (FRET), gel electrophoresis, and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

II. Antibodies which Bind to Same Epitope as or Cross-Compete with Anti-LAP Antibodies Anti-LAP antibodies which bind to the same or similar epitopes to the antibodies disclosed herein (and thus also cross-compete with the antibodies disclosed herein) may be raised using immunization protocols. The resulting antibodies can be screened for high affinity binding to human LAP-TGFβ1. Selected antibodies can then be studied, e.g., in yeast display assay in which sequence variants of LAP-TGFβ1 are presented on the surface of yeast cells, or by hydrogen-deuterium exchange experiments, to determine the precise epitope bound by the antibody.

Antibodies which bind to the same epitope as the anti-LAP antibodies described herein can also be generated using chimeric constructs, e.g., chicken-human chimeras of LAP-TGFβ1. Since human and chicken sequences can be combined to yield a LAP-TGFβ1 protein that folds correctly (as described in Example 2), the method can be used to generate immunogens to specific epitopes of interest on LAP-TGFβ1. With this strategy, the majority of the sequence would be taken from chicken LAP-TGFβ1, with small sections of human LAP-TGFβ1 inserted in regions containing the desired epitope. Exemplary epitopes on LAP-TGFβ1 that can be targeted using this strategy include, for example, the lower arm of LAP-TGFβ1, the latency loop of LAP-TGFβ1, or an epitope comprising amino acids 82-130 of human LAP-TGFβ1. Exemplary chicken-human chimera constructs are described in Example 3. This chimeric protein could be used to immunize chickens to yield monoclonal antibodies. Since the chicken LAP-TGFβ1 would be recognized as self, the immune response will be focused on the human sequence. Antibodies generated using this approach can be tested for various functions/properties (e.g., binding to LAP-TGFβ1, inhibiting TGFβ1 activation, binding to ECM, binding to cells such as immunosuppressive cells) using standard methods known in the art, e.g., the methods described herein.

The epitope to which an antibody binds can be determined using art-recognized methods. An anti-LAP antibody is considered to bind to the same epitope as a reference anti-LAP antibody if it, e.g., contacts one or more of the same residues on human LAP-TGFβ1 as the reference antibody; contacts one or more of the same residues within at least one region of human LAP-TGFβ1 as the reference antibody; contacts a majority of residues within at least one region of human LAP-TGFβ1 as the reference antibody; contacts a majority of the same residues within each region of human LAP-TGFβ1 as the reference antibody; contacts a majority of the same residues along the entire length of human LAP-TGFβ1 as the reference antibody; contacts all of the same distinct regions of human LAP-TGFβ1 as the reference antibody; contacts all of the same residues at any one region on human LAP-TGFβ1 as the reference antibody; or contacts all of the same residues at all of the same regions of human LAP-TGFβ1 as the reference antibody.

Techniques for determining antibodies that bind to the "same epitope on human LAP-TGFβ1" with the anti-LAP antibodies described herein include x-ray analyses of crystals of antigen:antibody complexes, which provides atomic resolution of the epitope. Other methods monitor the binding of the antibody to antigen fragments or mutated variations of the antigen where loss of binding due to an amino acid modification within the antigen sequence indicates the epitope component. Methods may also rely on the ability of an antibody of interest to affinity isolate specific short peptides (either in native three-dimensional form or in denatured form) from combinatorial phage display peptide libraries or from a protease digest of the target protein. The peptides are then regarded as leads for the definition of the epitope corresponding to the antibody used to screen the peptide library. For epitope mapping, computational algorithms have also been developed that have been shown to map conformational discontinuous epitopes.

The epitope or region comprising the epitope can also be identified by screening for binding to a series of overlapping peptides spanning human LAP-TGFβ1. Alternatively, the method of Jespers et al. (1994) Biotechnology 12:899 may be used to guide the selection of antibodies having the same epitope and therefore similar properties to the anti-LAP antibodies described herein. Using phage display, first, the heavy chain of the anti-LAP antibody is paired with a repertoire of (e.g., human) light chains to select a LAP-binding antibody, and then the new light chain is paired with a repertoire of (e.g., human) heavy chains to select a (e.g., human) LAP-binding antibody having the same epitope or epitope region as an anti-LAP antibody described herein. Alternatively, variants of an antibody described herein can be obtained by mutagenesis of cDNA sequences encoding the heavy and light chains of the antibody.

Alanine scanning mutagenesis, as described by Cunningham & Wells (1989) Science 244: 1081, or some other form of point mutagenesis of amino acid residues in LAP-TGFβ1 may also be used to determine the functional epitope for an anti-LAP antibody.

The epitope or epitope region (an "epitope region" is a region comprising the epitope or overlapping with the epitope) bound by a specific antibody may also be determined by assessing binding of the antibody to peptides comprising LAP-TGFβ1 fragments. A series of overlapping peptides encompassing the LAP-TGFβ1 sequence may be synthesized and screened for binding, e.g. in a direct ELISA, a competitive ELISA (where the peptide is assessed for its ability to prevent binding of an antibody to LAP-TGFβ1 bound to a well of a microtiter plate), or on a chip. Such peptide screening methods may not be capable of detecting some discontinuous functional epitopes.

An epitope may also be identified by MS-based protein footprinting, such as HDX-MS and Fast Photochemical Oxidation of Proteins (FPOP), structural methods such as X-ray crystal structure determination, molecular modeling, and nuclear magnetic resonance spectroscopy.

Single particle cryo electron microscopy (SP-Cryo-EM) can also be used to identify the epitope to which an antibody binds. SP-Cryo-EM is a technique for macromolecular structure analysis which uses a high intensity electron beam to image biological specimens in their native environment at cryogenic temperature. In recent years, SP-cryo-EM has emerged as a complementary technique to crystallography and NMR for determining near-atomic level structures suitable for application in drug discovery (Renaud et al. *Nat Rev Drug Discov* 2018; 17:471-92; Scapin et al. *Cell Chem Biol* 2018; 25:1318-25; Ceska et al. *Biochemical Society Transactions* 2019: p. BST20180267). In addition to high resolution information, SP-Cryo-EM has the further advantage of allowing access to larger and more complex biological systems, with the possibility of characterizing multiple conformational or compositional solution states from the same sample, providing insights into more biologically relevant states of the macromolecule. For imaging, a small volume of sample (e.g., 3 µl aliquot) is applied onto a grid and flash-frozen in a liquid ethane bath. The frozen grid is then loaded into the microscope and hundreds to thousands of images of different areas of the grids are collected. These images contain two-dimensional projections of the biological macromolecule (particles): using mathematical tools and GPU powered algorithms, the particles are identified, extracted, and classified; in the subsequent step, the different classes are used to compute one or more 3D reconstructions, corresponding to different conformations, oligomerization or binding states if they coexist in the same sample. The individual reconstructions can then be refined to high resolution.

III. Nucleic Acid Molecules

Also provided herein are nucleic acid molecules that encode the anti-LAP antibodies or antigen binding fragments described herein. The nucleic acids may be present in whole cells, in a cell lysate, or in a partially purified or substantially pure form. A nucleic acid described herein can be, for example, DNA or RNA and may or may not contain intronic sequences. In certain embodiments, the nucleic acid is a cDNA molecule. The nucleic acids described herein can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

In some embodiments, provided herein are nucleic acid molecules that encode the VH and/or VL sequences, or heavy and/or light chain sequences, of any of the anti-LAP antibodies or antigen binding fragments described herein. Host cells comprising the nucleotide sequences (e.g., nucleic acid molecules) described herein are encompassed herein. Once DNA fragments encoding VH and VL segments are obtained, these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (hinge, CH1, CH2 and/or CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region.

Also provided herein are nucleic acid molecules with conservative substitutions that do not alter the resulting amino acid sequence upon translation of the nucleic acid molecule.

IV. Methods of Production

Monoclonal antibodies can be prepared using a wide variety of techniques known in the art including the use of hybridoma, recombinant, and phage display technologies, or a combination thereof.

Various methods for making monoclonal antibodies described herein are available in the art. For example, the monoclonal antibodies can be made using the hybridoma method first described by Kohler et al., Nature, 256:495 (1975), or any later developments thereof, or by recombinant DNA methods (U.S. Pat. No. 4,816,567). For example, monoclonal antibodies can be produced using hybridoma techniques including those known in the art and taught, for example, in Harlow et al, Antibodies: A Laboratory Manual, (Cold Spring Harbor Laboratory Press, 2nd ed., 1988); Hammer-ling, et al., in: Monoclonal Antibodies and T-Cell Hybridomas 563-681 (Elsevier, N.Y., 1981) (said references incorporated by reference in their entireties). Methods for producing and screening for specific antibodies using hybridoma technology are routine and well known in the art. In another example, antibodies useful in the methods and compositions described herein can also be generated using various phage display methods known in the art, such as isolation from antibody phage libraries generated using the techniques described in McCafferty et al., Nature, 348:552-554 (1990). Clackson et al., Nature, 352:624-628 (1991) and Marks et al., J. Mol. Biol, 222:581-597 (1991) describe the isolation of murine and human antibodies, respectively, using phage libraries. Subsequent publications describe the production of high affinity (e.g., nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

Human antibodies can be made by a variety of methods known in the art, including phage display methods described above using antibody libraries derived from human immunoglobulin sequences. See also, U.S. Pat. Nos. 4,444,887 and 4,716,111; and PCT publication numbers WO 98/46645, WO 98/50433, WO 98/24893, WO 98/16654, WO 96/34096, WO 96/33735, and WO 91/10741, the contents of which are herein incorporated by reference in their entireties. Human antibodies can also be produced using transgenic mice which express human immunoglobulin genes, and upon immunization are capable of producing a full repertoire of human antibodies in the absence of endogenous immunoglobulin production. For an overview of this technology for producing human antibodies, see, Lonberg and Huszar, 1995, Int. Rev. Immunol. 13:65-93. Phage display technology (McCafferty et al., Nature 348:552-553 (1990)) also can be used to produce human antibodies and antibody fragments in vitro, from immunoglobulin variable (V) domain gene repertoires from unimmunized donors. Human antibodies can also be generated by in vitro activated B cells (see U.S. Pat. Nos. 5,567,610 and 5,229,275, the contents of which are herein incorporated by reference in their entireties). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., 1994, Bio/technology 12:899-903).

Chimeric antibodies can be prepared based on the sequence of a murine monoclonal antibody. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.).

Humanized forms of anti-LAP antibodies (e.g., humanized forms of mouse anti-LAP antibodies) are chimeric antibodies which contain minimal sequence derived from non-human immunoglobulin. Humanized antibodies are typically human immunoglobulins (recipient antibody) in which residues from a CDR or hypervariable region of the recipient are replaced by residues from a CDR or hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Humanized antibodies can comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin consensus sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

The framework and CDR regions of a humanized antibody need not correspond precisely to the parental sequences, e.g., the donor antibody CDR or the consensus framework can be mutagenized by substitution, insertion and/or deletion of at least one amino acid residue so that the CDR or framework residue at that site does not correspond exactly to either the donor antibody or the consensus framework. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see e.g., Winnaker, From Genes to Clones (Veriagsgesellschaft, Weinheim, Germany 1987). In a family of immunoglobulins, each position in the consensus sequence is occupied by the amino acid occurring most frequently at that position in the family. Where two amino acids occur equally frequently, either can be included in the consensus sequence. As used herein, "Vernier zone" refers to a subset of framework residues that may adjust CDR structure and fine-tune the fit to antigen as described by Foote and Winter (1992, J. Mol. Biol. 224:487-499, which is incorporated herein by reference). Vernier zone residues form a layer underlying the CDRs and can impact on the structure of CDRs and the affinity of the antibody. Human immunoglobulin (Ig) sequences that can be used as a recipient are well known in the art.

Framework residues in the human framework regions can be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, including, but not limited to, those described in Jones et al., Nature 321:522 (1986); Verhoeyen et al., Science 239: 1534 (1988), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), Padlan, Molecular Immunology 28(4/5):489-498 (1991); Studnicka et al., Protein Engineering 7(6):805-814 (1994); Roguska. et al., PNAS 91:969-973 (1994); PCT publication number WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766,886, 5,714,352, 6,204,023, 6,180,370, 5,693,762, 5,530, 101, 5,585,089, 5,225,539; 4,816,567, each entirely incorporated herein by reference.

The anti-LAP antibodies generated using the methods described above can be tested for desired functions, such as particular binding specificities, binding affinities, targeted cell populations, using methods known in the art and described in the Examples, for example, art-recognized protein-protein binding assays, biochemical screening assays, immunoassays, and cell-based assays. An aspect of the invention provides molecules that may be used to screen for an antibody or antigen binding fragment that binds LAP, a complex comprising LAP, and/or a complex comprising LAP-TGFβ1. For example, the molecules in Table 4 (i.e., molecules having the amino acid sequence of any of SEQ ID NO: 1, and 198-210) are used to screen or determine binding of at least one binding protein. In various embodiments, the at least one molecule in Table 4 (i.e., a molecule having the amino acid sequence of any of SEQ ID NO: 1, and 198-210) and Table 6 (i.e., a molecule having the amino acid sequence of any of SEQ ID NOs: 211-213) are used to screen or determine binding of at least one antibody or antigen binding fragment.

Exemplary assays include, but are not limited to, immunoprecipitation or by an in vitro binding assay, such as radioimmunoassay (RIA), FACS, enzyme-linked immunoabsorbent assay (ELISA), bio-layer interferometry (e.g., ForteBio assay), and Scatchard analysis.

Antibody Engineering

Further included are embodiments in which the anti-LAP antibodies or antigen-binding fragments thereof are engineered antibodies to include modifications to framework residues within the variable domains of the parental monoclonal antibody, e.g., to improve the properties of the antibody or fragment. Typically, such framework modifications are made to decrease the immunogenicity of the antibody or fragment. This is usually accomplished by replacing non-CDR residues in the variable domains (i.e., framework residues) in a parental (e.g., rodent) antibody or fragment with analogous residues from the immune repertoire of the species in which the antibody is to be used, e.g., human residues in the case of human therapeutics. Such an antibody or fragment is referred to as a "humanized" antibody or fragment. In some cases it is desirable to increase the affinity, or alter the specificity of an engineered (e.g., humanized) antibody. One approach is to "backmutate" one or more framework residues to the corresponding germline sequence. More specifically, an antibody or fragment that has undergone somatic mutation can contain framework residues that differ from the germline sequence from which the antibody is derived. Such residues can be identified by comparing the antibody or fragment framework sequences to the germline sequences from which the antibody or fragment is derived. Another approach is to revert to the original parental (e.g., rodent) residue at one or more positions of the engineered (e.g. humanized) antibody, e.g. to restore binding affinity that may have been lost in the process of replacing the framework residues. (See, e.g., U.S. Pat. Nos. 5,693,762, 5,585,089 and 5,530,101.)

In certain embodiments, the anti-LAP antibodies and antigen-binding fragments thereof are engineered (e.g., humanized) to include modifications in the framework and/or CDRs to improve their properties. Such engineered changes can be based on molecular modeling. A molecular model for the variable region for the parental (non-human) antibody sequence can be constructed to understand the structural features of the antibody and used to identify potential regions on the antibody that can interact with the antigen. Conventional CDRs are based on alignment of immunoglobulin sequences and identifying variable regions. Kabat et al., (1991) Sequences of Proteins of Immunological Interest, Kabat, et al.; National Institutes of Health, Bethesda, Md.; 5th ed.; NIH Publ. No. 91-3242; Kabat (1978) Adv. Prot. Chem. 32:1-75; Kabat, et al., (1977) J. Biol. Chem. 252:6609-6616. Chothia and coworkers carefully examined conformations of the loops in crystal structures of antibodies and proposed hypervariable loops. Chothia, et al., (1987) J Mol. Biol. 196:901-917 or Chothia, et al., (1989) Nature 342:878-883. There are variations between regions classified as "CDRs" and "hypervariable loops". Later studies (Raghunathan et al., (2012) J. Mol Recog. 25, 3, 103-113) analyzed several antibody—antigen crystal complexes and observed that the antigen binding regions in antibodies do not necessarily conform strictly to the "CDR" residues or "hypervariable" loops. The molecular model for the variable region of the non-human antibody can be used to guide the selection of regions that can potentially bind to the antigen. In practice, the potential antigen binding regions based on model differ from the conventional "CDR"s or "hyper variable" loops. Commercial scientific software such as MOE (Chemical Computing Group) can be used for molecular modeling. Human frameworks can be selected based on best matches with the non-human sequence both in the frameworks and in the CDRs. For FR4 (framework 4) in VH, VJ regions for the human germlines are compared with the corresponding non-human region. In the case of FR4 (framework 4) in VL, J-kappa and J-Lambda regions of human germline sequences are compared with the corresponding non-human region. Once suitable human frameworks are identified, the CDRs are grafted into the selected human frameworks. In some cases certain residues in the VL-VH interface can be retained as in the non-human (parental) sequence. Molecular models can also be used for identifying residues that can potentially alter the CDR conformations and hence binding to antigen. In some cases, these residues are retained as in the non-human (parental) sequence. Molecular models can also be used to identify solvent exposed amino acids that can result in unwanted effects such as glycosylation, deamidation and oxidation. Developability filters can be introduced early on in the design stage to eliminate/minimize these potential problems.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Pat. No. 7,125,689.

In particular embodiments, it will be desirable to change certain amino acids containing exposed side-chains to another amino acid residue in order to provide for greater chemical stability of the final antibody, so as to avoid deamidation or isomerization. The deamidation of asparagine may occur on NG, DG, NG, NS, NA, NT, QG or QS sequences and result in the creation of an isoaspartic acid residue that introduces a kink into the polypeptide chain and decreases its stability (isoaspartic acid effect). Isomerization can occur at DG, DS, DA or DT sequences. In certain embodiments, the antibodies of the present disclosure do not contain deamidation or asparagine isomerism sites. For example, an asparagine (Asn) residue may be changed to Gln or Ala to reduce the potential for formation of isoaspartate at any Asn-Gly sequences, particularly within a CDR.

A similar problem may occur at a Asp-Gly sequence. Reissner and Aswad (2003) Cell. Mol. Life Sci. 60:1281. Isoaspartate formation may debilitate or completely abrogate binding of an antibody to its target antigen. See, Presta (2005) J. Allergy Clin. Immunol. 116:731 at 734.

In various embodiment, the asparagine is changed to glutamine (Gln). It may also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) J. Chromatog. 662:261. In addition, any methionine residues (typically solvent exposed Met) in CDRs may be changed to Lys, Leu, Ala, or Phe or other amino acids in order to reduce the possibility that the methionine sulfur would oxidize, which could reduce antigen-binding affinity and also contribute to molecular heterogeneity in the final antibody preparation. Id. Additionally, in order to prevent or minimize potential scissile Asn-Pro peptide bonds, it may be desirable to alter any Asn-Pro combinations found in a CDR to Gln-Pro, Ala-Pro, or Asn-Ala. Antibodies with such substitutions are subsequently screened to ensure that the substitutions do not decrease the affinity or specificity of the antibody for LAP, or other desired biological activity to unacceptable levels. See Table 1A for exemplary stabilizing CDR variants.

TABLE 1A

Exemplary stabilizing CDR variants

| CDR Residue | Stabilizing Variant Sequence |
| --- | --- |
| Asn-Gly | Gln-Gly, Ala-Gly, or Asn-Ala |
| (N-G) | (Q-G), (A-G), or (N-A) |
| Asp-Gly | Glu-Gly, Ala-Gly or Asp-Ala |
| (D-G) | (E-G), (A-G), or (D-A) |
| Met | Lys, Leu, Ala, or Phe |
| (M) | (K), (L), (A), or (F) |
| Asn | Gln or Ala |
| (N) | (Q) or (A) |
| Asn-Pro | Gln-Pro, Ala-Pro, or Asn-Ala |
| (N-P) | (Q-P), (A-P), or (N-A) |

Antibody Engineering of the Fc Region

The antibodies (e.g., humanized antibodies) and antigen-binding fragments thereof disclosed herein (e.g., antibody 20E6 and humanized versions thereof and antibody and 28G11 and humanized versions thereof) can also be engineered to include modifications within the Fc region, typically to alter one or more properties of the antibody, such as serum half-life, complement fixation, Fc receptor binding, and/or effector function (e.g., antigen-dependent cellular cytotoxicity). Furthermore, the antibodies and antigen-binding fragments thereof disclosed herein (e.g., antibody 20E6 and humanized versions thereof) can be chemically modified (e.g., one or more chemical moieties can be attached to the antibody) or be modified to alter its glycosylation, again to alter one or more properties of the antibody or fragment. Each of these embodiments is described in further detail below. The numbering of residues in the Fc region is that of the EU index of Kabat.

The antibodies and antigen-binding fragments thereof disclosed herein (e.g., antibody 20E6 and humanized versions thereof) also include antibodies and fragments with modified (or blocked) Fc regions to provide altered effector functions. See, e.g., U.S. Pat. No. 5,624,821; and PCT Publication numbers WO2003/086310; WO2005/120571; WO2006/0057702. Such modifications can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc regions. Changes to the Fc can also alter the half-life of antibodies in therapeutic antibodies, enabling less frequent dosing and thus increased convenience and decreased use of material. See Presta (2005) J. Allergy Clin. Immunol. 116:731 at 734-35.

In one embodiment, the antibody or antigen-binding fragment of the invention (e.g., antibody 20E6 and humanized versions thereof) is an IgG4 isotype antibody or fragment comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system).

In one embodiment of the invention, the hinge region of CH1 is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the Fc hinge region of an antibody or antigen-binding fragment of the invention (e.g., antibody 20E6 and humanized versions thereof and antibody 22F9 and humanized versions thereof) is mutated to decrease the biological half-life of the antibody or fragment. More specifically, one or more amino acid mutations are introduced into the CH2-CH3 domain interface region of the Fc-hinge fragment such that the antibody or fragment has impaired Staphylococcyl protein A (SpA) binding relative to native Fc-hinge domain SpA binding. This approach is described in further detail in U.S. Pat. No. 6,165,745.

In another embodiment, the antibody or antigen-binding fragment of the invention (e.g., antibody 20E6 and humanized versions thereof and antibody 20E6 and humanized versions thereof) is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antibody or antigen-binding fragment. For example, one or more amino acids selected from amino acid residues 234, 235, 236, 237, 297, 318, 320 and 322 can be replaced with a different amino acid residue such that the antibody has an altered affinity for an effector ligand and retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551.

In another example, one or more amino acid residues within amino acid positions 231 and 239 are altered to thereby alter the ability of the antibody to fix complement. This approach is described further in PCT Publication number WO 94/29351.

In yet another example, the Fc region is modified to decrease the ability of the antibody or antigen-binding fragment of the invention (e.g., antibody 20E6 and humanized versions thereof and antibody 20E6 and humanized versions thereof) to mediate antibody dependent cellular cytotoxicity (ADCC) and/or to decrease the affinity of the antibody or fragment for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication number WO 00/42072. Moreover, the binding sites on human IgG1 for FcγR1, FcγRII, FcγRIII and FcRn have been mapped and variants with improved binding have been described (see Shields et al. (2001) J. Biol. Chem. 276:6591-6604).

In one embodiment of the invention, the Fc region is modified to decrease the ability of the antibody of the invention (e.g., antibody 20E6 and humanized versions thereof) to mediate effector function and/or to increase anti-inflammatory properties by modifying residues 243 and 264. In one embodiment, the Fc region of the antibody or fragment is modified by changing the residues at positions 243 and 264 to alanine. In one embodiment, the Fc region is modified to decrease the ability of the antibody or fragment to mediate effector function and/or to increase anti-inflammatory properties by modifying residues 243, 264, 267 and 328.

Altered Effector Function

In some embodiments, the Fc region of an anti-LAP antibody is modified to increase or reduce the ability of the antibody or antigen-binding fragment to mediate effector function and/or to increase/decrease their binding to the Fcgamma receptors (FcγRs).

The interaction between the constant region of an antigen binding protein and various Fc receptors (FcR) including FcgammaRI (CD64), FcgammaRII (CD32) and FcgammaRIII (CD16) is believed to mediate the effector functions, such as ADCC and CDC, of the antigen binding protein. The Fc receptor is also important for antibody cross-linking, which can be important for anti-tumor immunity.

Effector function can be measured in a number of ways including for example via binding of the FcgammaRIII to Natural Killer cells or via FcgammaRI to monocytes/macrophages to measure for ADCC effector function. For example, an antigen binding protein of the present invention can be assessed for ADCC effector function in a Natural Killer cell assay. Examples of such assays can be found in Shields et al., 2001 J. Biol. Chem., Vol. 276, p 6591-6604; Chappel et al., 1993 J. Biol. Chem., Vol 268, p 25124-25131; Lazar et al., 2006 PNAS, 103; 4005-4010.

Human IgG1 constant regions containing specific mutations or altered glycosylation on residue Asn297 have been shown to reduce binding to Fc receptors. In other cases, mutations have also been shown to enhance ADCC and CDC (Lazar et al. PNAS 2006, 103; 4005-4010; Shields et al. J Biol Chem 2001, 276; 6591-6604; Nechansky et al. Mol Immunol, 2007, 44; 1815-1817).

In one embodiment of the present invention, such mutations are in one or more of positions selected from 239, 332 and 330 (IgG1), or the equivalent positions in other IgG isotypes. Examples of suitable mutations are S239D and I332E and A330L. In one embodiment, the antigen binding protein of the invention herein described is mutated at positions 239 and 332, for example S239D and I332E or in a further embodiment it is mutated at three or more positions selected from 239 and 332 and 330, for example S239D and I332E and A330L. (EU index numbering).

In an alternative embodiment of the present invention, there is provided an antibody comprising a heavy chain constant region with an altered glycosylation profile such that the antigen binding protein has enhanced effector function. For example, wherein the antibody has enhanced ADCC or enhanced CDC or wherein it has both enhanced ADCC and CDC effector function. Examples of suitable methodologies to produce antigen binding proteins with an altered glycosylation profile are described in PCT Publication numbers WO2003011878 and WO2006014679 and European patent number EP1229125.

In a further aspect, the present invention provides "non-fucosylated" or "afucosylated" antibodies. Non-fucosylated antibodies harbor a tri-mannosyl core structure of complex-type N-glycans of Fc without fucose residue. These glyco-engineered antibodies that lack core fucose residue from the Fc N-glycans may exhibit stronger ADCC than fucosylated equivalents due to enhancement of FcgammaRIIIa binding capacity.

The present invention also provides a method for the production of an antibody according to the invention comprising the steps of: a) culturing a recombinant host cell comprising an expression vector comprising the isolated nucleic acid as described herein, wherein the recombinant host cell does not comprise an alpha-1,6-fucosyltransferase; and b) recovering the antigen binding protein. The recombinant host cell may not normally contain a gene encoding an alpha-1,6-fucosyltransferase (for example yeast host cells such as *Pichia* sp.) or may have been genetically modified to inactivate an alpha-1,6-fucosyltransferase. Recombinant host cells which have been genetically modified to inactivate the FUT8 gene encoding an alpha-1,6-fucosyltransferase are available. See, e.g., the POTELLIGENT™ technology system available from BioWa, Inc. (Princeton, N.J.) in which CHOK1SV cells lacking a functional copy of the FUT8 gene produce monoclonal antibodies having enhanced antibody dependent cell mediated cytotoxicity (ADCC) activity that is increased relative to an identical monoclonal antibody produced in a cell with a functional FUT8 gene. Aspects of the POTELLIGENT™ technology system are described in U.S. Pat. Nos. 7,214,775 and 6,946,292, and PCT Publication numbers WO0061739 and WO0231240. Those of ordinary skill in the art will also recognize other appropriate systems.

It will be apparent to those skilled in the art that such modifications may not only be used alone but may be used in combination with each other in order to further enhance or decrease effector function.

Production of Antibodies with Modified Glycosylation

In still another embodiment, the antibodies or antigen-binding fragments of the invention (e.g., antibody 20E6 and humanized versions thereof) comprise a particular glycosylation pattern. For example, an afucosylated or an aglycosylated antibody or fragment can be made (i.e., the antibody lacks fucose or glycosylation, respectively). The glycosylation pattern of an antibody or fragment may be altered to, for example, increase the affinity or avidity of the antibody or fragment for a LAP antigen. Such modifications can be accomplished by, for example, altering one or more of the glycosylation sites within the antibody or fragment sequence. For example, one or more amino acid substitutions can be made that result in removal of one or more of the variable region framework glycosylation sites to thereby eliminate glycosylation at that site. Such aglycosylation may increase the affinity or avidity of the antibody or fragment for antigen. See, e.g., U.S. Pat. Nos. 5,714,350 and 6,350,861.

Antibodies and antigen-binding fragments disclosed herein (e.g., antibody 20E6 and humanized versions thereof and antibody 28G11 and humanized versions thereof) may further include those produced in lower eukaryote host cells, in particular fungal host cells such as yeast and filamentous fungi have been genetically engineered to produce glycoproteins that have mammalian- or human-like glycosylation patterns (See for example, Choi et al, (2003) *Proc. Natl. Acad. Sci.* 100: 5022-5027; Hamilton et al., (2003) *Science* 301: 1244-1246; Hamilton et al., (2006) *Science* 313: 1441-1443; Nett et al., *Yeast* 28(3):237-52 (2011); Hamilton et al., *Curr Opin Biotechnol*. October; 18(5):387-92 (2007)). A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures (See for example, Li et al., (2006) *Nat. Biotechnol.* 24: 210-215).

In particular embodiments, the antibodies and antigen-binding fragments thereof disclosed herein (e.g., antibody 20E6 and humanized versions thereof) further include those produced in lower eukaryotic host cells and which comprise fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the antibodies and antigen-binding fragments thereof provided herein (e.g., antibody 20E6 and humanized versions thereof) may comprise antibodies or fragments having at least one hybrid N-glycan selected from the group consisting of $GlcNAcMan_5GlcNAc_2$; $GalGlcNAcMan_5GlcNAc_2$; and $NANAGalGlcNAcMan_5GlcNAc_2$. In particular aspects, the hybrid N-glycan is the predominant N-glycan species in the composition.

In particular embodiments, the antibodies and antigen-binding fragments thereof provided herein (e.g., antibody 20E6 and humanized versions thereof and antibody 28G11 and humanized versions thereof) comprise antibodies and fragments having at least one complex N-glycan selected from the group consisting of $GlcNAcMan_3GlcNAc_2$; $GalGlcNAcMan_3GlcNAc_2$; $NANAGalGlcNAcMan_3GlcNAc_2$; $GlcNAc_2Man_3GlcNAc_2$; $GalGlcNAc_2Man_3GlcNAc_2$; $Gal_2GlcNAc_2Man_3GlcNAc_2$; $NANAGal_2GlcNAc_2Man_3GlcNAc_2$; and $NANA_2Gal_2GlcNAc_2Man_3GlcNAc_2$. In particular aspects, the complex N-glycan are the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In one embodiment, the antibody and antigen binding fragments thereof provided herein comprise complex N-glycans, wherein at least 50%, 60%, 70%, 80%, 90%, 95%, 97%, 98%, 99%, or 100% of the complex N-glycans comprise the structure $NANA_2Gal_2GlcNAc_2Man_3GlcNAc_2$, wherein such structure is afucosylated. Such structures can be produced, e.g., in engineered *Pichia pastoris* host cells.

In particular embodiments, the N-glycan is fucosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan. Therefore, in particular aspects of the above the glycoprotein compositions, the glycoform is in an α1,3-linkage or α1,6-linkage fucose to produce a glycoform selected from the group consisting of $Man_5GlcNAc_2(Fuc)$, $GlcNAcMan_5GlcNAc_2(Fuc)$, $Man_3GlcNAc_2(Fuc)$, $GlcNAcMan_3GlcNAc_2(Fuc)$, $GlcNAc_2Man_3GlcNAc_2(Fuc)$, $GalGlcNAc_2Man_3GlcNAc_2(Fuc)$, $Gal_2GlcNAc_2Man_3GlcNAc_2(Fuc)$, NANAGal$_2$GlcNAc$_2$Man$_3$GlcNAc$_2$(Fuc), and NANA$_2$Gal$_2$GlcNAc$_2$Man$_3$GlcNAc$_2$(Fuc); in an α1,3-linkage or α1,4-linkage fucose to produce a glycoform selected from the group consisting of GlcNAc(Fuc)Man$_5$GlcNAc$_2$, GlcNAc(Fuc)Man$_3$GlcNAc$_2$, GlcNAc$_2$(Fuc$_{1-2}$) Man$_3$GlcNAc$_2$, GalGlcNAc$_2$(Fuc$_{1-2}$)Man$_3$GlcNAc$_2$, Gal$_2$GlcNAc$_2$(Fuc1-2)Man$_3$GlcNAc$_2$, NANAGal$_2$GlcNAc$_2$ (Fuc$_{1-2}$)Man$_3$GlcNAc$_2$, and NANA$_2$Gal$_2$GlcNAc$_2$(Fuc$_{1-2}$) Man$_3$GlcNAc$_2$; or in an α1,2-linkage fucose to produce a glycoform selected from the group consisting of Gal(Fuc) GlcNAc$_2$Man$_3$GlcNAc$_2$, Gal$_2$(Fuc$_{1-2}$) GlcNAc$_2$Man$_3$GlcNAc$_2$, NANAGal$_2$(Fuc$_{1-2}$) GlcNAc$_2$Man$_3$GlcNAc$_2$, and NANA$_2$Gal$_2$(Fuc$_{1-2}$) GlcNAc$_2$Man$_3$GlcNAc$_2$.

In further aspects, the antibodies (e.g., humanized antibodies) or antigen-binding fragments thereof comprise high mannose N-glycans, including but not limited to, Man$_8$GlcNAc$_2$, Man$_7$GlcNAc$_2$, Man$_6$GlcNAc$_2$, Man$_5$GlcNAc$_2$, Man$_4$GlcNAc$_2$, or N-glycans that consist of the Man$_3$GlcNAc$_2$ N-glycan structure.

In further aspects of the above, the complex N-glycans further include fucosylated and non-fucosylated bisected and multiantennary species.

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues post-translationally in the Golgi apparatus for N-linked glycoproteins. N-glycans have a common pentasaccharide core of Man$_3$GlcNAc$_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the Man$_3$GlcNAc$_2$ ("Man$_3$") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms".

With respect to complex N-glycans, the terms "G-2", "G-1", "G0", "G1", "G2", "A1", and "A2" mean the following. "G-2" refers to an N-glycan structure that can be characterized as Man$_3$GlcNAc$_2$; the term "G-1" refers to an N-glycan structure that can be characterized as GlcNAcMan$_3$GlcNAc$_2$; the term "G0" refers to an N-glycan structure that can be characterized as GlcNAc$_2$Man$_3$GlcNAc$_2$; the term "G1" refers to an N-glycan structure that can be characterized as GalGlcNAc$_2$Man$_3$GlcNAc$_2$; the term "G2" refers to an N-glycan structure that can be characterized as Gal$_2$GlcNAc$_2$Man$_3$GlcNAc$_2$; the term "A1" refers to an N-glycan structure that can be characterized as NANAGal$_2$GlcNAc$_2$Man$_3$GlcNAc$_2$; and, the term "A2" refers to an N-glycan structure that can be characterized as NANA$_2$Gal$_2$GlcNAc$_2$Man$_3$GlcNAc$_2$. Unless otherwise indicated, the terms G-2", "G-1", "G0", "G1", "G2", "A1", and "A2" refer to N-glycan species that lack fucose attached to the GlcNAc residue at the reducing end of the N-glycan. When the term includes an "F", the "F" indicates that the N-glycan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas GlcNAc$_{(2-4)}$Man$_3$GlcNAc$_2$, Gal$_{(1-4)}$GlcNAc$_{(2-4)}$Man$_3$GlcNAc$_2$, or NANA$_{(1-4)}$Gal$_{(1-4)}$GlcNAc$_{(2-4)}$Man$_3$GlcNAc$_2$. The term "1-4" refers to 1, 2, 3, or 4 residues. With respect to bisected N-glycans, the term "bisected N-glycan" refers to N-glycans in which a GlcNAc residue is linked to the mannose residue at the reducing end of the N-glycan. A bisected N-glycan can be characterized by the formula GlcNAc$_3$Man$_3$GlcNAc$_2$ wherein each mannose residue is linked at its non-reducing end to a GlcNAc residue. In contrast, when a multiantennary N-glycan is characterized as GlcNAc$_3$Man$_3$GlcNAc$_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

Antibody Physical Properties

The antibodies and antigen-binding fragments thereof disclosed herein (e.g., antibody 20E6 and humanized versions thereof) may further contain one or more glycosylation sites in either the light or heavy chain immunoglobulin variable region. Such glycosylation sites may result in increased immunogenicity of the antibody or fragment or an alteration of the pK of the antibody due to altered antigen-binding (Marshall et al. (1972) *Annu Rev Biochem* 41:673-702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316: 452-7; Mimura et al. (2000) *Mol Immunol* 37:697-706). Glycosylation has been known to occur at motifs containing an N-X-S/T sequence.

Each antibody or antigen-binding fragment (e.g., 20E6 or humanized versions thereof) will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8.

Each antibody or antigen-binding fragment (e.g., 20E6 or humanized versions thereof) will have a characteristic melting temperature, with a higher melting temperature indicating greater overall stability in vivo (Krishnamurthy R and Manning M C (2002) *Curr Pharm Biotechnol* 3:361-71). In general, the $T_{M1}$ (the temperature of initial unfolding) may be greater than 60° C., greater than 65° C., or greater than 70° C. The melting point of an antibody or fragment can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9). In a further embodiment, antibodies and antigen-binding fragments thereof (e.g., antibody 20E6 and humanized versions thereof) are selected that do not degrade rapidly. Degradation of an antibody or fragment can be measured using capillary electrophoresis (CE) and MALDI-MS (Alexander A J and Hughes D E (1995) *Anal Chem* 67:3626-32).

In a further embodiment, antibodies (e.g., antibody 20E6 and humanized versions thereof) and antigen-binding fragments thereof are selected that have minimal aggregation effects, which can lead to the triggering of an unwanted immune response and/or altered or unfavorable pharmacokinetic properties. Generally, antibodies and fragments are acceptable with aggregation of 25% or less, 20% or less, 15% or less, 10% or less, or 5% or less. Aggregation can be measured by several techniques, including size-exclusion column (SEC), high performance liquid chromatography (HPLC), and light scattering.

V. Multispecific antibodies

Multispecific antibodies (e.g., bispecific antibodies) provided herein include at least one binding region for a particular epitope on LAP-TGFβ1 (e.g., human LAP-TGFβ1) as described herein, and at least one other binding region (e.g., a cancer antigen). Multispecific antibodies can be prepared as full length antibodies or antibody fragments (e.g. F(ab')₂ antibodies).

Methods for making multispecific antibodies are well known in the art (see, e.g., PCT Publication numbers WO 05117973 and WO 06091209). For example, production of full length multispecific antibodies can be based on the co-expression of two paired immunoglobulin heavy chain-light chains, where the two chains have different specificities. Various techniques for making and isolating multispecific antibody fragments directly from recombinant cell culture have also been described. For example, multispecific antibodies can be produced using leucine zippers. Another strategy for making multispecific antibody fragments by the use of single-chain Fv (sFv) dimers has also been reported.

Examples of suitable multispecific molecule platforms include, but are not limited to, Dual Targeting (DT)-Ig (GSK/Domantis), Two-in-one Antibody (Genentech), Cross-linked Mabs (Karmanos Cancer Center), Fcab and mAb² (F-Star), CovX-body (CovX/Pfizer), Dual Variable Domain (DVD)-Ig (Abbott), IgG-like Bispecific (ImClone/Eli Lilly), Ts2Ab (MedImmune/AZ) and BsAb (Zymogenetics), HERCULES (Biogen Idec), TvAb (Roche), ScFv/Fc Fusions, SCORPION (Emergent BioSolutions/Trubion, Zymogenetics/BMS), Dual Affinity Retargeting Technology (Fc-DART) (MacroGenics), Dual(ScFv)2-Fab (National Research Center for Antibody Medicine—China), F(ab)2 (Medarex/AMGEN), Dual-Action or Bis-Fab (Genentech), Dock-and-Lock (DNL) (ImmunoMedics), Bivalent Bispecific (Biotecnol), SEED (EMD Serono), mAb² (F-star), Fab-Fv (UCB-Celltech), Bispecific T Cell Engager (BiTE) (Micromet, Tandem Diabody (Tandab) (Affimed), Dual Affinity Retargeting Technology (DART) (MacroGenics), Single-chain Diabody (Academic), TCR-like Antibodies (AIT, ReceptorLogics), COMBODY (Epigen Biotech), dual targeting nanobodies (Ablynx), and Fc-engineered IgG1 (Xencor).

In a particular embodiment, the multispecific antibody comprises a first antibody (or binding portion thereof) which binds to LAP-TGFβ1 derivatized or linked to another functional molecule, e.g., another peptide or protein (e.g., another antibody or ligand for a receptor) to generate a multispecific molecule that binds to LAP-TGFβ1 and a non-LAP target molecule. An antibody may be derivatized or linked to more than one other functional molecule to generate multispecific molecules that bind to more than two different binding sites and/or target molecules. To create a multispecific molecule, an antibody disclosed herein can be functionally linked (e.g., by chemical coupling, genetic fusion, noncovalent association or otherwise) to one or more other binding molecules, such as another antibody, antibody fragment, peptide, receptor, or binding mimetic, such that a multispecific molecule results.

Accordingly, multispecific molecules, for example, bispecific antibodies and bifunctional antibodies, comprising at least one first binding specificity for a particular epitope on LAP-TGFβ1 (e.g., human LAP-TGFβ1) and a second binding specificity for a second target are contemplated. In some embodiments, the second target is the second binding region specifically binds to a tumor-associated antigen. Tumor-associated antigens are well known in the art. Exemplary tumor-associated antigens include, but are not limited to, AFP, ALK, BAGE proteins, β-catenin, brc-abl, BRCA1, BORIS, CA9, carbonic anhydrase IX, caspase-8, CCR5, CD19, CD20, CD30, CDK4, CEA, cyclin-B1, CYP1B1, EGFR, EGFRvIII, ErbB2/Her2, ErbB3, ErbB4, ETV6-AML, EpCAM, EphA2, Fra-1, FOLR1, GAGE proteins (e.g., GAGE-1, -2), GD2, GD3, GloboH, glypican-3, GM3, gp100, Her2, HLA/B-raf, HLA/k-ras, HLA/MAGE-A3, hTERT, LMP2, MAGE proteins (e.g., MAGE-1, -2, -3, -4, -6, and -12), MART-1, mesothelin, ML-IAP, Muc1, Muc2, Muc3, Muc4, Muc5, Muc16 (CA-125), MUM1, NA17, NY-BR1, NY-BR62, NY-BR85, NY-ESO1, OX40, p15, p53, PAP, PAX3, PAX5, PCTA-1, PLAC1, PRLR, PRAME, PSMA (FOLH1), RAGE proteins, Ras, RGS5, Rho, SART-1, SART-3, Steap-1, Steap-2, STn, survivin, TAG-72, TGF-β, TMPRSS2, Tn, TRP-1, TRP-2, tyrosinase, and uroplakin-3.

In some embodiments, the second binding region of the bispecific antibody specifically binds to CD4, CD8, CD45, CD56, CD14, CD16, CD19, CD20, CD25, CD38, CD11b, CD22, CD30, CD39, CD114, CD23, CD73, CD163, CD206, CD203, CD200R, PD-1, PD-L1, PD-L2, CTLA-4, IDO, TIM-3, LAG-3, TIGIT, PVR, PVRL2, B7H3, B7H4, CSF-1R, VISTA, KIR, OX-40, GITR, 4-1BB, CD40, CD40L, CD27/CD70, CD28, ICOS, CD3, CD56, NKG2DA, NKG2DB, NKG2DC, NKG2DD, NKG2DF, NKG2DH, CD94, NKP46, NKP30, CD33, CD73, CD47, LILRB1, CD91, calreticulin, CD122, GARP, LRRC33, LAP2, LAP3, TGFβ1, TGFβ2, TGFβ3, FAP, cadherin 11 and stanniocalcin 1. In some embodiments, the second binding region has agonistic properties when binding to a target, e.g., a TNF family member agonist, OX40 ligand, CD137 ligand, CD137 agonist, STING agonist, GITR agonist, ICOS agonist, and CD28 agonist.

In some embodiments, the antibody is a trispecific antibody comprising a first, second, and third binding region, wherein the first binding region comprises the binding specificity (e.g., antigen-binding region) of an anti-LAP antibody described herein, and the second and third binding regions bind to two different targets (or different epitopes on the same target), for example, the targets described above.

In some embodiments, the antibody is a bifunctional antibody comprising an anti-LAP antibody described herein and a receptor molecule (i.e., a receptor trap construct such as a TGFβ superfamily ligand receptor (e.g., ActRIIB and variants thereof) or VEGFR).

In one embodiment, the multispecific molecules comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778.

The multispecific molecules can be prepared by conjugating the constituent binding specificities, e.g., the anti-FcR and anti-LAP binding specificities, using methods known in the art. For example, each binding specificity of the multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the multispecific molecule is a mAb×mAb, mAb×Fab, Fab×F(ab')$_2$ or ligand x Fab fusion protein. A multispecific molecule can be a single chain molecule comprising one single chain antibody and a binding determinant, or a single chain bispecific molecule comprising two binding determinants. Multispecific molecules may comprise at least two single chain molecules. Methods for preparing multispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the multispecific molecules to their specific targets can be confirmed by, for example, enzyme-linked immunosorbent assay (ELISA), radioimmunoassay (RIA), FACS analysis, bioassay (e.g., growth inhibition), or western blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA). The radioactive isotope can be detected by such means as the use of a αγ-β counter or a scintillation counter or by autoradiography.

VI. Immunoconjugates

Immunoconjugates comprising the anti-LAP antibodies or antigen binding fragments thereof described herein can be formed by conjugating the antibodies to another therapeutic agent to form, e.g., an antibody-drug conjugate (ADC). Suitable agents include, for example, a cytotoxic agent (e.g., a chemotherapeutic agent), a toxin (e.g. an enzymatically active toxin of bacterial, fungal, plant or animal origin, or fragments thereof), and/or a radioactive isotope (i.e., a radioconjugate). Additional suitable agents include, e.g., antimetabolites, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In some embodiments, ADCs with the anti-LAP antibodies or antigen binding fragment thereof described herein (e.g., conjugated to a cytotoxic agent) that bind to immunosuppressive cells (e.g., regulatory T cells) can be used to deplete the immunosuppressive cells from, e.g., the tumor microenvironment.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, neomycin, and the tricothecenes. Additional examples of cytotoxins or cytotoxic agents include, e.g., taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

In the ADC, the antibody and therapeutic agent preferably are conjugated via a cleavable linker such as a peptidyl, disulfide, or hydrazone linker. More preferably, the linker is a peptidyl linker such as Val-Cit, Ala-Val, Val-Ala-Val, Lys-Lys, Pro-Val-Gly-Val-Val (SEQ ID NO: 214), Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publication numbers WO 02/096910; WO 07/038658; WO 07/051081; WO 07/059404; WO 08/083312; and WO 08/103693; U.S. Patent Publication numbers 20060024317;

20060004081; and 20060247295; the disclosures of which are incorporated herein by reference.

A variety of radionuclides are available for the production of radioconjugated anti-LAP, antibodies. Examples include $^{212}Bi$, $^{131}I$, $^{131}In$, $^{90}Y$ and $^{186}Re$.

Immunoconjugates can also be used to modify a given biological response, and the drug moiety is not to be construed as limited to classical chemical therapeutic agents. For example, the drug moiety may be a protein or polypeptide possessing a desired biological activity (e.g., lymphokines, tumor necrosis factor, IFNγ, growth factors).

Immunoconjugates can be made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of radionucleotide to the antibody (see, e.g., PCT publication number WO94/11026).

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

The anti-LAP antibodies or antigen binding fragments described herein also are used for diagnostic purposes. Such antibodies or antigen binding fragments can be conjugated to an appropriate detectable agent to form an immunoconjugate. For diagnostic purposes, appropriate agents are detectable labels that include radioisotopes, for whole body imaging, and radioisotopes, enzymes, fluorescent labels and other suitable antibody tags for sample testing.

The detectable labels can be any of the various types used currently in the field of in vitro diagnostics, including particulate labels, isotopes, chromophores, fluorescent markers, luminescent markers, metal labels (e.g., for CyTOF, imaging mass cytometry), phosphorescent markers and the like, as well as enzyme labels that convert a given substrate to a detectable marker, and polynucleotide tags that are revealed following amplification such as by polymerase chain reaction. Suitable enzyme labels include horseradish peroxidase, alkaline phosphatase and the like. For instance, the label can be the enzyme alkaline phosphatase, detected by measuring the presence or formation of chemiluminescence following conversion of 1,2 dioxetane substrates such as adamantyl methoxy phosphoryloxy phenyl dioxetane (AMPPD), disodium 3-(4-(methoxyspiro{1,2-dioxetane-3, 2'-(5'-chloro)tricyclo{3.3.1.1 3,7}decan}-4-yl) phenyl phosphate (CSPD), as well as CDP and CDP-Star® or other luminescent substrates well-known to those in the art, for example the chelates of suitable lanthanides such as Terbium (III) and Europium(III). The detection means is determined by the chosen label. Appearance of the label or its reaction products can be achieved using the naked eye, in the case where the label is particulate and accumulates at appropriate levels, or using instruments such as a spectrophotometer, a luminometer, a fluorimeter, and the like, all in accordance with standard practice.

Preferably, conjugation methods result in linkages which are substantially (or nearly) non-immunogenic, e.g., peptide-(i.e. amide-), sulfide-, (sterically hindered), disulfide-, hydrazone-, and ether linkages. These linkages are nearly non-immunogenic and show reasonable stability within serum (see e.g. Senter, P. D., Curr. Opin. Chem. Biol. 13 (2009) 235-244; and PCT Publication numbers WO 2009/059278 and WO 95/17886).

Depending on the biochemical nature of the moiety and the antibody, different conjugation strategies can be employed. In case the moiety is naturally occurring or recombinant of between 50 to 500 amino acids, there are standard procedures in text books describing the chemistry for synthesis of protein conjugates, which can be easily followed by the skilled artisan (see e.g. Hackenberger, C. P. R., and Schwarzer, D., Angew. Chem. Int. Ed. Engl. 47 (2008) 10030-10074). In one embodiment the reaction of a maleinimido moiety with a cysteine residue within the antibody or the moiety is used. This is an especially suited coupling chemistry in case e.g. a Fab or Fab'-fragment of an antibody is used. Alternatively in one embodiment coupling to the C-terminal end of the antibody or moiety is performed. C-terminal modification of a protein, e.g. of a Fab-fragment can e.g. be performed as described (Sunbul, M. and Yin, J., Org. Biomol. Chem. 7 (2009) 3361-3371).

In general, site specific reaction and covalent coupling is based on transforming a natural amino acid into an amino acid with a reactivity which is orthogonal to the reactivity of the other functional groups present. For example, a specific cysteine within a rare sequence context can be enzymatically converted in an aldehyde (see Frese, M. A., and Dierks, T., ChemBioChem. 10 (2009) 425-427). It is also possible to obtain a desired amino acid modification by utilizing the specific enzymatic reactivity of certain enzymes with a natural amino acid in a given sequence context (see, e.g., Taki, M. et al., Prot. Eng. Des. Sel. 17 (2004) 119-126; Gautier, A. et al. Chem. Biol. 15 (2008) 128-136; and Protease-catalyzed formation of C—N bonds is used by Bordusa, F., Highlights in Bioorganic Chemistry (2004) 389-403). Site specific reaction and covalent coupling can also be achieved by the selective reaction of terminal amino acids with appropriate modifying reagents. The reactivity of an N-terminal cysteine with benzonitrils (see Ren, H. et al., Angew. Chem. Int. Ed. Engl. 48 (2009) 9658-9662) can be used to achieve a site-specific covalent coupling. Native chemical ligation can also rely on C-terminal cysteine residues (Taylor, E. Vogel; Imperiali, B, Nucleic Acids and Molecular Biology (2009), 22 (Protein Engineering), 65-96).

The moiety may also be a synthetic peptide or peptide mimic. In case a polypeptide is chemically synthesized, amino acids with orthogonal chemical reactivity can be incorporated during such synthesis (see e.g. de Graaf, A. J. et al., Bioconjug. Chem. 20 (2009) 1281-1295). Since a great variety of orthogonal functional groups is at stake and can be introduced into a synthetic peptide, conjugation of such peptide to a linker is standard chemistry.

In some embodiments, the moiety attached to an anti-LAP antibody or antigen binding fragment is selected from the group consisting of a detectable moiety, binding moiety, a labeling moiety, and a biologically active moiety.

VII. Assays

The anti-LAP antibodies or antigen binding fragments disclosed herein can be tested for desired properties, e.g., those described herein, using a variety of assays known in the art.

In one embodiment, the antibodies are or antigen binding fragments tested for specific binding to LAP-TGFβ1 (e.g., human LAP-TGFβ1). Methods for analyzing binding affinity, cross-reactivity, and binding kinetics of various anti-LAP antibodies or antigen binding fragments include standard assays known in the art, for example, Biacore™ surface plasmon resonance (SPR) analysis using a Biacore™ 2000 SPR instrument (Biacore AB, Uppsala, Sweden) or bio-layer interferometry (e.g., ForteBio assay), as described in the Examples. In some embodiments, the LAP used in the binding assay is complexed with TGFβ1. In some embodiments, the LAP used in the binding assay is not complexed with TGFβ1. In some embodiments, the LAP used in the binding assay is complexed with TGFβ1 and GARP or a fragment of GARP or LRRC33 or a fragment of LRRC33. In some embodiments the LAP used in the binding assay is complexed with TGFβ1 and LTBP (e.g., LTBP1, LTBP3, or LTBP4) or a fragment of LTBP.

In one embodiment, the antibodies or antigen binding fragments are tested for the ability to bind to cells that have been transfected with LAP-TGFβ1. In some embodiments the cells have also been transfected with GARP or LRRC33.

In one embodiment, the antibodies or antigen binding fragments are screened for the ability to bind to the surface of beads that have been coated with LAP.

In one embodiment, the antibodies or antigen binding fragments are screened for the ability to bind to LAP on cells expressing a heparin sulfate glycoprotein such as syndecan-4. For example, heparin sulfate glycoprotein-expressing cells are incubated with LAP or with LAP complexed to LTBP (e.g., LTBP1, LTBP3, or LTBP4) and the antibodies are screened for binding by flow cytometry.

In one embodiment, the antibodies or antigen binding fragments are tested for the ability to bind or affect TGFβ1. In one embodiment, the antibodies are screened for the ability to bind or affect TGFβ2. In one embodiment, the antibodies are tested for the ability to bind or affect TGFβ3.

In another embodiment, the antibodies or antigen binding fragments are tested for their effects on TGFβ activation (e.g., inhibition, stimulation, or no effect). In some embodiments, TGFβ1 activation is mediated by the binding of integrins including, but not limited, to αvβ6, αvβ8, αvβ3, or αvβ1. In some embodiments, TGFβ1 activation is mediated by matrix metalloproteases including, but not limited to, MMP2 and MMP9. In some embodiments, TGFβ1 activation is mediated by thrombospondin. In some embodiments, TGFβ1 activation is mediated by serum proteases. In some embodiments, TGFβ1 activation is mediated by heat, by shear forces, by a shift in pH or by ionizing radiation. In some embodiments, TGFβ1 activation is mediated by reactive oxygen species (ROS). The source of LAP in the activation assays can be LAP on the surface of a transfected cell line, LAP on the surface of a cell population that expresses LAP endogenously or in response to specific stimuli, LAP bound to extracellular matrix, LAP in solution (e.g., recombinant LAP), either complexed with TGFβ1 or without TGFβ1 or complexed with TGFβ1 and an anchor protein, such as GARP, LRRC33, LTBP1, LTBP3, or LTBP4. LAP-TGFβ1 can be purchased from R&D Systems or can be isolated from cell supernatants. The effect an antibody has on TGFβ1 activation can be determined, for example, using an ELISA (e.g., as described in Example 4) which measures levels of active TGFβ1 under different conditions (e.g., with or without antibody). The effect an antibody has on LAP-TGFβ1 activation can also be determined using a reporter cell line that expresses TGFβ receptor and responds to mature TGFβ.

In another embodiment, the antibodies or antigen binding fragments are tested for the ability to bind LAP in the extracellular matrix. Suitable methods for determining whether antibodies bind to LAP in the extracellular matrix include in vitro assays, wherein cells (e.g., P3U1 cells transfected with LAP-TGFβ) are cultured to lay down ECM on culture plates and subsequently removed, and labeled antibodies are tested for their ability to bind to the LAP and ECM left on the culture plate surface (e.g., as described in Example 5). Similar assays can be run using fibroblast cell lines or other cells that are known to secrete LAP-TGFβ and extracellular matrix components. In some embodiments, whether or not the anti-LAP antibodies bind to or do not bind to ECM can be determined by an ELISA, where the ECM has been shown to express latent TGFβ using commercially available antibodies.

In another embodiment, the antibodies or antigen binding fragments are tested for their ability to bind to particular cell types, e.g., immune cells (e.g., immunosuppressive cells, leukocytes) or platelets. The binding of antibodies or antigen binding fragments to certain leukocyte populations (e.g., Tregs, macrophages, MDSCs, GARP-negative cells) can be determined using flow cytometry, for example, as described in Examples 7.

Antibodies or antigen binding fragments can also be tested for their ability to inhibit the proliferation or viability of cells (either in vivo or in vitro), such as tumor cells, using art-recognized methods (e.g., 3H-thymidine incorporation, immunohistochemistry with proliferation markers, animal cancer models).

Antibodies or antigen binding fragments can also be tested for their anti-tumor activity in vivo (e.g., as monotherapy or combination therapy), using syngeneic tumor models well known in the art, such as the CT26 colorectal tumor model, EMT6 breast cancer model, and 4T1 breast cancer tumor metastasis model. Anti-LAP antibodies can also be tested in tumor xenogragft models which are known to be inhibited by anti-TGFβ antibodies (e.g., Detroit 562 tumor xenograft model). Exemplary methods for treating these models with anti-LAP antibodies are described, e.g., in Examples 12-16.

Exemplary criteria for determining whether an anti-LAP antibody or antigen binding fragment exhibits certain properties (e.g., binding, inhibition of activation, activation) are shown in Table 1B.

TABLE 1B

| Antibody Property | Positive |
|---|---|
| Binding to cells or ECM, as assessed by ELISA | 2 SD above the mean of a negative control |
| Binding to cell types, as assessed by flow cytometry | 2 SD above the mean (MFI on a homogeneous cell line or cell population) of a negative control |

TABLE 1B-continued

| Antibody Property | Positive |
|---|---|
| Binding to TGFβ by a binding assay (e.g., bio-layer interferometry | ≥100-fold difference in affinity relative to a negative control |
| Inhibition of TGFβ1 activation | ≥50% reduction in mature TGFβ1 levels in an in vitro culture relative to negative control when tested at antibody concentrations of 8 ug/mL |
| Activation of TGFβ1 | ≥2-fold increase in mature TGFβ1 levels in an in vitro culture relative to negative control when tested at antibody concentrations of 8 ug/mL |

VIII. Compositions

Also provided herein are compositions (e.g., pharmaceutical compositions) comprising the anti-LAP antibodies or antigen binding fragments described herein, immunoconjugates comprising the same, or bispecific antibodies comprising the same, and a carrier (e.g., pharmaceutically acceptable carrier). Such compositions are useful for various therapeutic applications.

In some embodiments, pharmaceutical compositions disclosed herein can include other compounds, drugs, and/or agents used for the treatment of various diseases (e.g., cancer, fibrosis, autoimmune diseases). Such compounds, drugs, and/or agents can include, for example, an anti-cancer agent, a chemotherapeutic agent, an immunosuppressive agent, an immunostimulatory agent, an immune checkpoint inhibitor, and/or an anti-inflammatory agent. Exemplary compounds, drugs, and agents that can be formulated together or separately with the anti-LAP antibodies or antigen binding fragments described herein are described in the next section (i.e., Section IX; Uses and Methods).

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein may also include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions described herein is contemplated. A pharmaceutical composition may comprise a preservative or may be devoid of a preservative. Supplementary active compounds can be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated herein. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody or antigen binding fragment, the dosage ranges from about 0.0001 to 100 mg/kg, and more usually 0.01 to 5 or 10 mg/kg, of the host body weight. An exemplary treatment regime entails administration once per week, once every two weeks, once every three weeks, once every four weeks, once a month, once every 3 months or once every three to 6 months.

An antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions described herein may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The therapeutically effective dosage of an anti-LAP antibody or antigen binding fragment in various embodiments results in a decrease in severity of disease symptoms, an increase in frequency and duration of disease symptom-free periods, or a prevention of impairment or disability due to the disease affliction. In the context of cancer, a therapeutically effective dose preferably results in increased survival, and/or prevention of further deterioration of physical symptoms associated with cancer. A therapeutically effective dose may prevent or delay onset of cancer, such as may be desired when early or preliminary signs of the disease are present.

A composition described herein can be administered via one or more routes of administration using one or more of a variety of methods known in the art. As will be appreciated by the skilled artisan, the route and/or mode of administration will vary depending upon the desired results. Preferred routes of administration for antibodies described herein include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody or antigen binding fragment described herein can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use with anti-LAP antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the anti-LAP antibodies or antigen binding fragments described herein can be formulated to ensure proper distribution in vivo. For example, the blood-brain barrier (BBB) excludes many highly hydrophilic compounds. To ensure that the therapeutic compounds described herein cross the BBB (if desired, e.g., for brain cancers), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

IX. Uses and Methods

The antibodies, antibody compositions, and methods described herein have numerous in vitro and in vivo utilities.

For example, provided herein is a method of treating cancer comprising administering to a subject in need thereof an anti-LAP antibody or antigen binding fragment described herein, such that the subject is treated, e.g., such that growth of cancerous tumors is inhibited or reduced and/or that the tumors regress and/or that prolonged survival is achieved.

In one embodiment, provided herein is a method of treating cancer comprising administering to a subject in need thereof an effective amount (e.g., a therapeutically effective amount) of an anti-LAP antibody described herein (or a bispecific antibody or immunoconjugate comprising the antibody). In some embodiments, the subject is administered a further therapeutic agent. In some embodiments, the further therapeutic agent is selected from the group consisting of: an anti-PD-1 antibody or an antigen binding fragment thereof, an anti-LAG3 antibody or an antigen biding portion thereof, an anti-VISTA antibody or an antigen binding fragment thereof, an anti-BTLA antibody or an antigen binding fragment thereof, an anti-TIM3 antibody or an antigen binding fragment thereof, an anti-CTLA4 antibody or an antigen binding fragment thereof, an anti-HVEM antibody or an antigen binding fragment thereof, an anti-CD27 antibody or an antigen binding fragment thereof, an anti-CD137 antibody or an antigen binding fragment thereof, an anti-OX40 antibody or an antigen binding fragment thereof, an anti-CD28 antibody or an antigen binding fragment thereof, an anti-PDL1 antibody or an antigen binding fragment thereof, an anti-PDL2 antibody or an antigen binding fragment thereof, an anti-GITR antibody or an antigen binding fragment thereof, an anti-ICOS antibody or an antigen binding fragment thereof, an anti-SIRPα antibody or an antigen binding fragment thereof, an anti-ILT2 antibody or an antigen binding fragment thereof, an anti-ILT3 antibody or an antigen binding fragment thereof, an anti-ILT4 antibody or an antigen binding fragment thereof, an anti-ILT5 antibody or an antigen binding fragment thereof, and an anti-4-1BB antibody or an antigen binding fragment thereof. In some embodiments, anti-PD1 antibody or antigen binding fragment thereof is pembrolizumab or an antigen biding fragment thereof. The heavy and light chain sequences of pembrolizumab are set forth in SEQ ID NOs: 240 and 241, respectively. In some embodiments, the further therapeutic agent is nivolumab. In various embodiments, the heavy and light chain sequences of nivolumab are set forth in comprising SEQ ID NOs: 246 and 247.

In some embodiments, the cancer is characterized by abnormal TGFβ activity. In some embodiments, the cancer is associated with fibrosis. In some embodiments, the cancer is associated with infiltration of CD4+ regulatory T cells. In some embodiments, the cancer is associated with infiltration of CD8+ regulatory T cells. In some embodiments, the cancer is associate with infiltration of regulatory B cells. In some embodiments, the cancer is associated with infiltration of myeloid-derived suppressor cells. In some embodiments, the cancer is associated with infiltration of tumor-associated macrophages. In some embodiments, the cancer is associated with infiltration of innate lymphoid cells. In some embodiments, the cancer is associated with infiltration of cancer-associated fibroblasts. In some embodiments, the cancer is associated with a radiation-related increase in the above cell types.

In some embodiments, the cancer is associated with an increased TGFβ1 activation signature. In some embodiments the cancer is associated with an EMT or an EMT signature. In some embodiments the cancer is associated with a tumor exhibiting an EMT or an EMT signature and immune infiltration. In some embodiments the cancer is associated with a tumor profile of immune exclusion. In some embodiments, the cancer is associated with increased LAP expression. In some embodiments, the cancer is associated with increased GARP expression. In some embodiments, the cancer is associated with increased LRRC33 expression.

Cancers whose growth may be inhibited using the anti-LAP antibodies described herein include, but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer (e.g. estrogen-receptor positive breast cancer HER2-positive breast cancer; triple negative breast cancer); cancer of the peritoneum; cervical cancer; cholangiocarcinoma; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; liver cancer (e.g. hepatocellular carcinoma; hepatoma); intra-epithelial neoplasm; kidney or renal cancer; larynx cancer; leukemia; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; teratocarcinoma; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblasts leukemia; and post-transplant lymphoproliferative disorder (PTLD), as well as abnormal vascular proliferation associated with phakomatoses, edema (such as that associated with brain tumors), tumors of primitive origins and Meigs' syndrome.

Additional cancers which can be treated using the anti-LAP antibodies or antigen binding fragments described herein include metastatic pancreatic cancer, metastatic adenocarcinoma of the pancreas, stomach cancer, fibrotic cancer, glioma, malignant glioma, diffuse intrinsic pontine glioma, recurrent childhood brain neoplasm renal cell carcinoma, clear-cell metastatic renal cell carcinoma, metastatic castration resistant prostate cancer, stage IV prostate cancer, metastatic melanoma, malignant melanoma, recurrent melanoma of the skin, melanoma brain metastases, malignant melanoma of head and neck, squamous cell non-small cell lung cancer, metastatic breast cancer, follicular lymphoma, advanced B-cell NHL, HL including diffuse large B-cell lymphoma (DLBCL), multiple myeloma, chronic myeloid leukemia, adult acute myeloid leukemia in remission, adult acute myeloid leukemia with Inv(16) (p13.1q22), CBFB-MYH11, adult acute myeloid leukemia with t(16:16) (p13.1:q22), CBFB-MYH11, adult acute myeloid leukemia with t(8:21)(d22:q22), RUNX1-RUNX1T1, adult acute myeloid leukemia with t(9:11)(p22:q23), MLLT3-MLL, adult acute promyelocytic leukemia with t015:17)(q22:q12), PML-RARA, alkylating agent-related acute myeloid leukemia, Richter's syndrome, adult glioblastoma, adult gliosarcoma, recurrent glioblastoma, recurrent childhood rhabdomyosarcoma, recurrent ewing sarcoma/peripheral primitive neuroectodermal tumor, recurrent neuroblastoma, recurrent osteosarcoma, colorectal cancer, MSI positive colorectal cancer, MSI negative colorectal cancer, nasopharyngeal nonkeratinizing carcinoma, recurrent nasopharyngeal undifferentiated carcinoma, cervical adenocarcinoma, cervical adenosquamous carcinoma; cervical squamous cell carcinoma, recurrent cervical carcinoma, anal canal squamous cell carcinoma, metastatic anal canal carcinoma, recurrent anal canal carcinoma, recurrent head and neck cancer, squamous cell of head and neck, head and neck squamous cell carcinoma (HNSCC), ovarian carcinoma, colon cancer, advanced GI cancer, gastric adenocarcinoma, gastroesophageal junction adenocarcinoma, bone neoplasms, soft tissue sarcoma, bone sarcoma, thymic carcinoma, urothelial carcinoma, merkel cell carcinoma, recurrent merkel cell carcinoma, mycosis fungoides, Sezary syndrome, neuroendocrine cancer, nasopharyngeal cancer, basal cell skin cancer, squamous cell skin cancer, dermatofibrosarcoma trotuberans, glioma, mesothelioma, myelodysplastic syndromes (MDS), myelofibrosis (MF), myeloproliferative neoplasms, and acute myeloid leukemia (AML).

Cancers may be metastatic or may be primary cancers. Cancers may be desmoplastic or non-desmoplastic. Cancers may be recurrent cancers.

In some embodiments, the anti-LAP antibodies or antigen binding fragments described herein are used to treat myelodysplastic syndromes (MDS). MDS are a diverse group of malignant disorders marked by bone marrow failure due to defective hematopoiesis and production of dysplastic cells. TGFβ is a primary driver in MDS (Geyh et al., Haematologica 2018; 103:1462-71) and agents that inhibit the function of TGFβ have been proposed as therapeutics (Mies et al., Curr Hematol Malig Rep 2016; 11:416-24). Furthermore, MDSCs are known to be dysregulated in MDS (Chen et al., JCI 2013; 123:4595-611) and agents that reduce MDSC levels in the bone marrow are potential therapeutics.

In some embodiments, the anti-LAP antibodies or antigen binding fragments described herein are used to treat myelofibrosis, which is another myeloid malignancy in which TGFβ1 plays a central role (Mascarenhas et al., Leukemia & Lymphoma 2014; 55:450-2).

In some embodiments, the cancer is resistant to checkpoint inhibitor(s). In some embodiments, the cancer is intrinsically refractory or resistant (e.g., resistant to a PD-1 pathway inhibitor, PD-1 pathway inhibitor, or CTLA-4 pathway inhibitor). In some embodiments, the resistance or refractory state of the cancer is acquired. In some embodiments, the anti-LAP antibodies or antigen binding fragments described herein can be used in combination with checkpoint inhibitors to overcome resistance of the cancer to the checkpoint inhibitors. In some embodiments, the anti-LAP antibodies or antigen binding fragments described herein can be used to treat tumors with a mesenchymal and/or EMT signature together with checkpoint inhibitors in combination or sequentially with agents that induce a mesenchymal phenotype, such as MAPK pathway inhibitors.

In some embodiments, the anti-LAP antibodies or antigen binding fragments described herein are used to enhance the viability of immune cells ex vivo, e.g., in adoptive NK cell transfer. Accordingly, in some embodiments, anti-LAP antibodies are used in combination with adoptively transferred NK cells to treat cancer.

In some embodiments, the anti-LAP antibodies or antigen binding fragments described herein are used to treat tumors with MHC loss or MHC down-regulation, as monotherapy or in combination with NK activating or enhancing treatment. In some embodiments, the anti-LAP antibodies described herein are used to treat checkpoint inhibitor resistant tumors in combination with NK activating or enhancing treatment.

Also provided herein is a method of treating cancer associated with an increased number of circulating platelets or an increased platelet to lymphocyte ratio comprising administering to a subject in need thereof an effective amount of an antibody or antigen binding fragment which specifically binds to LAP, wherein the antibody binds to platelets but does not cause platelet aggregation or platelet degranulation.

The ability of a compound to inhibit cancer can be evaluated in an animal model system predictive of efficacy in human tumors. Alternatively, this property of a composition can be evaluated by examining the ability of the compound to inhibit using in vitro assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

Also encompassed are methods for detecting the presence of LAP-TGFβ1 in a sample (e.g., a tumor biopsy sample), or measuring the amount of LAP-TGFβ1 in sample, comprising contacting the sample (e.g., tumor tissue) and a control sample (e.g., corresponding healthy tissue) with an antibody (e.g., monoclonal antibody) or antigen binding fragment which specifically binds to LAP-TGFβ1 under conditions that allow for formation of a complex between the antibody or portion thereof and LAP-TGFβ1. The formation of a complex is then detected, wherein a difference in complex formation between the sample compared to the control sample is indicative of the presence of LAP-TGFβ1 in the sample. The anti-LAP antibodies or antigen binding fragments described herein can also be used to purify LAP-TGFβ1 via immunoaffinity purification.

Diagnostic applications of the anti-LAP antibodies described herein are also contemplated.

In one embodiment, provided herein is a method of diagnosing a cancer associated with regulatory T cell infiltration comprising contacting a biological sample from a patient afflicted with the cancer with an anti-LAP antibody or antigen binding fragment described herein which binds to regulatory T cells, wherein positive staining with the antibody indicates the cancer is associated with regulatory T cell infiltration.

In another embodiment, provided herein is a method of diagnosing a cancer associated with GARP-negative suppressive cells comprising contacting a biological sample from a patient afflicted with the cancer with an anti-LAP antibody or antigen binding fragment described herein which binds to GARP-negative suppressive cells, wherein positive staining with the antibody and negative staining with an anti-GARP antibody indicates the cancer is associated with GARP-negative suppressive cells.

In another embodiment, provided herein is a method of selecting a patient afflicted with cancer for treatment with an anti-LAP antibody or antigen binding fragment described herein, comprising contacting a biological sample from the patient with the antibody, wherein positive staining with the antibody indicates the cancer is amenable to treatment with the antibody.

In another embodiment, provided herein is a method of determining the response of a patient afflicted with cancer to treatment with an anti-LAP antibody or antigen binding fragment described herein comprising contacting a biological sample from the patient with the antibody, wherein reduced staining with the antibody indicates the cancer is responding to treatment with the antibody.

In another embodiment, provided herein is a method of determining whether a cancer in a patient has metastasized comprising (a) identifying a patient having a cancer, (b) administering a labeled (e.g., radiolabeled) anti-LAP antibody or antigen binding fragment described herein to the patient and determining the biodistribution of the labeled anti-LAP antibody, and (c) periodically repeating step (b) to determine whether the biodistribution of the labeled anti-LAP antibody has changed, wherein a change in the biodistribution of the labeled anti-LAP antibody is indicative that the cancer has metastasized.

Also provided are methods of treating fibrosis with the anti-LAP antibodies described herein. In one embodiment, provided herein is a method of treating fibrosis comprising administering to a subject in need thereof an effective amount of an antibody or antigen binding fragment described herein. In some embodiments, the fibrosis is associated with cancer. In some embodiments, the fibrosis is associated with increased levels of myeloid-derived suppressor cells (e.g. Fernandez et al., Eur Respir J 2016; 48:1171-83).

Exemplary fibrotic disorders which can be treated with any of the anti-LAP antibodies or antigen binding fragment described herein include, but are not limited to, heart fibrosis, muscle fibrosis, skin fibrosis, liver fibrosis, soft tissue (e.g., mediastinum or retroperitoneum) fibrosis, renal fibrosis, bone marrow fibrosis, intestinal fibrosis, joint (e.g., knee, shoulder or other joints) fibrosis, pulmonary fibrosis, idiopathic pulmonary fibrosis, cystic fibrosis, endomyocardial fibrosis, mediastinal fibrosis, myelofibrosis, retroperitoneal fibrosis, progressive massive fibrosis, pipestem fibrosis, nephrogenic systemic fibrosis, Crohn's disease, keloid, old myocardial infarction, scleroderma/systemic sclerosis, subepithelial fibrosis, arthrofibrosis, some forms of adhesive capsulitis, proliferative fibrosis, viral hepatitis induced fibrosis, drug-induced fibrosis, radiation-induced fibrosis, and fibrosis associated with cancer.

Also provided herein is a method of reducing the number of immunosuppressive cells in a patient before, during, or after transplantation comprising administering an effective amount of any of the anti-LAP antibodies or antigen binding fragments described herein to a patient before undergoing transplantation, during transplantation, and/or after transplantation. In some embodiments, the anti-LAP antibodies or antigen binding fragments improve graft survival.

Inhibition of TGFβ has been shown to restore regenerative failure by reducing senescence and enhancing liver regeneration, in a model of acute liver disease (acetaminophen injury mouse model) (Bird et al., Sci Transl Med 2018; 10:eaan1230). Accordingly, also provided herein is a method of increasing the regenerative response in acute organ injury (e.g., acute liver injury) comprising administering to a subject with acute organ injury an effective amount of the anti-LAP antibodies or antigen binding fragments described herein.

Aberrant activation of TGFβ has been shown to initiate the onset of temporomandibular joint osteoarthritis (Zheng et al., Bone Res 2018; 6:26). Accordingly, also provided herein is a method of treating a patient with temporomandibular joint osteoarthritis comprising administering to the patient an effective amount of the anti-LAP antibodies or antigen binding fragments described herein to treat the temporomandibular joint osteoarthritis.

LAP-TGFβ1 has also been shown to mediate the differentiation of CD4+ effector cells into productively and latently infected central memory T cells during HIV-1 infection (Cheung et al., J Viol 2018; 92:e01510-17). Accordingly, also provided herein is a method of treating a patient with HIV-1 infection (or a patient at risk of developing HIV-1 infection) comprising administering to the patient an effective amount of the anti-LAP antibodies or antigen binding fragments described herein to treat the HIV-1 infection (e.g., inhibit differentiation of CD4+ effector cells into productively and latently infected central memory T cells).

TGFβ-expressing macrophages and suppressive regulatory T cells have been shown to be altered in the peritoneal fluid of patients with endometriosis (Hanada et al., Reprod Biol Endocrinol 2018; 16:9), suggesting that targeting LAP-TGFb1 expressed on these cells may be beneficial for treating the disorder. Accordingly, also provided herein is a method of treating a patient with endometriosis comprising administering to the patient an effective amount of the anti-LAP antibodies or antigen binding fragments described herein to treat the endometriosis.

LAP-TGFβ1-expressing CD4+ T cells and CD14+ monocytes and macrophages have been shown to be increased in patients carrying multidrug resistant *Mycobacterium tuberculosis* (Basile et al., Clin Exp Immunol 2016; 187:160), suggesting that targeting LAP-TGFβ1 expressed on these cells may be beneficial for treating the infection. Accordingly, also provided herein is a method of treating a patient with multidrug resistant *Mycobacterium tuberculosis* comprising administering to the patient an effective amount of the anti-LAP antibodies or antigen binding fragments described herein (e.g., anti-LAP antibodies which inhibit LAP-TGFβ1 activation) to treat the infection.

In some embodiments, the anti-LAP antibodies or antigen binding fragments described herein are used to treat β-thalassemia, a disorder in which TGFβ superfamily members have been implicated in defective erythropoiesis (Dussiot et al. Nat Med 2014; 20:398-407).

In certain embodiments, the anti-LAP antibody or antigen binding fragment can be used as monotherapy to treat a disease or disorder (e.g., cancer). Alternatively, an anti-LAP antibody or antigen binding fragment can be used in conjunction with another agent or therapy, e.g., an anti-cancer agent, a chemotherapeutic agent, an immunosuppressive agent, an immunostimulatory agent, an immune checkpoint inhibitor, an anti-inflammatory agent, or a cell therapy, as described in more detail below.

Combination Therapy

The anti-LAP antibodies or antigen binding fragments described herein can be used in combination with various treatments or agents (or in the context of a multispecific antibody or bifunctional partner) known in the art for the treatment of cancer, as described below.

Suitable anti-cancer agents for use in combination therapy with the anti-LAP antibodies or antigen binding fragments described herein include, but are not limited to, surgery, chemotherapeutic agents, growth inhibitory agents, cytotoxic agents, radiotherapy and agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC (Imatinib Mesylate)), a COX-2 inhibitor (e.g., celecoxib), interferons, cytokines, antagonists (e.g., neutralizing antibodies) that bind to one or more of the following targets PD 1, PDL1, PDL2 (e.g., pembrolizumab; nivolumab; MK-3475; AMP-224; MPDL3280A; MEDI0680; MSB0010718C; and/or MEDI4736); CTLA4 (e.g., tremelimumab (PFIZER) and ipilimumab); LAG3 (e.g., BMS-986016); CD 103; TIM-3 and/or other TIM family members; CEACAM-1 and/or other CEACAM family members, ErbB2, ErbB3, ErbB4, PDGFR-beta, BlyS, APRIL, BCMA or VEGF receptor(s), TRAIL/Apo2, PARP inhibitors (e.g., AZD-2281, Lynparza Olaparib, Rubraca Rucaparib; (Zejula) niraparib), DNA damage repair inhibitors (e.g., ATMi, ATRi, DNAPKi), and other bioactive and organic chemical agents. Combinations thereof are also specifically contemplated for the methods described herein.

Suitable chemotherapeutic agents for use in combination therapy with the anti-LAP antibodies or antigen binding fragments described herein include, but are not limited to, alkylating agents such as thiotepa and CYTOXAN® cyclosphosphamide; temozolomide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, 111), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin, vinblastine; platinum; etoposide (VP-16); ifosfamide; mitoxantrone; vincristine; NAVELBINE, vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (TYKERB); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

Also suitable for use in combination with the anti-LAP antibodies or antigen binding fragments described herein are drugs targeting epigenetic regulators, such as HDAC inhibitors, bromodomain inhibitors, and E3 ligase (e.g., cereblon) inhibitors (e.g., lenalidomide, pomalidomide, and thalidomide).

Suitable anti-inflammatory agents for use in combination therapy with the anti-LAP antibodies or antigen binding fragments described herein include, but are not limited to, aspirin and other salicylates, Cox-2 inhibitors (e.g., rofecoxib and celecoxib), NSAIDs (such as ibuprofen, fenoprofen, naproxen, sulindac, diclofenac, piroxicam, ketoprofen, diflunisal, nabumetone, etodolac, oxaprozin, and indomethacin), anti-IL6R antibodies, anti-IL8 antibodies, anti-IL15 antibodies, anti-IL15R antibodies, anti-CD4 antibodies, anti-CD11a antibodies (e.g., efalizumab), anti-alpha-4/beta-1 integrin (VLA4) antibodies (e.g., natalizumab), CTLA4-Ig for the treatment of inflammatory diseases, prednisolone, prednisone, disease modifying antirheumatic drugs (DMARDs) such as methotrexate, hydroxychloroquine, sulfasalazine, pyrimidine synthesis inhibitors (e.g., leflunomide), IL-1 receptor blocking agents (e.g., anakinra), TNF-α blocking agents (e.g., etanercept, infliximab, and adalimumab), and the like.

Suitable immunomodulatory agents (e.g., immunostimulatory and immunosuppressive agents) include, but are not limited to, cyclosporine, azathioprine, mycophenolic acid, mycophenolate mofetil, corticosteroids such as prednisone, methotrexate, gold salts, sulfasalazine, antimalarials, brequinar, leflunomide, mizoribine, 15-deoxyspergualine, 6-mercaptopurine, cyclophosphamide, rapamycin, tacrolimus (FK-506), OKT3, anti-thymocyte globulin, thymopentin, thymosin-a, antibodies that bind to p75 of the IL-2 receptor, antibodies that bind to MHC, CD2, CD3, CD4, CD7, CD28, B7, CD40, CD45, IFN-γ, TNF-α, IL-4, IL-5, IL-6R, IL-6, IGF, IGFR1, IL-7, IL-8, IL-10, CD11a, or CD58, or antibodies binding to their ligands, soluble IL-15R, IL-10, B7 molecules (B7-1, B7-2, variants thereof, and fragments thereof), ICOS, OX40, an inhibitor of a negative T cell regulator (such as an antibody against CTLA4), and the like.

Additional immunosuppressive agents include, for example, anti-TNF agents such as etanercept, adalimumab and infliximab, and steroids. Examples of specific natural and synthetic steroids include, for example: aldosterone, beclomethasone, betamethasone, budesonide, cloprednol, cortisone, cortivazol, deoxycortone, desonide, desoximetasone, dexamethasone, difluorocortolone, fluclorolone, flumethasone, flunisolide, fluocinolone, fluocinonide, fluocortin butyl, fluorocortisone, fluorocortolone, fluorometholone, flurandrenolone, fluticasone, halcinonide, hydrocortisone, icomethasone, meprednisone, methylprednisolone, paramethasone, prednisolone, prednisone, tixocortol, and triamcinolone.

Suitable immunostimulatory agents for use in combination therapy with the anti-LAP antibodies or antigen binding fragments described herein include, for example, compounds capable of stimulating antigen presenting cells (APCs), such as dendritic cells (DCs) and macrophages. For example, suitable immunostimulatory agents are capable of stimulating APCs, so that the maturation process of the APCs is accelerated, the proliferation of APCs is increased, and/or the recruitment or release of co-stimulatory molecules (e.g., CD80, CD86, ICAM-1, MHC molecules and CCR7) and pro-inflammatory cytokines (e.g., IL-1β, IL-6, IL-12, IL-15, and IFN-γ) is upregulated. Suitable immunostimulatory agents are also capable of increasing T cell proliferation. Such immunostimulatory agents include, but are not be limited to, CD40 ligand; FLT 3 ligand; cytokines, such as IFN-α, IFN-β, IFN-γ and IL-2; colony-stimulating factors, such as G-CSF (granulocyte colony-stimulating factor) and GM-CSF (granulocyte-macrophage colony-stimulating factor); an anti-CTLA-4 antibody, anti-PD1 antibody, anti-41BB antibody, or anti-OX-40 antibody; LPS (endotoxin); ssRNA; dsRNA; Bacille Calmette-Guerin (BCG); Levamisole hydrochloride; and intravenous immune globulins. In one embodiment an immunostimulatory agent may be a Toll-like Receptor (TLR) agonist. For example the immunostimulatory agent may be a TLR3 agonist such as double-stranded inosine:cytosine polynucleotide (Poly I:C, for example available as Ampligen™ from Hemispherx Bipharma, PA, US or Poly IC:LC from Oncovir) or Poly A:U; a TLR4 agonist such as monophosphoryl lipid A (MPL) or RC-529 (for example as available from GSK, UK); a TLR5 agonist such as flagellin; a TLR7 or TLR8 agonist such as an imidazoquinoline TLR7 or TLR 8 agonist, for example imiquimod (e.g., Aldara™) or resiquimod and related imidazoquinoline agents (e.g., as available from 3M Corporation); or a TLR 9 agonist such as a deoxynucleotide with unmethylated CpG motifs ("CpGs", e.g., as available from Coley Pharmaceutical). In another embodiment, the immunostimulatory molecule is a STING agonist. Such immunostimulatory agents may be administered simultaneously, separately or sequentially with the anti-LAP antibodies or antigen binding fragments described herein.

Suitable immune checkpoint blockers include, but are not limited to, agents (e.g., antibodies) that bind to PD-1, PD-L1, PD-L2, LAG-3, CTLA4, TIGIT, ICOS, OX40, PVR, PVRIG, VISTA, and TIM3. Non-limiting examples of antibodies that bind to PD-1, PD-L1, and PD-L2 include pembrolizumab; nivolumab; MK-3475; MPDL32; MEDI0680; MEDI4736; AMP-224; and MSB0010718C.

In some embodiments, the anti-LAP antibody or antigen binding fragment is administered with an agent that targets a stimulatory or inhibitory molecule that is a member of the immunoglobulin super family (IgSF). For example, the anti-LAP antibodies or antigen binding fragments described herein, may be administered to a subject with an agent that targets a member of the IgSF family to increase an immune response. For example, an anti-LAP antibody or antigen binding fragment may be administered with an agent that targets a member of the B7 family of membrane-bound ligands that includes B7-1, B7-2, B7-H1 (PD-L1), B7-DC (PD-L2), B7-H2 (ICOS-L), B7-H3, B7-H4, B7-H5 (VISTA), and B7-H6 or a co-stimulatory or co-inhibitory receptor binding specifically to a B7 family member.

An anti-LAP antibody or antigen binding fragment may also be administered with an agent that targets a member of the TNF and TNFR family of molecules (ligands or receptors), such as CD40 and CD40L, OX-40, OX-40L, CD70, CD27L, CD30, CD30L, 4-1BBL, CD137, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDA1, EDA2, TNFR1, Lymphotoxin α/TNFβ, TNFR2, TNFα, LTβR, Lymphotoxin a 102, FAS, FASL, RELT, DR6, TROY, and NGFR (see, e.g., Tansey (2009) Drug Discovery Today 00:1).

T cell responses can be stimulated by a combination of anti-LAP antibodies or antigen binding fragments described herein and one or more of the following agents:
  (1) An antagonist (inhibitor or blocking agent) of a protein that inhibits T cell activation (e.g., immune checkpoint inhibitors), such as CTLA-4, PD-1, PD-L1, PD-L2, and LAG-3, as described above, and any of the following proteins: TIM-3, Galectin 9, CEACAM-1, BTLA, CD69, Galectin-1, TIGIT, CD113, CD155, GPR56, VISTA, B7-H3, B7-H4, 2B4, CD48, GARP, PD1H, LAIR1, TIM-1, and TIM-4; and/or
  (2) An agonist of a protein that stimulates T cell activation, such as B7-1, B7-2, CD28, 4-1BB (CD137), 4-1BBL, GITR, ICOS, ICOS-L, OX40, OX40L, CD70, CD27, CD40, DR3 and CD28H.

Exemplary agents that modulate the above proteins and may be combined with the anti-LAP antibodies or antigen binding fragments described herein for treating cancer, include: Yervoy™ (ipilimumab) or Tremelimumab (to CTLA-4), galiximab (to B7.1), BMS-936558 (to PD-1), MK-3475 (to PD-1), AMP224 (to B7DC), BMS-936559 (to B7-H1), MPDL3280A (to B7-H1), MEDI-570 (to ICOS), AMG557 (to B7H2), MGA271 (to B7H3), IMP321 (to LAG-3), BMS-663513 (to CD137), PF-05082566 (to CD137), CDX-1127 (to CD27), anti-OX40 (Providence Health Services), huMAbOX40L (to OX40L), Atacicept (to TACI), CP-870893 (to CD40), Lucatumumab (to CD40), Dacetuzumab (to CD40), Muromonab-CD3 (to CD3), Ipilumumab (to CTLA-4).

Other molecules that can be combined with anti-LAP antibodies or antigen binding fragments for the treatment of cancer include antagonists of inhibitory receptors on NK cells or agonists of activating receptors on NK cells. For example, anti-LAP antibodies or antigen binding fragments can be combined with antagonists of KIR (e.g., lirilumab).

T cell activation is also regulated by soluble cytokines, and anti-LAP antibodies may be administered to a subject, e.g., having cancer, with antagonists of cytokines that inhibit T cell activation or agonists of cytokines that stimulate T cell activation.

In certain embodiments, anti-LAP antibodies or antigen binding fragments can be used in combination with (i) antagonists (or inhibitors or blocking agents) of proteins of the IgSF family or B7 family or the TNF family that inhibit T cell activation or antagonists of cytokines that inhibit T cell activation (e.g., IL-6, IL-10, TGF-β, VEGF; "immunosuppressive cytokines") and/or (ii) agonists of stimulatory receptors of the IgSF family, B7 family or the TNF family or of cytokines that stimulate T cell activation, for stimulating an immune response, e.g., for treating proliferative diseases, such as cancer.

Yet other agents for combination therapies include agents that inhibit or deplete macrophages or monocytes, including but not limited to CSF-1R antagonists such as CSF-1R antagonist antibodies including RG7155 (see PCT publication numbers WO11/70024, WO11/107553, WO11/131407, WO13/87699, WO13/119716, and WO13/132044) or FPA-008 (see PCT publication numbers WO11/140249; WO13169264; and WO14/036357).

Additional agents that may be combined with anti-LAP antibodies or antigen binding fragments include agents that enhance tumor antigen presentation, e.g., dendritic cell vaccines, GM-CSF secreting cellular vaccines, CpG oligonucleotides, and imiquimod, or therapies that enhance the immunogenicity of tumor cells (e.g., anthracyclines).

Another therapy that may be combined with anti-LAP antibodies is a therapy that inhibits a metabolic enzyme such as indoleamine dioxygenase (IDO), tryptophan-2,3-dioxygenase, dioxygenase, arginase, or nitric oxide synthetase.

Another class of agents that may be used with anti-LAP antibodies includes agents that inhibit the formation of adenosine or inhibit the adenosine A2A receptor, for example, anti-CD73 antibodies, anti-CD39 antibodies, and adenosine A2A/A2b inhibitors.

Other therapies that may be combined with anti-LAP antibodies or antigen binding fragments for treating cancer include therapies that reverse/prevent T cell anergy or exhaustion and therapies that trigger an innate immune activation and/or inflammation at a tumor site.

The anti-LAP antibodies or antigen binding fragments may be combined with a combinatorial approach that targets multiple elements of the immune pathway, such as one or more of the following: a therapy that enhances tumor antigen presentation (e.g., dendritic cell vaccine, GM-CSF secreting cellular vaccines, CpG oligonucleotides, imiquimod); a therapy that inhibits negative immune regulation e.g., by inhibiting CTLA-4 and/or PD1/PD-L1/PD-L2 pathway and/or depleting or blocking regulatory T cells or other immune suppressing cells; a therapy that stimulates positive immune regulation, e.g., with agonists that stimulate the CD-137 and/or GITR pathway and/or stimulate T cell effector function; a therapy that increases systemically the frequency of anti-tumor T cells; a therapy that depletes or inhibits regulatory T cells using an antagonist of CD25 (e.g., daclizumab) or by ex vivo anti-CD25 bead depletion; a therapy that impacts the function of suppressor myeloid cells in the tumor; a therapy that enhances immunogenicity of tumor cells (e.g., anthracyclines); cell therapy with adoptive T cell or NK cell transfer including genetically modified cells, e.g., cells modified by chimeric antigen receptors (CAR-T therapy); a therapy that inhibits a metabolic enzyme such as indoleamine dioxygenase (IDO), dioxygenase, arginase, or nitric oxide synthetase; a therapy that reverses/prevents T cell anergy or exhaustion; a therapy that triggers an innate immune activation and/or inflammation at a tumor site; administration of immune stimulatory cytokines; or blocking of immunosuppressive or immunorepressive cytokines.

The anti-LAP antibodies or antigen binding fragments described herein can be combined with proinflammatory cytokines, for example, IL-12 and IL-2. These cytokines can be modified to enhance half-life and tumor targeting.

The anti-LAP antibodies or antigen binding fragments described herein can be combined with immune cell engagers such as NK cell engagers or T cell engagers.

The anti-LAP antibodies or antigen binding fragments described herein can be combined with indoleamine dioxygenase (IDO) inhibitors, tryptophan-2,3-dioxygenase (TDO) inhibitors, and dual IDO/TDO inhibitors.

The anti-LAP antibodies or antigen binding fragments described herein can be combined with kynurine inhibitors.

The anti-LAP antibodies or antigen binding fragments described herein can be combined with CD47 and/or SIRPa blocking therapies.

The anti-LAP antibodies or antigen binding fragments described herein can be combined with JAK inhibitors and JAK pathway inhibitors (e.g., STAT3 inhibitors), e.g., for the treatment of myelofibrosis and myeloproliferative neoplasms.

The anti-LAP antibodies or antigen binding fragments described herein can be combined with DNA damage repair inhibitors.

The anti-LAP antibodies or antigen binding fragments described herein can be combined with erythropoietin and drugs that stimulate hematopoiesis.

The anti-LAP antibodies or antigen binding fragments described herein can be combined with angiogenesis inhibitors.

The anti-LAP antibodies or antigen binding fragments described herein can be combined with anti-viral drugs, such as neuramidase inhibitors.

Bispecific antibodies which have a first binding region with the specificity of the anti-LAP antibodies or antigen binding fragments described herein and a second binding region which binds to an immune checkpoint blocker (e.g., PD-1, PD-L1) can be used in combination with at least one additional anti-cancer agent (e.g., radiation, chemotherapeutic agents, biologics, vaccines) to inhibit tumor growth.

The anti-LAP antibodies or antigen binding fragments described herein can be combined with one or more immunostimulatory antibodies, such as an anti-PD-1 antagonist antibody, an anti-PD-L1 antagonist antibody, an antagonist anti-CTLA-4 antibody, an antagonistic anti-TIM3 antibody, and/or an anti-LAG3 antagonist antibody, such that an immune response is stimulated in the subject, for example to inhibit tumor growth.

Exemplary anti-PD-1 antibodies include nivolumab, pembrolizumab(also known as MK-3475, Lambrolizumab) described in WO2012/145493; AMP-514 described in WO 2012/145493, as well as PD-1 antibodies and other PD-1 inhibitors described in WO 2009/014708, WO 03/099196, WO 2009/114335, WO 2011/066389, WO 2011/161699, WO 2012/145493, U.S. Pat. Nos. 7,635,757 and 8,217,149, and U.S. Patent Publication No. 2009/0317368.

Exemplary anti-PD-L1 antibodies include MEDI4736 (also known as Anti-B7-H1), MPDL3280A (also known as RG7446), MSB0010718C (WO2013/79174), rHigM12B7, as well as any of the anti-PD-L1 antibodies disclosed in WO2013/173223, WO2011/066389, WO2012/145493, U.S. Pat. Nos. 7,635,757 and 8,217,149 and U.S. Publication No. 2009/145493.

Exemplary anti-CTLA-4 antibodies include Yervoy™ (ipilimumab), tremelimumab (formerly ticilimumab, CP-675,206), or an anti-CTLA-4 antibody described in any of the following publications: WO 98/42752; WO 00/37504; U.S. Pat. No. 6,207,156; Hurwitz et al. (1998) Proc. Natl. Acad. Sci. USA 95(17):10067-10071; Camacho et al. (2004) J. Clin. Oncology 22(145): Abstract No. 2505 (antibody CP-675206); and Mokyr et al. (1998) Cancer Res. 58:5301-5304.

Exemplary anti-LAG3 antibodies include IMP731 and IMP-321, described in US Publication No. 2011/007023, and PCT publication numbers WO08/132601, and WO09/44273, as well as antibodies described in U.S. Patent Publication No. US2011/0150892, and international patent publication numbers WO10/19570 and WO2014/008218.

Anti-LAP antibodies or antigen binding fragments can also be combined with immune-oncology agents such as CD137 (4-1BB) agonists (e.g., an agonistic CD137 antibody such as urelumab or PF-05082566 (see PCT publication number WO12/32433)); GITR agonists (e.g., an agonistic anti-GITR antibody), CD40 agonists (e.g., an agonistic CD40 antibody); CD40 antagonists (e.g., an antagonistic CD40 antibody such as lucatumumab (HCD122), dacetuzumab (SGN-40), CP-870,893 or Chi Lob 7/4); CD27 agonists (e.g., an agonistic CD27 antibody such as varlilumab (CDX-1127)), MGA271 (to B7H3) (WO11/109400)); KIR antagonists (e.g., lirilumab); IDO antagonists (e.g., INCB-024360 (WO2006/122150, WO07/75598, WO08/36653, WO08/36642), indoximod, NLG-919 (WO09/73620, WO09/1156652, WO11/56652, WO12/142237) or F001287); Toll-like receptor agonists (e.g., TLR2/4 agonists (e.g., Bacillus Calmette-Guerin); TLR7 agonists (e.g., Hiltonol or Imiquimod); TLR7/8 agonists (e.g., Resiquimod); or TLR9 agonists (e.g., CpG7909)); and TGF-β inhibitors (e.g., GC1008, LY2157299, TEW7197, or IMC-TR1).

The anti-LAP antibodies or antigen binding fragments described herein can also be combined with an immunogenic agent, such as cancerous cells, purified tumor antigens (including recombinant proteins, peptides, and carbohydrate molecules), cells, and cells transfected with genes encoding immune stimulating cytokines (He et al. (2004) J. Immunol. 173:4919-28). Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF (discussed further below).

The anti-LAP antibodies or antigen binding fragments described herein can also be combined with an anti-neoplastic antibody, such as Rituxan® (rituximab), Herceptin® (trastuzumab), Bexxar® (tositumomab), Zevalin® (ibritumomab), Campath® (alemtuzumab), Lymphocide® (epratuzumab), Avastin® (bevacizumab), and Tarceva® (erlotinib), and the like.

Several experimental treatment protocols involve ex vivo activation and expansion of antigen specific T cells and adoptive transfer of these cells into recipients in order to antigen-specific T cells against tumor (Greenberg & Riddell, supra). Ex vivo activation in the presence of the anti-LAP antibodies described herein with or without an additional immunostimulating therapy (e.g., an immune checkpoint blocker) can be expected to increase the frequency and activity of the adoptively transferred T cells.

The anti-LAP antibody or antigen binding fragment may also be administered with a standard of care treatment, or another treatment, such as radiation, surgery, or chemotherapy. The anti-LAP antibody or antigen binding fragment may be combined with a vaccination protocol. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sci U.S.A. 90: 3539-43).

Dendritic cells (DC) are potent antigen presenting cells that can be used to prime antigen-specific responses. DC's can be produced ex vivo and loaded with various protein and peptide antigens as well as tumor cell extracts (Nestle et al. (1998) Nature Medicine 4: 328-332). DCs can also be transduced by genetic means to express these tumor antigens as well. DCs have also been fused directly to tumor cells for the purposes of immunization (Kugler et al. (2000) *Nature Medicine* 6:332-336). As a method of vaccination, DC immunization can be effectively combined with the anti-LAP antibodies or antigen binding fragments described herein to activate more potent anti-tumor responses.

In some embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially.

X. Kits

Also provided are kits comprising the anti-LAP antibodies or antigen binding fragments, multispecific molecules, or immunoconjugates disclosed herein, optionally contained in a single vial or container, and include, e.g., instructions for use in treating or diagnosing a disease (e.g., cancer). The kits may include a label indicating the intended use of the contents of the kit. The term label includes any writing, marketing materials or recorded material supplied on or with the kit, or which otherwise accompanies the kit. Such kits may comprise the antibody, multispecific molecule, or immunoconjugate in unit dosage form, such as in a single dose vial or a single dose pre-loaded syringe.

The present disclosure is further illustrated by the following examples, which should not be construed as further limiting. The contents of all figures and all references, Genbank sequences, patents, and published patent applications cited throughout this application are expressly incorporated herein by reference.

EXAMPLES

Commercially available reagents referred to in the Examples below were used according to manufacturer's instructions unless otherwise indicated. Unless otherwise noted, the present invention uses standard procedures of recombinant DNA technology, such as those described hereinabove and in the following textbooks: Sambrook et al., supra; Ausubel et al., *Current Protocols in Molecular Biology* (Green Publishing Associates and Wiley Interscience, N.Y., 1989); Innis et al., *PCR Protocols: A Guide to Methods and Applications* (Academic Press, Inc.: N.Y., 1990); Harlow et al., *Antibodies: A Laboratory Manual* (Cold Spring Harbor Press: Cold Spring Harbor, 1988); Gait, *Oligonucleotide Synthesis* (IRL Press: Oxford, 1984); Freshney, *Animal Cell Culture*, 1987; Coligan et al., *Current Protocols in Immunology*, 1991.

The following Examples describe the characterization of anti-LAP antibodies 28G11, 22F9, 20E6 (also referred to as 26E10), 17G8, and 24E3, which were generated by immunizing TGFβ1 knock-out mice with mouse TGFβ1, as described in Oida et al. (*PLoS One* 2010; 5(11):e15523). The CDR sequences, variable region sequences, and full-length heavy and light chain sequences of anti-LAP antibodies 28G11, 22F9, 20E6, 17G8, and 24E3 are provided in Table 34. These antibodies were prepared in murine antibody format with an mIgG2a constant region, chimeric format with a human IgG constant region, and/or in humanized format.

To generate the antibodies with mIgG2a constant regions, the variable region sequences of each antibody were fused to a murine IgG2a constant region. The murine VH domains were fused to a codon-optimized gene for the murine IgG2a constant domains (UniProt accession # P01863) using overlap extension PCR. The murine VL domains were fused to a codon-optimized gene for the murine kappa constant domain (UniProt accession # P01837) using overlap extension PCR. The complete heavy-chain and light-chain sequences were individually TOPO-TA cloned into pcDNA3.4 for expression in ExpiCHO cells.

To generate the antibodies in chimeric format, the variable region sequences of the murine parental clones were fused to the human IgG1 constant region sequences. The murine VH domains were fused to a codon-optimized gene for the human IgG1 constant domains (UniProt accession # P01857) using overlap extension PCR. The murine VL domains were fused to a codon-optimized gene for the human kappa constant domain (UniProt accession # P01834) using overlap extension PCR. The complete heavy-chain and light-chain sequences were individually TOPO-TA cloned into pcDNA3.4 for expression in ExpiCHO cells.

Details regarding the humanization of the antibodies are described in Examples 8-11.

The designation of antibodies will follow the format described in Table 2.

TABLE 2

| Designation | Description |
| --- | --- |
| Antibody clone_(hyb) (e.g., 28G11_(hyb)) | Parental murine antibody |
| Antibody_mIgG2a (e.g., 28G11_IgG2a) | Murine variable region of parental antibody fused to murine IgG2a constant region |
| Antibody_hIgG1 (e.g., 28G11_hIgG1) | Chimeric antibody with murine variable region of parental antibody and human IgG1 constant region |
| Antibody_H(X)L(Y) (e.g., 28G11_H2L3) | Humanized antibody with X referring to particular humanized heavy chain and Y referring to particular humanized light chain |

Example 1: Binding of Anti-LAP Antibodies to Human and Murine LAP-TGFβ1

This Example describes the ability of anti-LAP antibodies 28G11_hIgG1, 22F9_hIgG1, and 20E6_hIgG1 to bind to human and murine LAP-TGFβ1 using bio-layer interferometry.

The chimeric antibodies were biotinylated using EZ-Link SulfoNHS-LC-Biotin (ThermoFisher). A streptavidin-functionalized tip was equilibrated in binding buffer (10 mM sodium phosphate, 150 mM sodium chloride, 1% (w/v) bovine serum albumin, 0.05% (w/v) sodium azide, pH 7.4). The tip was dipped in a 10 μg/mL solution of biotinylated, chimeric anti-LAP in binding buffer for 15 seconds to load the tip with antibody. The antibody-loaded tip was then washed in binding buffer and placed in a solution containing 0-24 nM of LAP-TGFβ1 (either a fusion protein containing a human IgG1 Fc domain fused to human LAP-TGFβ1 or a murine LAP-TGFβ1 with a C-terminal polyhistidine purification tag). The antigen was allowed to bind to antibody for 5 minutes (association phase), and then the tip was moved to binding buffer (dissociation phase). The association and dissociation phases were fit to a 1:1 binding model to determine the binding rate constants.

As shown in Table 3, 28G11_hIgG1, 22F9_hIgG1, and 20E6_hIgG1 bind with sub-nanomolar affinity to both human and murine LAP-TGFβ1. These data demonstrate that the antibodies bind to human and murine LAP-TGFβ1 in the absence of an anchor protein.

TABLE 1

| Antibody | $k_{on}$ (×10$^6$ M$^{-1}$s$^{-1}$) | $k_{off}$ (×10$^4$ s$^{-1}$) | $K_D$ (nM) |
|---|---|---|---|
| Mouse LAP-TGFβ1 | | | |
| 28G11_hIgG1 | 0.84 | 1.58 | 0.19 |
| 22F9_hIgG1 | 1.21 | 4.44 | 0.37 |
| 20E6_hIgG1 | 1.39 | 5.01 | 0.36 |
| Human LAP-TGFβ1 | | | |
| 28G11_hIgG1 | 0.54 | 3.60 | 0.67 |
| 22F9_hIgG1 | 1.01 | 7.68 | 0.76 |
| 20E6_hIgG1 | 1.04 | 6.06 | 0.58 |

Example 2: Binding of Anti-LAP Antibodies to LAP-TGFβ Isoforms and LAP-TGFβ Variants This Example describes the binding of anti-LAP antibodies to LAP-TGFβ isoforms and LAP-TGFβ variants. In addition to antibodies 28G11_hIgG1, 22F9_hIgG1, and 20E6_hIgG1, anti-LAP antibodies 17G8_hIgG1, 24E3_hIgG1, and 2C9_(hyb) were also tested in this experiment. Briefly, 4×10$^5$ each of (a) HT1080 cells, (b) HT1080 cells overexpressing human LAP-TGFβ1, (c) HT1080 cells overexpressing human LAP-TGFβ2, (d) HT1080 cells overexpressing human LAP-TGFβ3, (e) HT1080 cells overexpressing murine LAP-TGFβ1, (f) P3U1 cells, (g) P3U1 cells overexpressing LAP-TGFβ1 and GARP, and (h) P3U1 cells overexpressing LAP-TGFβ1 and LRRC33 were cultured in 96-well plates. The plates were centrifuged for 5 min at 1,500 rpm, liquid was removed, and cells were resuspended with 200 μL FACS buffer. The plates were centrifuged again, diluted primary antibody was added to each well, and the plates were incubated on ice for 20 minutes, followed by centrifugation. The cells were resuspended in 200 μL FACS buffer, centrifuged again, and resuspended in 50 μL diluted secondary antibody (Alexa647-anti-Human IgG or APC-anti-Mouse IgG). The plates were incubated on ice for 20 minutes in the dark, washed twice with 200 μL FACS buffer, and cells from each well (in 200 μL FACS buffer) were read on the Attune NXT instrument.

As shown in FIGS. 1A-1F, all tested antibodies bind to HT1080 cell lines overexpressing human LAP-TGFβ1, but not to control HT1080 cells or cells overexpressing human LAP-TGFβ2 or LAP-TGFβ3. All tested antibodies bind to P3U1-hTGFβ1 cells, and the binding was enhanced when either human GARP or LRRC33 was co-expressed. Antibodies 28G11_hIgG1, 22F9_hIgG1, 20E6_hIgG1, 17G8_hIgG1, and 24E3_hIgG1, but not 2C9_(hyb), bind to HT1080 cells overexpressing mouse LAP-TGFβ1. These results indicate that antibodies 28G11_hIgG1, 22F9_hIgG1, 20E6_hIgG1, 17G8_hIgG1, and 24E3_hIgG1 bind specifically to the LAP-TGFβ1 isoform of TGFβ.

The ability of the anti-LAP antibodies to bind variants of TGFβ1 that either prevent TGFβ1 activation by integrins ("closed" conformation) or favor release ("open" conformation), chimeric TGFβ1 sequences containing residues from chicken TGFβ1, and the LAP-only TGFβ1 variant (i.e., human TGFβ1 variant which does not contain the mature cytokine) was tested.

Briefly, 4×10$^5$ each of (a) HT1080 cells, (b) HT1080 cells overexpressing human LAP-TGFβ1, (c) HT1080 cells overexpressing LAP-TGFβ1 with K27C and Y75C mutations, (d) HT1080 cells overexpressing LAP-TGFβ1 with a Y74T mutation, (e) HT1080 cells overexpressing chimeric LAP-TGFβ1 in which exon 2.3 (residues 131-164) of human LAP-TGFβ1 have been replaced with corresponding residues from chicken LAP-TGFβ1 (UniProt accession # H9CX01), (f) HT1080 cells overexpressing chimeric LAP-TGFβ1 in which exon 4 (residues 183-208) of human LAP-TGFβ1 has been replaced with exon 4 from chicken LAP-TGFβ1, (g) HT1080 cells overexpressing chimeric LAP-TGFβ1 in which exon 2.2 (residues 108-130) of human LAP-TGFβ1 has been replaced with exon 2.2 from chicken LAP-TGFβ1, and (h) HT1080 cells overexpressing the LAP-only variant (i.e., "empty LAP") were cultured in 96-well plates. Cells were processed for flow cytometry in the same manner described above for the isoform-specific binding experiments.

As shown in FIGS. 2A-2F, while none of the tested anti-LAP antibodies bind to untransduced HT1080 cells, all tested antibodies bind to HT1080 cells overexpressing wild-type human LAP-TGFβ1. Antibodies 28G11_hIgG1, 22F9_hIgG1, 20E6_hIgG1, 17G8_hIgG1, and 24E3_hIgG1 bind to the K27C/Y75C ("closed") LAP-TGFβ1 variant, but not to the Y74T ("open") LAP-TGFβ1 variant. In contrast, antibody 2C9_(hyb) binds to both the K27C/Y75C and Y74T LAP-TGFβ1 variants. Antibodies 28G11_hIgG1, 22F9_hIgG1, 20E6_hIgG1, 17G8_hIgG1, and 24E3_hIgG1, but not 2C9_(hyb), bind to chimeric LAP-TGFβ1 containing chicken exons #2.3 and #4. Furthermore, as shown in FIGS. 3A-3F, while all tested antibodies bind to HT1080 cells overexpressing wild-type human LAP-TGFβ1, antibodies 28G11_hIgG1, 22F9_hIgG1, 20E6_hIgG1, 17G8_hIgG1, and 24E3_hIgG1 did not bind to the LAP-only variant or to chimeric LAP-TGFβ1 containing chicken exon #2.2.

Figure 4:
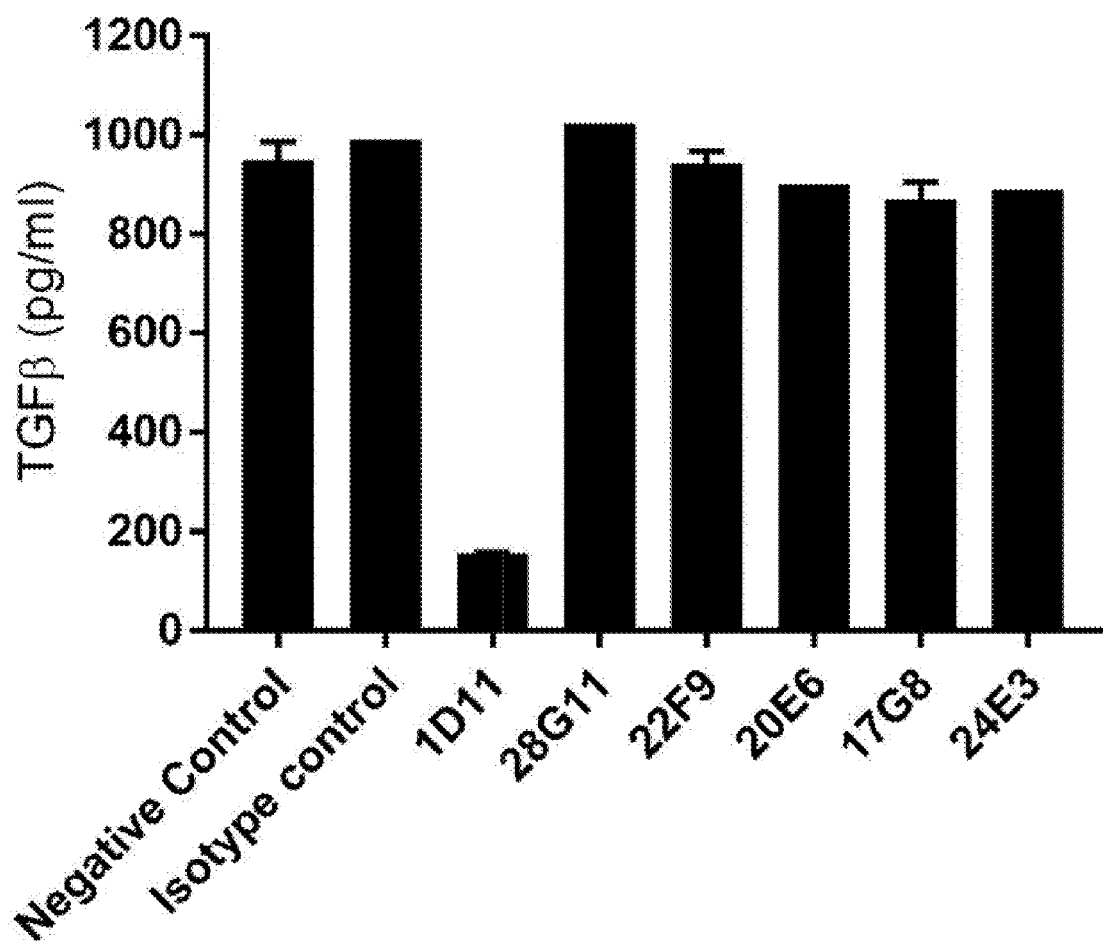
FIG. 4 is a graph showing the binding of antibodies 28G11_hIgG1, 22F9_hIgG1, 20E6_hIgG1, 17G8_hIgG1, 24E3_hIgG1, and 1D11 to mature TGFβ (i.e., TGFβ without LAP), as measured by an ELISA assay in which inhibition of signal reflects binding to mature TGFβ.
Figure 5A:
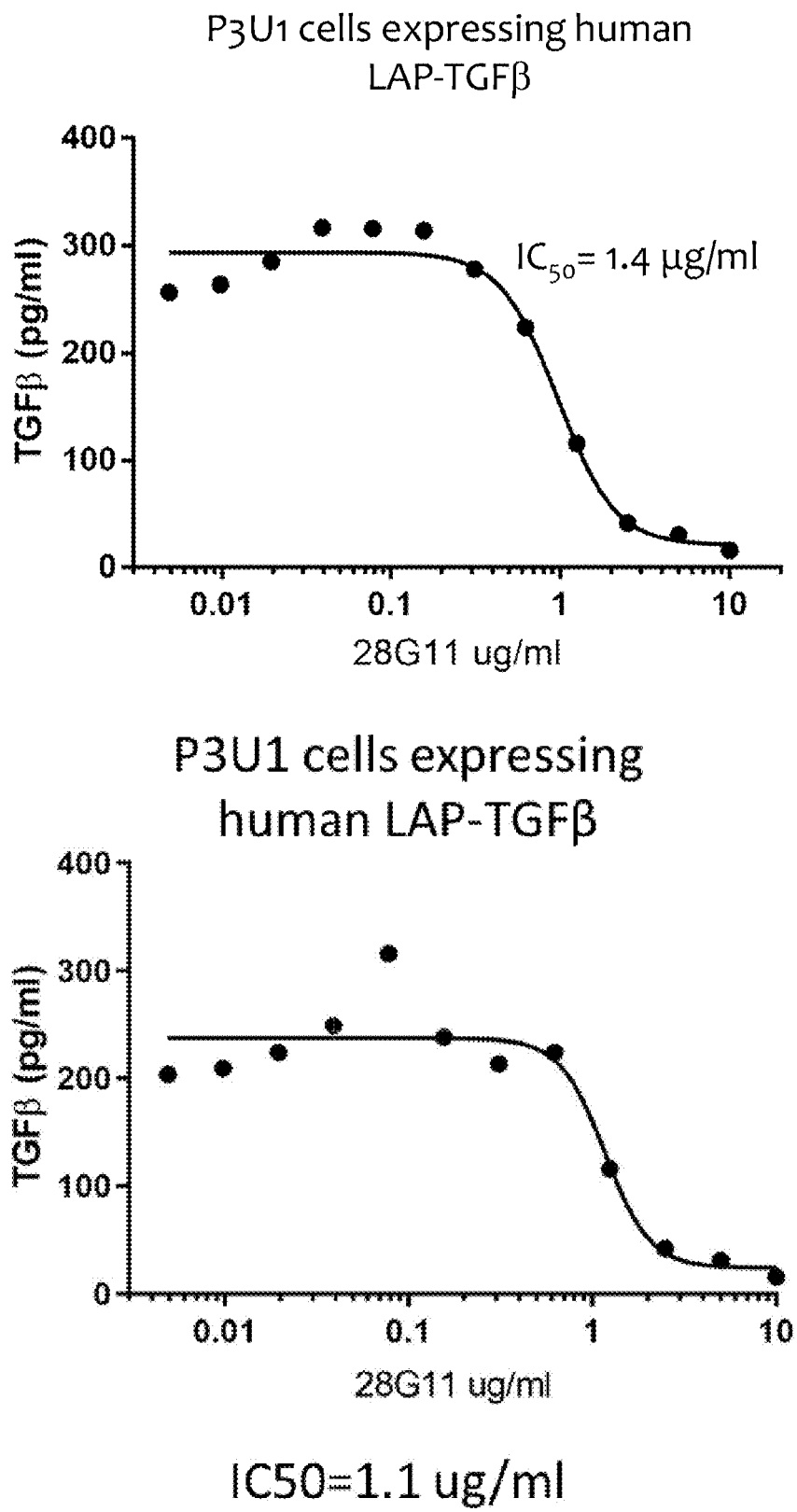

To determine whether anti-LAP antibodies 28G11_hIgG1, 22F9_hIgG1, 20E6_hIgG1, 17G8_hIgG1, and 24E3_hIgG1, bind to free human TGFβ1 (i.e., mature TGFβ1 that lacks LAP), the ability of the antibodies to inhibit an anti-TGFβ ELISA was evaluated. Briefly, mature TGFβ1 (1000 pg) was incubated with the indicated anti-LAP antibodies at 10m/mL, an isotype control antibody as a negative control or the commercially available anti-TGFβ antibody 1D11 as a positive control for 10 minutes on ice. For example, the 1D11 antibody is commercially available from any number of sellers, for example Bio x Cell Inc. (West Lebanon, N.H.). Supernatants were assayed in a TGFβ1 ELISA (R&D Systems) according to the manufacturer instructions to measure free TGFβ1. As shown in FIG. 4, the anti-TGFβ antibody 1D11 bound to the mature TGFβ and inhibited the ELISA, while no inhibition was seen with 28G11_hIgG1, 22F9_hIgG1, 20E6_hIgG1, 17G8_hIgG1, and 24E3_hIgG1. These data demonstrate that 28G11_hIgG1, 22F9_hIgG1, 20E6_hIgG1, 17G8_hIgG1, and 24E3_hIgG1 antibodies do not bind to mature TGFβ1 that lacks LAP. Note that Figure and FIG. are used interchangeably in this application.

In summary, these results suggest that antibodies 28G11_hIgG1, 22F9_hIgG1, 20E6_hIgG1, 17G8_hIgG1, and 24E3_hIgG1 share a related epitope. All anti-LAP antibodies tested bind to HT1080 cells overexpressing wild-type human LAP-TGFβ1 (HT1080-hβ1), but not to untransduced HT1080 cells. Antibodies 28G11_hIgG1, 22F9_hIgG1, 20E6_hIgG1, 17G8_hIgG1, and 24E3_hIgG1 did not bind to the LAP-only construct or the chimera containing chicken exon #2.2. Antibody 2C9_(hyb) binds to both the LAP-only construct, but not to the exon #2.2 chimera. This compilation of data indicates that antibodies 28G11_hIgG1, 22F9_hIgG1, 20E6_hIgG1, 17G8_hIgG1, and 24E3_hIgG1 only bind to LAP that contains the mature cytokine, and this is supported by the results shown in FIG. 4. However, chimeras with chicken exons #6 and #7, which encompass the mature cytokine, were bound by 28G11_hIgG1 (data not shown), initially suggesting that 28G11_hIgG1, 22F9_hIgG1, 20E6_hIgG1, 17G8_hIgG1, and 24E3_hIgG1 do not bind the mature cytokine directly, but rather are sensitive to conformational changes in the LAP region induced by the presence or absence of the mature cytokine. In contrast, 2C9 binds to all variants of LAP, including the "open" and "closed" conformation variants, as well as LAP in the presence or absence of the mature cytokine.

The binding epitope for 28G11 was mapped by assessing binding of cell-surface chimeric human/chicken LAP-TGFβ1 molecules using flow cytometry. The use of these binding data to determine epitopes was based on the following assumptions:

1. Anti-LAP antibodies will not bind to chicken LAP-TGFβ sequence
2. Human/chicken chimeras are expressed and displayed properly on the cell surface
3. If an anti-LAP antibody does bind to a chimera, none of the residues in that exon are part of the epitope.
4. If an anti-LAP antibody does not bind to a chimera, at least one residue in that exon is part of the epitope, or the presence of chicken sequence in that exon causes a conformational change in another part of LAP-TGFβ that disrupts the epitope.

Chimeric LAP-TGFβ1 molecules were made by replacing individual exons in human LAP-TGFβ1 with the homologous chicken LAP-TGFβ1 sequence (Table 4). Human and chicken LAP-TGFβ1 share ~50% sequence identity. The amino acid sequences of the tested LAP-TGFβ1 sequences are shown in Table 34.

TABLE 4

LAP-TGFβ1 sequences used for epitope mapping

| SEQ ID | Name | Description |
|---|---|---|
| 1 | human LAP-TGFβ1 (huB1) | Wild-type human LAP-TGFβ1 sequence |
| 198 | chicken LAP-TGFβ1 (chB1) | Wild-type chicken LAP-TGFβ1 sequence |
| 199 | chimera #1 | chimeric LAP-TGFβ1 in which exon 1 (residues 1-89) of human LAP-TGFβ1 has been replaced with exon 1 from chicken LAP-TGFβ1 |
| 200 | chimera #1.2 | chimeric LAP-TGFβ1 in which exon 1.2 (residues 30-50) of human LAP-TGF+62 1 has been replaced with exon 1.2 from chicken LAP-TGFβ1 |
| 201 | chimera #1.3 | chimeric LAP-TGFβ1 in which exon 1.3 (residues 51-81) of human LAP-TGFβ1 has been replaced with exon 1.3 from chicken LAP-TGFβ1 |
| 202 | chimera #2 | chimeric LAP-TGFβ1 in which exon 2 (residues 90-143) of human LAP-TGFβ1 has been replaced with exon 2 from chicken LAP-TGFβ1 |
| 203 | chimera #2.1 | chimeric LAP-TGFβ1 in which exon 2.1 (residues 82-107) of human LAP-TGFβ1 has been replaced with exon 2.1 from chicken LAP-TGFβ1 |
| 204 | chimera #2.2 | chimeric LAP-TGFβ1 in which exon 2.2 (residues 108-130) of human LAP-TGFβ1 has been replaced with exon 2.2 from chicken LAP-TGFβ1 |
| 205 | chimera #2.3 | chimeric LAP-TGFβ1 in which exon 2.3 (residues 131-164) of human LAP-TGFβ1 have been replaced with corresponding residues from chicken LAP-TGFβ1 |
| 206 | chimera #3 | chimeric LAP-TGFβ1 in which exon 3 (residues 144-182) of human LAP-TGFβ1 have been replaced with corresponding residues from chicken LAP-TGFβ1 |
| 207 | chimera #4 | chimeric LAP-TGFβ1 in which exon 4 (residues 183-208) of human LAP-TGFβ1 has been replaced with exon 4 from chicken LAP-TGFβ1 |
| 208 | chimera #5 | chimeric LAP-TGFβ1 in which exon 5 (residues 209-257) of human LAP-TGFβ1 have been replaced with corresponding residues from chicken LAP-TGFβ1 |
| 209 | chimera #6 | chimeric LAP-TGFβ1 in which exon 6 (residues 258-309) of human LAP-TGFβ1 have been replaced with corresponding residues from chicken LAP-TGFβ1 |
| 210 | chimera #7 | chimeric LAP-TGFβ1 in which exon 7 (residues 310-361) of human LAP-TGF+62 1 have been replaced with corresponding residues from chicken LAP-TGFβ1 |

These constructs were subcloned into lentivirus and transduced into HT1080 cells. Successful gene integration was confirmed by expression of a green fluorescent protein (GFP) reporter gene. LAP-TGFβ1 expression was evaluated by flow cytometry using a rabbit monoclonal antibody (Rmab) raised against a peptide from the mature cytokine (residues 250-361) domain (Abcam cat # ab179695), 28G11_(hyb) and 2C9_(hyb). Briefly, $4 \times 10^5$ each of (a) HT1080 cells, (b) HT1080 cells overexpressing human LAP-TGFβ1, (c) HT1080 cells overexpressing chicken LAP-TGFβ1, and (d) HT1080 cells overexpressing human/chicken chimeras #1-#7 were cultured in 96-well plates. The plates were centrifuged for 5 min at 1,500 rpm, liquid was removed, and cells were resuspended with 200 μL FACS buffer. The plates were centrifuged again, diluted primary antibody was added to each well, and the plates were incubated on ice for 20 minutes, followed by centrifugation. The cells were resuspended in 200 μL FACS buffer, centrifuged again, and resuspended in 50 μL diluted secondary antibody (APC-anti-Mouse IgG). The plates were incubated on ice for 20 minutes in the dark, washed twice with 200 μL FACS buffer, and cells from each well (in 200 μL FACS buffer) were read on the Attune NXT instrument. The antibodies were considered to be binding if >10% of cells were GFP+/APC+ and there was visible correlation between the GFP and allophycocyanin (APC) signals (Table 5).

TABLE 5

% GFP +/APC + cells by flow cytometry

| HT1080 Variant | Rmab | 28G11 (hyb) | 2C9 (hyb) |
|---|---|---|---|
| null | 0.7% | 0.0% | 0.0% |
| huB1 | 68.9% | 98.3% | 72.4% |
| chB1 | 0.5% | 0.3% | 1.1% |
| chimera #1 | 7.5% | 0.2% | 7.6% |
| chimera #1.2 | 78.3% | 84.1% | 81.8% |
| chimera #1.3 | 65.2% | 83.0% | 82.6% |
| chimera #2 | 1.5% | 0.2% | 4.1% |
| chimera #2.1 | 79.1% | 3.5% | 5.6% |
| chimera #2.2 | 47.2% | 0.5% | 0.2% |
| chimera #2.3 | ND | 94.7% | 0.3% |
| chimera #3 | 46.3% | 32.2% | 34.0% |
| chimera #4 | 56.2% | 76.2% | 2.8% |
| chimera #5 | 11.9% | 41.7% | 4.0% |
| chimera #6 | 76.7% | 84.9% | 87.6% |
| chimera #7 | 0.6% | 44.4% | 63.9% |

All three antibodies bound to the positive control HT1080 cell line overexpressing human LAP-TGFβ1. No binding was observed with the negative control strain (HT1080-null). None of the antibodies bound chicken LAP-TGFβ1, indicating that the sequence differences between human and chicken homologues were sufficient to disrupt the epitopes recognized by these antibodies. Chimeras #1 and #2 were not recognized by any antibody, suggesting that these constructs were not efficiently expressed. To test this hypothesis, smaller portions of chicken sequence were inserted into exon #1 or #2 in the human sequence (chimeras #1.2, 1.3, 2.1, 2.2, and 2.3). The constructs with these smaller replacements were recognized by the Rmab antibody, indicating that they were robustly expressed in HT1080 cells. Chimera #7 was not bound by the Rmab antibody, but was recognized by both 28G11_(hyb) and 2C9_(hyb), showing that this construct is expressed on the cell surface, and that the epitope for Rmab is likely in this region of the protein.

The 28G11 (hyb) antibody bound to chimeras #1.2, 1.3, 2.3, 3, 4, 5, 6 and 7, indicating that those regions are not involved in the epitope for this antibody. In contrast, chimeras #2.1 and #2.2 were not bound by 28G11 (hyb), suggesting that this antibody binds to human LAP-TGFβ1 within the sequence VLMVETHNEIYDKFKQSTHSIYMFFNTSELREAVPEPVLLSRAE (SEQ ID NO: 215).

The 2C9_(hyb) binding was disrupted by the chicken residues present in chimeras #2.1, 2.2, 2.3, 4 and 5. This suggests that this antibody binds to a discontinuous epitope that incorporates portions of each of these insertions that are distant in sequence, but adjacent in the three-dimensional structure of the antigen.

Example 3. Generation of Antibodies Binding to Specific Epitopes of Interest on LAP-TGFβ1

Figure 6A:
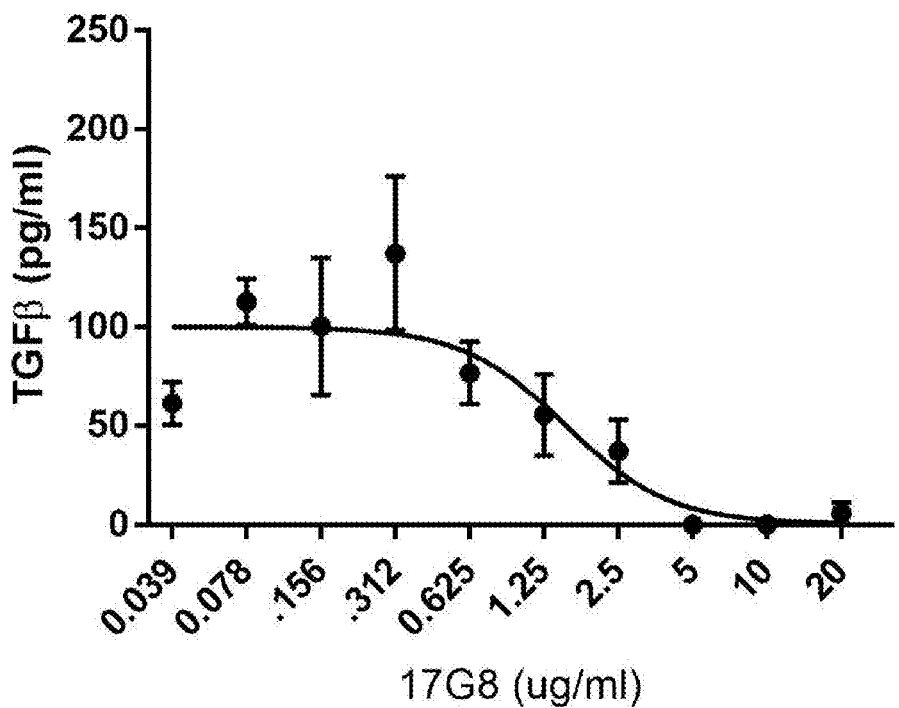
FIGS. 6A-6F are graphs showing the effects of antibodies) 17G8 (FIG. 6A for human LAP-TGFβ1 and FIG. 6B for mouse LAP-TGFβ1), 24E3 (FIG. 6C for human LAP-TGFβ1 and FIG. 6D for murine LAP-TGFβ1), 22F9 (FIG. 6E for human LAP-TGFβ1), 20E6 (FIG. 6F for human LAP-TGFβ1 on TGFβ1 activation in P3U1 cells expressing human or mouse LAP-TGFβ1.
Figure 6B:
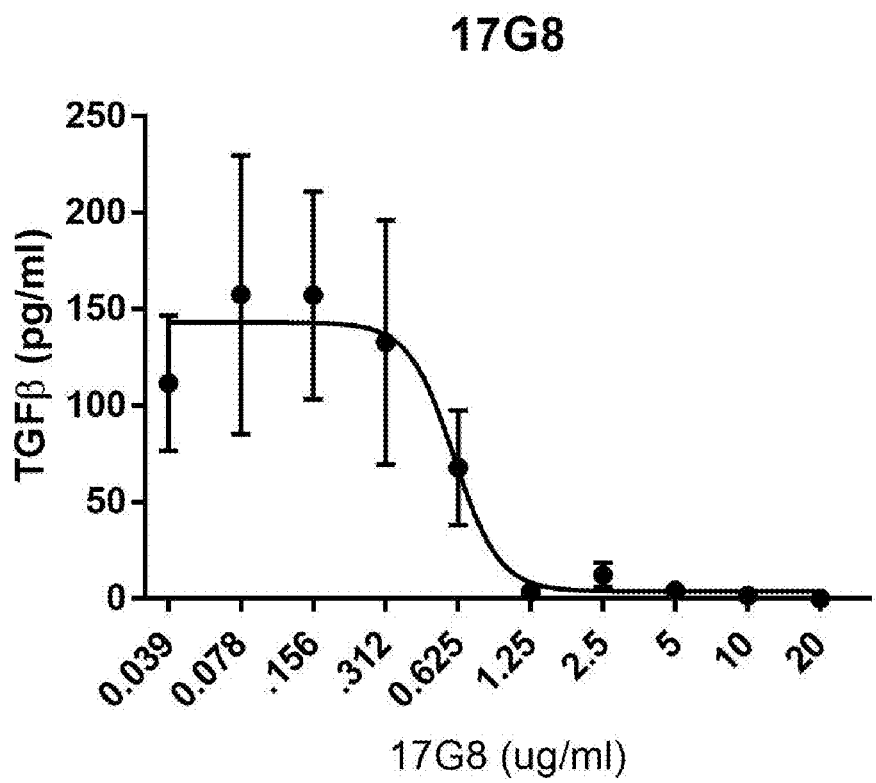
Figure 6C:
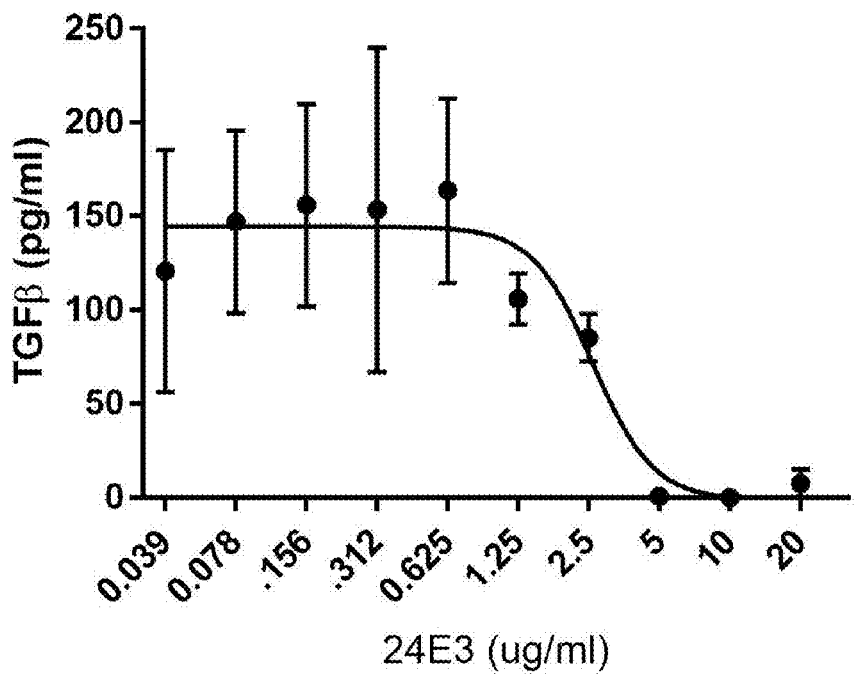
Figure 6D:
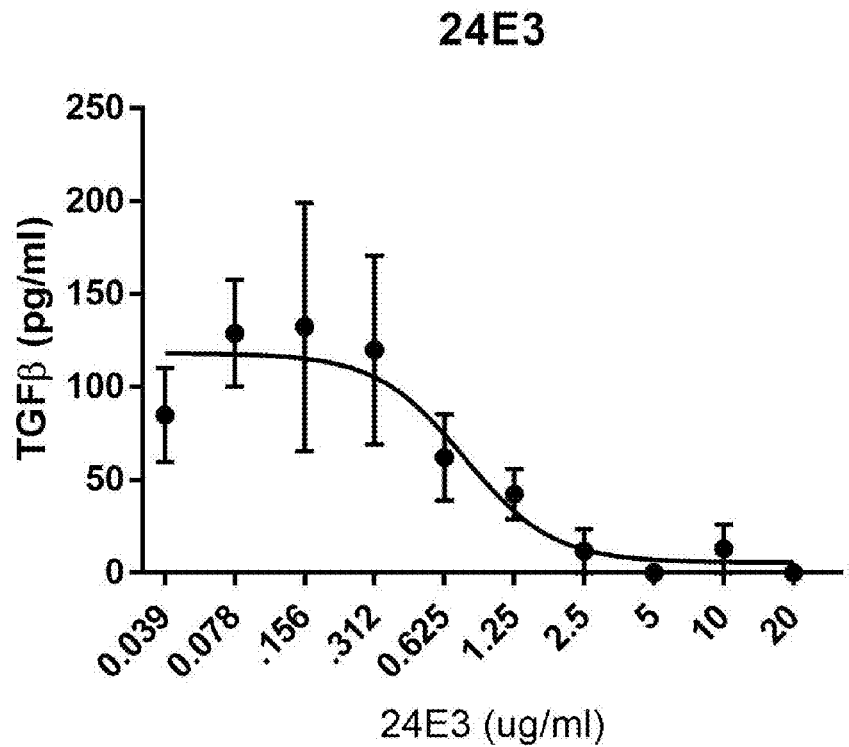
Figure 6E:
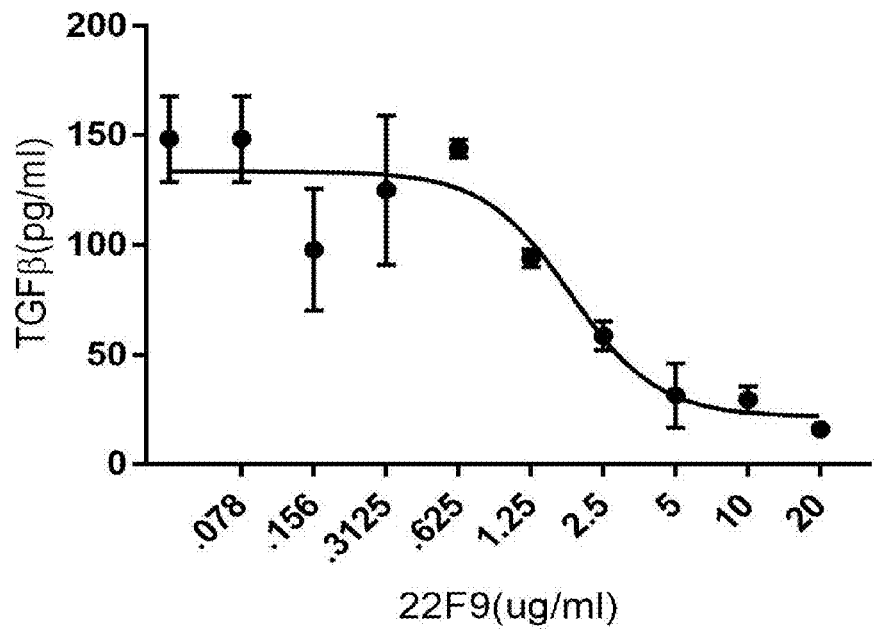
Figure 6F:
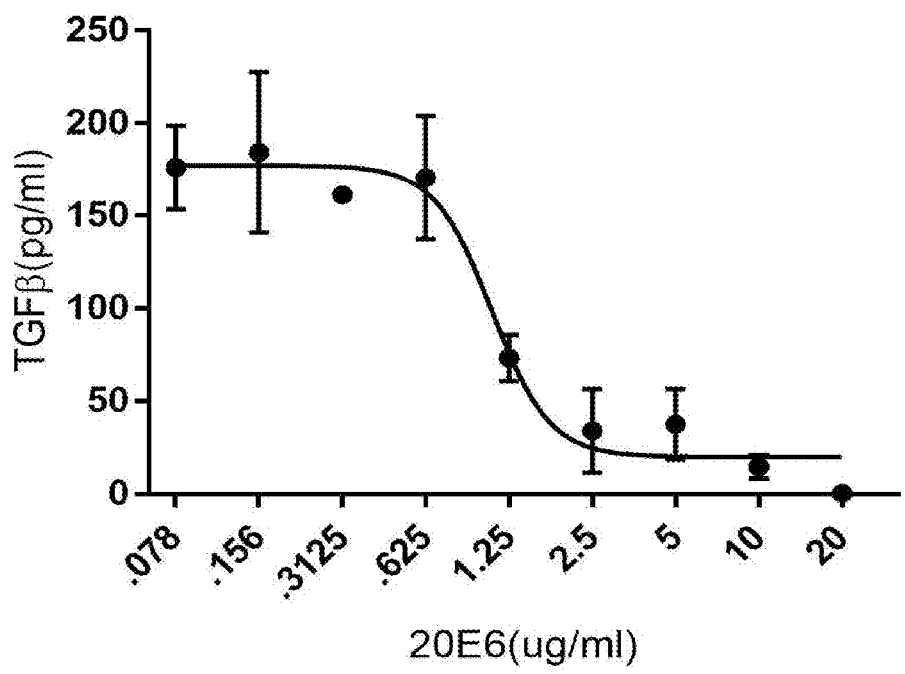

As described in Example 2, constructs with combinations of human and chicken sequence are able to fold into the correct structure. Accordingly, additional chimeras can be generated that could be used as immunogens to target specific epitopes of interest on LAP-TGFβ1. These constructs would be the inverse of the constructs described in Example 2. That is, the majority of the sequence would be taken from chicken LAP-TGFβ1, with small sections of human LAP-TGFβ1 inserted in regions containing the desired epitope. Exemplary epitopes on LAP-TGFβ1 that can be targeted using this strategy include, for example, an epitope comprising amino acids 82-130 of human LAP-TGFβ1, the lower arm of LAP-TGFβ1, or the latency loop of LAP-TGFβ1. This chimeric protein could be used to immunize chickens to yield monoclonal antibodies. Since the chicken LAP-TGFβ1 would be recognized as self, the immune response will be focused on the human sequence. Exemplary chicken-human chimeras which can be used to immunize chickens is shown in Table 6. The sequences of these chimeras are provided in Table 34. Anti-LAP antibodies generated in this manner can be tested for various functions (e.g., binding to human LAP-TGFβ1, inhibition of TGFβ1 activation, binding to immune cells) using the methods described herein.

TABLE 6

Chicken-human chimera for immunization

| SEQ ID | Name | Description |
|---|---|---|
| 211 | chB1ex2.1_2.2 | Chimeric LAP-TGFβ1 in which exons 2.1 and 2.2 (residues 83-128) of chicken LAP-TGFβ1 has been replaced with exons 2.1 and 2.2 from human LAP-TGFβ1. This chimera can be used to generate antibodies that target amino acid residues 82-130 of human LAP-TGFβ1. |
| 212 | chB1ex1.3 | Chimeric LAP-TGFβ1 in which exon 1.3 (residues 50-82) of chicken LAP-TGFβ1 has been replaced with exon 1.3 from human LAP-TGFβ1. This chimera can be used to generate antibodies that target amino acid residues 50-81 of human LAP-TGFβ1 |
| 213 | chB1 ex1.2 | Chimeric LAP-TGFβ1 in which exon 1.2 (residues 30-50) of chicken LAP-TGFβ1 has been replaced with exon 1.2 from human LAP-TGFβ1. This chimera can be used to generate antibodies that target amino acid residues 30-50 of human LAP-TGFβ1 |

Example 4: Effect of Anti-LAP Antibodies on TGFβ1 Activation

This Example describes the effect of anti-LAP antibodies 28G11_hIgG1, 28G11_mIgG2a, 17G8_hIgG1, 24E3_hIgG1, 22F9_hIgG1, 22F9_mIgG2a, 20E6_hIgG1, and 20E6_mIgG2a antibodies on TGFβ1 activation.

Briefly, P3U1 cells expressing human LAP-TGFβ1 or P3U1 cells expressing murine LAP-TGFβ1 were cultured overnight in serum free advanced DMEM in round bottom tissue culture plates and treated the following day with anti-LAP antibody (2-fold serial dilutions starting with a high of 20 ug/ml) for 24 hours. Active TGFβ1 was detected in the supernatant of cell cultures by utilizing a commercially available human TGFβ1 ELISA kit (R&D Systems) according to the manufacturer instructions.

FIGS. 5A and 5B show that 28G11_hIgG1 inhibited TGFβ1 activation in both P3U1 cells expressing human LAP-TGFβ1 (IC50=1.4 ug/ml) and murine LAP-TGFβ (IC50=1 ug/ml).

As with the experiment using 28G11 in FIG. 5, the tested antibodies inhibited TGFβ1 activation in P3U1 cells expressing human LAP-TGFβ1. Data are shown in the following Figures; IC50 values are as shown for antibody 17G8 (FIG. 6A for human TGFβ1 (IC50=1.5 ug/ml) and 6B for mouse TGFβ1 (IC50=0.59 ug/ml)), antibody 24E3 (FIG. 6C for human TGFβ1 (IC50=2.6 ug/ml) and 6D for mouse TGFβ1 (IC50=0.76 ug/ml)), antibody 22F9 (FIG. 6E for human TGFβ1 (IC50=1.8 ug/ml)), and antibody 20E6 (FIG. 6F for human TGFβ1 (IC50=1.08 ug/ml)).

Additional experiments were performed to further confirm that the antibodies inhibited activation in P3U1 cells expressing human LAP-TGFβ1 or P3U1 cells expressing murine LAP-TGFβ1. Data are shown in the following Figures; IC50 values are as shown: antibody 28G11_mIgG2a (FIG. 6G: IC50=1.6 ug/ml for human TGFβ1 and 0.8 ug/ml for mouse TGFβ1), antibody 20E6_mIgG2a (FIG. 6H: IC50=1.4 ug/ml for human TGFβ1 and 1.0 ug/ml for mouse TGFβ1), antibody 22F9_mIgG2a (FIG. 6I: IC50=1.8 ug/ml for human TGFβ1 and 1.0 ug/ml for mouse TGFβ1), antibody 24E3_hIgG1 (FIG. 6J: IC50=2.5 ug/ml for human TGFβ1 and 1.1 ug/ml for mouse TGFβ1), antibody 17G8_hIgG1 (FIG. 6K: IC50=1.0/ml for human TGFβ1 and 1.4 ug/ml for mouse TGFβ1), antibody 20E6_H0.2aL1 (FIG. 6L: IC50=1.3 ug/ml for human TGFβ1 and 1.7 ug/ml for mouse TGFβ1).

Consistent with the above results, in a separate experiment using the P3U1 cell-based assay, 28G11_hIgG1, 22F9_hIgG1, and 20E6_hIgG1 potently inhibited human TGFβ1 activation (Table 7).

TABLE 7

Inhibition of human TGFβ1 activation (IC$_{50}$)

| 28G11_hIgG1 | 22F9_hIgG1 | 20E6_hIgG1 |
|---|---|---|
| 2.3 µg/mL | 3.9 µg/mL | 4.7 µg/mL |

Thus multiple experiments described in this example showed that the anti-LAP antibodies described herein had an inhibitory effect on TGFβ1 activation.

Example 5: Binding of Anti-LAP Antibodies to Extracellular Matrix

This Example describes the ability of 28G11_hIgG1, 22F9_hIgG1, 20E6_hIgG1, 2C9_mIgG2a, 16B4_mIgG2a, 17G8_hIgG1, and 24E3_hIgG1 antibodies to bind LAP-TGFβ1 in ECM.

Briefly, to evaluate antibody binding to ECM, P3U1 cells were incubated in round bottom tissue culture plates for 48 hours. Cells were then removed, leaving behind ECM on the surface of the plates. Three different groups were compared: (a) P3U1 cells expressing human LAP-TGFβ1, (b) P3U1 cells expressing murine LAP-TGFβ1, and (c) P3U1 cells without LAP-TGFβ1 (null cells). Binding of antibody to LAP-TGFβ1/ECM was then determined using biotinylated anti-LAP antibodies followed by incubation with streptavidin horseradish peroxidase (HRP) and 3',5,5'-tetramethylbenzidine (TMB) substrate.

Figure 7:
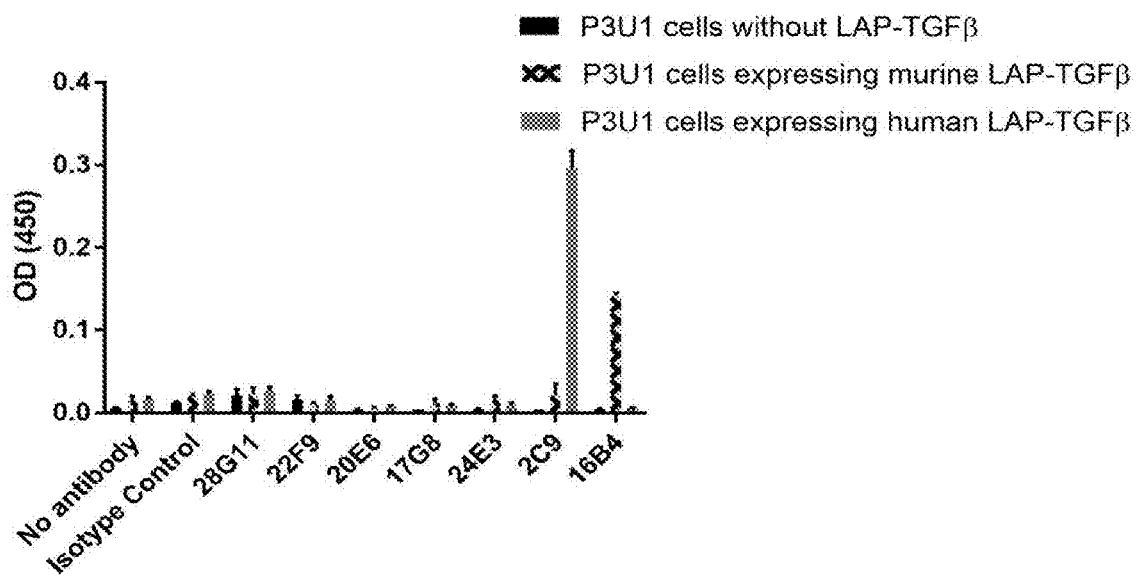
FIG. 7 is a graph showing binding of the indicated anti-LAP antibodies to extracellular matrix (ECM) deposited by P3U1 cells. Three cell types were tested: P3U1 cells without LAP-TGFβ, P3U1 cells expressing human LAP-TGFβ1, and P3U1 cells expressing murine LAP-TGFβ1. Antibodies were used at a concentration of 2 μg/mL.

As shown in FIG. 7, 28G11_hIgG1, 22F9_hIgG1, 20E6_hIgG1, 17G8_hIgG1, and 24E3_hIgG1 antibodies did not bind to LAP-TGFβ1/ECM. In contrast, anti-LAP antibody 16B4 showed strong binding to murine LAP-TGFβ1 in LAP-TGFβ1/ECM and anti-LAP antibody 2C9 showed strong binding to human LAP-TGFβ1 in LAP-TGFβ1/ECM. This result suggests that, while 28G11_hIgG1, 22F9_hIgG1, 20E6_hIgG1, 17G8_hIgG1, and 24E3_hIgG1 bind strongly to cells expressing murine or human LAP-TGFβ1, they did not bind to murine or human LAP-TGFβ1 in ECM.

Example 6: Binding of Anti-LAP Antibodies to Platelets

This Example describes the binding of anti-LAP antibodies to platelets and their effects on platelet degranulation.

Figure 8:
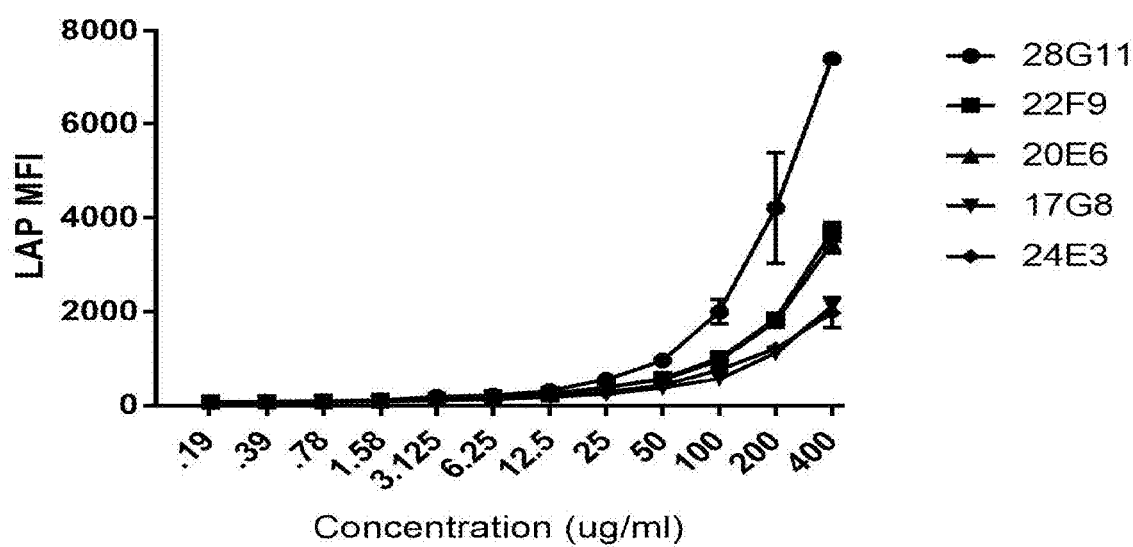
FIG. 8 is a graph showing the dose-response relationship in binding of the indicated anti-LAP antibodies (i.e., antibodies 28G11, 22F9, 20E6, 17G8, and 24E3) to human platelets.
Figure 9A:
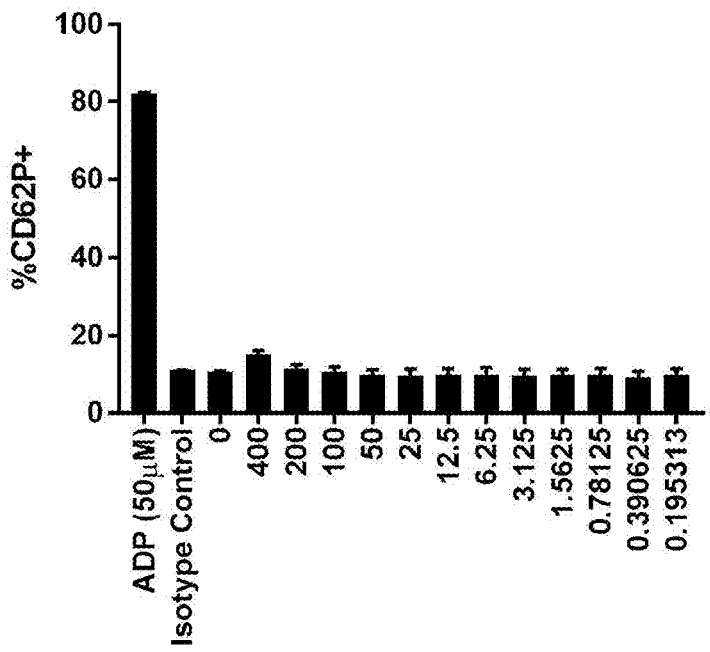
FIGS. 9A-9E are graphs showing the effects of anti-LAP antibodies 28G11_hyb (FIG. 9A), 20E6_IgG2a (FIG. 9B), 22F9_IgG2a (FIG. 9C), 17G8_hIgG1 (FIG. 9D), and 24E3_hIgG1 (FIG. 9E) on human platelet degranulation.
Figure 9B:
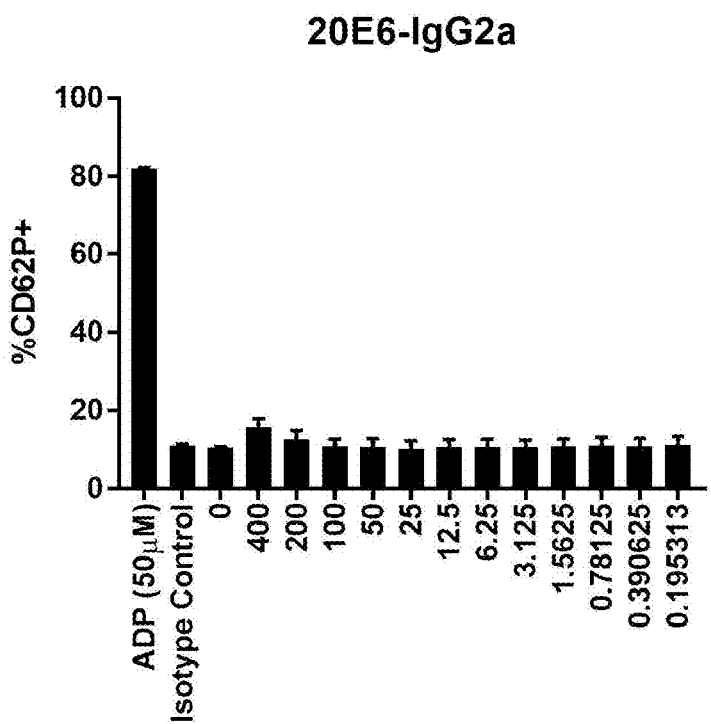
Figure 9C:
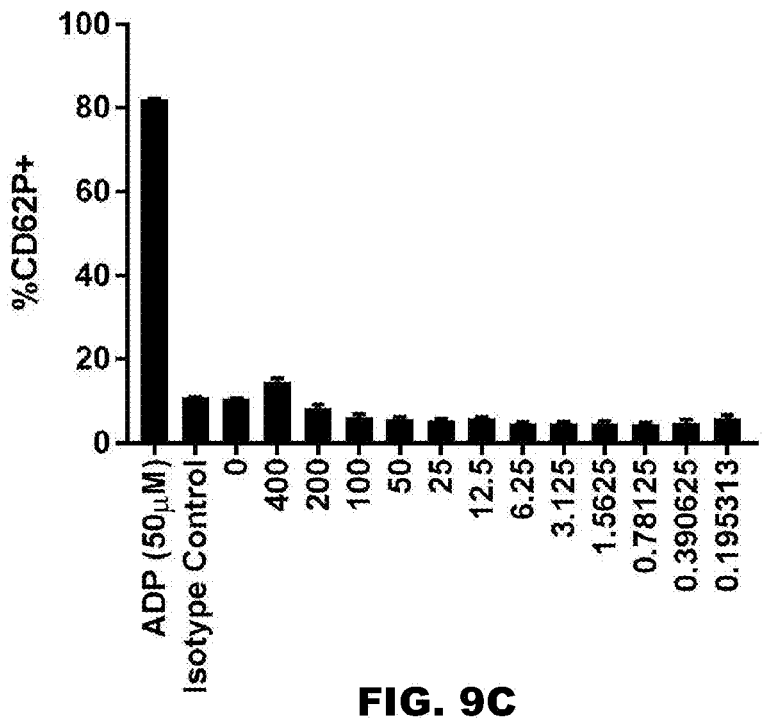
Figure 9D:
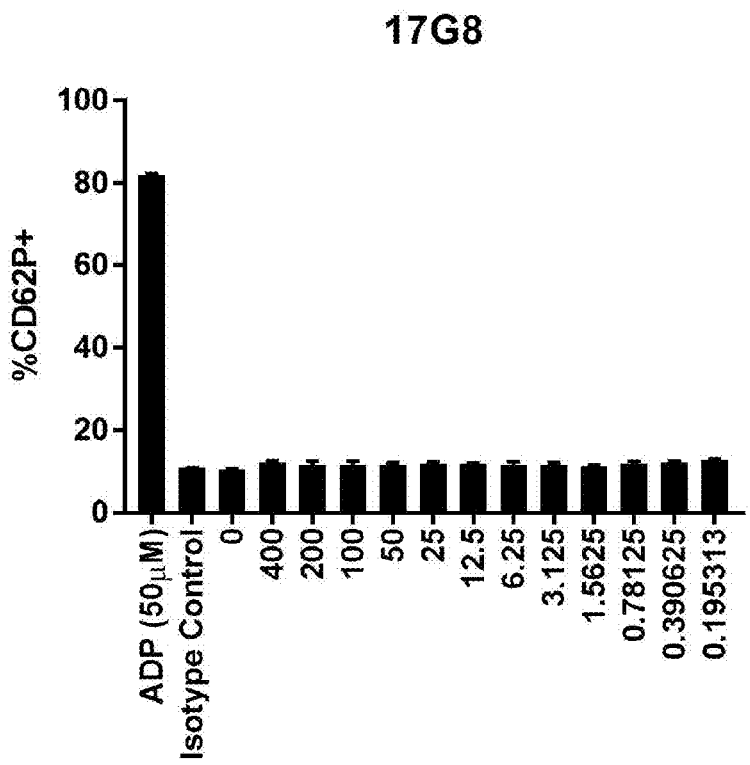
Figure 9E:
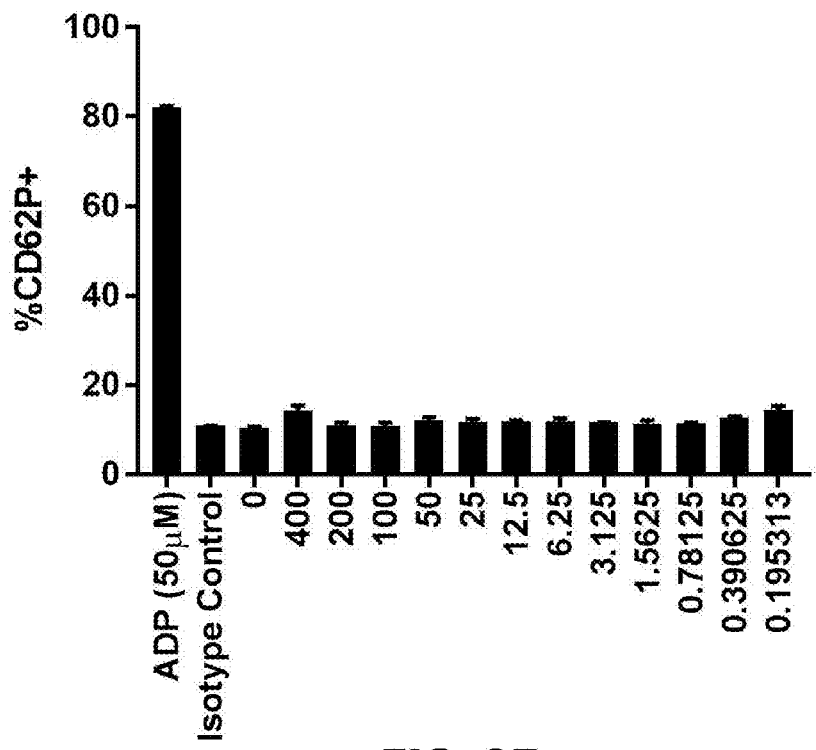

Briefly, a direct platelet binding assay was performed by flow cytometry. Diluted whole human blood was incubated with the indicated concentrations of directly conjugated anti-LAP antibodies (28G11_(hyb), 20E6_mIgG2a, 22F9_mIgG2a, 17G8_hIgG1, and 24E3_hIgG1) for 15 minutes. The reactions were then incubated for an additional 15 minutes with a commercially available directly conjugated antibody against CD61 (BioLegend), and analyzed by flow cytometry. The data represents the anti-LAP mean fluorescence intensity of CD61 positive platelets. As shown in FIG. 8, anti-LAP antibodies 28G11, 20E6, 22F9, 17G8, and 24E3 showed binding to platelets in a dose-responsive manner.

These anti-LAP antibodies were further tested for platelet degranulation. Briefly, diluted whole human blood was incubated with the indicated concentrations of anti-LAP antibodies or adenosine diphosphate (ADP) as a positive control for 15 minutes. The reactions were then incubated for an additional 15 minutes with directly conjugated antibodies against CD61, to detect whole blood platelets, and CD62P (BioLegend) to detect degranulated platelets. The samples were analyzed by flow cytometry to determine the percentage of CD62P+ platelets.

As shown in FIGS. 9A-9E, none of the tested antibodies, i.e., 28G11, 20E6, 22F9, 17G8, and 24E3, induced significant platelet degranulation, even at the highest dose tested.

Example 7: Differential Binding of Anti-LAP Antibodies to Immune Cells

This Example describes the binding of anti-LAP antibodies to different types of immune cells.

Figure 10A:
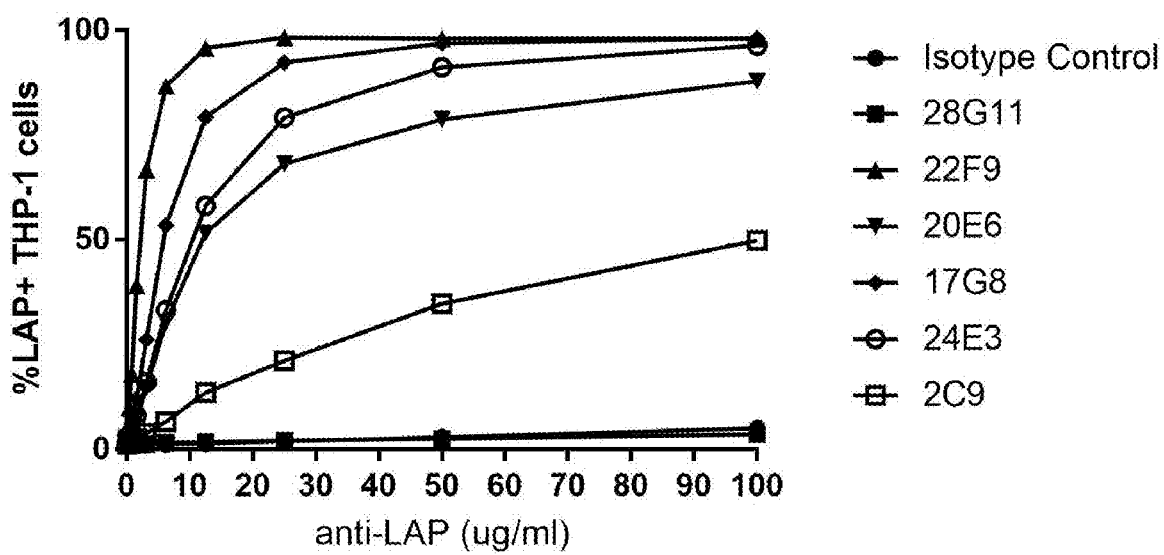
FIGS. 10A and 10B are graphs showing the binding of the indicated anti-LAP antibodies to THP-1 cells. THP cell binding is expressed as the percentage (%) of LAP+ cells in FIG. 10A and as median fluorescent intensity (MFI) in FIG. 10B.
Figure 10B:
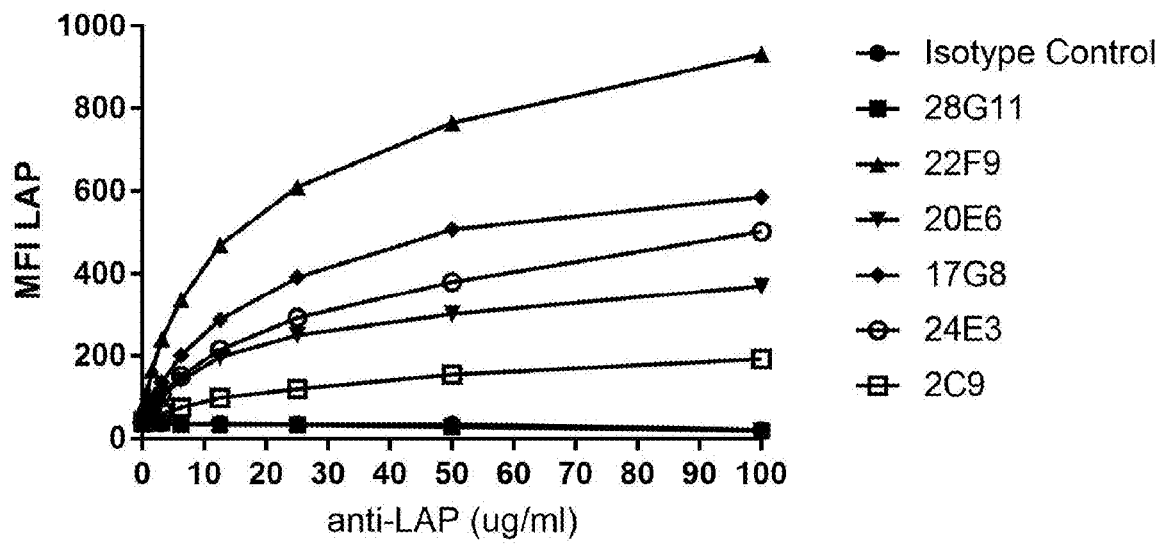
Figure 10C:
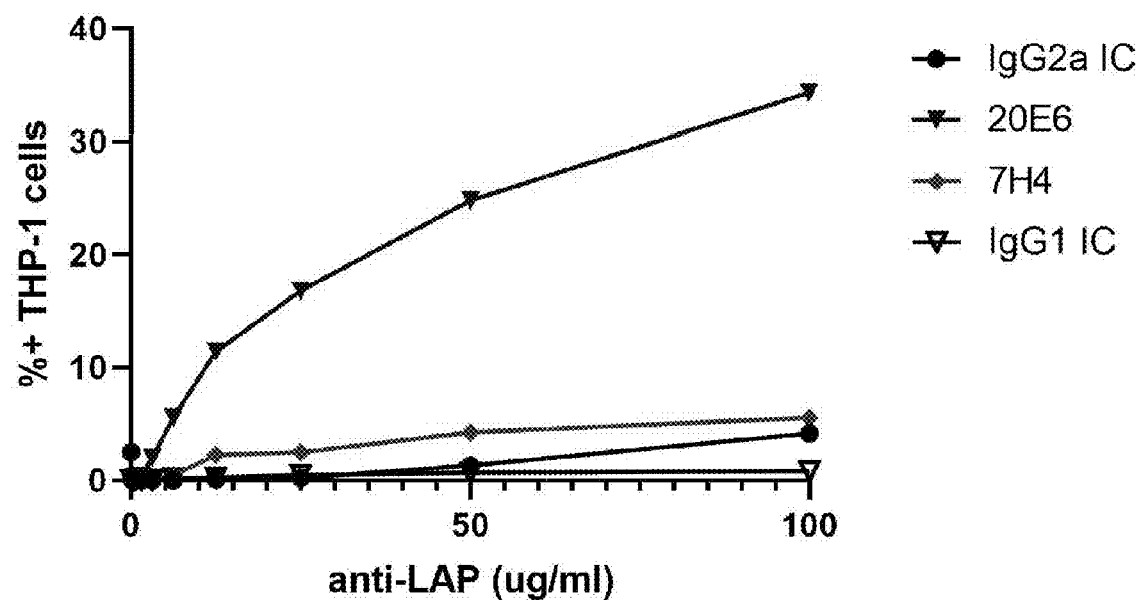
FIG. 10C is a graph showing the binding of the indicated anti-LAP antibodies to THP-1 cells. THP cell binding is expressed as the % of LAP+ cells.
Figure 10D:
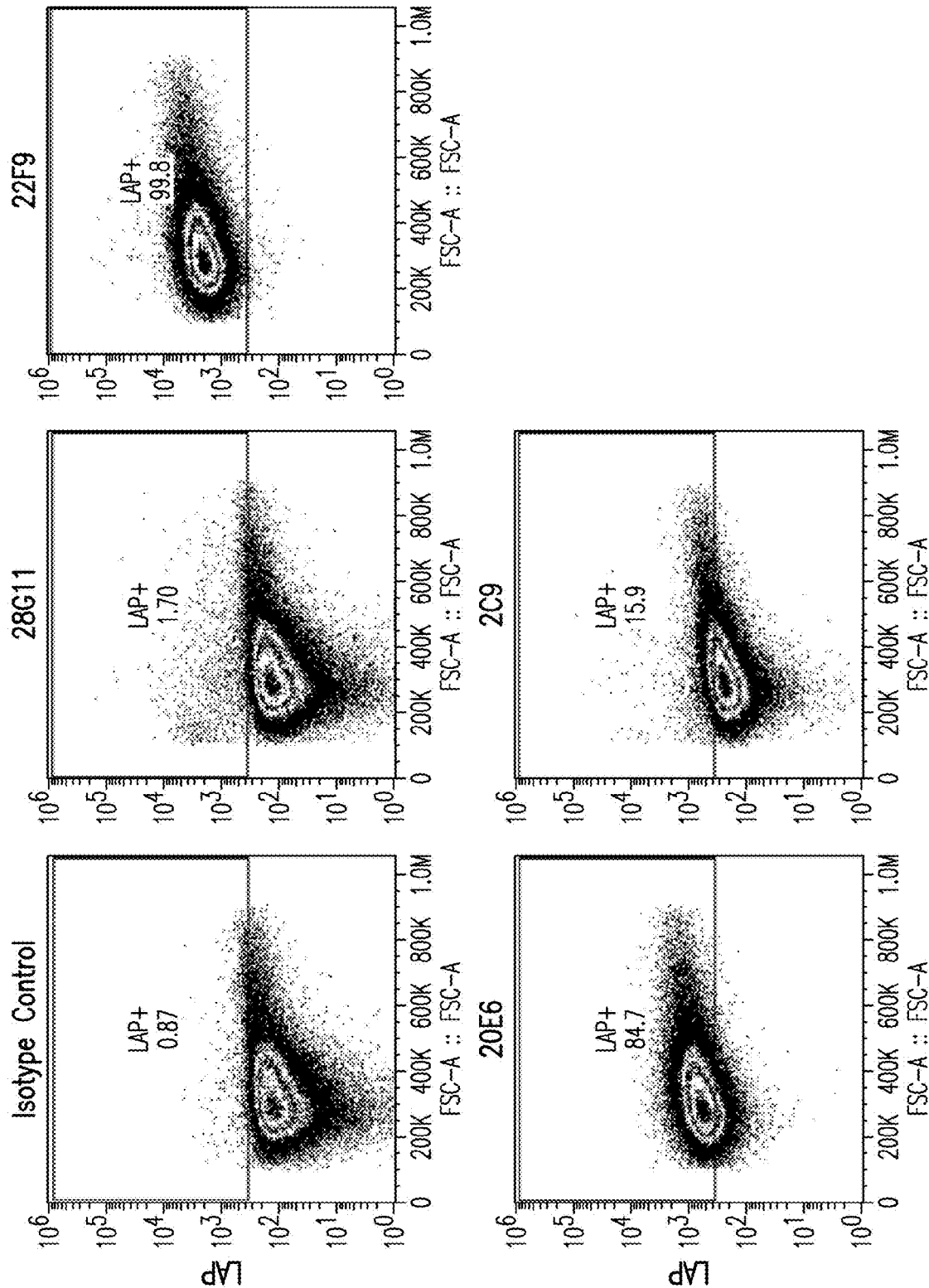
FIG. 10D shows dot plots for the binding of the indicated anti-LAP antibodies to THP-1 cells.

Anti-LAP antibodies were tested for their ability to bind to THP-1 cells, a cell line derived from a patient with acute monocytic leukemia that is reported to express LRRC33. THP-1 cells were incubated with FACS buffer and human Fc block followed by incubation with varying concentrations of Alexa 647 conjugated 28G11_(hyb), 22F9_mIgG2a, 20E6_mIgG2a, 17G8_hIgG1, 24E3_hIgG1, 2C9_mIgG2a, or mIgG2a isotype control. Cells were analyzed by flow cytometry and graphed as percent positive THP-1 cells or median fluorescence intensity (MFI) of anti-LAP binding. As shown in FIGS. 10A and 10B, antibodies 22F9, 17G8, 24E3, 20E6, and 2C9 display strong binding to THP-1 cells. No binding above background was seen for anti-LAP antibody 28G11. In another experiment, the binding of 20E6_mIgG2a and 7H4 hyb to THP-1 cells was compared using the methods described above. As shown in FIG. 10C, and consistent with FIGS. 10A and 10B, 20E6 showed strong binding to THP-1 cells, whereas 7H4 showed no binding. In a separate experiment THP-1 cells were incubated with FACS buffer and human Fc block followed by incubation with 5 ug/ml of Alexa 647 conjugated 28G11_hyb, 22F9_mIgG2a, 20E6_mIgG2a, 2C9_mIgG2a, or IgG2a isotype control. Cells were analyzed by flow cytometry and gated as single cells. Representative dot plots are shown in FIG. 10D; in these plots, antibodies were at 5 ug/ml.

Figure 10E:
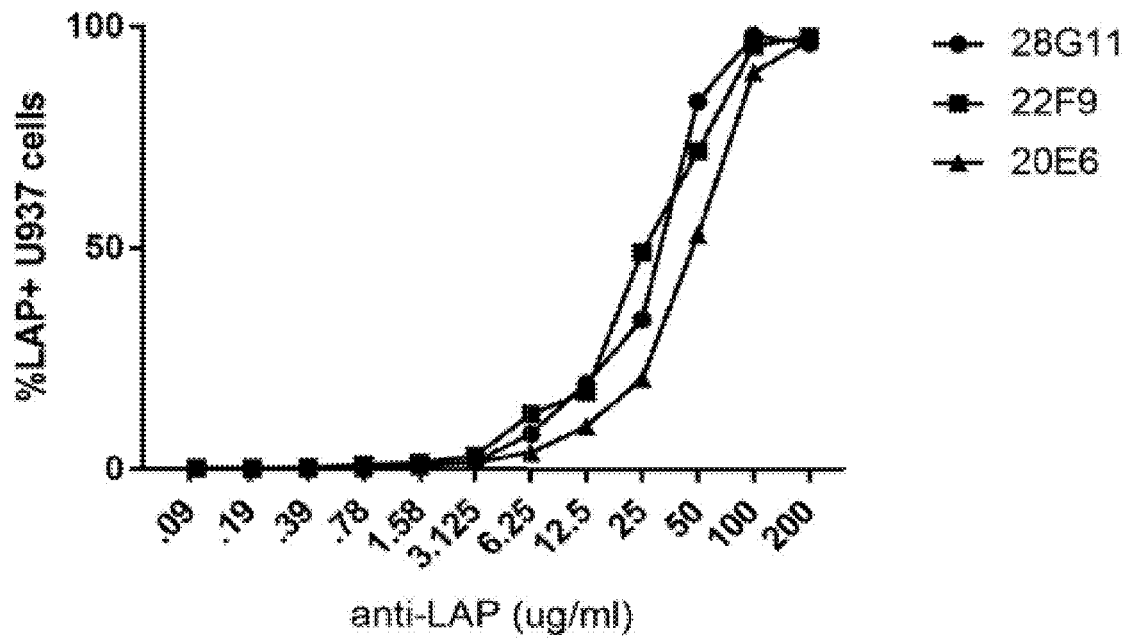
FIGS. 10E and 10F are graphs showing the binding of the indicated anti-LAP antibodies to U937 cells. U937 cell binding is expressed as the % of LAP+ cells in FIG. 10E and as MFI in FIG. 10F.
Figure 10F:
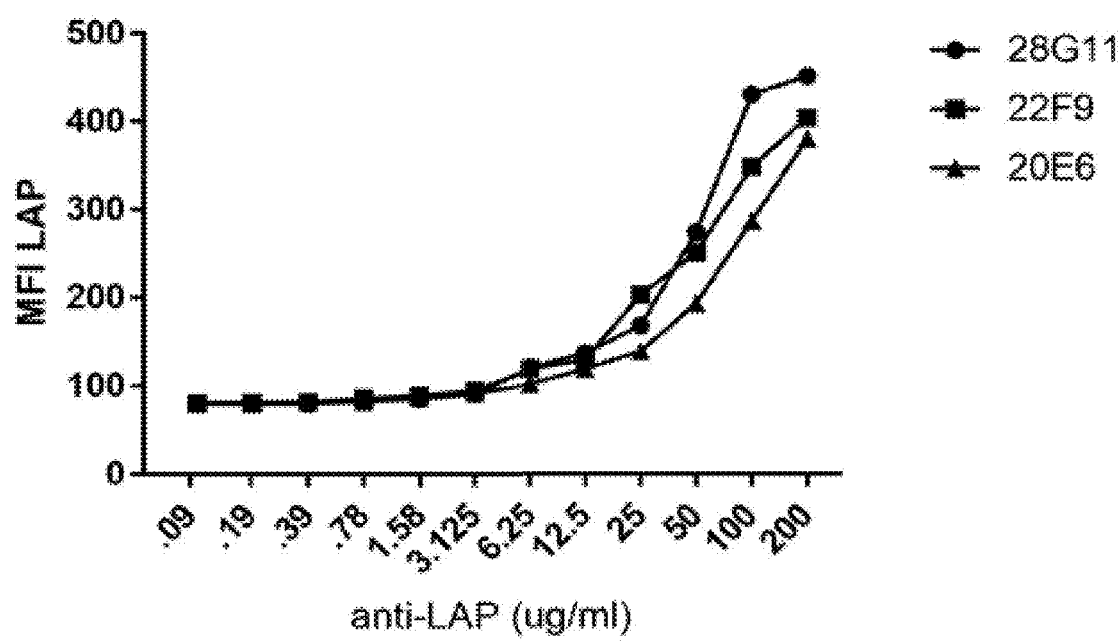
Figure 10G:
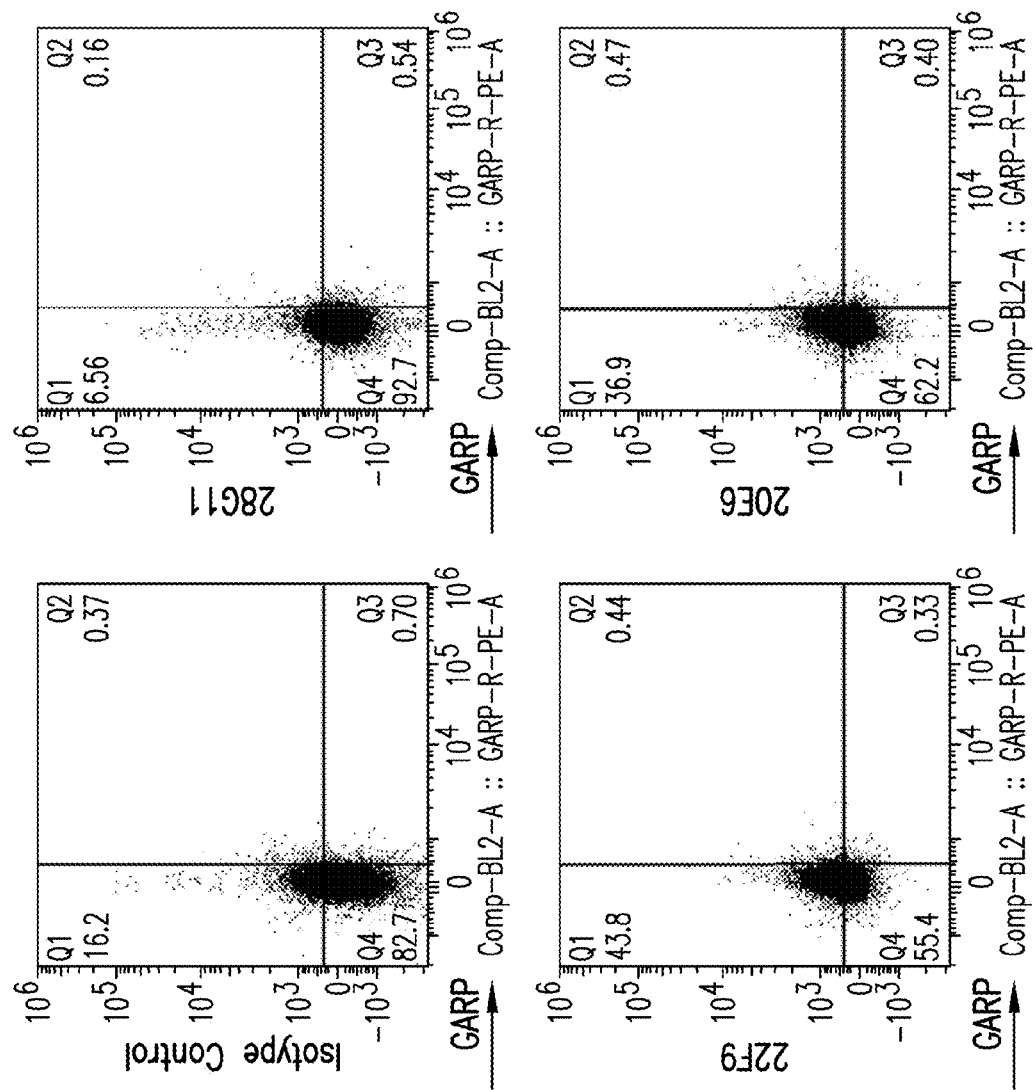
FIG. 10G shows dot plots for the binding of the indicated anti-LAP antibodies to U937 cells.

Anti-LAP antibodies were tested for their ability to bind to U937 cells, a myeloid cell line derived from a patient with histiocytic lymphoma. U937 cells were incubated with FACS buffer and human Fc block followed by incubation with varying concentrations of Alexa 647 conjugated 28G11_hyb, 22F9_mIgG2a, or 20E6_mIgG2a. In a separate experiment U937 cells were incubated with FACS buffer and human Fc block followed by incubation with 10 ug/ml of Alexa 647 conjugated 28G11_hyb, 22F9_mIgG2a, 20E6_mIgG2a or mIgG2a isotype control (FIGS. 10E and 10F). Representative dot plots are shown in FIG. 10G; in these plots, antibodies were at 10 ug/ml. The anti-LAP antibodies 28G11, 22F9, and 20E6 were shown to bind similarly to the U937 cells, both by MFI and the dose response of binding.

These data demonstrate that the anti-LAP antibodies 28G11, 22F9, and 20E6 display comparable binding to one LAP+ myeloid cell line but dramatically different binding to another LAP+ myeloid cell line. The following experiments were performed to determine whether that same differential binding could be observed in non-transformed cell populations.

Anti-LAP antibodies were tested for their ability to bind to immune cells isolated from mice carrying CT26 tumors. Briefly, 1×10$^6$ CT26 cells were injected into the flank region of 6 male Balb/C mice. When mean tumor volumes reached about 80 mm³, mice were treated with either IgG2a or IgG1 isotype control antibodies at 10 mg/kg (this was originally part of an experiment in which mice were treated with therapeutic antibodies and these animals were intended to serve as controls). Mice were treated again 3 days later and harvested 7 days post first injection. Tumor tissue was disassociated in a GentlMACS dissociator and digested with Collagenase IV/DNase1, strained through a 70-µm cell strainer and counted. Spleen tissue was dissociated by passing through a 70-µm cell strainer and counted. Cells were analyzed by flow cytometry using the following scheme: Gate on live cells→Gate on single cells→Gate on CD45+ cells→Gate on CD41-population→Gate on appropriate immune cell subsets as follows:

CD4 T cells—CD45+, CD3+, CD4+

Regulatory T cells—CD45+, CD3+, CD4+, Foxp3+

CD8 T cells—CD45+, CD3+, CD8+

CD11b—CD45+, CD11b+

M2 macrophages—CD45+, CD11b+, F4/80+, CD206+

Dendritic cells—CD45+, F4/80−, CD11c+

M-MDSC—CD45+, CD11b+, F4/80−, Ly6G−, Ly6C high

G-MDSC—CD45+, CD11b+, F4/80−, Ly6G+

M1 macrophages—CD45+, CD11b+, F4/80+, MHC II high, CD206−

NK cells—CD45+, CD49b+

Figure 11:
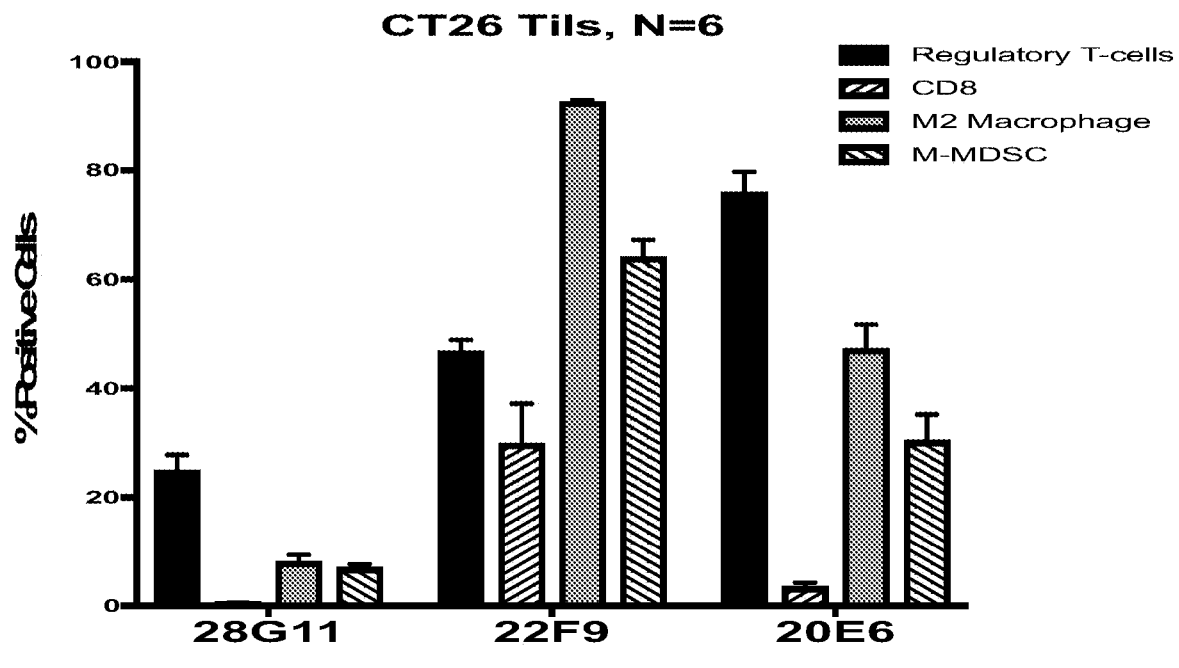
FIG. 11 is a graph showing the binding of anti-LAP antibodies 28G11, 22F9, and 20E6 to regulatory T cells, CD8 cells, M2 macrophages, and M-MDSCs from CT26 TILs, expressed as the percentage of positive cells.

Binding of the anti-LAP antibodies was analyzed using Alexa 647-labeled 28G11-IgG2a, 22F9-IgG2a, and 20E6-IgG2a. A summary of the data is shown in Table 8 and in FIG. 11. The three anti-LAP antibodies 28G11, 22F9 and 20E6 display very different binding profiles to clinically relevant immune cell subsets in tumor tissue. Most notably, 22F9 and 20E6 bind to a higher percentage of regulatory T cells, M2 macrophages, and M-MDSCs compared to 28G11. These data indicate that, although these three antibodies all have similarities in their binding and functional properties (see Examples 1, 2, and 4-6), the antibodies display large differences in their binding to cell populations known to be important in the immunosuppressive tumor microenvironment. For example, both 22F9 and 20E6 bind a higher percentage of regulatory T cells, M2 macrophages, and M-MDSC than does 28G11. This supports the superiority of 22F9 and 20E6 over 28G11 for the modulation of these important immunosuppressive cell populations in tumors. Moreover, the differences in binding of 22F9 and 20E6 support the potential preferential use of one or the other antibody in a given tumor depending on the makeup of the infiltrating leukocyte population.

TABLE 8

Binding to immune cells in tumor
(expressed as % positive ± SEM of the 6 individual mice)

| Immune cell type | 28G11 | 22F9 | 20E6 |
|---|---|---|---|
| CD4 | 5.1 ± 1.0 | 44.2 ± 2.0 | 66.8 ± 2.4 |
| Regulatory T cells | 24.8 ± 3.0 | 46.7 ± 2.2 | 75.8 ± 3.9 |
| CD8 | 0.5 ± 0.1 | 29.8 ± 7.4 | 3.4 ± 0.9 |
| CD11b | 16.8 ± 2.3 | 70.2 ± 3.2 | 50.7 ± 5.6 |
| M2 macrophages | 8.0 ± 1.4 | 92.5 ± 0.5 | 47.2 ± 4.5 |
| Dendritic cells | 7.8 ± 1.3 | 50.4 ± 4.0 | 27.6 ± 4.5 |

TABLE 8-continued

Binding to immune cells in tumor
(expressed as % positive ± SEM of the 6 individual mice)

| Immune cell type | 28G11 | 22F9 | 20E6 |
|---|---|---|---|
| M-MDSC | 6.9 ± 0.8 | 64.0 ± 3.2 | 30.3 ± 4.9 |
| G-MDSC | 2.4 ± 0.6 | 21.9 ± 2.1 | 7.0 ± 1.9 |

Splenocytes from the same mice were analyzed by flow cytometry in parallel with the tumor tissue. As shown in Table 9, antibodies 28G11, 22F9, and 20E6 bind a lower percentage of immune cells in the spleen of tumor bearing mice than they do of the tumors from those same mice (Table 8). These data demonstrate the tumor selectivity of all three antibodies. Some differences between the antibodies were observed, with 22F9 displaying the strongest binding in the spleen. This supports the superiority of 20E6 in settings where a maximal selectivity for the tumor environment is preferred.

TABLE 9

Binding to immune cells in spleen
(expressed as % positive ± SEM of the 6 individual mice)

| Immune cell type | 28G11 | 22F9 | 20E6 |
|---|---|---|---|
| CD4 | 1.6 ± 0.05 | 2.9 ± 0.06 | 1.7 ± 0.06 |
| Regulatory T cells | 4.0 ± 0.4 | 6.1 ± 0.5 | 3.6 ± 0.3 |
| CD8 | 0.9 ± 0.02 | 1.9 ± 0.1 | 0.9 ± 0.05 |
| CD11b | 4.0 ± 0.5 | 17.2 ± 1.1 | 4.2 ± 0.2 |
| M2 macrophages | 1.8 ± 0.6 | 11.3 ± 1.7 | 2.6 ± 0.5 |
| Dendritic cells | 4.9 ± 0.5 | 21.5 ± 1.1 | 6.3 ± 0.5 |
| M-MDSC | 8.2 ± 0.6 | 21.7 ± 2.2 | 4.9 ± 0.3 |
| G-MDSC | 1.6 ± 0.4 | 8.0 ± 0.4 | 2.1 ± 0.2 |
| M1 macrophages | 1.0 ± 0.3 | 11.7 ± 1.3 | 1.7 ± 0.4 |
| NK cells | 3.0 ± 0.2 | 13.4 ± 1.2 | 4.5 ± 0.2 |

The ability of antibodies 28G11, 22F9, 20E6, 17G8, 24E3, and 2F8 to bind to human macrophage subsets was also examined. Briefly, CD14+ cells were obtained from StemExpress where they were isolated from whole blood of a donor via magnetic negative selection. Cells were cultured for 6 days in Immunocult macrophage medium (StemCell tech)+M-CSF (50 ng/ml) with the following additions to skew the cells to specific macrophage subtypes (M1 macrophages: 50 ng/ml h-IFN-γ+10 ng/ml LPS; M2a macrophages: 10 ng/ml h-IL4; M2b macrophages: immobilized IgG+100 ng/ml LPS; M2c macrophages: 10 ng/ml IL10+20 ng/ml TGFβ). Cells were stained with CD14 and Alexa 647-labeled anti-LAP antibodies 28G11_mIgG2a, 22F9_mIgG2a, 20E6_mIgG2a, 17G8_hIgG1, 24E3_hIgG1, 2F8_(hyb), mIgG2a isotype control, or hIgG1 isotype control. Cells were gated as live, single cell prior to analysis.

As shown in Table 10, the anti-LAP antibodies displayed very different binding patterns to isolated human macrophage subsets. Notably, 22F9 bound a much higher percentage of all macrophage subpopulations than did 28G11 or 20E6. 20E6 bound a higher percentage of M1 macrophages than did 28G11.

TABLE 10

Binding to immune cells from healthy donors (expressed as % positive)

| Immune cell type | 28G11 | 22F9 | 20E6 | 17G8 | 24E3 | 2F8 | Isotype control |
|---|---|---|---|---|---|---|---|
| Macrophages | 55.8% | 85.0% | 51.8% | 24.8% | 50.8% | 40.0% | 1.04% |
| M1 macrophages | 15.2% | 86.4% | 46.1% | 52.2% | 50.1% | 0.91% | 2.34% |
| M2a macrophages | 55.6% | 85.0% | 51.5% | 20.6% | 34.3% | 29.1% | 3.53% |
| M2b macrophages | 24.5% | 90.8% | 20.4% | 50.7% | 66.7% | 26.9% | 2.14% |
| M2c macrophages | 29.1% | 99.1% | 28.2% | 72.8% | 84.5% | 5.1% | 1.26% |

In a separate experiment, the binding of the anti-LAP antibodies to activated human CD4+ T cell populations was also assessed. CD4+ cells were isolated from PBMCs using magnetic negative selection according to instructions provided by the manufacturer (StemCell Tech). Cells were activated using a 1:1 ratio of Dynabeads (Thermo) to cells and cultured in advanced RPMI+10% FBS+30 U/ml human IL2 for 48 hours. Cells were stained with live/dead dye followed by CD4, CD25, and 28G11-IgG2a, 22F9-IgG2a, 20E6-IgG2a, 17G8-hIgG1, 24E3-hIgG1, 2F8_(hyb), IgG1 isotype control, or IgG2a isotype control for LAP expression. Cells were fixed and permeabilized for Foxp3 staining according to the manufacturer recommendations (Ebiosciences) and stained for Foxp3. Cells were gated as live, single cells, CD4+ and CD25+ prior to analysis. 22F9 was found to bind a higher percentage of activated CD4+ cells than did the other tested anti-LAP antibodies.

Increased binding to specific cell populations is expected to be associated with direct clinical benefit. The antibodies described here inhibit TGFβ activation and release of the mature cytokine. Because TGFβ acts in an autocrine or near-paracrine manner, selective binding to specific cell populations will result in inhibition of the production of mature TGFβ in the immediate proximity of the indicated cell population. Thus, for example, the increased binding of anti-LAP antibody 20E6 when compared to antibody 28G11 to regulatory T cells would be expected to result in selectively reduced TGFβ levels at the surface of those same regulatory T cells. Given that TGFβ is a major driver of regulatory T cell generation, this is expected to result in reduced numbers of regulatory T cells in the tumor microenvironment and increased clinical efficacy of 20E6 over 28G11. In a second example, the increased binding of anti-LAP antibody 22F9 when compared to antibody 28G11 to macrophage subsets would be expected to result in selectively reduced TGFβ levels at the surface of those same macrophages. Given that TGFβ is a primary mechanism of cell-contact dependent macrophage inhibition of effector T cell function, this is expected to result in reduced macrophage-mediated inhibition and increased effector T cell function in the tumor microenvironment and increased clinical efficacy of 20E6 over 28G11.

In some embodiments, the anti-LAP antibodies are of an isotype with active effector function and enhanced binding of a specific anti-LAP antibody to a given cell population will result in increased depletion of that cell population by ADCC or CDC. Thus, for example, the increased binding of anti-LAP antibody 20E6 when compared to antibody 28G11 to regulatory T cells would be expected to result in increased ADCC or CDC-mediated depletion of those regulatory T cells in the tumor microenvironment and increased clinical efficacy of 20E6 over 28G11. In a second example, the increased binding of anti-LAP antibody 22F9 when compared to antibody 28G11 to macrophage subsets would be expected to result in increased ADCC- or CDC-mediated depletion of those macrophage subsets in the tumor microenvironment and increased clinical efficacy of 22F9 over 28G11.

The data presented in this example demonstrate that the finding that the anti-LAP antibodies described here bind differently to immune cell subpopulations can be demonstrated in both murine and human systems and in both primary cell populations and transformed cell lines.

Example 8: Generation of Humanized Anti-LAP Antibodies

This Example describes the humanization of anti-LAP antibodies 28G11, 22F9, and 20E6.

Models of 28G11, 22F9, and 26E10 (also referred to as 20E6) variable regions were built using Modeller, a program which uses multiple structure templates to assemble a structural model. PDB code 3dv6 was chosen as the template for the 28G11 heavy chain (86% sequence identity with the 28G11 VH domain) and 2zjs was chosen as the template for the 28G11 light chain (97% sequence identity with 28G11 VL domain). PDB code 1a6v was chosen as the template for the 22F9 heavy chain (89% sequence identity with the 22F9 V region), and PDB code 2xqy was chosen as the template for the 22F9 light chain (94% identity with the 22F9 V region). PDB code 1a6v was chosen as the template for the 26E10 (20E6) heavy chain (93% sequence identity with the 26E10 (20E6) V region), and PDB code 1jv5 was chosen as the template for the 26E10 (20E6) light chain (96% identity with the 26E10 V region). Structural models of the variable domains were assembled and refined with Modeller.

To choose antibody acceptor framework sequences for the light and heavy chains, an antibody sequence database and query tools were used to identify suitable templates with the highest similarity to the murine 28G11, 22F9, and 26E10 (20E6) sequences in canonical, interface, and Vernier zone residues; the same length CDRs if possible (except CDR-H3); and a minimum required number of back mutations (i.e., changes of framework residue types from that of the human acceptor to that of the mature murine antibody). Human germline sequences filled in with human consensus residues in the FR4 framework region were considered as well.

Based on the above analysis, CDR sequences of 28G11 were grafted onto IGHV3-72*01(H0) and IGKV1-27*01 (L0) germlines. For humanization of 22F9, CDR sequences of 22F9 were grafted onto IGHV1-46*01(H0) and IGKV1-39*01(L0) germlines. For humanization of 20E6, CDR sequences of 20E6 were grafted onto human IGHV1-2*05

(H0) and IGKV1-33*01(L0) germlines. Back substitutions to mouse sequences in the heavy and/or light chains of these humanized antibodies were introduced based on analysis of homology models. Substitutions were also introduced (as discussed in the Examples that follow) to remove potential deamidation and isomerization sites. Each of these candidates were tested for various functions, including binding to cells overexpressing LAP-TGFβ1, as described in the Examples below.

Example 9: Characterization of Humanized 28G11 Candidates and Liability Site-Removed 28G11 Variants In this Example, the characteristics of various humanized 28G11 candidates were examined to identify humanized antibodies that retained the function of the parental antibodies (e.g., binding to TGFβ1). Also examined were deamidation/isomerization site-removed 28G11 variants. Table 11 summarizes the various humanized 28G11 constructs (heavy and light chain sequences) used in this Example. The sequences of these constructs are provided in Table 34.

TABLE 11

Exemplary 28G11 antibodies and antigen binding fragments

| SEQ ID | Name | Description |
|---|---|---|
| 32 | 28G11_H0 | Humanized 28G11 heavy chain sequence with CDR1, CDR2 and CDR3 sequences from parental murine antibody inserted into the human IGHV3-72*01 germline with a consensus framework 4 sequence |
| 34 | 28G11_H1 | Humanized_28G11_H0 heavy chain sequence which includes amino substitutions S30T and V48L |
| 36 | 28G11_H2 | Humanized 28G11_H0 heavy chain sequence which includes amino substitutions S30T, V48L, D73N, K75Q, N76S, and V109L |
| 39 | 28G11_H2.1 | Humanized 28G11_H2 heavy chain sequence which includes amino substitution N56Q |
| 41 | 28G11_H2a | Humanized 28G11_H0 heavy chain sequence which includes amino substitutions S30T and D73N |
| 43 | 28G11_H2b | Humanized 28G11_H0 heavy chain sequence which includes amino substitutions S30T, N56Q and D73N |
| 45 | 28G11_H2b_hIgG4mut | H2b heavy chain with a variant human IgG4 constant region; the variant human IgG4 constant region has the sequence of SEQ ID NO: 197. |
| 217 | 28G11_L0 | Humanized 28G11 light chain sequence with CDR1, CDR2 and CDR3 sequences from parental murine antibody inserted into the human IGKV1-27*01 germline with a huIGKJ2 framework 4 sequence |
| 47 | 28G11_L1 | Humanized 28G11_L0 light chain sequence which includes amino substitutions F7lY and Y87F |
| 49 | 28G11_L2 | Humanized 28G11_L0 light chain sequence which includes amino substitutions V43T, P44V, F71Y, and Y87F |
| 51 | 28G11_L3 | Humanized 28G11_L0 light chain sequence which includes amino substitutions V19L, T22S, V43T, P44V, F71Y, and Y87F |
| 53 | 28G11_L3a | Humanized 28G11_L0 light chain sequence which includes amino substitutions V19L, T22S, P44V, and F71Y. |

In the first experiment, the various humanized 28G11 candidates were tested for retention of binding to human LAP-TGFβ1 by competition with biotin-28G11 in a flow cytometry assay.

P3U1 cells over-expressing human GARP and LAP-TGFβ1 were placed in a round-bottom 96-well plate at density of 40,000 cells/well. The cells were washed with FACS buffer (25 mM HEPES, 2 mM EDTA, 2% fetal bovine serum in Hank's Balanced Salt Solution). 50 µL of 1:200 diluted TruStain Mouse FcX (BioLegend) was added to each well, followed by 50 µL of 100 ng/µL of humanized 28G11 construct (H0L0, H0L1, H0L2, H0L3, H1L0, H1L1, H1L2, H1L3, H2L0, H2L1, H2L2, H2L3). See Table 34. The antibody was allowed to bind for 10 minutes. 50 µL of 6.2 ng/µL of biotinylated murine hybridoma 28G11_(hyb) was added to each well. The biotinylated antibody was allowed to bind for 10 minutes, and then the cells were washed twice with FACS buffer. The cells were labeled for 15 minutes with allophytocyanin-streptavidin (BioLegend), washed twice with FACS buffer, and analyzed by flow cytometry.

Figure 12:
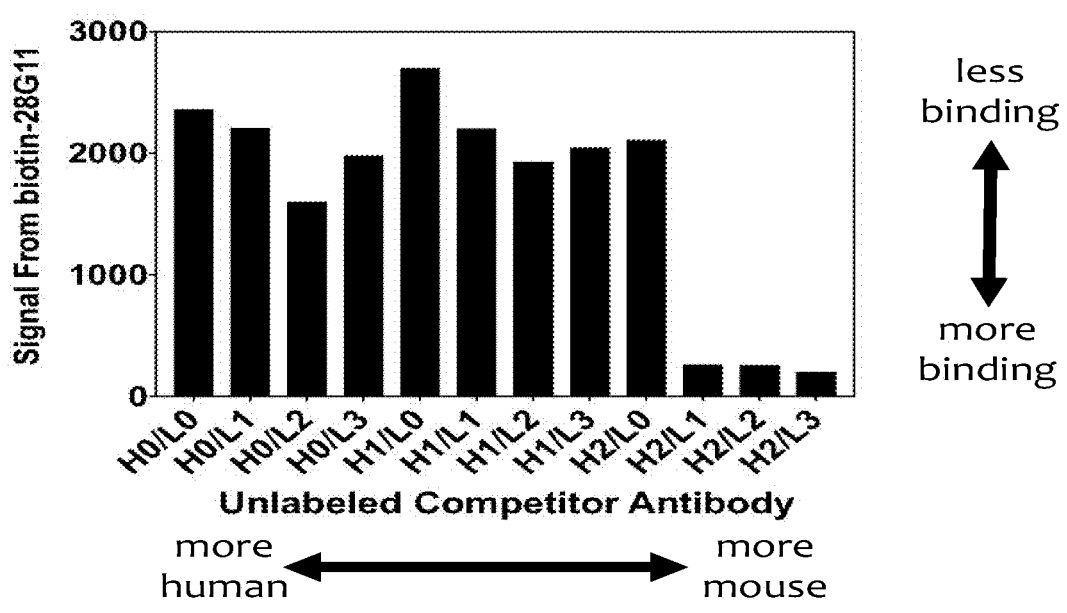
FIG. 12 is a graph showing the ability of humanized 28G11 variants to compete with murine 28G11 parental antibody for binding to P3U1 cells over-expressing human GARP and LAP-TGFβ1. H0-H2 are variant humanized heavy chains, and L0-L3 are variant humanized light chains.

As shown in FIG. 12, all constructs with H0, H1, or L0 failed to block biotin-28G11 binding to human LAP-TGFβ1, indicating that these humanized frameworks do not allow the CDR loops to adopt the correct structure for tight LAP-TGFβ1 binding. 28G11_H2L1, 28G11_H2L2, and 28G11_H2L3 did compete with the parental murine antibody. These constructs were biotinylated to confirm specific binding.

Figure 13:
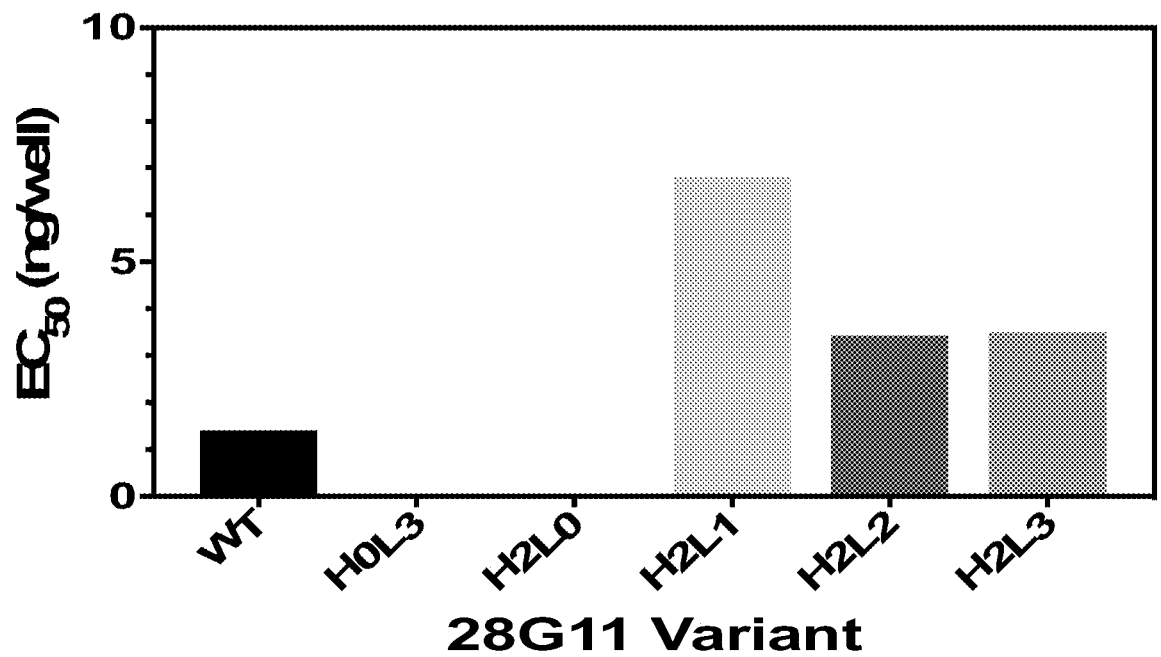
FIG. 13 is a graph showing the binding of the indicated humanized 28G11 variants to P3U1 cells over-expressing human GARP and LAP-TGFβ1.
Figure 14A:
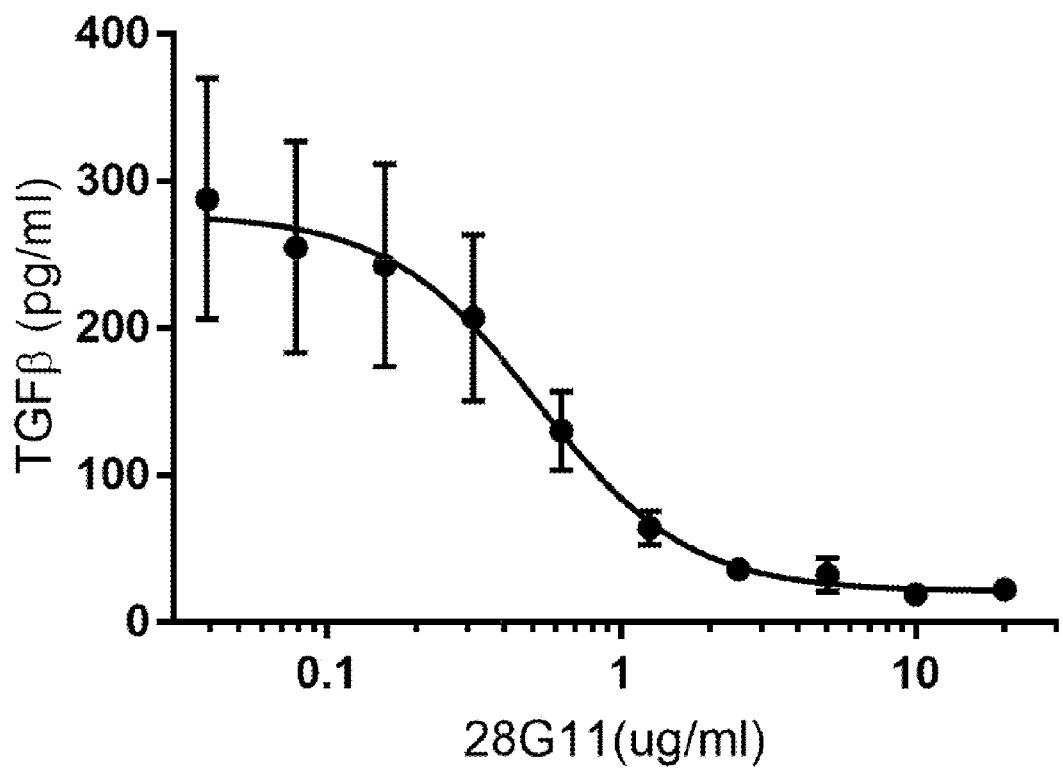
FIGS. 14A-14D are graphs showing the inhibition of TGFβ1 activation by the indicated humanized 28G11 variants by ELISA.
Figure 14B:
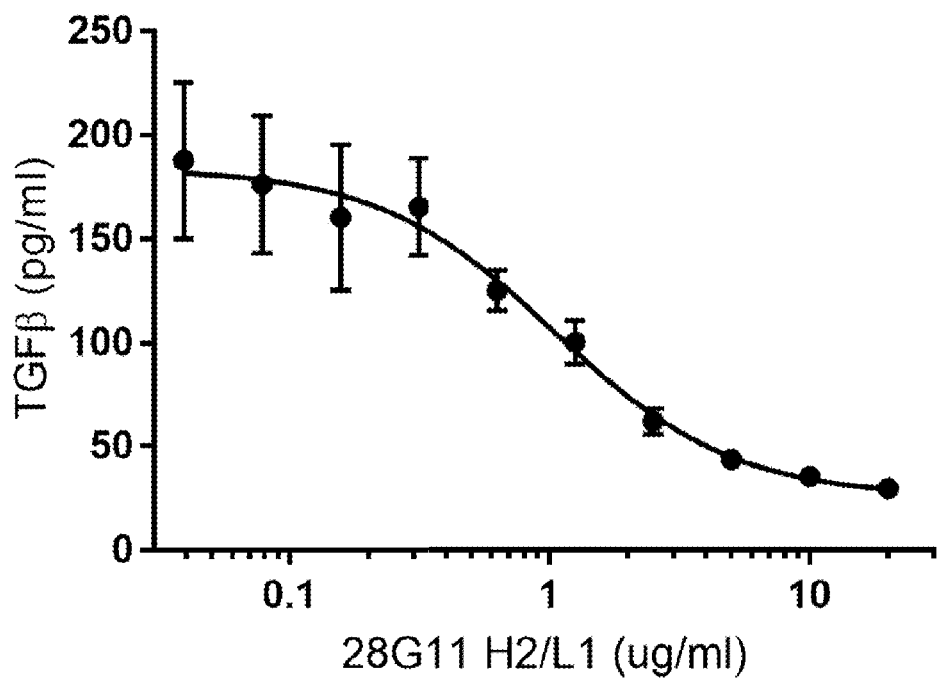
Figure 14C:
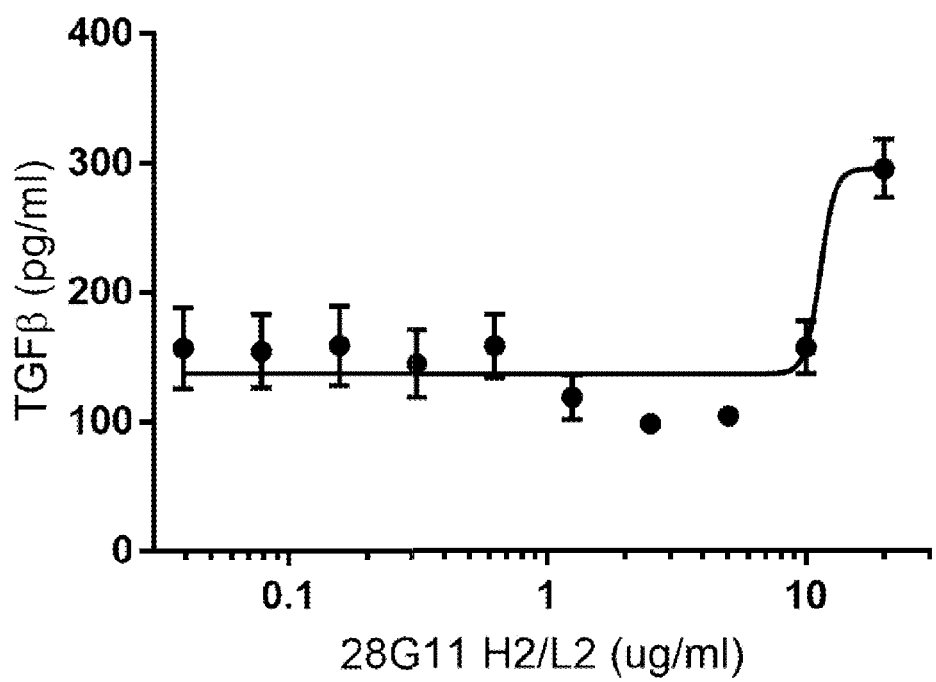
Figure 14D:
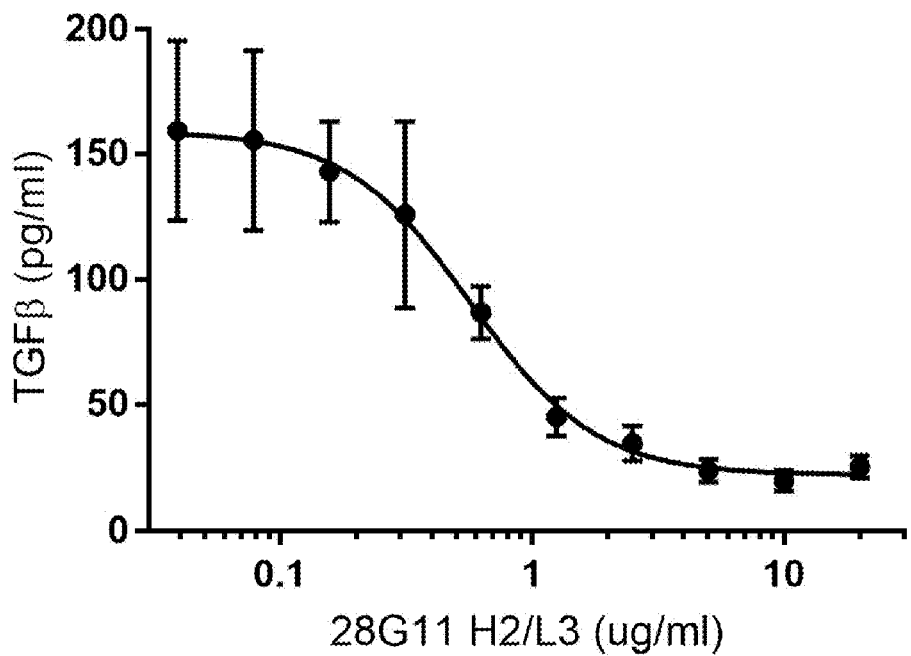

Next, direct binding of the humanized 28G11 variants to P3U1 cells over-expressing human GARP and LAP-TGFβ1 was tested. Briefly, P3U1 cells overexpressing human GARP and LAP-TGFβ1 were plated, washed and FcX-treated as described above. The cells were incubated with 10 µg/mL biotinylated 28G11_H0L3, 28G11_H2L0, 28G11_H2L1, 28G11_H2L2 or 28G11_H2L3 for 20 minutes at 4° C. The cells were washed, stained with APC-streptavidin, washed again and analyzed by flow cytometry as described above. Consistent with the competition experiment, 28G11_H0L3 and 28G11_H2L0 did not bind, but 28G11_H2L1, 28G11_H2L2 and 28G11_H2L3 showed potent binding to human LAP-TGFβ1 (FIG. 13).

The ability of 28G11_H2L1, 28G11_H2L2, and 28G11_H2L3, which showed the most potent binding among the humanized 28G11 variants tested in the studies described above, to inhibit TGFβ1 activation was tested in an ELISA-based assay. Briefly, P3U1 cells expressing human TGFβ were cultured overnight in serum free advanced medium in round bottom tissue culture plates and treated the following day with the humanized 28G11 variants (2-fold serial dilutions starting with 20 ug/ml) for 24 hours. Active TGFβ1 was detected in the supernatant of cell cultures by utilizing a commercially available human TGFβ1 ELISA kit (R&D Systems) according to the manufacturer instructions. As shown in FIGS. 14A-14D, 28G11_(hyb), 28G11_H2L1, and 28G11_H2L3, but not 28G11_H2L2, inhibited TGFβ1 activation.

Based on the studies described above, the best binding was observed with 28G11_H2L3. As shown below, both the H2 heavy chain and L3 light chain include 6 positions that are back-mutated to murine residues from the human framework (back-mutated residues are in lower case letters and underlined.

28G11_H2:
(SEQ ID NO: 35)
EVQLVESGGGLVQPGGSLRLSCAAS GFTFtDYYMS

WVRQAPGKGLEWlG FIRNKPNGYTTEYSASVKGRFTISRDnSqsSLYL

QMNSLKTEDTAVYYCAR YTGGGYFDY WGQGTLlTVSS

28G11_L3:
(SEQ ID NO: 50)
DIQMTQSPSSLSASVGDR_lTI_sC RASQDISNYLN

WYQQKPGK_tvKLLIY YTSRLHS GVPSRFSGSGSGTD_yTLTISSLQPE

DVATY_fC QQGDTLPWT FGQGTKLEIK

Figure 15A:
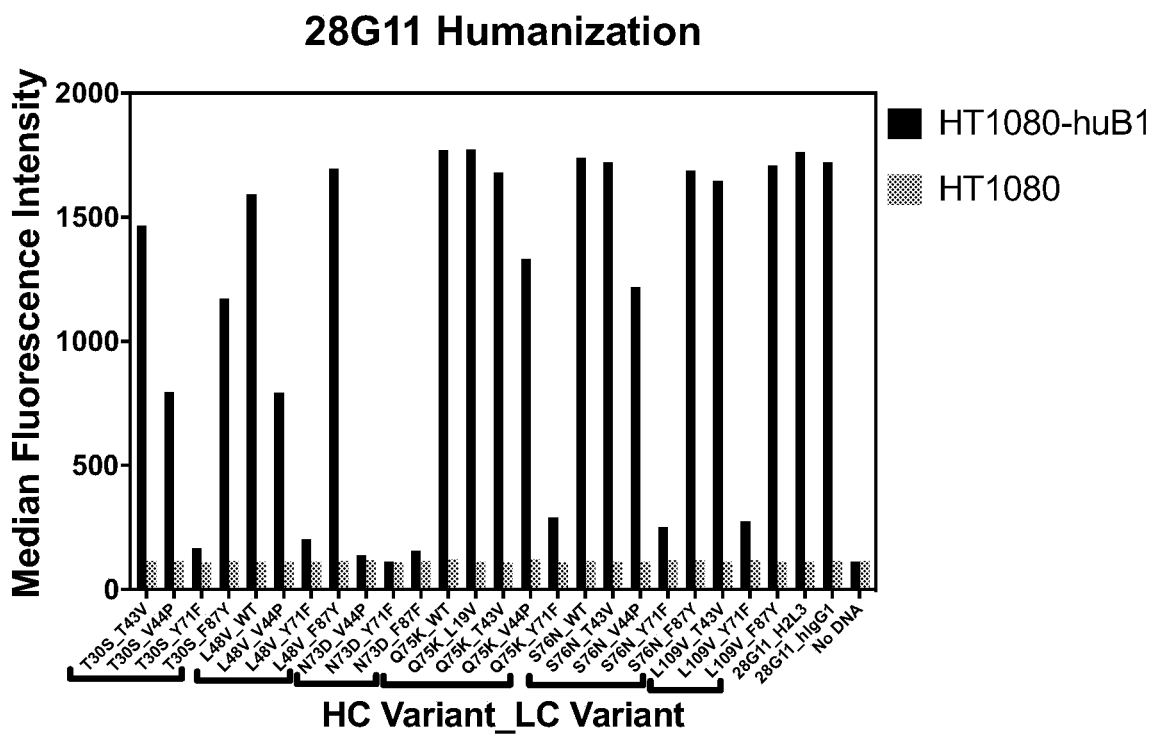
FIG. 15A is a graph showing the effects that various combinations of reversions in the humanized 28G11_H2L3 variant back to human residues have on binding to HT1080 cells overexpressing human LAP-TGFβ1. The various antibodies tested are listed as HC variant_LC variant.
Figure 15B:
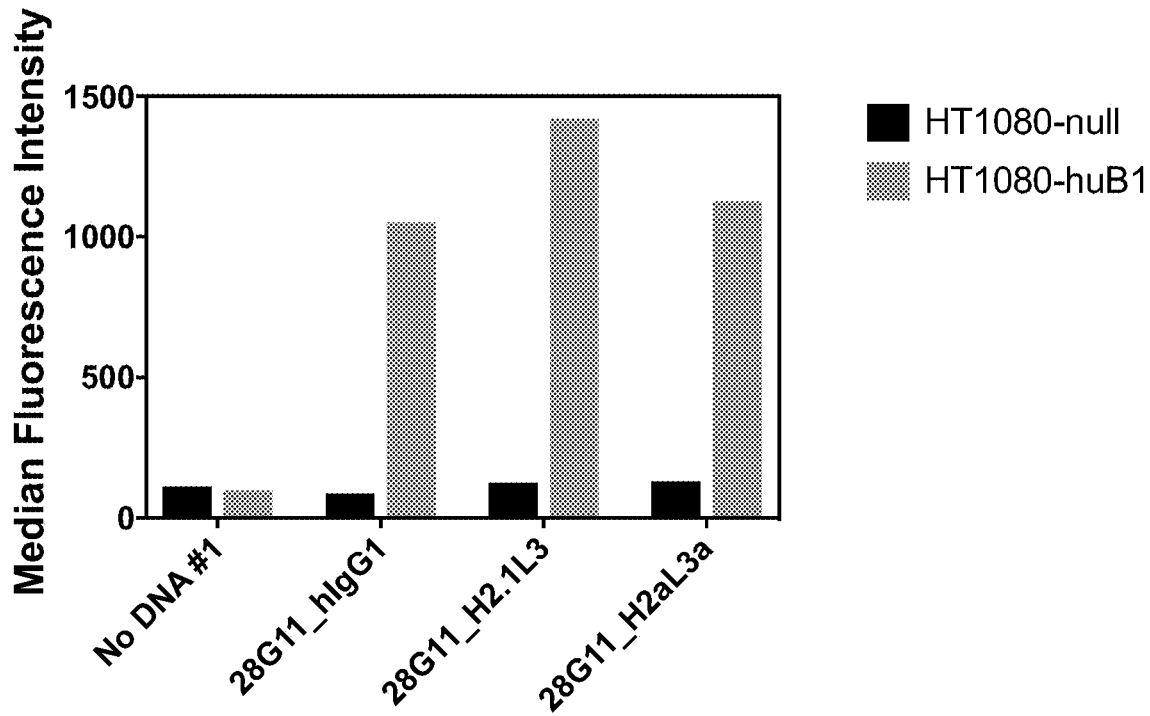
FIG. 15B is a graph showing the effects that the 28G11_H2.1L3 and 28G11_H2aL3a variants have on binding to HT1080 cells overexpressing human LAP-TGFβ1. Black bars correspond to antibody binding to HT1080 cells over-expressing human LAP-TGFβ1. Gray bars correspond to antibody binding to control HT1080 cells which do not over-express human LAP-TGFβ1.

28G11_H2L3 was used as the basis for adding back individual substitutions to determine which of the back-mutated positions could tolerate human residues. FIGS. 15A and 15B show the effects that various combinations of reversions back to human residues had on binding to HT1080 cells overexpressing human LAP-TGFβ1. For example, the combination of HC_N73D+LC_Y71F eliminated binding, and the combination of HC_T30S+LC_V44P had reduced binding. The LC_L19V construct was poorly expressed. From the data in FIG. 15A, it was concluded that the L48V, Q75K, S76N, and L109V substitutions could be tolerated on the heavy chain (resulting in sequence 28G11_H2a) and the T43V and F87Y could be tolerated on the light chain (resulting in sequence 28G11 L3a). 28G11_H2aL3a was tested for binding to HT1080 cells over-expressing human LAP-TGFβ1. See Table 12 and Table 34. As shown in FIG. 15B, this construct binds as well as a mouse-human chimera containing the original variable region domains of the parental murine 28G11 antibody.

The 28G11_H2L3 sequence contains a 'NG' dipeptide in the CDR2 region that can undergo a deamidation reaction to produce aspartate or iso-aspartate at the position of the asparagine residue. To prevent this, a N56Q substitution was introduced into the sequence (28G11_H2.1L3). This antibody binds HT1080-huB1 cells slightly better than the original sequence (FIG. 15B).

Example 10: Characterization of Humanized 22F9 Candidates and Liability Site-Removed 22F9 Variants In this Example, the characteristics of various humanized 22F9 candidates were examined to identify humanized antibodies that retained the function of the parental antibodies (e.g., binding to TGFβ1). Also examined were deamidation/isomerization site-removed 22F9 variants. Table 12 summarizes the various 22F9 variants used in this Example. The sequences of these constructs are provided in Table 34.

TABLE 12

Exemplary 22F9 antibodies and antigen binding fragments

| SEQ ID | Name | Description |
|---|---|---|
| 72 | 22F9_H0 | Humanized 22F9 heavy chain sequence which the CDR1, CDR2 and CDR3 sequences of the parental murine antibody are inserted into the IGHV1-46*01 germline with a consensus framework 4 sequence |
| 74 | 22F9_H0.1 | Humanized 22F9_H0 heavy chain sequence which includes amino substitutions S7P, K12V, V20L, R38K, A40R, N54Q, R66K, V67A, M69L, T73K, T75S, V78A, and D102A |
| 76 | 22F9_H1 | Humanized 22F9_H0 heavy chain sequence which includes amino substitutions M48I, R71V, and R94Y |
| 78 | 22F9_H1.1 | Humanized 22F9_H0 heavy chain sequence which includes amino substitutions S7P, K12V, V20L, R38K, A40R, M48I, N54Q, R66K, V67A, R71V, T73K, T75S, R94Y, and D102A |
| 81 | 22F9_H2 | Humanized 22F9_H0 heavy chain sequence which includes amino substitutions M48I, M69L, R71V, V78A, and R94Y |
| 83 | 22F9_H2.1 | Humanized 22F9_H0 heavy chain sequence which includes amino substitutions S7P, K12V, V20L, R38K, A40R, M48I, N54Q, R66K, V67A, M69L, R71V, T73K, V78A, R94Y, and D102A |
| 86 | 22F9_H3 | Humanized 22F9_H0 heavy chain sequence which includes amino substitutions M48I, M69L, R71V, T73K, T75S, V78A, and R94Y |
| 88 | 22F9_H3.1 | Humanized 22F9_H0 heavy chain sequence which includes amino substitutions S7P, K12V, V20L, M48I, N54Q, M69L, R71V, T73K, T75S, V78A, R94Y, and D102A |
| 91 | 22F9_H4 | Humanized 22F9_H0 heavy chain sequence which includes amino substitutions R38K, A40R, M48I, R66K, V67A, M69L, R71V, T73K, T75S, V78A, and R94Y |
| 93 | 22F9_H5 | Humanized 22F9_H0 heavy chain sequence which includes amino substitutions S7P, K12V, V20L, R38K, A40R, M48I, R66K, V67A, M69L, R71V, T73K, T75S, V78A, and R94Y |
| 96 | 22F9_H5.2 | Humanized_22F9_H0 heavy chain sequence which includes amino substitutions S7P, K12V, V20L, R38K, A40R, M48I, N54Q, R66K, V67A, M69L, R71V, T73K, T75S, V78A, R94Y, and D102A |
| 99 | 22F9_H7 | Humanized 22F9_H0 heavy chain sequence which includes amino substitutions S7P, K12V, V20L, M48I, N54Q, R71V, T73K, R94Y, and D102A |
| 100 | 22F9_H7_hIgG4mut | 22F9_H7 heavy chain with a variant human IgG4 constant region; the variant human IgG4 constant region has the sequence of SEQ ID NO: 197. |
| 102 | 22F9_H7a | Humanized 22F9_H0 heavy chain sequence which includes amino substitutions Q1E, S7P, K12V, V20L, M48I, N54Q, R71V, T73K, R94Y, and D102A |
| 103 | 22F9_H7a_hIgG4mut | 22F9_H7a heavy chain with a variant human IgG4 constant region; the variant human IgG4 constant region has the sequence of SEQ ID NO: 197. |
| 105 | 22F9_L0 | Humanized 22F9 light chain sequence which the CDR1, CDR2 and CDR3 sequences of the parental murine antibody are inserted into the IGKV1-39 × 01 germline with a IGKJ4 framework 4 sequence |
| 107 | 22F9_L1 | Humanized 22F9_L0 light chain sequence which includes amino acidsubstitutions A43P and D70H |
| 109 | 22F9_L2 | Humanized 22F9_L0 light chain sequence which includes amino acid substitutions A13V, V19A, A43P, D70H, L78V, and V104L |

Figure 16:
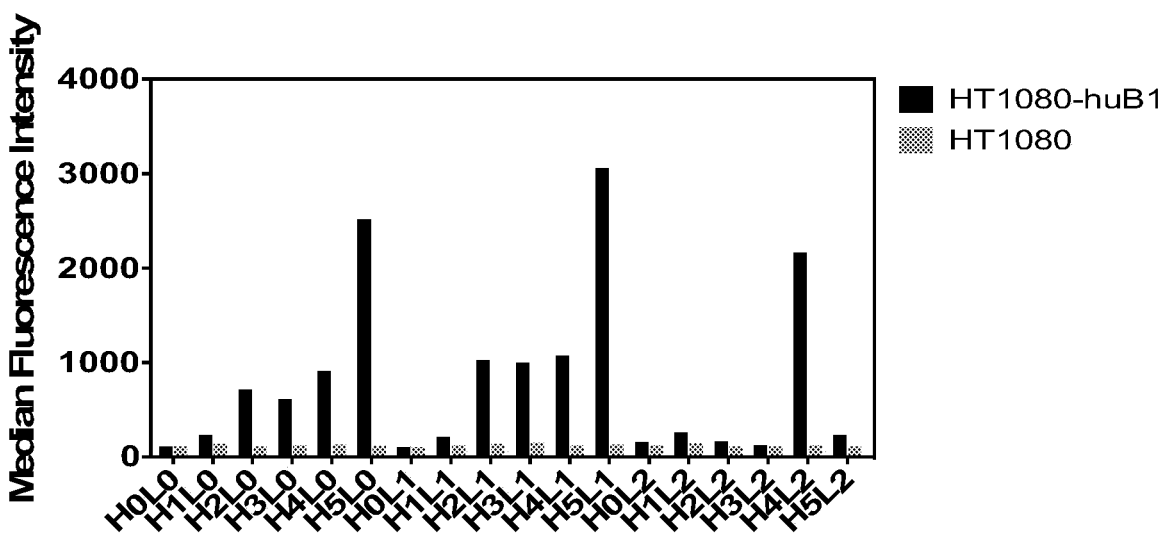
FIG. 16 is a graph showing the binding of the indicated humanized 22F9 variants to HT1080 cells over-expressing human LAP-TGFβ1. Black bars correspond to antibody binding to HT1080 cells over-expressing human LAP-TGFβ1. Gray bars correspond to antibody binding to control HT1080 cells which do not over-express human LAP-TGFβ1.

First, the ability of 22F9_H0L0, H1L0, H2L0, H3L0, H4L0, H5L0, H0L1, H1L1, H2L1, H3L1, H4L1, H5L1, H0L2, H1L2, H2L2, H3L3, H4L2, and H5L2 to bind to HT1080 cells overexpressing human TGFβ1 was tested by flow cytometry. HT1080 cells over-expressing human LAP-TGFβ1 were placed in a round-bottom 96-well plate at density of 40,000 cells/well. The cells were washed with FACS buffer (25 mM HEPES, 2 mM EDTA, 2% fetal bovine serum in Hank's Balanced Salt Solution). 50 μL of 1:200 diluted TruStain Human FcX (BioLegend) was added to each well, followed by 50 μL of 100 ng/μL of humanized 22F9 construct. The antibody was allowed to bind for 20 minutes. The cells were washed twice with FACS buffer. The cells were labeled for 15 minutes with Alexa647-anti Human IgG (Jackson Immunoresearch), washed twice with FACS buffer, and analyzed by flow cytometry. As shown in FIG. 16, 22F9_H2L0, H3L0, H4L0, H5L0, H2L1, H3L1, H4L1, H5L1, and H4L2 showed some binding relative to control HT1080 cells and 22F9_H0L0. The strongest binding was observed with antibodies containing the H5 heavy-chain sequence.

Binding to human TGFβ1 of a subset of candidates was also tested by bio-layer interferometry (Octet). A streptavidin coated tip was equilibrated for 60 seconds in binding buffer (10 mM sodium phosphate, 150 mM sodium chloride, 1% bovine serum albumin, 0.05% sodium azide). The tip was then dipped in 10 μg/mL biotinylated antibody in binding buffer. After 15 seconds, the tip was washed in binding buffer for 60 seconds, and then dipped in 0-24 nM Fc-human LAP. Analyte association was measured for 5 minutes. The tip was transferred to binding buffer alone, and analyte dissociation was measured for 5 minutes. The association and dissociation data were fit to a 1:1 binding model. As shown in Table 13, of the candidates tested, 22F9_H5L0 showed the highest signal change on binding, and 22F9_H4L0 showed the tightest affinity.

TABLE 13

Binding data for 22F9 antibodies and antigen binding fragments

| Antibody | $k_{on}$ ($\times 10^5$ M$^{-1}$s$^{-1}$) | $k_{off}$ ($\times 10^{-3}$ s$^{-1}$) | $K_D$ (nM) | Loading (nm) | Binding (nm) |
|---|---|---|---|---|---|
| 22F9_hIgG1 | 4.50 | 1.68 | 3.74 | 1.13 | 0.27 |
| 22F9_H3L0 | 7.78 | 2.14 | 2.75 | 0.99 | 0.023 |
| 22F9_H4L0 | 8.10 | 1.32 | 1.63 | 0.90 | 0.057 |
| 22F9_H4L2 | 5.98 | 1.37 | 2.30 | 1.17 | 0.07 |
| 22F9_H5L0 | 5.10 | 1.7 | 3.35 | 1.22 | 0.13 |
| 22F9_H5L1 | 5.19 | 1.22 | 2.34 | 1.29 | 0.08 |
| 22F9_H5L2 | 6.29 | 2.46 | 3.91 | 1.25 | 0.06 |

In another experiment, size exclusion chromatography (SEC) was used to assess aggregation of the candidates. Each protein was diluted to 1 mg/mL in phosphate buffered saline, pH 7.4. A Sepax SEC-300 column was equilibrated with 10 mM sodium phosphate, 150 mM sodium chloride, 0.05% (v/v) sodium azide, pH 7.4. 10 μL of 1 mg/mL antibody was injected onto the column. Eluted proteins were detected by absorbance at 280 nm. The IgG monomer peak was identified by comparing its retention time against a set of gel-filtration molecular weight standards (Bio-Rad). The results are shown in Table 14.

TABLE 14

22F9 chromatographic data

| Antibody | RT (min) | Area (mAU*s) | % monomer |
|---|---|---|---|
| 22F9_mIgG2a | 7.956 | 341 | >99% |
| 22F9_hIgG1 | 8.035 | 259 | >99% |
| 22F9_H0L0 | 7.93 | 160 | 77% |
| 22F9_H4L0 | 8.083 | 168 | >99% |
| 22F9_H4L1 | 8.178 | 180 | >99% |
| 22F9_H4L2 | 8.161 | 214 | >99% |
| 22F9_H5L0 | 8.02 | 220 | >99% |
| 22F9_H5L1 | 8.106 | 219 | >99% |
| 22F9_H5L2 | 8.11 | 206 | >99% |

Figure 17A:
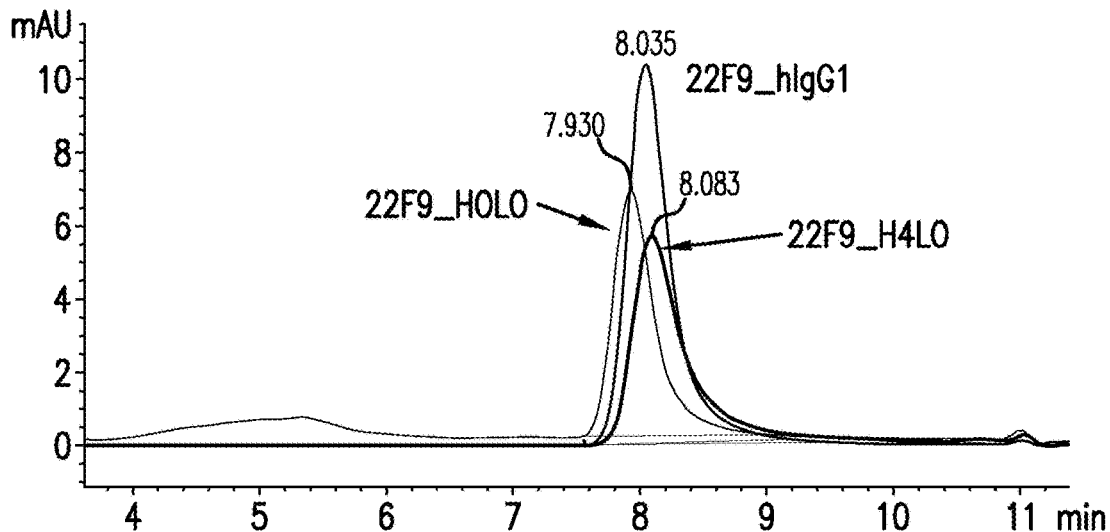
FIGS. 17A and 17B are chromatograms from size exclusion high-performance liquid chromatography (SE-HPLC) for the indicated antibody 22F9 and variants.
Figure 17B:
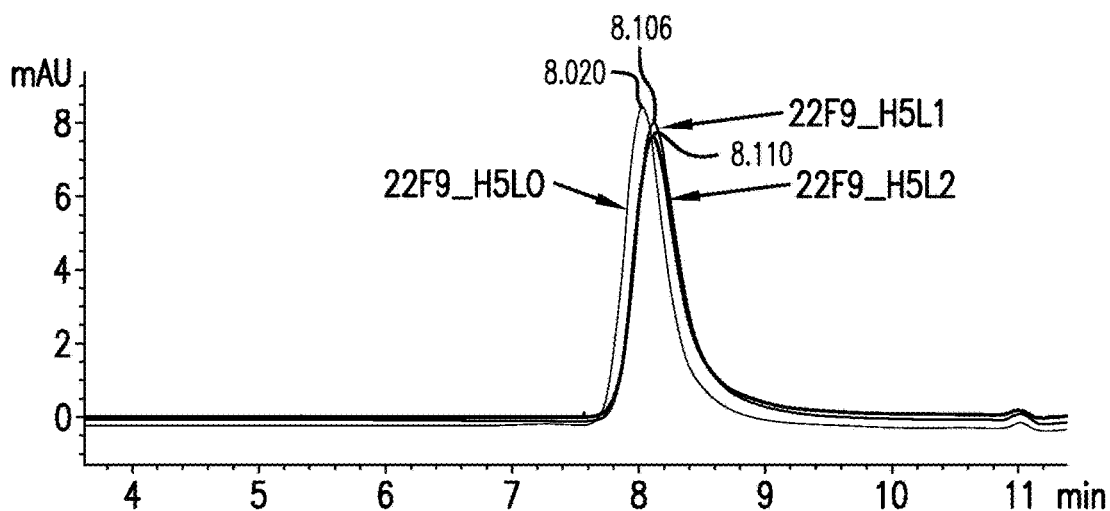

Most of the tested candidates showed little aggregation, as reflected in the high percentage of monomers (>99%). Candidates with lower than expected Octet binding signals also had smaller SEC peaks. The significantly lower total area for 22F9_H4L0 implies the aggregates are too large to enter the column, whereas all 22F9_H5 constructs were well behaved. FIG. 17A shows size exclusion-high performance liquid chromatography (SE-HPLC) results for 22F9_hIgG1, 22F9_H0L0, and 22F9_H4L0, and FIG. 17B shows the results for 22F9_H5L0, H5L1, and H5L2.

The H5L0 candidate, the sequence of which is provided below, was further characterized by reverting murine residues back to the corresponding human residue by single-site substitution to determine which murine residues are essential. Additional substitutions were made to remove potential deamidation sites (N54S, N54H, N54A, N54Q) and isomerization sites (D102E, D102A, D102G).

22F9_H5:

(SEQ ID NO: 92)

QVQLVQpGAEVvKPGASVKlSCKAS GYTFTSYWMH

WVkQrPGQGLEWiG MINPNSGSTNYNEKFKS kaTlTvDkSsSTaYM

ELSSLRSEDTAVYYCAy YDY<sup>D</sup>GFFDV WGQGTLVTVSS

Figure 18A:
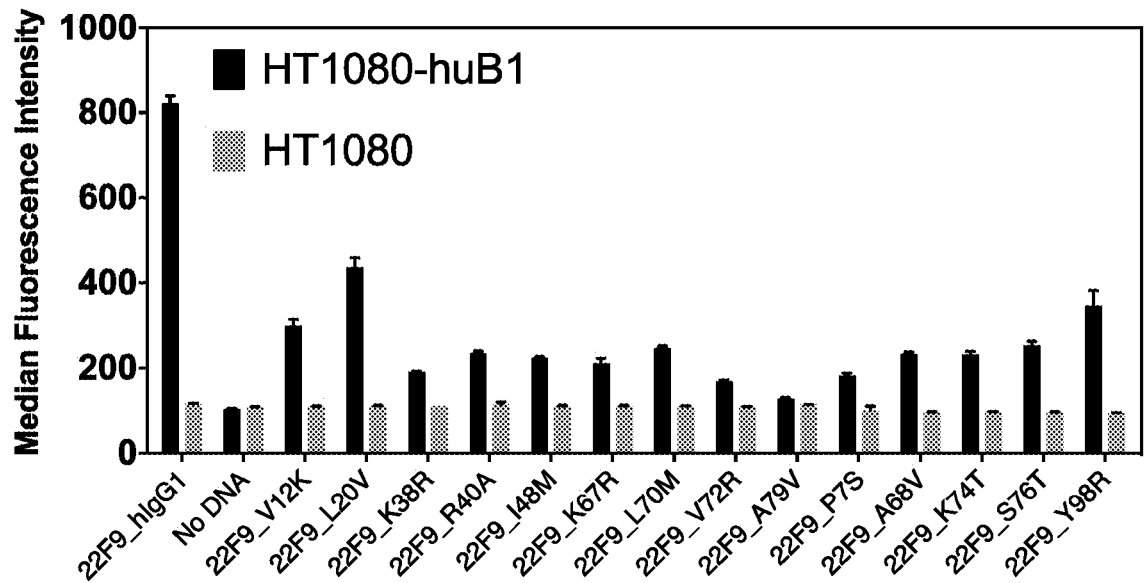
FIG. 18A is a graph showing the effects of reverting murine residues in the heavy chain of 22F9_H5L0 back to corresponding human residues on binding to HT1080 cells over-expressing human LAP-TGFβ1.
Figure 18B:
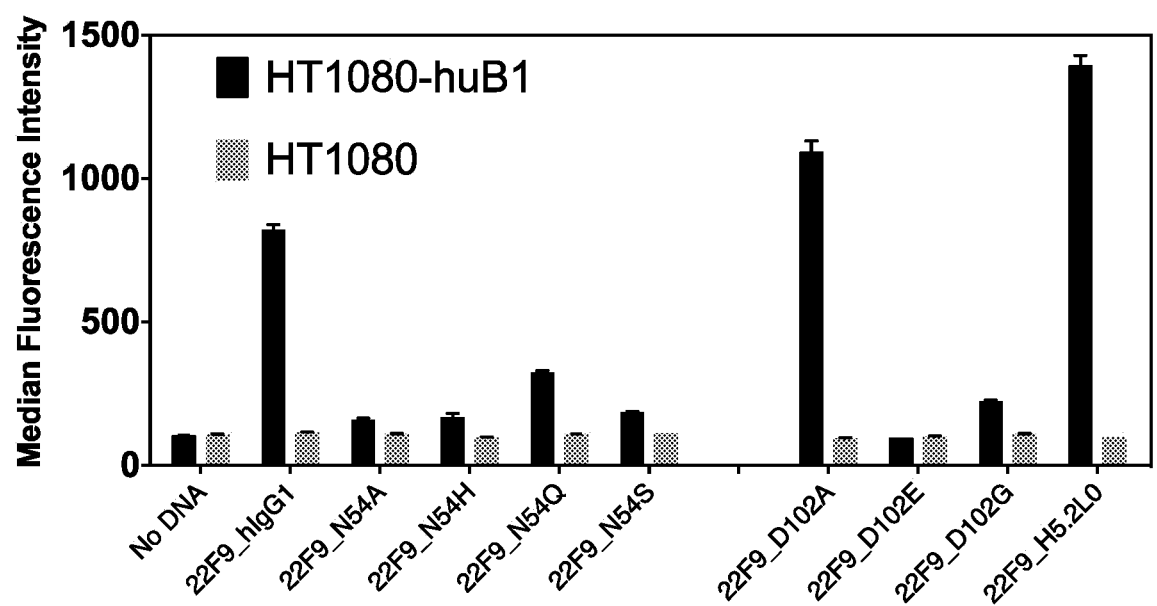
FIG. 18B is a graph showing the effects of substitutions to remove potential deamidation and/or isomerization sites in 22F9_H5L0 on binding to HT1080 cells over-expressing human LAP-TGFβ1. 22F9_H5.2L0 corresponds to 22F9_H5L0 with the double N54Q/D102A mutation.

As shown in FIG. 18A, all single-site substitutions reverting murine framework residues back to human substantially reduced binding to LAP-TGFβ1. As shown in FIG. 18B, the N54Q and D102A substitutions retained the most binding activity of all substitutions at those positions, and a double N54Q/D102A variant (22F9_H5.2) had the strongest binding signal of all antibodies tested in this assay. See also Table 12 and Table 34.

Figure 18C:
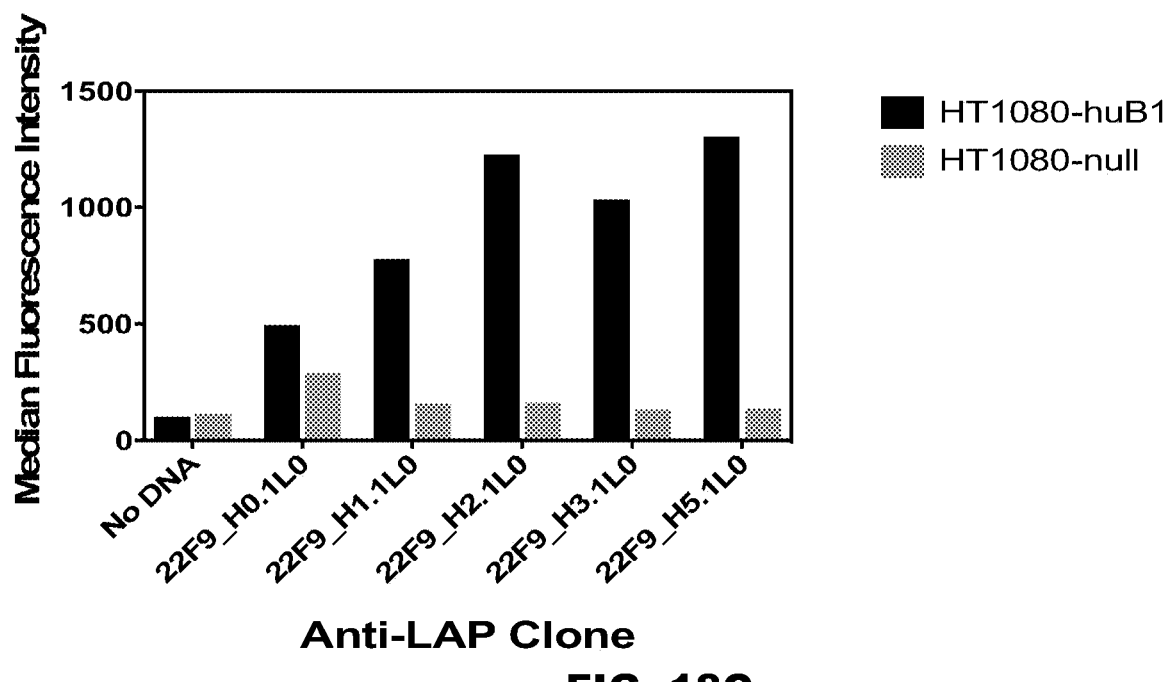
FIG. 18C is a graph showing the binding of 22F9_H0.1, 22F9_H1.1, 22F9_H2.1, and 22F9_H3.1 variants to HT1080 cells over-expressing human LAP-TGFβ1. Black bars correspond to antibody binding to HT1080 cells over-expressing human LAP-TGFβ1. Gray bars correspond to antibody binding to control HT1080 cells which do not over-express human LAP-TGFβ1.

As the single variants did not yield any reduction in the number of murine residues, an alternative strategy was employed to make amino-acid substitutions in groups. These constructs, labeled 22F9_H0.1, 22F9_H1.1, 22F9_H2.1, and 22F9_H3.1, were assayed for binding to HT1080 cells over-expressing human LAP-TGFβ1 as described above. As shown in FIG. 18C, the 22F9_H0.1 variant did not bind human LAP-TGFβ1, while the 22F9_H1.1, 22F9_H2.1 and 22F9_H3.1 variants did bind human LAP-TGFβ1.

Example 11: Characterization of Humanized 20E6 Candidates and Liability Site-Removed 20E6 Variants In this Example, the characteristics of various humanized 20E6 candidates were examined to identify humanized antibodies that retained the function of the parental antibodies (e.g., binding to TGFβ1). Also examined were deamidation/isomerization site-removed 20E6 variants. Table 15 summarizes the various 20E6 variants used in this Example. The sequences of these constructs are provided in Table 34. Notably, L1 includes 3 murine back-substitutions, i.e., P44V (which is at the VH/VL interface and could potentially affect domain pairing and stability), F71Y (a canonical residue which could potentially affect the structure of CDR L2), and Y87F (which is at the VH/VL interface and could potentially affect domain pairing and stability).

TABLE 15

Exemplary 20E6 antibodies and antigen binding fragments

| SEQ ID | Name | Description |
|---|---|---|
| 128 | 20E6_H0 | Humanized 20E6 heavy chain sequence which the CDR1, CDR2 (extended definition) and CDR3 sequences of the parental murine antibody are inserted into the IGHV1-2*02 germline with a consensus framework 4 sequence |
| 131 | 20E6_H0.1 | Humanized 20E6 heavy chain sequence which the CDR1, CDR2 and CDR3 sequences of the parental murine antibody are inserted into the IGHV1-2*02 germline with a consensus framework 4 sequence |
| 134 | 20E6_H0.2 | Humanized 20E6_H0.1 heavy chain sequence which includes the amino acid substitution N54Q |
| 219 | 20E6_H0.2a | Humanized 20E6_H0.1 heavy chain sequence which includes the amino acid substitutions Q1E and N54Q |
| 136 | 20E6_H0.3 | Humanized 20E6_H0.1 heavy chain sequence which includes the amino acid substitution N54G |
| 137 | 20E6_H0.4 | Humanized 20E6_H0.1 heavy chain sequence which includes the amino acid substitution N54A |
| 138 | 20E6_H0.5 | Humanized 20E6_H0.1 heavy chain sequence which includes the amino acid substitution N54S |
| 139 | 20E6_H0.6 | Humanized 20E6_H0.1 heavy chain sequence which includes the amino acid substitution N54H |
| 140 | 20E6_H0.7 | Humanized 20E6_H0.1 heavy chain sequence which includes the amino acid substitution N54L |
| 141 | 20E6_H0.8 | Humanized 20E6_H0.1 heavy chain sequence which includes the amino acid substitution N54D |
| 135 | 20E6_H0.2_hIgG4 mut | 20E6_H0.2 heavy chain with a variant human IgG4 constant region; the variant human IgG4 constant region has the sequence of SEQ ID NO: 197. |
| 220 | 20E6_H0.2a_hIgG4 mut | 20E6_H0.2a heavy chain with a variant human IgG4 constant region; the variant human IgG4 constant region has the sequence of SEQ ID NO: 197. |
| 145 | 20E6_H1 | Humanized 20E6_H0 heavy chain sequence which includes amino acid substitutions M48I, M69L, R71V |
| 147 | 20E6_H2 | Humanized 20E6_H0 heavy chain sequence which includes amino acid substitutions M48I, M69L, R71V, T73K, T75S |
| 149 | 20E6_H3 | Humanized 20E6_H0 heavy chain sequence which includes amino acid substitutions R38K, A40R, M48I, R66K, V67A, M69L, R71V, T73K, T75S |
| 151 | 20E6_H4 | Humanized 20E6_H0 heavy chain sequence which includes amino acid substitutions S7P, K12V, V20L, R38K, A40R, M48I, R66K, V67A, M69L, R71V, T73K, T75S |
| 153 | 20E6_L0 | Humanized 20E6 light chain sequence which the CDR1, CDR2 and CDR3 sequences of the parental murine antibody are inserted into the IGKV1-39*01 germline with a IGKJ2 framework 4 sequence |
| 155 | 20E6_L1 | Humanized 20E6_L0 light chain sequence which includes amino acid substitutions P44V, F71Y, Y87F |
| 157 | 20E6_L0_P44V | 20E6_L0 having a P to V mutation at position 44 |
| 159 | 20E6_L0_F71Y | 20E6_L0 having a F to Y mutation at position 71 |
| 161 | 20E6_L0_Y87F | 20E6_L0 having a Y to F mutation at position 87 |

Figure 19A:
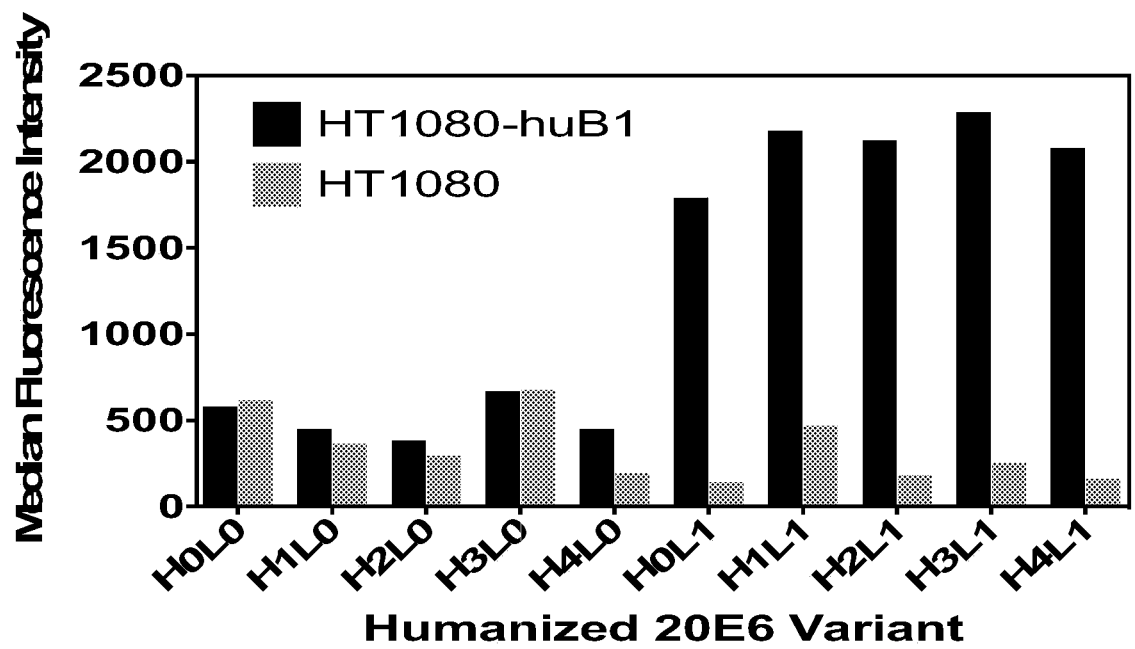
FIGS. 19A and 19B are graphs showing the binding of the indicated humanized 20E6 variants to human LAP-TGFβ1. Black bars correspond to antibody binding to HT1080 cells over-expressing human LAP-TGFβ1. Gray bars correspond to antibody binding to control HT1080 cells which do not over-express human LAP-TGFβ1.
Figure 19B:
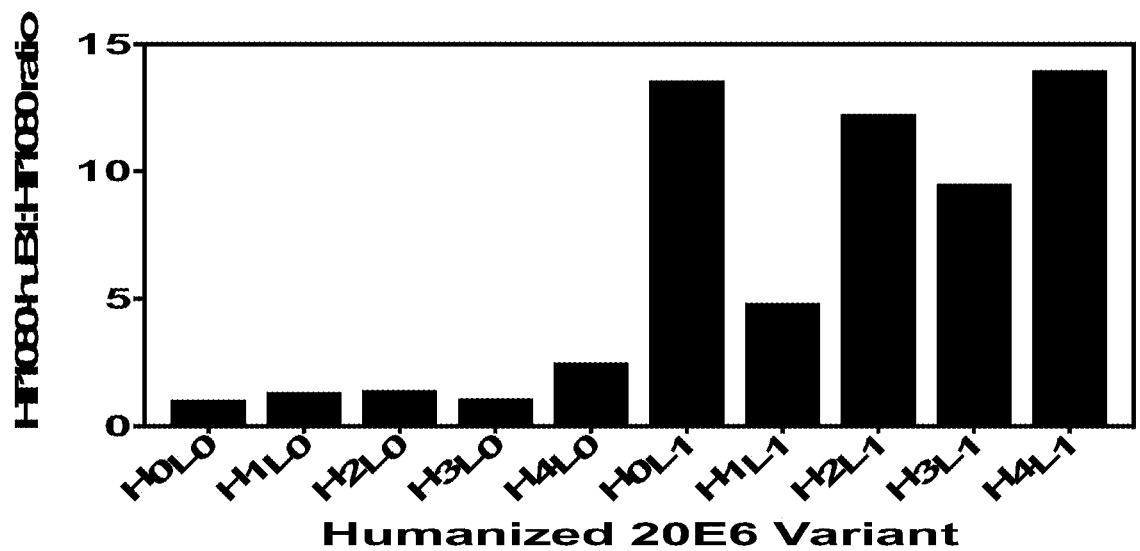

First, the ability of the humanized 20E6 candidates to bind to HT1080 cells overexpressing human TGFβ1 was tested by flow cytometry. HT1080 cells over-expressing human LAP-TGFβ1 were placed in a round-bottom 96-well plate at density of 40,000 cells/well. The cells were washed with FACS buffer (25 mM HEPES, 2 mM EDTA, 2% fetal bovine serum in Hank's Balanced Salt Solution). A volume (50 µL) of 1:200 diluted TruStain Human FcX (BioLegend) was added to each well, followed by 50 µL of 100 ng/µL of humanized 20E6 antibody construct. The antibody was allowed to bind for 20 minutes. The cells were washed twice with FACS buffer. The cells were labeled for 15 minutes with Alexa647-anti Human IgG (Jackson Immunoresearch), washed twice with FACS buffer, and analyzed by flow cytometry. As shown in FIGS. 19A and 19B, candidates which include the L1 light chain showed greater binding to HT1080-huβ1 cells than to control HT1080 cells.

The binding of humanized 20E6 candidates to human LAP-TGFβ1 was also tested by bio-layer interferometry (Octet). As shown in Table 16, 20E6_H(0-4)L1 had comparable binding kinetics, consistent with the flow cytometry results.

TABLE 16

Octet binding data for 20E6

| Antibody | $k_{on}$ ($\times 10^5$ M$^{-1}$s$^{-1}$) | $k_{off}$ ($\times 10^{-3}$ s$^{-1}$) | $K_D$ (nM) |
|---|---|---|---|
| 20E6_hIgG1 | 0.98 | 9.97 | 1.02 |
| 20E6_H0L1 | 1.59 | 8.14 | 0.51 |
| 20E6_H1L1 | 1.41 | 6.77 | 0.48 |
| 20E6_H2L1 | 1.57 | 7.47 | 0.48 |

TABLE 16-continued

Octet binding data for 20E6

| Antibody | $k_{on}$ ($\times 10^5$ M$^{-1}$s$^{-1}$) | $k_{off}$ ($\times 10^{-3}$ s$^{-1}$) | $K_D$ (nM) |
|---|---|---|---|
| 20E6_H3L1 | 1.48 | 7.02 | 0.47 |
| 20E6_H4L1 | 1.56 | 7.29 | 0.47 |

Figure 20A:
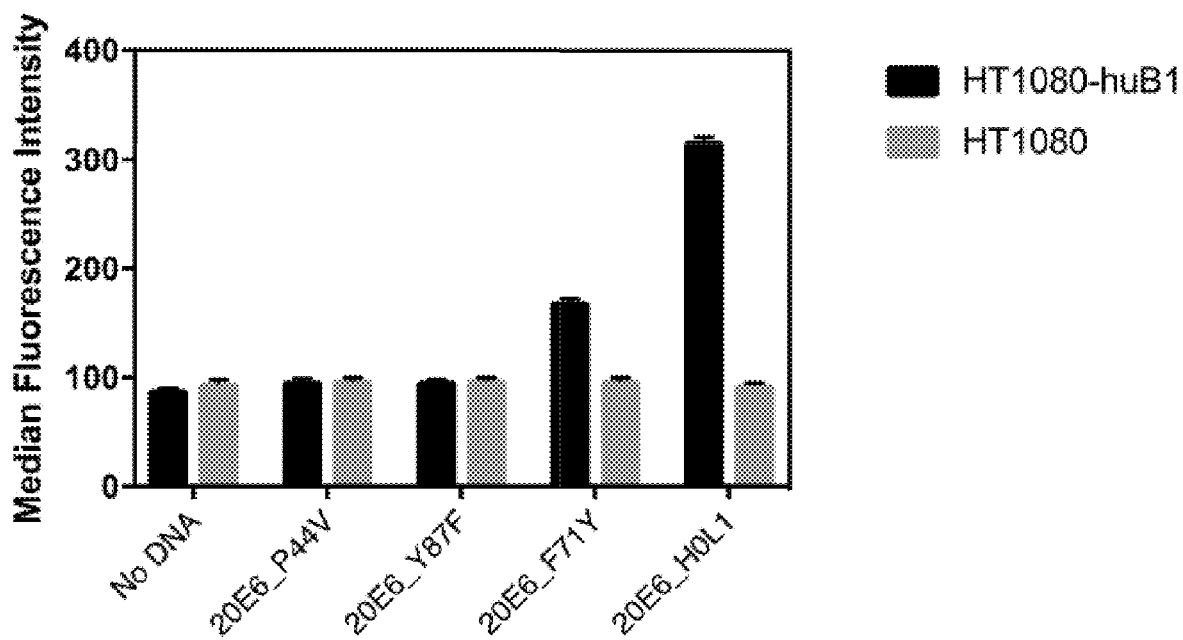
FIG. 20A is a graph showing the effects of murine back-substitutions to the L1 light chain of 20E6 on binding to human LAP-TGFβ1.

As discussed above, the L1 light chain has 3 murine back-substitutions, i.e., P44V, F71Y, and Y87F. To determine whether all three of these murine back-substitutions are necessary for binding to LAP-TGFβ1, each substitution was introduced individually into the L0 light chain and compared to 20E6_H0L1. As shown in FIG. 20A, all three murine back-substitutions are necessary for binding to HT1080 cells over-expressing LAP-TGFβ1.

Figure 20B:
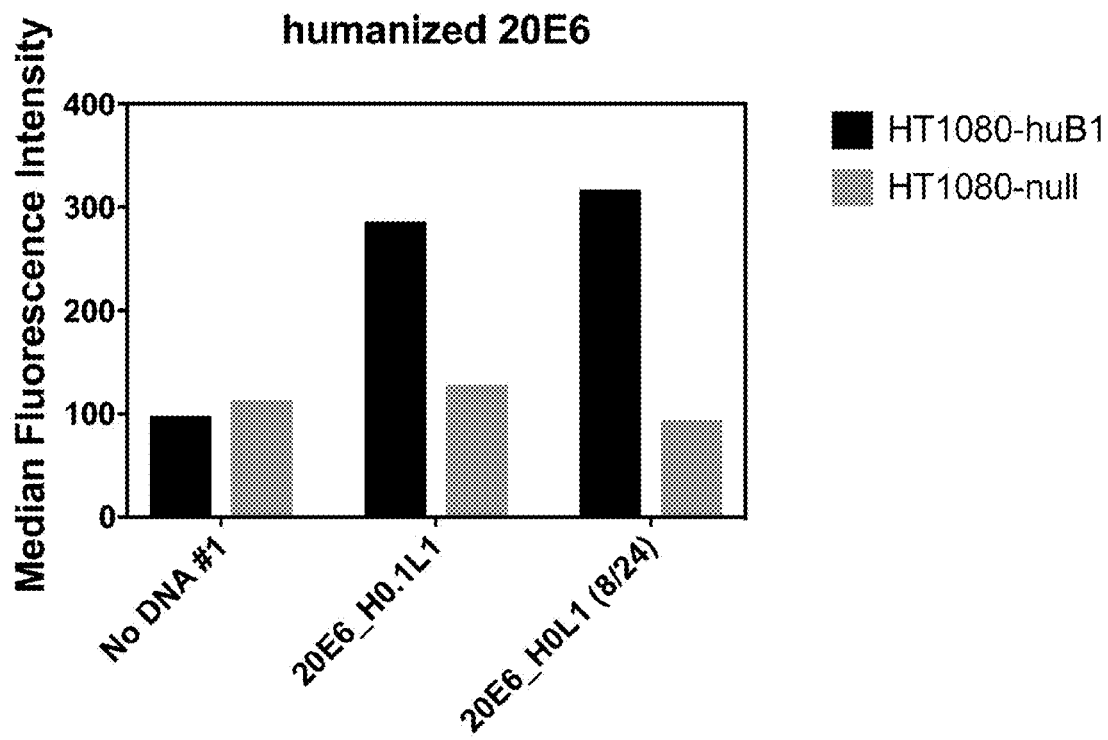
FIG. 20B is a graph showing the binding of the 20E6_H0 heavy chain variant with reduced immunogenicity on binding to human LAP-TGFβ1. Black bars correspond to antibody binding to HT1080 cells over-expressing human LAP-TGFβ1. Gray bars correspond to antibody binding to control HT1080 cells which do not over-express human LAP-TGFβ1.

The CDR grafting used to generate the 20E6_H0 sequence used an extended definition of the heavy-chain CDR2, which resulted in the incorporation of additional murine residues in 20E6_H0. To reduce the risk of immunogenicity, a variant of 20E6_H0 was made with the traditional (Kabat) definition for heavy-chain CDR2. This construct, 20E6_H0.1, bound to human LAP-TGFβ1, as well as 20E6_H0, indicating that these murine residues are not needed (FIG. 20B).

Example 12: Binding of Anti-LAP Antibodies to Human LAP-TGFβ1, 2 and 3

This Example describes testing the specificity of humanized 20E6 (20E6_H0.2aL1_IgG1) antibody, which has the heavy and light chain sequences of SEQ ID NOs: 219 and 155, respectively) for binding to human LAP-TGFβ isoforms 1, 2, and 3 using bio-layer interferometry.

Figure 21A:
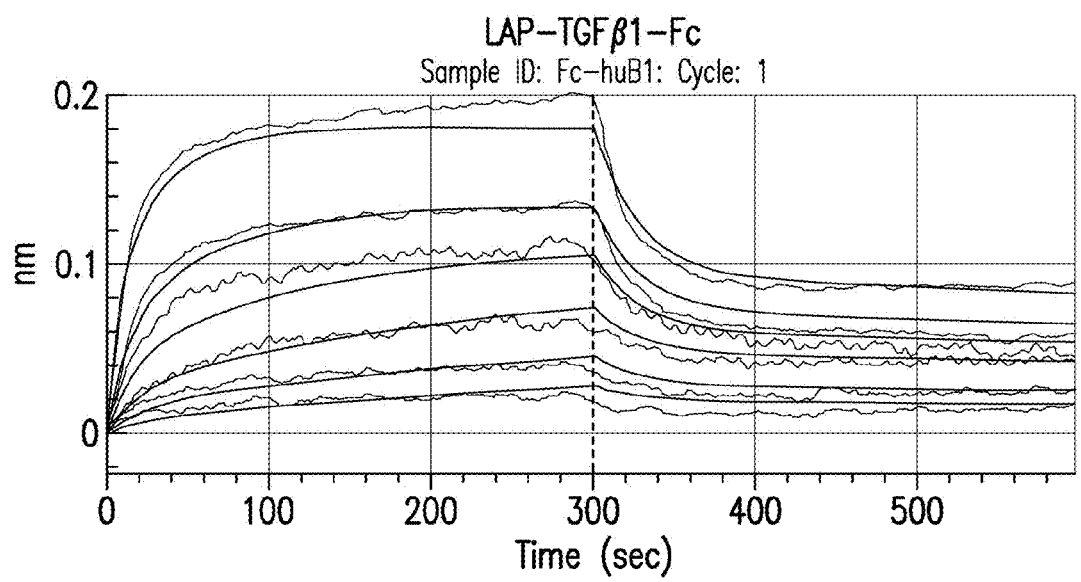
FIGS. 21A-21C are bio-layer interferometry curves showing the binding of 20E6_H0.2aL1_hIgG1 antibody to Fc fusions comprising either human LAP-TGFβ1, LAP-TGFβ2, or LAP-TGFβ3.
Figure 21B:
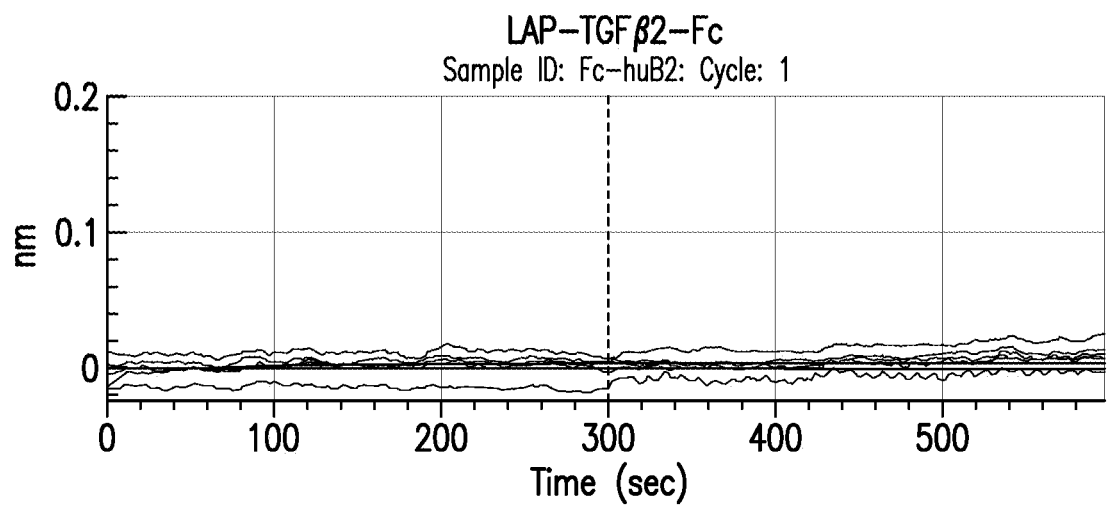
Figure 21C:
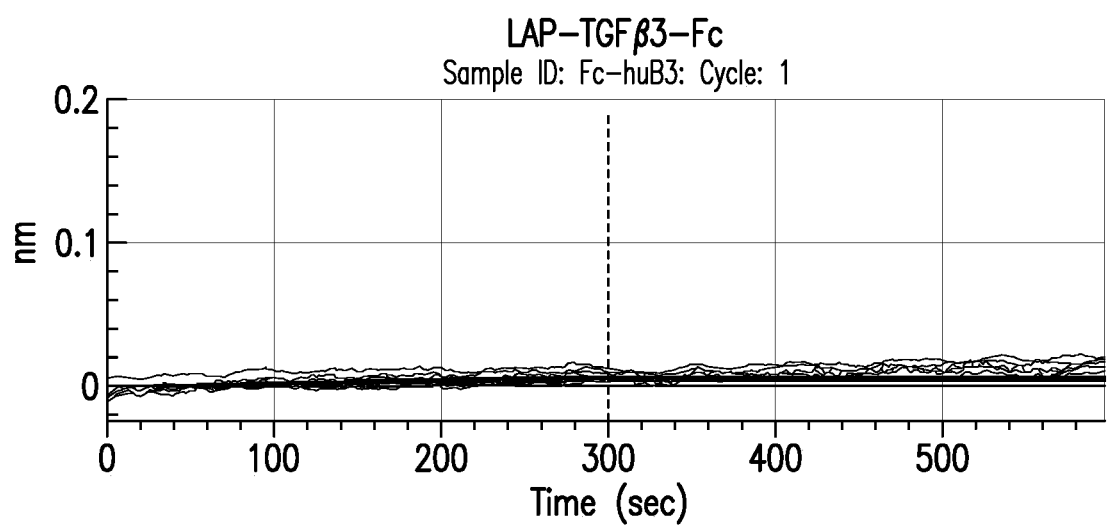
Figure 22A:
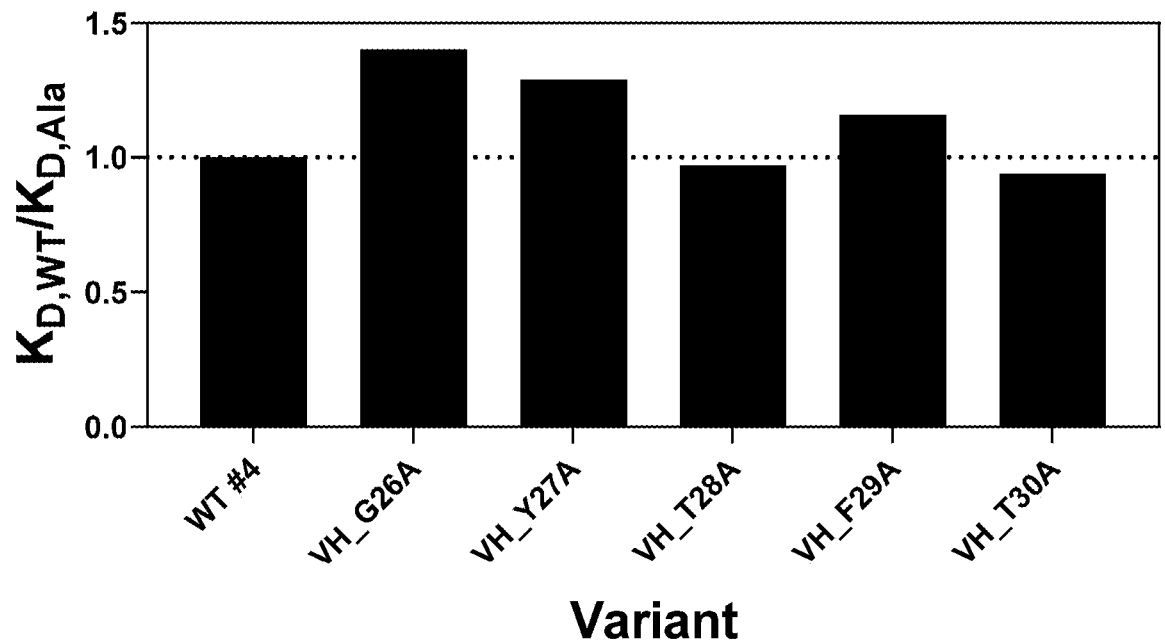
FIGS. 22A-22D are graphs showing the binding of multiple heavy and light chain CDR variants of 20E6_H0.2aL1_hIgG1 antibody to human LAP-TGFβ1.
Figure 22B:
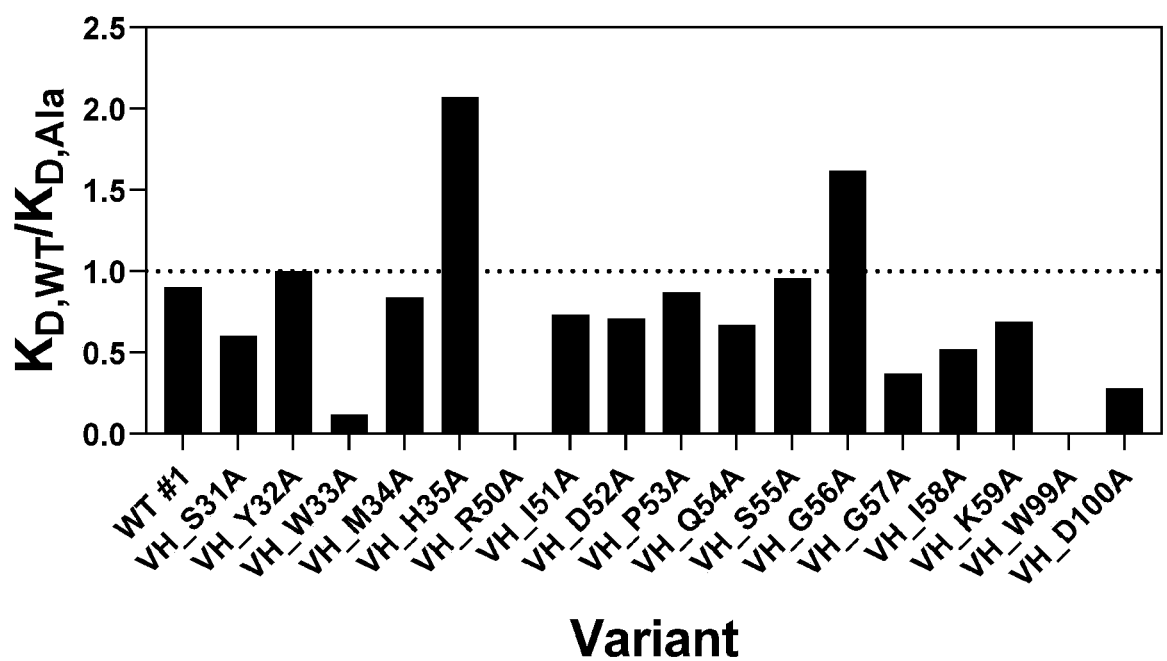
Figure 22C:
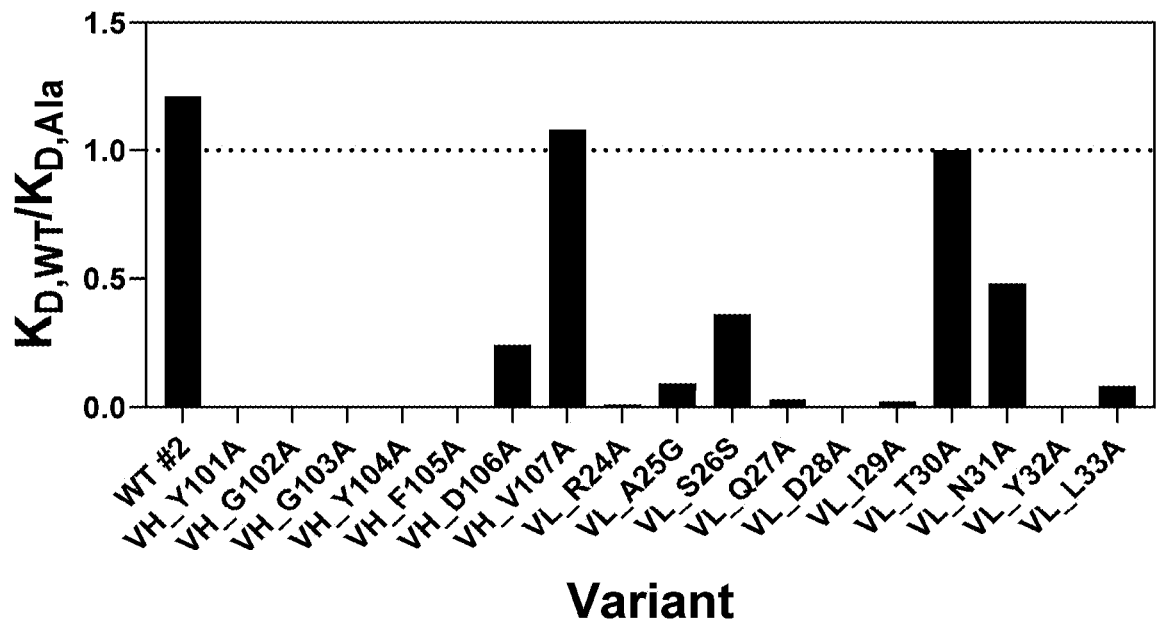
Figure 22D:
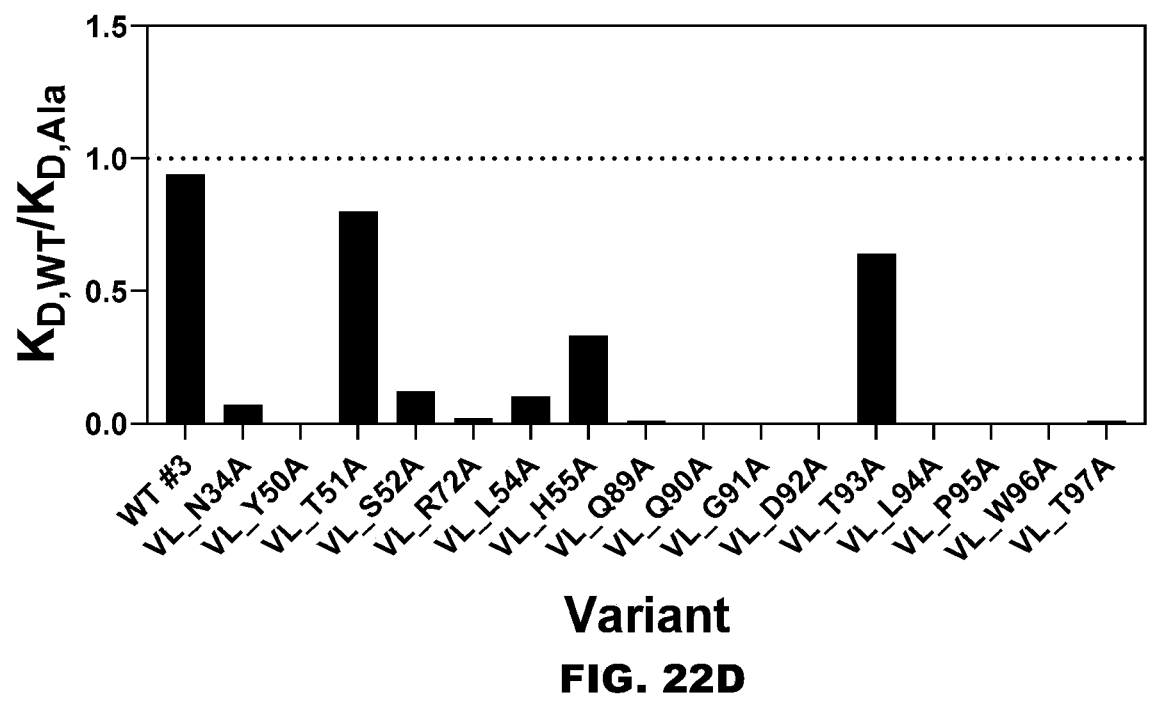

The 20E6_H0.2aL1_IgG1 antibody was biotinylated using EZ-Link SulfoNHS-LC-Biotin (ThermoFisher). A streptavidin-functionalized tip was equilibrated in binding buffer (10 mM sodium phosphate, 150 mM sodium chloride, 1% (w/v) bovine serum albumin, 0.05% (w/v) sodium azide, pH 7.4) and dipped in a 10 μg/mL solution of biotinylated anti-LAP in binding buffer for 30 seconds to load the tip with antibody. The antibody-loaded tip was then washed in binding buffer and placed in a solution containing 0-24 nM of a fusion protein having a human IgG1 Fc domain fused to either human LAP-TGFβ1, human LAP-TGFβ2 or human LAP-TGFβ3. The antigen was allowed to bind to antibody for 5 minutes (association phase), and then the tip was moved to binding buffer (dissociation phase). The association and dissociation phases were fit to a 2:1 heterogenous ligand binding model to determine the binding rate constants. As shown in FIG. 21A and Table 17, 20E6_H0.2aL1_IgG1 bound with sub-nanomolar affinity to human LAP-TGFβ1, but not to human LAP-TGFβ2 (FIG. 21B) or LAP-TGFβ3 (FIG. 21C). These data demonstrated that the 20E6_H0.2aL1_IgG1 antibody specifically binds to human LAP-TGFβ1 and there was no binding to LAP-TGFβ2 and LAP-TGFβ3.

TABLE 17

Binding of anti-LAP antibody 20E6_H0.2aL1_IgG1 to human LAP-TGFβ1, 2 and 3

| Sample ID | $k_{on}$ ($\times 10^6$ M$^{-1}$s$^{-1}$) | $k_{off}$ ($\times 10^{-4}$ s$^{-1}$) | $K_D$ (nM) | $k_{on,2}$ ($\times 10^6$ M$^{-1}$s$^{-1}$) | $k_{off,2}$ ($\times 10^{-4}$ s$^{-1}$) | $K_{D,2}$ (nM) |
|---|---|---|---|---|---|---|
| Fc-huB1 | 3.24 | 369 | 11.4 | 1.18 | 4.09 | 0.35 |
| Fc-huB2 | — | — | — | — | — | — |
| Fc-huB3 | — | — | — | — | — | — |

Example 13: Binding of Anti-LAP Antibodies to Mouse, Rat, Cynomolgus Monkey, and Human LAP-TGFβ1

This Example describes the testing of species specificity of 20E6_H0.2aL1_hIgG1 antibody and 20E6_H0.2aL1_hIgG4mut antibody (which has the heavy and light chain sequences of SEQ ID NOs: 220 and 155, respectively) to bind to LAP-TGFβ1 from several species using bio-layer interferometry.

The binding of 20E6_H0.2aL1_IgG1 antibody and 20E6_H0.2aL1_hIgG4mut antibody to LAP-TGFβ1 of various species was examined by bio-layer interferometry using the method described in Example 12, except that the antibody-loaded tip was placed in a solution containing 0-24 nM of a fusion protein having a human IgG1 Fc domain fused to either mouse, rat, cynomolgus monkey, or human LAP-TGFβ1. As shown in Tables 18 and 19, respectively, 20E6_H0.2aL1_hIgG1 antibody and 20E6_H0.2aL1_hIgG4mut antibody bound with nanomolar affinity to LAP-TGFβ1 from all species tested.

TABLE 18

Binding data of 20E6_H0.2aL1_IgG1 antibody to LAP-TGFβ1 of various species

| LAP-TGFβ1 | $K_D$ (nM) | $k_{on}$ ($\times 10^6$ M$^{-1}$ s$^{-1}$) | $k_{off}$ ($\times 10^{-4}$ s$^{-1}$) | $K_{D,2}$ (nM) | $k_{on,2}$ ($\times 10^6$ M$^{-1}$ s$^{-1}$) | $k_{off,2}$ ($\times 10^{-4}$ s$^{-1}$) |
|---|---|---|---|---|---|---|
| Human | 16.51 ± 0.01[a] | 2.15 ± 0.18 | 355 ± 14 | 0.97 ± 0.10 | 0.68 ± 0.02 | 6.57 ± 0.67 |
| Cyno | 15.85 ± 0.01 | 2.49 ± 0.30 | 394 ± 22 | 0.71 ± 0.13 | 1.03 ± 0.06 | 7.28 ± 1.24 |
| Rat | 13.38 ± 0.01 | 3.30 ± 0.25 | 441 ± 16 | 0.68 ± 0.07 | 1.14 ± 0.05 | 7.68 ± 0.77 |
| Mouse | 14.19 ± 0.01 | 2.42 ± 0.26 | 343 ± 19 | 0.56 ± 0.14 | 0.70 ± 0.04 | 3.90 ± 0.98 |

[a]All values reported as average ± standard deviation from triplicate measurements

TABLE 19

Binding data of 20E6_H0.2aL1_hIgG4mut antibody to LAP-TGFβ1 of various species LAP-TGFβ1

| | $K_D$ (nM) | $k_{on}$ (×10$^6$ M$^{-1}$ s$^{-1}$) | $k_{off}$ (×10$^{-4}$ s$^{-1}$) | $K_{D,2}$ (nM) | $k_{on,2}$ (×10$^6$ M$^{-1}$ s$^{-1}$) | $k_{off,2}$ (×10$^{-4}$ s$^{-1}$) |
|---|---|---|---|---|---|---|
| Human | 10.72 ± 0.01 | 2.8 ± 0.3 | 303 ± 16 | 0.51 ± 0.12 | 0.70 ± 0.03 | 3.6 ± 0.8 |
| Cyno | 26.14 ± 0.05 | 2.0 ± 0.4 | 524 ± 36 | 1.53 ± 0.18 | 0.94 ± 0.06 | 14.3 ± 1.4 |
| Rat | 11.14 ± 0.01 | 3.6 ± 0.4 | 406 ± 20 | 0.51 ± 0.06 | 1.70 ± 0.08 | 8.7 ± 0.9 |
| Mouse | 16.88 ± 0.02 | 2.8 ± 0.4 | 478 ± 27 | 1.31 ± 0.11 | 0.84 ± 0.04 | 11.0 ± 0.8 |

$^a$All values reported as average ± standard deviation from triplicate measurements

Example 14: Alanine Scanning Mutagenesis of CDRs in Humanized 20E6

This Example describes the testing of binding of human LAP-TGFβ1 to variants of 20E6_H0.2aL1_IgG1 antibody using bio-layer interferometry.

A total of 49 single alanine substitutions were made in the heavy and light chain CDRs of the antibody to identify critical residues for human LAP-TGFβ1 binding. In addition, residue A25 in the light chain was substituted with glycine. Plasmid DNA for these variants was transfected into ExpiCHO cells in 1 mL cultures on 24-well plates, along with wells containing no DNA (negative control) and wells transfected with DNA for the wild-type antibody (positive control). IgG concentrations in each well were determined by binding to Protein A-functionalized tips. Tips were dipped into wells containing the supernatants from each culture. IgG concentrations were determined by comparing the rate of signal change for each well against the rate of signal change for a standard curve of purified 20E6_H0.2aL1_hIgG1 antibody diluted into ExpiCHO media. CHO supernatants were diluted to 0.6m/mL in media. A streptavidin-functionalized tip was equilibrated in binding buffer (10 mM sodium phosphate, 150 mM sodium chloride, 1% (w/v) bovine serum albumin, 0.05% (w/v) sodium azide, pH 7.4) and then dipped in a 5 µg/mL solution of biotinylated human LAP-TGFβ1 in binding buffer for 60 seconds to load the tip with antigen. The antigen-loaded tip was then washed in binding buffer and placed in the diluted CHO supernatant. The antigen was allowed to bind to antibody for 5 minutes (association phase), and then the tip was moved to binding buffer (dissociation phase). The association and dissociation phases were fit to a 1:1 binding model to determine binding rate constants.

As shown in FIGS. 22A-22D and Table 20, alanine substitutions at positions 50, 99, 101, 102, 103, 104, 105 in the heavy chain, and positions 24, 28, 29, 32, 50, 53, 89, 90, 91, 92, 94, 95, 96 and 97 in the light chain had modest to severe impacts on binding affinity, indicating that these residues are involved in binding to human LAP-TGFβ1.

Example 15: Mono-Vs. Bi-Valent Binding of Anti-LAP Antibodies to Human LAP-TGFβ1

This Example compared the monovalent binding and bivalent binding of 20E6_H0.2aL1_hIgG1 antibody to human LAP-TGFβ1.

Figure 23A:
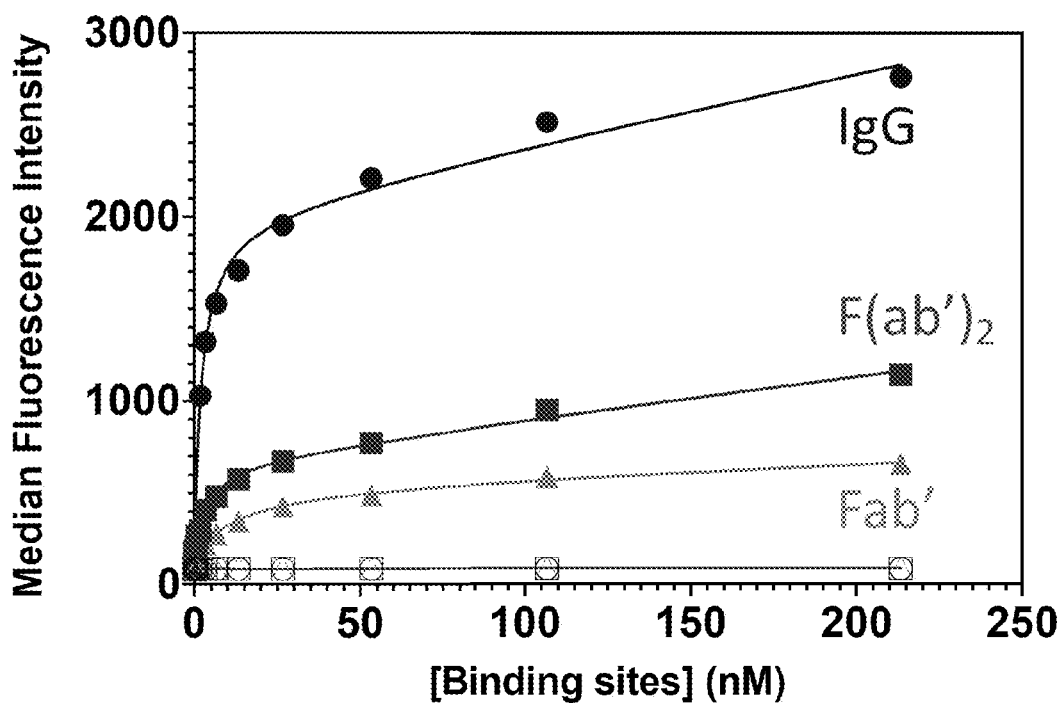
FIGS. 23A and 23B are graphs showing the binding of F(ab')2 fragments and Fab' fragments of 20E6_H0.2aL1_hIgG1 to P3U1 cells overexpressing GARP and LAP-TGFβ1.
Figure 23B:
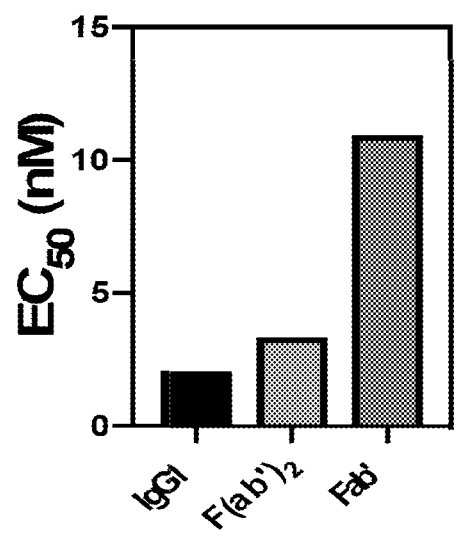

F(ab')2 fragments of 20E6_H0.2aL1_hIgG1 antibody were generated with the FragIT kit (Genovis) following the manufacturer's instructions. The F(ab')2 was then treated with 10 mM 2-Mercaptoethylamine-HCl (2-MEA) to generate Fab' fragments. To test binding to cells over-expressing human LAP-TGFβ1, 4×10$^5$ each of (a) P3U1 cells and (b) P3U1 cells overexpressing human GARP and human LAP-TGFβ1 were cultured in 96-well plates. The plates were centrifuged for 5 min at 1,500 rpm, liquid was removed, and cells were resuspended with 200 µL FACS buffer. The plates were centrifuged again, diluted primary antibody was added to each well, and the plates were incubated on ice for 20 minutes, followed by centrifugation. The cells were resuspended in 200 µL FACS buffer, centrifuged again, and resuspended in 50 µL diluted secondary antibody (Alexa647-anti-Human IgG). The plates were incubated on ice for 20 minutes in the dark, washed twice with 200 µL FACS buffer, and cells from each well (in 200 µL FACS buffer) were read on the Attune NXT instrument. As shown in FIGS. 23A and 23B, all three constructs bound the P3U1 cells over-expressing GARP and LAP-TGFβ1.

Example 16: Binding of Anti-LAP Antibodies to Human LAP-TGFβ1 in the Presence of Anchor Proteins This Example describes the testing of the binding of 20E6_H0.2aL1_hIgG1 antibody to human LAP-TGFβ1 in the presence of anchor proteins.

LAP-TGFβ is anchored to the extracellular matrix through LTBP, and to the surface of immunosuppressive cells via GARP or LRRC33. Soluble forms of human LTBP1 and GARP were prepared to assess the influence of the anchor protein on anti-LAP antibody binding. The ECR3E fragment (described in Annes et al. *JCB* 2004; 165:723) consists of the third cysteine-rich domain of human LTBP1, flanked by EGFR-like domains. This construct contains all of the elements necessary for covalent attachment to LAP-TGFβ, forming a soluble complex. A soluble GARP-LAP-TGFβ complex was prepared by co-expressing human LAP-TGFβ1 with a chimera comprised of the extracellular domain of human GARP with the transmembrane and cytosolic domains of meprina (described in Fridrich et al. *PLoS ONE*. 2016; 11(4): e0153290).

A streptavidin-functionalized tip was equilibrated in binding buffer (10 mM sodium phosphate, 150 mM sodium chloride, 1% (w/v) bovine serum albumin, 0.05% (w/v) sodium azide, pH 7.4) and dipped in a 5 µg/mL solution of biotinylated antibody (i.e., 20E6_H0.2aL1_hIgG1, murine 16F4, or MHG8, a GARP-specific murine IgG2a described in Lienart et al. *Science* 2018; 362:952-956) in binding buffer for 30 seconds to load the tip with antibody. The antibody-loaded tip was then washed in binding buffer and placed in a solution containing 0-24 nM of a fusion protein containing a human IgG1 Fc domain fused to either human LAP-TGFβ1, the soluble GARP-LAP-TGFβ1 complex, or the soluble ECR3E-LAP-TGFβ1 complex. The antigen was allowed to bind to antibody for 5 minutes (association phase), and then the tip was moved to binding buffer (dissociation phase). The binding and dissociation data for 16F4 and MHG8 were well-fit by a 1:1 binding model. The association and dissociation phases for 20E6_H0.2aL1_hIgG1 antibody were fit to a 2:1 heterogenous ligand binding model to determine the binding rate constants.

Figure 24:
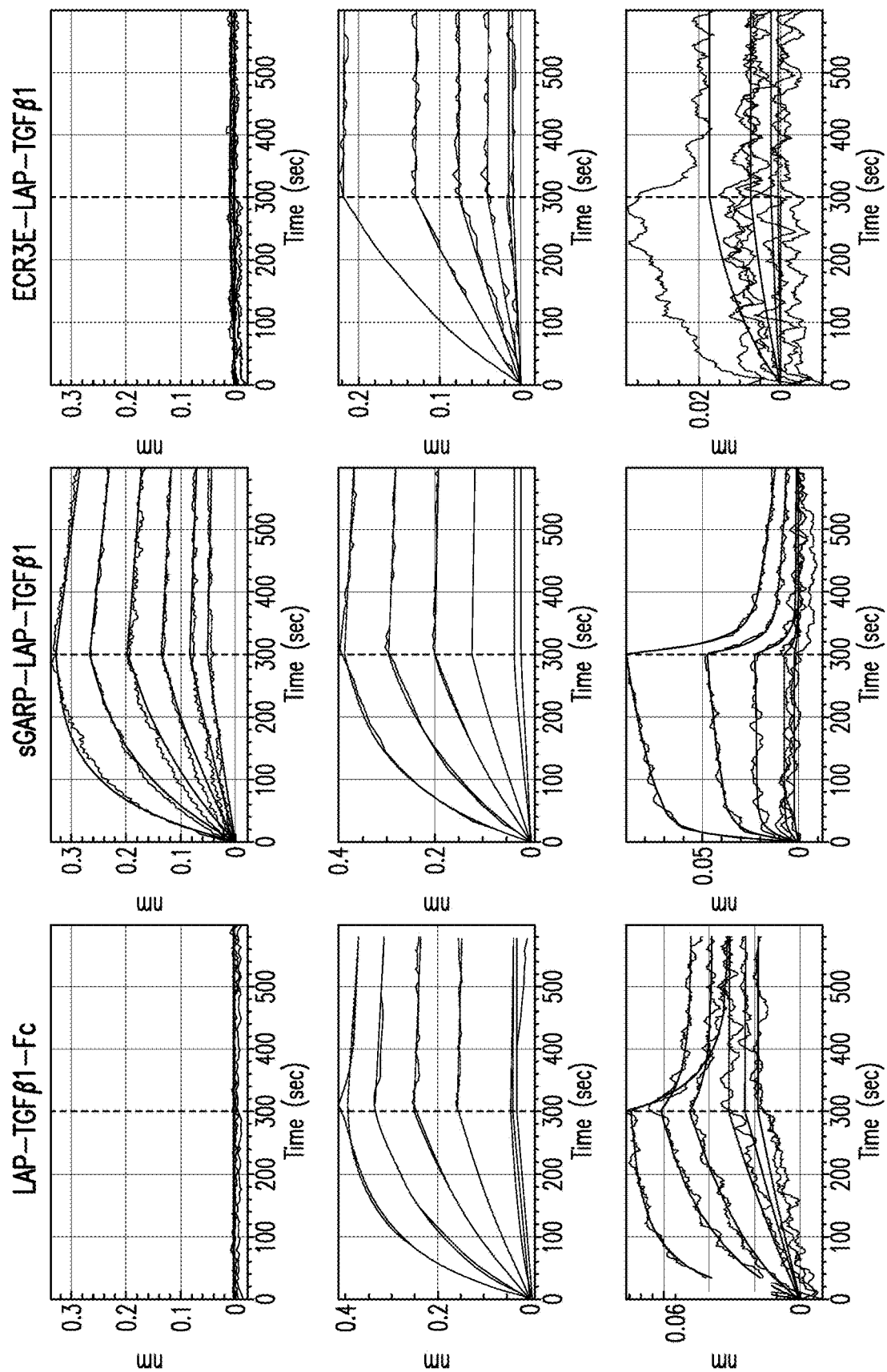
FIG. 24 is a series of bio-layer interferometry curves showing the binding of MHG8 (a GARP-specific murine IgG2a) antibody, 16F4 (an anti-LAP) antibody, and humanized 20E6 antibody to soluble LAP-TGFβ1, sGARP-LAP-TGFβ1, and ECR3E-LAP-TGFβ1 complexes.

As shown in FIG. 24 and Table 21, the 20E6_H0.2aL1_hIgG1 antibody bound to free LAP-TGFβ1 and the soluble GARP-LAP-TGFβ1 complex with nanomolar affinity, but not to the ECR3E-LAP-TGFβ1 complex. As expected, the anti-GARP antibody (MHG8) bound to the GARP-LAP-TGFβ1 complex, but not to free LAP-TGFβ1 or the ECR3E-LAP-TGFβ1 complex. 16F4 bound tightly to all three constructs.

in binding buffer and placed in a solution containing 24 nM of the sGARP-LAP-TGFβ1 complex. The antigen was allowed to bind to antibody for 5 minutes (association phase), and then the tip was moved to wells containing binding buffer alone, or 24 nM of unmodified antibody. Binding of the second, unmodified antibody was assessed by the signal change after 5 minutes of incubation.

As shown in Table 22, all four antibodies blocked binding of the same antibody, as expected. The 20E6_H0.2aL1_hIgG1 (h12_hIgG1) antibody competed for binding with 28G11 antibody, but not 16F4 antibody or MHG8 antibody.

TABLE 20

Human LAP-TGFb1 binding effects of CDR substitutions in 20E6_H0.2aL1_hIgG1

| Variant | $K_{D,WT}/K_{D,Ala}$ | Variant | $K_{D,WT}/K_{D,Ala}$ | Variant | $K_{D,WT}/K_{D,Ala}$ | Variant | $K_{D,WT}/K_{D,Ala}$ |
|---|---|---|---|---|---|---|---|
| WT #4 | 1.00 | WT #1 | 0.90 | WT #2 | 1.21 | WT #3 | 0.94 |
| VH_G26A | 1.40 | VH_S31A | 0.60 | VH_Y101A | 0.00 | VL_N34A | 0.07 |
| VH_Y27A | 1.29 | VH_Y32A | 1.00 | VH_G102A | 0.00 | VL_Y50A | 0.00 |
| VH_T28A | 0.97 | VH_W33A | 0.12 | VH_G103A | 0.00 | VL_T51A | 0.80 |
| VH_F29A | 1.16 | VH_M34A | 0.84 | VH_Y104A | 0.00 | VL_S52A | 0.12 |
| VH_T30A | 0.94 | VH_H35A | 2.07 | VH_F105A | 0.00 | VL_R53A | 0.02 |
|  |  | VH_R50A | 0.00 | VH_D106A | 0.24 | VL_L54A | 0.10 |
|  |  | VH_I51A | 0.73 | VH_V107A | 1.08 | VL_H55A | 0.33 |
|  |  | VH_D52A | 0.71 | VL_R24A | 0.01 | VL_Q89A | 0.01 |
|  |  | VH_P53A | 0.87 | VL_A25G | 0.09 | VL_Q90A | 0.00 |
|  |  | VH_Q54A | 0.67 | VL_S26S | 0.36 | VL_G91A | 0.00 |
|  |  | VH_S55A | 0.96 | VL_Q27A | 0.03 | VL_D92A | 0.00 |
|  |  | VH_G56A | 1.62 | VL_D28A | 0.00 | VL_T93A | 0.64 |
|  |  | VH_G57A | 0.37 | VL_I29A | 0.02 | VL_L94A | 0.00 |
|  |  | VH_I58A | 0.52 | VL_T30A | 1.00 | VL_P95A | 0.00 |
|  |  | VH_K59A | 0.69 | VL_N31A | 0.48 | VL_W96A | 0.00 |
|  |  | VH_W99A | 0.00 | VL_Y32A | 0.00 | VL_T97A | 0.01 |
|  |  | VH_D100A | 0.28 | VL_L33A | 0.08 |  |  |

TABLE 21

Binding affinity for 20E6_H0.2aL1_hIgG1 antibody to free LAP-TGFβ1 complex, the soluble GARP-LAP-TGFβ1 complex, and ECR3E-LAP-TGFβ1 complex

| Sample | $K_{D,1}$ (nM) | $k_{on,1}$ (×10$^6$ M$^{-1}$ s$^{-1}$) | $k_{off,1}$ (×10$^{-3}$ s$^{-1}$) | $K_{D,2}$ (nM) | $k_{on,2}$ (×10$^6$ M$^{-1}$ s$^{-1}$) | $k_{off,2}$ (×10$^{-3}$ s$^{-1}$) |
|---|---|---|---|---|---|---|
| Fc-LAP | 16.16 ± 0.01 | 2.51 ± 0.25 | 40.58 ± 1.81 | 0.96 ± 0.09 | 0.96 ± 0.04 | 0.92 ± 0.07 |
| ECR3E-LAP | No binding | — | — | — | — | — |
| sGARP-LAP | 18.71 ± 0.05 | 2.77 ± 1.01 | 51.81 ± 6.84 | — | — | — |

Figure 25:
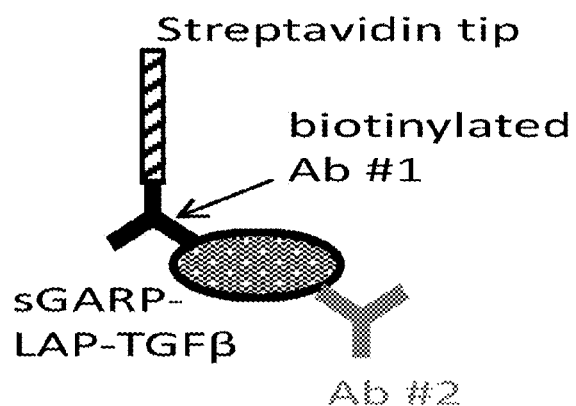
FIG. 25 is a schematic of the competition experiment used to compare binding epitopes of murine 28G11, 16F4, and MHG8, as described in Example 17.

Example 17: Competition Between Humanized 20E6 and Other Anti-LAP Antibodies for Binding to Soluble Human GARP-LAP-TGFβ1 Complex Murine 28G11, 16F4, and MHG8 antibodies bind tightly to a soluble complex consisting of the extracellular domain of human GARP and human LAP-TGFβ1 (sGARP-LAP-TGFβ1). It was observed that 20E6_H0.2aL1_hIgG1 antibody also binds tightly to this complex. Competition experiments, as shown in FIG. 25, were performed to compare the binding epitopes of these four antibodies.

A streptavidin-functionalized tip was equilibrated in binding buffer (10 mM sodium phosphate, 150 mM sodium chloride, 1% (w/v) bovine serum albumin, 0.05% (w/v) sodium azide, pH 7.4) and dipped in a 5 μg/mL solution of biotinylated antibody (i.e., either 20E6_H0.2aL1_hIgG1 antibody, murine 16F4 antibody, murine 28G11 antibody, or MHG8 antibody) in binding buffer for 30 seconds to load the tip with antibody. The antibody-loaded tip was then washed

TABLE 22

Competition binding data of anti-LAP antibodies to soluble human GARP-LAP-TGFβ1 complex

|  | MHG8 | 16F4 | h12_hIgG1 | 28G11 |
|---|---|---|---|---|
| MHG8 | 0.00 | 0.30 | 0.25 | 0.28 |
| 16F4 | 0.46 | 0.00 | 0.43 | 0.43 |
| h12 hIgG1 | 0.07 | 0.08 | 0.00 | 0.00 |
| 28G11 | 0.29 | 0.20 | −0.01 | 0.00 |

Example 18: Optimized 7H4 Variant Antibodies

This Example describes the optimization of antibody 7H4 (e.g., removal of potential liability sites in the heavy chain). Specifically, position 55 in the heavy chain of 7H4, which is located in the CDR2, is a potential isomerization site. To remove this potential liability site, the aspartic acid at position 55 is mutated to an amino acid other than aspartic acid, for example, glycine, alanine, or glutamic acid, as described in Table 23. The sequences are provided in Table 34.

These 7H4 variant antibodies can be tested for various functions (e.g., binding to human LAP-TGFβ1, inhibition of TGFβ1 activation, binding to immune cells) using the methods described herein.

TABLE 23

Multiple variants of 7H4 antibody sequences and antigen binding fragments

| SEQ ID | Name | Description |
|---|---|---|
| 221 | 7H4_HC (hyb) | Murine 7H4 heavy chain sequence |
| 222 | 7H4_LC (hyb) | Murine 7H4 light chain sequence |
| 231 | 7H4_HCDR2 (D55G) | Murine 7H4 heavy chain CDR2 with potential isomerization site removed (D55G) |
| 232 | 7H4_HCDR2 (D55A) | Murine 7H4 heavy chain CDR2 with potential isomerization site removed (D55A) |
| 233 | 7H4_HCDR2 (D55E) | Murine 7H4 heavy chain CDR2 with potential isomerization site removed (D55E) |
| 234 | 7H4_VHmut#1 (D55G) | Murine 7H4 heavy chain variable region with potential isomerization site removed (D55G) |
| 235 | 7H4_VHmut#2 (D55A) | Murine 7H4 heavy chain variable region with potential isomerization site removed (D55A) |
| 236 | 7H4_VHmut#3 (D55E) | Murine 7H4 heavy chain variable region with potential isomerization site removed (D55E) |
| 224 | 7H4_VL | Murine 7H4 light chain variable region sequence |
| 237 | 7H4_HCmut#1 (D55G) | Murine 7H4 heavy chain with potential isomerization site removed (D55G). |
| 238 | 7H4_HCmut#2 (D55A) | Murine 7H4 heavy chain with potential isomerization site removed (D55A). |
| 239 | 7H4_HCmut#3 (D55E) | Murine 7H4 heavy chain with potential isomerization site removed (D55E). |

Example 19: Cryo-EM Structure of Humanized 20E6 in Complex with LAP-TGFβ1

This Example describes the identification of the epitope on LAP-TGFβ1 to which humanized 20E6 binds, as well as the paratope of humanized 20E6, by single particle cryo electron microscopy (SP-Cryo-EM).
Sample and Grids Preparation.

Humanized 20E6 mAb (20E6_H0.2aL1_hIgG1) and Fab were generated as described in Example 11. Human biotinylated LAP-TGFβ1-Fc and GARP-LAP-TGFβ1 were generated as described in Example 16. Human LAP-TGFβ1 was purchased from R&D and supplied in phosphate buffered saline (PBS) buffer (10 mM sodium phosphate, 150 mM sodium chloride, pH 7.4) containing 50% glycerol. Several different samples were prepared, with the different proteins at different concentrations, ratio, and incubation time. The following five samples were used to generate the final reconstruction:

1) Sample A: 20 microliters (also referred to as μl or ul) of LAP-TGFβ1-Fc (10.3 micromolar (μM or uM) in PBS (10 mM sodium phosphate, 150 mM sodium chloride, pH 7.4)) were mixed with 4 ul of humanized 20E6 (26 μM in PBS) for a final solution of 4.25 μM LAP-TGFβ1-Fc and 4.3 μM humanized 20E6-Mab (1 Mab per dimer ratio); the mixture was left on ice for 45 min and then used to prepare grids.
2) Sample B: 1:5 dilution of Sample A: 4 μl Sample A+16 μl HEPES buffered saline (HBS; 20 mM Hepes, 150 mM NaCl, pH 7.0).
3) Sample C: 8 μl of LAP-TGFβ1-Fc (10.3 μM in PBS) were mixed with 8 μl of humanized 20E6 (8.6 μM in PBS) for a final solution of 2.34 μM LAP-TGFβ1-Fc and 4.7 μM of humanized 20E6-Fab; the mixture was left on ice for 30 min then diluted 1:1 with HBS.
4) Sample D: LAP-TGFβ1 in PBS with 50% glycerol was buffer exchanged into a no-glycerol buffer (i.e., PBS), and complexed in a 2 dimer:1 Mab ratio with humanized 20E6-Mab, then concentrated to 30 μM (for HDX studies). For cryo-EM studies, the sample was diluted 10-fold with PBS.
5) Sample E: 1.2 μl of GARP-LAP-TGFβ1 (19.3 μM in PBS) was mixed with 1.3 μl of humanized 20E6-Fab (8.6 μM in PBS) and 2.6 μl of HBS buffer for a final solution of 4.4 μM GARP-LAP-TGFβ1 and 2.2 μM humanized 20E6-Fab (1 Fab per 2 dimers of GARP-LAP-TGFβ1). The mixture was left for 30-60 mins on ice and diluted 1:10 with HBS buffer.

Grids (C-flat carbon on gold, 300 mesh, 1.3/1.2) were prepared using a Vitrobot Mark 4 (ThermoFisher) using standard procedures: grids were glow discharged using a Pelco easyGlow unit (Ted Pella, Inc.) with the factory suggested values for plasma cleaning (0.39 mbar, lower level 15 mA, hold 10", glow 30"). The Vitrobot was set with a chamber humidity between 90-100%; a chamber temperature of 4° C.; a wait time of 0 sec; a blot time of 3 sec; a blot force of 0. Three (3) μl of sample were applied to the grid, blotted, and then plunged into a liquid ethane bath; the frozen grid was then transferred to liquid nitrogen (LN2) and kept at LN2 temperature for all subsequent steps (clipping, transferring to the microscope cassette, and data collection).
Data Collection and Structure Determination.

All data sets were collected on a ThermoFisher Titan Krios G3 equipped with a Gatan K3 Direct Electron Detector. Data collection was done using the Gatan Latitude software. Five data sets (one per each prepared sample) were collected. Table 24 summarizes the microscope and camera parameters used for data collection, and the total number of movies collected for each sample. The entire data collection (for the 5 samples) spanned two weeks.

TABLE 24

Cryo-EM details for 20E6 humanized antibody and Fab

| Sample | # of Movies | Voltage | Magnification | Detector pixel size (Å) | Dose (e−/Å²) | Defocus (μm) |
|---|---|---|---|---|---|---|
| A) LAP-TGFβ1-FC + Humanized 20E6-Mab, 1 Mab/dimer | 2690 | 300 | 81,000 | 1.07 | 62.5 | −0.8 to −1.8 |
| B) LAP-TGFβ1-FC + Humanized 20E6-Mab, 1 Mab/dimer (1:5 dilution) | 1994 | 300 | 81,000 | 1.07 | 62.5 | −1.2 to −1.6 |

TABLE 24-continued

Cryo-EM details for 20E6 humanized antibody and Fab

| Sample | # of Movies | Voltage | Magnification | Detector pixel size (Å) | Dose ($e^-/Å^2$) | Defocus (μm) |
|---|---|---|---|---|---|---|
| C) LAP-TGFβ1-FC + Humanized 20E6-Fab, 2 Fab/Dimer | 2647 | 300 | 81,000 | 1.07 | 62.5 | −1.2 to −1.6 |
| D) LAP-TGFβ1 + Humanized 20E6-Mab (1:10 dilution) | 4545 | 300 | 81,000 | 1.07 | 62.5 | −0.8 to −1.8 |
| E) GARP-LAP-TGFl31 + Humanized 20E6-Fab (1 Fab/1 dimer) 1:10 dilution | 9366 | 300 | 81,000 | 1.07 | 62.5 | −0.8 to −1.8 |

Data Processing and Map Reconstruction.

The entire data processing and map reconstruction were carried out with Cryosparc V2 (Structura Biotechnology Inc., Toronto, Canada; Punjani et al. Nature Methods 2017; 14:290-6; Brubaker et al. IEEE Trans Pattern Anal Mach Intell 2017; 39:706-18). Initial stages of the processing pipeline (Movie alignment, CTF estimation, particle picking, and 2D classes determination) was carried out individually for each data set. Cleaned particles from the individual data sets were merged together in three stages.

1) Particles from the first three data sets (samples A-C), were merged and processed together but the best map was only at 5 Å.
2) Using particles from sample D it was possible to generate a 3.8 Ang map. Templates from sample D were then used for a new particle picking for samples A-C. Selected particles were then subjected to one round of 2D classification and merged with the best particle set from Sample D for a total of 533,297 particles. After one round of 2D classification, the best classes (436,918 particles) were used to run a homogeneous refinement job. The resulting map was subjected to one round of non-uniform refinement (NU-refinement) which resulted in a map with a resolution of 3.5 Å.
3) A set of ~1.2M particles from sample E was merged with the latest (best) set from 2. After 2 rounds of 2D classification, the best 2D classes (864,958 particles) were used to calculate a map that (after NU refinement) had a nominal resolution of 3.4 Å.

Figure 26A:
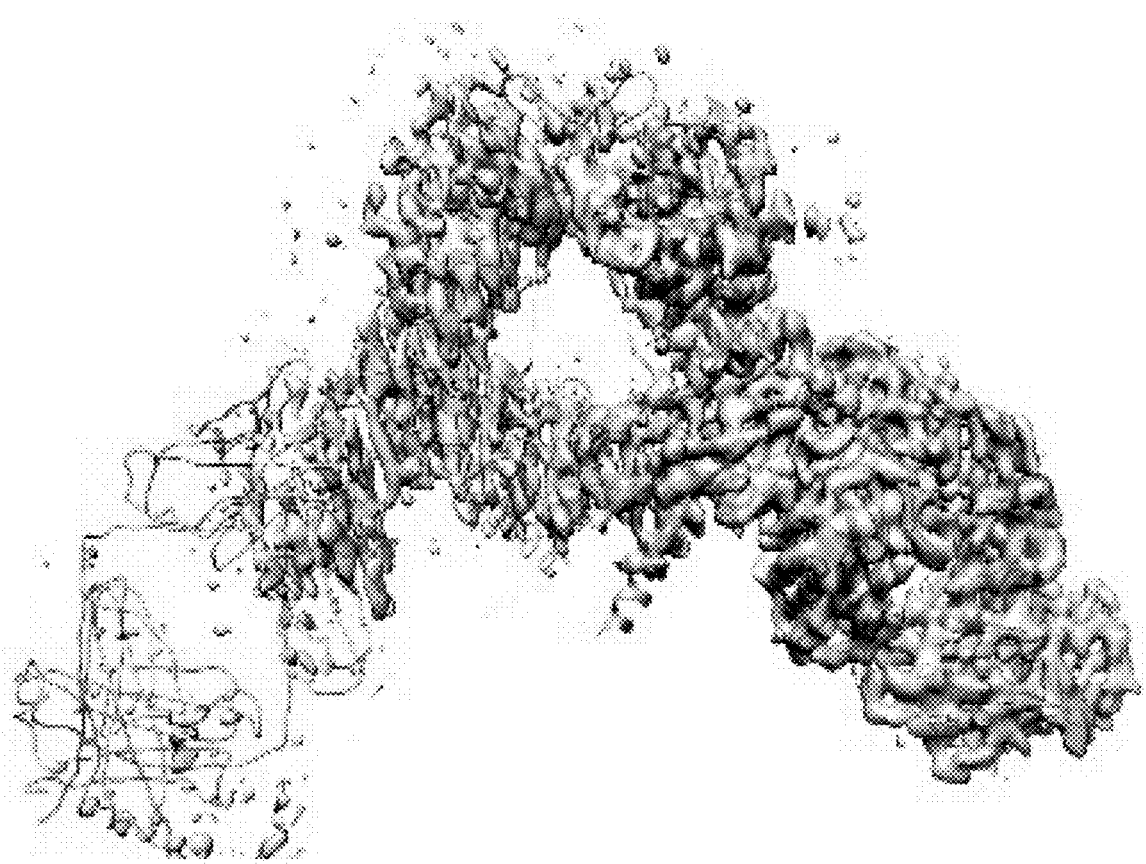
FIG. 26A shows an example of a cryo-EM map used to build the humanized 20E6-Fab/LAP-TGFβ1 model.
Figure 26B:
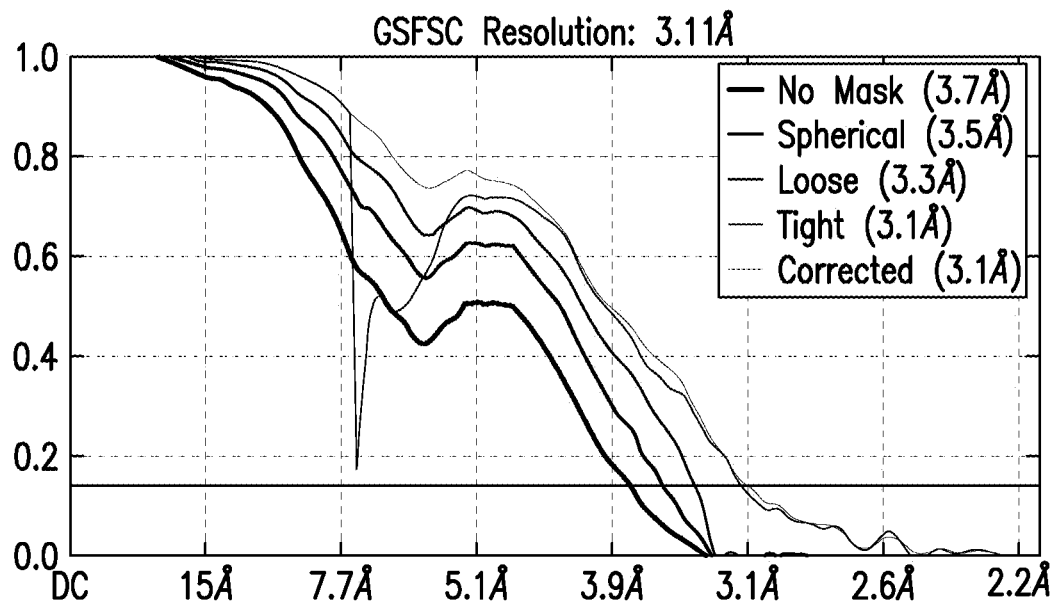
FIG. 26B is a plot of the FSC curve versus resolution.
Figure 26C:
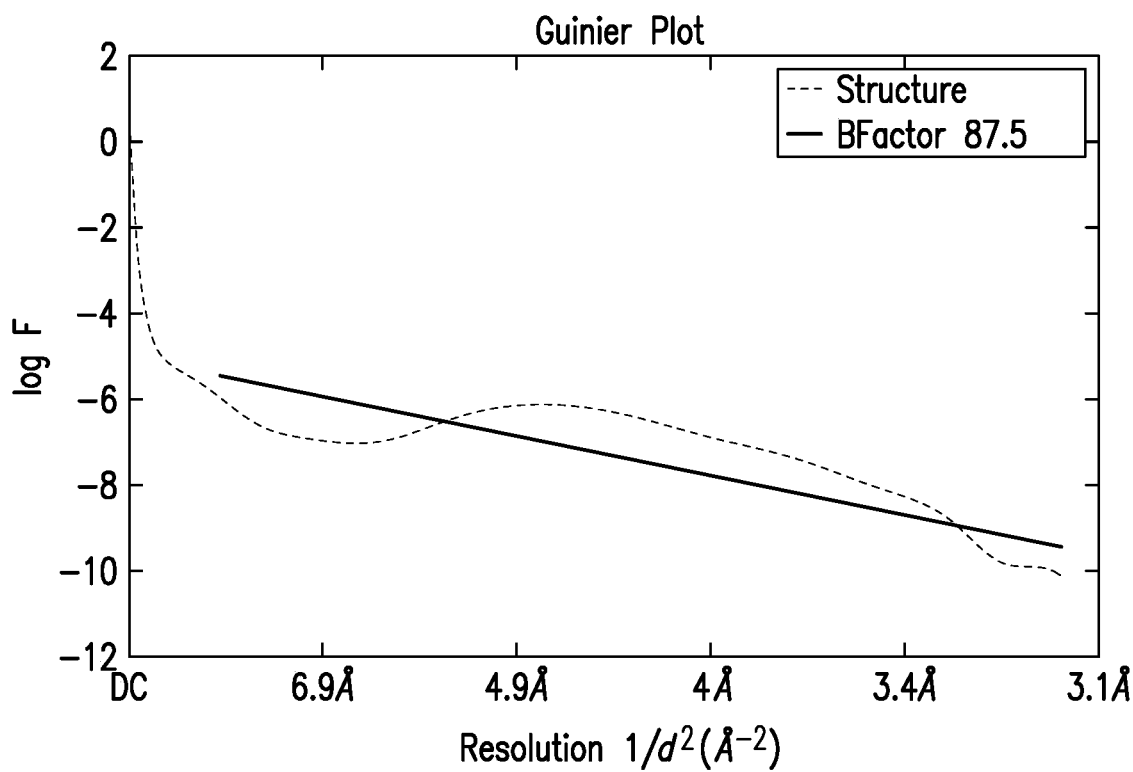
FIG. 26C is the B-factor estimation using a Guinier plot.

Another 2 rounds of 2D classification on the 864,958 particles were then used to generate a set containing 802,256 particles and a non-uniform (NU_-refined map at 3.3 Å. Throughout the whole process, visual inspection of the resulting maps (density improvement, continuity in density, lack of (or reduction on) preferred orientation artifacts) was used to decide subsequent steps. The latest map clearly pointed to the fact that, while two Fabs/LAP-TGFβ1 dimer are present, one is much more better defined than the other (FIG. 26A), and thus particle subtraction and local refinement procedures were applied. The resulting final map had a nominal resolution of 3.1 Å. This map was used to build and refine the final model. FIGS. 26B and 26C show the FSC plot and the Guinier plot for the final map.

Model Building and Refinement.

All model building and refinement were carried out using COOT (Emsley et al. *Acta Crystallogr D-Biological Crystallography* 2010; 66:486-501) and PHENIX (Afonine et al. *Acta Crystallogr D Struct Biol* 2018; 74 6:531-44). LAP-TGFβ1 coordinates were obtained from PDB entry 3RJR, and Fab coordinates were obtained from a homology model generated using MOE 2019.0101 (Chemical Computing Group ULC). LAP/TGFβ1 and the Fab model were initially positioned into the map as rigid bodies using COOT, and the density was used to rebuild some of the loops and assign the correct sequences. The PHENIX real space refinement module was carried out to optimize the model geometry. Table 25 summarizes model refinement and statistics:

TABLE 25

| Model refinement and statistics for the cryo-EM of humanized 20E6 Fab and LAP-TGFβ1 | |
|---|---|
| Symmetry Imposed | C1 |
| Particle used | 802,256 |
| Map resolution (Å) | 3.1 |
| FSC threshold | 0.143 |
| Map Resolution Range (Å) | 3-19 |
| Refinement | |
| Map sharpening B-factor ($Å^2$) | 87.5 |
| Model composition | |
| Non Hydrogen Atoms | 8,757 |
| Protein residues | 1,110 |
| CC_mask: | 0.655 |
| CC_volume: | 0.638 |
| CC_peaks: | 0.525 |
| rmsd (bonds) (Å): | 0.01 |
| rmsd (angles) (°): | 0.98 |
| All-atom clashscore | 5.41 |
| Ramachandran plot: | |
| outliers: | 0.00% |
| allowed: | 7.16% |
| favored: | 92.84% |
| Rotamer outliers: | 0.20% |

The final model contained two chains for the LAP-TGFβ1 dimer (chains A and B, each one containing residues 1-61+ 70-208+216-241+250-361; numbering for antigen assumes absence of signal peptide, i.e. Leu 1=Leu 30 in complete sequence); two chains (heavy chain (VH), residues 1-221 and light chain (VL), residues 2-214) for the humanized 20E6-Fab. One sugar moiety (NAG) was modeled at one of the glycosylation sites (Asn A53); for all the other possible glycosylation positions (A107, A147, B53, B107, and B147) the density was not sufficient to warrant the sugar addition).

Structural Analysis.

Figure 27A:
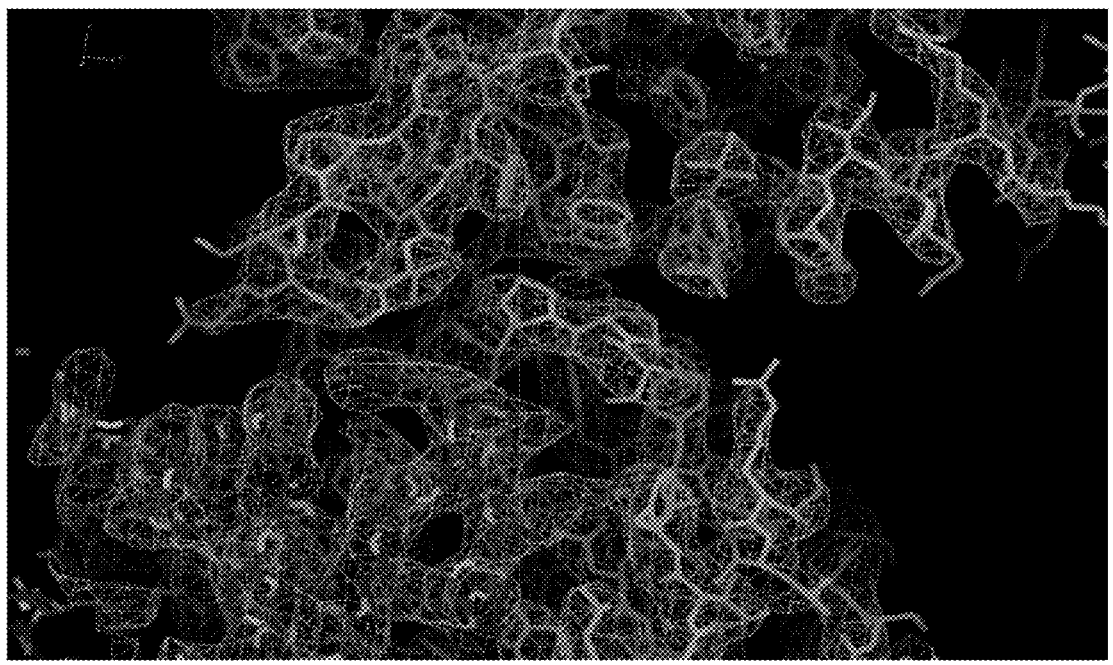
FIG. 27A is a cryo-EM map of the humanized 20E6 antibody complexed with LAP-TGFβ1 at 3.1 Å resolution.
Figure 27B:
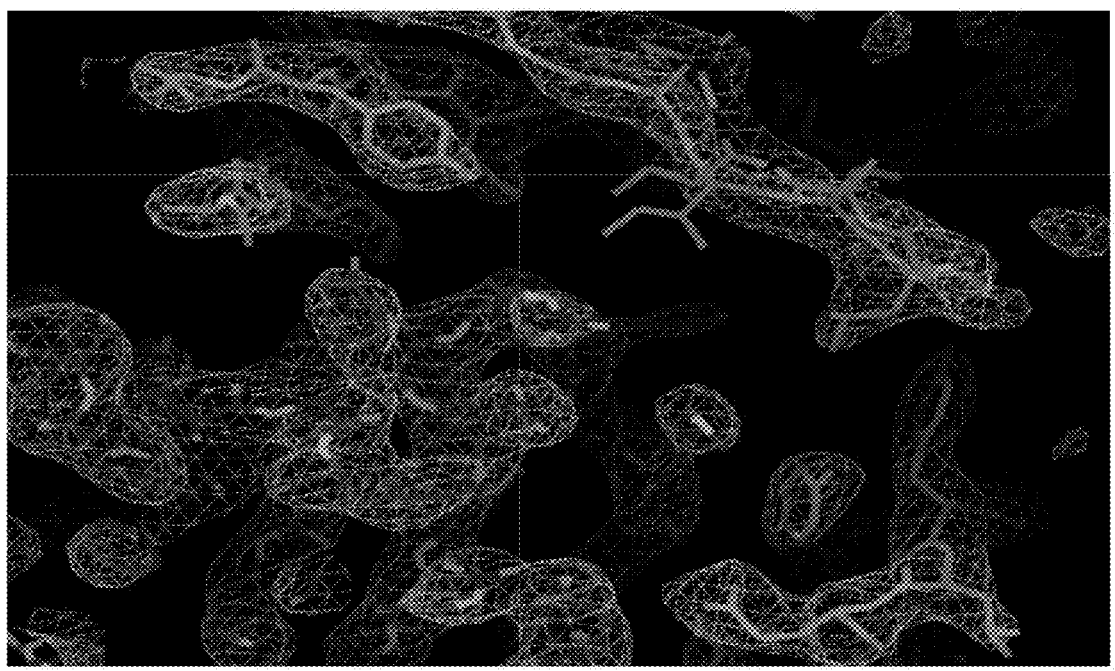
FIG. 27B shows the electron density for PDB entry 5jxe at 2.9 Å resolution.

The structure of the LAP-TGFβ1 dimer in complex with humanized 20E6-Fab was determined to 3.1 Å resolution. The quality of the cryo-EM map was such that assignment of side chains for both the antigen and the Fab was unequivocal. At the antigen-antibody interface, the quality of the map is comparable to that of x-ray derived electron density maps calculated at comparable resolution (FIG. 27A: cryo-EM map at 3.1 Å resolution; FIG. 27B: electron density for Protein Data Bank (PDB) entry 5jxe at 2.9 Å resolution).

Due to the intrinsic characteristics of cryo-EM maps (Cardone G, et. Al, J Struct Biol. 2013; 184:226-236), there is a clear gradient between the LAP-TGFβ1:Fab interface and the rest of the molecule. A lower level density is present for a second, symmetrically bound Fab, which could be docked into the final map (FIG. 26A).

Figure 28A:
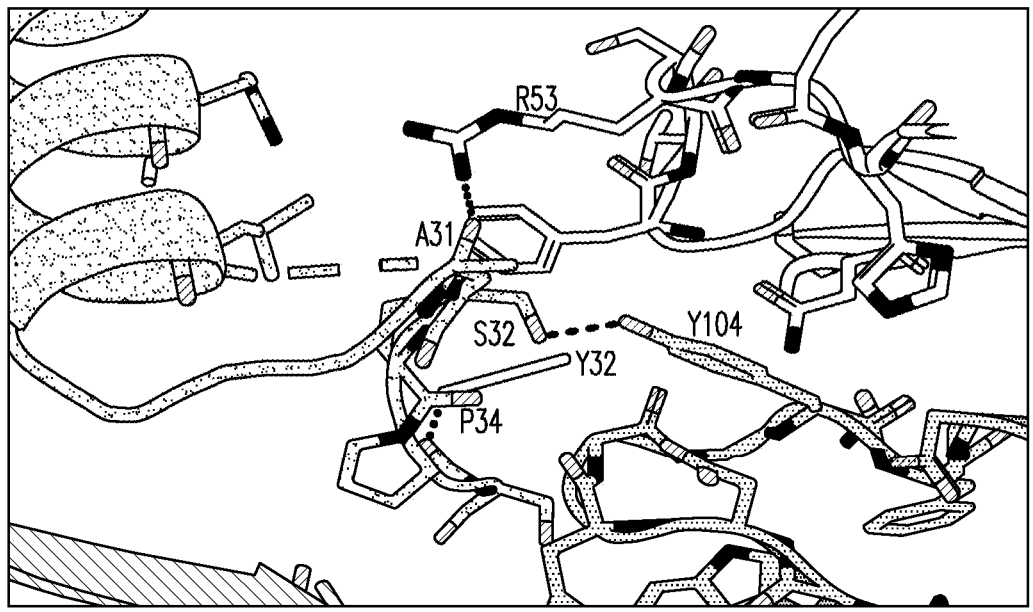
FIG. 28A shows interactions between LAP and the VL and VH of the humanized 20E6 Fab.
Figure 28B:
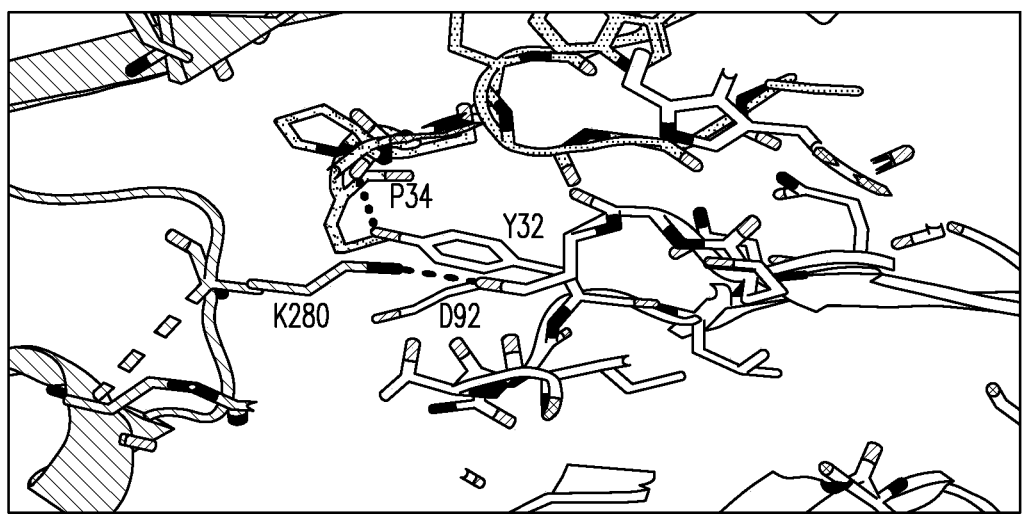
FIG. 28B shows interactions between TGFβ1 and the humanized 20E6 VL and VH portions of the Fab.
Figure 28C:
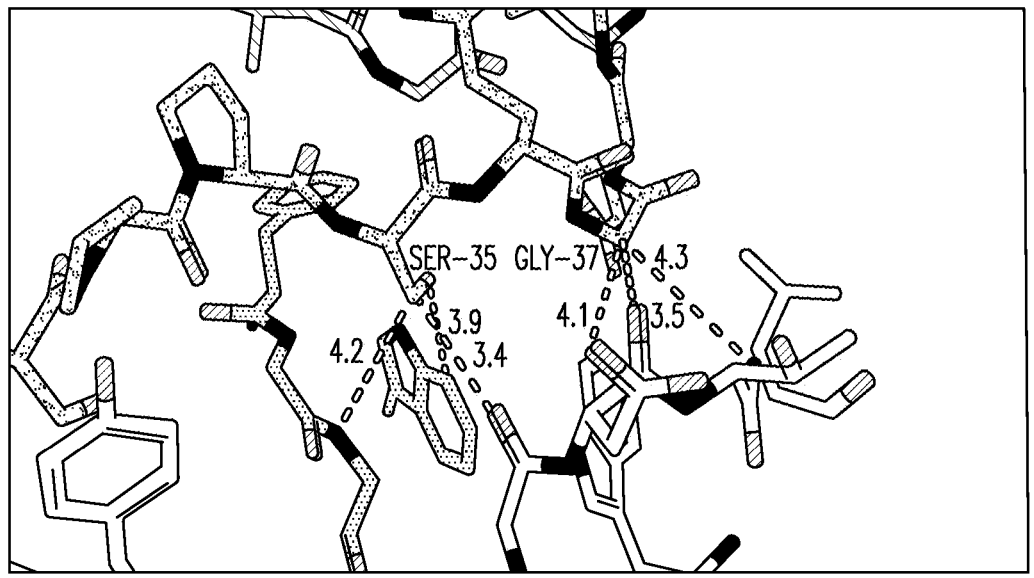
FIG. 28C and FIG. 28D show additional interactions between LAP-TGFβ1 and the 20E6 VL portion of the 20E6 Fab. Constructs and interactions are shown in grayscale.
Figure 28D:
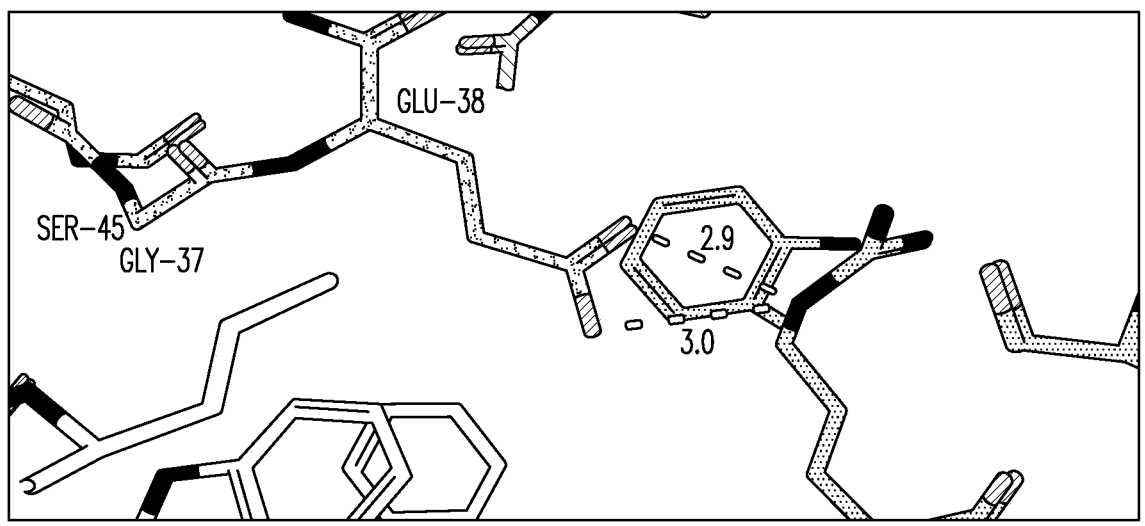

The humanized 20E6-Fab paratope and LAP-TGFβ1 epitope residues that comprise the interaction interface are shown in FIGS. 28A and 28B, and summarized in Table 26. The interface is made up of van der Waals and electrostatic interactions, and corresponds to ~800 Å² of buried surface, as calculated by Protein interfaces, surfaces and assemblies (PISA), (Krissinel et al, *J Mol Biol* 2007; 372:774-97). The epitope is formed by residues A31-P40 from chain A (LAP residues) and Y340-R343 and R274-K280 from chain B (TGFβ1 residues). The fact that both LAP and TGFβ1 residues are required for interactions with humanized 20E6-Fab explains why the antibody is specific for the closed form of the LAP-TGFβ1 complex, and does not bind to empty LAP or to mature TGFβ1. The paratope is formed by light chain (VL) residues: T30, Y32, Y49-Y50, R53, G91-L94, W96, and heavy chain (VH) residues W33, R50, I58-K59, W99, and Y101-G103. Epitopes determined by the cryo-EM analysis are in agreement with the hydrogen deuterium exchange mass spectrometry (HDX-MS) analysis described in Example 22. Paratopes are in agreement with residues identified by alanine scanning experiments described in Example 14. See also FIGS. 28C-D.

TABLE 26

Epitope and paratope of LAP-TGFβ1 and humanized 20E6-Fab*

| VH | TGFβ1 | VL |
|---|---|---|
|  | R274 | T30 |
|  | G278 | T30 |
|  | W279 | Y50, Y50 |
|  | K280 | D92 |
| Y101 | V341 |  |
| Y101, W33 | G342 |  |

| VH | LAP | VL |
|---|---|---|
|  | A31 | Y49, R53 |
| Y104, Y104 | S32 | Y49, Y50 |
| G102 | P33 | Y32 |
|  | P34 | Y32 |
| G102, W99, | S35 | G91, Y32 |
|  | Q36 | D92 |
|  | G37 | L94, D92 |
| R50, K59, W33 | E38 | L94, W96 |

*Residues from humanized 20E6-Fab VH or VL that interact with LAP-TGFβ1 residues are indicated.
Hydrogen bonding interactions are indicated in bold (interaction cut-off set to 4.5 Å; hydrogen bond interactions cut-off set to 3.5 Å).

Example 20: Cryo-EM Structure of Humanized 28G11 in Complex with LAP-TGFβ1

The structure of humanized 28G11 Fab in complex with human LAP-TGFβ1 was determined by cryo-EM to identify the epitope on LAP-TGFβ1 to which the antibody binds, and the paratope of humanized 28G11-Fab.

Sample and Grids Preparation.

Humanized 28G11 mAb (28G11_H2bL3a_hIgG1, which has heavy and light chain variable region sequences of SEQ ID NOs: 43 and 53, respectively) and GARP-LAP-TGFβ1 were generated as described in Examples 9 and 16, and supplied in PBS buffer (10 mM sodium phosphate, 150 mM sodium chloride, pH 7.4). The sample used for cryo-EM experiments was prepared by mixing 2.0 µl of GARP-LAP-TGFβ1 (38.7 µM), 0.5 µl of humanized 28G11 (77.3 µM), and 17.5 µl of HBS buffer (20 mM Hepes, 150 mM NaCl, pH 7.0) for a final concentration of 3.87 µM for GARP-LAP-TGFβ1 and 1.95 µM for humanized 28G11. The sample was further diluted 1:1 with HBS before preparing the grids. The complex containing GARP (rather than LAP-TGFβ1 alone) was used to disrupt the preferred orientation issues observed in data collected from samples of humanized 28G11:LAP-TGFβ1.

Grids (C-flat carbon on gold, 300 mesh, 1.3/1.2) were prepared using a Vitrobot Mark 4 (ThermoFisher) using standard procedures. Grids were glow discharged using a Pelco easyGlow unit (Ted Pella, Inc.) with the factory suggested values for plasma cleaning (0.39 mbar, lower level 15 mA, hold 10", glow 30"). The Vitrobot was set with a chamber humidity between 90-100%; a chamber temperature of 4C°; a blot time of 3 sec; a wait time of 0 sec; a blot force of 0. Three (3) µl of sample were applied to the grid, blotted, and then plunged into a liquid ethane bath; the frozen grid was then transferred to liquid nitrogen (LN2) and kept at LN2 temperature for all subsequent steps (clipping, transferring to the microscope cassette, and data collection).

Data Collection and Structure Determination.

The data set was collected on a ThermoFisher 300 KeV Titan Krios G3 equipped with a ThermoFisher Falcon 3 Direct Electron Detector. Data collection was done using the ThermoFisher EPU software. 4267 movies were collected at a nominal magnification of 75,000×; the defocus range was set to be between −1.4 and −2.0 µm. The detector pixel size was 1.06 Å and the dose was 37.74 e⁻/Å².

Data Processing and Map Reconstruction.

The entire data processing and map reconstruction was carried out with Cryosparc V2. The initial particle picking identified 2.9M particles. After two 2D classification jobs, about 620K particles were used to calculate an initial map (nominal resolution 3.81 Ang). The particle stack was further cleaned up using two more 2D classifications, and the resulting set of particles (505,582 particles) were used to generate a map that after a NU-refinement had a nominal resolution of 3.48 Ang. Local (masked) refinement was then used to improve the resolution at the epitope-paratope interface. The result of the local refinement (after particle subtraction) was a 3.38 Ang map in which the details at the interface were greatly improved. This map was used to build the model.

Model Building and Refinement.

All model building and refinement were carried out using COOT. The complex between LAP-TGFβ1 and humanized 20E6 Fab was used as the starting model; LAP-TGFβ1 and humanized 28G11-Fab were initially positioned into the map as rigid bodies using COOT, and the density was used to rebuild some of the loops and assign the correct sequences. The PHENIX real space refinement module was carried out to optimize the model geometry. Table 27 summarizes the model refinement and statistics:

TABLE 27

Model refinement and statistics of humanized 28G11-Fab and LAP-TGFβ1

| | |
|---|---|
| Symmetry Imposed | C1 |
| Particle used | 505,582 |
| Map resolution (Å) | 3.4 |
| FSC threshold | 0.143 |
| Map Resolution Range (Å) | 3.0-14.0 |
| Refinement | |
| Map sharpening B-factor (Å$^2$) | 105.6 |
| Model composition | |
| Non Hydrogen Atoms | 8,960 |
| Protein residues | 1,113 |
| CC_mask: | 0.716 |
| CC_volume: | 0.702 |
| CC_peaks: | 0.628 |
| rmsd (bonds) (Å): | 0.007 |
| rmsd (angles) (°): | 0.81 |
| All-atom clashscore | 19.8 |
| Ramachandran plot: | |
| outliers: | 0.00% |
| allowed: | 15.58% |
| favored: | 84.42% |
| Rotamer outliers: | 0.20% |

The final model contained two chains for the LAP-TGFβ1 dimer (chains A and B, each one containing residues 1-61+ 70-208+216-241+250-361; numbering for antigen assumes absence of signal peptide, i.e. Leu 1=Leu 30 in complete sequence) and one molecule (heavy chain (VH), residues 1-221 and light chain (VL), residues 2-214) for the humanized 28G11-Fab. One sugar moiety N-acetylglucosamine (NAG) was modeled at one of the glycosylation sites (Asn A53); for all the other possible glycosylation positions (Asn A107, Asn A147, Asn B53, Asn B107, and Asn B147) the density was not sufficient to warrant the sugar addition).

Structural Analysis.

The structure of the LAP-TGFβ1 dimer in complex with humanized 28G11-Fab was determined to 3.4 Å resolution. The quality of the cryo-EM map was such that assignment of side chains for both the antigen and the Fab was unequivocal.

Figure 29A:
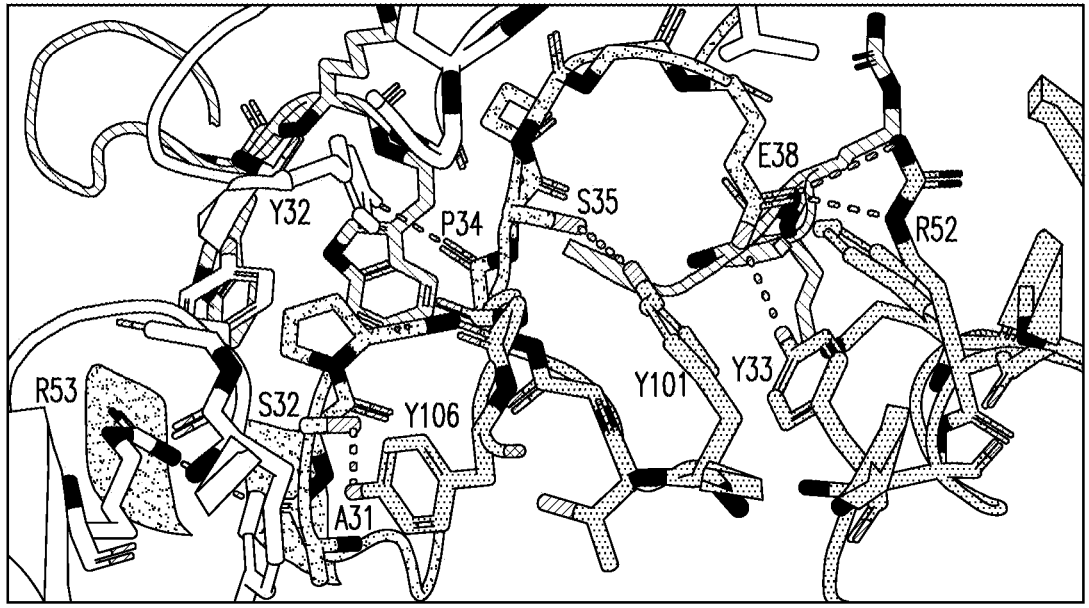
FIG. 29A shows interactions between LAP and the VL and VH of the 28G11 humanized Fab.
Figure 29B:
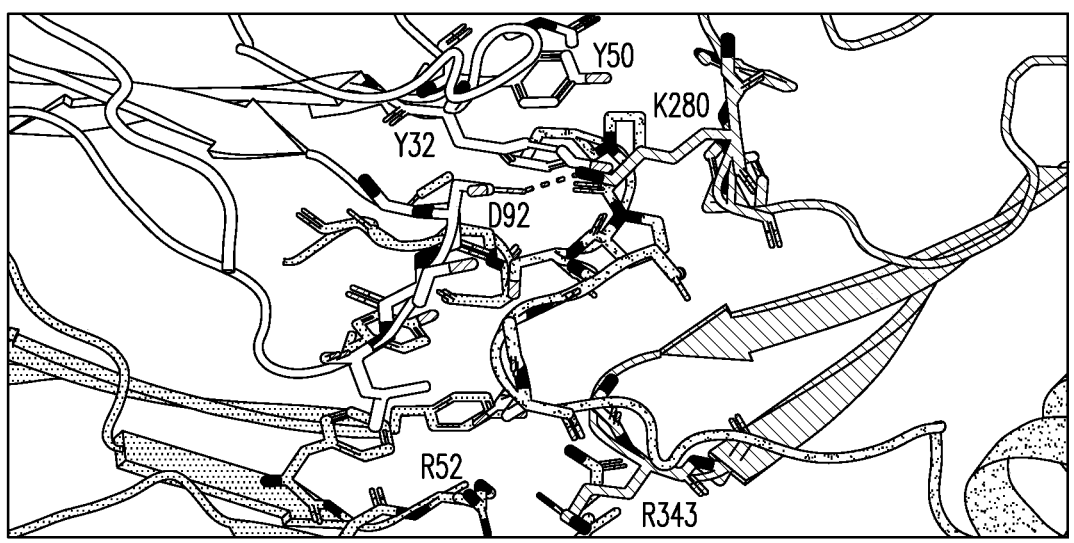
FIG. 29B shows interactions between TGFβ1 and the humanized 28G11 VL and VH portions of the Fab.
Figure 29C:
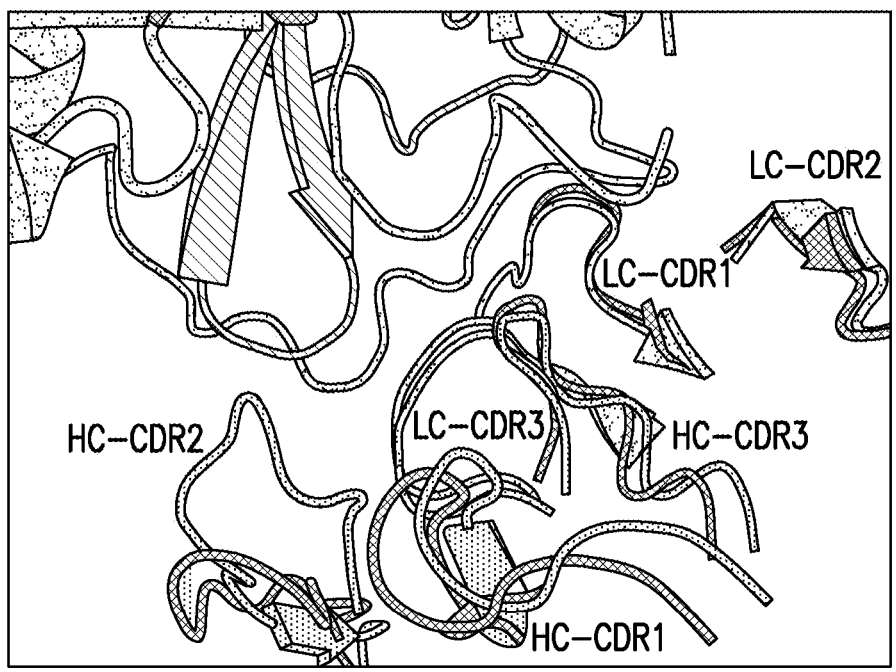
FIG. 29C shows the repositioning of CDRs in humanized 28G11 and humanized 20E6.
Figure 29D:
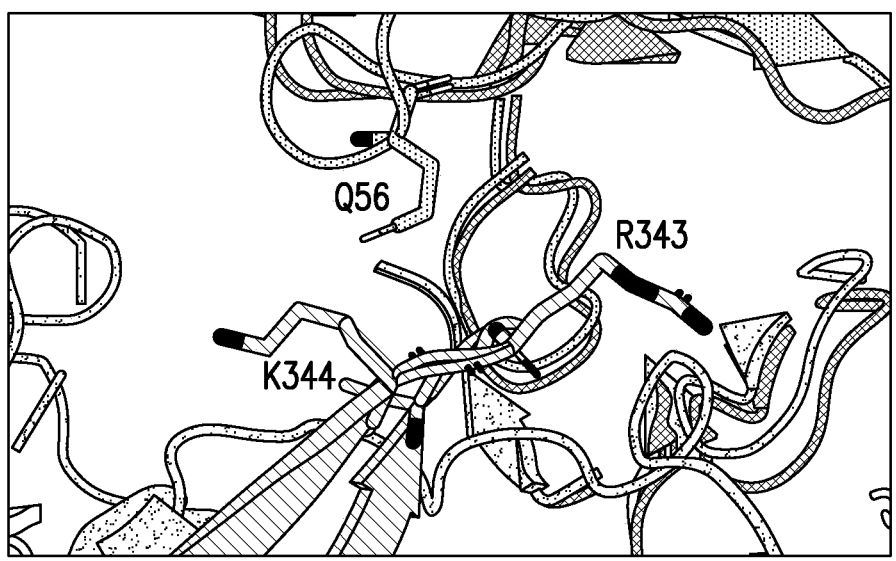
FIG. 29D shows that Q56 in humanized 28G11 is ideally positions to interact with the TGFβ1 loop spanning residues V342-K344.
Figure 29E:
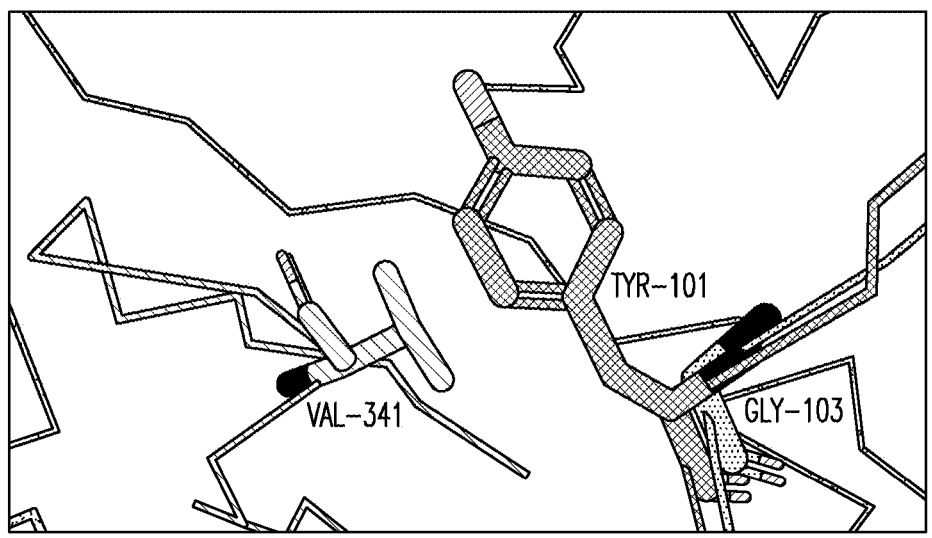
FIG. 29E shows that, in humanized 28G11, a Tyr residue is replaced by Gly, resulting in loss of interactions with the side chain of V341. Constructs and interactions are shown in grayscale.

The humanized 28G11-Fab paratope and LAP-TGFβ1 epitope residues that comprise the interaction interface are shown in FIGS. 29A and 29B, and summarized in Table 28. See also FIGS. 29C-E. The interface is made up of van der Waals and electrostatic interactions, and corresponds to ~800 Å$^2$ of buried surface, as calculated by PISA. The epitope is formed by residues A31-E38 from chain A (LAP residues) and G342-K344 and G278-W281 from chain B (TGFβ1 residues). The fact that both LAP and TGFβ1 residues are required for interactions with h20E6-Fab explains why the antibody is specific for the closed form of the LAP-TGFβ1 complex, and does not bind to empty LAP or to the mature TGFβ1. The paratope is formed by light chain (VL) residues: Y32, Y49-Y50, R53, and G91-L94, and heavy chain (VH) residues W33, F50-N53, Q56, and Y101-Y106.

TABLE 28

Epitope and paratope of LAP-TGFβ1 and 28G11-Fab*

| VH | TGFβ1 | VL |
|---|---|---|
| | G278 | S30 |
| | W279 | Y50 |
| | K280 | D92 |
| | W281 | Y32 |
| Q56, W33 | G342 | |
| R52, Q56 | R343 | |
| Q56 | K344 | |

| VH | LAP | VL |
|---|---|---|
| | A31 | Y49, R53 |
| Y106, Y106 | S32 | Y49, Y50, R53 |
| | G104 | P33 | Y32, Y50 |
| | P34 | Y32, Y32 |
| Y101, G104 | S35 | Y32, G91 |
| | Q36 | D92 |
| | G37 | D92, T93, L94 |
| F50, R52, R52, Y33, Y33 | E38 | L94 |

*Residues from 28G11-Fab VH or VL that interact with LAP-TGFβ1 residues are indicated.
Hydrogen bonding interactions are indicated in bold (interaction cut-off set to 4.5 Å; hydrogen bond interactions cut-off set to 3.5 Å).

Example 21: Cryo-EM Structure of Murine 22F9 in Complex with LAP-TGFβ1

The structure of murine 22F9-Fab (referred to in the Example as 22F9) in complex with human LAP-TGFβ1 was determined by SP-Cryo-EM to identify the epitope on LAP-TGFβ1 to which the antibody binds, and the paratope of 22F9-Fab.

Sample and Grids Preparation.

The murine 22F9 mAb used in this experiment was 22F9_N54Q_D102A_mIgG2a, which has heavy and light chain variable region sequences of SEQ ID NOs: 248 and 249, respectively. Human LAP-TGFβ1 was purchased from R&D and supplied in PBS buffer (10 mM sodium phosphate, 150 mM sodium chloride, pH 7.4) containing 50% glycerol. The sample was prepared as follows: LAP-TGFβ1 in PBS with 50% glycerol was buffer exchanged into a no-glycerol buffer (i.e., PBS), and complexed in a 1 dimer:1 Mab ratio with 22F9-Mab, then diluted 10-fold with PBS.

Grids (C-flat carbon on gold, 300 mesh, 1.3/1.2) were prepared using a Vitrobot Mark 4 (ThermoFisher) using standard procedures. Specifically, grids were glow discharged using a Pelco easyGlow unit (Ted Pella, Inc.) with the factory suggested values for plasma cleaning (0.39 mbar, lower level 15 mA, hold 10", glow 30"). The Vitrobot was set with a chamber humidity between 90-100%; a chamber temperature of 4C°; a blot time of 3 sec; a wait time of 0 sec; a blot force of 0. Three (3) µl of sample were applied to the grid, blotted, and then plunged into a liquid ethane bath. The frozen grid was then transferred to liquid nitrogen (LN2) and kept at LN2 temperature for all subsequent steps (clipping, transferring to the microscope cassette, and data collection).

Data Collection and Structure Determination.

The data set was collected on a ThermoFisher 300 KeV Titan Krios G3 equipped with a Gatan K3 Direct Electron Detector. Data collection was done using Gatan Latitude software. 3741 movies were collected at a nominal magnification of 81,000x; the defocus range was set to be between −0.8 and −1.8 µm. The detector pixel size was 1.07 Å and the dose was 62.5 e−/Å$^2$.

Data Processing and Map Reconstruction.

Figure 30A:
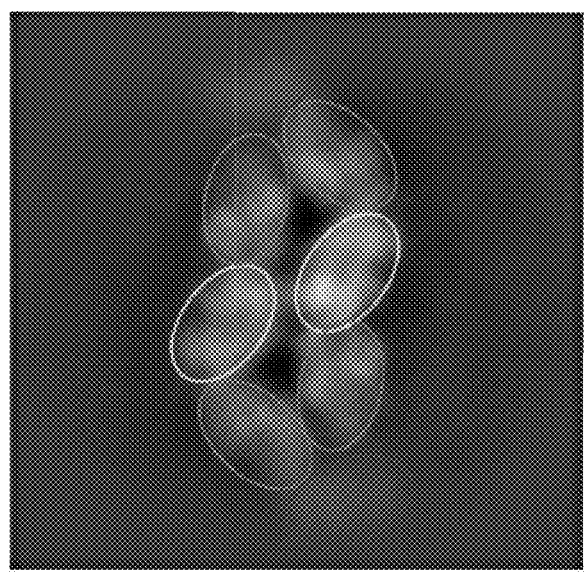
FIG. 30A shows the 2Mab:2TGFβ1 complex identified in cryo-EM (Mab refers to 22F9 Fab). Constructs are: LAP-TGFβ1 dimer; 22F9-Fabs; 22F9-Fcs.
Figure 30B:
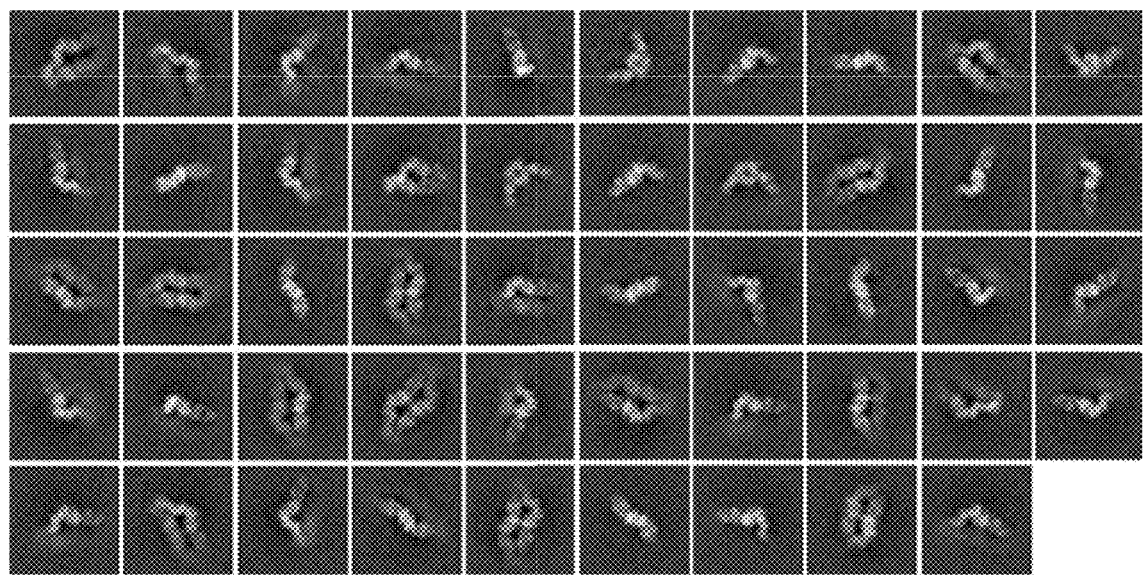
FIG. 30B provides examples of the 2D classes. Constructs and interactions are shown in grayscale.

The entire data processing and map reconstruction was carried out with Cryosparc V2. Initial processing identified 2.9M particles. Several 2D classification jobs were run to clean up the particle stack and remove outliers. At the end, 522,208 particles were used in a homogeneous refinement job which yielded a 3.68 Ang map. Non-uniform refinement yielded a 3.43 Ang map that was used to build the model. The 2D classes clearly showed the presence of a 2Mab: 2TGFβ1 complex, confirming the stoichiometry suggested by SEC-MAL experiments (FIGS. 30A and 30B).

Model Building and Refinement.

All model building and refinement were carried out using COOT and PHENIX (Afonine et al. *Acta Crystallogr D Struct Biol* 2018; 74 6:531-44). The complex between LAP/TGFβ1 and humanized 20E6 was used as starting model; LAP-TGFβ1 and humanized 20E6-Fab were initially positioned into the map as rigid bodies using COOT, and the density was used to rebuild some of the loops and assign the correct sequences. The PHENIX real space refinement module was carried out to optimize the model geometry. Table 29 summarizes the model refinement and statistics:

TABLE 29

Model refinement and statistics of humanized 22F9-Fab and LAP-TGFβ1

| | |
|---|---|
| Symmetry Imposed | C2 |
| Particle used | 522,208 |
| Map resolution (Å) | 3.4 |
| FSC threshold | 0.143 |
| Map Resolution Range (Å) | 3-14 |
| Refinement | |
| Map sharpening B-factor (Å$^2$) | 116.0 |
| Model composition | |
| Non Hydrogen Atoms | 11926 |
| Protein residues | 1530 |
| CC_mask: | 0.689 |
| CC_volume: | 0.680 |
| CC_peaks: | 0.615 |
| rmsd (bonds) (Å): | 0.007 |
| rmsd (angles) (°): | 0.91 |
| All-atom clashscore | 25.1 |
| Ramachandran plot: | |
| outliers: | 0.40% |
| allowed: | 18.1% |
| favored: | 81.5% |
| Rotamer outliers: | 1.95% |

The final model contained two chains for the LAP-TGFβ1 dimer (chains A and B, each one containing residues 1-61+ 70-208+216-241+250-361; numbering for antigen assumes absence of signal peptide, i.e., Leu 1=Leu 30 in complete sequence); two chains (heavy chain (VH), residues 1-221 and light chain (VL), residues 2-214) for the 22F9-Fab. One sugar moiety (NAG) was modeled at glycosylation sites Asn A53 and Asn B53); the density was not sufficient to warrant the sugar addition for all other possible glycosylation positions (A107, A147, B107, and B147).

Structural Analysis.

The structure of the LAP-TGFβ1 dimer in complex with the 22F9-Fab was determined to 3.4 Å resolution. The quality of the cryo-EM map was such that assignment of side chains for both the antigen and the Fab was unequivocal.

Figure 31A:
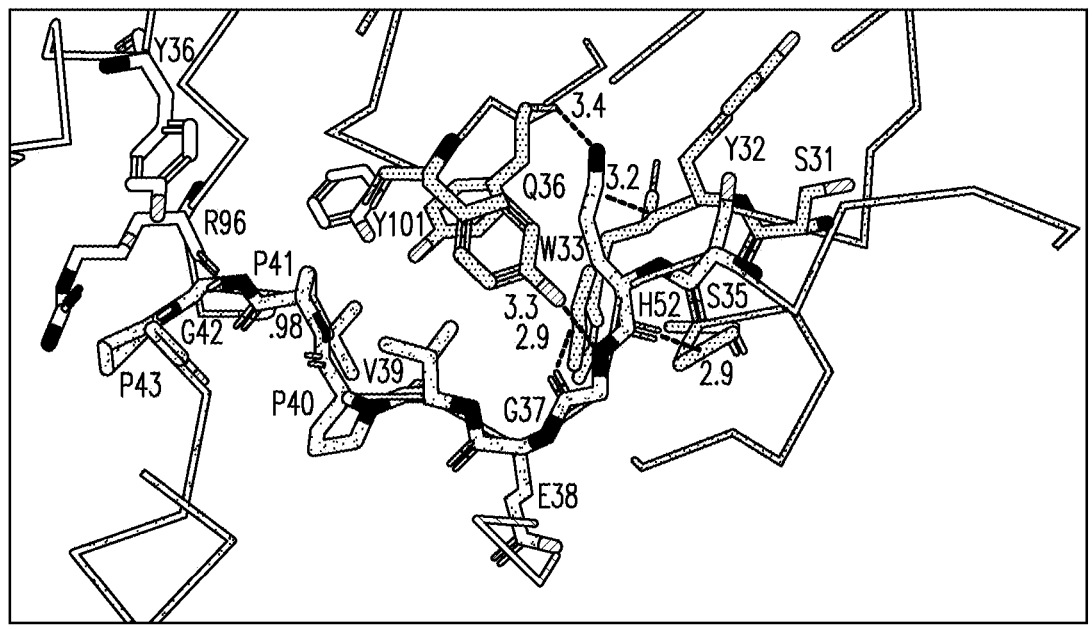
FIG. 31A shows interactions between LAP and the VL and VH portions of the 22F9 Fab.
Figure 31B:
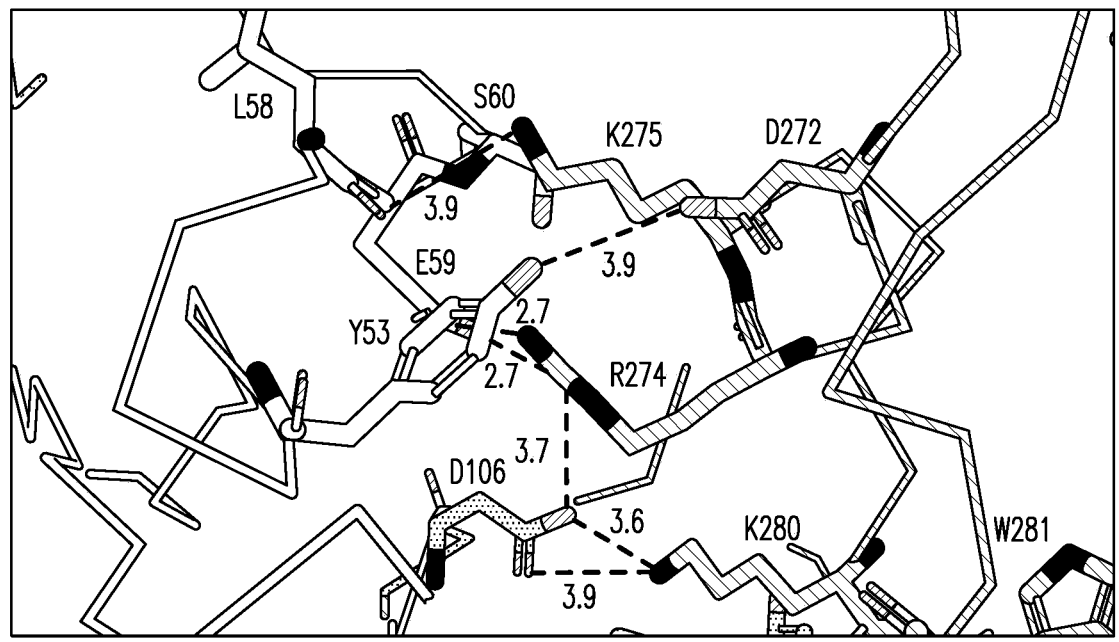
FIG. 31B shows interactions between TGFβ and 22F9 VL and VH.

The 22F9-Fab paratope and LAP-TGFβ1 epitope residues that comprise the interaction interface are shown in FIGS. 31A and 31B and summarized in Table 30.

The interface is made up of van der Waals and electrostatic interactions, and corresponds to ~900 Å$^2$ of buried surface, as calculated by PISA. The epitope is formed by residues S35-P43 from chain A (LAP residues) and D272-K275, K280-H283, and Y340 from chain B (TGFβ1 residues).

Figure 31C:
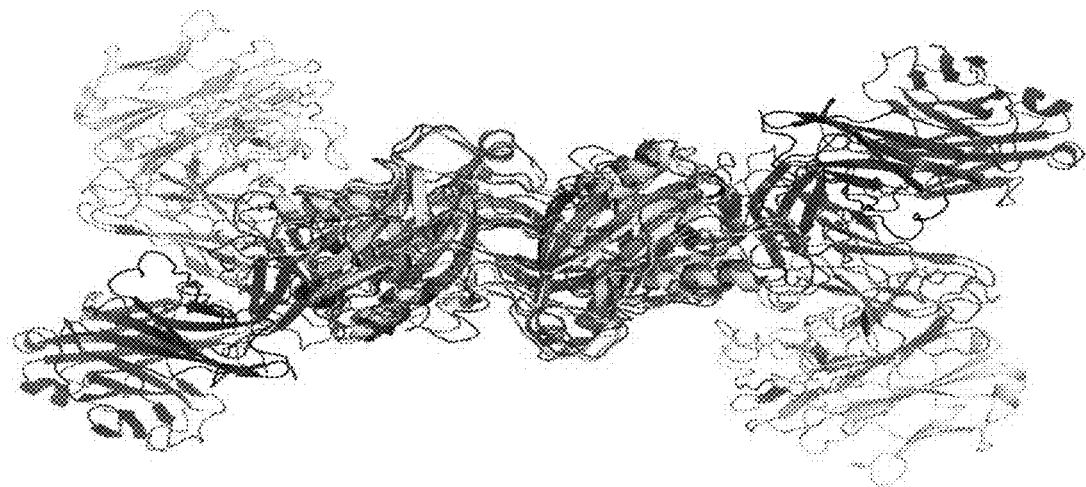
FIG. 31C shows an overlay of 22F9-Fab+LAP-TGFβ1 complex and humanized 20E6-Fab+LAP-TGFβ1 (Fabs) and the different orientation of humanized 20E6-Fabs and 22F9-Fabs with respect to the antigen.
Figure 31D:
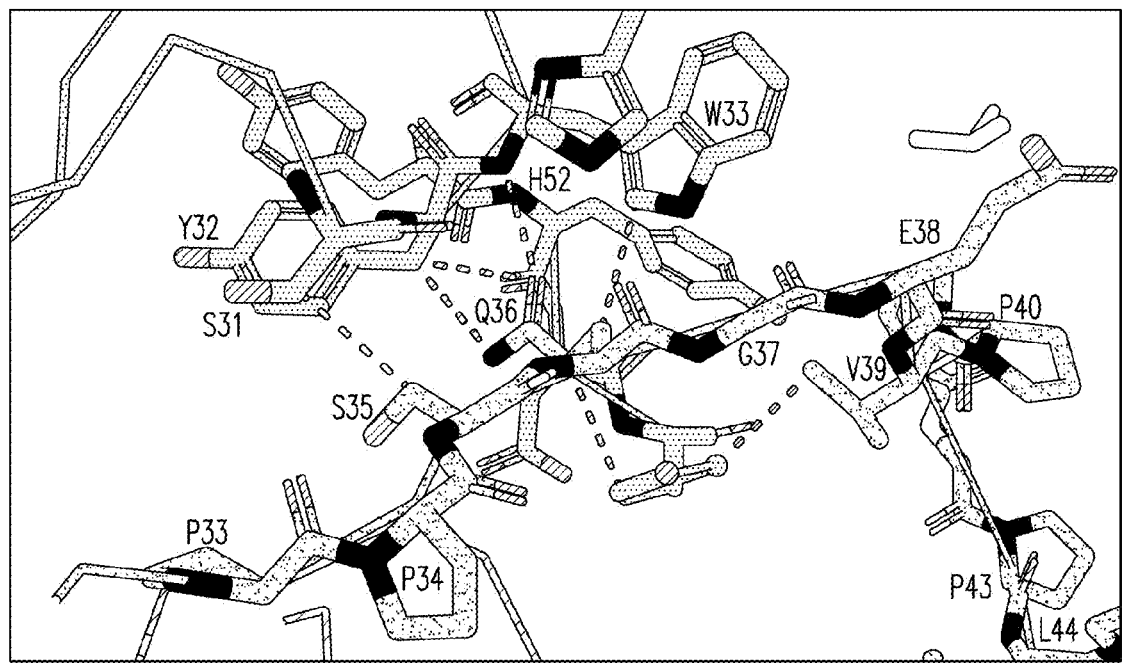
FIG. 31D and FIG. 31E show additional interactions between LAP-TGFβ1 and portions of the 20E6 Fab. Constructs and interactions are shown in grayscale.
Figure 31E:
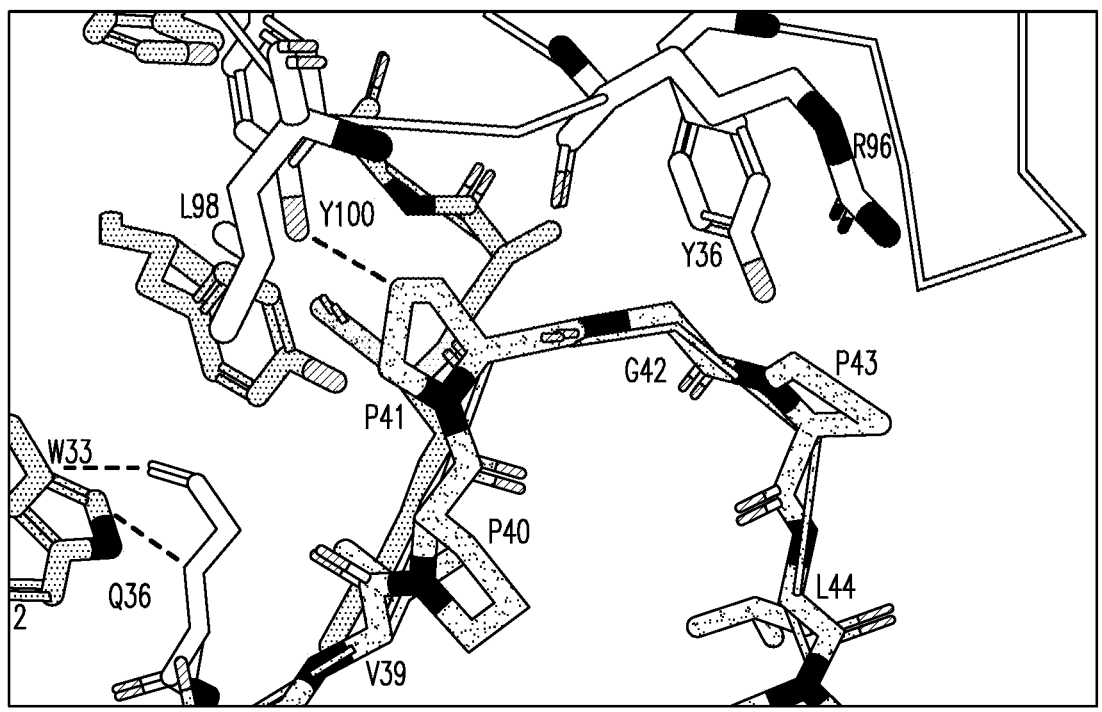

The 22F9 paratope is formed by light chain (VL) residues: Y36, Y53, L58-S60, and R98-Y100, and heavy chain (VH) residues S31-W33, H52, and Y98-D106. See FIGS. 31C-E.

TABLE 30

Epitope and paratope of LAP-TGFβ1 and 22F9-Fab*

| VH | TGFβ1 | VL |
|---|---|---|
| | D272 | Y53 |
| D100, Y104, D106 | R274 | Y53, E59 |
| | K275 | Y53, L58, E59, S60 |
| Y32, Y98, Y99, D100, Y101, D106 | K280 | |
| Y101 | W281 | |
| Y101 | H283 | |
| Y101 | Y340 | |

| VH | LAP | VL |
|---|---|---|
| S31, Y32 | S35 | |
| W33, W33, Y32, H52 Y99, Y99, | Q36 | |
| W33, W33, | G37 | |
| | E38 | |
| M50, Y101, Y99 | V39 | |
| Y99 | P41 | Y100, R96, E97, L98 |
| | G42 | R96, R96, Y36, Y36 |
| | P43 | T31, Y36, R96 |

*Residues from 22F9-Fab VH or VL that interact with LAP-TGFβ1 residues are indicated. Hydrogen bonding interactions are indicated with bold type (interaction cut-off set to 4.5 Å; hydrogen bond interactions cut-off set to 3.5 Å).

Example 22: Analysis of a Humanized 20E6 Antibody by Hydrogen Deuterium Exchange Mass Spectrometry Contact areas between the humanized anti-LAP antibody 20E6_H0.2_hIgG4mut (referred to as "humanized 20E6" in this Example) and human LAP-TGFβ1 were determined by hydrogen deuterium exchange mass spectrometry (HDX-MS). HDX-MS measures the exchange of deuterium with hydrogen into the amide backbone of the protein. One factor influencing the exchange rate is the hydrogen's exposure to solvent. Comparison of the exchange levels in the antigen when the antibody is bound can identify regions of the protein where the antibody is binding.

Materials

Human LAP-TGFβ1 protein was purchased from R&D Systems and consists of an N-terminal 249 aa latency-associated peptide (LAP) and a C-terminal 112 aa mature TGFβ1 protein. The protein was buffer exchanged and concentrated to 40 µM in 10 mM sodium phosphate, 150 mM sodium chloride, pH 7.4.

Humanized anti-LAP-TGFβ1 antibody (20E6_H0.2_hIgG4mut) was generated as described in Example 11. The antibody was diluted from 7.1 mg/mL to 5.8 mg/mL, equivalent to 40 µM.

Liquid Chromatography-Mass Spectrometry

A Waters Synapt G2Si Quadrupole Time-of-flight (TOF) mass spectrometer was used. For peptide identification and measurement of deuterium labeled samples, the mass spectrometer was set to acquire one full scan MS data (low energy) and one MS(e) data (high energy) in the TOF-only mode. The scan time was set to 0.4 seconds. Ramp trap collision energy was from 15 to 45 volts.

The liquid chromatography system was a Waters nano-Acquity binary pump for the analytical column gradient and auxiliary pump for sample digestion and loading. For sample digestion and loading, the buffer used was 100% water and 0.1% formic acid at a flow rate of 100 μL/minute. For the analytical gradient, the buffers were Buffer A (0.1% formic acid in water) and Buffer B (0.1% formic acid in acetonitrile).

The gradient was at 40 μL/minute from 5% B to 35% B in 9 minutes, followed by a ramp to 85% B in one minute, a wash of 85% B for one minute, and a re-equilibration at 5% B for one minute. The column was then washed by cycling the gradient between 5% and 95% B, four times with one minute at each step, followed by a final equilibration at 5% B for one minute. The trapping column was a Waters Vanguard BEH C18 1.7 μm Guard Column and the analytical column was a Waters BEH C18, 1.7 μm 1×50 mm column.

Sample handling for the deuterium labeling was done by a Waters HDX unit which consists of Leaptec H/D-X PAL system and a Waters HDX chamber for column cooling. The labeling sample tray was set to a temperature of 10° C., the quenching tray was set to 1.5° C., and the trap and analytical column chamber was set to 1.5° C. The immobilized protease type XIII/pepsin column (w/w, 1:1) from NovaBioassays was kept at 20° C. in the enzyme column chamber.

Deuterium Labeling

Human LAP-TGFβ1 was mixed with humanized 20E6 to final concentrations of 20 μM for human LAP-TGFβ1 and 10 μM for humanized 20E6. An unbound control was prepared by incubating human LAP-TGFβ1 in 10 mM sodium phosphate, 150 mM sodium chloride, pH 7.4. The antibody bound sample and the unbound control were incubated at room temperature for one hour before beginning the labeling experiment.

To deuterium label the samples, 6 μL of sample was mixed with 54 μL of 10 mM sodium phosphate, 150 mM sodium chloride in deuterium oxide pD 7.4. Labeling time points were 0, 10, 60, 600, 6000, and 14,400 seconds. After each time point, 50 μL of the labeling mixture was added to 50 μL of cold quench buffer (500 mM tris(2-carboxyethyl) phosphine (TCEP) in phosphate buffer, pH 2.5). After mixing once, 90 μL was then injected into the column cooling chamber where the sample was passed over the protease type XIII/pepsin column and the resulting peptides loaded onto the trapping column. After 4 minutes, a valve switch took the protease type XIII/pepsin column out of line. The trap was then switched in-line with the analytical column and the analytical gradient and the mass spectrometer data acquisition was started. Each time point was acquired in duplicate.

Data Analysis

Liquid chromatography-tandem mass spectrometry (LC-MS/MS) data was acquired of unlabeled bound and unbound samples in quadruplicate, and database searches with ProteinLynx Global Server 3.0 (Waters Corporation) were performed to verify successful digestion of the proteins and to generate a list of peptides from the dual-enzyme digestion. The protein database used was human LAP-TGFβ1 combined with a randomized human LAP-TGFβ1 sequence to reduce false identification.

Mass spectrometry (MS) data from the deuterium labeling experiment was processed by DynamX (version 3.0.0, Waters Corporation). For each peptide, the mass, retention time, and charge state selected by the software were verified manually.

Results

Figure 32:
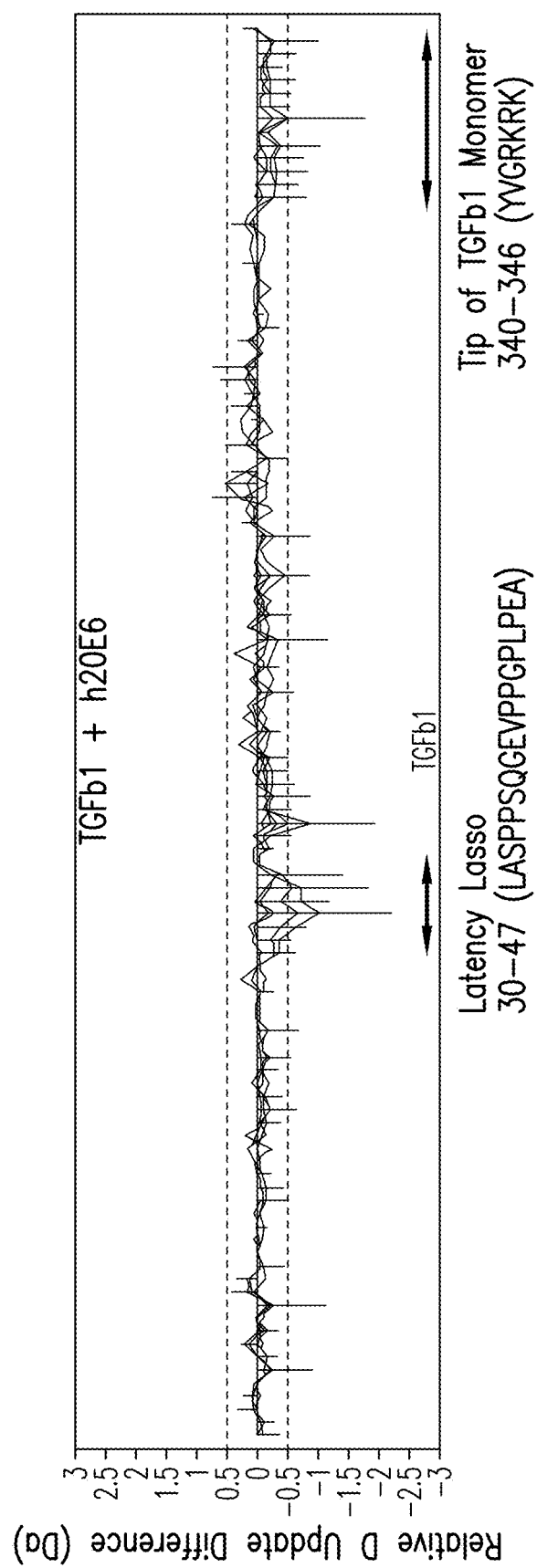
FIG. 32 is a H/D Difference Plot showing deuterium uptake protection upon humanized 20E6 antibody binding to human LAP-TGFβ1 protein.

The human LAP-TGFβ1 peptides protected by humanized 20E6 are shown in an H/D Difference Plot (FIG. 32).

Example 23: Epitope Mapping of Murine 28G11, 22F9, 20E6, and 2F8 Antibodies by HDX-MS Contact areas between murine anti-LAP-TGFβ1 antibodies 28G11, 22F9, 20E6, and 2F8 and human LAP-TGFβ1 were determined by HDX-MS, as described below.

Methods

Materials used were as follows:
Human LAP-TGFβ1 protein was purchased from R&D Systems and consists of an N-terminal 249 aa latency-associated peptide (LAP) and a C-terminal 112 aa mature TGFβ1 protein. The protein was buffer exchanged and concentrated to 40 μM in 10 mM sodium phosphate and 150 mM sodium chloride, pH 7.4.
Murine 28G11_mIgG2a, murine 22F9_mIgG2a, and murine 20E6_mIgG2a were diluted to 40 μM. The heavy and light chain variable region sequences of 28G11(hyb), 22F9 (hyb), and 20E6 (hyb) (provided in Table 34) were fused to an mIgG2a constant Murine 2F8 (IgG1) was purchased from BioLegend and concentrated from 0.5 mg/mL to 40 μM.

Liquid chromatography-mass spectrometry was performed in the manner described in Example 22, except that, in the sample handling for deuterium labeling, the labeling sample tray was set to a temperature of 25° C. instead of 10° C. Deuterium labeling was also performed as described in Example 22, except that human LAP-TGFb1 was mixed with the antibody to final concentrations of 20 μM for human LAP-TGFβ1 and 20 μM for the antibody. Data analysis was performed as described in Example 22.

Results

Figure 33:
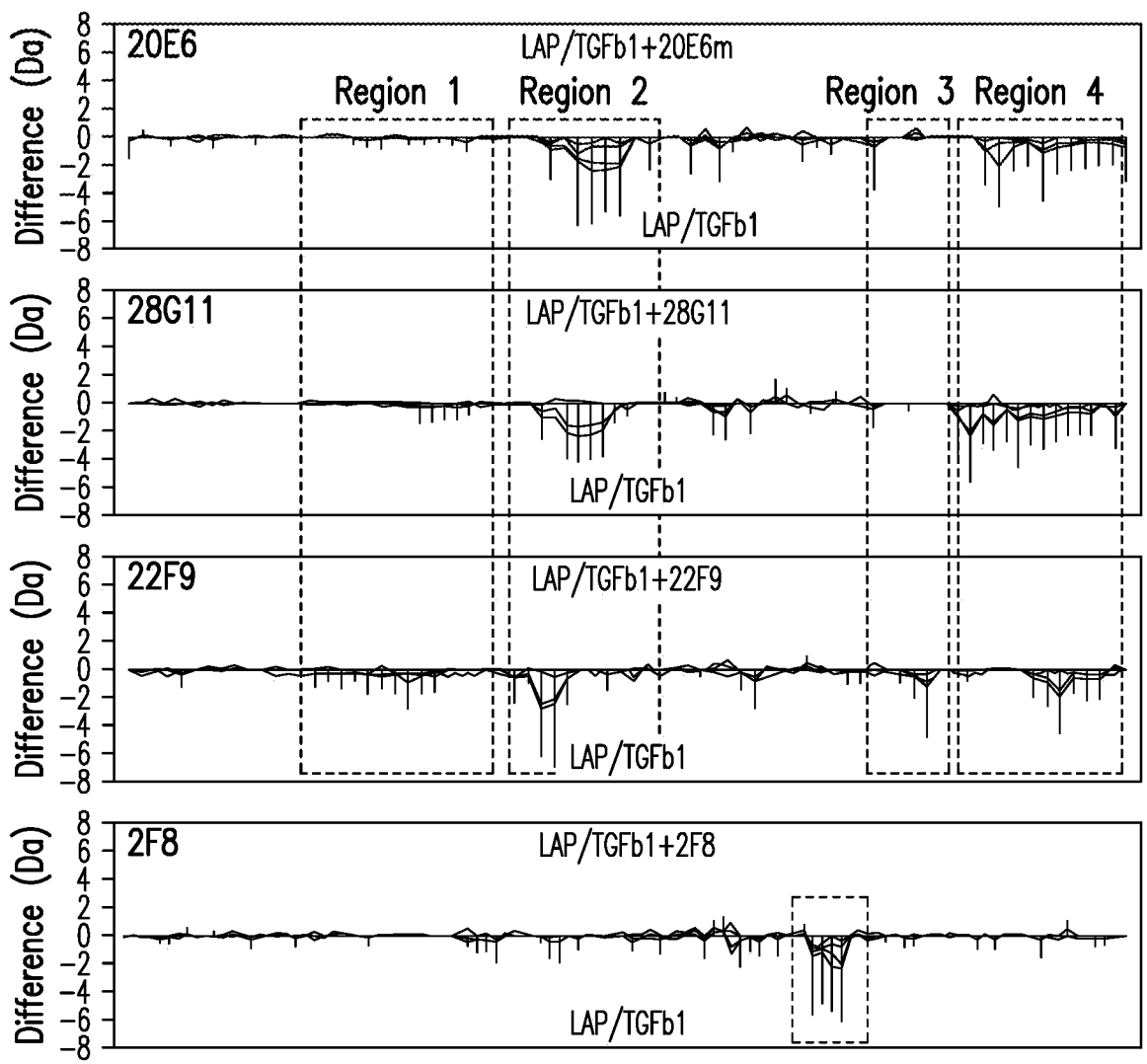
FIG. 33 is a H/D Difference Plot showing deuterium uptake protection upon antibody binding to human LAP-TGFβ1 protein.

Human LAP-TGFβ1 peptides protected by the antibodies are illustrated in the H/D Difference Plots shown in FIG. 33. Binding epitopes for 28G11, 22F9, and 20E6 covered four regions in the LAP-TGFβ1 protein: amino acid residues 14-25 (RKRIEAIRGQIL, region 1; SEQ ID NO: 250), 30-39 (LASPPSQGEV, region 2; SEQ ID NO: 251), 278-286 (GWKWIHEPK, region 3; SEQ ID NO: 252), and 340-346 (YVGRKPK, region 4; SEQ ID NO:253). Regions 1 and 2 are in the LAP domain, and region 3 and 4 are in the mature TGFβ1 domain.

Differences in the degree of deuterium exchange protection were detected among the antibodies. For example, in comparing 20E6 with 28G11 and 22F9, 20E6 showed no deuterium exchange protection at region 1, while 28G11 and 22F9 had detectable changes upon antibody binding (approximately 1.3 and 1.9 Da, respectively). Slight differences in deuterium exchange were also observed for regions 2 and 3. Specifically, in region 2, a 6 Da difference was detected for 20E6, but the difference for 28G11 was only 4 Da. In region 3, a 4 Da difference was detected for 20E6, but only a 2 Da difference was detected for 28G11. Notably, the interaction at region 1 detected by HDX was not observed in the cryo-EM structure, suggesting that deuterium exchange protection at region 1 is not due to direct antibody:antigen binding, but from changes in local solution dynamics as a result of slightly different binding interactions between these antibodies and LAP-TGFβ1. Taken together, the HDX data are consistent with the cryo-EM structures.

It was observed that antibody 2F8 bound to residues 205-225 (amino acids VDINGFTTGRRGDLATIHGMN; SEQ ID NO: 254).

The amino acid sequences of murine and human LAP-TGFβ1 are 89% identical. Epitopes identified are all in the homologous region (FIG. 34).

Example 24: Binding Stoichiometry of Human LAP-TGFβ1 or GARP-LAP-TGFβ1 Complexed with a Humanized 20E6 Antibody by Size-Exclusion Chromatography and Multi-Angle Light Scattering The binding stoichiometry of human LAP-TGFβ1 or GARP-LAP-TGFβ1 complexed with 20E6_H0.2_hIgG4mut was determined by size-exclusion chromatography and multi-angle light scattering (SEC-MALS). Due to differences in size, human LAP-TGFβ1 alone, 20E6_H0.2_hIgG4mut alone, and the complex elute at different times on SEC chromatogram. The MALS detector helps determine the molecular weight for each detected peak. Based on the molecular weight of individual proteins and the protein complex, binding stoichiometry can be determined.

Materials
- Human LAP/TGFβ1 protein was purchased from R&D Systems and consists of an N-terminal 249 aa latency-associated peptide (LAP) and a C-terminal 112 aa mature TGFβ1 protein. The protein was buffer exchanged and concentrated to 40 μM in 10 mM sodium phosphate, 150 mM sodium chloride, pH 7.4.
- Human GARP-LAP-TGFβ1 was generated as described in Example 16.
- Anti-human LAP-TGFβ1 antibody (20E6_H0.2_hIgG4mut) was generated as described in Example 11. The antibody was diluted from 7.1 mg/mL to 5.8 mg/mL equivalent to 40 μM.

Size-Exclusion Chromatography—Multi-Angle Light Scattering

Size-exclusion chromatography was performed using an Agilent 1200 HPLC connected to a photodiode array detector and a Wyatt light scattering detector. Superdex 200 Increase 5/150 GL column was run at a 0.2 mL/minutes flow rate using 10 mM sodium phosphate, 150 mM sodium chloride, pH 7.4 buffer under an isocratic gradient.

Human LAP-TGFβ1 was mixed with antibody 20E6_H0.2_hIgG4mut to final concentrations of 5 μM for human LAP-TGFβ1 and antibody 2.5 μM for 20E6_H0.2_hIgG4mut. Thirty μL of 5 μM human LAP/TGFβ1 alone, 5 μM 20E6_H0.2_hIgG4mut alone, and LAP-TGFβ1:20E6 complex were analyzed using the SEC-MALS system including a gel filtration standard and bovine serum albumin standard. The following samples were also analyzed: 30 μL of 7.5 μM human LAP-TGFβ1 alone, 7.5 μM antibody 20E6_H0.2_hIgG4mut alone, and GARP-LAP-TGFβ1:20E6_H0.2_hIgG4mut complex.

Data Analysis

All chromatograms were plotted using ChemStation (Version A.01.08.108, Agilent Technologies) at 280 nM UV absorbance. The light scattering data was analyzed using ASTRA (Version 6.1.2.84, Wyatt Technologies). All peaks were integrated cross full width at half height.

Results

Figure 35B:
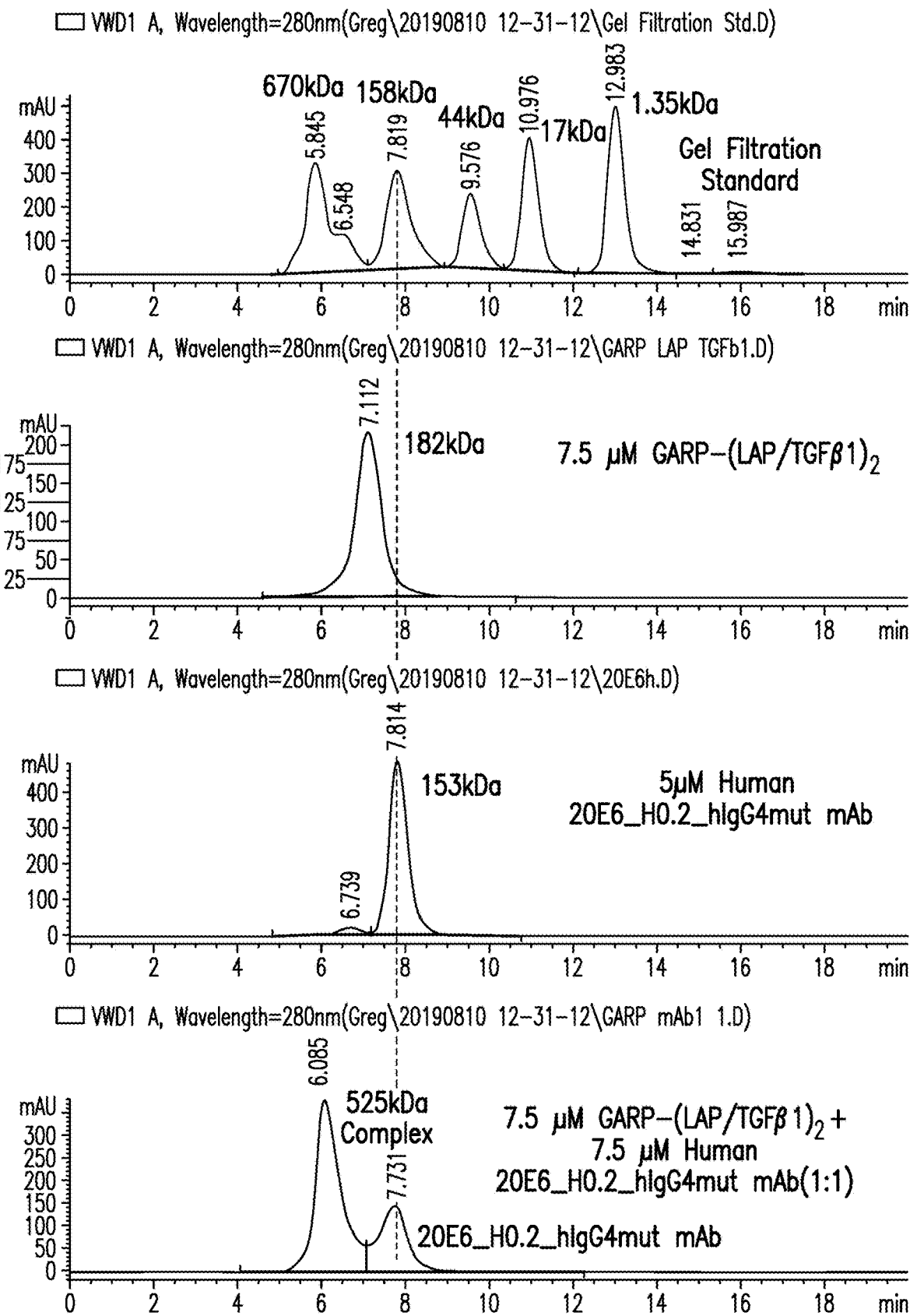

SEC-MALS analysis for LAP-TGFβ1:20E6_H0.2_hIgG4mut complex and GARP-LAP-TGFβ1 complex are shown in FIGS. 35A and 35B, respectively. Based on the molecular weight of each protein and the protein complex, the binding stoichiometry for the LAP-TGFβ1 complex is 2:2 molar ratio, i.e., two copies of LAP-TGFβ1 dimer bind to two copies of 20E6_H0.2_hIgG4mut antibody; the binding stoichiometry for the GARP-LAP-TGFβ1 complex is 2:1 molar ratio. In the presence of GARP, only one binding site in LAP-TGFβ1 dimer is able to interact with the antibody.

Example 25: Efficacy of Anti-LAP Antibodies in CT26 Syngeneic Model

This Example describes the efficacy of anti-LAP antibodies in combination with anti-PD-1 antibodies in the CT26 colorectal cancer tumor model, a syngeneic model of cancer. In this experiment, variants of the anti-LAP antibodies were used in which the Fc portion of the antibody was the IgG2a isotype rather than the isotype found in the parental hybridoma.

Briefly, 6-8 week-old Balb/c mice were subcutaneously implanted with $3 \times 10^5$ CT26 colorectal cancer cells. Tumors were grown until an average size of 48 $mm^2$ at which point tumor-bearing animals were randomized to groups of 10 animals each.

One set of animals was dosed intraperitoneally with either rat anti-PD-1 clone RMP1-14-IgG2a at 3 mg/kg or a combination of anti-PD-1 and antibody 28G11-IgG2a at 10 mg/kg on days 0, 3, 6, 9, and 12. Animal groups were also dosed with isotype control antibodies (rat-IgG2a and/or mouse IgG2a, not shown).

Another set of animals was dosed intraperitoneally with either rat anti-PD-1 clone RMP1-14-IgG2a at 3 mg/kg, antibody 16B4-IgG2a at 10 mg/kg, or a combination of anti-PD-1 and antibody 16B4-IgG2a at 10 mg/kg on days 0, 3, 6, 9, and 12. Animal groups were also dosed with isotype control antibodies (rat-IgG2a and/or mouse IgG2a, not shown).

Survival was assessed daily and tumor volumes were measured 3 times per week by caliper using the formula $V=W2 \times L/2$. Animals were followed for 53 days post dosing.

Figure 36A:
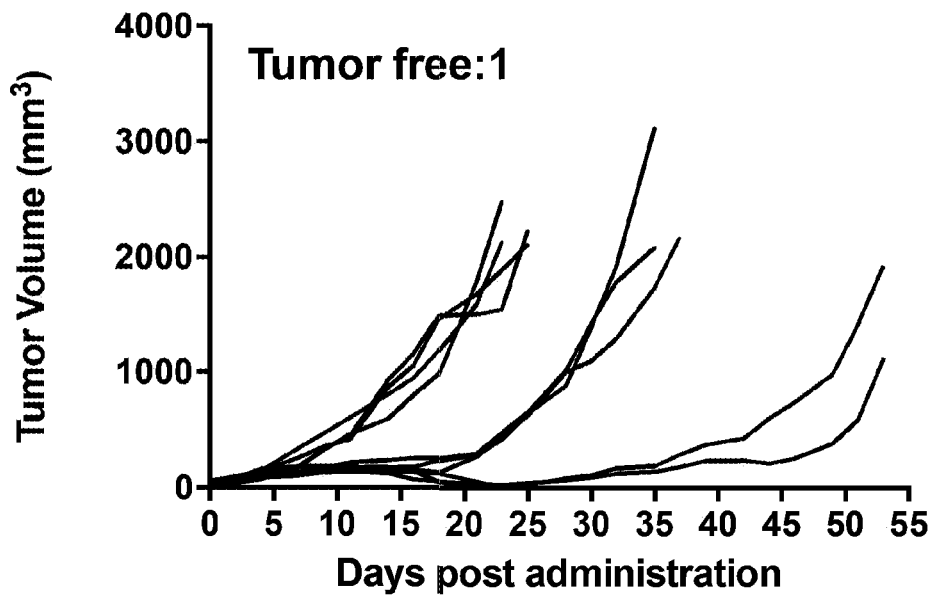
FIGS. 36A-36F are a series of graphs that show the effects of anti-LAP antibodies 28G11 and 16B4 in combination with an anti-PD-1 antibody on tumor volume in a syngeneic CT26 colorectal cancer tumor model. The data shown in the figures are.
Figure 36B:
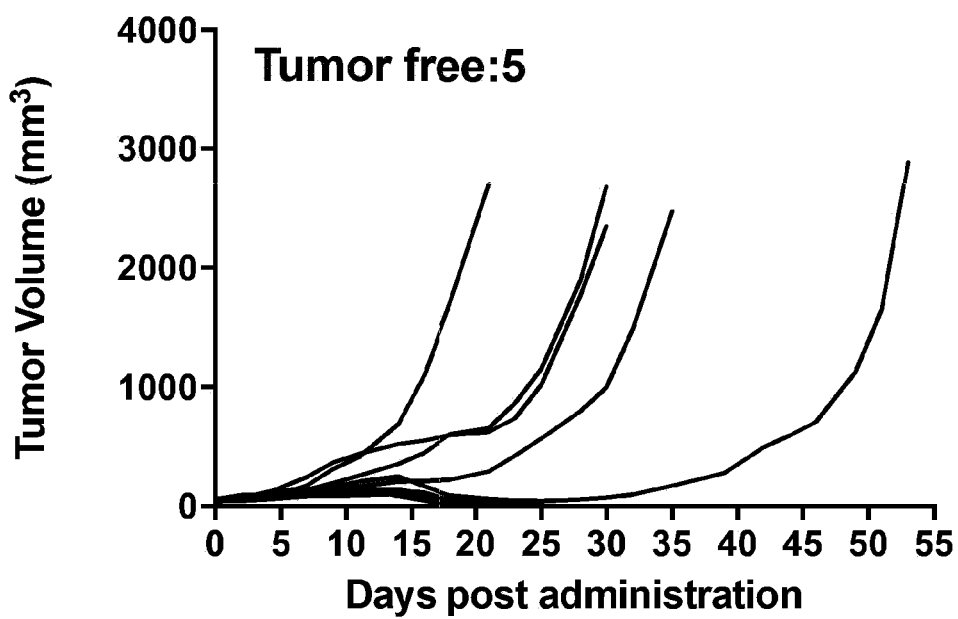
Figure 36C:
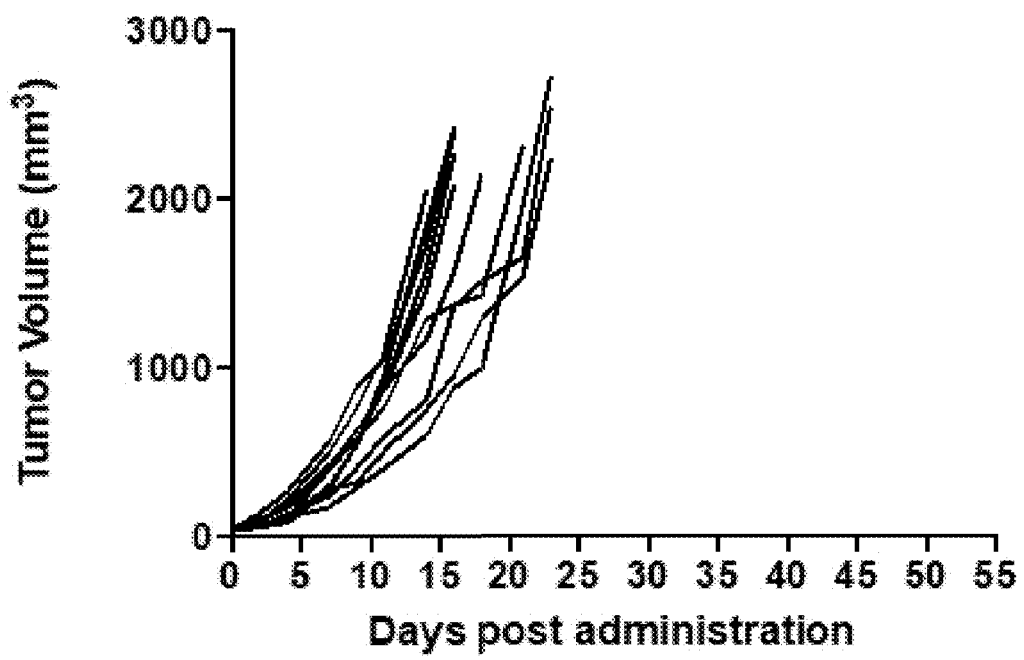
Figure 36D:
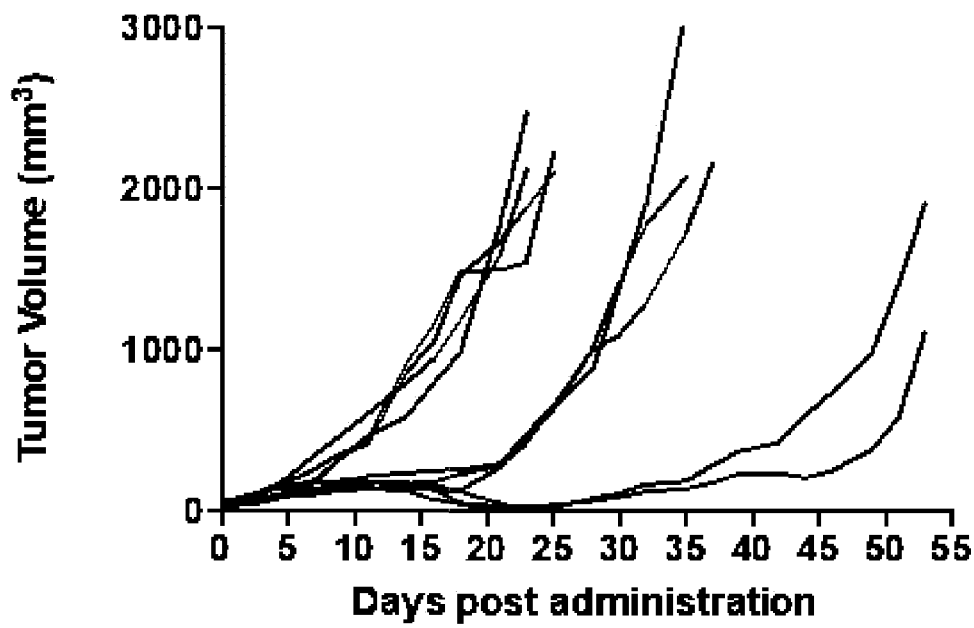
Figure 36E:
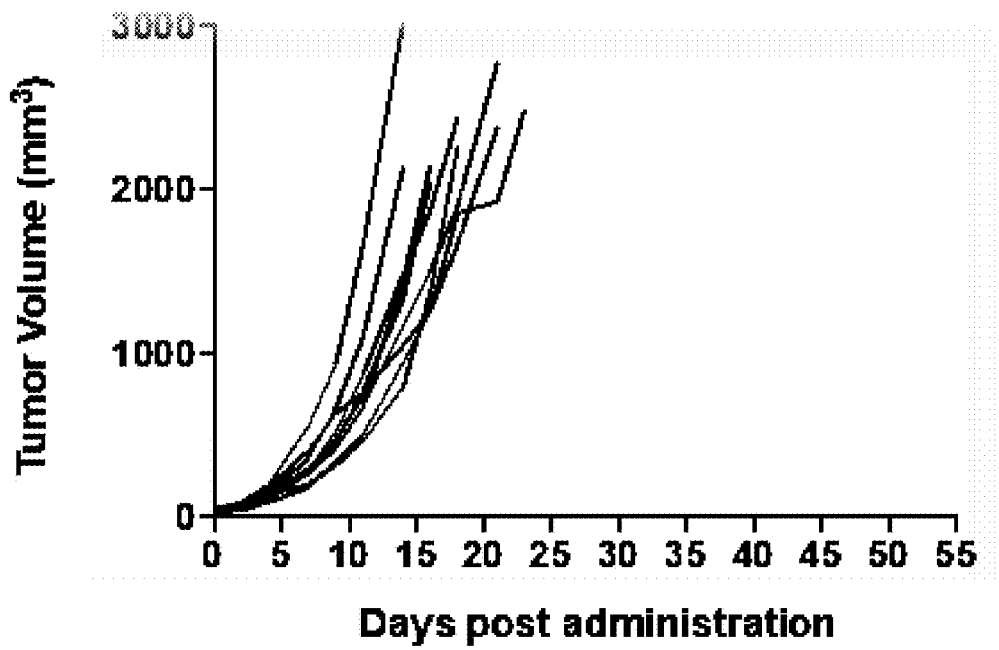
Figure 36F:
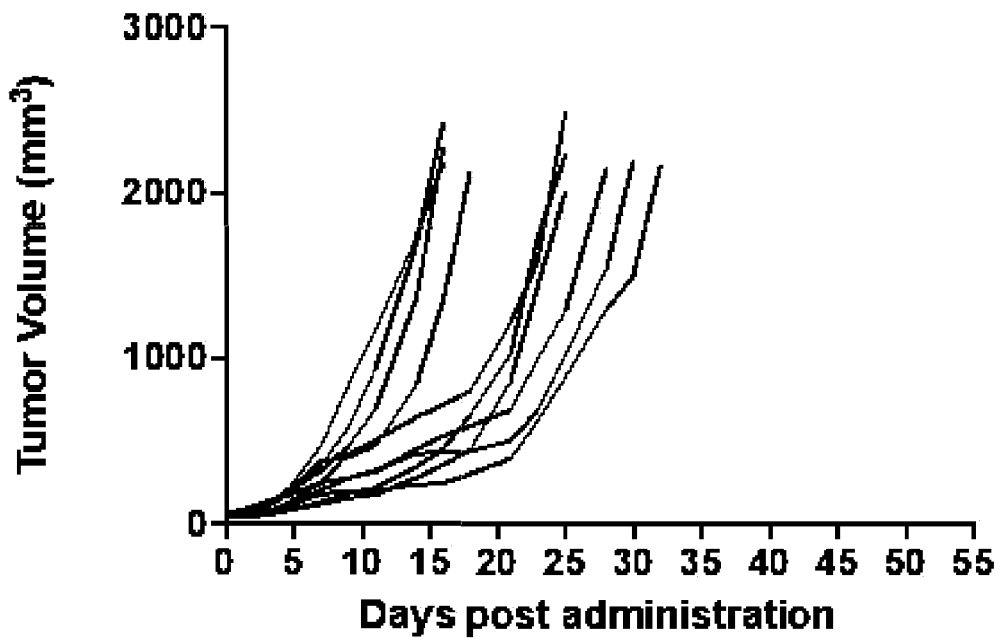

As shown in FIGS. 36A and 36B, treatment of this syngeneic model with antibody 28G11 resulted in a 5-fold increase in complete response rate over anti-PD-1 alone. In contrast, as shown in FIGS. 36C-36F, treatment of animals with antibody 16B4 had no effect on tumor growth. In fact, treatment of animals with a combination of 16B4 and anti-PD-1 resulted in a reduction of the response rate seen with anti-PD-1 antibody alone. These data establish that the two anti-LAP antibodies 28G11 and 16B4 have different functional properties in a mouse tumor model.

Example 26: Efficacy of Anti-LAP Antibodies in EMT6 Syngeneic Model

This Example describes the efficacy of anti-LAP antibodies in combination with anti-PD-1 antibodies in another syngeneic model of cancer, i.e., the EMT6 breast cancer tumor model.

Briefly, 6-8 week-old Balb/c mice were subcutaneously implanted into the right hind flank with $3 \times 10^5$ EMT6 breast cancer cells. Tumors were grown until an average size of 75 $mm^2$, at which point tumor-bearing animals were randomized to 10 groups of 10 animals each, and dosed intraperitoneally on days 0, 3, 6, 9, 12, 15, 18, and 21 according to the following:

TABLE 31

Antibody and dosing information for the EMT6 syngeneic model

| Group | Description | Dose |
| --- | --- | --- |
| 1 | Rat IgG2a | 5 mg/kg |
|   | Mouse IgG2a | 15 mg/kg |
| 2 | Rat anti-PD-1 RMP1-14-IgG2a | 5 mg/kg |
|   | Mouse IgG2a | 15 mg/kg |
| 3 | 28G11_IgG2a | 10 mg/kg |

TABLE 31-continued

Antibody and dosing information for the EMT6 syngeneic model

| Group | Description | Dose |
|---|---|---|
| | Rat IgG2a | 5 mg/kg |
| 4 | Rat anti-PD-1 RMP1-14-IgG2a | 5 mg/kg |
| | 28G11_IgG2a | 10 mg/kg |
| 5 | 22F9_IgG2a | 10 mg/kg |
| | Rat IgG2a | 5 mg/kg |
| 6 | 22F9_IgG2a | 15 mg/kg |
| 7 | Rat anti-PD-1 RMP1-14-IgG2a | 5 mg/kg |
| | 22F9_IgG2a | 10 mg/kg |
| 8 | Rat anti-PD-1 RMP1-14-IgG2a | 5 mg/kg |
| | 22F9_IgG2a | 15 mg/kg |
| 9 | 20E6_IgG2a | 10 mg/kg |
| | Rat IgG2a | 5 mg/kg |
| 10 | Rat anti-PD-1 RMP1-14-IgG2a | 5 mg/kg |
| | 20E6_IgG2a | 10 mg/kg |

Survival was assessed daily and tumor volumes were measured 3 times per week by caliper using the formula V=W2×L/2. Animals were followed for 28 days post dosing. Data is graphed as mean tumor volume+/−SEM.

Figure 37:
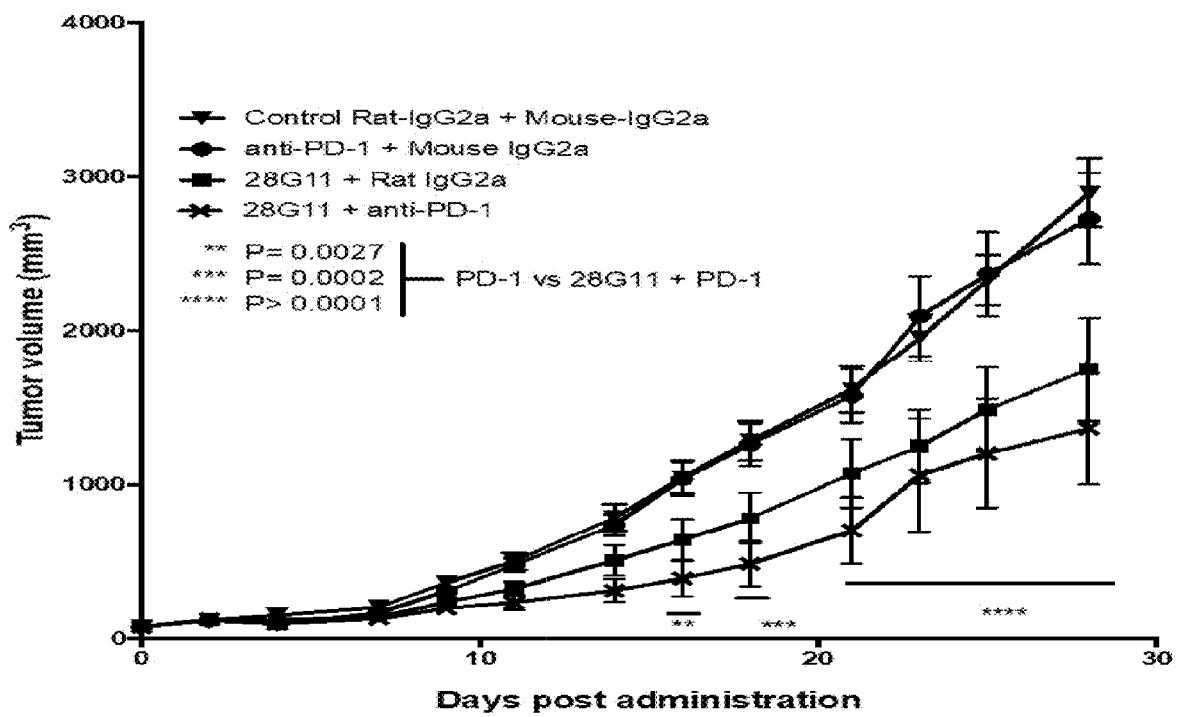
FIG. 37 is a graph that shows the effects of anti-LAP antibody 28G11 in combination with an anti-PD-1 antibody on tumor volume in a syngeneic EMT6 breast cancer tumor model. The anti-PD-1 antibody was a rat anti-PD-1 (clone RMP1-14)-IgG2a antibody. The statistical test used was two-way ANOVA.
Figure 38:
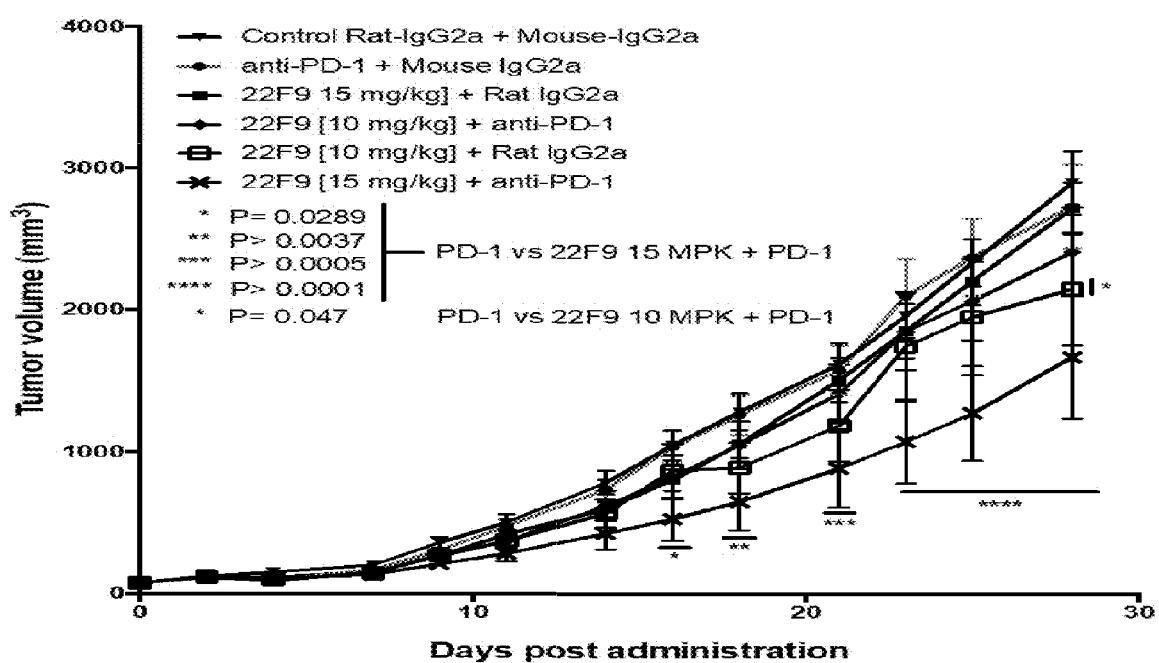
FIG. 38 is a graph that shows the effects of anti-LAP antibody 22F9 in combination with an anti-PD-1 antibody on tumor volume in a syngeneic EMT6 breast cancer tumor model. The anti-PD-1 antibody was a rat anti-PD-1 (clone RMP1-14)-IgG2a antibody. The statistical test used was two-way ANOVA.
Figure 39:
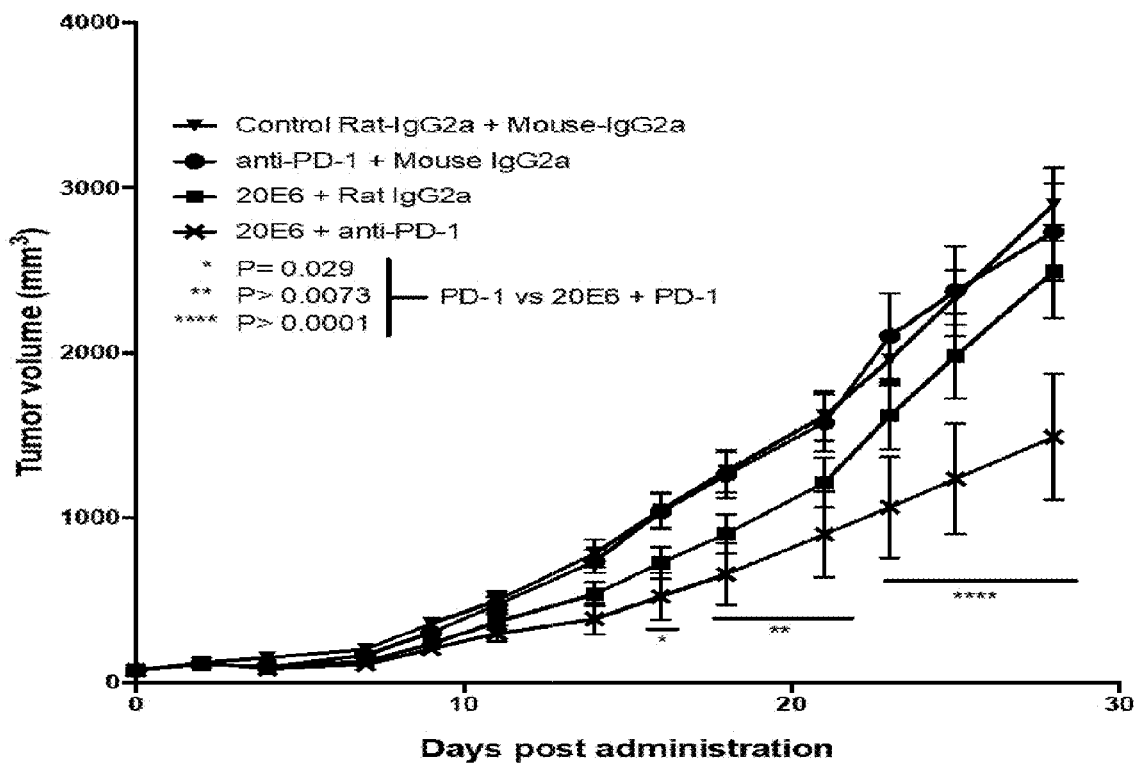
FIG. 39 is a graph that shows the effects of anti-LAP antibody 20E6 in combination with an anti-PD-1 antibody on tumor volume in a syngeneic EMT6 breast cancer tumor model. The anti-PD-1 antibody was a rat anti-PD-1 (clone RMP1-14)-IgG2a antibody. The statistical test used was two-way ANOVA.

As shown in FIG. 37, treatment of animals with antibody 28G11 either alone or in combination with anti-PD-1 resulted in a statistically significant reduction in tumor growth relative to isotype control antibody or anti-PD-1 alone. Similarly, treatment of animals with antibody 22F9 (FIG. 38) and 20E6 (FIG. 39), either alone or in combination with anti-PD-1, resulted in a statistically significant reduction in tumor growth relative to isotype control antibody or anti-PD-1 alone. These data demonstrate that 28G11, 22F9 and 20E6 are all active in combination with anti-PD-1 antibody in the EMT6 mouse model.

Example 27: Efficacy of Anti-LAP Antibodies in 4T1 Breast Cancer Tumor Metastasis Model This Example describes the efficacy of anti-LAP antibodies as monotherapy in a model of tumor metastasis, i.e., the 4T1 breast cancer tumor metastasis model.

Briefly, 1×10$^5$ 4 T1 breast cancer cells were implanted into the mammary fat pad of 6-8 week-old Balb/c mice. One day after implantation, animals were randomized to groups of 7 animals each. Animals were dosed with mouse IgG1 isotype control antibody, mouse-IgG2a control antibody, anti-TGFβ clone 1D11-IgG1, and anti-LAP antibodies 28G11 and 16B4. All animals were dosed intraperitoneally at 10 mg/kg on days 0, 3, 6, 9, and 12. On day 29 post dosing, animals were sacrificed and metastatic lung tumor nodules were counted. Data is graphed as mean lung nodule count ±SEM.

Figure 40:
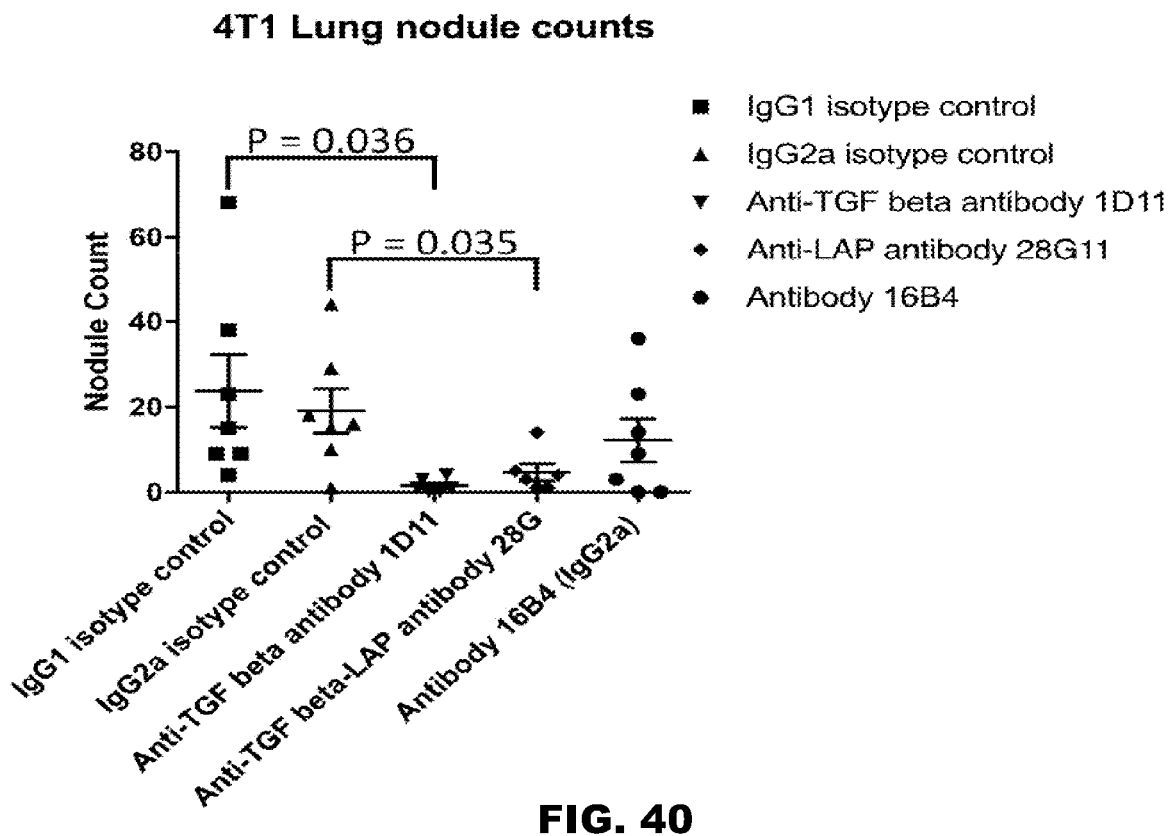
FIG. 40 is a graph that shows the effects of anti-LAP antibodies 28G11_IgG2a and 16B4_IgG2a, and the anti-TGFβ antibody 1D11_IgG1, as monotherapy on lung nodule counts in the 4T1 breast cancer tumor metastasis model ($p<0.05$, unpaired T test following removal of outliers).

As shown in FIG. 40, treatment of animals with anti-TGFβ antibodies 1D11 and 28G11, but not 16B4, resulted in a statistically significant reduction of metastatic lung nodules relative to isotype control antibody treated animals (p<0.05, unpaired T test following removal of outliers). These data demonstrate that the two anti-LAP antibodies 28G11 and 16B4 have different functional effects in a mouse model of tumor metastasis. The finding that 28G11 has comparable efficacy to the anti-TGFβ antibody 1D11 is consistent with the effects of 28G11 being due to effects on the TGFβ pathway.

Example 28: Efficacy of Anti-LAP Antibodies in the CT26 Syngeneic Model in Combination with Radiation This Example describes the efficacy of anti-LAP antibodies in combination with radiation in a syngeneic CT26 tumor model.

Briefly, 1×10$^6$ CT26 colorectal cancer cells were implanted into 6-8 week-old Balb/c mice. Eight days after implantation, animals were randomized into 6 groups of 16 animals each when mean tumor volume was 300 mm$^2$ (day 0). Starting on day 0, animals were dosed with mouse IgG2a isotype control antibody (Group 1), anti-LAP antibody 28G11-IgG2a (Group 2), 12 Gy radiotherapy and mouse IgG2a isotype control antibody (Group 3), 20 Gy radiotherapy and mouse IgG2a isotype control antibody (Group 4), 12 Gy radiotherapy and anti-LAP antibody 28G11-IgG2a (Group 5), or 20 Gy radiotherapy and anti-LAP antibody 28G11-IgG2a (Group 6). All antibodies were dosed intraperitoneally at 10 mg/kg. Groups 1 and 2 received a total of 3 doses of antibody on days 0, 3, and 6 and those animals were sacrificed at day 7 due to large tumor burden. Groups 3-6 received a total of 5 doses of antibody on days 0, 3, 6, 9, and 12. Three random animals from Groups 3-6 were also sacrificed on day 7 and the remaining animals were followed to day 19. In all cases where animals received radiation therapy, radiation was dosed only once on day 0. Survival was assessed daily and tumor volumes were measured 3 times per week by caliper using the formula V=W2×L/2. Data is presented as mean tumor volume+/−SEM of surviving animals.

Figure 41A:
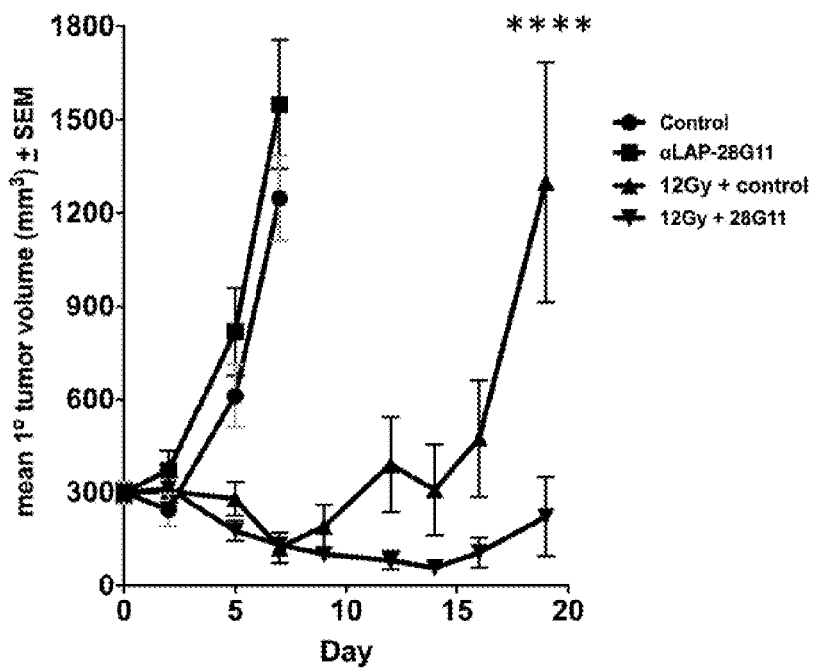
FIGS. 41A and 41B are graphs that show the effects of anti-LAP antibody 28G11_IgG2a in combination with 12 Gy (FIG. 41A) and 20 Gy (FIG. 41B) radiation on tumor volume in the syngeneic CT26 tumor model. The statistical test used was 2-way ANOVA. **$P<0.0001$, *$P=0.0004$.
Figure 41B:
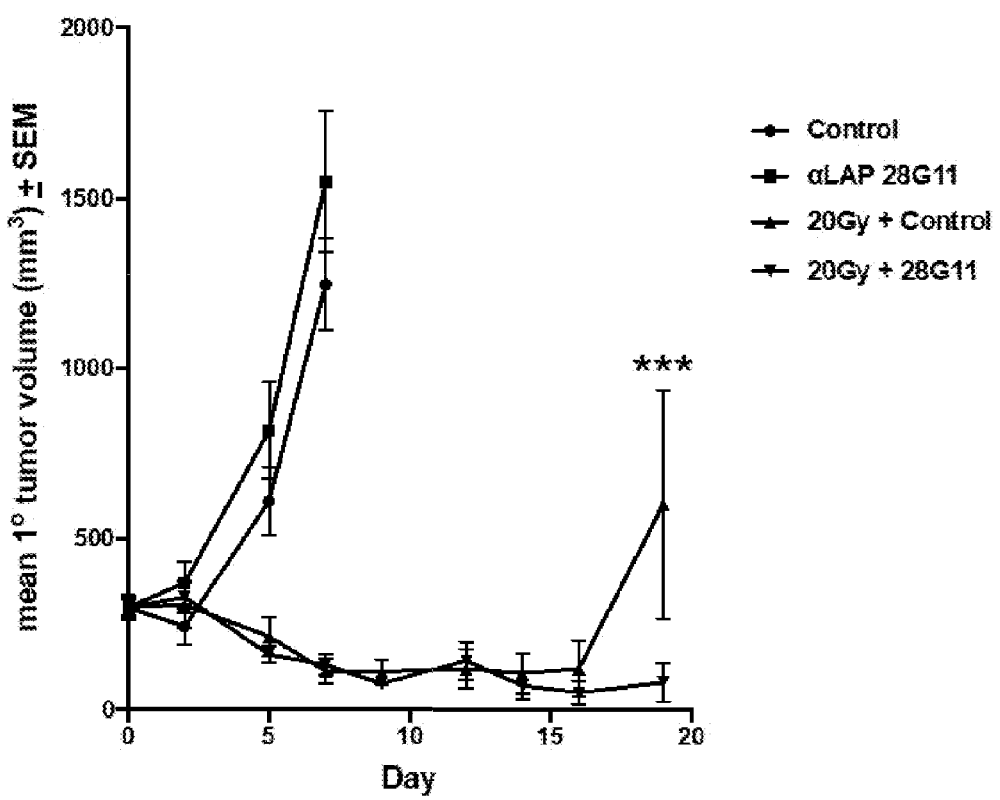

As shown in FIGS. 41A and 41B, treatment of animals with 12 or 20 Gy radiation alone resulted in a delay in tumor growth. Co-administration of 28G11 at 12 Gy radiation dose resulted in a statistically significant reduction in tumor growth relative to radiation treatment alone (**P<0.0001, *P=0.0004, 2-way ANOVA). Co-administration of 28G11 at 20 Gy radiation dose also resulted in a reduction relative to radiation treatment alone, and that effect also was statistically significant.

Example 29: Effects of Anti-LAP Antibodies on CD73 Expression

In this Example, the effect of anti-LAP antibodies on CD73 expression in the tumor microenvironment was examined. CD73 is a cell surface enzyme that processes adenosine monophosphate (AMP) to adenosine, a molecule with known immunosuppressive effects in the tumor microenvironment.

CT26 tumors were grown in Balb/c mice to 300 mm$^2$ (designated day 0), and antibody 28G11 was dosed at 10 mg/kg on days 0, 3, and 6. Mice were treated with targeted radiation (12 Gy or 20 Gy) at a single dose on day 0. CD73 expression on monocytic myeloid-derived suppressor cells (mMDSCs), M2 macrophages, and dendritic cells was examined by flow cytometry on day 7 after radiation. Groupings were as follows:
  Group 1: isotype control, no radiation (n=5)
  Group 2: 28G11, no radiation (n=5)
  Group 3: isotype control, 12 Gy radiation (N=3)
  Group 4: isotype control, 20 Gy radiation (N=3)
  Group 5: 28G11, 12 Gy radiation (N=2)
  Group 6: 28G11, 20 Gy radiation (N=3)

Figure 42A:
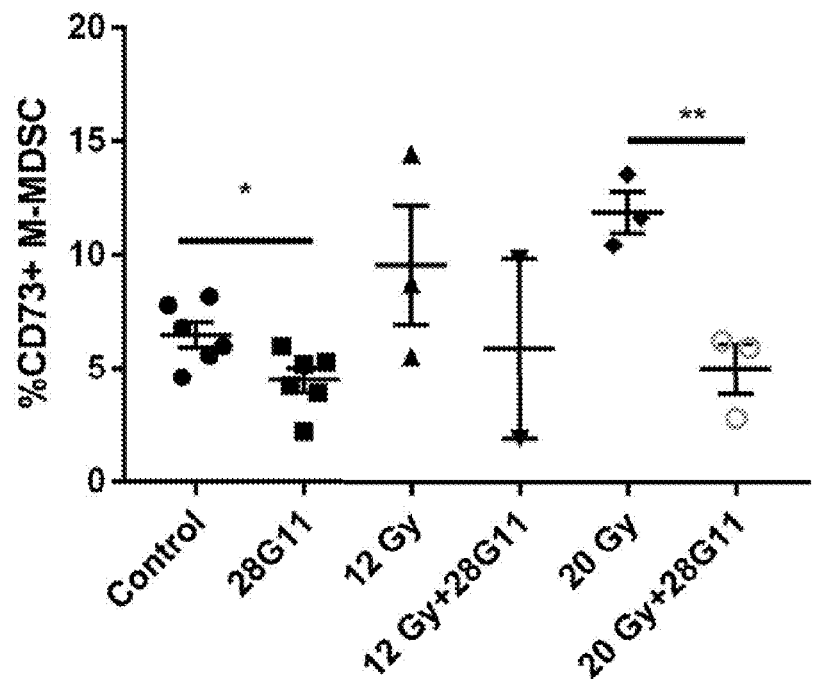
FIGS. 42A-42C are graphs that show the effects of anti-LAP antibody 28G11_IgG2a on CD73 expression in M-MDSCs (FIG. 42A), M2 macrophages (FIG. 42B), and dendritic cells (FIG. 42C), with or without 12 Gy or 20 Gy radiation.
Figure 42B:
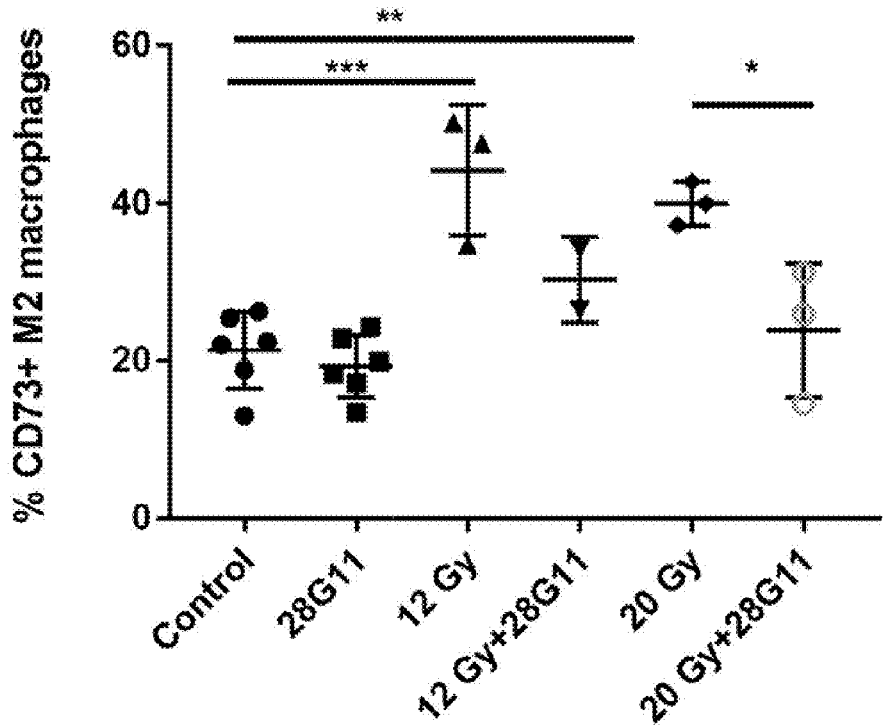
Figure 42C:
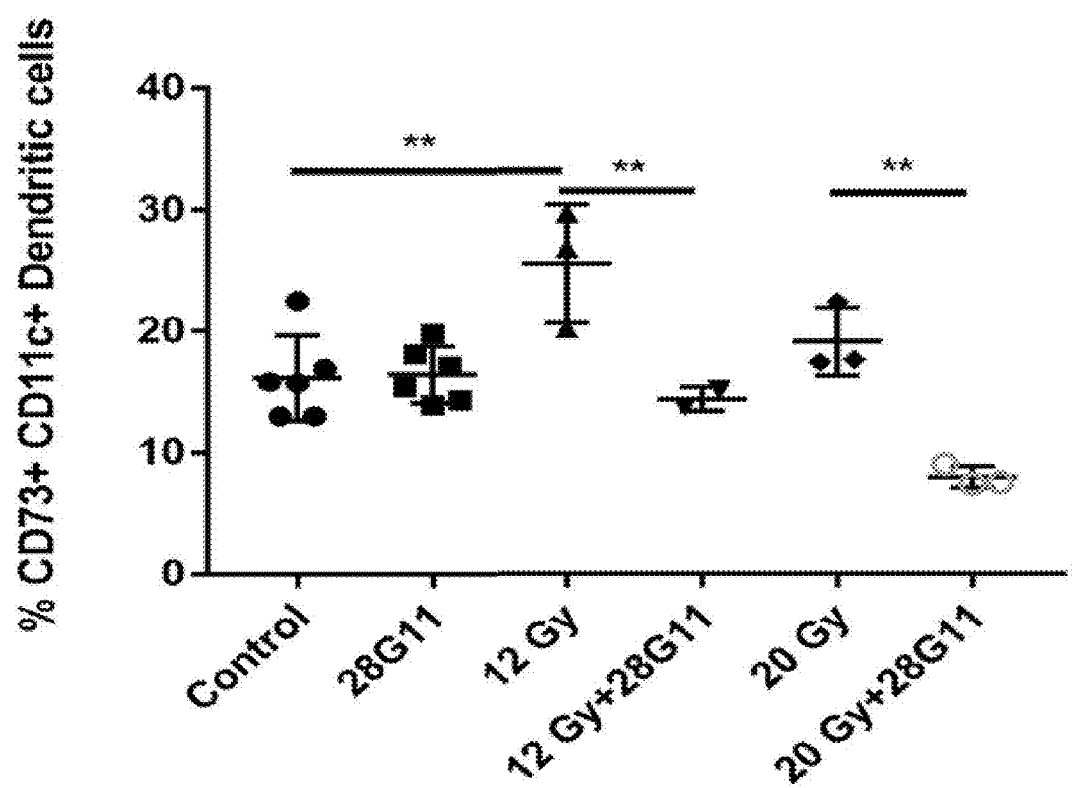
Figure 43A:
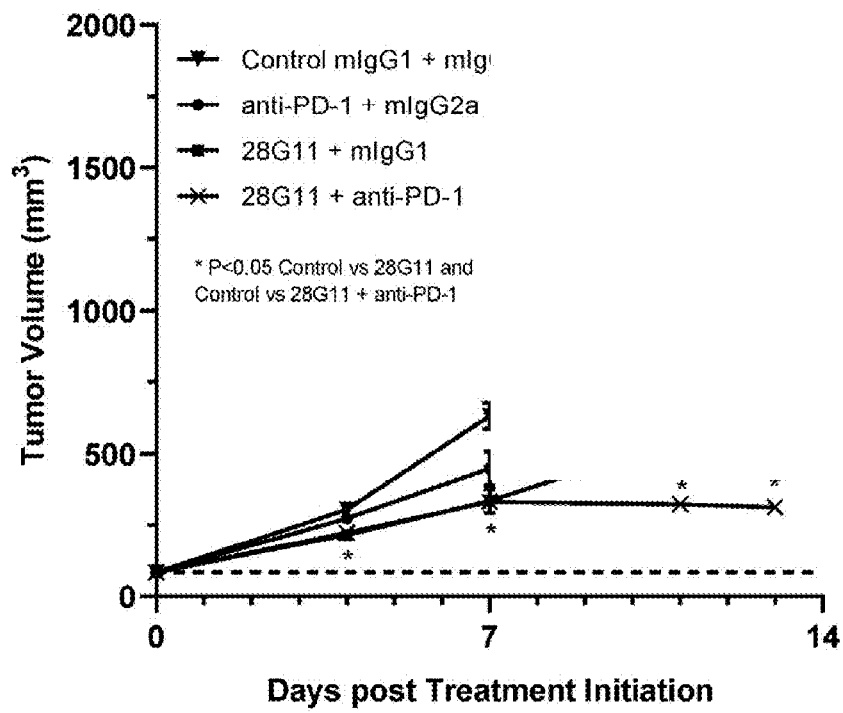
FIGS. 43A-43H are a series of graphs that show effects of anti-LAP antibodies 28G11-mIgG2a and 20E6-mIgG2a alone and in combination with anti-PD-1 antibody on tumor volume in a syngeneic EMT6 mouse breast cancer tumor model. The data shown in the figures are.
Figure 43B:
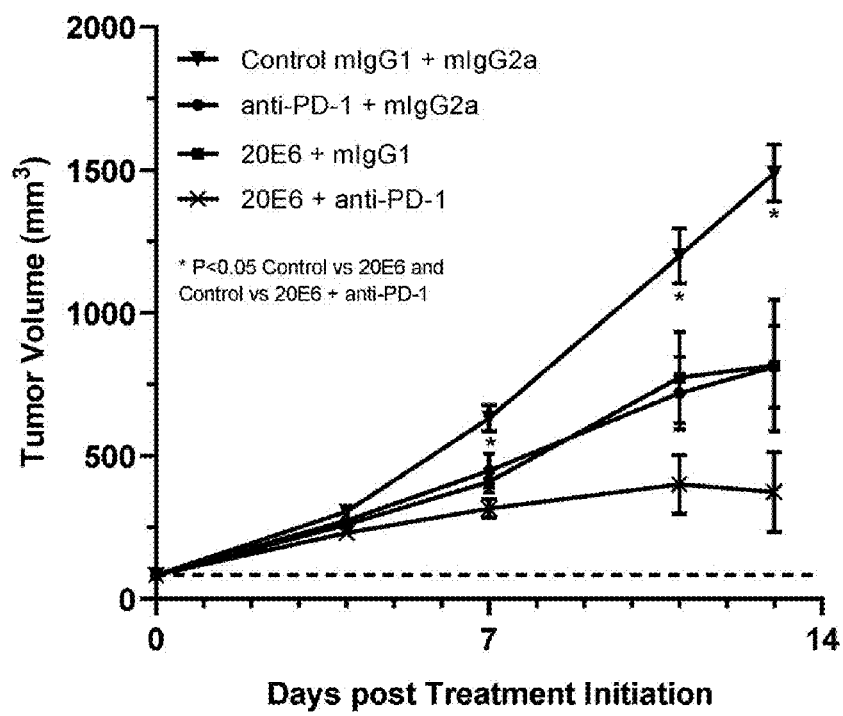
Figure 43C:
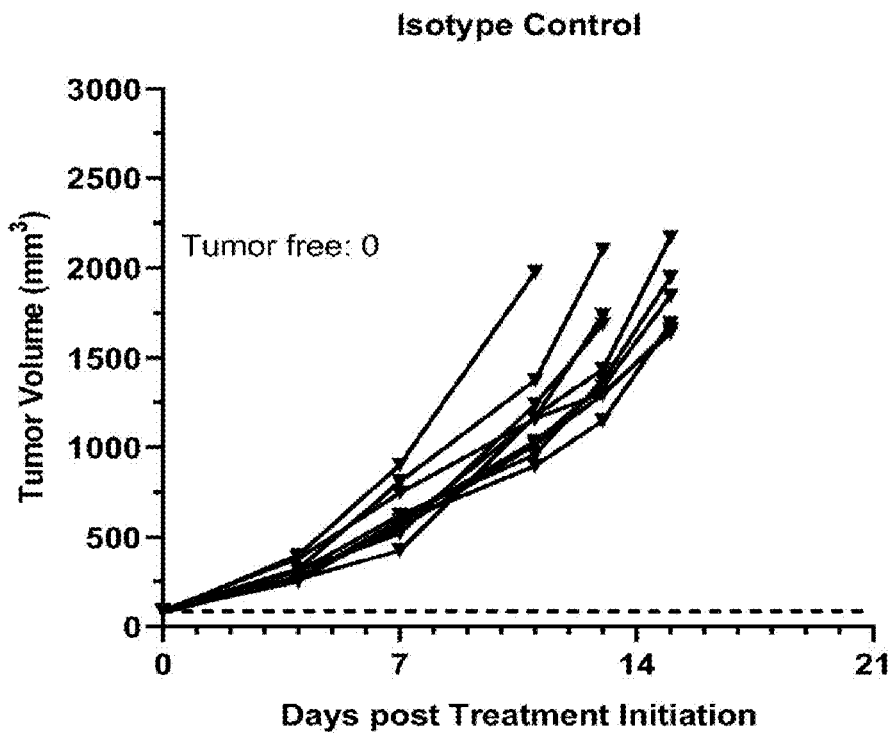
Figure 43D:
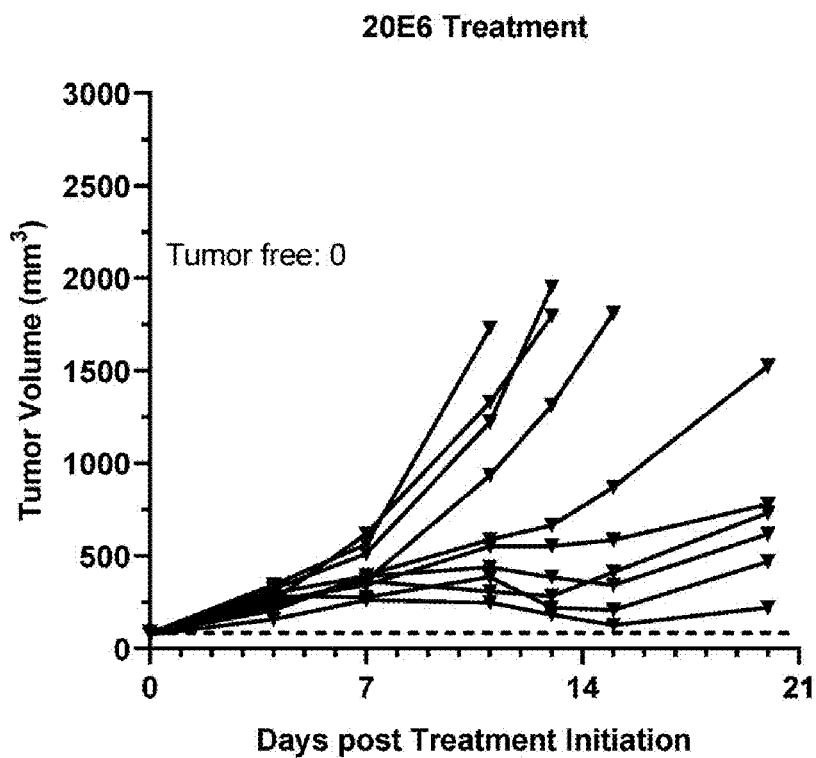
Figure 43E:
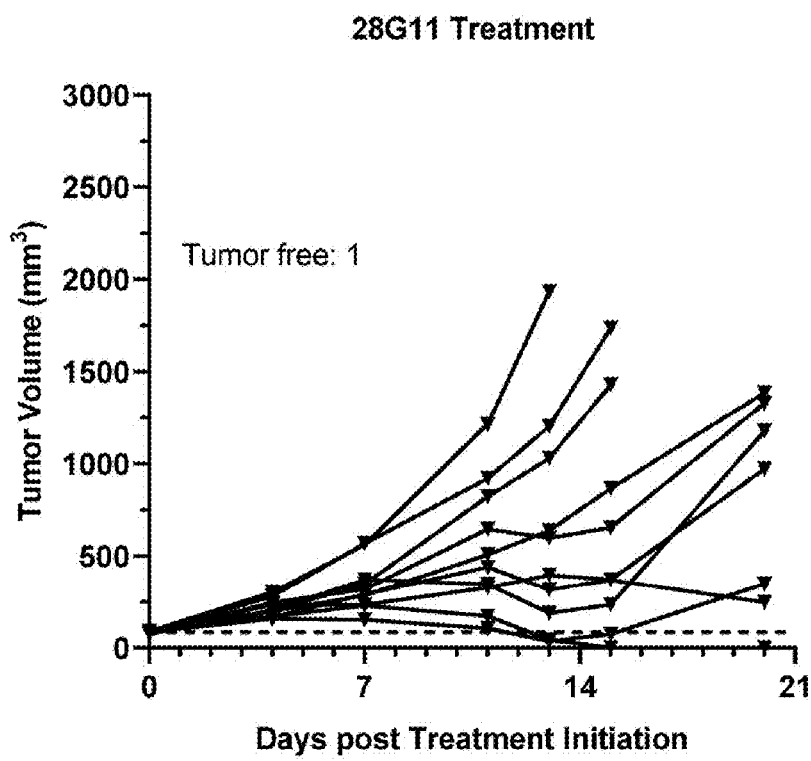
Figure 43F:
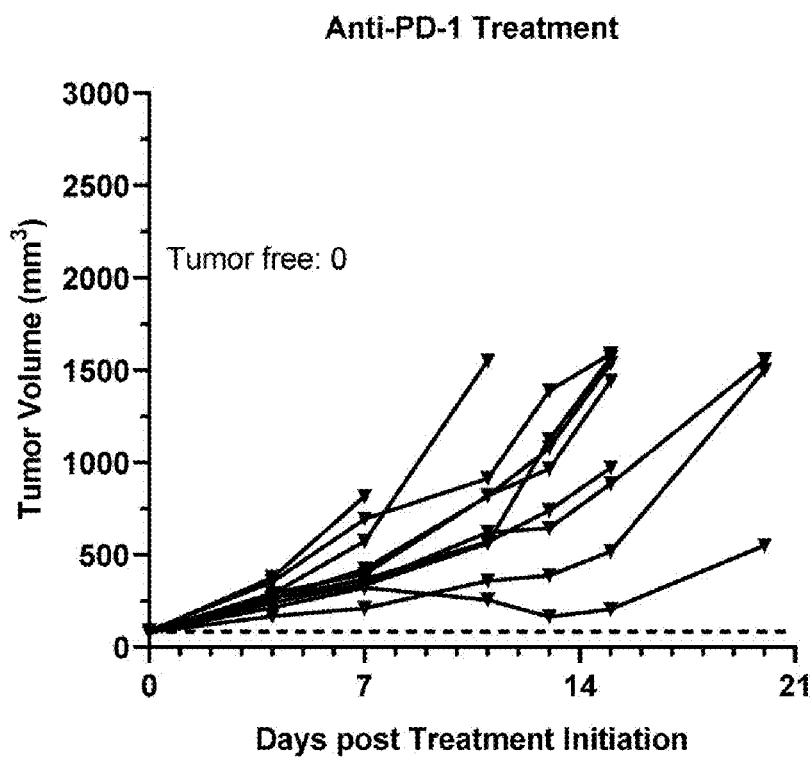
Figure 43G:
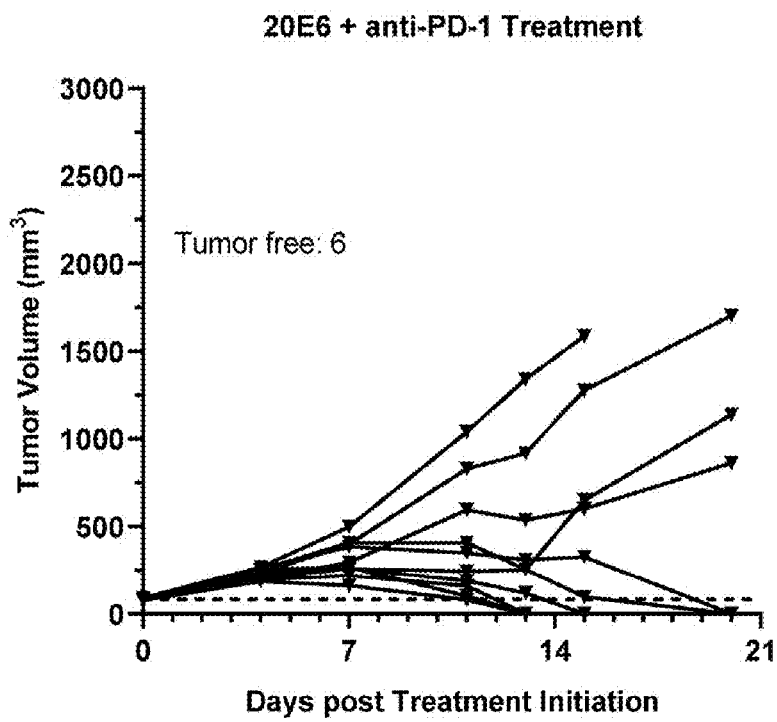
Figure 43H:
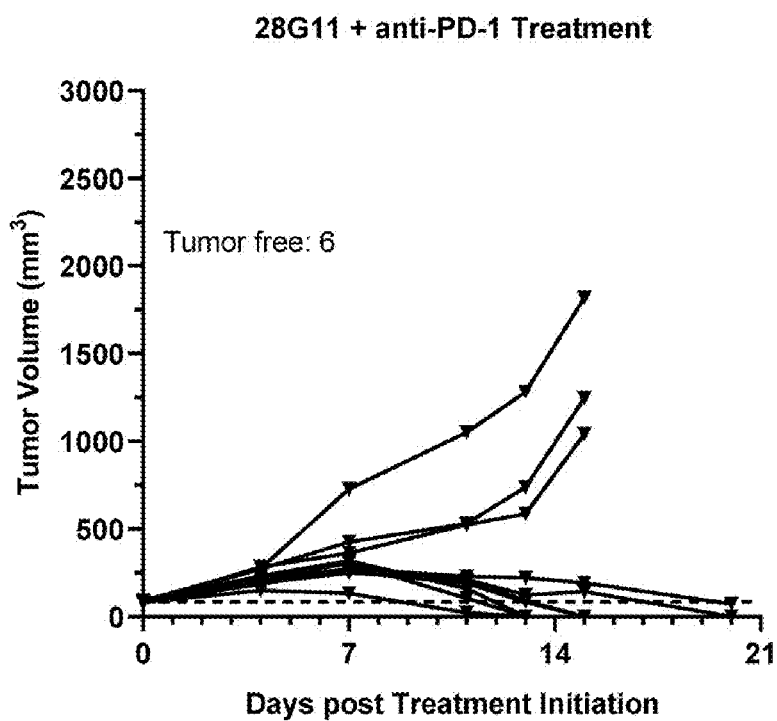

As shown in FIGS. 42A-42C, radiation at both doses (12 Gy and 20 Gy) induced CD73 expression on mMDSCs, M2 macrophages, and dendritic cells. This increase in CD73 expression was attenuated by treatment with 28G11. Moreover, 28G11 reduced CD73 expression to below baseline levels in mMDSCs of mice which were not treated with radiation (FIG. 42A). These results demonstrate that anti-LAP antibody treatment reduced both the number and immunosuppressive ability of inhibitory cell populations, as reflected in the reduced proportion of CD73 positive mMD-SCs, M2 macrophages, and dendritic cells.

Example 30: Biodistribution of Anti-LAP Antibodies

In this Example, the biodistribution of anti-LAP antibodies in mice harboring tumors was examined.

Briefly, 3 Balb/C mice were implanted with $1\times10^6$ CT26 cells and tumors were allowed to grow until they reached a mean tumor volume of 150 mm$^3$. Animals were dosed with a single injection of 28G11_hIgG1 at 10 mg/kg. Three days post-injection, animals were sacrificed and blood was collected. Mice were perfused with PBS and heart, liver, kidney, bone, colon, lung, and spleen tissue were harvested. Tissue was placed in 10% Neutral buffered formalin, stored overnight at 4° C., and transferred to 80% ethanol. Tissue samples were sectioned and stained with anti-human IgG1 to identify the location of 28G11 within the animal. There was minimal staining observed in most tissues, with the strongest staining observed in tumor tissue.

Example 31. Efficacy of 20E6 and 28G11 Alone and in Combination with Anti-PD-1 in Animal Models of Cancer This Example describes the testing the efficacy of 20E6 and 28G11 antibodies alone and in combination with anti-PD-1 in the EMT6 mouse breast cancer tumor model. The antibodies used are listed below:
Mouse x [LAP-TGFb1_H] mAb (28G11_VH_N56Q) mIgG2a/Kappa (CX): 28G11_mIgG2a
Mouse x [LAP-TGFb1_H] mAb (20E6_Q1E_N54Q) IgG2a/Kappa (CX): 20E6_mIgG2a
Mouse x [HEXON_Ad] mAb (TC31.27F11.C2) IgG2a/Kappa (CC): isotype control antibody Briefly, 6-8 weeks-old Balb/c mice were inoculated subcutaneously with $0.3\times10^6$ EMT6 mouse breast cancer cells. Animals were stratified into 6 treatment groups of 10 animals each when the tumors grew to an average size of ~85 mm$^3$, at which point treatment was initiated. All antibodies were administered intraperitoneally. Antibodies 20E6 and 28G11 were dosed at 10 mg/kg twice per week, while anti-PD1 was dosed at 5 mg/kg every 5 days. The vehicle-control group consisted of a murine IgG1 isotype control dosed at 5 mg/kg, and a murine IgG2a isotype control dosed at 10 mg/kg. Tumors were measured 2-3 times per week and tumor volume was calculated using the following formula: V=(tumor width) x (tumor length)/2. It was observed that treatment of subjects with antibody 20E6 and antibody 28G11 alone resulted in significant tumor growth inhibition compared to subjects treated with the isotype control antibody. Furthermore, the combination treatment of either antibody 20E6 or antibody 28G11 with anti-PD-1 antibody resulted in 6 complete responses where animals did not have any residual tumors. See FIGS. 43A-43H. All treatments were observed to be well tolerated and did not cause any bodyweight loss.

Example 32: Binding of Anti-LAP F(Ab') to Human LAP-TGFβ Isoforms 1, 2, and 3

To avoid the interference of avidity in the affinity measurement, this Example analyzed the binding kinetics of 20E6 F(ab') binding protein to human LAP-TGFβ. This Example describes the isoform specificity of humanized 20E6 F(ab') binding protein to bind to human LAP-TGFβ isoforms 1, 2, and 3 using surface plasmon resonance.

A Series S CM4 sensor chip (GE Healthcare, catalog BR100534) was immobilized with an anti-human Fc capture antibody following the kit protocol (GE Healthcare, catalog BR100839) on a Biacore T200 instrument with 1×HBS-EP+ (Teknova, catalog H8022). Kinetic binding interactions between human LAP-TGFβ isoforms 1, 2, and 3 and humanized 20E6 F(ab') were performed in 1×HBS-EP+ with 0.1 mg/mL BSA (Jackson Immunoresearch, catalog 001-000-162) at 25° C. Approximately 50-65 RU of human LAP-TGFβ-Fc isoforms were captured to the anti-human Fc surface followed by injection of 1:3 serially diluted humanized 20E6 F(ab') from 3000 nM to 1.37 nM and including 0 nM F(ab'). The binding data was double referenced by subtraction of signal from a reference (capture surface only) flow cell and the 0 nM F(ab') injection. Binding rate constants were determined by fitting the data with a 1:1 binding model (GE Healthcare Biacore T200 Evaluation software 2.0).

As shown in the figures and Table 32, the humanized 20E6 IgG1 antibody, when captured to the anti-human Fc capture sensor chip, exhibited a non-1:1 binding profile due to the bivalent nature of both the IgG1 and bivalent epitopes presented by the LAP-TGFβ1 molecule. See FIG. 44A. Also it was observed that monovalent humanized 20E6 F(ab') bound with nanomolar affinity to human LAP-TGFβ1 (FIG. 44B), but no appreciable signal increase was observed for human LAP-TGFβ2 (FIG. 44C) or LAP-TGFβ3 (FIG. 44D). These data demonstrate that the humanized 20E6 F(ab') specifically bound to human LAP-TGFβ1.

TABLE 32

Binding parameters for humanized 20E6 F(ab') binding to human TGFβ isoforms

| Isoform | $k_{on}$ ($\times10^6$ M$^{-1}$s$^{-1}$) | $k_{off}$ ($\times10^{-2}$ s$^{-1}$) | $K_D$ (nM) |
|---|---|---|---|
| LAP-TGFβ1 | 1.96 | 8.00 | 40.8 |
| LAP-TGFβ2 | — | — | — |
| LAP-TGFβ3 | — | — | — |

Example 33: Binding of Anti-LAP F(Ab') to Human, Cynomolgus Monkey, Rat, and Mouse LAP-TGFβ1

This Example describes the species specificity of humanized 20E6 F(ab') binding protein to bind to LAP-TGFβ1 from several species using surface plasmon resonance.

A Series S CM4 sensor chip (GE Healthcare, catalog BR100534) was immobilized with an anti-human Fc capture antibody following the kit protocol (GE Healthcare, catalog BR100839) on a Biacore T200 instrument with 1×HBS-EP+ (Teknova, catalog H8022). Kinetic binding interactions between human, cynomolgus monkey, rat, and mouse LAP-TGFβ1 and humanized 20E6 F(ab') were performed in 1×HBS-EP+ with 0.1 mg/mL BSA (Jackson Immunoresearch, catalog 001-000-162) at 25° C. Approximately 60-95 RU of human, cynomolgus monkey, rat, and mouse LAP-TGFβ-Fc were captured to the anti-human Fc surface followed by injection of 1:3 serially diluted humanized 20E6 F(ab') from 3000 nM to 1.37 nM and including 0 nM F(ab'). The binding data was double referenced by subtraction of signal from a reference (capture surface only) flow cell and the 0 nM F(ab') injection. Binding rate constants were determined by fitting the data with a 1:1 binding model (GE Healthcare Biacore T200 Evaluation software 2.0).

As shown in the figures and Table 33, humanized 20E6 F(ab') bound with nanomolar affinity to human LAP-TGFβ1 (FIG. 45A), cynomolgus monkey LAP-TGFβ1 (FIG. 45B), rat LAP-TGFβ1 (FIG. 45C), and mouse LAP-TGFβ1 (FIG. 45D).

TABLE 33

Binding parameters for humanized 20E6 F(ab') binding to LAP-TGFβ1 from multiple species

| Species | $k_{on}$ ($\times 10^6$ M$^{-1}$s$^{-1}$) | $k_{off}$ ($\times 10^{-2}$ s$^{-1}$) | $K_D$ (nM) |
|---|---|---|---|
| Human | 1.91 ± 0.53 | 9.39 ± 2.35 | 49.5 ± 1.4 |
| Cynomolgus | 1.58 ± 0.03 | 9.50 ± 0.12 | 60.3 ± 0.9 |
| Rat | 1.79 ± 0.42 | 10.6 ± 2.57 | 59.4 ± 0.7 |
| Mouse | 1.64 ± 0.04 | 7.90 ± 0.11 | 48.3 ± 0.9 |

Figure 46:
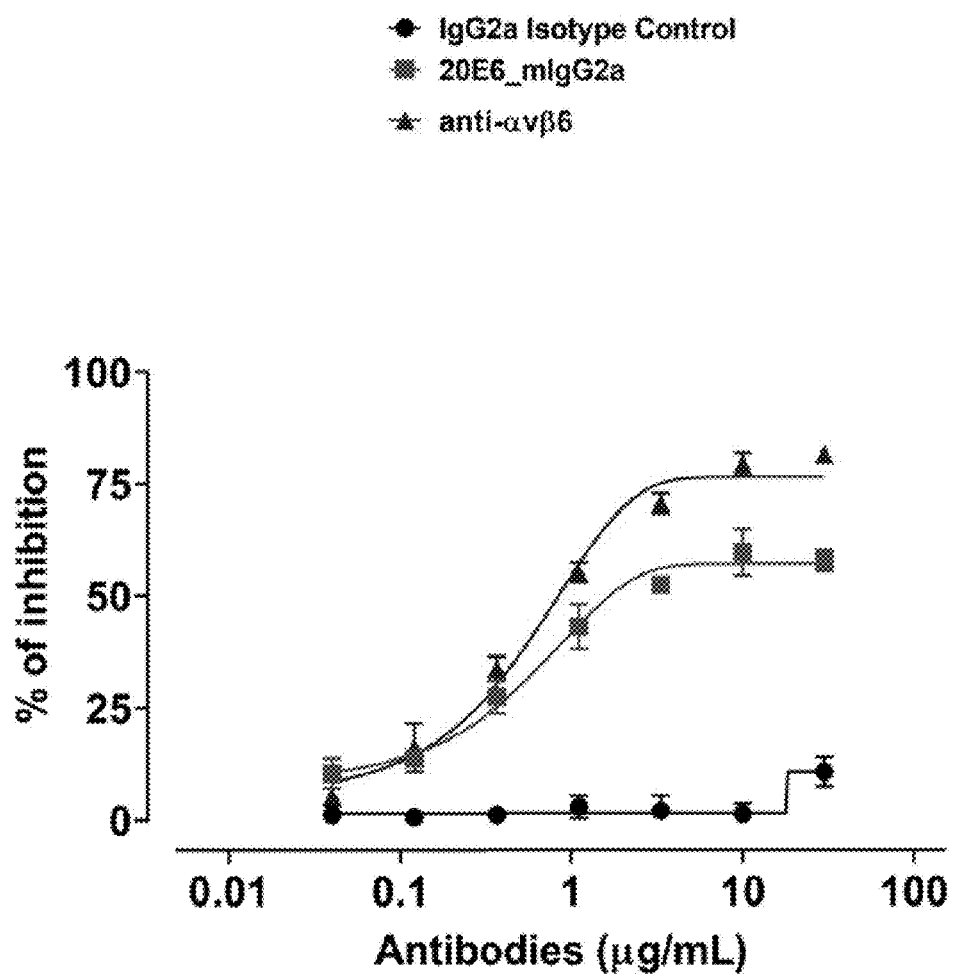
FIG. 46 is a graph showing inhibition of integrin (avb6) activation of LAP-TGFb1 using 20E6_mIgG2a antibody, isotype control antibody or anti-αVβ6 (10D5) antibody.

All values reported as average ± standard deviation from triplicate measurements Example 34: Inhibition of Integrin (Avb6) Activation of LAP-TGFb1 with This Examples examined the inhibition of integrin (avb6) activation of LAP-TGFb1 using a LAP antibody 20E6_mIgG2a. Recombinant human aVβ6 integrin (R&D Systems; cat. #3817-AV) was coated in a 96 well flat bottom tissue culture plate at 2 ug/ml in serum free RPMI for 2 hours at 37C. Wells were treated with a 3-fold serial dilution (high of 30 ug/ml) of 20E6_mIgG2a, isotype control or anti-aVβ6 (10D5; commercially available from Millipore Sigma). Immediately after treatment P3U1 cells expressing human LAP-TGFβ1 (5×10$^4$/well) were added to the plate followed by HEK-Blue TGFβ (2×10$^4$/well) cells. (HEK-Blue TGFβ cells contain a SMAD binding element responsive SEAP reporter resulting in secretion of SEAP when bioactive TGFβ binds to receptor.) The plates were then incubated overnight at 37° C. and the following day 125 μL of supernatant was taken and plated in a 96-well v-bottom plate and spun again at 500G for 5 minutes to remove cells. Secreted Alkaline Phosphatase (SEAP) levels in the supernatant (25 μL) were detected utilizing the Great EscAPe Chemiluminescence Kit 2.0 (Takara Bio; cat. #631736) according to the manufacturer protocol. Data show that the 20E6_mIgG2a effectively inhibited integrin avb6 activation of LAP-TGFb1 as compared to the isotype control antibody and the anti-aVβ6 (10D5) antibody (FIG. 46).

TABLE 34

Summary table of sequences

| SEQ ID | Description | Sequence |
|---|---|---|
| | | Protein sequences |
| 1 | human LAP-TGFβ1 | LSTCKTIDMELVKRKRIEAIRGQILSKLRLASPPSQGEVPPGP LPEAVLALYNSTRDRVAGESAEPEPEPEADYYAKEVTRVLMVE THNEIYDKFKQSTHSIYMFFNTSELREAVPEPVLLSRAELRLL RLKLKVEQHVELYQKYSNNSWRYLSNRLLAPSDSPEWLSFDVT GVVRQWLSRGGEIEGFRLSAHCSCDSRDNTLQVDINGFTGRR GDLATIHGMNRPFLLLMATPLERAQHLQSSRHRRALDTNYCFS STEKNCCVRQLYIDFRKDLGWKWIHEPKGYHANFCLGPCPYIW SLDTQYSKVLALYNQHNPGASAAPCCVPQALEPLPIVYYVGRK PKVEQLSNMIVRSCKCS |
| 2 | LAP region of human LAP-TGFβ1 | LSTCKTIDMELVKRKRIEAIRGQILSKLRLASPPSQGEVPPGP LPEAVLALYNSTRDRVAGESAEPEPEPEADYYAKEVTRVLMVE THNEIYDKFKQSTHSIYMFFNTSELREAVPEPVLLSRAELRLL RLKLKVEQHVELYQKYSNNSWRYLSNRLLAPSDSPEWLSFDVT GVVRQWLSRGGEIEGFRLSAHCSCDSRDNTLQVDINGFTTGRR GDLATIHGMNRPFLLLMATPLERAQHLQSSRHR |
| 3 | human LAP-TGFβ2 | LSTCSTLDMDQFMRKRIEAIRGQILSKLKLTSPPEDYPEPEEV PPEVISIYNSTRDLLQEKASRRAAACERERSDEEYYAKEVYKI DMPPFFPSENAIPPTFYRPYFRIVRFDVSAMEKNASNLVKAEF RVFRLQNPKARVPEQRIELYQILKSKDLTSPTQRYIDSKVVKT RAEGEWLSFDVTDAVHEWLHHKDRNLGFKISLHCPCCTFVPSN NYIIPNKSEELEARFAGIDGTSTYTSGDQKTIKSTRKKNSGKT PHLLLMLLPSYRLESQQTNRRKKRALDAAYCFRNVQDNCCLRP LYIDFKRDLGWKWIHEPKGYNANFCAGACPYLWSSDTQHSRVL SLYNTINPEASASPCCVSQDLEPLTILYYIGKTPKIEQLSNMI VKSCKCS |
| 4 | LAP region of human LAP-TGFβ2 | LSTCSTLDMDQFMRKRIEAIRGQILSKLKLTSPPEDYPEPEEV PPEVISIYNSTRDLLQEKASRRAAACERERSDEEYYAKEVYKI DMPPFFPSENAIPPTFYRPYFRIVRFDVSAMEKNASNLVKAEF RVFRLQNPKARVPEQRIELYQILKSKDLTSPTQRYIDSKVVKT RAEGEWLSFDVTDAVHEWLHHKDRNLGFKISLHCPCCTFVPSN NYIIPNKSEELEARFAGIDGTSTYTSGDQKTIKSTRK KNSGKTPHLLLMLLPSYRLESQQTNRRKKR |
| 5 | human LAP-TGFβ3 | LSTCTTLDFGHIKKKRVEAIRGQILSKLRLTSPPEPTVMTHVP YQVLALYNSTRELLEEMHGEREEGCTQENTESEYYAKEIHKFD MIQGLAEHNELAVCPKGITSKVFRFNVSSVEKNRTNLFRAEFR VLRVPNPSSKRNEQRIELFQILRPDEHIAKQRYIGGKNLPTRG TAEWLSFDVTDTVREWLLRRESNLGLEISIHCPCHTFQPNGDI LENIHEVMEIKFKGVDNEDDHGRGDLGRLKKQKDHHNPHLILM MIPPHRLDNPGQGGQRKKRALDTNYCFRNLEENCCVRPLYIDF RQDLGWKWVHEPKGYYANFCSGPCPYLRSADTTHSTVLGLYNT LNPEASASPCCVPQDLEPLTILYYVGRTPKVEQLSNMVVKSCK CS |

TABLE 34-continued

Summary table of sequences

| SEQ ID | Description | Sequence |
|---|---|---|
| 6 | LAP region of human LAP-TGFβ3 | LSTCTTLDFGHIKKKRVEAIRGQILSKLRLTSPPEPTVMTHVPYQVLALYNSTRELLEEMHGEREEGCTQENTESEYYAKEIHKFDMIQGLAEHNELAVCPKGITSKVFRFNVSSVEKNRTNLFRAEFRVLRVPNPSSKRNEQRIELFQILRPDEHIAKQRYIGGKNLPTRGTAEWLSFDVTDTVREWLLRRESNLGLEISIHCPCHTFQPNGDILENIHEVMEIKFKGVDNEDDHGRGDLGRLKKQKDHHNPHLILMMIPPHRLDNPGQGGQRKKR |
| 7 | mouse LAP-TGFβ1 | LSTCKTIDMELVKRKRIEAIRGQILSKLRLASPPSQGEVPPGPLPEAVLALYNSTRDRVAGESADPEPEPEADYYAKEVTRVLMVDRNNAIYEKTKDISHSIYMFFNTSDIREAVPEPPLLSRAELRLQRLKSSVEQHVELYQKYSNNSWRYLGNRLLTPTDTPEWLSFDVTGVVRQWLNQGDGIQGFRFSAHCSCDSKDNKLHVEINGISPKRRGDLGTIHDMNRPFLLLMATPLERAQHLSSRHRRALDTNYCFSSTEKNCCVRQLYIDFRKDLGWKWIHEPKGYHANFCLGPCPYIWSLDTQYSKVLALYNQHNPGASASPCCVPQALEPLPIVYYVGRKPKVEQLSNMIVRSCKCS |
| 8 | LAP region of mouse LAP-TGFβ1 | LSTCKTIDMELVKRKRIEAIRGQILSKLRLASPPSQGEVPPGPLPEAVLALYNSTRDRVAGESADPEPEPEADYYAKEVTRVLMVDRNNAIYEKTKDISHSIYMFFNTSDIREAVPEPPLLSRAELRLQRLKSSVEQHVELYQKYSNSWRYLGNRLLTPTDTPEWLSFDVTGVVRQWLNQGDGIQGFRFSAHCSCDSKDNKLHVEINGISPKRRGDLGTIHDMNRPFLLLMATPLERAQHLSSRHRR |
| 9 | mouse LAP-TGFβ2 | LSTCSTLDMDQFMRKRIEAIRGQILSKLKLTSPPEDYPEPDEVPPEVISIYNSTRDLLQEKASRRAAACERERSDEEYYAKEVYKIDMPSHLPSENAIPPTFYRPYFRIVRFDVSTMEKNASNLVKAEFRVFRLQNPKARVAEQRIELYQILKSKDLTSPTQRYIDSKVVKTRAEGEWLSFDVTDAVQEWLHHKDRNLGFKISLHCPCCTFVPSNNYIIPNKSEELEARFAGIDGTSTYASGDQKTIKSTRKKTSGKTPHLLLMLLPSYRLESQQSSRRKKRALDAAYCFRNVQDNCCLRPLYIDFKRDLGWKWIHEPKGYNANFCAGACPYLWSSDTQHTKVLSLYNTINPEASASPCCVSQDLEPLTILYYIGNTPKIEQLSNMIVKSCKCS |
| 10 | LAP region of mouse LAP-TGFβ2 | LSTCSTLDMDQFMRKRIEAIRGQILSKLKLTSPPEDYPEPDEVPPEVISIYNSTRDLLQEKASRRAAACERERSDEEYYAKEVYKIDMPSHLPSENAIPPTFYRPYFRIVRFDVSTMEKNASNLVKAEFRVFRLQNPKARVAEQRIELYQILKSKDLTSPTQRYIDSKVVKTRAEGEWLSFDVTDAVQEWLHHKDRNLGFKISLHCPCCTFVPSNNYIIPNKSEELEARFAGIDGTSTYASGDQKTIKSTRKKTSGKTPHLLLMLLPSYRLESQQSSRRKKR |
| 11 | mouse LAP-TGFβ3 | LSTCTTLDFGHIKKKRVEAIRGQILSKLRLTSPPEPSVMTHVPYQVLALYNSTRELLEEMHGEREEGCTQETSESEYYAKEIHKFDMIQGLAEHNELAVCPKGITSKVFRFNVSSVEKNGTNLFRAEFRVLRVPNPSSKRTEQRIELFQILRPDEHIAKQRYIGGKNLPTRGTAEWLSFDVTDTVREWLLRRESNLGLEISIHCPCHTFQPNGDILENVHEVMEIKFKGVDNEDDHGRGDLGRLKKQKDHHNPHLILMMIPPHRLDSPGQGSQRKKRALDTNYCFRNLEENCCVRPLYIDFRQDLGWKWVHEPKGYYANFCSGPCPYLRSADTTHSTVLGLYNTLNPEASASPCCVPQDLEPLTILYYVGRTPKVEQLSNMVVKSCKCS |
| 12 | LAP region of mouse LAP-TGFβ3 | LSTCTTLDFGHIKKKRVEAIRGQILSKLRLTSPPEPSVMTHVPYQVLALYNSTRELLEEMHGEREEGCTQETSESEYYAKEIHKFDMIQGLAEHNELAVCPKGITSKVFRFNVSSVEKNGTNLFRAEFRVLRVPNPSSKRTEQRIELFQILRPDEHIAKQRYIGGKNLPTRGTAEWLSFDVTDTVREWLLRRESNLGLEISIHCPCHTFQPNGDILENVHEVMEIKFKGVDNEDDHGRGDLGRLKKQKDHHNPHLILMMIPPHRLDSPGQGSQRKKR |
| 13 | human LAP-TGFβ1 "open conformation" | LSTCKTIDMELVKRKRIEAIRGQILSKLRLASPPSQGEVPPGPLPEAVLALYNSTRDRVAGESAEPEPEPEADTYAKEVTRVLMVETHNEIYDKFKQSTHSIYMFFNTSELREAVPEPVLLSRAELRLLRLKLKVEQHVELYQKYSNNSWRYLSNRLLAPSDSPEWLSFDVTGVVRQWLSRGGEIEGFRLSAHCSCDSRDNTLQVDINGFTTGRRGDLATIHGMNRPFLLLMATPLERAQHLQSSRHRALDTNYCFSSTEKNCCVRQLYIDFRKDLGWKWIHEPKGYHANFCLGPCPYIWSLDTQYSKVLALYNQHNPGASAAPCCVPQALEPLPIVYYVGRKPKVEQLSNMIVRSCKCS |
| 14 | human LAP-TGFβ1 "closed conformation" | LSTCKTIDMELVKRKRIEAIRGQILSCLRLASPPSQGEVPPGPLPEAVLALYNSTRDRVAGESAEPEPEPEADYCAKEVTRVLMVETHNEIYDKFKQSTHSIYMFFNTSELREAVPEPVLLSRAELRLLRLKLKVEQHVELYQKYSNNSWRYLSNRLLAPSDSPEWLSFDVTGVVRQWLSRGGEIEGFRLSAHCSCDSRDNTLQVDINGFTTGRRGDLATIHGMNRPFLLLMATPLERAQHLQSSRHRALDTNYCFSSTEKNCCVRQLYIDFRKDLGWKWIHEPKGYHANFCLGPCPYIWSLDTQYSKVLALYNQHNPGASAAPCCVPQALEPLPIVYYVGRKPKVEQLSNMIVRSCKCS |

TABLE 34-continued

Summary table of sequences

| SEQ ID | Description | Sequence |
|---|---|---|
| 15 | human free TGFβ1 (mature TGFβ1 without LAP) | ALDTNYCFSSTEKNCCVRQLYIDFRKDLGWKWIHEPKGYHANF CLGPCPYIWSLDTQYSKVLALYNQHNPGASAAPCCVPQALEPL PIVYYVGRKPKVEQLSNMIVRSCKCS |
| 257 | Human LAP-TGFβ1 in FIG. 34 | LSTCKTIDMELVKRKRIEAIRGQILSKLRLASPPSQGEVPPGP LPEAVLALYNSTRDRVAGESAEPEPEPEADYYAKEVTRVLMVE THNEIYDKFKQSTHSIYMFFNTSELREAVPEPVLLSRAELRLL RLKLKVEQHVELYQKYSNNSWRYLSNRLLAPSDSPEWLSFDVT GVVRQWLSRGGEIEGFRLSAHCSCDSRDNTLQVDINAGFTTGR RGDLATIHGMNRPFLLLMATPLERAQHLQSSRHRRALDTNYCF SSTEKNCCVRQLYIDFRKDLGWKWIHEPKGYHANFCLGPCPYI WSLDTQYSKVLALYNQHNPGASAAPCCVPQALEPLPIVYYVGR KPKVEQLSNMIVRSCKCS |

Binding protein, antibody and antigen binding fragments

| SEQ ID | Description | Sequence |
|---|---|---|
| 16 | 28G11(hyb)VHCDR1 | DYYMS |
| 17 | 28G11(hyb)VHCDR2 (extended definition of VHCDR2 used for humanization) | FIRNKPNGYTTE |
| 18 | 28G11(hyb)VHCDR3 | YTGGGYFDY |
| 19 | 28G11(hyb)VLCDR1 | RASQDISNYLN |
| 20 | 28G11(hyb)VLCDR2 | YTSRLHS |
| 21 | 28G11(hyb)VLCDR3 | QQGDTLPWT |
| 22 | 28G11(hyb) VH | EVKLVESGGGLVQPGGSLSLSCAASGFTFTDYYMSWVRQPPGK ALEWLGFIRNKPNGYTTEYSASVKGRFTISRDNSQSILYLQMN VLRAEDSATYYCARYTGGGYFDYWGQGTTLTVSS |
| 23 | 28G11(hyb) VL | DIQMTQTTSSLSASLGDRLTISCRASQDISNYLNWYQQKPDGT VKLLIYYTSRLHSGVPSRFSGSGSGTDYSLTISNLEQADIATY FCQQGDTLPWTFGGGTKLEIK |
| 24 | 28G11(hyb) heavy chain | EVKLVESGGGLVQPGGSLSLSCAASGFTFTDYYMSWVRQPPGK ALEWLGFIRNKPNGYTTEYSASVKGRFTISRDNSQSILYLQMN VLRAEDSATYYCARYTGGGYFDYWGQGTTLTVSSAKTTPPSVY PLAPGCGDTTGSSVTLGCLVKGYFPESVTVTWNSGSLSSSVHT FPALLQSGLYTMSSSVTVPSSTWPSQTVTCSVAHPASSTTVDK KLEPSGPISTINPCPPCKECHKCPAPNLEGGPSVFIFPPNIKD VLMISLTPKVTCVVVDVSEDDPDVQISWFVNNVEVHTAQTQTH REDYNSTIRVVSTLPIQHQDWMSGKEFKCKVNNKDLPSPIERT ISKIKGLVRAPQVYILPPPAEQLSRKDVSLTCLVVGFNPGDIS VEWTSNGHTEENYKDTAPVLDSDGSYFIYSKLNMKTSKWEKTD SFSCNVRHEGLKNYYLKKTISRSPGK |
| 25 | 28G11(hyb) light chain | DIQMTQTTSSLSASLGDRLTISCRASQDISNYLNWYQQKPDGT VKLLIYYTSRLHSGVPSRFSGSGSGTDYSLTISNLEQADIATY FCQQGDTLPWTFGGGTKLEIKRADAAPTVSIFPPSSEQLTSGG ASVVCFLNNFYPKDINVKWKIDGSERQNGVLNSWTDQDSKDST YSMSSTLTLTKDEYERHNSYTCEATHKTSTSPIVKSFNRNEC |
| 26 | 28G11 VHCDR2 N56Q | FIRNKPQGYTTE |
| 27 | 28G11 VHCDR2 N56S | FIRNKPSGYTTE |
| 28 | 28G11 VHCDR2 N56H | FIRNKPHGYTTE |
| 29 | 28G11 VHCDR2 N56L | FIRNKPLGYTTE |
| 30 | 28G11 VHCDR2 N56D | FIRNKPDGYTTE |
| 31 | 28G11_H0 VH | EVQLVESGGGLVQPGGSLRLSCAASGFTFSDYYMSWVRQAPGK GLEWVGFIRNKPNGYTTEYSASVKGRFTISRDDSKNSLYLQMN SLKTEDTAVYYCARYTGGGYFDYWGQGTLVTVSS |
| 32 | 28G11_H0_IgG1 | EVQLVESGGGLVQPGGSLRLSCAASGFTFSDYYMSWVRQAPGK GLEWVGFIRNKPNGYTTEYSASVKGRFTISRDDSKNSLYLQMN SLKTEDTAVYYCARYTGGGYFDYWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVD KKVEPKSCDKTHTCPPCPAPELLGGPSVFLFPPKPKDTLMISR TPEVTCVVVDVSHEDPEVKFNWYVDGVEVHNAKTKPREEQYNS TYRVVSVLTVLHQDWLNGKEYKCKVSNKALPAPIEKTISKAKG QPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPGK |
| 33 | 28G11_H1 VH | EVQLVESGGGLVQPGGSLRLSCAASGFTFTDYYMSWVRQAPGK GLEWLGFIRNKPNGYTTEYSASVKGRFTISRDDSKNSLYLQMN SLKTEDTAVYYCARYTGGGYFDYWGQGTLVTVSS |
| 34 | 28G11_H1_IgG1 | EVQLVESGGGLVQPGGSLRLSCAASGFTFTDYYMSWVRQAPGK GLEWLGFIRNKPNGYTTEYSASVKGRFTISRDDSKNSLYLQMN SLKTEDTAVYYCARYTGGGYFDYWGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVD KKVEPKSCDKTHTCPPCPAPELLGGPSVFLFPPKPKDTLMISR TPEVTCVVVDVSHEDPEVKFNWYVDGVEVHNAKTKPREEQYNS TYRVVSVLTVLHQDWLNGKEYKCKVSNKALPAPIEKTISKAKG |

TABLE 34-continued

Summary table of sequences

| SEQ ID | Description | Sequence |
|---|---|---|
| | | QPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPGK |
| 35 | 28G11_H2 VH | EVQLVESGGGLVQPGGSLRLSCAAS<u>GFTFTDYYMS</u>WVRQAPGK GLEWLG<u>FIRNKPNGYTTE</u>YSASVKGRFTISRDNSQSSLYLQMN SLKTEDTAVYYCARY<u>TGGGYFDY</u>WGQGTLLTVSS |
| 36 | 28G11_H2_IgG1 | EVQLVESGGGLVQPGGSLRLSCAAS<u>GFTFTDYYMS</u>WVRQAPGK GLEWLG<u>FIRNKPNGYTTE</u>YSASVKGRFTISRDNSQSSLYLQMN SLKTEDTAVYYCARY<u>TGGGYFDY</u>WGQGTLLTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVD KKVEPKSCDKTHTCPPCPAPELLGGPSVFLFPPKPKDTLMISR TPEVTCVVVDVSHEDPEVKFNWYVDGVEVHNAKTKPREEQYNS TYRVVSVLTVLHQDWLNGKEYKCKVSNKALPAPIEKTISKAKG QPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPGK |
| 37 | 28G11_H2_IgG4mut | EVQLVESGGGLVQPGGSLRLSCAAS<u>GFTFTDYYMS</u>WVRQAPGK GLEWLG<u>FIRNKPNGYTTE</u>YSASVKGRFTISRDNSQSSLYLQMN SLKTEDTAVYYCARY<u>TGGGYFDY</u>WGQGTLLTVSSASTKGPSVF PLAPCSRSTSESTAALGCLVKDYFPEPVTVSWNSGALTSGVHT FPAVLQSSGLYSLSSVVTVPSSSLGTKTYTCNVDHKPSNTKVD KRVESKYGPPCPPCPAPEAAGGPSVFLFPPKPKDTLMISRTPE VTCVVVDVSQEDPEVQFNWYVDGVEVHNAKTKPREEQFNSTYR VVSVLTVLHQDWLNGKEYKCKVSNKGLPSSIEKTISKAKGQPR EPQVYTLPPSQEEMTKNQVSLTCLVKGFYPSDIAVEWESNGQP ENNYKTTPPVLDSDGSFFLYSRLTVDKSRWQEGNVFSCSVMHE ALHNHYTQKSLSLSLGK |
| 38 | 28G11_H2.1 VH | EVQLVESGGGLVQPGGSLRLSCAAS<u>GFTFTDYYMS</u>WVRQAPGK GLEWLG<u>FIRNKPQGYTTE</u>YSASVKGRFTISRDNSQSSLYLQMN SLKTEDTAVYYCARY<u>TGGGYFDY</u>WGQGTLLTVSS |
| 39 | 28G11_H2.1_IgG1 | EVQLVESGGGLVQPGGSLRLSCAAS<u>GFTFTDYYMS</u>WVRQAPGK GLEWLG<u>FIRNKPQGYTTE</u>YSASVKGRFTISRDNSQSSLYLQMN SLKTEDTAVYYCARY<u>TGGGYFDY</u>WGQGTLLTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVD KKVEPKSCDKTHTCPPCPAPELLGGPSVFLFPPKPKDTLMISR TPEVTCVVVDVSHEDPEVKFNWYVDGVEVHNAKTKPREEQYNS TYRVVSVLTVLHQDWLNGKEYKCKVSNKALPAPIEKTISKAKG QPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPGK |
| 40 | 28G11_H2a VH | EVQLVESGGGLVQPGGSLRLSCAAS<u>GFTFTDYYMS</u>WVRQAPGK GLEWVG<u>FIRNKPNGYTTE</u>YSASVKGRFTISRDNSKNSLYLQMN SLKTEDTAVYYCARY<u>TGGGYFDY</u>WGQGTLVTVSS |
| 41 | 28G11_H2a_IgG1 | EVQLVESGGGLVQPGGSLRLSCAAS<u>GFTFTDYYMS</u>WVRQAPGK GLEWVG<u>FIRNKPNGYTTE</u>YSASVKGRFTISRDNSKNSLYLQMN SLKTEDTAVYYCARY<u>TGGGYFDY</u>WGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVD KKVEPKSCDKTHTCPPCPAPELLGGPSVFLFPPKPKDTLMISR TPEVTCVVVDVSHEDPEVKFNWYVDGVEVHNAKTKPREEQYNS TYRVVSVLTVLHQDWLNGKEYKCKVSNKALPAPIEKTISKAKG QPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPGK |
| 42 | 28G11_H2b VH | EVQLVESGGGLVQPGGSLRLSCAAS<u>GFTFTDYYMS</u>WVRQAPGK GLEWVG<u>FIRNKPQGYTTE</u>YSASVKGRFTISRDNSKNSLYLQMN SLKTEDTAVYYCARY<u>TGGGYFDY</u>WGQGTLVTVSS |
| 43 | 28G11_H2b_IgG1 | EVQLVESGGGLVQPGGSLRLSCAAS<u>GFTFTDYYMS</u>WVRQAPGK GLEWVG<u>FIRNKPQGYTTE</u>YSASVKGRFTISRDNSKNSLYLQMN SLKTEDTAVYYCARY<u>TGGGYFDY</u>WGQGTLVTVSSASTKGPSVF PLAPSSKSTSGGTAALGCLVKDYFPEPVTVSWNSGALTSGVHT FPAVLQSSGLYSLSSVVTVPSSSLGTQTYICNVNHKPSNTKVD KKVEPKSCDKTHTCPPCPAPELLGGPSVFLFPPKPKDTLMISR TPEVTCVVVDVSHEDPEVKFNWYVDGVEVHNAKTKPREEQYNS TYRVVSVLTVLHQDWLNGKEYKCKVSNKALPAPIEKTISKAKG QPREPQVYTLPPSRDELTKNQVSLTCLVKGFYPSDIAVEWESN GQPENNYKTTPPVLDSDGSFFLYSKLTVDKSRWQQGNVFSCSV MHEALHNHYTQKSLSLSPGK |
| 44 | 28G11_H2b_hIgG4mut VH | EVQLVESGGGLVQPGGSLRLSCAAS<u>GFTFTDYYMS</u>WVRQAPGK GLEWVG<u>FIRNKPQGYTTE</u>YSASVKGRFTISRDNSKNSLYLQMN SLKTEDTAVYYCARY<u>TGGGYFDY</u>WGQGTLVTVSS |
| 45 | 28G11_H2b_hIgG4mut | EVQLVESGGGLVQPGGSLRLSCAAS<u>GFTFTDYYMS</u>WVRQAPGK GLEWVG<u>FIRNKPQGYTTE</u>YSASVKGRFTISRDNSKNSLYLQMN SLKTEDTAVYYCARY<u>TGGGYFDY</u>WGQGTLVTVSSASTKGPSVF |

TABLE 34-continued

Summary table of sequences

| SEQ ID | Description | Sequence |
|---|---|---|
| | | PLAPCSRSTSESTAALGCLVKDYFPEPVTVSWNSGALTSGVHT FPAVLQSSGLYSLSSVVTVPSSSLGTKTYTCNVDHKPSNTKVD KRVESKYGPPCPPCPAPEAAGGPSVFLFPPKPKDTLMISRTPE VTCVVVDVSQEDPEVQFNWYVDGVEVHNAKTKPREEQFNSTYR VVSVLTVLHQDWLNGKEYKCKVSNKGLPSSIEKTISKAKGQPR EPQVYTLPPSQEEMTKNQVSLTCLVKGFYPSDIAVEWESNGQP ENNYKTTPPVLDSDGSFFLYSRLTVDKSRWQEGNVFSCSVMHE ALHNHYTQKSLSLSLGK |
| 46 | 28G11_L1 VL | DIQMTQSPSSLSASVGDRVTITCRASQDISNYLNWYQQKPGKV PKLLIYYTSRLHSGVPSRFSGSGSGTDYTLTISSLQPEDVATY FCQQGDTLPWTFGQGTKLEIK |
| 47 | 28G11_L1 | DIQMTQSPSSLSASVGDRVTITCRASQDISNYLNWYQQKPGKV PKLLIYYTSRLHSGVPSRFSGSGSGTDYTLTISSLQPEDVATY FCQQGDTLPWTFGQGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| 48 | 28G11_L2 VL | DIQMTQSPSSLSASVGDRVTITCRASQDISNYLNWYQQKPGKV VKLLIYYTSRLHSGVPSRFSGSGSGTDYTLTISSLQPEDVATY FCQQGDTLPWTFGQGTKLEIK |
| 49 | 28G11_L2 | DIQMTQSPSSLSASVGDRVTITCRASQDISNYLNWYQQKPGKT VKLLIYYTSRLHSGVPSRFSGSGSGTDYTLTISSLQPEDVATY FCQQGDTLPWTFGQGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| 50 | 28G11_L3 VL | DIQMTQSPSSLSASVGDRLTISCRASQDISNYLNWYQQKPGKT VKLLIYYTSRLHSGVPSRFSGSGSGTDYTLTISSLQPEDVATY FCQQGDTLPWTFGQGTKLEIK |
| 51 | 28G11_L3 | DIQMTQSPSSLSASVGDRLTISCRASQDISNYLNWYQQKPGKT VKLLIYYTSRLHSGVPSRFSGSGSGTDYTLTISSLQPEDVATY FCQQGDTLPWTFGQGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| 52 | 28G11_L3a VL | DIQMTQSPSSLSASVGDRLTISCRASQDISNYLNWYQQKPGKV VKLLIYYTSRLHSGVPSRFSGSGSGTDYTLTISSLQPEDVATY YCQQGDTLPWTFGQGTKLEIK |
| 53 | 28G11_L3a | DIQMTQSPSSLSASVGDRLTISCRASQDISNYLNWYQQKPGKV VKLLIYYTSRLHSGVPSRFSGSGSGTDYTLTISSLQPEDVATY YCQQGDTLPWTFGQGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| 54 | 22F9(hyb)VHCDR1 | GYTFTSYWMH |
| 55 | 22F9(hyb)VHCDR2 | MIHPNSGSTN |
| 56 | 22F9(hyb)VHCDR3 | YDYDGFFDV |
| 57 | 22F9(hyb)VLCDR1 | RASKSVSTSGYSYMH |
| 58 | 22F9(hyb)VLCDR2 | LASNLES |
| 59 | 22F9(hyb)VLCDR3 | QHSRELPYT |
| 60 | 22F9(hyb )VH | QVQLQQPGAELVKPGASVKLSCKASGYTFTSYWMHWVKQRPGQ GLEWIGMIHPNSGSTNYNEKFKSKATLTVDKSSSTAYMQLSSL TSEDSAVYYCAYYDYDGFFDVWGTGTTVTSS |
| 61 | 22F9(hyb) VL | DIVLTQSPASLDVSLGQRATISCRASKSVSTSGYSYMHWYQQK SGQPPKLLIYLASNLESGVPARFSGSGSGTHFTLNIHPVEEED AATYYCQHSRELPYTFGGGTKLEIK |
| 62 | 22F9(hyb) heavy chain | QVQLQQPGAELVKPGASVKLSCKASGYTFTSYWMHWVKQRPGQ GLEWIGMIHPNSGSTNYNEKFKSKATLTVDKSSSTAYMQLSSL TSEDSAVYYCAYYDYDGFFDVWGTGTTVTSSAKTTPPSVYPL APGSAAQTNSMVTLGCLVKGYFPEPVTVTWNSGSLSSGVHTFP AVLQSDLYTLSSSVTVPSSPRPSETVTCNVAHPASSTKVDKKI VPRDCGCKPCICTVPEVSSVFIFPPKPKDVLTITLTPKVTCVV VDISKDDPEVQFSWFVDDVEVHTAQTQPREEQFNSTFRSVSEL PIMHQDWLNGKEFKCRVNSAAFPAPIEKTISKTKGRPKAPQVY TIPPPKEQMAKDKVSLTCMITDFFPEDITVEWQWNGQPAENYK NTQPIMNTNGSYFVYSKLNVQKSNWEAGNTFTCSVLHEGLHNH HTEKSLSHSPGK |
| 63 | 22F9(hyb) light chain | DIVLTQSPASLDVSLGQRATISCRASKSVSTSGYSYMHWYQQK SGQPPKLLIYLASNLESGVPARFSGSGSGTHFTLNIHPVEEED AATYYCQHSRELPYTFGGGTKLEIKRADAAPTVSIFPPSSEQL TSGGASVVCFLNNFYPKDINVKWKIDGSERQNGVLNSWTDQDS KDSTYSMSSTLTLTKDEYERHNSYTCEATHKTSTSPIVKSFNR NEC |
| 64 | 22F9 VHCDR2 N54A | MIHPASGSTN |
| 65 | 22F9 VHCDR2 N54H | MIHPHSGSTN |
| 66 | 22F9 VHCDR2 N54Q | MIHPQSGSTN |
| 67 | 22F9 VHCDR2 N54S | MIHPSSGSTN |
| 68 | 22F9 VHCDR3 D102A | YDYAGFFDV |
| 69 | 22F9 VHCDR3 D102E | YDYEGFFDV |
| 70 | 22F9 VHCDR3 D102G | YDYGGFFDV |

TABLE 34-continued

Summary table of sequences

| SEQ ID | Description | Sequence |
|---|---|---|
| 71 | 22F9_H0 VH | QVQLVQSGAEVKKPGASVKVSCKAS<u>GYTFTSYWMH</u>WVRQAPGQ GLEWMG<u>MIHPNSGSTN</u>YNEKFKSRVTMTRDTSTSTVYMELSSL RSEDTAVYYCAR<u>YDYDGFFDV</u>WGQGTLVTVSS |
| 72 | 22F9_H0_IgG1 | QVQLVQSGAEVKKPGASVKVSCKAS<u>GYTFTSYWMH</u>WVRQAPGQ GLEWMG<u>MIHPNSGSTN</u>YNEKFKSRVTMTRDTSTSTVYMELSSL RSEDTAVYYCAR<u>YDYDGFFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 73 | 22F9_H0.1 VH | QVQLVQpGAEVvKPGASVKlSCKAS<u>GYTFTSYWMH</u>WVkQrPGQ GLEWMG<u>MIHPqSGSTN</u>YNEKFKSkaTlTRDkSsSTaYMELSSL RSEDTAVYYCAR<u>YDYaGFFDV</u>WGQGTLVTVSS |
| 74 | 22F9_H0.1_IgG1 | QVQLVQpGAEVvKPGASVKlSCKAS<u>GYTFTSYWMH</u>WVkQrPGQ GLEWMG<u>MIHPqSGSTN</u>YNEKFKSkaTlTRDkSsSTaYMELSSL RSEDTAVYYCAR<u>YDYaGFFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 75 | 22F9_H1 VH | QVQLVQSGAEVKKPGASVKVSCKAS<u>GYTFTSYWMH</u>WVRQAPGQ GLEWiG<u>MIHPNSGSTN</u>YNEKFKSRVTMTvDTSTSTVYMELSSL RSEDTAVYYCAy<u>YDYDGFFDV</u>WGQGTLVTVSS |
| 76 | 22F9_H1_IgG1 | QVQLVQSGAEVKKPGASVKVSCKAS<u>GYTFTSYWMH</u>WVRQAPGQ GLEWiG<u>MIHPNSGSTN</u>YNEKFKSRVTMTvDTSTSTVYMELSSL RSEDTAVYYCAy<u>YDYDGFFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 77 | 22F9_H1.1 VH | QVQLVQpGAEVvKPGASVKlSCKAS<u>GYTFTSYWMH</u>WVkQrPGQ GLEWIG<u>MIHPqSGSTN</u>YNEKFKSkaTMTVDkSsSTVYMELSSL RSEDTAVYYCAY<u>YDYaGFFDV</u>WGQGTLVTVSS |
| 78 | 22F9_H1.1_IgG1 | QVQLVQpGAEVvKPGASVKlSCKAS<u>GYTFTSYWMH</u>WVkQrPGQ GLEWIG<u>MIHPqSGSTN</u>YNEKFKSkaTMTVDkSsSTVYMELSSL RSEDTAVYYCAY<u>YDYaGFFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 79 | 22F9_H1.1_IgG4mut | QVQLVQpGAEVvKPGASVKlSCKAS<u>GYTFTSYWMH</u>WVkQrPGQ GLEWIG<u>MIHPqSGSTN</u>YNEKFKSkaTMTVDkSsSTVYMELSSL RSEDTAVYYCAY<u>YDYaGFFDV</u>WGQGTLVTVSSASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEAAGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLGK |
| 80 | 22F9_H2 VH | QVQLVQSGAEVKKPGASVKVSCKAS<u>GYTFTSYWMH</u>WVRQAPGQ GLEWiG<u>MIHPNSGSTN</u>YNEKFKSRVTlTvDTSTSTaYMELSSL RSEDTAVYYCAy<u>YDYDGFFDV</u>WGQGTLVTVSS |
| 81 | 22F9_H2_IgG1 | QVQLVQSGAEVKKPGASVKVSCKAS<u>GYTFTSYWMH</u>WVRQAPGQ GLEWiG<u>MIHPNSGSTN</u>YNEKFKSRVTlTvDTSTSTaYMELSSL RSEDTAVYYCAy<u>YDYDGFFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP |

TABLE 34-continued

Summary table of sequences

| SEQ ID | Description | Sequence |
|---|---|---|
| | | EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 82 | 22F9_H2.1 VH | QVQLVQpGAEVvKPGASVKlSCKAS<u>GYTFTSYWMH</u>WVkQrPGQ GLEWIG<u>MIHPqSGSTN</u>YNEKFKSkaTLTVDkSTSTAYMELSSL RSEDTAVYYCAY<u>YDYaGFFDV</u>WGQGTLVTVSS |
| 83 | 22F9_H2.1_IgG1 | QVQLVQpGAEVvKPGASVKlSCKAS<u>GYTFTSYWMH</u>WVkQrPGQ GLEWIG<u>MIHPqSGSTN</u>YNEKFKSkaTLTVDkSTSTAYMELSSL RSEDTAVYYCAY<u>YDYaGFFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 84 | 22F9_H2.1_IgG4mut | QVQLVQpGAEVvKPGASVKlSCKAS<u>GYTFTSYWMH</u>WVkQrPGQ GLEWIG<u>MIHPqSGSTN</u>YNEKFKSkaTLTVDkSTSTAYMELSSL RSEDTAVYYCAY<u>YDYaGFFDV</u>WGQGTLVTVSSASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEAAGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLGK |
| 85 | 22F9_H3 VH | QVQLVQSGAEVKKPGASVKVSCKAS<u>GYTFTSYWMH</u>WVRQAPGQ GLEWiG<u>MIHPNSGSTN</u>YNEKFKSRVTlTvDkSsSTaYMELSSL RSEDTAVYYCAy<u>YDYDGFFDV</u>WGQGTLVTVSS |
| 86 | 22F9_H3_IgG1 | QVQLVQSGAEVKKPGASVKVSCKAS<u>GYTFTSYWMH</u>WVRQAPGQ GLEWiG<u>MIHPNSGSTN</u>YNEKFKSRVTlTvDkSsSTaYMELSSL RSEDTAVYYCAy<u>YDYDGFFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 87 | 22F9_H3.1 VH | QVQLVQpGAEVvKPGASVKlSCKAS<u>GYTFTSYWMH</u>WVRQAPGQ GLEWIG<u>MIHPqSGSTN</u>YNEKFKSRVTLTVDKSSSTAYMELSSL RSEDTAVYYCAY<u>YDYaGFFDV</u>WGQGTLVTVSS |
| 88 | 22F9_H3.1_IgG1 | QVQLVQpGAEVvKPGASVKlSCKAS<u>GYTFTSYWMH</u>WVRQAPGQ GLEWIG<u>MIHPqSGSTN</u>YNEKFKSRVTLTVDKSSSTAYMELSSL RSEDTAVYYCAY<u>YDYaGFFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 89 | 22F9_H3.1_IgG4mut | QVQLVQpGAEVvKPGASVKlSCKAS<u>GYTFTSYWMH</u>WVRQAPGQ GLEWIG<u>MIHPqSGSTN</u>YNEKFKSRVTLTVDKSSSTAYMELSSL RSEDTAVYYCAY<u>YDYaGFFDV</u>WGQGTLVTVSSASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEAAGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLGK |
| 90 | 22F9_H4 VH | QVQLVQSGAEVKKPGASVKVSCKAS<u>GYTFTSYWMH</u>WVkQrPGQ GLEWiG<u>MIHPNSGSTN</u>YNEKFKSkaTlTvDkSsSTaYMELSSL RSEDTAVYYCAy<u>YDYDGFFDV</u>WGQGTLVTVSS |
| 91 | 22F9_H4_IgG1 | QVQLVQSGAEVKKPGASVKVSCKAS<u>GYTFTSYWMH</u>WVkQrPGQ GLEWiG<u>MIHPNSGSTN</u>YNEKFKSkaTlTvDkSsSTaYMELSSL RSEDTAVYYCAy<u>YDYDGFFDV</u>WGQGTLVTVSSASTKGPSVFPL APSSKSTSGGTAALGCLVKDYFPEPVTVSWNSGALTSGVHTFP |

TABLE 34-continued

Summary table of sequences

| SEQ ID | Description | Sequence |
|---|---|---|
| | | AVLQSSGLYSLSSVVTVPSSSLGTQTYICNVNHKPSNTKVDKK |
| | | VEPKSCDKTHTCPPCPAPELLGGPSVFLFPPKPKDTLMISRTP |
| | | EVTCVVVDVSHEDPEVKFNWYVDGVEVHNAKTKPREEQYNSTY |
| | | RVVSVLTVLHQDWLNGKEYKCKVSNKALPAPIEKTISKAKGQP |
| | | REPQVYTLPPSRDELTKNQVSLTCLVKGFYPSDIAVEWESNGQ |
| | | PENNYKTTPPVLDSDGSFFLYSKLTVDKSRWQQGNVFSCSVMH |
| | | EALHNHYTQKSLSLSPGK |
| 92 | 22F9_H5 VH | QVQLVQpGAEVvKPGASVKlSCKAS<u>GYTFTSYWMH</u>WVkQrPGQ |
| | | GLEWi<u>GMIHPNSGSTN</u>YNEKFKSkaTlTvDkSsSTaYMELSSL |
| | | RSEDTAVYYCAy<u>YDYDGFFDV</u>WGQGTLVTVSS |
| 93 | 22F9_H5_IgG1 | QVQLVQpGAEVvKPGASVKlSCKAS<u>GYTFTSYWMH</u>WVkQrPGQ |
| | | GLEWi<u>GMIHPNSGSTN</u>YNEKFKSkaTlTvDkSsSTaYMELSSL |
| | | RSEDTAVYYCAy<u>YDYDGFFDV</u>WGQGTLVTVSSASTKGPSVFPL |
| | | APSSKSTSGGTAALGCLVKDYFPEPVTVSWNSGALTSGVHTFP |
| | | AVLQSSGLYSLSSVVTVPSSSLGTQTYICNVNHKPSNTKVDKK |
| | | VEPKSCDKTHTCPPCPAPELLGGPSVFLFPPKPKDTLMISRTP |
| | | EVTCVVVDVSHEDPEVKFNWYVDGVEVHNAKTKPREEQYNSTY |
| | | RVVSVLTVLHQDWLNGKEYKCKVSNKALPAPIEKTISKAKGQP |
| | | REPQVYTLPPSRDELTKNQVSLTCLVKGFYPSDIAVEWESNGQ |
| | | PENNYKTTPPVLDSDGSFFLYSKLTVDKSRWQQGNVFSCSVMH |
| | | EALHNHYTQKSLSLSPGK |
| 94 | 22F9_H5_IgG4mut | QVQLVQpGAEVvKPGASVKlSCKAS<u>GYTFTSYWMH</u>WVkQrPGQ |
| | | GLEWi<u>GMIHPNSGSTN</u>YNEKFKSkaTlTvDkSsSTaYMELSSL |
| | | RSEDTAVYYCAy<u>YDYDGFFDV</u>WGQGTLVTVSSASTKGPSVFPL |
| | | APCSRSTSESTAALGCLVKDYFPEPVTVSWNSGALTSGVHTFP |
| | | AVLQSSGLYSLSSVVTVPSSSLGTKTYTCNVDHKPSNTKVDKR |
| | | VESKYGPPCPPCPAPEAAGGPSVFLFPPKPKDTLMISRTPEVT |
| | | CVVVDVSQEDPEVQFNWYVDGVEVHNAKTKPREEQFNSTYRVV |
| | | SVLTVLHQDWLNGKEYKCKVSNKGLPSSIEKTISKAKGQPREP |
| | | QVYTLPPSQEEMTKNQVSLTCLVKGFYPSDIAVEWESNGQPEN |
| | | NYKTTPPVLDSDGSFFLYSRLTVDKSRWQEGNVFSCSVMHEAL |
| | | HNHYTQKSLSLSLGK |
| 95 | 22F9_H5.2 VH | QVQLVQpGAEVvKPGASVKlSCKAS<u>GYTFTSYWMH</u>WVkQrPGQ |
| | | GLEWi<u>GMIHPQSGSTN</u>YNEKFKSkaTlTvDkSsSTaYMELSSL |
| | | RSEDTAVYYCAy<u>YDYAGFFDV</u>WGQGTLVTVSS |
| 96 | 22F9_H5.2_IgG1 | QVQLVQpGAEVvKPGASVKlSCKAS<u>GYTFTSYWMH</u>WVkQrPGQ |
| | | GLEWi<u>GMIHPQSGSTN</u>YNEKFKSkaTlTvDkSsSTaYMELSSL |
| | | RSEDTAVYYCAy<u>YDYAGFFDV</u>WGQGTLVTVSSASTKGPSVFPL |
| | | APSSKSTSGGTAALGCLVKDYFPEPVTVSWNSGALTSGVHTFP |
| | | AVLQSSGLYSLSSVVTVPSSSLGTQTYICNVNHKPSNTKVDKK |
| | | VEPKSCDKTHTCPPCPAPELLGGPSVFLFPPKPKDTLMISRTP |
| | | EVTCVVVDVSHEDPEVKFNWYVDGVEVHNAKTKPREEQYNSTY |
| | | RVVSVLTVLHQDWLNGKEYKCKVSNKALPAPIEKTISKAKGQP |
| | | REPQVYTLPPSRDELTKNQVSLTCLVKGFYPSDIAVEWESNGQ |
| | | PENNYKTTPPVLDSDGSFFLYSKLTVDKSRWQQGNVFSCSVMH |
| | | EALHNHYTQKSLSLSPGK |
| 97 | 22F9_H5.2_IgG4mut | QVQLVQpGAEVvKPGASVKlSCKAS<u>GYTFTSYWMH</u>WVkQrPGQ |
| | | GLEWi<u>GMIHPQSGSTN</u>YNEKFKSkaTlTvDkSsSTaYMELSSL |
| | | RSEDTAVYYCAy<u>YDYAGFFDV</u>WGQGTLVTVSSASTKGPSVFPL |
| | | APCSRSTSESTAALGCLVKDYFPEPVTVSWNSGALTSGVHTFP |
| | | AVLQSSGLYSLSSVVTVPSSSLGTKTYTCNVDHKPSNTKVDKR |
| | | VESKYGPPCPPCPAPEAAGGPSVFLFPPKPKDTLMISRTPEVT |
| | | CVVVDVSQEDPEVQFNWYVDGVEVHNAKTKPREEQFNSTYRVV |
| | | SVLTVLHQDWLNGKEYKCKVSNKGLPSSIEKTISKAKGQPREP |
| | | QVYTLPPSQEEMTKNQVSLTCLVKGFYPSDIAVEWESNGQPEN |
| | | NYKTTPPVLDSDGSFFLYSRLTVDKSRWQEGNVFSCSVMHEAL |
| | | HNHYTQKSLSLSLGK |
| 98 | 22F9_H7 VH | QVQLVQpGAEVvKPGASVKlSCKAS<u>GYTFTSYWMH</u>WVRQAPGQ |
| | | GLEWi<u>GMIHPqSGSTN</u>YAQKFQGRVTMTvDkSTSTVYMELSSL |
| | | RSEDTAVYYCAy<u>YDYaGFFDV</u>WGQGTLVTVSS |
| 99 | 22F9_H7_IgG1 | QVQLVQpGAEVvKPGASVKlSCKAS<u>GYTFTSYWMH</u>WVRQAPGQ |
| | | GLEWi<u>GMIHPqSGSTN</u>YAQKFQGRVTMTvDkSTSTVYMELSSL |
| | | RSEDTAVYYCAy<u>YDYaGFFDV</u>WGQGTLVTVSSASTKGPSVFPL |
| | | APSSKSTSGGTAALGCLVKDYFPEPVTVSWNSGALTSGVHTFP |
| | | AVLQSSGLYSLSSVVTVPSSSLGTQTYICNVNHKPSNTKVDKK |
| | | VEPKSCDKTHTCPPCPAPELLGGPSVFLFPPKPKDTLMISRTP |
| | | EVTCVVVDVSHEDPEVKFNWYVDGVEVHNAKTKPREEQYNSTY |
| | | RVVSVLTVLHQDWLNGKEYKCKVSNKALPAPIEKTISKAKGQP |
| | | REPQVYTLPPSRDELTKNQVSLTCLVKGFYPSDIAVEWESNGQ |
| | | PENNYKTTPPVLDSDGSFFLYSKLTVDKSRWQQGNVFSCSVMH |
| | | EALHNHYTQKSLSLSPGK |
| 100 | 22F9_H7_IgG4mut | QVQLVQpGAEVvKPGASVKlSCKAS<u>GYTFTSYWMH</u>WVRQAPGQ |
| | | GLEWi<u>GMIHPqSGSTN</u>YAQKFQGRVTMTvDkSTSTVYMELSSL |
| | | RSEDTAVYYCAy<u>YDYaGFFDV</u>WGQGTLVTVSSASTKGPSVFPL |
| | | APCSRSTSESTAALGCLVKDYFPEPVTVSWNSGALTSGVHTFP |
| | | AVLQSSGLYSLSSVVTVPSSSLGTKTYTCNVDHKPSNTKVDKR |

TABLE 34-continued

Summary table of sequences

| SEQ ID | Description | Sequence |
|---|---|---|
| | | VESKYGPPCPPCPAPEAAGGPSVFLFPPKPKDTLMISRTPEVT
CVVVDVSQEDPEVQFNWYVDGVEVHNAKTKPREEQFNSTYRVV
SVLTVLHQDWLNGKEYKCKVSNKGLPSSIEKTISKAKGQPREP
QVYTLPPSQEEMTKNQVSLTCLVKGFYPSDIAVEWESNGQPEN
NYKTTPPVLDSDGSFFLYSRLTVDKSRWQEGNVFSCSVMHEAL
HNHYTQKSLSLSLGK |
| 101 | 22F9_H7a VH | EVQLVQpGAEVvKPGASVKlSCKAS<u>GYTFTSYWMH</u>WVRQAPGQ
GLEWi<u>MIHPqSGSTN</u>YAQKFQGRVTMTvDkSTSTVYMELSSL
RSEDTAVYYCAy<u>YDYaGFFDV</u>WGQGTLVTVSS |
| 102 | 22F9_H7a_IgG1 | EVQLVQpGAEVvKPGASVKlSCKAS<u>GYTFTSYWMH</u>WVRQAPGQ
GLEWi<u>MIHPqSGSTN</u>YAQKFQGRVTMTvDkSTSTVYMELSSL
RSEDTAVYYCAy<u>YDYaGFFDV</u>WGQGTLVTVSSASTKGPSVFPL
APSSKSTSGGTAALGCLVKDYFPEPVTVSWNSGALTSGVHTFP
AVLQSSGLYSLSSVVTVPSSSLGTQTYICNVNHKPSNTKVDKK
VEPKSCDKTHTCPPCPAPELLGGPSVFLFPPKPKDTLMISRTP
EVTCVVVDVSHEDPEVKFNWYVDGVEVHNAKTKPREEQYNSTY
RVVSVLTVLHQDWLNGKEYKCKVSNKALPAPIEKTISKAKGQP
REPQVYTLPPSRDELTKNQVSLTCLVKGFYPSDIAVEWESNGQ
PENNYKTTPPVLDSDGSFFLYSKLTVDKSRWQQGNVFSCSVMH
EALHNHYTQKSLSLSPGK |
| 103 | 22F9_H7a_IgG4mut | EVQLVQpGAEVvKPGASVKlSCKAS<u>GYTFTSYWMH</u>WVRQAPGQ
GLEWi<u>MIHPqSGSTN</u>YAQKFQGRVTMTvDkSTSTVYMELSSL
RSEDTAVYYCAy<u>YDYaGFFDV</u>WGQGTLVTVSSASTKGPSVFPL
APCSRSTSESTAALGCLVKDYFPEPVTVSWNSGALTSGVHTFP
AVLQSSGLYSLSSVVTVPSSSLGTKTYTCNVDHKPSNTKVDKR
VESKYGPPCPPCPAPEAAGGPSVFLFPPKPKDTLMISRTPEVT
CVVVDVSQEDPEVQFNWYVDGVEVHNAKTKPREEQFNSTYRVV
SVLTVLHQDWLNGKEYKCKVSNKGLPSSIEKTISKAKGQPREP
QVYTLPPSQEEMTKNQVSLTCLVKGFYPSDIAVEWESNGQPEN
NYKTTPPVLDSDGSFFLYSRLTVDKSRWQEGNVFSCSVMHEAL
HNHYTQKSLSLSLGK |
| 104 | 22F9_L0 VL | DIQLTQSPSSLSASVGDRVTITC<u>RASKSVSTSGYSYMH</u>WYQQK
PGKAPKLLIY<u>LASNLES</u>GVPSRFSGSGSGTDFTLTISSLQPED
FATYYC<u>QHSRELPYT</u>FGGGTKVEIK |
| 105 | 22F9_L0 | DIQLTQSPSSLSASVGDRVTITC<u>RASKSVSTSGYSYMH</u>WYQQK
PGKAPKLLIY<u>LASNLES</u>GVPSRFSGSGSGTDFTLTISSLQPED
FATYYC<u>QHSRELPYT</u>FGGGTKVEIKRTVAAPSVFIFPPSDEQL
KSGTASVVCLLNNFYPREAKVQWKVDNALQSGNSQESVTEQDS
KDSTYSLSSTLTLSKADYEKHKVYACEVTHQGLSSPVTKSFNR
GEC |
| 106 | 22F9_L1 VL | DIQLTQSPSSLSASVGDRVTITC<u>RASKSVSTSGYSYMH</u>WYQQK
PGKpPKLLIY<u>LASNLES</u>GVPSRFSGSGSGThFTLTISSLQPED
FATYYC<u>QHSRELPYT</u>FGGGTKVEIK |
| 107 | 22F9_L1 | DIQLTQSPSSLSASVGDRVTITC<u>RASKSVSTSGYSYMH</u>WYQQK
PGKpPKLLIY<u>LASNLES</u>GVPSRFSGSGSGThFTLTISSLQPED
FATYYC<u>QHSRELPYT</u>FGGGTKVEIKRTVAAPSVFIFPPSDEQL
KSGTASVVCLLNNFYPREAKVQWKVDNALQSGNSQESVTEQDS
KDSTYSLSSTLTLSKADYEKHKVYACEVTHQGLSSPVTKSFNR
GEC |
| 108 | 22F9_L2 VL | DIQLTQSPSSLSvSVGDRaTITC<u>RASKSVSTSGYSYMH</u>WYQQK
PGKpPKLLIY<u>LASNLES</u>GVPSRFSGSGSGThFTLTISSvQPED
FATYYC<u>QHSRELPYT</u>FGGGTKlEIK |
| 109 | 22F9_L2 | DIQLTQSPSSLSvSVGDRaTITC<u>RASKSVSTSGYSYMH</u>WYQQK
PGKpPKLLIY<u>LASNLES</u>GVPSRFSGSGSGThFTLTISSvQPED
FATYYC<u>QHSRELPYT</u>FGGGTKlEIKRTVAAPSVFIFPPSDEQL
KSGTASVVCLLNNFYPREAKVQWKVDNALQSGNSQESVTEQDS
KDSTYSLSSTLTLSKADYEKHKVYACEVTHQGLSSPVTKSFNR
GEC |
| 110 | 20E6(hyb)VHCDR1 | GYTFTSYWMH |
| 111 | 20E6(hyb)VHCDR2 | RIDPNSGGIK |
| 112 | 20E6(hyb)VHCDR3 | WDYGGYFDV |
| 113 | 20E6(hyb)VLCDR1 | RASQDITNYLN |
| 114 | 20E6(hyb)VLCDR2 | YTSRLHS |
| 115 | 20E6(hyb)VLCDR3 | QQGDTLPWT |
| 116 | 20E6(hyb) VH | QVQLQQPGAELVKPGASVKLSCKAS<u>GYTFTSYWMH</u>WVKQRPGR
GLEWIG<u>RIDPNSGGI</u>KYNEKFKSKATLTVDKSSSTAYMQLSSL
TSEDSAVYYCAR<u>WDYGGYFDV</u>WGTGTTVTVSS |
| 117 | 20E6(hyb) VL | DIQMTQTTSSLSASLGDRVTISC<u>RASQDITNYLN</u>WYQQKPDGA
VKLLIY<u>YTSRLHS</u>GVPSRFSGSGSGTDYSLTISNLEQEDIATY
FC<u>QQGDTLPWT</u>FGGGTKLEIK |
| 118 | 20E6(hyb) heavy chain | QVQLQQPGAELVKPGASVKLSCKAS<u>GYTFTSYWMH</u>WVKQRPGR
GLEWIG<u>RIDPNSGGI</u>KYNEKFKSKATLTVDKSSSTAYMQLSSL
TSEDSAVYYCAR<u>WDYGGYFDV</u>WGTGTTVTVSSQSFPNVFPLV
SCESPLSDKNLVAMGCLARDFLPSTISFTWNYQNNTEVIQGIR
TFPTLRTGGKYLATSQVLLSPKSILEGSDEYLVCKIHYGGKNR
DLHVPIPAVAEMNPNVNVFVPPRDGFSGPAPRKSKLICEATNF |

TABLE 34-continued

Summary table of sequences

| SEQ ID | Description | Sequence |
|---|---|---|
|  |  | TPKPITVSWLKDGKLVESGFTTDPVTIENKGSTPQTYKVISTL TISEIDWLNLNVYTCRVDHRGLTFLKNVSSTCAASPSTDILTF TIPPSFADIFLSKSANLTCLVSNLATYETLNISWASQSGEPLE TKIKIMESHPNGTFSAKGVASVCVEDWNNRKEFVCTVTHRDLP SPQKKFISKPNEVHKHPPAVYLLPPAREQLNLRESATVTCLVK GFSPADISVQWLQRGQLLPQEKYVTSAPMPEPGAPGFYFTHSI LTVTEEEWNSGETYTCVVGHEALPHLVTERTVDKSTGKPTLYN VSLIMSDTGGTCY |
| 119 | 20E6(hyb) light chain | DIQMTQTTSSLSASLGDRVTISC<u>RASQDITNYLN</u>WYQQKPDGA VKLLIY<u>YTSRLHS</u>GVPSRFSGSGSGTDYSLTISNLEQEDIATY FC<u>QQGDTLPWT</u>FGGGTKLEIKRADAAPTVSIFPPSSEQLTSGG ASVVCFLNNFYPKDINVKWKIDGSERQNGVLNSWTDQDSKDST YSMSSTLTLTKDEYERHNSYTCEATHKTSTSPIVKSFNRNEC |
| 120 | 20E6(hyb)VHCDR2 N54Q | RIDPQSGGIK |
| 121 | 20E6(hyb)VHCDR2 N54G | RIDPGSGGIK |
| 122 | 20E6(hyb)VHCDR2 N54A | RIDPASGGIK |
| 123 | 20E6(hyb)VHCDR2 N54S | RIDPSSGGIK |
| 124 | 20E6(hyb)VHCDR2 N54H | RIDPHSGGIK |
| 125 | 20E6(hyb)VHCDR2 N54L | RIDPLSGGIK |
| 126 | 20E6(hyb)VHCDR2 N54D | RIDPDSGGIK |
| 127 | 20E6_H0 VH | QVQLVQSGAEVKKPGASVKVSCKASGYTFT<u>SYWMH</u>WVRQAPGQ GLEWMG<u>RIDPNSGGI</u>KYNEKFKSRVTMTRDTSISTAYMELSRL RSDDTAVYYCAR<u>WDYGGYFDV</u>WGQGTLVTVSS |
| 128 | 20E6_H0_IgG1 | QVQLVQSGAEVKKPGASVKVSCKAS<u>GYTFTSYWMH</u>WVRQAPGQ GLEWMG<u>RIDPNSGGI</u>KYNEKFKSRVTMTRDTSISTAYMELSRL RSDDTAVYYCAR<u>WDYGGYFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 129 | 20E6_H0_IgG4mut | QVQLVQSGAEVKKPGASVKVSCKASGYTFT<u>SYWMH</u>WVRQAPGQ GLEWMG<u>RIDPNSGGI</u>KYNEKFKSRVTMTRDTSISTAYMELSRL RSDDTAVYYCAR<u>WDYGGYFDV</u>WGQGTLVTVSSASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEAAGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLGK |
| 130 | 20E6_H0.1 VH | QVQLVQSGAEVKKPGASVKVSCKAS<u>GYTFTSYWMH</u>WVRQAPGQ GLEWMG<u>RIDPNSGGI</u>KYAQKFQGRATLTVDTSTSTAYMELSRL RSDDTAVYYCAR<u>WDYGGYFDV</u>WGQGTLVTVSS |
| 131 | 20E6_H0.1_IgG1 | QVQLVQSGAEVKKPGASVKVSCKAS<u>GYTFTSYWMH</u>WVRQAPGQ GLEWMG<u>RIDPNSGGI</u>KYAQKFQGRATLTVDTSTSTAYMELSRL RSDDTAVYYCAR<u>WDYGGYFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 132 | 20E6_H0.13gG4mut | QVQLVQSGAEVKKPGASVKVSCKAS<u>GYTFTSYWMH</u>WVRQAPGQ GLEWMG<u>RIDPNSGGI</u>KYAQKFQGRATLTVDTSTSTAYMELSRL RSDDTAVYYCAR<u>WDYGGYFDV</u>WGQGTLVTVSSASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEAAGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLGK |
| 133 | 20E6_H0.2 VH | QVQLVQSGAEVKKPGASVKVSCKAS<u>GYTFTSYWMH</u>WVRQAPGQ GLEWMG<u>RIDPQSGGI</u>KYAQKFQGRATLTVDTSTSTAYMELSRL RSDDTAVYYCAR<u>WDYGGYFDV</u>WGQGTLVTVSS |
| 134 | 20E6_H0.2_IgG1 | QVQLVQSGAEVKKPGASVKVSCKAS<u>GYTFTSYWMH</u>WVRQAPGQ GLEWMG<u>RIDPQSGGI</u>KYAQKFQGRATLTVDTSTSTAYMELSRL RSDDTAVYYCAR<u>WDYGGYFDV</u>WGQGTLVTVSSASTKGPSVFPL |

TABLE 34-continued

Summary table of sequences

| SEQ ID | Description | Sequence |
|---|---|---|
| | | APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 135 | 20E6_H0.2_IgG4mut | QVQLVQSGAEVKKPGASVKVSCKAS<u>GYTFTSYWMH</u>WVRQAPGQ GLEWM<u>GRIDPQSGGI</u>KYAQKFQGRATLTVDTSTSTAYMELSRL RSDDTAVYYCAR<u>WDYGGYFDV</u>WGQGTLVTVSSASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEAAGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLGK |
| 136 | 20E6_H0.3_IgG1 | QVQLVQSGAEVKKPGASVKVSCKAS<u>GYTFTSYWMH</u>WVRQAPGQ GLEWM<u>GRIDPqSGGI</u>KYAQKFQGRATLTVDTSTSTAYMELSRL RSDDTAVYYCAR<u>WDYGGYFDV</u>WGQGTLVTVSS |
| 137 | 20E6_H0.4_IgG1 | QVQLVQSGAEVKKPGASVKVSCKAS<u>GYTFTSYWMH</u>WVRQAPGQ GLEWM<u>GRIDPaSGGI</u>KYAQKFQGRATLTVDTSTSTAYMELSRL RSDDTAVYYCAR<u>WDYGGYFDV</u>WGQGTLVTVSS |
| 138 | 20E6_H0.5_IgG1 | QVQLVQSGAEVKKPGASVKVSCKAS<u>GYTFTSYWMH</u>WVRQAPGQ GLEWM<u>GRIDPsSGGI</u>KYAQKFQGRATLTVDTSTSTAYMELSRL RSDDTAVYYCAR<u>WDYGGYFDV</u>WGQGTLVTVSS |
| 139 | 20E6_H0.6_IgG1 | QVQLVQSGAEVKKPGASVKVSCKAS<u>GYTFTSYWMH</u>WVRQAPGQ GLEWM<u>GRIDPhSGGI</u>KYAQKFQGRATLTVDTSTSTAYMELSRL RSDDTAVYYCAR<u>WDYGGYFDV</u>WGQGTLVTVSS |
| 140 | 20E6_H0.7_IgG1 | QVQLVQSGAEVKKPGASVKVSCKAS<u>GYTFTSYWMH</u>WVRQAPGQ GLEWM<u>GRIDPlSGGI</u>KYAQKFQGRATLTVDTSTSTAYMELSRL RSDDTAVYYCAR<u>WDYGGYFDV</u>WGQGTLVTVSS |
| 141 | 20E6_H0.8_IgG1 | QVQLVQSGAEVKKPGASVKVSCKAS<u>GYTFTSYWMH</u>WVRQAPGQ GLEWM<u>GRIDPdSGGI</u>KYAQKFQGRATLTVDTSTSTAYMELSRL RSDDTAVYYCAR<u>WDYGGYFDV</u>WGQGTLVTVSS |
| 142 | 20E6_H0.2_hIgG4mut VH | QVQLVQSGAEVKKPGASVKVSCKAS<u>GYTFTSYWMH</u>WVRQAPGQ GLEWM<u>GRIDPQSGGI</u>KYAQKFQGRATLTVDTSTSTAYMELSRL RSDDTAVYYCAR<u>WDYGGYFDV</u>WGQGTLVTVSS |
| 143 | 20E6_H0.2_hIgG4mut | QVQLVQSGAEVKKPGASVKVSCKAS<u>GYTFTSYWMH</u>WVRQAPGQ GLEWM<u>GRIDPQSGGI</u>KYAQKFQGRATLTVDTSTSTAYMELSRL RSDDTAVYYCAR<u>WDYGGYFDV</u>WGQGTLVTVSSASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEAAGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLGK |
| 144 | 20E6_H1 VH | QVQLVQSGAEVKKPGASVKVSCKAS<u>GYTFTSYWMH</u>WVRQAPGQ GLEWi<u>GRIDPNSGGI</u>KYNEKFKSRVTlTvDTSISTAYMELSRL RSDDTAVYYCAR<u>WDYGGYFDV</u>WGQGTLVTVSS |
| 145 | 20E6_H1_IgG1 | QVQLVQSGAEVKKPGASVKVSCKAS<u>GYTFTSYWMH</u>WVRQAPGQ GLEWi<u>GRIDPNSGGI</u>KYNEKFKSRVTlTvDTSISTAYMELSRL RSDDTAVYYCAR<u>WDYGGYFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 146 | 20E6_H2 VH | QVQLVQSGAEVKKPGASVKVSCKAS<u>GYTFTSYWMH</u>WVRQAPGQ GLEWi<u>GRIDPNSGGI</u>KYNEKFKSRVTlTvDkSsSTAYMELSRL RSDDTAVYYCAR<u>WDYGGYFDV</u>WGQGTLVTVSS |
| 147 | 20E6_H2_IgG1 | QVQLVQSGAEVKKPGASVKVSCKAS<u>GYTFTSYWMH</u>WVRQAPGQ GLEWi<u>GRIDPNSGGI</u>KYNEKFKSRVTlTvDkSsSTAYMELSRL RSDDTAVYYCAR<u>WDYGGYFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP |

TABLE 34-continued

Summary table of sequences

| SEQ ID | Description | Sequence |
|---|---|---|
| | | REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 148 | 20E6_H3 VH | QVQLVQSGAEVKKPGASVKVSCKAS<u>GYTFTSYWMH</u>WVkQrPGQ GLEWi<u>GRIDPNSGGI</u>KYNEKFKSkaTlTvDkSsSTAYMELSRL RSDDTAVYYCAR<u>WDYGGYFDV</u>WGQGTLVTVSS |
| 149 | 20E6_H3_IgG1 | QVQLVQSGAEVKKPGASVKVSCKAS<u>GYTFTSYWMH</u>WVkQrPGQ GLEWi<u>GRIDPNSGGI</u>KYNEKFKSkaTlTvDkSsSTAYMELSRL RSDDTAVYYCAR<u>WDYGGYFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 150 | 20E6_H4 VH | QVQLVQpGAEVvKPGASVKlSCKAS<u>GYTFTSYWMH</u>WVkQrPGQ GLEWi<u>GRIDPNSGGI</u>KYNEKFKSkaTlTvDkSsSTAYMELSRL RSDDTAVYYCAR<u>WDYGGYFDV</u>WGQGTLVTVSS |
| 151 | 20E6_H4_IgG1 | QVQLVQpGAEVvKPGASVKlSCKAS<u>GYTFTSYWMH</u>WVkQrPGQ GLEWi<u>GRIDPNSGGI</u>KYNEKFKSkaTlTvDkSsSTAYMELSRL RSDDTAVYYCAR<u>WDYGGYFDV</u>WGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 152 | 20E6_L0 VL | DIQMTQSPSSLSASVGDRVTITC<u>RASQDITNYLN</u>WYQQKPGKA PKLLIY<u>YTSRLHS</u>GVPSRFSGSGSGTDFTLTISSLQPEDFATY YC<u>QQGDTLPWT</u>FGQGTKLEIK |
| 153 | 20E6_L0 | DIQMTQSPSSLSASVGDRVTITC<u>RASQDITNYLN</u>WYQQKPGKA PKLLIY<u>YTSRLHS</u>GVPSRFSGSGSGTDFTLTISSLQPEDFATY YC<u>QQGDTLPWT</u>FGQGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| 154 | 20E6_L1 VL | DIQMTQSPSSLSASVGDRVTITC<u>RASQDITNYLN</u>WYQQKPGKA vKLLIY<u>YTSRLHS</u>GVPSRFSGSGSGTDyTLTISSLQPEDFATY fC<u>QQGDTLPWT</u>FGQGTKLEIK |
| 155 | 20E6_L1 | DIQMTQSPSSLSASVGDRVTITC<u>RASQDITNYLN</u>WYQQKPGKA vKLLIY<u>YTSRLHS</u>GVPSRFSGSGSGTDyTLTISSLQPEDFATY fC<u>QQGDTLPWT</u>FGQGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| 156 | 20E6_L0_P44V VL | DIQMTQSPSSLSASVGDRVTITC<u>RASQDITNYLN</u>WYQQKPGKA VKLLIY<u>YTSRLHS</u>GVPSRFSGSGSGTDFTLTISSLQPEDFATY YC<u>QQGDTLPWT</u>FGQGTKLEIK |
| 157 | 20E6_L0_P44V | DIQMTQSPSSLSASVGDRVTITC<u>RASQDITNYLN</u>WYQQKPGKA VKLLIY<u>YTSRLHS</u>GVPSRFSGSGSGTDFTLTISSLQPEDFATY YC<u>QQGDTLPWT</u>FGQGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| 158 | 20E6_L0_F71YVL | DIQMTQSPSSLSASVGDRVTITC<u>RASQDITNYLN</u>WYQQKPGKA PKLLIY<u>YTSRLHS</u>GVPSRFSGSGSGTDYTLTISSLQPEDFATY YC<u>QQGDTLPWT</u>FGQGTKLEIK |
| 159 | 20E6_L0_F71Y | DIQMTQSPSSLSASVGDRVTITC<u>RASQDITNYLN</u>WYQQKPGKA PKLLIY<u>YTSRLHS</u>GVPSRFSGSGSGTDYTLTISSLQPEDFATY YC<u>QQGDTLPWT</u>FGQGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| 160 | 20E6_L0_Y87F VL | DIQMTQSPSSLSASVGDRVTITC<u>RASQDITNYLN</u>WYQQKPGKA PKLLIY<u>YTSRLHS</u>GVPSRFSGSGSGTDFTLTISSLQPEDFATY FC<u>QQGDTLPWT</u>FGQGTKLEIK |
| 161 | 20E6_L0_Y87F | DIQMTQSPSSLSASVGDRVTITC<u>RASQDITNYLN</u>WYQQKPGKA PKLLIY<u>YTSRLHS</u>GVPSRFSGSGSGTDFTLTISSLQPEDFATY FC<u>QQGDTLPWT</u>FGQGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| 162 | 17G8(hyb)VHCDR1 | GFTFTDYYMS |
| 163 | 17G8(hyb)VHCDR2 | FIRNKANGYTTE |
| 164 | 17G8(hyb)VHCDR3 | YKLGGYFDV |
| 165 | 17G8(hyb)VLCDR1 | RASQDISNYLN |
| 166 | 17G8(hyb)VLCDR2 | YTSRLHS |

TABLE 34-continued

Summary table of sequences

| SEQ ID | Description | Sequence |
|---|---|---|
| 167 | 17G8(hyb)VLCDR3 | QQGNTLPWT |
| 168 | 17G8(hyb )VH | EVKLVESGGGLVQPGGSLSLSCAASGFTFTDYYMSWVRQPPGKALEWLGFIRNKANGYTTEYSASVKGRFTISRDNSQSILYLQMNALRAEDSATYYCARYKLGGYFDVWGTGTTVTVSS |
| 169 | 17G8(hyb) VL | DIQMTQTTSSLSASLGDRVTISCRASQDISNYLNWYQQKPDGTVKLLIYYTSRLHSGVPSRFSGSGSGTDYSLTISNLEQEDIATYFCQQGNTLPWTFGGGTKLEIK |
| 170 | 17G8(hyb) heavy chain | EVKLVESGGGLVQPGGSLSLSCAASGFTFTDYYMSWVRQPPGKALEWLGFIRNKANGYTTEYSASVKGRFTISRDNSQSILYLQMNALRAEDSATYYCARYKLGGYFDVWGTGTTVTVSSQSFPNVFPLVSCESPLSDKNLVAMGCLARDFLPSTISFTWNYQNNTEVIQGIRTFPTLRTGGKYLATSQVLLSPKSILEGSDEYLVCKIHYGGKNRDLHVPIPAVAEMNPNVNVFVPPRDGFSGPAPRKSKLICEATNFTPKPITVSWLKDGKLVESGFTTDPVTIENKGSTPQTYKVISTLTISEIDWLNLNVYTCRVDHRGLTFLKNVSSTCAASPSTDILTFTIPPSFADIFLSKSANLTCLVSNLATYETLNISWASQSGEPLETKIKIMESHPNGTFSAKGVASVCVEDWNNRKEFVCTVTHRDLPSPQKKFISKPNEVHKHPPAVYLLPPAREQLNLRESATVTCLVKGFSPADISVQWLQRGQLLPQEKYVTSAPMPEPGAPGFYFTHSILTVTEEEWNSGETYTCVVGHEALPHLVTERTVDKSTGKPTLYNVSLIMSDTGGTCY |
| 171 | 17G8(hyb) light chain | DIQMTQTTSSLSASLGDRVTISCRASQDISNYLNWYQQKPDGTVKLLIYYTSRLHSGVPSRFSGSGSGTDYSLTISNLEQEDIATYFCQQGNTLPWTFGGGTKLEIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC |
| 172 | 17G8(hyb)VHCDR2 N54Q | FIRNKAQGYTTE |
| 173 | 17G8(hyb)VHCDR2 N54G | FIRNKAGGYTTE |
| 174 | 17G8(hyb)VHCDR2 N54A | FIRNKAAGYTTE |
| 175 | 17G8(hyb)VHCDR2 N54S | FIRNKASGYTTE |
| 176 | 17G8(hyb)VHCDR2 N54H | FIRNKAHGYTTE |
| 177 | 17G8(hyb)VHCDR2 N54L | FIRNKALGYTTE |
| 178 | 17G8(hyb)VHCDR2 N54D | FIRNKADGYTTE |
| 179 | 24E3(hyb)VHCDR1 | GYTFTSYNMH |
| 180 | 24E3(hyb)VHCDR2 | AIYPGNGDTS |
| 181 | 24E3(hyb)VHCDR3 | WDWGGYFDV |
| 182 | 24E3(hyb)VLCDR1 | RASQDISNYLN |
| 183 | 24E3(hyb)VLCDR2 | YTSRLHS |
| 184 | 24E3(hyb)VLCDR3 | QQGDTLPWTF |
| 185 | 24E3(hyb)VH | QAYLQQSGAELVRPGASVKMSCKASGYTFTSYNMHWVKQTPRQGLEWIGAIYPGNGDTSYNPKFKGKATLTVDKSSSTAYMQLSSLTSEDSAVYFCTRWDWGGYFDVWGTGTTVTVSS |
| 186 | 24E3(hyb) VL | DIQMTQTTSSLSASLGDRVTISCRASQDISNYLNWYQQKPDGTVKLLIYYTSRLHSGVPSRFSGSGSGTDYSLTISNLEQEDIATYFCQQGDTLPWTFGGGTKLGIK |
| 187 | 24E3(hyb) heavy chain | QAYLQQSGAELVRPGASVKMSCKASGYTFTSYNMHWVKQTPRQGLEWIGAIYPGNGDTSYNPKFKGKATLTVDKSSSTAYMQLSSLTSEDSAVYFCTRWDWGGYFDVWGTGTTVTVSSQSFPNVFPLVSCESPLSDKNLVAMGCLARDFLPSTISFTWNYQNNTEVIQGIRTFPTLRTGGKYLATSQVLLSPKSILEGSDEYLVCKIHYGGKNRDLHVPIPAVAEMNPNVNVFVPPRDGFSGPAPRKSKLICEATNFTPKPITVSWLKDGKLVESGFTTDPVTIENKGSTPQTYKVISTLTISEIDWLNLNVYTCRVDHRGLTFLKNVSSTCAASPSTDILTFTIPPSFADIFLSKSANLTCLVSNLATYETLNISWASQSGEPLETKIKIMESHPNGTFSAKGVASVCVEDWNNRKEFVCTVTHRDLPSPQKKFISKPNEVHKHPPAVYLLPPAREQLNLRESATVTCLVKGFSPADISVQWLQRGQLLPQEKYVTSAPMPEPGAPGFYFTHSILTVTEEEWNSGETYTCVVGHEALPHLVTERTVDKSTGKPTLYNVSLIMSDTGGTCY |
| 188 | 24E3(hyb) light chain | DIQMTQTTSSLSASLGDRVTISCRASQDISNYLNWYQQKPDGTVKLLIYYTSRLHSGVPSRFSGSGSGTDYSLTISNLEQEDIATYFCQQGDTLPWTFGGGTKLGIKRADAAPTVSIFPPSSEQLTSGGASVVCFLNNFYPKDINVKWKIDGSERQNGVLNSWTDQDSKDSTYSMSSTLTLTKDEYERHNSYTCEATHKTSTSPIVKSFNRNEC |
| 189 | 24E3(hyb)VHCDR2 N54Q | AIYPGQGDTS |
| 190 | 24E3(hyb)VHCDR2 N54G | AIYPGGGDTS |
| 191 | 24E3(hyb)VHCDR2 N54A | AIYPGAGDTS |
| 192 | 24E3(hyb)VHCDR2 N54S | AIYPGSGDTS |
| 193 | 24E3(hyb)VHCDR2 N54H | AIYPGHGDTS |
| 194 | 24E3(hyb)VHCDR2 N54L | AIYPGLGDTS |
| 195 | 24E3(hyb)VHCDR2 N54D | AIYPGDGDTS |
| 196 | Human IgG1 constant region | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPI |

TABLE 34-continued

Summary table of sequences

| SEQ ID | Description | Sequence |
|---|---|---|
| 197 | Human IgG4 variant constant region (also referred to as "IgG4mut") | EKTISKAKGQPREPQVYTLPPSRDELTKNQVSLTCLVKGFYPS DIAVEWESNGQPENNYKTTPPVLDSDGSFFLYSKLTVDKSRWQ QGNVFSCSVMHEALHNHYTQKSLSLSPGK ASTKGPSVFPLAPCSRSTSESTAALGCLVKDYFPEPVTVSWNS GALTSGVHTFPAVLQSSGLYSLSSVVTVPSSSLGTKTYTCNVD HKPSNTKVDKRVESKYGPPCPPCPAPEAAGGPSVFLFPPKPKD TLMISRTPEVTCVVVDVSQEDPEVQFNWYVDGVEVHNAKTKPR EEQFNSTYRVVSVLTVLHQDWLNGKEYKCKVSNKGLPSSIEKT ISKAKGQPREPQVYTLPPSQEEMTKNQVSLTCLVKGFYPSDIA VEWESNGQPENNYKTTPPVLDSDGSFFLYSRLTVDKSRWQEGN VFSCSVMHEALHNHYTQKSLSLSLGK |
| 198 | chicken LAP-TGFβ1 | LSTCQRLDLEAAKKKRIEAVRGQILSKLRLTAPPPASETPPRP LPDDVRALYNSTQELLKQRARLRPPPDGPDEYWAKELRRIPME TTWDGPMEHWQPQSHSIFFVFNVSRVRAEVGGRALLHRAELRM LRQKAAADSAGTEQRLELYQGYGNASWRYLHGRSVRATADDEW LSFDVTDAVHQWLSGSELLGVFKLSVHCPCEMGPGHADEMRIS IEGFEQQRGDMQSIAKKHRRVPYVLAMALPAERANELHSARRR RDLDTDYCFGPGTDEKNCCVRPLYIDFRKDLQWKIHEPKGYM ANFCMGPCPYIWSADTQYTKVLALYNQHNPGASAAPCCVPQTL DPLPIIYYVGRNVRVEQLSNMVVRACKCS |
| 199 | human-chicken LAP-TGFβ1 chimera #1 | LSTCQRLDLEAAKKKRIEAVRGQILSKLRLTAPPPASETPPRP LPDDVRALYNSTQELLKQRARLRPPPDGPDEYWAKELRRIPME TTWDEIYDKFKQSTHSIYMFFNTSELREAVPEPVLLSRAELRL LRLKLKVEQHVELYQKYSNNSWRYLSNRLLAPSDSPEWLSFDV TGVVRQWLSRGGEIEGFRLSAHCSCDSRDNTLQVDINGFTTGR RGDLATIHGMNRPFLLLMATPLERAQHLQSSRHRRALDTNYCF SSTEKNCCVRQLYIDFRKDLGWKIHEPKGYHANFCLGPCPYI WSLDTQYSKVLALYNQHNPGASAAPCCVPQALEPLPIVYYVGR KPKVEQLSNMIVRSCKCS |
| 200 | human-chicken LAP-TGFβ1 chimera #1.2 | LSTCKTIDMELVKRKRIEAIRGQILSKLRLTAPPPASETPPRP LPDDVRALYNSTRDRVAGESAEPEPEPEADYYAKEVTRVLMVE THNEIYDKFKQSTHSIYMFFNTSELREAVPEPVLLSRAELRLL RLKLKVEQHVELYQKYSNNSWRYLSNRLLAPSDSPEWLSFDVT GVVRQWLSRGGEIEGFRLSAHCSCDSRDNTLQVDINGFTTGRR GDLATIHGMNRPFLLLMATPLERAQHLQSSRHRRALDTNYCFS STEKNCCVRQLYIDFRKDLGWKIHEPKGYHANFCLGPCPYIW SLDTQYSKVLALYNQHNPGASAAPCCVPQALEPLPIVYYVGRK PKVEQLSNMIVRSCKCS |
| 201 | human-chicken LAP-TGFβ1 chimera #1.3 | LSTCKTIDMELVKRKRIEAIRGQILSKLRLASPPSQGEVPPGP LPEAVLALYNSTQELLKQRARLRPPPDGPDEYWAKELRRVLMV ETHNEIYDKFKQSTHSIYMFFNTSELREAVPEPVLLSRAELRL LRLKLKVEQHVELYQKYSNNSWRYLSNRLLAPSDSPEWLSFDV TGVVRQWLSRGGEIEGFRLSAHCSCDSRDNTLQVDINGFTTGR RGDLATIHGMNRPFLLLMATPLERAQHLQSSRHRRALDTNYCF SSTEKNCCVRQLYIDFRKDLGWKIHEPKGYHANFCLGPCPYI WSLDTQYSKVLALYNQHNPGASAAPCCVPQALEPLPIVYYVGR KPKVEQLSNMIVRSCKCS |
| 202 | human-chicken LAP-TGFβ1 chimera #2 | LSTCKTIDMELVKRKRIEAIRGQILSKLRLASPPSQGEVPPGP LPEAVLALYNSTRDRVAGESAEPEPEPEADYYAKEVTRVLMVE THNGPMEHWQPQSHSIFFVFNVSRVRAEVGGRALLHRAELRML RQKAAADSAGTEQRLELYQKYSNNSWRYLSNRLLAPSDSPEWL SFDVTGVVRQWLSRGGEIEGFRLSAHCSCDSRDNTLQVDINGF TTGRRGDLATIHGMNRPFLLLMATPLERAQHLQSSRHRRALDT NYCFSSTEKNCCVRQLYIDFRKDLGWKIHEPKGYHANFCLGP CPYIWSLDTQYSKVLALYNQHNPGASAAPCCVPQALEPLPIVY YVGRKPKVEQLSNMIVRSCKCS |
| 203 | human-chicken LAP-TGFβ1 chimera #2.1 | LSTCKTIDMELVKRKRIEAIRGQILSKLRLASPPSQGEVPPGP LPEAVLALYNSTRDRVAGESAEPEPEPEADYYAKEVTRIPMET TWDGPMEHWQPQSHSIFFVFNTSELREAVPEPVLLSRAELRLL RLKLKVEQHVELYQKYSNNSWRYLSNRLLAPSDSPEWLSFDVT GVVRQWLSRGGEIEGFRLSAHCSCDSRDNTLQVDINGFTTGRR GDLATIHGMNRPFLLLMATPLERAQHLQSSRHRRALDTNYCFS STEKNCCVRQLYIDFRKDLGWKIHEPKGYHANFCLGPCPYIW SLDTQYSKVLALYNQHNPGASAAPCCVPQALEPLPIVYYVGRK PKVEQLSNMIVRSCKCS |
| 204 | human-chicken LAP-TGFβ1 chimera #2.2 | LSTCKTIDMELVKRKRIEAIRGQILSKLRLASPPSQGEVPPGP LPEAVLALYNSTRDRVAGESAEPEPEPEADYYAKEVTRVLMVE THNEIYDKFKQSTHSIYMFFNVSRVRAEVGGRALLHRAELRML RLLRLKLKVEQHVELYQKYSNNSWRYLSNRLLAPSDSPEWLSF DVTGVVRQWLSRGGEIEGFRLSAHCSCDSRDNTLQVDINGFTT GRRGDLATIHGMNRPFLLLMATPLERAQHLQSSRHRRALDTNY CFSSTEKNCCVRQLYIDFRKDLGWKIHEPKGYHANFCLGPCP YIWSLDTQYSKVLALYNQHNPGASAAPCCVPQALEPLPIVYYV GRKPKVEQLSNMIVRSCKCS |

TABLE 34-continued

Summary table of sequences

| SEQ ID | Description | Sequence |
|---|---|---|
| 205 | human-chicken LAP-TGFβ1 chimera #2.3 | LSTCKTIDMELVKRKRIEAIRGQILSKLRLASPPSQGEVPPGPLPEAVLALYNSTRDRVAGESAEPEPEPEADYYAKEVTRVLMVETHNEIYDKFKQSTHSIYMFFNTSELREAVPEPVLLSRAELRMLRQKAAADSAGTEQRLELYQGYGNASWRYLHGRSVRATADDEWLSFDVTGVVRQWLSRGGEIEGFRLSAHCSCDSRDNTLQVDINGFTTGRRGDLATIHGMNRPFLLLMATPLERAQHLQSSRHRRALDTNYCFSSTEKNCCVRQLYIDFRKDLGWKWIHEPKGYHANFCLGPCPYIWSLDTQYSKVLALYNQHNPGASAAPCCVPQALEPLPIVYYVGRKPKVEQLSNMIVRSCKCS |
| 206 | human-chicken LAP-TGFβ1 chimera #3 | LSTCKTIDMELVKRKRIEAIRGQILSKLRLASPPSQGEVPPGPLPEAVLALYNSTRDRVAGESAEPEPEPEADYYAKEVTRVLMVETHNEIYDKFKQSTHSIYMFFNTSELREAVPEPVLLSRAELRLLRLKLKVEQHVELYQGYGNASWRYLHGRSVRATADDEWLSFDVTDAVHQWLSGGEIEGFRLSAHCSCDSRDNTLQVDINGFTTGRRGDLATIHGMNRPFLLLMATPLERAQHLQSSRHRRALDTNYCFSSTEKNCCVRQLYIDFRKDLGWKWIHEPKGYHANFCLGPCPYIWSLDTQYSKVLALYNQHNPGASAAPCCVPQALEPLPIVYYVGRKPKVEQLSNMIVRSCKCS |
| 207 | human-chicken LAP-TGFβ1 chimera #4 | LSTCKTIDMELVKRKRIEAIRGQILSKLRLASPPSQGEVPPGPLPEAVLALYNSTRDRVAGESAEPEPEPEADYYAKEVTRVLMVETHNEIYDKFKQSTHSIYMFFNTSELREAVPEPVLLSRAELRLLRLKLKVEQHVELYQKYSNNSWRYLSNRLLAPSDSPEWLSFDVTGVVRQWLSRGSELLGVFKLSVHCPCEMGPGHADEMRISIEGFTTGRRGDLATIHGMNRPFLLLMATPLERAQHLQSSRHRRALDTNYCFSSTEKNCCVRQLYIDFRKDLGWKWIHEPKGYHANFCLGPCPYIWSLDTQYSKVLALYNQHNPGASAAPCCVPQALEPLPIVYYVGRKPKVEQLSNMIVRSCKCS |
| 208 | human-chicken LAP-TGFβ1 chimera #5 | LSTCKTIDMELVKRKRIEAIRGQILSKLRLASPPSQGEVPPGPLPEAVLALYNSTRDRVAGESAEPEPEPEADYYAKEVTRVLMVETHNEIYDKFKQSTHSIYMFFNTSELREAVPEPVLLSRAELRLLRLKLKVEQHVELYQKYSNNSWRYLSNRLLAPSDSPEWLSFDVTGVVRQWLSRGGEIEGFRLSAHCSCDSRDNTLQVDINGFEQQRGDMQSIAKKHRRVPYVLAMALPAERANELHSARRRDLDTDYCFSSTEKNCCVRQLYIDFRKDLGWKWIHEPKGYHANFCLGPCPYIWSLDTQYSKVLALYNQHNPGASAAPCCVPQALEPLPIVYYVGRKPKVEQLSNMIVRSCKCS |
| 209 | human-chicken LAP-TGFβ1 chimera #6 | LSTCKTIDMELVKRKRIEAIRGQILSKLRLASPPSQGEVPPGPLPEAVLALYNSTRDRVAGESAEPEPEPEADYYAKEVTRVLMVETHNEIYDKFKQSTHSIYMFFNTSELREAVPEPVLLSRAELRLLRLKLKVEQHVELYQKYSNNSWRYLSNRLLAPSDSPEWLSFDVTGVVRQWLSRGGEIEGFRLSAHCSCDSRDNTLQVDINGFTTGRRGDLATIHGMNRPFLLLMATPLERAQHLQSSRHRRALDTNYCFGPGTDEKNCCVRPLYIDFRKDLQWKWIHEPKGYMANFCMGPCPYIWSADTQYTKVLALYNQHNPGASAAPCCVPQALEPLPIVYYVGRKPKVEQLSNMIVRSCKCS |
| 210 | human-chicken LAP-TGFβ1 chimera #7 | LSTCKTIDMELVKRKRIEAIRGQILSKLRLASPPSQGEVPPGPLPEAVLALYNSTRDRVAGESAEPEPEPEADYYAKEVTRVLMVETHNEIYDKFKQSTHSIYMFFNTSELREAVPEPVLLSRAELRLLRLKLKVEQHVELYQKYSNNSWRYLSNRLLAPSDSPEWLSFDVTGVVRQWLSRGGEIEGFRLSAHCSCDSRDNTLQVDINGFTTGRRGDLATIHGMNRPFLLLMATPLERAQHLQSSRHRRALDTNYCFSSTEKNCCVRQLYIDFRKDLGWKWIHEPKGYHANFCLGPCPYIWSLDTQYSKVLALYNQHNPGASAAPCCVPQTLDPLPIIYYVGRNVRVEQLSNMVVRACKCS |
| 211 | Chicken-human LAP-TGFβ1 chimera chB1ex2.1_2.2 | LSTSQRLDLEAAKKKRIEAVRGQILSKLRLTAPPPASETPPRPLPDDVRALYNSTQELLKQRARLRPPPDGPDEYWAKELRRVLMVETHNEIYDKFKQSTHSIYMFFNTSELREAVPEPVLLSRAELRLLRLKLKVEQHVELYQKYGNASWRYLHGRSVRATADDEWLSFDVTDAVHQWLSGSELLGVFKLSVHCPCEMGPGHADEMRISIEGFEQQRGDMQSIAKKHRRVPYVLAMALPAERANELHSARRRDLDTDYCFGPGTDEKNCCVRPLYIDFRKDLQWKWIHEPKGYMANFCMGPCPYIWSADTQYTKVLALYNQHNPGASAAPCCVPQTLDPLPIIYYVGRNVRVEQLSNMVVRACKCS |
| 212 | Chicken-human LAP-TGFβ1 chimera chB1ex1.3 | LSTSQRLDLEAAKKKRIEAVRGQILSKLRLTAPPPASETPPRPLPDDVRALYNSTRDRVAGESAEPEPEPEADYYAKEVTRIPMETTWDGPMEHWQPQSHSIFFVFNVSRVRAEVGGRALLHRAELRMLRQKAAADSAGTEQRLELYQGYGNASWRYLHGRSVRATADDEWLSFDVTDAVHQWLSGSELLGVFKLSVHCPCEMGPGHADEMRISIEGFEQQRGDMQSIAKKHRRVPYVLAMALPAERANELHSARRRRDLDTDYCFGPGTDEKNCCVRPLYIDFRKDLQWKWIHEPKGYMANFCMGPCPYIWSADTQYTKVLALYNQHNPGASAAPCCVPQTLDPLPIIYYVGRNVRVEQLSNMVVRACKCS |
| 213 | Chicken-human LAP-TGFβ1 chimera chB1_ex1.2 | LSTSQRLDLEAAKKKRIEAVRGQILSKLRLASPPSQGEVPPGPLPEAVLALYNSTQELLKQRARLRPPPDGPDEYWAKELRRIPMETTWDGPMEHWQPQSHSIFFVFNVSRVRAEVGGRALLHRAELRMLRQKAAADSAGTEQRLELYQGYGNASWRYLHGRSVRATADDEW |

TABLE 34-continued

Summary table of sequences

| SEQ ID | Description | Sequence |
|---|---|---|
|  |  | LSFDVTDAVHQWLSGSELLGVFKLSVHCPCEMGPGHADEMRIS IEGFEQQRGDMQSIAKKHRRVPYVLAMALPAERANELHSARRR RDLDTDYCFGPGTDEKNCCVRPLYIDFRKDLQWKIHEPKGYM ANFCMGPCPYIWSADTQYTKVLALYNQHNPGASAAPCCVPQTL DPLPIIYYVGRNVRVEQLSNMVVRACKCS |
| 214 | Linker | PVGVV |
| 215 | LAP-TGFβ1 epitope | VLMVETHNEIYDKFKQSTHSIYMFFNTSELREAVPEPVLLSRA E |
| 216 | 28G11_L0 VL | DIQMTQSPSSLSASVGDRVTITCRASQDISNYLNWYQQKPGKV PKLLIYYTSRLHSGVPSRFSGSGSGTDFTLTISSLQPEDVATY YCQQGDTLPWTFGQGTKLEIK |
| 217 | 28G11_L0 | DIQMTQSPSSLSASVGDRVTITCRASQDISNYLNWYQQKPGKV PKLLIYYTSRLHSGVPSRFSGSGSGTDFTLTISSLQPEDVATY YCQQGDTLPWTFGQGTKLEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| 218 | 20E6_H0.2a VH | EVQLVQSGAEVKKPGASVKVSCKASGYTFTSYWMHWVRQAPGQ GLEWMGRIDPQSGGIKYAQKFQGRATLTVDTSTSTAYMELSRL RSDDTAVYYCARWDYGGYFDVWGQGTLVTVSS |
| 219 | 20E6_H0.2a_IgG1 | EVQLVQSGAEVKKPGASVKVSCKASGYTFTSYWMHWVRQAPGQ GLEWMGRIDPQSGGIKYAQKFQGRATLTVDTSTSTAYMELSRL RSDDTAVYYCARWDYGGYFDVWGQGTLVTVSSASTKGPSVFPL APSSKSTSGGTAALGCLVKDYFPEPVTVSWNSGALTSGVHTFP AVLQSSGLYSLSSVVTVPSSSLGTQTYICNVNHKPSNTKVDKK VEPKSCDKTHTCPPCPAPELLGGPSVFLFPPKPKDTLMISRTP EVTCVVVDVSHEDPEVKFNWYVDGVEVHNAKTKPREEQYNSTY RVVSVLTVLHQDWLNGKEYKCKVSNKALPAPIEKTISKAKGQP REPQVYTLPPSRDELTKNQVSLTCLVKGFYPSDIAVEWESNGQ PENNYKTTPPVLDSDGSFFLYSKLTVDKSRWQQGNVFSCSVMH EALHNHYTQKSLSLSPGK |
| 220 | 20E6_H0.2a_IgG4mut | EVQLVQSGAEVKKPGASVKVSCKASGYTFTSYWMHWVRQAPGQ GLEWMGRIDPQSGGIKYAQKFQGRATLTVDTSTSTAYMELSRL RSDDTAVYYCARWDYGGYFDVWGQGTLVTVSSASTKGPSVFPL APCSRSTSESTAALGCLVKDYFPEPVTVSWNSGALTSGVHTFP AVLQSSGLYSLSSVVTVPSSSLGTKTYTCNVDHKPSNTKVDKR VESKYGPPCPPCPAPEAAGGPSVFLFPPKPKDTLMISRTPEVT CVVVDVSQEDPEVQFNWYVDGVEVHNAKTKPREEQFNSTYRVV SVLTVLHQDWLNGKEYKCKVSNKGLPSSIEKTISKAKGQPREP QVYTLPPSQEEMTKNQVSLTCLVKGFYPSDIAVEWESNGQPEN NYKTTPPVLDSDGSFFLYSRLTVDKSRWQEGNVFSCSVMHEAL HNHYTQKSLSLSLGK |
| 221 | 7H4_HC (hyb) | DVQLQESGPGLVKPSQSLSLTCSVTGYSITSGYYWNWIRQFPG NKLEWMGYISYDGTNNYNPSLKNRISITRDTSKHQFFLKLNSV TTEDTATYYCARSFYNNYFDFWGQGTTLTVSSAKTTPPSVYPL APGCGDTTGSSVTLGCLVKGYFPESVTVTWNSGSLSSSVHTFP ALLQSGLYTMSSSVTVPSSTWPSQTVTCSVAHPASSTTVDKKL EPSGPISTINPCPPCKECHKCPAPNLEGGPSVFIFPPNIKDVL MISLTPKVTCVVVDVSEDDPDVQISWFVNNVEVHTAQTQTHRE DYNSTIRVVSTLPIQHQDWMSGKEFKCKVNNKDLPSPIERTIS KIKGLVRAPQVYILPPPAEQLSRKDVSLTCLVVGFNPGDISVE WTSNGHTEENYKDTAPVLDSDGSYFIYSKLNMKTSKWEKTDSF SCNVRHEGLKNYYLKKTISRSPGK |
| 222 | 7H4_LC (hyb) | DIQMTQSPSSLSASLGGKVTITCKASQDIDKYIAWYQHKPGKG PRLLIHYTSTLQPGIPSRFSGSGSGRDYSFNISNLEPEDIATY YCLQYDNLRTFGGGTKLEIKRADAAPTVSIFPPSSEQLTSGGA SVVCFLNNFYPKDINVKWKIDGSERQNGVLNSWTDQDSKDSTY SMSSTLTLTKDEYERHNSYTCEATHKTSTSPIVKSFNRNEC |
| 223 | 7H4_VH | DVQLQESGPGLVKPSQSLSLTCSVTGYSITSGYYWNWIRQFPG NKLEWMGYISYDGTNNYNPSLKNRISITRDTSKHQFFLKLNSV TTEDTATYYCARSFYNNYFDFWGQGTTLTVSS |
| 224 | 7H4_VL | DIQMTQSPSSLSASLGGKVTITCKASQDIDKYIAWYQHKPGKG PRLLIHYTSTLQPGIPSRFSGSGSGRDYSFNISNLEPEDIATY YCLQYDNLRTFGGGTKLEIK |
| 225 | 7H4_HCDR1 | GYSITSGYYWN |
| 226 | 7H4_HCDR2 | YISYDGTNNYNPSLKN |
| 227 | 7H4_HCDR3 | SFYNNYFDF |
| 228 | 7H4_LCDR1 | KASQDIDKYIA |
| 229 | 7H4_LCDR2 | YTSTLQP |
| 230 | 7H4_LCDR3 | LQYDNLRT |
| 231 | 7H4_HCDR2 (D55G) | YISYGGTNNYNPSLKN |
| 232 | 7H4_HCDR2 (D55A) | YISYAGTNNYNPSLKN |
| 233 | 7H4_HCDR2 (D55E) | YISYEGTNNYNPSLKN |
| 234 | 7H4_VHmut#1 (D55G) | DVQLQESGPGLVKPSQSLSLTCSVTGYSITSGYYWNWIRQFPG NKLEWMGYISYGGTNNYNPSLKNRISITRDTSKHQFFLKLNSV TTEDTATYYCARSFYNNYFDFWGQGTTLTVSS |

TABLE 34-continued

Summary table of sequences

| SEQ ID | Description | Sequence |
|---|---|---|
| 235 | 7H4_VHmut#2 (D55A) | DVQLQESGPGLVKPSQSLSLTCSVTGYSITSGYYWNWIRQFPG NKLEWMGYISYAGTNNYNPSLKNRISITRDTSKHQFFLKLNSV TTEDTATYYCARSFYNNYFDFWGQGTTLTVSS |
| 236 | 7H4_VHmut#3 (D55E) | DVQLQESGPGLVKPSQSLSLTCSVTGYSITSGYYWNWIRQFPG NKLEWMGYISYEGTNNYNPSLKNRISITRDTSKHQFFLKLNSV TTEDTATYYCARSFYNNYFDFWGQGTTLTVSS |
| 237 | 7H4_HCmut#1 (D55G) | DVQLQESGPGLVKPSQSLSLTCSVTGYSITSGYYWNWIRQFPG NKLEWMGYISYGGTNNYNPSLKNRISITRDTSKHQFFLKLNSV TTEDTATYYCARSFYNNYFDFWGQGTTLTVSSAKTTPPSVYPL APGCGDTTGSSVTLGCLVKGYFPESVTVTWNSGSLSSSVHTFP ALLQSGLYTMSSSVTVPSSTWPSQTVTCSVAHPASSTTVDKKL EPSGPISTINPCPPCKECHKCPAPNLEGGPSVFIFPPNIKDVL MISLTPKVTCVVVDVSEDDPDVQISWFVNNVEVHTAQTQTHRE DYNSTIRVVSTLPIQHQDWMSGKEFKCKVNNKDLPSPIERTIS KIKGLVRAPQVYILPPPAEQLSRKDVSLTCLVVGFNPGDISVE WTSNGHTEENYKDTAPVLDSDGSYFIYSKLNMKTSKWEKTDSF SCNVRHEGLKNYYLKKTISRSPGK |
| 238 | 7H4_HCmut#2 (D55A) | DVQLQESGPGLVKPSQSLSLTCSVTGYSITSGYYWNWIRQFPG NKLEWMGYISYAGTNNYNPSLKNRISITRDTSKHQFFLKLNSV TTEDTATYYCARSFYNNYFDFWGQGTTLTVSSAKTTPPSVYPL APGCGDTTGSSVTLGCLVKGYFPESVTVTWNSGSLSSSVHTFP ALLQSGLYTMSSSVTVPSSTWPSQTVTCSVAHPASSTTVDKKL EPSGPISTINPCPPCKECHKCPAPNLEGGPSVFIFPPNIKDVL MISLTPKVTCVVVDVSEDDPDVQISWFVNNVEVHTAQTQTHRE DYNSTIRVVSTLPIQHQDWMSGKEFKCKVNNKDLPSPIERTIS KIKGLVRAPQVYILPPPAEQLSRKDVSLTCLVVGFNPGDISVE WTSNGHTEENYKDTAPVLDSDGSYFIYSKLNMKTSKWEKTDSF SCNVRHEGLKNYYLKKTISRSPGK |
| 239 | 7H4_HCmut#3 (D55E) | DVQLQESGPGLVKPSQSLSLTCSVTGYSITSGYYWNWIRQFPG NKLEWMGYISYEGTNNYNPSLKNRISITRDTSKHQFFLKLNSV TTEDTATYYCARSFYNNYFDFWGQGTTLTVSSAKTTPPSVYPL APGCGDTTGSSVTLGCLVKGYFPESVTVTWNSGSLSSSVHTFP ALLQSGLYTMSSSVTVPSSTWPSQTVTCSVAHPASSTTVDKKL EPSGPISTINPCPPCKECHKCPAPNLEGGPSVFIFPPNIKDVL MISLTPKVTCVVVDVSEDDPDVQISWFVNNVEVHTAQTQTHRE DYNSTIRVVSTLPIQHQDWMSGKEFKCKVNNKDLPSPIERTIS KIKGLVRAPQVYILPPPAEQLSRKDVSLTCLVVGFNPGDISVE WTSNGHTEENYKDTAPVLDSDGSYFIYSKLNMKTSKWEKTDSF SCNVRHEGLKNYYLKKTISRSPGK |
| 240 | Pembrolizumab heavy chain | QVQLVQSGVEVKKPGASVKVSCKASGYTFTNYYMYWVRQAPGQ GLEWMGGINPSNGGTNFNEKFKNRVTLTTDSSTTTAYMELKSL QFDDTAVYYCARRDYRFDMGFDYWGQGTTVTVSSASTKGPSVF PLAPCSRSTSESTAALGCLVKDYFPEPVTVSWNSGALTSGVHT FPAVLQSSGLYSLSSVVTVPSSSLGTKTYTCNVDHKPSNTKVD KRVESKYGPPCPPCPAPEFLGGPSVFLFPPKPKDTLMISRTPE VTCVVVDVSQEDPEVQFNWYVDGVEVHNAKTKPREEQFNSTYR VVSVLTVLHQDWLNGKEYKCKVSNKGLPSSIEKTISKAKGQPR EPQVYTLPPSQEEMTKNQVSLTCLVKGFYPSDIAVEWESNGQP ENNYKTTPPVLDSDGSFFLYSRLTVDKSRWQEGNVFSCSVMHE ALHNHYTQKSLSLSLGK |
| 241 | Pembrolizumab light chain | EIVLTQSPATLSLSPGERATLSCRASKGVSTSGYSYLHWYQQK PGQAPRLLIYLASYLESGVPARFSGSGSGTDFTLTISSLEPED FAVYYCQHSRDLPLTFGGGTKVEIKRTVAAPSVFIFPPSDEQL KSGTASVVCLLNNFYPREAKVQWKVDNALQSGNSQESVTEQDS KDSTYSLSSTLTLSKADYEKHKVYACEVTHQGLSSPVTKSFNR GEC |
| 242 | 20E6 VHCDR3 consensus | WX$_1$YGGYFX$_2$X$_3$ (X$_1$–X$_3$ can be any amino acid) |
| 243 | 20E6 VLCDR3 consensus | QQGDX$_1$LPWT (X$_1$ can be any amino acid) |
| 244 | Human_IgG1_ P01857_L234A_L235A | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEaaGGPSVFLFPPK PKDTLMISRTPEVTCVVVDVSHEDPEVKFNWYVDGVEVHNAKT KPREEQYNSTYRVVSVLTVLHQDWLNGKEYKCKVSNKALPAPI EKTISKAKGQPREPQVYTLPPSRDELTKNQVSLTCLVKGFYPS DIAVEWESNGQPENNYKTTPPVLDSDGSFFLYSKLTVDKSRWQ QGNVFSCSVMHEALHNHYTQKSLSLSPGK |
| 245 | Human_IgG1_ P01857_L234A_L235A_ D265S | ASTKGPSVFPLAPSSKSTSGGTAALGCLVKDYFPEPVTVSWNS GALTSGVHTFPAVLQSSGLYSLSSVVTVPSSSLGTQTYICNVN HKPSNTKVDKKVEPKSCDKTHTCPPCPAPEaaGGPSVFLFPPK PKDTLMISRTPEVTCVVVsVSHEDPEVKFNWYVDGVEVHNAKT KPREEQYNSTYRVVSVLTVLHQDWLNGKEYKCKVSNKALPAPI EKTISKAKGQPREPQVYTLPPSRDELTKNQVSLTCLVKGFYPS DIAVEWESNGQPENNYKTTPPVLDSDGSFFLYSKLTVDKSRWQ QGNVFSCSVMHEALHNHYTQKSLSLSPGK |

TABLE 34-continued

Summary table of sequences

| SEQ ID | Description | Sequence |
|---|---|---|
| 246 | Nivolumab heavy chain | QVQLVESGGGVVQPGRSLRLDCKASGITFSNSGMHWVRQAPGK GLEWVAVIWYDGSKRYYADSVKGRFTISRDNSKNTLFLQMNSL RAEDTAVYYCATNDDYWGQGTLVTVSSASTKGPSVFPLAPCSR STSESTAALGCLVKDYFPEPVTVSWNSGALTSGVHTFPAVLQS SGLYSLSSVVTVPSSSLGTKTYTCNVDHKPSNTKVDKRVESKY GPPCPPCPAPEFLGGPSVFLFPPKPKDTLMISRTPEVTCVVVD VSQEDPEVQFNWYVDGVEVHNAKTKPREEQFNSTYRVVSVLTV LHQDWLNGKEYKCKVSNKGLPSSIEKTISKAKGQPREPQVYTL PPSQEEMTKNQVSLTCLVKGFYPSDIAVEWESNGQPENNYKTT PPVLDSDGSFFLYSRLTVDKSRWQEGNVFSCSVMHEALHNHYT QKSLSLSLGK |
| 247 | Nivolumab light chain | EIVLTQSPATLSLSPGERATLSCRASQSVSSYLAWYQQKPGQA PRLLIYDASNRATGIPARFSGSGSGTDFTLTISSLEPEDFAVY YCQQSSNWPRTFGQGTKVEIKRTVAAPSVFIFPPSDEQLKSGT ASVVCLLNNFYPREAKVQWKVDNALQSGNSQESVTEQDSKDST YSLSSTLTLSKADYEKHKVYACEVTHQGLSSPVTKSFNRGEC |
| 248 | 22F9_N54Q_D102A heavy chain | QVQLQQPGAELVKPGASVKLSCKASGYTFTSYWMHWVKQRPGQ GLEWIGMIHPQSGSTNYNEKFKSKATLTVDKSSSTAYMQLSSL TSEDSAVYYCAYYDYAGFFDVWGTGTTVTVSSAKTTAPSVYPL APVCGDTTGSSVTLGCLVKGYFPEPVTLTWNSGSLSSGVHTFP AVLQSDLYTLSSSVTVTSSTWPSQSITCNVAHPASSTKVDKKI EPRGPTIKPCPPCKCPAPNLLGGPSVFIFPPKIKDVLMISLSP IVTCVVVDVSEDDPDVQISWFVNNVEVHTAQTQTHREDYNSTL RVVSALPIQHQDWMSGKEFKCKVNNKDLPAPIERTISKPKGSV RAPQVYVLPPPEEEMTKKQVTLTCMVTDFMPEDIYVEWTNNGK TELNYKNTEPVLDSDGSYFMYSKLRVEKKNWVERNSYSCSVVH EGLHNHHTTKSFSRTPGK |
| 249 | 22F9_N54Q_D102A light chain | DIVLTQSPASLDVSLGQRATISCRASKSVSTSGYSYMHWYQQK SGQPPKLLIYLASNLESGVPARFSGSGSGTHFTLNIHPVEEED AATYYCQHSRELPYTFGGGTKLEIKRADAAPTVSIFPPSSEQL TSGGASVVCFLNNFYPKDINVKWKIDGSERQNGVLNSWTDQDS KDSTYSMSSTLTLTKDEYERHNSYTCEATHKTSTSPIVKSFNR NEC |
| 250 | Region 1 of LAP-TGFβ1 | RKRIEAIRGQIL |
| 251 | Region 2 of LAP-TGFβ1 | LASPPSQGEV |
| 252 | Region 3 of LAP-TGFβ1 | GWKWIHEPK |
| 253 | Region 4 of LAP-TGFβ1 | YVGRKPK |
| 254 | 2F8 binding region | VDINGFTTGRRGDLATIHGMN |
| 255 | 7H4_HCmut #3 (D55G) | DVQLQESGPGLVKPSQSLSLTCSVTGYSITSGYYWNWIRQFPG NKLEWMGYISYGGTNNYNPSLKNRISITRDTSKHQFFLKLNSV TTEDTATYYCARSFYNNYFDFWGQGTTLTVSSAKTTPPSVYPL APGCGDTTGSSVTLGCLVKGYFPESVTVTWNSGSLSSSVHTFP ALLQSGLYTMSSSVTVPSSTWPSQTVTCSVAHPASSTTVDKKL EPSGPISTINPCPPCKECHKCPAPNLEGGPSVFIFPPNIKDVL MISLTPKVTCVVVDVSEDDPDVQISWFVNNVEVHTAQTQTHRE DYNSTIRVVSTLPIQHQDWMSGKEFKCKVNNKDLPSPIERTIS KIKGLVRAPQVYILPPPAEQLSRKDVSLTCLVVGFNPGDISVE WTSNGHTEENYKDTAPVLDSDGSYFIYSKLNMKTSKWEKTDSF SCNVRHEGLKNYYLKKTISRSPGK |
| 256 | Kappa light chain constant domain | VAAPSVFIFPPSDEQLKSGTASVVCLLNNFYPREAKVQWKVDN ALQSGNSQESVTEQDSKDSTYSLSSTLTLSKADYEKHKVYACE VTHQGLSSPVTKSFNRGEC |

In this Table and previous Tables, unless indicated otherwise, it is understood that underlined underlining indicates the CDRs in the binding protein (e.g., antibody or antigen binding fragment thereof). Note that a CDR might be defined and identified by any of the methods and systems described herein (e.g., Chothia, Kabat, and IMGT).

EQUIVALENTS

Those skilled in the art will recognize, or be able to ascertain using no more than routine experimentation, many equivalents of the specific embodiments disclosed herein. Such equivalents are intended to be encompassed by the following claims.

The invention claimed is:

1. An isolated antibody or antigen binding fragment thereof which specifically binds to LAP comprising:

(a) a heavy chain variable region comprising CDR1, CDR2, and CDR3 regions comprising the amino acid sequences of SEQ ID NOs: 110, 120, and 112, respectively, and a light chain variable region comprising CDR1, CDR2, and CDR3 regions comprising the amino acid sequences of SEQ ID NOs: 113, 114, and 115, respectively;

(b) a heavy chain variable region comprising CDR1, CDR2, and CDR3 regions comprising the amino acid sequences of SEQ ID NOs: 110, 111, and 112, respectively, and a light chain variable region comprising CDR1, CDR2, and CDR3 regions comprising the amino acid sequences of SEQ ID NOs: 113, 114, and 115, respectively;
(c) a heavy chain variable region comprising CDR1, CDR2, and CDR3 regions comprising the amino acid sequences of SEQ ID NOs: 16, 26, and 18, respectively, and a light chain variable region comprising CDR1, CDR2, and CDR3 regions comprising the amino acid sequences of SEQ ID NOs: 19, 20, and 21, respectively;
(d) a heavy chain variable region comprising CDR1, CDR2, and CDR3 regions comprising the amino acid sequences of SEQ ID NOs: 54, 55, and 56, respectively, and a light chain variable region comprising CDR1, CDR2, and CDR3 regions comprising the amino acid sequences of SEQ ID NOs: 57, 58, and 59, respectively;
(e) a heavy chain variable region comprising CDR1, CDR2, and CDR3 regions comprising the amino acid sequences of SEQ ID NOs: 54, 66, and 56, respectively, and a light chain variable region comprising CDR1, CDR2, and CDR3 regions comprising the amino acid sequences of SEQ ID NOs: 57, 58, and 59, respectively;
(f) a heavy chain variable region comprising CDR1, CDR2, and CDR3 regions comprising the amino acid sequences of SEQ ID NOs: 54, 55, and 68, respectively, and a light chain variable region comprising CDR1, CDR2, and CDR3 regions comprising the amino acid sequences of SEQ ID NOs: 57, 58, and 59, respectively; or
(g) a heavy chain variable region comprising CDR1, CDR2, and CDR3 regions comprising the amino acid sequences of SEQ ID NOs: 54, 66, and 68, respectively, and a light chain variable region comprising CDR1, CDR2, and CDR3 regions comprising the amino acid sequences of SEQ ID NOs: 57, 58, and 59, respectively.

2. The antibody or antigen binding fragment thereof of claim 1 which comprises heavy and light chain variable region sequences which are at least 85%, 90%, 95%, 98%, or 99% identical to the amino acid sequences selected from the group consisting of: (a) SEQ ID NOs: 218 and 154, respectively; (b) SEQ ID NOs: 133 and 154, respectively; (c) SEQ ID NOs: 42 and 52, respectively; (d) SEQ ID NOs: 101 and 104, respectively; and (e) SEQ ID NOs: 98 and 104, respectively; or
which comprises a heavy chain variable region comprising the amino acid sequence of SEQ ID NO: 218 or a heavy chain variable region comprising the amino acid sequence of SEQ ID NO:218 with 1-5, 5-10, 10-15, 15-20, or 20-25 amino acid substitutions; and a light chain variable region comprising the amino acid sequence of SEQ ID NO: 154 or a light chain variable region comprising the amino acid sequence of SEQ ID NO: 154 with 1-5, 5-10, 10-15, 15-20, or 20-25 amino acid substitutions.

3. The antibody or antigen binding fragment thereof of claim 1 which comprises heavy and light chain sequences which are at least 85%, 90%, 95%, 98%, or 99% identical to the amino acid sequences selected from the group consisting of: (a) SEQ ID NOs: 219 and 155, respectively; (b) SEQ ID NOs: 220 and 155, respectively; (c) SEQ ID NOs: 134 and 155, respectively; (d) SEQ ID NOs: 135 and 155, respectively; (e) SEQ ID NOs: 43 and 53, respectively; (f) SEQ ID NOs: 45 and 53, respectively; (g) SEQ ID NOs: 102 and 105, respectively; (h) SEQ ID NOs: 103 and 105, respectively; (i) SEQ ID NOs: 99 and 105, respectively; and (j) SEQ ID NOs: 100 and 105, respectively.

4. The antibody or antigen binding fragment of claim 1, wherein the antibody binds to human LAP and inhibits TGFβ1 activation.

5. The antibody of claim 1, wherein the antibody comprises an IgG constant region or variant thereof and/or wherein the antibody is a chimeric, human or humanized antibody.

6. An isolated antibody which binds to human LAP and comprises a heavy chain variable region comprising CDR1, CDR2, and CDR3 regions comprising the amino acid sequences of SEQ ID NOs: 110, 120, and 112, respectively, and a light chain variable region comprising CDR1, CDR2, and CDR3 regions comprising the amino acid sequences of SEQ ID NOs: 113, 114, and 115, respectively, wherein the antibody further comprises a human IgG1 constant region.

7. An isolated antibody which binds to human LAP and comprises a heavy chain variable region comprising CDR1, CDR2, and CDR3 regions comprising the amino acid sequences of SEQ ID NOs: 110, 120, and 112, respectively, and a light chain variable region comprising CDR1, CDR2, and CDR3 regions comprising the amino acid sequences of SEQ ID NOs: 113, 114, and 115, respectively, wherein the antibody further comprises a mutant human IgG4 constant region comprising the amino acid sequence of SEQ ID NO: 197.

8. The antibody of claim 6, wherein the antibody comprises heavy and light chain variable regions comprising the amino acid sequences of SEQ ID NOs: 218 and 154, respectively.

9. An immunoconjugate comprising the antibody or antigen binding fragment of claim 1, linked to a detectable moiety, a binding moiety, a labeling moiety, or a biologically active moiety.

10. A pharmaceutical composition comprising the antibody or antigen binding fragment of claim 1, and a pharmaceutically acceptable carrier.

11. A kit comprising the antibody or antigen binding fragment of claim 1, and instructions for use.

12. The antibody or antigen binding fragment of claim 1, wherein the antibody binds to human LAP with a KD of 60 nM or less, 50 nM or less, 40 nM or less, 30 nM or less, 20 nM or less, or 10 nM or less.

13. The pharmaceutical composition of claim 10, further comprising one or more additional therapeutic agents.

14. The pharmaceutical composition of claim 13, wherein the one or more additional therapeutic agents is selected from the group consisting of an anti-cancer agent, a chemotherapeutic agent, an immunosuppressive agent, an immunostimulatory agent, an anti-inflammatory agent, and an immune checkpoint inhibitor.

15. The pharmaceutical composition of claim 14, wherein the immune checkpoint blocker is selected from the group consisting of: an anti-PD1 antibody, an anti-PD-L1 antibody, an anti-LAG-3 antibody, an anti-CTLA-4 antibody, an anti-TIGIT antibody, and an anti-TIM3 antibody.

16. The pharmaceutical composition of claim 14, wherein the PD-1 antibody is pembrolizumab.

17. The antibody or antigen binding fragment thereof of claim 1 which is an antibody that comprises heavy and light chain variable region sequences selected from the group consisting of: (a) SEQ ID NOs: 218 and 154, respectively; (b) SEQ ID NOs: 133 and 154, respectively; (c) SEQ ID NOs: 42 and 52, respectively; (d) SEQ ID NOs: 101 and 104, respectively; and (e) SEQ ID NOs: 98 and 104, respectively.

18. The antibody or antigen binding fragment thereof of claim 1 which is an antibody that comprises heavy and light chain sequences selected from the group consisting of: (a) SEQ ID NOs: 219 and 155, respectively; (b) SEQ ID NOs: 220 and 155, respectively; (c) SEQ ID NOs: 134 and 155, respectively; (d) SEQ ID NOs: 135 and 155, respectively; (e) SEQ ID NOs: 43 and 53, respectively; (f) SEQ ID NOs: 45 and 53, respectively; (g) SEQ ID NOs: 102 and 105, respectively; (h) SEQ ID NOs: 103 and 105, respectively; (i) SEQ ID NOs: 99 and 105, respectively; and (j) SEQ ID NOs: 100 and 105, respectively.

* * * * *

SEQUENCE LISTING

<160> NUMBER OF SEQ ID NOS: 257

<210> SEQ ID NO 1
<211> LENGTH: 361
<212> TYPE: PRT
<213> ORGANISM: Artificial Sequence
<220> FEATURE:

<223> OTHER INFORMATION: Synthetic: human LAP-TGF-beta-1

<400> SEQUENCE: 1

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
    290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
        355                 360

<210> SEQ ID NO 2
<211> LENGTH: 248
<212> TYPE: PRT
<213> ORGANISM: Artificial Sequence
<220> FEATURE:

<223> OTHER INFORMATION: Synthetic: LAP region of human LAP-TGF-beta-1

<400> SEQUENCE: 2

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
                20                  25                  30

Pro Pro Ser Gln Gly Glu Val Pro Pro Gly Pro Leu Pro Glu Ala Val
            35                  40                  45

Leu Ala Leu Tyr Asn Ser Thr Arg Asp Arg Val Ala Gly Glu Ser Ala
        50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
                100                 105                 110

Glu Ala Val Pro Glu Pro Val Leu Leu Ser Arg Ala Glu Leu Arg Leu
            115                 120                 125

Leu Arg Leu Lys Leu Lys Val Glu Gln His Val Glu Leu Tyr Gln Lys
        130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
                180                 185                 190

His Cys Ser Cys Asp Ser Arg Asp Asn Thr Leu Gln Val Asp Ile Asn
            195                 200                 205

Gly Phe Thr Thr Gly Arg Arg Gly Asp Leu Ala Thr Ile His Gly Met
        210                 215                 220

Asn Arg Pro Phe Leu Leu Leu Met Ala Thr Pro Leu Glu Arg Ala Gln
225                 230                 235                 240

His Leu Gln Ser Ser Arg His Arg
                245
```

<210> SEQ ID NO 3
<211> LENGTH: 394
<212> TYPE: PRT
<213> ORGANISM: Artificial Sequence
<220> FEATURE:
<223> OTHER INFORMATION: Synthetic: human LAP-TGF-beta-2

<400> SEQUENCE: 3

```
Leu Ser Thr Cys Ser Thr Leu Asp Met Asp Gln Phe Met Arg Lys Arg
1               5                   10                  15

Ile Glu Ala Ile Arg Gly Gln Ile Leu Ser Lys Leu Lys Leu Thr Ser
                20                  25                  30

Pro Pro Glu Asp Tyr Pro Glu Pro Glu Glu Val Pro Pro Glu Val Ile
            35                  40                  45

Ser Ile Tyr Asn Ser Thr Arg Asp Leu Leu Gln Glu Lys Ala Ser Arg
        50                  55                  60

Arg Ala Ala Ala Cys Glu Arg Glu Arg Ser Asp Glu Glu Tyr Tyr Ala
65                  70                  75                  80

Lys Glu Val Tyr Lys Ile Asp Met Pro Pro Phe Phe Pro Ser Glu Asn
                85                  90                  95
```

```
Ala Ile Pro Pro Thr Phe Tyr Arg Pro Tyr Phe Arg Ile Val Arg Phe
            100                 105                 110

Asp Val Ser Ala Met Glu Lys Asn Ala Ser Asn Leu Val Lys Ala Glu
            115                 120                 125

Phe Arg Val Phe Arg Leu Gln Asn Pro Lys Ala Arg Val Pro Glu Gln
            130                 135                 140

Arg Ile Glu Leu Tyr Gln Ile Leu Lys Ser Lys Asp Leu Thr Ser Pro
145                 150                 155                 160

Thr Gln Arg Tyr Ile Asp Ser Lys Val Val Lys Thr Arg Ala Glu Gly
            165                 170                 175

Glu Trp Leu Ser Phe Asp Val Thr Asp Ala Val His Glu Trp Leu His
            180                 185                 190

His Lys Asp Arg Asn Leu Gly Phe Lys Ile Ser Leu His Cys Pro Cys
            195                 200                 205

Cys Thr Phe Val Pro Ser Asn Asn Tyr Ile Ile Pro Asn Lys Ser Glu
            210                 215                 220

Glu Leu Glu Ala Arg Phe Ala Gly Ile Asp Gly Thr Ser Thr Tyr Thr
225                 230                 235                 240

Ser Gly Asp Gln Lys Thr Ile Lys Ser Thr Arg Lys Lys Asn Ser Gly
            245                 250                 255

Lys Thr Pro His Leu Leu Leu Met Leu Leu Pro Ser Tyr Arg Leu Glu
            260                 265                 270

Ser Gln Gln Thr Asn Arg Arg Lys Lys Arg Ala Leu Asp Ala Ala Tyr
            275                 280                 285

Cys Phe Arg Asn Val Gln Asp Asn Cys Cys Leu Arg Pro Leu Tyr Ile
            290                 295                 300

Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
            325                 330                 335

Asp Thr Gln His Ser Arg Val Leu Ser Leu Tyr Asn Thr Ile Asn Pro
            340                 345                 350

Glu Ala Ser Ala Ser Pro Cys Cys Val Ser Gln Asp Leu Glu Pro Leu
            355                 360                 365

Thr Ile Leu Tyr Tyr Ile Gly Lys Thr Pro Lys Ile Glu Gln Leu Ser
            370                 375                 380

Asn Met Ile Val Lys Ser Cys Lys Cys Ser
385                 390

<210> SEQ ID NO 4
<211> LENGTH: 282
<212> TYPE: PRT
<213> ORGANISM: Artificial Sequence
<220> FEATURE:
<223> OTHER INFORMATION: Synthetic: LAP region of human LAP-TGF-beta-2

<400> SEQUENCE: 4

Leu Ser Thr Cys Ser Thr Leu Asp Met Asp Gln Phe Met Arg Lys Arg
1               5                   10                  15

Ile Glu Ala Ile Arg Gly Gln Ile Leu Ser Lys Leu Lys Leu Thr Ser
            20                  25                  30

Pro Pro Glu Asp Tyr Pro Glu Pro Glu Glu Val Pro Pro Glu Val Ile
            35                  40                  45

Ser Ile Tyr Asn Ser Thr Arg Asp Leu Leu Gln Glu Lys Ala Ser Arg
        50                  55                  60
```

```
Arg Ala Ala Ala Cys Glu Arg Glu Arg Ser Asp Glu Glu Tyr Tyr Ala
 65                  70                  75                  80

Lys Glu Val Tyr Lys Ile Asp Met Pro Pro Phe Phe Pro Ser Glu Asn
                 85                  90                  95

Ala Ile Pro Pro Thr Phe Tyr Arg Pro Tyr Phe Arg Ile Val Arg Phe
            100                 105                 110

Asp Val Ser Ala Met Glu Lys Asn Ala Ser Asn Leu Val Lys Ala Glu
            115                 120                 125

Phe Arg Val Phe Arg Leu Gln Asn Pro Lys Ala Arg Val Pro Glu Gln
130                 135                 140

Arg Ile Glu Leu Tyr Gln Ile Leu Lys Ser Lys Asp Leu Thr Ser Pro
145                 150                 155                 160

Thr Gln Arg Tyr Ile Asp Ser Lys Val Val Lys Thr Arg Ala Glu Gly
                165                 170                 175

Glu Trp Leu Ser Phe Asp Val Thr Asp Ala Val His Glu Trp Leu His
            180                 185                 190

His Lys Asp Arg Asn Leu Gly Phe Lys Ile Ser Leu His Cys Pro Cys
            195                 200                 205

Cys Thr Phe Val Pro Ser Asn Asn Tyr Ile Ile Pro Asn Lys Ser Glu
210                 215                 220

Glu Leu Glu Ala Arg Phe Ala Gly Ile Asp Gly Thr Ser Thr Tyr Thr
225                 230                 235                 240

Ser Gly Asp Gln Lys Thr Ile Lys Ser Thr Arg Lys Lys Asn Ser Gly
                245                 250                 255

Lys Thr Pro His Leu Leu Leu Met Leu Leu Pro Ser Tyr Arg Leu Glu
            260                 265                 270

Ser Gln Gln Thr Asn Arg Arg Lys Lys Arg
            275                 280
```

<210> SEQ ID NO 5
<211> LENGTH: 389
<212> TYPE: PRT
<213> ORGANISM: Artificial Sequence
<220> FEATURE:
<223> OTHER INFORMATION: Synthetic: human LAP-TGF-beta-3

<400> SEQUENCE: 5

```
Leu Ser Thr Cys Thr Thr Leu Asp Phe Gly His Ile Lys Lys Lys Arg
 1               5                  10                  15

Val Glu Ala Ile Arg Gly Gln Ile Leu Ser Lys Leu Arg Leu Thr Ser
                20                  25                  30

Pro Pro Glu Pro Thr Val Met Thr His Val Pro Tyr Gln Val Leu Ala
            35                  40                  45

Leu Tyr Asn Ser Thr Arg Glu Leu Leu Glu Glu Met His Gly Glu Arg
 50                 55                  60

Glu Glu Gly Cys Thr Gln Glu Asn Thr Glu Ser Glu Tyr Tyr Ala Lys
 65                 70                  75                  80

Glu Ile His Lys Phe Asp Met Ile Gln Gly Leu Ala Glu His Asn Glu
                85                  90                  95

Leu Ala Val Cys Pro Lys Gly Ile Thr Ser Lys Val Phe Arg Phe Asn
            100                 105                 110

Val Ser Ser Val Glu Lys Asn Arg Thr Asn Leu Phe Arg Ala Glu Phe
            115                 120                 125

Arg Val Leu Arg Val Pro Asn Pro Ser Ser Lys Arg Asn Glu Gln Arg
130                 135                 140
```

```
Ile Glu Leu Phe Gln Ile Leu Arg Pro Asp Glu His Ile Ala Lys Gln
145                 150                 155                 160

Arg Tyr Ile Gly Gly Lys Asn Leu Pro Thr Arg Gly Thr Ala Glu Trp
            165                 170                 175

Leu Ser Phe Asp Val Thr Asp Thr Val Arg Glu Trp Leu Leu Arg Arg
            180                 185                 190

Glu Ser Asn Leu Gly Leu Glu Ile Ser Ile His Cys Pro Cys His Thr
            195                 200                 205

Phe Gln Pro Asn Gly Asp Ile Leu Glu Asn Ile His Glu Val Met Glu
            210                 215                 220

Ile Lys Phe Lys Gly Val Asp Asn Glu Asp Asp His Gly Arg Gly Asp
225                 230                 235                 240

Leu Gly Arg Leu Lys Lys Gln Lys Asp His His Asn Pro His Leu Ile
            245                 250                 255

Leu Met Met Ile Pro Pro His Arg Leu Asp Asn Pro Gly Gln Gly Gly
            260                 265                 270

Gln Arg Lys Lys Arg Ala Leu Asp Thr Asn Tyr Cys Phe Arg Asn Leu
            275                 280                 285

Glu Glu Asn Cys Cys Val Arg Pro Leu Tyr Ile Asp Phe Arg Gln Asp
            290                 295                 300

Leu Gly Trp Lys Trp Val His Glu Pro Lys Gly Tyr Tyr Ala Asn Phe
305                 310                 315                 320

Cys Ser Gly Pro Cys Pro Tyr Leu Arg Ser Ala Asp Thr Thr His Ser
            325                 330                 335

Thr Val Leu Gly Leu Tyr Asn Thr Leu Asn Pro Glu Ala Ser Ala Ser
            340                 345                 350

Pro Cys Cys Val Pro Gln Asp Leu Glu Pro Leu Thr Ile Leu Tyr Tyr
            355                 360                 365

Val Gly Arg Thr Pro Lys Val Glu Gln Leu Ser Asn Met Val Val Lys
            370                 375                 380

Ser Cys Lys Cys Ser
385

<210> SEQ ID NO 6
<211> LENGTH: 277
<212> TYPE: PRT
<213> ORGANISM: Artificial Sequence
<220> FEATURE:
<223> OTHER INFORMATION: Synthetic: LAP region of human LAP-TGF-beta-3

<400> SEQUENCE: 6

Leu Ser Thr Cys Thr Thr Leu Asp Phe Gly His Ile Lys Lys Lys Arg
1               5                   10                  15

Val Glu Ala Ile Arg Gly Gln Ile Leu Ser Lys Leu Arg Leu Thr Ser
            20                  25                  30

Pro Pro Glu Pro Thr Val Met Thr His Val Pro Tyr Gln Val Leu Ala
            35                  40                  45

Leu Tyr Asn Ser Thr Arg Glu Leu Leu Glu Glu Met His Gly Glu Arg
            50                  55                  60

Glu Glu Gly Cys Thr Gln Glu Asn Thr Glu Ser Glu Tyr Tyr Ala Lys
65                  70                  75                  80

Glu Ile His Lys Phe Asp Met Ile Gln Gly Leu Ala Glu His Asn Glu
            85                  90                  95

Leu Ala Val Cys Pro Lys Gly Ile Thr Ser Lys Val Phe Arg Phe Asn
            100                 105                 110
```

```
Val Ser Ser Val Glu Lys Asn Arg Thr Asn Leu Phe Arg Ala Glu Phe
        115                 120                 125

Arg Val Leu Arg Val Pro Asn Pro Ser Ser Lys Arg Asn Glu Gln Arg
    130                 135                 140

Ile Glu Leu Phe Gln Ile Leu Arg Pro Asp Glu His Ile Ala Lys Gln
145                 150                 155                 160

Arg Tyr Ile Gly Gly Lys Asn Leu Pro Thr Arg Gly Thr Ala Glu Trp
                165                 170                 175

Leu Ser Phe Asp Val Thr Asp Thr Val Arg Glu Trp Leu Leu Arg Arg
            180                 185                 190

Glu Ser Asn Leu Gly Leu Glu Ile Ser Ile His Cys Pro Cys His Thr
        195                 200                 205

Phe Gln Pro Asn Gly Asp Ile Leu Glu Asn Ile His Glu Val Met Glu
    210                 215                 220

Ile Lys Phe Lys Gly Val Asp Asn Glu Asp Asp His Gly Arg Gly Asp
225                 230                 235                 240

Leu Gly Arg Leu Lys Lys Gln Lys Asp His His Asn Pro His Leu Ile
                245                 250                 255

Leu Met Met Ile Pro Pro His Arg Leu Asp Asn Pro Gly Gln Gly Gly
            260                 265                 270

Gln Arg Lys Lys Arg
        275

<210> SEQ ID NO 7
<211> LENGTH: 361
<212> TYPE: PRT
<213> ORGANISM: Artificial Sequence
<220> FEATURE:
<223> OTHER INFORMATION: Synthetic: mouse LAP-TGF-beta-1

<400> SEQUENCE: 7

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
        115                 120                 125

Gln Arg Leu Lys Ser Ser Val Glu Gln His Val Glu Leu Tyr Gln Lys
    130                 135                 140

Tyr Ser Asn Asn Ser Trp Arg Tyr Leu Gly Asn Arg Leu Leu Thr Pro
145                 150                 155                 160

Thr Asp Thr Pro Glu Trp Leu Ser Phe Asp Val Thr Gly Val Val Arg
                165                 170                 175

Gln Trp Leu Asn Gln Gly Asp Gly Ile Gln Gly Phe Arg Phe Ser Ala
            180                 185                 190
```

```
His Cys Ser Cys Asp Ser Lys Asp Asn Lys Leu His Val Glu Ile Asn
            195                 200                 205

Gly Ile Ser Pro Lys Arg Arg Gly Asp Leu Gly Thr Ile His Asp Met
210                 215                 220

Asn Arg Pro Phe Leu Leu Leu Met Ala Thr Pro Leu Glu Arg Ala Gln
225                 230                 235                 240

His Leu His Ser Ser Arg His Arg Arg Ala Leu Asp Thr Asn Tyr Cys
            245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
            275                 280                 285

His Ala Asn Phe Cys Leu Gly Pro Cys Pro Tyr Ile Trp Ser Leu Asp
            290                 295                 300

Thr Gln Tyr Ser Lys Val Leu Ala Leu Tyr Asn Gln His Asn Pro Gly
305                 310                 315                 320

Ala Ser Ala Ser Pro Cys Cys Val Pro Gln Ala Leu Glu Pro Leu Pro
            325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
            355                 360

<210> SEQ ID NO 8
<211> LENGTH: 248
<212> TYPE: PRT
<213> ORGANISM: Artificial Sequence
<220> FEATURE:
<223> OTHER INFORMATION: Synthetic: LAP region of mouse LAP-TGF-beta-1

<400> SEQUENCE: 8

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
            35                  40                  45

Leu Ala Leu Tyr Asn Ser Thr Arg Asp Arg Val Ala Gly Glu Ser Ala
        50                  55                  60

Asp Pro Glu Pro Glu Pro Glu Ala Asp Tyr Tyr Ala Lys Glu Val Thr
65                  70                  75                  80

Arg Val Leu Met Val Asp Arg Asn Asn Ala Ile Tyr Glu Lys Thr Lys
                85                  90                  95

Asp Ile Ser His Ser Ile Tyr Met Phe Phe Asn Thr Ser Asp Ile Arg
            100                 105                 110

Glu Ala Val Pro Glu Pro Pro Leu Leu Ser Arg Ala Glu Leu Arg Leu
            115                 120                 125

Gln Arg Leu Lys Ser Ser Val Glu Gln His Val Glu Leu Tyr Gln Lys
        130                 135                 140

Tyr Ser Asn Ser Trp Arg Tyr Leu Gly Asn Arg Leu Leu Thr Pro Thr
145                 150                 155                 160

Asp Thr Pro Glu Trp Leu Ser Phe Asp Val Thr Gly Val Val Arg Gln
                165                 170                 175

Trp Leu Asn Gln Gly Asp Gly Ile Gln Gly Phe Arg Phe Ser Ala His
            180                 185                 190
```

Cys Ser Cys Asp Ser Lys Asp Asn Lys Leu His Val Glu Ile Asn Gly
            195                 200                 205

Ile Ser Pro Lys Arg Arg Gly Asp Leu Gly Thr Ile His Asp Met Asn
    210                 215                 220

Arg Pro Phe Leu Leu Leu Met Ala Thr Pro Leu Glu Arg Ala Gln His
225                 230                 235                 240

Leu His Ser Ser Arg His Arg Arg
                245

<210> SEQ ID NO 9
<211> LENGTH: 394
<212> TYPE: PRT
<213> ORGANISM: Artificial Sequence
<220> FEATURE:
<223> OTHER INFORMATION: Synthetic: mouse LAP-TGF-beta-2

<400> SEQUENCE: 9

Leu Ser Thr Cys Ser Thr Leu Asp Met Asp Gln Phe Met Arg Lys Arg
1               5                   10                  15

Ile Glu Ala Ile Arg Gly Gln Ile Leu Ser Lys Leu Lys Leu Thr Ser
            20                  25                  30

Pro Pro Glu Asp Tyr Pro Glu Pro Asp Glu Val Pro Pro Glu Val Ile
        35                  40                  45

Ser Ile Tyr Asn Ser Thr Arg Asp Leu Leu Gln Glu Lys Ala Ser Arg
    50                  55                  60

Arg Ala Ala Ala Cys Glu Arg Glu Arg Ser Asp Glu Glu Tyr Tyr Ala
65                  70                  75                  80

Lys Glu Val Tyr Lys Ile Asp Met Pro Ser His Leu Pro Ser Glu Asn
                85                  90                  95

Ala Ile Pro Pro Thr Phe Tyr Arg Pro Tyr Phe Arg Ile Val Arg Phe
            100                 105                 110

Asp Val Ser Thr Met Glu Lys Asn Ala Ser Asn Leu Val Lys Ala Glu
        115                 120                 125

Phe Arg Val Phe Arg Leu Gln Asn Pro Lys Ala Arg Val Ala Glu Gln
    130                 135                 140

Arg Ile Glu Leu Tyr Gln Ile Leu Lys Ser Lys Asp Leu Thr Ser Pro
145                 150                 155                 160

Thr Gln Arg Tyr Ile Asp Ser Lys Val Val Lys Thr Arg Ala Glu Gly
                165                 170                 175

Glu Trp Leu Ser Phe Asp Val Thr Asp Ala Val Gln Glu Trp Leu His
            180                 185                 190

His Lys Asp Arg Asn Leu Gly Phe Lys Ile Ser Leu His Cys Pro Cys
        195                 200                 205

Cys Thr Phe Val Pro Ser Asn Asn Tyr Ile Ile Pro Asn Lys Ser Glu
    210                 215                 220

Glu Leu Glu Ala Arg Phe Ala Gly Ile Asp Gly Thr Ser Thr Tyr Ala
225                 230                 235                 240

Ser Gly Asp Gln Lys Thr Ile Lys Ser Thr Arg Lys Lys Thr Ser Gly
                245                 250                 255

Lys Thr Pro His Leu Leu Leu Met Leu Leu Pro Ser Tyr Arg Leu Glu
            260                 265                 270

Ser Gln Gln Ser Ser Arg Arg Lys Lys Arg Ala Leu Asp Ala Ala Tyr
        275                 280                 285

Cys Phe Arg Asn Val Gln Asp Asn Cys Cys Leu Arg Pro Leu Tyr Ile
    290                 295                 300

```
Asp Phe Lys Arg Asp Leu Gly Trp Lys Trp Ile His Glu Pro Lys Gly
305                 310                 315                 320

Tyr Asn Ala Asn Phe Cys Ala Gly Ala Cys Pro Tyr Leu Trp Ser Ser
            325                 330                 335

Asp Thr Gln His Thr Lys Val Leu Ser Leu Tyr Asn Thr Ile Asn Pro
            340                 345                 350

Glu Ala Ser Ala Ser Pro Cys Cys Val Ser Gln Asp Leu Glu Pro Leu
            355                 360                 365

Thr Ile Leu Tyr Tyr Ile Gly Asn Thr Pro Lys Ile Glu Gln Leu Ser
370                 375                 380

Asn Met Ile Val Lys Ser Cys Lys Cys Ser
385                 390
```

<210> SEQ ID NO 10
<211> LENGTH: 282
<212> TYPE: PRT
<213> ORGANISM: Artificial Sequence
<220> FEATURE:
<223> OTHER INFORMATION: Synthetic: LAP region of mouse LAP-TGF-beta-2

<400> SEQUENCE: 10

```
Leu Ser Thr Cys Ser Thr Leu Asp Met Asp Gln Phe Met Arg Lys Arg
1               5                   10                  15

Ile Glu Ala Ile Arg Gly Gln Ile Leu Ser Lys Leu Lys Leu Thr Ser
            20                  25                  30

Pro Pro Glu Asp Tyr Pro Glu Pro Asp Glu Val Pro Pro Glu Val Ile
            35                  40                  45

Ser Ile Tyr Asn Ser Thr Arg Asp Leu Leu Gln Glu Lys Ala Ser Arg
50                  55                  60

Arg Ala Ala Ala Cys Glu Arg Glu Arg Ser Asp Glu Glu Tyr Tyr Ala
65                  70                  75                  80

Lys Glu Val Tyr Lys Ile Asp Met Pro Ser His Leu Pro Ser Glu Asn
                85                  90                  95

Ala Ile Pro Pro Thr Phe Tyr Arg Pro Tyr Phe Arg Ile Val Arg Phe
            100                 105                 110

Asp Val Ser Thr Met Glu Lys Asn Ala Ser Asn Leu Val Lys Ala Glu
        115                 120                 125

Phe Arg Val Phe Arg Leu Gln Asn Pro Lys Ala Arg Val Ala Glu Gln
    130                 135                 140

Arg Ile Glu Leu Tyr Gln Ile Leu Lys Ser Lys Asp Leu Thr Ser Pro
145                 150                 155                 160

Thr Gln Arg Tyr Ile Asp Ser Lys Val Val Lys Thr Arg Ala Glu Gly
                165                 170                 175

Glu Trp Leu Ser Phe Asp Val Thr Asp Ala Val Gln Glu Trp Leu His
            180                 185                 190

His Lys Asp Arg Asn Leu Gly Phe Lys Ile Ser Leu His Cys Pro Cys
        195                 200                 205

Cys Thr Phe Val Pro Ser Asn Asn Tyr Ile Ile Pro Asn Lys Ser Glu
    210                 215                 220

Glu Leu Glu Ala Arg Phe Ala Gly Ile Asp Gly Thr Ser Thr Tyr Ala
225                 230                 235                 240

Ser Gly Asp Gln Lys Thr Ile Lys Ser Thr Arg Lys Lys Thr Ser Gly
                245                 250                 255

Lys Thr Pro His Leu Leu Leu Met Leu Leu Pro Ser Tyr Arg Leu Glu
            260                 265                 270
```

Ser Gln Gln Ser Ser Arg Arg Lys Lys Arg
        275                 280

<210> SEQ ID NO 11
<211> LENGTH: 389
<212> TYPE: PRT
<213> ORGANISM: Artificial Sequence
<220> FEATURE:
<223> OTHER INFORMATION: Synthetic: mouse LAP-TGF-beta-3

<400> SEQUENCE: 11

Leu Ser Thr Cys Thr Thr Leu Asp Phe Gly His Ile Lys Lys Lys Arg
1               5                   10                  15

Val Glu Ala Ile Arg Gly Gln Ile Leu Ser Lys Leu Arg Leu Thr Ser
            20                  25                  30

Pro Pro Glu Pro Ser Val Met Thr His Val Pro Tyr Gln Val Leu Ala
        35                  40                  45

Leu Tyr Asn Ser Thr Arg Glu Leu Leu Glu Glu Met His Gly Glu Arg
    50                  55                  60

Glu Glu Gly Cys Thr Gln Glu Thr Ser Glu Ser Glu Tyr Tyr Ala Lys
65                  70                  75                  80

Glu Ile His Lys Phe Asp Met Ile Gln Gly Leu Ala Glu His Asn Glu
                85                  90                  95

Leu Ala Val Cys Pro Lys Gly Ile Thr Ser Lys Val Phe Arg Phe Asn
            100                 105                 110

Val Ser Ser Val Glu Lys Asn Gly Thr Asn Leu Phe Arg Ala Glu Phe
        115                 120                 125

Arg Val Leu Arg Val Pro Asn Pro Ser Ser Lys Arg Thr Glu Gln Arg
    130                 135                 140

Ile Glu Leu Phe Gln Ile Leu Arg Pro Asp Glu His Ile Ala Lys Gln
145                 150                 155                 160

Arg Tyr Ile Gly Gly Lys Asn Leu Pro Thr Arg Gly Thr Ala Glu Trp
                165                 170                 175

Leu Ser Phe Asp Val Thr Asp Thr Val Arg Glu Trp Leu Leu Arg Arg
            180                 185                 190

Glu Ser Asn Leu Gly Leu Glu Ile Ser Ile His Cys Pro Cys His Thr
        195                 200                 205

Phe Gln Pro Asn Gly Asp Ile Leu Glu Asn Val His Glu Val Met Glu
    210                 215                 220

Ile Lys Phe Lys Gly Val Asp Asn Glu Asp Asp His Gly Arg Gly Asp
225                 230                 235                 240

Leu Gly Arg Leu Lys Lys Gln Lys Asp His His Asn Pro His Leu Ile
                245                 250                 255

Leu Met Met Ile Pro Pro His Arg Leu Asp Ser Pro Gly Gln Gly Ser
            260                 265                 270

Gln Arg Lys Lys Arg Ala Leu Asp Thr Asn Tyr Cys Phe Arg Asn Leu
        275                 280                 285

Glu Glu Asn Cys Cys Val Arg Pro Leu Tyr Ile Asp Phe Arg Gln Asp
    290                 295                 300

Leu Gly Trp Lys Trp Val His Glu Pro Lys Gly Tyr Tyr Ala Asn Phe
305                 310                 315                 320

Cys Ser Gly Pro Cys Pro Tyr Leu Arg Ser Ala Asp Thr Thr His Ser
                325                 330                 335

Thr Val Leu Gly Leu Tyr Asn Thr Leu Asn Pro Glu Ala Ser Ala Ser
            340                 345                 350

```
Pro Cys Cys Val Pro Gln Asp Leu Glu Pro Leu Thr Ile Leu Tyr Tyr
            355                 360                 365

Val Gly Arg Thr Pro Lys Val Glu Gln Leu Ser Asn Met Val Val Lys
    370                 375                 380

Ser Cys Lys Cys Ser
385

<210> SEQ ID NO 12
<211> LENGTH: 277
<212> TYPE: PRT
<213> ORGANISM: Artificial Sequence
<220> FEATURE:
<223> OTHER INFORMATION: Synthetic: LAP region of mouse LAP-TGF-beta-3

<400> SEQUENCE: 12

Leu Ser Thr Cys Thr Thr Leu Asp Phe Gly His Ile Lys Lys Lys Arg
1               5                   10                  15

Val Glu Ala Ile Arg Gly Gln Ile Leu Ser Lys Leu Arg Leu Thr Ser
            20                  25                  30

Pro Pro Glu Pro Ser Val Met Thr His Val Pro Tyr Gln Val Leu Ala
        35                  40                  45

Leu Tyr Asn Ser Thr Arg Glu Leu Leu Glu Glu Met His Gly Glu Arg
    50                  55                  60

Glu Glu Gly Cys Thr Gln Glu Thr Ser Glu Ser Glu Tyr Tyr Ala Lys
65                  70                  75                  80

Glu Ile His Lys Phe Asp Met Ile Gln Gly Leu Ala Glu His Asn Glu
                85                  90                  95

Leu Ala Val Cys Pro Lys Gly Ile Thr Ser Lys Val Phe Arg Phe Asn
            100                 105                 110

Val Ser Ser Val Glu Lys Asn Gly Thr Asn Leu Phe Arg Ala Glu Phe
        115                 120                 125

Arg Val Leu Arg Val Pro Asn Pro Ser Ser Lys Arg Thr Glu Gln Arg
    130                 135                 140

Ile Glu Leu Phe Gln Ile Leu Arg Pro Asp Glu His Ile Ala Lys Gln
145                 150                 155                 160

Arg Tyr Ile Gly Gly Lys Asn Leu Pro Thr Arg Gly Thr Ala Glu Trp
                165                 170                 175

Leu Ser Phe Asp Val Thr Asp Thr Val Arg Glu Trp Leu Leu Arg Arg
            180                 185                 190

Glu Ser Asn Leu Gly Leu Glu Ile Ser Ile His Cys Pro Cys His Thr
        195                 200                 205

Phe Gln Pro Asn Gly Asp Ile Leu Glu Asn Val His Glu Val Met Glu
    210                 215                 220

Ile Lys Phe Lys Gly Val Asp Asn Glu Asp Asp His Gly Arg Gly Asp
225                 230                 235                 240

Leu Gly Arg Leu Lys Lys Gln Lys Asp His His Asn Pro His Leu Ile
                245                 250                 255

Leu Met Met Ile Pro Pro His Arg Leu Asp Ser Pro Gly Gln Gly Ser
            260                 265                 270

Gln Arg Lys Lys Arg
        275

<210> SEQ ID NO 13
<211> LENGTH: 360
<212> TYPE: PRT
<213> ORGANISM: Artificial Sequence
```

```
<220> FEATURE:
<223> OTHER INFORMATION: Synthetic: human LAP-TGF-beta-1 open
      conformation

<400> SEQUENCE: 13

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Thr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
        275                 280                 285

Ala Asn Phe Cys Leu Gly Pro Cys Pro Tyr Ile Trp Ser Leu Asp Thr
    290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
        355                 360

<210> SEQ ID NO 14
<211> LENGTH: 360
<212> TYPE: PRT
```

<213> ORGANISM: Artificial Sequence
<220> FEATURE:
<223> OTHER INFORMATION: Synthetic: human LAP-TGF-beta-1 closed conformation

<400> SEQUENCE: 14

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Cys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Cys Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
    130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
    210                 215                 220

Asn Arg Pro Phe Leu Leu Leu Met Ala Thr Pro Leu Glu Arg Ala Gln
225                 230                 235                 240

His Leu Gln Ser Ser Arg His Arg Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
        275                 280                 285

Ala Asn Phe Cys Leu Gly Pro Cys Pro Tyr Ile Trp Ser Leu Asp Thr
    290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
        355                 360
```

<210> SEQ ID NO 15
<211> LENGTH: 112

<212> TYPE: PRT
<213> ORGANISM: Artificial Sequence
<220> FEATURE:
<223> OTHER INFORMATION: Synthetic: human free TGF-beta-1 (mature
    TGF-beta-1 without LAP)

<400> SEQUENCE: 15

```
Ala Leu Asp Thr Asn Tyr Cys Phe Ser Ser Thr Glu Lys Asn Cys Cys
1               5                   10                  15

Val Arg Gln Leu Tyr Ile Asp Phe Arg Lys Asp Leu Gly Trp Lys Trp
            20                  25                  30

Ile His Glu Pro Lys Gly Tyr His Ala Asn Phe Cys Leu Gly Pro Cys
        35                  40                  45

Pro Tyr Ile Trp Ser Leu Asp Thr Gln Tyr Ser Lys Val Leu Ala Leu
    50                  55                  60

Tyr Asn Gln His Asn Pro Gly Ala Ser Ala Ala Pro Cys Cys Val Pro
65                  70                  75                  80

Gln Ala Leu Glu Pro Leu Pro Ile Val Tyr Tyr Val Gly Arg Lys Pro
                85                  90                  95

Lys Val Glu Gln Leu Ser Asn Met Ile Val Arg Ser Cys Lys Cys Ser
            100                 105                 110
```

<210> SEQ ID NO 16
<211> LENGTH: 5
<212> TYPE: PRT
<213> ORGANISM: Artificial Sequence
<220> FEATURE:
<223> OTHER INFORMATION: Synthetic: 28G11(hyb)VHCDR1

<400> SEQUENCE: 16

```
Asp Tyr Tyr Met Ser
1               5
```

<210> SEQ ID NO 17
<211> LENGTH: 12
<212> TYPE: PRT
<213> ORGANISM: Artificial Sequence
<220> FEATURE:
<223> OTHER INFORMATION: Synthetic: 28G11(hyb)VHCDR2 (extended
    definition of VHCDR2 used for humanization)

<400> SEQUENCE: 17

```
Phe Ile Arg Asn Lys Pro Asn Gly Tyr Thr Thr Glu
1               5                   10
```

<210> SEQ ID NO 18
<211> LENGTH: 9
<212> TYPE: PRT
<213> ORGANISM: Artificial Sequence
<220> FEATURE:
<223> OTHER INFORMATION: Synthetic: 28G11(hyb)VHCDR3

<400> SEQUENCE: 18

```
Tyr Thr Gly Gly Gly Tyr Phe Asp Tyr
1               5
```

<210> SEQ ID NO 19
<211> LENGTH: 11
<212> TYPE: PRT
<213> ORGANISM: Artificial Sequence
<220> FEATURE:
<223> OTHER INFORMATION: Synthetic: 28G11(hyb)VLCDR1

<400> SEQUENCE: 19

```
Arg Ala Ser Gln Asp Ile Ser Asn Tyr Leu Asn
1               5                   10

<210> SEQ ID NO 20
<211> LENGTH: 7
<212> TYPE: PRT
<213> ORGANISM: Artificial Sequence
<220> FEATURE:
<223> OTHER INFORMATION: Synthetic: 28G11(hyb)VLCDR2

<400> SEQUENCE: 20

Tyr Thr Ser Arg Leu His Ser
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic: 28G11(hyb)VLCDR3

<400> SEQUENCE: 21

Gln Gln Gly Asp Thr Leu Pro Trp Thr
1               5

<210> SEQ ID NO 22
<211> LENGTH: 120
<212> TYPE: PRT
<213> ORGANISM: Artificial Sequence
<220> FEATURE:
<223> OTHER INFORMATION: Synthetic: 28G11(hyb) VH

<400> SEQUENCE: 22

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Pro Asn Gly Tyr Thr Thr Glu Tyr Ser Ala
    50                  55                  60

Ser Val Lys Gly Arg Phe Thr Ile Ser Arg Asp Asn Ser Gln Ser Ile
65                  70                  75                  80

Leu Tyr Leu Gln Met Asn Val Leu Arg Ala Glu Asp Ser Ala Thr Tyr
                85                  90                  95

Tyr Cys Ala Arg Tyr Thr Gly Gly Gly Tyr Phe Asp Tyr Trp Gly Gln
            100                 105                 110

Gly Thr Thr Leu Thr Val Ser Ser
        115                 120

<210> SEQ ID NO 23
<211> LENGTH: 107
<212> TYPE: PRT
<213> ORGANISM: Artificial Sequence
<220> FEATURE:
<223> OTHER INFORMATION: Synthetic: 28G11(hyb) VL

<400> SEQUENCE: 23

Asp Ile Gln Met Thr Gln Thr Thr Ser Ser Leu Ser Ala Ser Leu Gly
1               5                   10                  15

Asp Arg Leu Thr Ile Ser Cys Arg Ala Ser Gln Asp Ile Ser Asn Tyr
            20                  25                  30
```

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Ala Asp Ile Ala Thr Tyr Phe Cys Gln Gln Gly Asp Thr Leu Pro Trp
                 85                  90                  95

Thr Phe Gly Gly Gly Thr Lys Leu Glu Ile Lys
                100                 105

<210> SEQ ID NO 24
<211> LENGTH: 456
<212> TYPE: PRT
<213> ORGANISM: Artificial Sequence
<220> FEATURE:
<223> OTHER INFORMATION: Synthetic: 28G11(hyb) heavy chain

<400> SEQUENCE: 24

Glu Val Lys Leu Val Glu Ser Gly Gly Gly Leu Val Gln Pro Gly Gly
 1               5                  10                  15

Ser Leu Ser Leu Ser Cys Ala Ala Ser Gly Phe Thr Phe Thr Asp Tyr
                 20                  25                  30

Tyr Met Ser Trp Val Arg Gln Pro Pro Gly Lys Ala Leu Glu Trp Leu
             35                  40                  45

Gly Phe Ile Arg Asn Lys Pro Asn Gly Tyr Thr Thr Glu Tyr Ser Ala
     50                  55                  60

Ser Val Lys Gly Arg Phe Thr Ile Ser Arg Asp Asn Ser Gln Ser Ile
 65                  70                  75                  80

Leu Tyr Leu Gln Met Asn Val Leu Arg Ala Glu Asp Ser Ala Thr Tyr
                 85                  90                  95

Tyr Cys Ala Arg Tyr Thr Gly Gly Tyr Phe Asp Tyr Trp Gly Gln
            100                 105                 110

Gly Thr Thr Leu Thr Val Ser Ser Ala Lys Thr Thr Pro Pro Ser Val
            115                 120                 125

Tyr Pro Leu Ala Pro Gly Cys Gly Asp Thr Thr Gly Ser Ser Val Thr
        130                 135                 140

Leu Gly Cys Leu Val Lys Gly Tyr Phe Pro Glu Ser Val Thr Val Thr
145                 150                 155                 160

Trp Asn Ser Gly Ser Leu Ser Ser Val His Thr Phe Pro Ala Leu
            165                 170                 175

Leu Gln Ser Gly Leu Tyr Thr Met Ser Ser Ser Val Thr Val Pro Ser
            180                 185                 190

Ser Thr Trp Pro Ser Gln Thr Val Thr Cys Ser Val Ala His Pro Ala
        195                 200                 205

Ser Ser Thr Thr Val Asp Lys Lys Leu Glu Pro Ser Gly Pro Ile Ser
    210                 215                 220

Thr Ile Asn Pro Cys Pro Cys Lys Glu Cys His Lys Cys Pro Ala
225                 230                 235                 240

Pro Asn Leu Glu Gly Gly Pro Ser Val Phe Ile Phe Pro Pro Asn Ile
            245                 250                 255

Lys Asp Val Leu Met Ile Ser Leu Thr Pro Lys Val Thr Cys Val Val
            260                 265                 270

Val Asp Val Ser Glu Asp Asp Pro Asp Val Gln Ile Ser Trp Phe Val
        275                 280                 285

```
Asn Asn Val Glu Val His Thr Ala Gln Thr Gln Thr His Arg Glu Asp
    290                 295                 300

Tyr Asn Ser Thr Ile Arg Val Val Ser Thr Leu Pro Ile Gln His Gln
305                 310                 315                 320

Asp Trp Met Ser Gly Lys Glu Phe Lys Cys Lys Val Asn Asn Lys Asp
                325                 330                 335

Leu Pro Ser Pro Ile Glu Arg Thr Ile Ser Lys Ile Lys Gly Leu Val
            340                 345                 350

Arg Ala Pro Gln Val Tyr Ile Leu Pro Pro Ala Glu Gln Leu Ser
        355                 360                 365

Arg Lys Asp Val Ser Leu Thr Cys Leu Val Val Gly Phe Asn Pro Gly
    370                 375                 380

Asp Ile Ser Val Glu Trp Thr Ser Asn Gly His Thr Glu Glu Asn Tyr
385                 390                 395                 400

Lys Asp Thr Ala Pro Val Leu Asp Ser Asp Gly Ser Tyr Phe Ile Tyr
                405                 410                 415

Ser Lys Leu Asn Met Lys Thr Ser Lys Trp Glu Lys Thr Asp Ser Phe
            420                 425                 430

Ser Cys Asn Val Arg His Glu Gly Leu Lys Asn Tyr Tyr Leu Lys Lys
        435                 440                 445

Thr Ile Ser Arg Ser Pro Gly Lys
    450                 455

<210> SEQ ID NO 25
<211> LENGTH: 214
<212> TYPE: PRT
<213> ORGANISM: Artificial Sequence
<220> FEATURE:
<223> OTHER INFORMATION: Synthetic: 28G11(hyb) light chain

<400> SEQUENCE: 25

Asp Ile Gln Met Thr Gln Thr Thr Ser Ser Leu Ser Ala Ser Leu Gly
1               5                   10                  15

Asp Arg Leu Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Ala Asp Ile Ala Thr Tyr Phe Cys Gln Gln Gly Asp Thr Leu Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190
```

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 26
<211> LENGTH: 12
<212> TYPE: PRT
<213> ORGANISM: Artificial Sequence
<220> FEATURE:
<223> OTHER INFORMATION: Synthetic: 28G11 VHCDR2 N56Q

<400> SEQUENCE: 26

Phe Ile Arg Asn Lys Pro Gln Gly Tyr Thr Thr Glu
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic: 28G11 VHCDR2 N56S

<400> SEQUENCE: 27

Phe Ile Arg Asn Lys Pro Ser Gly Tyr Thr Thr Glu
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Synthetic: 28G11 VHCDR2 N56H

<400> SEQUENCE: 28

Phe Ile Arg Asn Lys Pro His Gly Tyr Thr Thr Glu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Synthetic: 28G11 VHCDR2 N56L

<400> SEQUENCE: 29

Phe Ile Arg Asn Lys Pro Leu Gly Tyr Thr Thr Glu
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic: 28G11 VHCDR2 N56D

<400> SEQUENCE: 30

Phe Ile Arg Asn Lys Pro Asp Gly Tyr Thr Thr Glu
1               5                   10

<210> SEQ ID NO 31
<211> LENGTH: 120
<212> TYPE: PRT
<213> ORGANISM: Artificial Sequence
<220> FEATURE:
<223> OTHER INFORMATION: Synthetic: 28G11_H0 VH

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Pro Asn Gly Tyr Thr Thr Glu Tyr Ser Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Thr Gly Gly Gly Tyr Phe Asp Tyr Trp Gly Gln
            100                 105                 110

Gly Thr Leu Val Thr Val Ser Ser
        115                 120

<210> SEQ ID NO 32
<211> LENGTH: 450
<212> TYPE: PRT
<213> ORGANISM: Artificial Sequence
<220> FEATURE:
<223> OTHER INFORMATION: Synthetic: 28G11_H0_IgG1

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Pro Asn Gly Tyr Thr Thr Glu Tyr Ser Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Thr Gly Gly Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly

```
                   225                 230                 235                 240
        Pro Ser Val Phe Leu Phe Pro Lys Pro Lys Asp Thr Leu Met Ile
                          245                 250                 255

Ser Arg Thr Pro Glu Val Thr Cys Val Val Val Asp Val Ser His Glu
                      260                 265                 270

Asp Pro Glu Val Lys Phe Asn Trp Tyr Val Asp Gly Val Glu Val His
                      275                 280                 285

Asn Ala Lys Thr Lys Pro Arg Glu Glu Gln Tyr Asn Ser Thr Tyr Arg
                      290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Ala Leu Pro Ala Pro Ile Glu
                          325                 330                 335

Lys Thr Ile Ser Lys Ala Lys Gly Gln Pro Arg Glu Pro Gln Val Tyr
                          340                 345                 350

Thr Leu Pro Pro Ser Arg Asp Glu Leu Thr Lys Asn Gln Val Ser Leu
                          355                 360                 365

Thr Cys Leu Val Lys Gly Phe Tyr Pro Ser Asp Ile Ala Val Glu Trp
                          370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Lys Leu Thr Val Asp
                          405                 410                 415

Lys Ser Arg Trp Gln Gln Gly Asn Val Phe Ser Cys Ser Val Met His
                          420                 425                 430

Glu Ala Leu His Asn His Tyr Thr Gln Lys Ser Leu Ser Leu Ser Pro
                          435                 440                 445

Gly Lys
            450

<210> SEQ ID NO 33
<211> LENGTH: 120
<212> TYPE: PRT
<213> ORGANISM: Artificial Sequence
<220> FEATURE:
<223> OTHER INFORMATION: Synthetic: 28G11_H1 VH

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Pro Asn Gly Tyr Thr Thr Glu Tyr Ser Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Thr Gly Gly Gly Tyr Phe Asp Tyr Trp Gly Gln
            100                 105                 110

Gly Thr Leu Val Thr Val Ser Ser
        115                 120
```

<210> SEQ ID NO 34
<211> LENGTH: 450
<212> TYPE: PRT
<213> ORGANISM: Artificial Sequence
<220> FEATURE:
<223> OTHER INFORMATION: Synthetic: 28G11_H1_IgG1

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Pro Asn Gly Tyr Thr Thr Glu Tyr Ser Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Thr Gly Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
```

```
                370                 375                 380
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 35
<211> LENGTH: 120
<212> TYPE: PRT
<213> ORGANISM: Artificial Sequence
<220> FEATURE:
<223> OTHER INFORMATION: Synthetic: 28G11_H2 VH

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Pro Asn Gly Tyr Thr Thr Glu Tyr Ser Ala
    50                  55                  60

Ser Val Lys Gly Arg Phe Thr Ile Ser Arg Asp Asn Ser Gln Ser Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Thr Gly Gly Gly Tyr Phe Asp Tyr Trp Gly Gln
            100                 105                 110

Gly Thr Leu Leu Thr Val Ser Ser
        115                 120

<210> SEQ ID NO 36
<211> LENGTH: 450
<212> TYPE: PRT
<213> ORGANISM: Artificial Sequence
<220> FEATURE:
<223> OTHER INFORMATION: Synthetic: 28G11_H2_IgG1

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Pro Asn Gly Tyr Thr Thr Glu Tyr Ser Ala
    50                  55                  60

Ser Val Lys Gly Arg Phe Thr Ile Ser Arg Asp Asn Ser Gln Ser Ser
65                  70                  75                  80

Leu Tyr Leu Gln Met Asn Ser Leu Lys Thr Glu Asp Thr Ala Val Tyr
                85                  90                  95
```

```
Tyr Cys Ala Arg Tyr Thr Gly Gly Gly Tyr Phe Asp Tyr Trp Gly Gln
            100                 105                 110
Gly Thr Leu Leu Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys
    450

<210> SEQ ID NO 37
<211> LENGTH: 447
<212> TYPE: PRT
<213> ORGANISM: Artificial Sequence
<220> FEATURE:
<223> OTHER INFORMATION: Synthetic: 28G11_H2_IgG4mut

<400> SEQUENCE: 37
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Pro Asn Gly Tyr Thr Thr Glu Tyr Ser Ala
    50                  55                  60

Ser Val Lys Gly Arg Phe Thr Ile Ser Arg Asp Asn Ser Gln Ser Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Thr Gly Gly Tyr Phe Asp Tyr Trp Gly Gln
            100                 105                 110

Gly Thr Leu Leu Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
        260                 265                 270

Val Gln Phe Asn Trp Tyr Val Asp Gly Val Glu Val His Asn Ala Lys
    275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Gln Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
```

<210> SEQ ID NO 38
<211> LENGTH: 120
<212> TYPE: PRT
<213> ORGANISM: Artificial Sequence
<220> FEATURE:
<223> OTHER INFORMATION: Synthetic: 28G11_H2.1 VH

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Pro Gln Gly Tyr Thr Thr Glu Tyr Ser Ala
    50                  55                  60

Ser Val Lys Gly Arg Phe Thr Ile Ser Arg Asp Asn Ser Gln Ser Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Thr Gly Gly Gly Tyr Phe Asp Tyr Trp Gly Gln
            100                 105                 110

Gly Thr Leu Leu Thr Val Ser Ser
        115                 120

<210> SEQ ID NO 39
<211> LENGTH: 450
<212> TYPE: PRT
<213> ORGANISM: Artificial Sequence
<220> FEATURE:
<223> OTHER INFORMATION: Synthetic: 28G11_H2.1_IgG1

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Leu
        35                  40                  45

Gly Phe Ile Arg Asn Lys Pro Gln Gly Tyr Thr Thr Glu Tyr Ser Ala
    50                  55                  60

Ser Val Lys Gly Arg Phe Thr Ile Ser Arg Asp Asn Ser Gln Ser Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Thr Gly Gly Gly Tyr Phe Asp Tyr Trp Gly Gln
            100                 105                 110

Gly Thr Leu Leu Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 40
<211> LENGTH: 120
<212> TYPE: PRT
<213> ORGANISM: Artificial Sequence
<220> FEATURE:
<223> OTHER INFORMATION: Synthetic: 28G11_H2a VH

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Pro Asn Gly Tyr Thr Thr Glu Tyr Ser Ala
    50                  55                  60

```
Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg Tyr Thr Gly Gly Tyr Phe Asp Tyr Trp Gly Gln
                100                 105                 110

Gly Thr Leu Val Thr Val Ser Ser
        115                 120

<210> SEQ ID NO 41
<211> LENGTH: 450
<212> TYPE: PRT
<213> ORGANISM: Artificial Sequence
<220> FEATURE:
<223> OTHER INFORMATION: Synthetic: 28G11_H2a_IgG1

<400> SEQUENCE: 41

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asp Tyr
             20                  25                  30

Tyr Met Ser Trp Val Arg Gln Ala Pro Gly Lys Gly Leu Glu Trp Val
         35                  40                  45

Gly Phe Ile Arg Asn Lys Pro Asn Gly Tyr Thr Thr Glu Tyr Ser Ala
     50                  55                  60

Ser Val Lys Gly Arg Phe Thr Ile Ser Arg Asp Asn Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg Tyr Thr Gly Gly Tyr Phe Asp Tyr Trp Gly Gln
                100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 42
<211> LENGTH: 120
<212> TYPE: PRT
<213> ORGANISM: Artificial Sequence
<220> FEATURE:
<223> OTHER INFORMATION: Synthetic: 28G11_H2b VH

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Pro Gln Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Thr Gly Gly Gly Tyr Phe Asp Tyr Trp Gly Gln
            100                 105                 110

Gly Thr Leu Val Thr Val Ser Ser
        115                 120

<210> SEQ ID NO 43
<211> LENGTH: 450
<212> TYPE: PRT
<213> ORGANISM: Artificial Sequence
<220> FEATURE:
<223> OTHER INFORMATION: Synthetic: 28G11_H2b_IgG1

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30
```

```
Tyr Met Ser Trp Val Arg Gln Ala Pro Gly Lys Gly Leu Glu Trp Val
        35                  40                  45
Gly Phe Ile Arg Asn Lys Pro Gln Gly Tyr Thr Thr Glu Tyr Ser Ala
    50                  55                  60
Ser Val Lys Gly Arg Phe Thr Ile Ser Arg Asp Asn Ser Lys Asn Ser
65                  70                  75                  80
Leu Tyr Leu Gln Met Asn Ser Leu Lys Thr Glu Asp Thr Ala Val Tyr
                85                  90                  95
Tyr Cys Ala Arg Tyr Thr Gly Gly Tyr Phe Asp Tyr Trp Gly Gln
                100                 105                 110
Gly Thr Leu Val Thr Val Ser Ser Ala Ser Thr Lys Gly Pro Ser Val
            115                 120                 125
Phe Pro Leu Ala Pro Ser Ser Lys Ser Thr Ser Gly Gly Thr Ala Ala
        130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
        275                 280                 285
Asn Ala Lys Thr Lys Pro Arg Glu Glu Gln Tyr Asn Ser Thr Tyr Arg
    290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Asp Glu Leu Thr Lys Asn Gln Val Ser Leu
        355                 360                 365
Thr Cys Leu Val Lys Gly Phe Tyr Pro Ser Asp Ile Ala Val Glu Trp
    370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
```

Gly Lys
    450

<210> SEQ ID NO 44
<211> LENGTH: 120
<212> TYPE: PRT
<213> ORGANISM: Artificial Sequence
<220> FEATURE:
<223> OTHER INFORMATION: Synthetic: 28G11_H2b_hIgG4mut VH

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Pro Gln Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Thr Gly Gly Gly Tyr Phe Asp Tyr Trp Gly Gln
            100                 105                 110

Gly Thr Leu Val Thr Val Ser Ser
        115                 120

<210> SEQ ID NO 45
<211> LENGTH: 447
<212> TYPE: PRT
<213> ORGANISM: Artificial Sequence
<220> FEATURE:
<223> OTHER INFORMATION: Synthetic: 28G11_H2b_hIgG4mut

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Tyr Met Ser Trp Val Arg Gln Ala Pro Gly Lys Gly Leu Glu Trp Val
        35                  40                  45

Gly Phe Ile Arg Asn Lys Pro Gln Gly Tyr Thr Thr Glu Tyr Ser Ala
    50                  55                  60

Ser Val Lys Gly Arg Phe Thr Ile Ser Arg Asp Asn Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg Tyr Thr Gly Gly Gly Tyr Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

```
Leu Gln Ser Ser Gly Leu Tyr Ser Leu Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 46
<211> LENGTH: 107
<212> TYPE: PRT
<213> ORGANISM: Artificial Sequence
<220> FEATURE:
<223> OTHER INFORMATION: Synthetic: 28G11_L1 VL

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Gln Gln Gly Asp Thr Leu Pro Trp
                85                  90                  95
```

```
Thr Phe Gly Gln Gly Thr Lys Leu Glu Ile Lys
            100                 105
```

<210> SEQ ID NO 47
<211> LENGTH: 214
<212> TYPE: PRT
<213> ORGANISM: Artificial Sequence
<220> FEATURE:
<223> OTHER INFORMATION: Synthetic: 28G11_L1

<400> SEQUENCE: 47

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Gln Gln Gly Asp Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 48
<211> LENGTH: 107
<212> TYPE: PRT
<213> ORGANISM: Artificial Sequence
<220> FEATURE:
<223> OTHER INFORMATION: Synthetic: 28G11_L2 VL

<400> SEQUENCE: 48

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
```

```
        65                  70                  75                  80

Glu Asp Val Ala Thr Tyr Phe Cys Gln Gln Gly Asp Thr Leu Pro Trp
                85                  90                  95

Thr Phe Gly Gln Gly Thr Lys Leu Glu Ile Lys
            100                 105

<210> SEQ ID NO 49
<211> LENGTH: 214
<212> TYPE: PRT
<213> ORGANISM: Artificial Sequence
<220> FEATURE:
<223> OTHER INFORMATION: Synthetic: 28G11_L2

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
                20                  25                  30

Leu Asn Trp Tyr Gln Gln Lys Pro Gly Lys Thr Val Lys Leu Leu Ile
            35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Gln Gln Gly Asp Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 50
<211> LENGTH: 107
<212> TYPE: PRT
<213> ORGANISM: Artificial Sequence
<220> FEATURE:
<223> OTHER INFORMATION: Synthetic: 28G11_L3 VL

<400> SEQUENCE: 50

Asp Ile Gln Met Thr Gln Ser Pro Ser Ser Leu Ser Ala Ser Val Gly
1               5                   10                  15

Asp Arg Leu Thr Ile Ser Cys Arg Ala Ser Gln Asp Ile Ser Asn Tyr
                20                  25                  30

Leu Asn Trp Tyr Gln Gln Lys Pro Gly Lys Thr Val Lys Leu Leu Ile
            35                  40                  45
```

```
Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Gln Gln Gly Asp Thr Leu Pro Trp
                85                  90                  95

Thr Phe Gly Gln Gly Thr Lys Leu Glu Ile Lys
            100                 105

<210> SEQ ID NO 51
<211> LENGTH: 214
<212> TYPE: PRT
<213> ORGANISM: Artificial Sequence
<220> FEATURE:
<223> OTHER INFORMATION: Synthetic: 28G11_L3

<400> SEQUENCE: 51

Asp Ile Gln Met Thr Gln Ser Pro Ser Ser Leu Ser Ala Ser Val Gly
1               5                   10                  15

Asp Arg Leu Thr Ile Ser Cys Arg Ala Ser Gln Asp Ile Ser Asn Tyr
                20                  25                  30

Leu Asn Trp Tyr Gln Gln Lys Pro Gly Lys Thr Val Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Gln Gln Gly Asp Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 52
<211> LENGTH: 107
<212> TYPE: PRT
<213> ORGANISM: Artificial Sequence
<220> FEATURE:
<223> OTHER INFORMATION: Synthetic: 28G11_L3a VL

<400> SEQUENCE: 52

Asp Ile Gln Met Thr Gln Ser Pro Ser Ser Leu Ser Ala Ser Val Gly
1               5                   10                  15

Asp Arg Leu Thr Ile Ser Cys Arg Ala Ser Gln Asp Ile Ser Asn Tyr
                20                  25                  30
```

```
Leu Asn Trp Tyr Gln Gln Lys Pro Gly Lys Val Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Gly Asp Thr Leu Pro Trp
                85                  90                  95

Thr Phe Gly Gln Gly Thr Lys Leu Glu Ile Lys
            100                 105

<210> SEQ ID NO 53
<211> LENGTH: 214
<212> TYPE: PRT
<213> ORGANISM: Artificial Sequence
<220> FEATURE:
<223> OTHER INFORMATION: Synthetic: 28G11_L3a

<400> SEQUENCE: 53

Asp Ile Gln Met Thr Gln Ser Pro Ser Ser Leu Ser Ala Ser Val Gly
1               5                   10                  15

Asp Arg Leu Thr Ile Ser Cys Arg Ala Ser Gln Asp Ile Ser Asn Tyr
            20                  25                  30

Leu Asn Trp Tyr Gln Gln Lys Pro Gly Lys Val Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Gln Gln Gly Asp Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 54
<211> LENGTH: 10
<212> TYPE: PRT
<213> ORGANISM: Artificial Sequence
<220> FEATURE:
<223> OTHER INFORMATION: Synthetic: 22F9(hyb)VHCDR1

<400> SEQUENCE: 54

Gly Tyr Thr Phe Thr Ser Tyr Trp Met His
```

```
<210> SEQ ID NO 55
<211> LENGTH: 10
<212> TYPE: PRT
<213> ORGANISM: Artificial Sequence
<220> FEATURE:
<223> OTHER INFORMATION: Synthetic: 22F9(hyb)VHCDR2

<400> SEQUENCE: 55

Met Ile His Pro Asn Ser Gly Ser Thr Asn
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Synthetic: 22F9(hyb)VHCDR3

<400> SEQUENCE: 56

Tyr Asp Tyr Asp Gly Phe Phe Asp Val
1               5

<210> SEQ ID NO 57
<211> LENGTH: 15
<212> TYPE: PRT
<213> ORGANISM: Artificial Sequence
<220> FEATURE:
<223> OTHER INFORMATION: Synthetic: 22F9(hyb)VLCDR1

<400> SEQUENCE: 57

Arg Ala Ser Lys Ser Val Ser Thr Ser Gly Tyr Ser Tyr Met His
1               5                   10                  15

<210> SEQ ID NO 58
<211> LENGTH: 7
<212> TYPE: PRT
<213> ORGANISM: Artificial Sequence
<220> FEATURE:
<223> OTHER INFORMATION: Synthetic: 22F9(hyb)VLCDR2

<400> SEQUENCE: 58

Leu Ala Ser Asn Leu Glu Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic: 22F9(hyb)VLCDR3

<400> SEQUENCE: 59

Gln His Ser Arg Glu Leu Pro Tyr Thr
1               5

<210> SEQ ID NO 60
<211> LENGTH: 118
<212> TYPE: PRT
<213> ORGANISM: Artificial Sequence
<220> FEATURE:
<223> OTHER INFORMATION: Synthetic: 22F9(hyb )VH

<400> SEQUENCE: 60

Gln Val Gln Leu Gln Gln Pro Gly Ala Glu Leu Val Lys Pro Gly Ala
1               5                   10                  15
```

```
Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Tyr Tyr Asp Tyr Asp Gly Phe Phe Asp Val Trp Gly Thr Gly Thr
                100                 105                 110

Thr Val Thr Val Ser Ser
            115

<210> SEQ ID NO 61
<211> LENGTH: 111
<212> TYPE: PRT
<213> ORGANISM: Artificial Sequence
<220> FEATURE:
<223> OTHER INFORMATION: Synthetic: 22F9(hyb) VL

<400> SEQUENCE: 61

Asp Ile Val Leu Thr Gln Ser Pro Ala Ser Leu Asp Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Ser Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr His Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Pro Tyr Thr Phe Gly Gly Gly Thr Lys Leu Glu Ile Lys
                100                 105                 110

<210> SEQ ID NO 62
<211> LENGTH: 442
<212> TYPE: PRT
<213> ORGANISM: Artificial Sequence
<220> FEATURE:
<223> OTHER INFORMATION: Synthetic: 22F9(hyb) heavy chain

<400> SEQUENCE: 62

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
```

```
                85                  90                  95
Ala Tyr Tyr Asp Tyr Asp Gly Phe Phe Asp Val Trp Gly Thr Gly Thr
            100                 105                 110

Thr Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Val Thr Val Pro Ser Ser Pro
            180                 185                 190

Arg Pro Ser Glu Thr Val Thr Cys Asn Val Ala His Pro Ala Ser Ser
        195                 200                 205

Thr Lys Val Asp Lys Lys Ile Val Pro Arg Asp Cys Gly Cys Lys Pro
    210                 215                 220

Cys Ile Cys Thr Val Pro Glu Val Ser Ser Val Phe Ile Phe Pro Pro
225                 230                 235                 240

Lys Pro Lys Asp Val Leu Thr Ile Thr Leu Thr Pro Lys Val Thr Cys
                245                 250                 255

Val Val Val Asp Ile Ser Lys Asp Asp Pro Glu Val Gln Phe Ser Trp
            260                 265                 270

Phe Val Asp Asp Val Glu Val His Thr Ala Gln Thr Gln Pro Arg Glu
        275                 280                 285

Glu Gln Phe Asn Ser Thr Phe Arg Ser Val Ser Glu Leu Pro Ile Met
    290                 295                 300

His Gln Asp Trp Leu Asn Gly Lys Glu Phe Lys Cys Arg Val Asn Ser
305                 310                 315                 320

Ala Ala Phe Pro Ala Pro Ile Glu Lys Thr Ile Ser Lys Thr Lys Gly
                325                 330                 335

Arg Pro Lys Ala Pro Gln Val Tyr Thr Ile Pro Pro Pro Lys Glu Gln
            340                 345                 350

Met Ala Lys Asp Lys Val Ser Leu Thr Cys Met Ile Thr Asp Phe Phe
        355                 360                 365

Pro Glu Asp Ile Thr Val Glu Trp Gln Trp Asn Gly Gln Pro Ala Glu
    370                 375                 380

Asn Tyr Lys Asn Thr Gln Pro Ile Met Asn Thr Asn Gly Ser Tyr Phe
385                 390                 395                 400

Val Tyr Ser Lys Leu Asn Val Gln Lys Ser Asn Trp Glu Ala Gly Asn
                405                 410                 415

Thr Phe Thr Cys Ser Val Leu His Glu Gly Leu His Asn His His Thr
            420                 425                 430

Glu Lys Ser Leu Ser His Ser Pro Gly Lys
        435                 440

<210> SEQ ID NO 63
<211> LENGTH: 218
<212> TYPE: PRT
<213> ORGANISM: Artificial Sequence
<220> FEATURE:
<223> OTHER INFORMATION: Synthetic: 22F9(hyb) light chain

<400> SEQUENCE: 63

Asp Ile Val Leu Thr Gln Ser Pro Ala Ser Leu Asp Val Ser Leu Gly
```

```
  1               5                  10                 15
Gln Arg Ala Thr Ile Ser Cys Arg Ala Ser Lys Ser Val Ser Thr Ser
                20                 25                 30
Gly Tyr Ser Tyr Met His Trp Tyr Gln Gln Lys Ser Gly Gln Pro Pro
                35                 40                 45
Lys Leu Leu Ile Tyr Leu Ala Ser Asn Leu Glu Ser Gly Val Pro Ala
                50                 55                 60
Arg Phe Ser Gly Ser Gly Ser Gly Thr His Phe Thr Leu Asn Ile His
 65                 70                 75                 80
Pro Val Glu Glu Glu Asp Ala Ala Thr Tyr Tyr Cys Gln His Ser Arg
                85                 90                 95
Glu Leu Pro Tyr Thr Phe Gly Gly Gly Thr Lys Leu Glu Ile Lys Arg
               100                105                110
Ala Asp Ala Ala Pro Thr Val Ser Ile Phe Pro Pro Ser Ser Glu Gln
               115                120                125
Leu Thr Ser Gly Gly Ala Ser Val Val Cys Phe Leu Asn Asn Phe Tyr
               130                135                140
Pro Lys Asp Ile Asn Val Lys Trp Lys Ile Asp Gly Ser Glu Arg Gln
145                150                155                160
Asn Gly Val Leu Asn Ser Trp Thr Asp Gln Asp Ser Lys Asp Ser Thr
               165                170                175
Tyr Ser Met Ser Ser Thr Leu Thr Leu Thr Lys Asp Glu Tyr Glu Arg
               180                185                190
His Asn Ser Tyr Thr Cys Glu Ala Thr His Lys Thr Ser Thr Ser Pro
               195                200                205
Ile Val Lys Ser Phe Asn Arg Asn Glu Cys
               210                215

<210> SEQ ID NO 64
<211> LENGTH: 10
<212> TYPE: PRT
<213> ORGANISM: Artificial Sequence
<220> FEATURE:
<223> OTHER INFORMATION: Synthetic: 22F9 VHCDR2 N54A

<400> SEQUENCE: 64

Met Ile His Pro Ala Ser Gly Ser Thr Asn
1               5                  10

<210> SEQ ID NO 65
<211> LENGTH: 10
<212> TYPE: PRT
<213> ORGANISM: Artificial Sequence
<220> FEATURE:
<223> OTHER INFORMATION: Synthetic: 22F9 VHCDR2 N54H

<400> SEQUENCE: 65

Met Ile His Pro His Ser Gly Ser Thr Asn
1               5                  10

<210> SEQ ID NO 66
<211> LENGTH: 10
<212> TYPE: PRT
<213> ORGANISM: Artificial Sequence
<220> FEATURE:
<223> OTHER INFORMATION: Synthetic: 22F9 VHCDR2 N54Q

<400> SEQUENCE: 66

Met Ile His Pro Gln Ser Gly Ser Thr Asn
1               5                  10
```

<210> SEQ ID NO 67
<211> LENGTH: 10
<212> TYPE: PRT
<213> ORGANISM: Artificial Sequence
<220> FEATURE:
<223> OTHER INFORMATION: Synthetic: 22F9 VHCDR2 N54S

<400> SEQUENCE: 67

Met Ile His Pro Ser Ser Gly Ser Thr Asn
1               5                   10

<210> SEQ ID NO 68
<211> LENGTH: 9
<212> TYPE: PRT
<213> ORGANISM: Artificial Sequence
<220> FEATURE:
<223> OTHER INFORMATION: Synthetic: 22F9 VHCDR3 D102A

<400> SEQUENCE: 68

Tyr Asp Tyr Ala Gly Phe Phe Asp Val
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic: 22F9 VHCDR3 D102E

<400> SEQUENCE: 69

Tyr Asp Tyr Glu Gly Phe Phe Asp Val
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic: 22F9 VHCDR3 D102G

<400> SEQUENCE: 70

Tyr Asp Tyr Gly Gly Phe Phe Asp Val
1               5

<210> SEQ ID NO 71
<211> LENGTH: 118
<212> TYPE: PRT
<213> ORGANISM: Artificial Sequence
<220> FEATURE:
<223> OTHER INFORMATION: Synthetic: 22F9_H0 VH

<400> SEQUENCE: 71

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Met Ile His Pro Asn Ser Gly Ser Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

```
                85                  90                  95
Ala Arg Tyr Asp Tyr Asp Gly Phe Phe Asp Val Trp Gly Gln Gly Thr
                100                 105                 110

Leu Val Thr Val Ser Ser
        115

<210> SEQ ID NO 72
<211> LENGTH: 448
<212> TYPE: PRT
<213> ORGANISM: Artificial Sequence
<220> FEATURE:
<223> OTHER INFORMATION: Synthetic: 22F9_H0_IgG1

<400> SEQUENCE: 72

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Met Ile His Pro Asn Ser Gly Ser Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Tyr Asp Tyr Asp Gly Phe Phe Asp Val Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
```

```
                    325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
                355                 360                 365
Leu Val Lys Gly Phe Tyr Pro Ser Asp Ile Ala Val Glu Trp Glu Ser
                370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
                435                 440                 445

<210> SEQ ID NO 73
<211> LENGTH: 118
<212> TYPE: PRT
<213> ORGANISM: Artificial Sequence
<220> FEATURE:
<223> OTHER INFORMATION: Synthetic: 22F9_H0.1 VH

<400> SEQUENCE: 73

Gln Val Gln Leu Val Gln Pro Gly Ala Glu Val Val Lys Pro Gly Ala
1               5                   10                  15
Ser Val Lys Leu Ser Cys Lys Ala Ser Gly Tyr Thr Phe Thr Ser Tyr
                20                  25                  30
Trp Met His Trp Val Lys Gln Arg Pro Gly Gln Gly Leu Glu Trp Met
            35                  40                  45
Gly Met Ile His Pro Gln Ser Gly Ser Thr Asn Tyr Asn Glu Lys Phe
        50                  55                  60
Lys Ser Lys Ala Thr Leu Thr Arg Asp Lys Ser Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Tyr Asp Tyr Ala Gly Phe Phe Asp Val Trp Gly Gln Gly Thr
                100                 105                 110
Leu Val Thr Val Ser Ser
            115

<210> SEQ ID NO 74
<211> LENGTH: 448
<212> TYPE: PRT
<213> ORGANISM: Artificial Sequence
<220> FEATURE:
<223> OTHER INFORMATION: Synthetic: 22F9_H0.1_IgG1

<400> SEQUENCE: 74

Gln Val Gln Leu Val Gln Pro Gly Ala Glu Val Val Lys Pro Gly Ala
1               5                   10                  15
Ser Val Lys Leu Ser Cys Lys Ala Ser Gly Tyr Thr Phe Thr Ser Tyr
                20                  25                  30
Trp Met His Trp Val Lys Gln Arg Pro Gly Gln Gly Leu Glu Trp Met
            35                  40                  45
Gly Met Ile His Pro Gln Ser Gly Ser Thr Asn Tyr Asn Glu Lys Phe
        50                  55                  60
```

-continued

```
Lys Ser Lys Ala Thr Leu Thr Arg Asp Lys Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Tyr Asp Tyr Ala Gly Phe Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 75
<211> LENGTH: 118
<212> TYPE: PRT
<213> ORGANISM: Artificial Sequence
<220> FEATURE:
<223> OTHER INFORMATION: Synthetic: 22F9_H1 VH

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Ser Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Asp Gly Phe Phe Asp Val Trp Gly Gln Gly Thr
            100                 105                 110

Leu Val Thr Val Ser Ser
        115

<210> SEQ ID NO 76
<211> LENGTH: 448
<212> TYPE: PRT
<213> ORGANISM: Artificial Sequence
<220> FEATURE:
<223> OTHER INFORMATION: Synthetic: 22F9_H1_IgG1

<400> SEQUENCE: 76

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Ser Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Asp Gly Phe Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 77
<211> LENGTH: 118
<212> TYPE: PRT
<213> ORGANISM: Artificial Sequence
<220> FEATURE:
<223> OTHER INFORMATION: Synthetic: 22F9_H1.1 VH

<400> SEQUENCE: 77

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Gln Ser Gly Ser Thr Asn Tyr Asn Glu Lys Phe
    50                  55                  60

Lys Ser Lys Ala Thr Met Thr Val Asp Lys Ser Ser Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser
        115

<210> SEQ ID NO 78
<211> LENGTH: 448

```
<212> TYPE: PRT
<213> ORGANISM: Artificial Sequence
<220> FEATURE:
<223> OTHER INFORMATION: Synthetic: 22F9_H1.1_IgG1

<400> SEQUENCE: 78
```

| | | | | | | | | | | | | | | |
|---|---|---|---|---|---|---|---|---|---|---|---|---|---|---|
| Gln | Val | Gln | Leu | Val | Gln | Pro | Gly | Ala | Glu | Val | Val | Lys | Pro | Gly | Ala |
| 1 | | | | 5 | | | | | 10 | | | | | 15 | |

| Ser | Val | Lys | Leu | Ser | Cys | Lys | Ala | Ser | Gly | Tyr | Thr | Phe | Thr | Ser | Tyr |
| | | | 20 | | | | | 25 | | | | | 30 | | |

| Trp | Met | His | Trp | Val | Lys | Gln | Arg | Pro | Gly | Gln | Gly | Leu | Glu | Trp | Ile |
| | | 35 | | | | | 40 | | | | | 45 | | | |

| Gly | Met | Ile | His | Pro | Gln | Ser | Gly | Ser | Thr | Asn | Tyr | Asn | Glu | Lys | Phe |
| | 50 | | | | | 55 | | | | | 60 | | | | |

| Lys | Ser | Lys | Ala | Thr | Met | Thr | Val | Asp | Lys | Ser | Ser | Ser | Thr | Val | Tyr |
| 65 | | | | | 70 | | | | | 75 | | | | | 80 |

| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |

| Ala | Tyr | Tyr | Asp | Tyr | Ala | Gly | Phe | Phe | Asp | Val | Trp | Gly | Gln | Gly | Thr |
| | | | 100 | | | | | 105 | | | | | 110 | | |

| Leu | Val | Thr | Val | Ser | Ser | Ala | Ser | Thr | Lys | Gly | Pro | Ser | Val | Phe | Pro |
| | | 115 | | | | | 120 | | | | | 125 | | | |

| Leu | Ala | Pro | Ser | Ser | Lys | Ser | Thr | Ser | Gly | Gly | Thr | Ala | Ala | Leu | Gly |
| | 130 | | | | | 135 | | | | | 140 | | | | |

| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |

| Ser | Gly | Ala | Leu | Thr | Ser | Gly | Val | His | Thr | Phe | Pro | Ala | Val | Leu | Gln |
| | | | | 165 | | | | | 170 | | | | | 175 | |

| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |

| Ser | Leu | Gly | Thr | Gln | Thr | Tyr | Ile | Cys | Asn | Val | Asn | His | Lys | Pro | Ser |
| | | 195 | | | | | 200 | | | | | 205 | | | |

| Asn | Thr | Lys | Val | Asp | Lys | Lys | Val | Glu | Pro | Lys | Ser | Cys | Asp | Lys | Thr |
| | 210 | | | | | 215 | | | | | 220 | | | | |

| His | Thr | Cys | Pro | Pro | Cys | Pro | Ala | Pro | Glu | Leu | Leu | Gly | Gly | Pro | Ser |
| 225 | | | | | 230 | | | | | 235 | | | | | 240 |

| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |

| Thr | Pro | Glu | Val | Thr | Cys | Val | Val | Val | Asp | Val | Ser | His | Glu | Asp | Pro |
| | | | 260 | | | | | 265 | | | | | 270 | | |

| Glu | Val | Lys | Phe | Asn | Trp | Tyr | Val | Asp | Gly | Val | Glu | Val | His | Asn | Ala |
| | | 275 | | | | | 280 | | | | | 285 | | | |

| Lys | Thr | Lys | Pro | Arg | Glu | Glu | Gln | Tyr | Asn | Ser | Thr | Tyr | Arg | Val | Val |
| | 290 | | | | | 295 | | | | | 300 | | | | |

| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |

| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |

| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |

| Pro | Pro | Ser | Arg | Asp | Glu | Leu | Thr | Lys | Asn | Gln | Val | Ser | Leu | Thr | Cys |
| | | 355 | | | | | 360 | | | | | 365 | | | |

| Leu | Val | Lys | Gly | Phe | Tyr | Pro | Ser | Asp | Ile | Ala | Val | Glu | Trp | Glu | Ser |
| | 370 | | | | | 375 | | | | | 380 | | | | |

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 79
<211> LENGTH: 445
<212> TYPE: PRT
<213> ORGANISM: Artificial Sequence
<220> FEATURE:
<223> OTHER INFORMATION: Synthetic: 22F9_H1.1_IgG4mut

<400> SEQUENCE: 79

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Gln Ser Gly Ser Thr Asn Tyr Asn Glu Lys Phe
    50                  55                  60

Lys Ser Lys Ala Thr Met Thr Val Asp Lys Ser Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300
```

```
Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
        420                 425                 430

His Tyr Thr Gln Lys Ser Leu Ser Leu Ser Leu Gly Lys
        435                 440                 445

<210> SEQ ID NO 80
<211> LENGTH: 118
<212> TYPE: PRT
<213> ORGANISM: Artificial Sequence
<220> FEATURE:
<223> OTHER INFORMATION: Synthetic: 22F9_H2 VH

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Ser Arg Val Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Tyr Tyr Asp Tyr Asp Gly Phe Phe Asp Val Trp Gly Gln Gly Thr
        100                 105                 110

Leu Val Thr Val Ser Ser
        115

<210> SEQ ID NO 81
<211> LENGTH: 448
<212> TYPE: PRT
<213> ORGANISM: Artificial Sequence
<220> FEATURE:
<223> OTHER INFORMATION: Synthetic: 22F9_H2_IgG1

<400> SEQUENCE: 81

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45
```

```
Gly Met Ile His Pro Asn Ser Gly Ser Thr Asn Tyr Asn Glu Lys Phe
    50                  55                  60
Lys Ser Arg Val Thr Leu Thr Val Asp Thr Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Tyr Tyr Asp Tyr Asp Gly Phe Phe Asp Val Trp Gly Gln Gly Thr
                100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 82
<211> LENGTH: 118
```

```
<212> TYPE: PRT
<213> ORGANISM: Artificial Sequence
<220> FEATURE:
<223> OTHER INFORMATION: Synthetic: 22F9_H2.1 VH

<400> SEQUENCE: 82
```

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Gln Ser Gly Ser Thr Asn Tyr Asn Glu Lys Phe
    50                  55                  60

Lys Ser Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser
        115

```
<210> SEQ ID NO 83
<211> LENGTH: 448
<212> TYPE: PRT
<213> ORGANISM: Artificial Sequence
<220> FEATURE:
<223> OTHER INFORMATION: Synthetic: 22F9_H2.1_IgG1

<400> SEQUENCE: 83
```

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Gln Ser Gly Ser Thr Asn Tyr Asn Glu Lys Phe
    50                  55                  60

Lys Ser Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

```
Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 84
<211> LENGTH: 445
<212> TYPE: PRT
<213> ORGANISM: Artificial Sequence
<220> FEATURE:
<223> OTHER INFORMATION: Synthetic: 22F9_H2.1_IgG4mut

<400> SEQUENCE: 84

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Gln Ser Gly Ser Thr Asn Tyr Asn Glu Lys Phe
    50                  55                  60

Lys Ser Lys Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser Ala Ser Thr Lys Gly Pro Ser Val Phe Pro
        115                 120                 125
```

```
Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Lys Thr Tyr Thr Cys Asn Val Asp His Lys Pro Ser
                195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
                260                 265                 270

Phe Asn Trp Tyr Val Asp Gly Val Glu Val His Asn Ala Lys Thr Lys
                275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Gln Glu Glu Met Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly Lys
                435                 440                 445

<210> SEQ ID NO 85
<211> LENGTH: 118
<212> TYPE: PRT
<213> ORGANISM: Artificial Sequence
<220> FEATURE:
<223> OTHER INFORMATION: Synthetic: 22F9_H3 VH

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Ile
            35                  40                  45
```

Gly Met Ile His Pro Asn Ser Gly Ser Thr Asn Tyr Asn Glu Lys Phe
            50                  55                  60

Lys Ser Arg Val Thr Leu Thr Val Asp Lys Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Tyr Tyr Asp Tyr Asp Gly Phe Phe Asp Val Trp Gly Gln Gly Thr
                100                 105                 110

Leu Val Thr Val Ser Ser
        115

<210> SEQ ID NO 86
<211> LENGTH: 448
<212> TYPE: PRT
<213> ORGANISM: Artificial Sequence
<220> FEATURE:
<223> OTHER INFORMATION: Synthetic: 22F9_H3_IgG1

<400> SEQUENCE: 86

Gln Val Gln Leu Val Gln Ser Gly Ala Glu Val Lys Lys Pro Gly Ala
 1               5                   10                  15

Ser Val Lys Val Ser Cys Lys Ala Ser Gly Tyr Thr Phe Thr Ser Tyr
                 20                  25                  30

Trp Met His Trp Val Arg Gln Ala Pro Gly Gln Gly Leu Glu Trp Ile
            35                  40                  45

Gly Met Ile His Pro Asn Ser Gly Ser Thr Asn Tyr Asn Glu Lys Phe
            50                  55                  60

Lys Ser Arg Val Thr Leu Thr Val Asp Lys Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Tyr Tyr Asp Tyr Asp Gly Phe Phe Asp Val Trp Gly Gln Gly Thr
                100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 87
<211> LENGTH: 118
<212> TYPE: PRT
<213> ORGANISM: Artificial Sequence
<220> FEATURE:
<223> OTHER INFORMATION: Synthetic: 22F9_H3.1 VH

<400> SEQUENCE: 87

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Met Ile His Pro Gln Ser Gly Ser Thr Asn Tyr Asn Glu Lys Phe
    50                  55                  60

Lys Ser Arg Val Thr Leu Thr Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser
        115

<210> SEQ ID NO 88
<211> LENGTH: 448
<212> TYPE: PRT
<213> ORGANISM: Artificial Sequence
<220> FEATURE:
<223> OTHER INFORMATION: Synthetic: 22F9_H3.1_IgG1

<400> SEQUENCE: 88

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr

```
            20                  25                  30
Trp Met His Trp Val Arg Gln Ala Pro Gly Gln Gly Leu Glu Trp Ile
            35                  40                  45
Gly Met Ile His Pro Gln Ser Gly Ser Thr Asn Tyr Asn Glu Lys Phe
            50                  55                  60
Lys Ser Arg Val Thr Leu Thr Val Asp Lys Ser Ser Thr Ala Tyr
65                  70                  75                  80
Met Glu Leu Ser Ser Leu Arg Ser Glu Asp Thr Ala Val Tyr Tyr Cys
                    85                  90                  95
Ala Tyr Tyr Asp Tyr Ala Gly Phe Phe Asp Val Trp Gly Gln Gly Thr
                100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
            130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                    165                 170                 175
Ser Ser Gly Leu Tyr Ser Leu Ser Ser Val Val Thr Val Pro Ser Ser
                180                 185                 190
Ser Leu Gly Thr Gln Thr Tyr Ile Cys Asn Val Asn His Lys Pro Ser
                195                 200                 205
Asn Thr Lys Val Asp Lys Lys Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                    245                 250                 255
Thr Pro Glu Val Thr Cys Val Val Val Asp Val Ser His Glu Asp Pro
                260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
            290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                    325                 330                 335
Ile Ser Lys Ala Lys Gly Gln Pro Arg Glu Pro Gln Val Tyr Thr Leu
                340                 345                 350
Pro Pro Ser Arg Asp Glu Leu Thr Lys Asn Gln Val Ser Leu Thr Cys
            355                 360                 365
Leu Val Lys Gly Phe Tyr Pro Ser Asp Ile Ala Val Glu Trp Glu Ser
            370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                    405                 410                 415
Arg Trp Gln Gln Gly Asn Val Phe Ser Cys Ser Val Met His Glu Ala
                420                 425                 430
Leu His Asn His Tyr Thr Gln Lys Ser Leu Ser Leu Ser Pro Gly Lys
            435                 440                 445
```

<210> SEQ ID NO 89
<211> LENGTH: 445
<212> TYPE: PRT
<213> ORGANISM: Artificial Sequence
<220> FEATURE:
<223> OTHER INFORMATION: Synthetic: 22F9_H3.1_IgG4mut

<400> SEQUENCE: 89

```
Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Met Ile His Pro Gln Ser Gly Ser Thr Asn Tyr Asn Glu Lys Phe
    50                  55                  60

Lys Ser Arg Val Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365
```

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 90
<211> LENGTH: 118
<212> TYPE: PRT
<213> ORGANISM: Artificial Sequence
<220> FEATURE:
<223> OTHER INFORMATION: Synthetic: 22F9_H4 VH

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Met Ile His Pro Asn Ser Gly Ser Thr Asn Tyr Asn Glu Lys Phe
        50                  55                  60

Lys Ser Lys Ala Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Asp Gly Phe Phe Asp Val Trp Gly Gln Gly Thr
            100                 105                 110

Leu Val Thr Val Ser Ser
        115

<210> SEQ ID NO 91
<211> LENGTH: 448
<212> TYPE: PRT
<213> ORGANISM: Artificial Sequence
<220> FEATURE:
<223> OTHER INFORMATION: Synthetic: 22F9_H4_IgG1

<400> SEQUENCE: 91

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
            35                  40                  45

Gly Met Ile His Pro Asn Ser Gly Ser Thr Asn Tyr Asn Glu Lys Phe
        50                  55                  60

Lys Ser Lys Ala Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Asp Gly Phe Phe Asp Val Trp Gly Gln Gly Thr

```
                100             105             110
Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 92
<211> LENGTH: 118
<212> TYPE: PRT
<213> ORGANISM: Artificial Sequence
<220> FEATURE:
<223> OTHER INFORMATION: Synthetic: 22F9_H5 VH

<400> SEQUENCE: 92

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
```

```
                20                  25                  30
Trp Met His Trp Val Lys Gln Arg Pro Gly Gln Gly Leu Glu Trp Ile
        35                  40                  45
Gly Met Ile His Pro Asn Ser Gly Ser Thr Asn Tyr Asn Glu Lys Phe
    50                  55                  60
Lys Ser Lys Ala Thr Leu Thr Val Asp Lys Ser Ser Ser Thr Ala Tyr
65                  70                  75                  80
Met Glu Leu Ser Ser Leu Arg Ser Glu Asp Thr Ala Val Tyr Tyr Cys
                85                  90                  95
Ala Tyr Tyr Asp Tyr Asp Gly Phe Phe Asp Val Trp Gly Gln Gly Thr
            100                 105                 110
Leu Val Thr Val Ser Ser
            115

<210> SEQ ID NO 93
<211> LENGTH: 448
<212> TYPE: PRT
<213> ORGANISM: Artificial Sequence
<220> FEATURE:
<223> OTHER INFORMATION: Synthetic: 22F9_H5_IgG1

<400> SEQUENCE: 93

Gln Val Gln Leu Val Gln Pro Gly Ala Glu Val Val Lys Pro Gly Ala
1               5                   10                  15
Ser Val Lys Leu Ser Cys Lys Ala Ser Gly Tyr Thr Phe Thr Ser Tyr
            20                  25                  30
Trp Met His Trp Val Lys Gln Arg Pro Gly Gln Gly Leu Glu Trp Ile
        35                  40                  45
Gly Met Ile His Pro Asn Ser Gly Ser Thr Asn Tyr Asn Glu Lys Phe
    50                  55                  60
Lys Ser Lys Ala Thr Leu Thr Val Asp Lys Ser Ser Ser Thr Ala Tyr
65                  70                  75                  80
Met Glu Leu Ser Ser Leu Arg Ser Glu Asp Thr Ala Val Tyr Tyr Cys
                85                  90                  95
Ala Tyr Tyr Asp Tyr Asp Gly Phe Phe Asp Val Trp Gly Gln Gly Thr
            100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
```

```
                260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
```

<210> SEQ ID NO 94
<211> LENGTH: 445
<212> TYPE: PRT
<213> ORGANISM: Artificial Sequence
<220> FEATURE:
<223> OTHER INFORMATION: Synthetic: 22F9_H5_IgG4mut

<400> SEQUENCE: 94

```
Gln Val Gln Leu Val Gln Pro Gly Ala Glu Val Val Lys Pro Gly Ala
1               5                   10                  15
Ser Val Lys Leu Ser Cys Lys Ala Ser Gly Tyr Thr Phe Thr Ser Tyr
            20                  25                  30
Trp Met His Trp Val Lys Gln Arg Pro Gly Gln Gly Leu Glu Trp Ile
        35                  40                  45
Gly Met Ile His Pro Asn Ser Gly Ser Thr Asn Tyr Asn Glu Lys Phe
    50                  55                  60
Lys Ser Lys Ala Thr Leu Thr Val Asp Lys Ser Ser Ser Thr Ala Tyr
65                  70                  75                  80
Met Glu Leu Ser Ser Leu Arg Ser Glu Asp Thr Ala Val Tyr Tyr Cys
                85                  90                  95
Ala Tyr Tyr Asp Tyr Asp Gly Phe Phe Asp Val Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Cys Ser Arg Ser Thr Ser Glu Ser Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
```

```
                180                 185                 190
Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
            210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 95
<211> LENGTH: 118
<212> TYPE: PRT
<213> ORGANISM: Artificial Sequence
<220> FEATURE:
<223> OTHER INFORMATION: Synthetic: 22F9_H5.2 VH

<400> SEQUENCE: 95

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Gln Ser Gly Ser Thr Asn Tyr Asn Glu Lys Phe
    50                  55                  60

Lys Ser Lys Ala Thr Leu Thr Val Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
```

Leu Val Thr Val Ser Ser
            115

<210> SEQ ID NO 96
<211> LENGTH: 448
<212> TYPE: PRT
<213> ORGANISM: Artificial Sequence
<220> FEATURE:
<223> OTHER INFORMATION: Synthetic: 22F9_H5.2_IgG1

<400> SEQUENCE: 96

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Gln Ser Gly Ser Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 97
<211> LENGTH: 445
<212> TYPE: PRT
<213> ORGANISM: Artificial Sequence
<220> FEATURE:
<223> OTHER INFORMATION: Synthetic: 22F9_H5.2_IgG4mut

<400> SEQUENCE: 97

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Gln Ser Gly Ser Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln

```
                    260                 265                 270
Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 98
<211> LENGTH: 118
<212> TYPE: PRT
<213> ORGANISM: Artificial Sequence
<220> FEATURE:
<223> OTHER INFORMATION: Synthetic: 22F9_H7 VH

<400> SEQUENCE: 98

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Met Ile His Pro Gln Ser Gly Ser Thr Asn Tyr Ala Gln Lys Phe
    50                  55                  60

Gln Gly Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser
        115

<210> SEQ ID NO 99
<211> LENGTH: 448
<212> TYPE: PRT
<213> ORGANISM: Artificial Sequence
<220> FEATURE:
<223> OTHER INFORMATION: Synthetic: 22F9_H7_IgG1

<400> SEQUENCE: 99
```

-continued

```
Gln Val Gln Leu Val Gln Pro Gly Ala Glu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
                35                  40                  45

Gly Met Ile His Pro Gln Ser Gly Ser Thr Asn Tyr Ala Gln Lys Phe
            50                  55                  60

Gln Gly Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
```

Leu His Asn His Tyr Thr Gln Lys Ser Leu Ser Leu Ser Pro Gly Lys
                 435                       440                     445

<210> SEQ ID NO 100
<211> LENGTH: 445
<212> TYPE: PRT
<213> ORGANISM: Artificial Sequence
<220> FEATURE:
<223> OTHER INFORMATION: Synthetic: 22F9_H7_IgG4mut

<400> SEQUENCE: 100

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Met Ile His Pro Gln Ser Gly Ser Thr Asn Tyr Ala Gln Lys Phe
    50                  55                  60

Gln Gly Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser

```
                340             345             350
Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
            435                 440                 445

<210> SEQ ID NO 101
<211> LENGTH: 118
<212> TYPE: PRT
<213> ORGANISM: Artificial Sequence
<220> FEATURE:
<223> OTHER INFORMATION: Synthetic: 22F9_H7a VH

<400> SEQUENCE: 101

Glu Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Met Ile His Pro Gln Ser Gly Ser Thr Asn Tyr Ala Gln Lys Phe
    50                  55                  60

Gln Gly Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser
        115

<210> SEQ ID NO 102
<211> LENGTH: 448
<212> TYPE: PRT
<213> ORGANISM: Artificial Sequence
<220> FEATURE:
<223> OTHER INFORMATION: Synthetic: 22F9_H7a_IgG1

<400> SEQUENCE: 102

Glu Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Met Ile His Pro Gln Ser Gly Ser Thr Asn Tyr Ala Gln Lys Phe
    50                  55                  60

Gln Gly Arg Val Thr Met Thr Val Asp Lys Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 103
<211> LENGTH: 445
<212> TYPE: PRT
<213> ORGANISM: Artificial Sequence
<220> FEATURE:
<223> OTHER INFORMATION: Synthetic: 22F9_H7a_IgG4mut

<400> SEQUENCE: 103
```

```
Glu Val Gln Leu Val Gln Pro Gly Ala Glu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
            35                  40                  45

Gly Met Ile His Pro Gln Ser Gly Ser Thr Asn Tyr Ala Gln Lys Phe
    50                  55                  60

Gln Gly Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Tyr Tyr Asp Tyr Ala Gly Phe Phe Asp Val Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Tyr Arg Val Val Ser Val Leu
            290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
```

His Tyr Thr Gln Lys Ser Leu Ser Leu Ser Leu Gly Lys
            435                 440                 445

<210> SEQ ID NO 104
<211> LENGTH: 111
<212> TYPE: PRT
<213> ORGANISM: Artificial Sequence
<220> FEATURE:
<223> OTHER INFORMATION: Synthetic: 22F9_L0 VL

<400> SEQUENCE: 104

Asp Ile Gln Leu Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Tyr Thr Phe Gly Gly Gly Thr Lys Val Glu Ile Lys
            100                 105                 110

<210> SEQ ID NO 105
<211> LENGTH: 218
<212> TYPE: PRT
<213> ORGANISM: Artificial Sequence
<220> FEATURE:
<223> OTHER INFORMATION: Synthetic: 22F9_L0

<400> SEQUENCE: 105

Asp Ile Gln Leu Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

```
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 106
<211> LENGTH: 111
<212> TYPE: PRT
<213> ORGANISM: Artificial Sequence
<220> FEATURE:
<223> OTHER INFORMATION: Synthetic: 22F9_L1 VL

<400> SEQUENCE: 106

Asp Ile Gln Leu Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Pro Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr His Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Tyr Thr Phe Gly Gly Gly Thr Lys Val Glu Ile Lys
            100                 105                 110

<210> SEQ ID NO 107
<211> LENGTH: 218
<212> TYPE: PRT
<213> ORGANISM: Artificial Sequence
<220> FEATURE:
<223> OTHER INFORMATION: Synthetic: 22F9_L1

<400> SEQUENCE: 107

Asp Ile Gln Leu Thr Gln Ser Pro Ser Ser Leu Ser Ala Ser Val Gly
1               5                   10                  15

Asp Arg Val Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Pro Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr His Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Leu Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160
```

```
Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
            210                 215

<210> SEQ ID NO 108
<211> LENGTH: 111
<212> TYPE: PRT
<213> ORGANISM: Artificial Sequence
<220> FEATURE:
<223> OTHER INFORMATION: Synthetic: 22F9_L2 VL

<400> SEQUENCE: 108

Asp Ile Gln Leu Thr Gln Ser Pro Ser Ser Leu Ser Val Ser Val Gly
1               5                   10                  15

Asp Arg Ala Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Pro Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr His Phe Thr Leu Thr Ile Ser
65                  70                  75                  80

Ser Val Gln Pro Glu Asp Phe Ala Thr Tyr Tyr Cys Gln His Ser Arg
                85                  90                  95

Glu Leu Pro Tyr Thr Phe Gly Gly Gly Thr Lys Leu Glu Ile Lys
            100                 105                 110

<210> SEQ ID NO 109
<211> LENGTH: 218
<212> TYPE: PRT
<213> ORGANISM: Artificial Sequence
<220> FEATURE:
<223> OTHER INFORMATION: Synthetic: 22F9_L2

<400> SEQUENCE: 109

Asp Ile Gln Leu Thr Gln Ser Pro Ser Ser Leu Ser Val Ser Val Gly
1               5                   10                  15

Asp Arg Ala Thr Ile Thr Cys Arg Ala Ser Lys Ser Val Ser Thr Ser
            20                  25                  30

Gly Tyr Ser Tyr Met His Trp Tyr Gln Gln Lys Pro Gly Lys Pro Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr His Phe Thr Leu Thr Ile Ser
65                  70                  75                  80

Ser Val Gln Pro Glu Asp Phe Ala Thr Tyr Tyr Cys Gln His Ser Arg
                85                  90                  95

Glu Leu Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
```

```
                130              135              140
Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 110
<211> LENGTH: 10
<212> TYPE: PRT
<213> ORGANISM: Artificial Sequence
<220> FEATURE:
<223> OTHER INFORMATION: Synthetic: 20E6(hyb)VHCDR1

<400> SEQUENCE: 110

Gly Tyr Thr Phe Thr Ser Tyr Trp Met His
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthetic: 20E6(hyb)VHCDR2

<400> SEQUENCE: 111

Arg Ile Asp Pro Asn Ser Gly Gly Ile Lys
1               5                   10

<210> SEQ ID NO 112
<211> LENGTH: 9
<212> TYPE: PRT
<213> ORGANISM: Artificial Sequence
<220> FEATURE:
<223> OTHER INFORMATION: Synthetic: 20E6(hyb)VHCDR3

<400> SEQUENCE: 112

Trp Asp Tyr Gly Gly Tyr Phe Asp Val
1               5

<210> SEQ ID NO 113
<211> LENGTH: 11
<212> TYPE: PRT
<213> ORGANISM: Artificial Sequence
<220> FEATURE:
<223> OTHER INFORMATION: Synthetic: 20E6(hyb)VLCDR1

<400> SEQUENCE: 113

Arg Ala Ser Gln Asp Ile Thr Asn Tyr Leu Asn
1               5                   10

<210> SEQ ID NO 114
<211> LENGTH: 7
<212> TYPE: PRT
<213> ORGANISM: Artificial Sequence
<220> FEATURE:
<223> OTHER INFORMATION: Synthetic: 20E6(hyb)VLCDR2

<400> SEQUENCE: 114
```

```
Tyr Thr Ser Arg Leu His Ser
1               5
```

<210> SEQ ID NO 115
<211> LENGTH: 9
<212> TYPE: PRT
<213> ORGANISM: Artificial Sequence
<220> FEATURE:
<223> OTHER INFORMATION: Synthetic: 20E6(hyb)VLCDR3

<400> SEQUENCE: 115

```
Gln Gln Gly Asp Thr Leu Pro Trp Thr
1               5
```

<210> SEQ ID NO 116
<211> LENGTH: 118
<212> TYPE: PRT
<213> ORGANISM: Artificial Sequence
<220> FEATURE:
<223> OTHER INFORMATION: Synthetic: 20E6(hyb) VH

<400> SEQUENCE: 116

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Arg Gly Leu Glu Trp Ile
            35                  40                  45

Gly Arg Ile Asp Pro Asn Ser Gly Ile Lys Tyr Asn Glu Lys Phe
50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Trp Asp Tyr Gly Gly Tyr Phe Asp Val Trp Gly Thr Gly Thr
            100                 105                 110

Thr Val Thr Val Ser Ser
        115
```

<210> SEQ ID NO 117
<211> LENGTH: 107
<212> TYPE: PRT
<213> ORGANISM: Artificial Sequence
<220> FEATURE:
<223> OTHER INFORMATION: Synthetic: 20E6(hyb) VL

<400> SEQUENCE: 117

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Tyr
                20                  25                  30

Leu Asn Trp Tyr Gln Gln Lys Pro Asp Gly Ala Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Trp
                85                  90                  95

Thr Phe Gly Gly Gly Thr Lys Leu Glu Ile Lys
```

<210> SEQ ID NO 118
<211> LENGTH: 572
<212> TYPE: PRT
<213> ORGANISM: Artificial Sequence
<220> FEATURE:
<223> OTHER INFORMATION: Synthetic: 20E6(hyb) heavy chain

<400> SEQUENCE: 118

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Ile Lys Tyr Asn Glu Lys Phe
    50                  55                  60

Lys Ser Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Tyr Cys
            85                  90                  95

Ala Arg Trp Asp Tyr Gly Gly Tyr Phe Asp Val Trp Gly Thr Gly Thr
        100                 105                 110

Thr Val Thr Val Ser Ser Ser Gln Ser Phe Pro Asn Val Phe Pro Leu
    115                 120                 125

Val Ser Cys Glu Ser Pro Leu Ser Asp Lys Asn Leu Val Ala Met Gly
130                 135                 140

Cys Leu Ala Arg Asp Phe Leu Pro Ser Thr Ile Ser Phe Thr Trp Asn
145                 150                 155                 160

Tyr Gln Asn Asn Thr Glu Val Ile Gln Gly Ile Arg Thr Phe Pro Thr
            165                 170                 175

Leu Arg Thr Gly Gly Lys Tyr Leu Ala Thr Ser Gln Val Leu Leu Ser
        180                 185                 190

Pro Lys Ser Ile Leu Glu Gly Ser Asp Glu Tyr Leu Val Cys Lys Ile
    195                 200                 205

His Tyr Gly Gly Lys Asn Arg Asp Leu His Val Pro Ile Pro Ala Val
210                 215                 220

Ala Glu Met Asn Pro Asn Val Asn Val Phe Val Pro Pro Arg Asp Gly
225                 230                 235                 240

Phe Ser Gly Pro Ala Pro Arg Lys Ser Lys Leu Ile Cys Glu Ala Thr
            245                 250                 255

Asn Phe Thr Pro Lys Pro Ile Thr Val Ser Trp Leu Lys Asp Gly Lys
        260                 265                 270

Leu Val Glu Ser Gly Phe Thr Thr Asp Pro Val Thr Ile Glu Asn Lys
    275                 280                 285

Gly Ser Thr Pro Gln Thr Tyr Lys Val Ile Ser Thr Leu Thr Ile Ser
290                 295                 300

Glu Ile Asp Trp Leu Asn Leu Asn Val Tyr Thr Cys Arg Val Asp His
305                 310                 315                 320

Arg Gly Leu Thr Phe Leu Lys Asn Val Ser Ser Thr Cys Ala Ala Ser
            325                 330                 335

Pro Ser Thr Asp Ile Leu Thr Phe Thr Ile Pro Pro Ser Phe Ala Asp
        340                 345                 350

Ile Phe Leu Ser Lys Ser Ala Asn Leu Thr Cys Leu Val Ser Asn Leu
```

```
            355                 360                 365
Ala Thr Tyr Glu Thr Leu Asn Ile Ser Trp Ala Ser Gln Ser Gly Glu
            370                 375                 380
Pro Leu Glu Thr Lys Ile Lys Ile Met Glu Ser His Pro Asn Gly Thr
385                 390                 395                 400
Phe Ser Ala Lys Gly Val Ala Ser Val Cys Val Glu Asp Trp Asn Asn
                405                 410                 415
Arg Lys Glu Phe Val Cys Thr Val Thr His Arg Asp Leu Pro Ser Pro
            420                 425                 430
Gln Lys Lys Phe Ile Ser Lys Pro Asn Glu Val His Lys His Pro Pro
            435                 440                 445
Ala Val Tyr Leu Leu Pro Pro Ala Arg Glu Gln Leu Asn Leu Arg Glu
        450                 455                 460
Ser Ala Thr Val Thr Cys Leu Val Lys Gly Phe Ser Pro Ala Asp Ile
465                 470                 475                 480
Ser Val Gln Trp Leu Gln Arg Gly Gln Leu Leu Pro Gln Glu Lys Tyr
                485                 490                 495
Val Thr Ser Ala Pro Met Pro Glu Pro Gly Ala Pro Gly Phe Tyr Phe
            500                 505                 510
Thr His Ser Ile Leu Thr Val Thr Glu Glu Glu Trp Asn Ser Gly Glu
            515                 520                 525
Thr Tyr Thr Cys Val Val Gly His Glu Ala Leu Pro His Leu Val Thr
        530                 535                 540
Glu Arg Thr Val Asp Lys Ser Thr Gly Lys Pro Thr Leu Tyr Asn Val
545                 550                 555                 560
Ser Leu Ile Met Ser Asp Gly Gly Thr Cys Tyr
                565                 570

<210> SEQ ID NO 119
<211> LENGTH: 214
<212> TYPE: PRT
<213> ORGANISM: Artificial Sequence
<220> FEATURE:
<223> OTHER INFORMATION: Synthetic: 20E6(hyb) light chain

<400> SEQUENCE: 119

Asp Ile Gln Met Thr Gln Thr Thr Ser Ser Leu Ser Ala Ser Leu Gly
1               5                   10                  15
Asp Arg Val Thr Ile Ser Cys Arg Ala Ser Gln Asp Ile Thr Asn Tyr
                20                  25                  30
Leu Asn Trp Tyr Gln Gln Lys Pro Asp Gly Ala Val Lys Leu Leu Ile
            35                  40                  45
Tyr Tyr Thr Ser Arg Leu His Ser Gly Val Pro Ser Arg Phe Ser Gly
        50                  55                  60
Ser Gly Ser Gly Thr Asp Tyr Ser Leu Thr Ile Ser Asn Leu Glu Gln
65                  70                  75                  80
Glu Asp Ile Ala Thr Tyr Phe Cys Gln Gln Gly Asp Thr Leu Pro Trp
                85                  90                  95
Thr Phe Gly Gly Gly Thr Lys Leu Glu Ile Lys Arg Ala Asp Ala Ala
                100                 105                 110
Pro Thr Val Ser Ile Phe Pro Pro Ser Ser Glu Gln Leu Thr Ser Gly
            115                 120                 125
Gly Ala Ser Val Val Cys Phe Leu Asn Asn Phe Tyr Pro Lys Asp Ile
        130                 135                 140
Asn Val Lys Trp Lys Ile Asp Gly Ser Glu Arg Gln Asn Gly Val Leu
```

```
                145                 150                 155                 160
Asn Ser Trp Thr Asp Gln Asp Ser Lys Asp Ser Thr Tyr Ser Met Ser
                165                 170                 175
Ser Thr Leu Thr Leu Thr Lys Asp Glu Tyr Glu Arg His Asn Ser Tyr
            180                 185                 190
Thr Cys Glu Ala Thr His Lys Thr Ser Thr Ser Pro Ile Val Lys Ser
        195                 200                 205
Phe Asn Arg Asn Glu Cys
    210

<210> SEQ ID NO 120
<211> LENGTH: 10
<212> TYPE: PRT
<213> ORGANISM: Artificial Sequence
<220> FEATURE:
<223> OTHER INFORMATION: Synthetic: 20E6(hyb)VHCDR2 N54Q

<400> SEQUENCE: 120

Arg Ile Asp Pro Gln Ser Gly Gly Ile Lys
1               5                   10

<210> SEQ ID NO 121
<211> LENGTH: 10
<212> TYPE: PRT
<213> ORGANISM: Artificial Sequence
<220> FEATURE:
<223> OTHER INFORMATION: Synthetic: 20E6(hyb)VHCDR2 N54G

<400> SEQUENCE: 121

Arg Ile Asp Pro Gly Ser Gly Gly Ile Lys
1               5                   10

<210> SEQ ID NO 122
<211> LENGTH: 10
<212> TYPE: PRT
<213> ORGANISM: Artificial Sequence
<220> FEATURE:
<223> OTHER INFORMATION: Synthetic: 20E6(hyb)VHCDR2 N54A

<400> SEQUENCE: 122

Arg Ile Asp Pro Ala Ser Gly Gly Ile Lys
1               5                   10

<210> SEQ ID NO 123
<211> LENGTH: 10
<212> TYPE: PRT
<213> ORGANISM: Artificial Sequence
<220> FEATURE:
<223> OTHER INFORMATION: Synthetic: 20E6(hyb)VHCDR2 N54S

<400> SEQUENCE: 123

Arg Ile Asp Pro Ser Ser Gly Gly Ile Lys
1               5                   10

<210> SEQ ID NO 124
<211> LENGTH: 10
<212> TYPE: PRT
<213> ORGANISM: Artificial Sequence
<220> FEATURE:
<223> OTHER INFORMATION: Synthetic: 20E6(hyb)VHCDR2 N54H

<400> SEQUENCE: 124

Arg Ile Asp Pro His Ser Gly Gly Ile Lys
1               5                   10
```

<210> SEQ ID NO 125
<211> LENGTH: 10
<212> TYPE: PRT
<213> ORGANISM: Artificial Sequence
<220> FEATURE:
<223> OTHER INFORMATION: Synthetic: 20E6(hyb)VHCDR2 N54L

<400> SEQUENCE: 125

Arg Ile Asp Pro Leu Ser Gly Gly Ile Lys
1               5                   10

<210> SEQ ID NO 126
<211> LENGTH: 10
<212> TYPE: PRT
<213> ORGANISM: Artificial Sequence
<220> FEATURE:
<223> OTHER INFORMATION: Synthetic: 20E6(hyb)VHCDR2 N54D

<400> SEQUENCE: 126

Arg Ile Asp Pro Asp Ser Gly Gly Ile Lys
1               5                   10

<210> SEQ ID NO 127
<211> LENGTH: 118
<212> TYPE: PRT
<213> ORGANISM: Artificial Sequence
<220> FEATURE:
<223> OTHER INFORMATION: Synthetic: 20E6_H0 VH

<400> SEQUENCE: 127

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Asp Pro Asn Ser Gly Gly Ile Lys Tyr Asn Glu Lys Phe
    50                  55                  60

Lys Ser Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser
        115

<210> SEQ ID NO 128
<211> LENGTH: 448
<212> TYPE: PRT
<213> ORGANISM: Artificial Sequence
<220> FEATURE:
<223> OTHER INFORMATION: Synthetic: 20E6_H0_IgG1

<400> SEQUENCE: 128

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Asp Pro Asn Ser Gly Gly Ile Lys Tyr Asn Glu Lys Phe
                50                  55                  60

Lys Ser Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Trp Asp Tyr Gly Gly Tyr Phe Asp Val Trp Gly Gln Gly Thr
                100                 105                 110

Leu Val Thr Val Ser Ser Ala Ser Thr Lys Gly Pro Ser Val Phe Pro
                115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
                290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
                370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445

<210> SEQ ID NO 129
<211> LENGTH: 445
<212> TYPE: PRT

<213> ORGANISM: Artificial Sequence
<220> FEATURE:
<223> OTHER INFORMATION: Synthetic: 20E6_H0_IgG4mut

<400> SEQUENCE: 129

| | | | | | | | | | | | | | | | |
|---|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Trp | Met | His | Trp | Val | Arg | Gln | Ala | Pro | Gly | Gln | Gly | Leu | Glu | Trp | Met |
| | | 35 | | | | | 40 | | | | | 45 | | | |
| Gly | Arg | Ile | Asp | Pro | Asn | Ser | Gly | Gly | Ile | Lys | Tyr | Asn | Glu | Lys | Phe |
| | 50 | | | | | 55 | | | | | 60 | | | | |
| Lys | Ser | Arg | Val | Thr | Met | Thr | Arg | Asp | Thr | Ser | Ile | Ser | Thr | Ala | Tyr |
| 65 | | | | | 70 | | | | | 75 | | | | | 80 |
| Met | Glu | Leu | Ser | Arg | Leu | Arg | Ser | Asp | Asp | Thr | Ala | Val | Tyr | Tyr | Cys |
| | | | | 85 | | | | | 90 | | | | | 95 | |
| Ala | Arg | Trp | Asp | Tyr | Gly | Gly | Tyr | Phe | Asp | Val | Trp | Gly | Gln | Gly | Thr |
| | | | 100 | | | | | 105 | | | | | 110 | | |
| Leu | Val | Thr | Val | Ser | Ser | Ala | Ser | Thr | Lys | Gly | Pro | Ser | Val | Phe | Pro |
| | | 115 | | | | | 120 | | | | | 125 | | | |
| Leu | Ala | Pro | Cys | Ser | Arg | Ser | Thr | Ser | Glu | Ser | Thr | Ala | Ala | Leu | Gly |
| | 130 | | | | | 135 | | | | | 140 | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Ser | Leu | Gly | Thr | Lys | Thr | Tyr | Thr | Cys | Asn | Val | Asp | His | Lys | Pro | Ser |
| | | 195 | | | | | 200 | | | | | 205 | | | |
| Asn | Thr | Lys | Val | Asp | Lys | Arg | Val | Glu | Ser | Lys | Tyr | Gly | Pro | Pro | Cys |
| | 210 | | | | | 215 | | | | | 220 | | | | |
| Pro | Pro | Cys | Pro | Ala | Pro | Glu | Ala | Ala | Gly | Gly | Pro | Ser | Val | Phe | Leu |
| 225 | | | | | 230 | | | | | 235 | | | | | 240 |
| Phe | Pro | Pro | Lys | Pro | Lys | Asp | Thr | Leu | Met | Ile | Ser | Arg | Thr | Pro | Glu |
| | | | | 245 | | | | | 250 | | | | | 255 | |
| Val | Thr | Cys | Val | Val | Val | Asp | Val | Ser | Gln | Glu | Asp | Pro | Glu | Val | Gln |
| | | | 260 | | | | | 265 | | | | | 270 | | |
| Phe | Asn | Trp | Tyr | Val | Asp | Gly | Val | Glu | Val | His | Asn | Ala | Lys | Thr | Lys |
| | | 275 | | | | | 280 | | | | | 285 | | | |
| Pro | Arg | Glu | Glu | Gln | Phe | Asn | Ser | Thr | Tyr | Arg | Val | Val | Ser | Val | Leu |
| | 290 | | | | | 295 | | | | | 300 | | | | |
| Thr | Val | Leu | His | Gln | Asp | Trp | Leu | Asn | Gly | Lys | Glu | Tyr | Lys | Cys | Lys |
| 305 | | | | | 310 | | | | | 315 | | | | | 320 |
| Val | Ser | Asn | Lys | Gly | Leu | Pro | Ser | Ser | Ile | Glu | Lys | Thr | Ile | Ser | Lys |
| | | | | 325 | | | | | 330 | | | | | 335 | |
| Ala | Lys | Gly | Gln | Pro | Arg | Glu | Pro | Gln | Val | Tyr | Thr | Leu | Pro | Pro | Ser |
| | | | 340 | | | | | 345 | | | | | 350 | | |
| Gln | Glu | Glu | Met | Thr | Lys | Asn | Gln | Val | Ser | Leu | Thr | Cys | Leu | Val | Lys |
| | | | | 355 | | | | | 360 | | | | | 365 | |
| Gly | Phe | Tyr | Pro | Ser | Asp | Ile | Ala | Val | Glu | Trp | Glu | Ser | Asn | Gly | Gln |
| | | 370 | | | | | 375 | | | | | 380 | | | |
| Pro | Glu | Asn | Asn | Tyr | Lys | Thr | Thr | Pro | Pro | Val | Leu | Asp | Ser | Asp | Gly |

```
                385                 390                 395                 400
Ser Phe Phe Leu Tyr Ser Arg Leu Thr Val Asp Lys Ser Arg Trp Gln
                    405                 410                 415

Glu Gly Asn Val Phe Ser Cys Ser Val Met His Glu Ala Leu His Asn
                    420                 425                 430

His Tyr Thr Gln Lys Ser Leu Ser Leu Ser Leu Gly Lys
                    435                 440                 445

<210> SEQ ID NO 130
<211> LENGTH: 118
<212> TYPE: PRT
<213> ORGANISM: Artificial Sequence
<220> FEATURE:
<223> OTHER INFORMATION: Synthetic: 20E6_H0.1 VH

<400> SEQUENCE: 130

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Arg Ile Asp Pro Asn Ser Gly Gly Ile Lys Tyr Ala Gln Lys Phe
        50                  55                  60

Gln Gly Arg Ala Thr Leu Thr Val Asp Thr Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
                100                 105                 110

Leu Val Thr Val Ser Ser
            115

<210> SEQ ID NO 131
<211> LENGTH: 448
<212> TYPE: PRT
<213> ORGANISM: Artificial Sequence
<220> FEATURE:
<223> OTHER INFORMATION: Synthetic: 20E6_H0.1_IgG1

<400> SEQUENCE: 131

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Arg Ile Asp Pro Asn Ser Gly Gly Ile Lys Tyr Ala Gln Lys Phe
        50                  55                  60

Gln Gly Arg Ala Thr Leu Thr Val Asp Thr Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
                100                 105                 110

Leu Val Thr Val Ser Ser Ala Ser Thr Lys Gly Pro Ser Val Phe Pro
            115                 120                 125
```

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 132
<211> LENGTH: 445
<212> TYPE: PRT
<213> ORGANISM: Artificial Sequence
<220> FEATURE:
<223> OTHER INFORMATION: Synthetic: 20E6_H0.1_IgG4mut

<400> SEQUENCE: 132

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Asp Pro Asn Ser Gly Gly Ile Lys Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 133
<211> LENGTH: 118
<212> TYPE: PRT

<213> ORGANISM: Artificial Sequence
<220> FEATURE:
<223> OTHER INFORMATION: Synthetic: 20E6_H0.2 VH

<400> SEQUENCE: 133

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Asp Pro Gln Ser Gly Gly Ile Lys Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser
        115
```

<210> SEQ ID NO 134
<211> LENGTH: 448
<212> TYPE: PRT
<213> ORGANISM: Artificial Sequence
<220> FEATURE:
<223> OTHER INFORMATION: Synthetic: 20E6_H0.2_IgG1

<400> SEQUENCE: 134

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Asp Pro Gln Ser Gly Gly Ile Lys Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 135
<211> LENGTH: 445
<212> TYPE: PRT
<213> ORGANISM: Artificial Sequence
<220> FEATURE:
<223> OTHER INFORMATION: Synthetic: 20E6_H0.2_IgG4mut

<400> SEQUENCE: 135

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Arg Ile Asp Pro Gln Ser Gly Gly Ile Lys Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 136
<211> LENGTH: 118
<212> TYPE: PRT
<213> ORGANISM: Artificial Sequence
<220> FEATURE:
<223> OTHER INFORMATION: Synthetic: 20E6_H0.3_IgG1

<400> SEQUENCE: 136

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

```
Gly Arg Ile Asp Pro Gly Ser Gly Ile Lys Tyr Ala Gln Lys Phe
     50                  55                  60

Gln Gly Arg Ala Thr Leu Thr Val Asp Thr Ser Thr Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Trp Asp Tyr Gly Gly Tyr Phe Asp Val Trp Gly Gln Gly Thr
             100                 105                 110

Leu Val Thr Val Ser Ser
            115

<210> SEQ ID NO 137
<211> LENGTH: 118
<212> TYPE: PRT
<213> ORGANISM: Artificial Sequence
<220> FEATURE:
<223> OTHER INFORMATION: Synthetic: 20E6_H0.4_IgG1

<400> SEQUENCE: 137

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Trp Met His Trp Val Arg Gln Ala Pro Gly Gln Gly Leu Glu Trp Met
             35                  40                  45

Gly Arg Ile Asp Pro Ala Ser Gly Ile Lys Tyr Ala Gln Lys Phe
     50                  55                  60

Gln Gly Arg Ala Thr Leu Thr Val Asp Thr Ser Thr Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Trp Asp Tyr Gly Gly Tyr Phe Asp Val Trp Gly Gln Gly Thr
             100                 105                 110

Leu Val Thr Val Ser Ser
            115

<210> SEQ ID NO 138
<211> LENGTH: 118
<212> TYPE: PRT
<213> ORGANISM: Artificial Sequence
<220> FEATURE:
<223> OTHER INFORMATION: Synthetic: 20E6_H0.5_IgG1

<400> SEQUENCE: 138

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Trp Met His Trp Val Arg Gln Ala Pro Gly Gln Gly Leu Glu Trp Met
             35                  40                  45

Gly Arg Ile Asp Pro Ser Ser Gly Ile Lys Tyr Ala Gln Lys Phe
     50                  55                  60

Gln Gly Arg Ala Thr Leu Thr Val Asp Thr Ser Thr Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Trp Asp Tyr Gly Gly Tyr Phe Asp Val Trp Gly Gln Gly Thr
             100                 105                 110
```

Leu Val Thr Val Ser Ser
        115

<210> SEQ ID NO 139
<211> LENGTH: 118
<212> TYPE: PRT
<213> ORGANISM: Artificial Sequence
<220> FEATURE:
<223> OTHER INFORMATION: Synthetic: 20E6_H0.6_IgG1

<400> SEQUENCE: 139

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Asp Pro His Ser Gly Gly Ile Lys Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser
        115

<210> SEQ ID NO 140
<211> LENGTH: 118
<212> TYPE: PRT
<213> ORGANISM: Artificial Sequence
<220> FEATURE:
<223> OTHER INFORMATION: Synthetic: 20E6_H0.7_IgG1

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Asp Pro Leu Ser Gly Gly Ile Lys Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser
        115

<210> SEQ ID NO 141
<211> LENGTH: 118
<212> TYPE: PRT
<213> ORGANISM: Artificial Sequence
<220> FEATURE:
<223> OTHER INFORMATION: Synthetic: 20E6_H0.8_IgG1

<400> SEQUENCE: 141

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Asp Pro Asp Ser Gly Gly Ile Lys Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser
        115

<210> SEQ ID NO 142
<211> LENGTH: 118
<212> TYPE: PRT
<213> ORGANISM: Artificial Sequence
<220> FEATURE:
<223> OTHER INFORMATION: Synthetic: 20E6_H0.2_ hIgG4mut VH

<400> SEQUENCE: 142

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Asp Pro Gln Ser Gly Gly Ile Lys Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser
        115

<210> SEQ ID NO 143
<211> LENGTH: 445
<212> TYPE: PRT
<213> ORGANISM: Artificial Sequence
<220> FEATURE:
<223> OTHER INFORMATION: Synthetic: 20E6_H0.2_ hIgG4mut

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Asp Pro Gln Ser Gly Ile Lys Tyr Ala Gln Lys Phe
 50                  55                  60

Gln Gly Arg Ala Thr Leu Thr Val Asp Thr Ser Thr Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Trp Asp Tyr Gly Gly Tyr Phe Asp Val Trp Gly Gln Gly Thr
             100                 105                 110

Leu Val Thr Val Ser Ser Ala Ser Thr Lys Gly Pro Ser Val Phe Pro
         115                 120                 125

Leu Ala Pro Cys Ser Arg Ser Thr Ser Glu Ser Thr Ala Ala Leu Gly
     130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 144
<211> LENGTH: 118

```
<212> TYPE: PRT
<213> ORGANISM: Artificial Sequence
<220> FEATURE:
<223> OTHER INFORMATION: Synthetic: 20E6_H1 VH

<400> SEQUENCE: 144
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Arg Ile Asp Pro Asn Ser Gly Gly Ile Lys Tyr Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser
        115

```
<210> SEQ ID NO 145
<211> LENGTH: 448
<212> TYPE: PRT
<213> ORGANISM: Artificial Sequence
<220> FEATURE:
<223> OTHER INFORMATION: Synthetic: 20E6_H1_IgG1

<400> SEQUENCE: 145
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Arg Ile Asp Pro Asn Ser Gly Gly Ile Lys Tyr Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

```
Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 146
<211> LENGTH: 118
<212> TYPE: PRT
<213> ORGANISM: Artificial Sequence
<220> FEATURE:
<223> OTHER INFORMATION: Synthetic: 20E6_H2 VH

<400> SEQUENCE: 146

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Arg Ile Asp Pro Asn Ser Gly Gly Ile Lys Tyr Asn Glu Lys Phe
    50                  55                  60

Lys Ser Arg Val Thr Leu Thr Val Asp Lys Ser Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser
        115
```

<210> SEQ ID NO 147
<211> LENGTH: 448
<212> TYPE: PRT
<213> ORGANISM: Artificial Sequence
<220> FEATURE:
<223> OTHER INFORMATION: Synthetic: 20E6_H2_IgG1

<400> SEQUENCE: 147

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Ile
        35                  40                  45

Gly Arg Ile Asp Pro Asn Ser Gly Gly Ile Lys Tyr Asn Glu Lys Phe
    50                  55                  60

Lys Ser Arg Val Thr Leu Thr Val Asp Lys Ser Ser Ser Thr Ala Tyr
65                  70                  75                  80

Met Glu Leu Ser Arg Leu Arg Ser Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

```
Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 148
<211> LENGTH: 118
<212> TYPE: PRT
<213> ORGANISM: Artificial Sequence
<220> FEATURE:
<223> OTHER INFORMATION: Synthetic: 20E6_H3 VH

<400> SEQUENCE: 148

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Arg Ile Asp Pro Asn Ser Gly Gly Ile Lys Tyr Asn Glu Lys Phe
    50                  55                  60

Lys Ser Lys Ala Thr Leu Thr Val Asp Lys Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser
        115

<210> SEQ ID NO 149
<211> LENGTH: 448
<212> TYPE: PRT
<213> ORGANISM: Artificial Sequence
<220> FEATURE:
<223> OTHER INFORMATION: Synthetic: 20E6_H3_IgG1

<400> SEQUENCE: 149

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Arg Ile Asp Pro Asn Ser Gly Gly Ile Lys Tyr Asn Glu Lys Phe
    50                  55                  60

Lys Ser Lys Ala Thr Leu Thr Val Asp Lys Ser Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Trp Asp Tyr Gly Gly Tyr Phe Asp Val Trp Gly Gln Gly Thr
```

```
            100                 105                 110
Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 150
<211> LENGTH: 118
<212> TYPE: PRT
<213> ORGANISM: Artificial Sequence
<220> FEATURE:
<223> OTHER INFORMATION: Synthetic: 20E6_H4 VH

<400> SEQUENCE: 150

Gln Val Gln Leu Val Gln Pro Gly Ala Glu Val Val Lys Pro Gly Ala
1               5                   10                  15

Ser Val Lys Leu Ser Cys Lys Ala Ser Gly Tyr Thr Phe Thr Ser Tyr
```

```
            20                  25                  30
Trp Met His Trp Val Lys Gln Arg Pro Gly Gln Gly Leu Glu Trp Ile
        35                  40                  45
Gly Arg Ile Asp Pro Asn Ser Gly Gly Ile Lys Tyr Asn Glu Lys Phe
    50                  55                  60
Lys Ser Lys Ala Thr Leu Thr Val Asp Lys Ser Ser Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Trp Asp Tyr Gly Gly Tyr Phe Asp Val Trp Gly Gln Gly Thr
            100                 105                 110
Leu Val Thr Val Ser Ser
            115

<210> SEQ ID NO 151
<211> LENGTH: 448
<212> TYPE: PRT
<213> ORGANISM: Artificial Sequence
<220> FEATURE:
<223> OTHER INFORMATION: Synthetic: 20E6_H4_IgG1

<400> SEQUENCE: 151

Gln Val Gln Leu Val Gln Pro Gly Ala Glu Val Val Lys Pro Gly Ala
1               5                   10                  15
Ser Val Lys Leu Ser Cys Lys Ala Ser Gly Tyr Thr Phe Thr Ser Tyr
            20                  25                  30
Trp Met His Trp Val Lys Gln Arg Pro Gly Gln Gly Leu Glu Trp Ile
        35                  40                  45
Gly Arg Ile Asp Pro Asn Ser Gly Gly Ile Lys Tyr Asn Glu Lys Phe
    50                  55                  60
Lys Ser Lys Ala Thr Leu Thr Val Asp Lys Ser Ser Ser Thr Ala Tyr
65                  70                  75                  80
Met Glu Leu Ser Arg Leu Arg Ser Asp Asp Thr Ala Val Tyr Tyr Cys
                85                  90                  95
Ala Arg Trp Asp Tyr Gly Gly Tyr Phe Asp Val Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
```

```
                    260                 265                 270
Glu Val Lys Phe Asn Trp Tyr Val Asp Gly Val Glu Val His Asn Ala
            275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 152
<211> LENGTH: 107
<212> TYPE: PRT
<213> ORGANISM: Artificial Sequence
<220> FEATURE:
<223> OTHER INFORMATION: Synthetic: 20E6_L0 VL

<400> SEQUENCE: 152

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Thr Asn Tyr
            20                  25                  30
Leu Asn Trp Tyr Gln Gln Lys Pro Gly Lys Ala Pro Lys Leu Leu Ile
        35                  40                  45
Tyr Tyr Thr Ser Arg Leu His Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Gly Asp Thr Leu Pro Trp
                85                  90                  95
Thr Phe Gly Gln Gly Thr Lys Leu Glu Ile Lys
            100                 105

<210> SEQ ID NO 153
<211> LENGTH: 214
<212> TYPE: PRT
<213> ORGANISM: Artificial Sequence
<220> FEATURE:
<223> OTHER INFORMATION: Synthetic: 20E6_L0

<400> SEQUENCE: 153

Asp Ile Gln Met Thr Gln Ser Pro Ser Ser Leu Ser Ala Ser Val Gly
1               5                   10                  15
```

Asp Arg Val Thr Ile Thr Cys Arg Ala Ser Gln Asp Ile Thr Asn Tyr
            20                  25                  30

Leu Asn Trp Tyr Gln Gln Lys Pro Gly Lys Ala Pro Lys Leu Leu Ile
             35                  40                  45

Tyr Tyr Thr Ser Arg Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Asp Thr Leu Pro Trp
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 154
<211> LENGTH: 107
<212> TYPE: PRT
<213> ORGANISM: Artificial Sequence
<220> FEATURE:
<223> OTHER INFORMATION: Synthetic: 20E6_L1 VL

<400> SEQUENCE: 154

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Thr Asn Tyr
            20                  25                  30

Leu Asn Trp Tyr Gln Gln Lys Pro Gly Lys Ala Val Lys Leu Leu Ile
             35                  40                  45

Tyr Tyr Thr Ser Arg Leu His Ser Gly Val Pro Ser Arg Phe Ser Gly
 50                  55                  60

Ser Gly Ser Gly Thr Asp Tyr Thr Leu Thr Ile Ser Ser Leu Gln Pro
 65                  70                  75                  80

Glu Asp Phe Ala Thr Tyr Phe Cys Gln Gln Gly Asp Thr Leu Pro Trp
                 85                  90                  95

Thr Phe Gly Gln Gly Thr Lys Leu Glu Ile Lys
            100                 105

<210> SEQ ID NO 155
<211> LENGTH: 214
<212> TYPE: PRT
<213> ORGANISM: Artificial Sequence
<220> FEATURE:
<223> OTHER INFORMATION: Synthetic: 20E6_L1

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Thr Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asp Thr Leu Pro Trp
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 156
<211> LENGTH: 107
<212> TYPE: PRT
<213> ORGANISM: Artificial Sequence
<220> FEATURE:
<223> OTHER INFORMATION: Synthetic: 20E6_L0_P44V VL

<400> SEQUENCE: 156

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Thr Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Trp
            85                  90                  95

Thr Phe Gly Gln Gly Thr Lys Leu Glu Ile Lys
            100                 105

<210> SEQ ID NO 157
<211> LENGTH: 214
<212> TYPE: PRT
<213> ORGANISM: Artificial Sequence

```
<220> FEATURE:
<223> OTHER INFORMATION: Synthetic: 20E6_L0_P44V

<400> SEQUENCE: 157

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Thr Asn Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asp Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 158
<211> LENGTH: 107
<212> TYPE: PRT
<213> ORGANISM: Artificial Sequence
<220> FEATURE:
<223> OTHER INFORMATION: Synthetic: 20E6_L0_F71Y VL

<400> SEQUENCE: 158

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asp Thr Leu Pro Trp
                85                  90                  95

Thr Phe Gly Gln Gly Thr Lys Leu Glu Ile Lys
            100                 105
```

-continued

<210> SEQ ID NO 159
<211> LENGTH: 214
<212> TYPE: PRT
<213> ORGANISM: Artificial Sequence
<220> FEATURE:
<223> OTHER INFORMATION: Synthetic: 20E6_L0_F71Y

<400> SEQUENCE: 159

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Gly Asp Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 160
<211> LENGTH: 107
<212> TYPE: PRT
<213> ORGANISM: Artificial Sequence
<220> FEATURE:
<223> OTHER INFORMATION: Synthetic: 20E6_L0_Y87F VL

<400> SEQUENCE: 160

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Asp Thr Leu Pro Trp
                85                  90                  95
```

```
Thr Phe Gly Gln Gly Thr Lys Leu Glu Ile Lys
            100                 105

<210> SEQ ID NO 161
<211> LENGTH: 214
<212> TYPE: PRT
<213> ORGANISM: Artificial Sequence
<220> FEATURE:
<223> OTHER INFORMATION: Synthetic: 20E6_L0_Y87F

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Gly Asp Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 162
<211> LENGTH: 10
<212> TYPE: PRT
<213> ORGANISM: Artificial Sequence
<220> FEATURE:
<223> OTHER INFORMATION: Synthetic: 17G8(hyb)VHCDR1

<400> SEQUENCE: 162

Gly Phe Thr Phe Thr Asp Tyr Tyr Met Ser
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Synthetic: 17G8(hyb)VHCDR2

<400> SEQUENCE: 163

Phe Ile Arg Asn Lys Ala Asn Gly Tyr Thr Thr Glu
```

```
1               5                   10

<210> SEQ ID NO 164
<211> LENGTH: 9
<212> TYPE: PRT
<213> ORGANISM: Artificial Sequence
<220> FEATURE:
<223> OTHER INFORMATION: Synthetic: 17G8(hyb)VHCDR3

<400> SEQUENCE: 164

Tyr Lys Leu Gly Gly Tyr Phe Asp Val
1               5

<210> SEQ ID NO 165
<211> LENGTH: 11
<212> TYPE: PRT
<213> ORGANISM: Artificial Sequence
<220> FEATURE:
<223> OTHER INFORMATION: Synthetic: 17G8(hyb)VLCDR1

<400> SEQUENCE: 165

Arg Ala Ser Gln Asp Ile Ser Asn Tyr Leu Asn
1               5                   10

<210> SEQ ID NO 166
<211> LENGTH: 7
<212> TYPE: PRT
<213> ORGANISM: Artificial Sequence
<220> FEATURE:
<223> OTHER INFORMATION: Synthetic: 17G8(hyb)VLCDR2

<400> SEQUENCE: 166

Tyr Thr Ser Arg Leu His Ser
1               5

<210> SEQ ID NO 167
<211> LENGTH: 9
<212> TYPE: PRT
<213> ORGANISM: Artificial Sequence
<220> FEATURE:
<223> OTHER INFORMATION: Synthetic: 17G8(hyb)VLCDR3

<400> SEQUENCE: 167

Gln Gln Gly Asn Thr Leu Pro Trp Thr
1               5

<210> SEQ ID NO 168
<211> LENGTH: 120
<212> TYPE: PRT
<213> ORGANISM: Artificial Sequence
<220> FEATURE:
<223> OTHER INFORMATION: Synthetic: 17G8(hyb )VH

<400> SEQUENCE: 168

Glu Val Lys Leu Val Glu Ser Gly Gly Leu Val Gln Pro Gly Gly
1               5                   10                  15

Ser Leu Ser Leu Ser Cys Ala Ala Ser Gly Phe Thr Phe Thr Asp Tyr
                20                  25                  30

Tyr Met Ser Trp Val Arg Gln Pro Pro Gly Lys Ala Leu Glu Trp Leu
            35                  40                  45

Gly Phe Ile Arg Asn Lys Ala Asn Gly Tyr Thr Thr Glu Tyr Ser Ala
        50                  55                  60

Ser Val Lys Gly Arg Phe Thr Ile Ser Arg Asp Asn Ser Gln Ser Ile
65                  70                  75                  80
```

Leu Tyr Leu Gln Met Asn Ala Leu Arg Ala Glu Asp Ser Ala Thr Tyr
                85                  90                  95

Tyr Cys Ala Arg Tyr Lys Leu Gly Gly Tyr Phe Asp Val Trp Gly Thr
            100                 105                 110

Gly Thr Thr Val Thr Val Ser Ser
        115                 120

<210> SEQ ID NO 169
<211> LENGTH: 107
<212> TYPE: PRT
<213> ORGANISM: Artificial Sequence
<220> FEATURE:
<223> OTHER INFORMATION: Synthetic: 17G8(hyb) VL

<400> SEQUENCE: 169

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105

<210> SEQ ID NO 170
<211> LENGTH: 574
<212> TYPE: PRT
<213> ORGANISM: Artificial Sequence
<220> FEATURE:
<223> OTHER INFORMATION: Synthetic: 17G8(hyb) heavy chain

<400> SEQUENCE: 170

Glu Val Lys Leu Val Glu Ser Gly Gly Gly Leu Val Gln Pro Gly Gly
1               5                   10                  15

Ser Leu Ser Leu Ser Cys Ala Ala Ser Gly Phe Thr Phe Thr Asp Tyr
            20                  25                  30

Tyr Met Ser Trp Val Arg Gln Pro Pro Gly Lys Ala Leu Glu Trp Leu
        35                  40                  45

Gly Phe Ile Arg Asn Lys Ala Asn Gly Tyr Thr Thr Glu Tyr Ser Ala
50                  55                  60

Ser Val Lys Gly Arg Phe Thr Ile Ser Arg Asp Asn Ser Gln Ser Ile
65                  70                  75                  80

Leu Tyr Leu Gln Met Asn Ala Leu Arg Ala Glu Asp Ser Ala Thr Tyr
                85                  90                  95

Tyr Cys Ala Arg Tyr Lys Leu Gly Gly Tyr Phe Asp Val Trp Gly Thr
            100                 105                 110

Gly Thr Thr Val Thr Val Ser Ser Gln Ser Phe Pro Asn Val Phe
        115                 120                 125

Pro Leu Val Ser Cys Glu Ser Pro Leu Ser Asp Lys Asn Leu Val Ala
    130                 135                 140

Met Gly Cys Leu Ala Arg Asp Phe Leu Pro Ser Thr Ile Ser Phe Thr
145                 150                 155                 160

```
Trp Asn Tyr Gln Asn Asn Thr Glu Val Ile Gln Gly Ile Arg Thr Phe
                165                 170                 175

Pro Thr Leu Arg Thr Gly Gly Lys Tyr Leu Ala Thr Ser Gln Val Leu
            180                 185                 190

Leu Ser Pro Lys Ser Ile Leu Glu Gly Ser Asp Glu Tyr Leu Val Cys
        195                 200                 205

Lys Ile His Tyr Gly Gly Lys Asn Arg Asp Leu His Val Pro Ile Pro
    210                 215                 220

Ala Val Ala Glu Met Asn Pro Asn Val Asn Val Phe Val Pro Pro Arg
225                 230                 235                 240

Asp Gly Phe Ser Gly Pro Ala Pro Arg Lys Ser Lys Leu Ile Cys Glu
                245                 250                 255

Ala Thr Asn Phe Thr Pro Lys Pro Ile Thr Val Ser Trp Leu Lys Asp
            260                 265                 270

Gly Lys Leu Val Glu Ser Gly Phe Thr Thr Asp Pro Val Thr Ile Glu
        275                 280                 285

Asn Lys Gly Ser Thr Pro Gln Thr Tyr Lys Val Ile Ser Thr Leu Thr
    290                 295                 300

Ile Ser Glu Ile Asp Trp Leu Asn Leu Asn Val Tyr Thr Cys Arg Val
305                 310                 315                 320

Asp His Arg Gly Leu Thr Phe Leu Lys Asn Val Ser Ser Thr Cys Ala
                325                 330                 335

Ala Ser Pro Ser Thr Asp Ile Leu Thr Phe Thr Ile Pro Pro Ser Phe
            340                 345                 350

Ala Asp Ile Phe Leu Ser Lys Ser Ala Asn Leu Thr Cys Leu Val Ser
        355                 360                 365

Asn Leu Ala Thr Tyr Glu Thr Leu Asn Ile Ser Trp Ala Ser Gln Ser
    370                 375                 380

Gly Glu Pro Leu Glu Thr Lys Ile Lys Ile Met Glu Ser His Pro Asn
385                 390                 395                 400

Gly Thr Phe Ser Ala Lys Gly Val Ala Ser Val Cys Val Glu Asp Trp
                405                 410                 415

Asn Asn Arg Lys Glu Phe Val Cys Thr Val Thr His Arg Asp Leu Pro
            420                 425                 430

Ser Pro Gln Lys Lys Phe Ile Ser Lys Pro Asn Glu Val His Lys His
        435                 440                 445

Pro Pro Ala Val Tyr Leu Leu Pro Pro Ala Arg Glu Gln Leu Asn Leu
    450                 455                 460

Arg Glu Ser Ala Thr Val Thr Cys Leu Val Lys Gly Phe Ser Pro Ala
465                 470                 475                 480

Asp Ile Ser Val Gln Trp Leu Gln Arg Gly Gln Leu Leu Pro Gln Glu
                485                 490                 495

Lys Tyr Val Thr Ser Ala Pro Met Pro Glu Pro Gly Ala Pro Gly Phe
            500                 505                 510

Tyr Phe Thr His Ser Ile Leu Thr Val Thr Glu Glu Trp Asn Ser
        515                 520                 525

Gly Glu Thr Tyr Thr Cys Val Val Gly His Glu Ala Leu Pro His Leu
    530                 535                 540

Val Thr Glu Arg Thr Val Asp Lys Ser Thr Gly Lys Pro Thr Leu Tyr
545                 550                 555                 560

Asn Val Ser Leu Ile Met Ser Asp Thr Gly Gly Thr Cys Tyr
                565                 570
```

<210> SEQ ID NO 171
<211> LENGTH: 214
<212> TYPE: PRT
<213> ORGANISM: Artificial Sequence
<220> FEATURE:
<223> OTHER INFORMATION: Synthetic: 17G8(hyb) light chain

<400> SEQUENCE: 171

```
Asp Ile Gln Met Thr Gln Thr Thr Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 172
<211> LENGTH: 12
<212> TYPE: PRT
<213> ORGANISM: Artificial Sequence
<220> FEATURE:
<223> OTHER INFORMATION: Synthetic: 17G8(hyb)VHCDR2 N54Q

<400> SEQUENCE: 172

```
Phe Ile Arg Asn Lys Ala Gln Gly Tyr Thr Thr Glu
1               5                   10
```

<210> SEQ ID NO 173
<211> LENGTH: 12
<212> TYPE: PRT
<213> ORGANISM: Artificial Sequence
<220> FEATURE:
<223> OTHER INFORMATION: Synthetic: 17G8(hyb)VHCDR2 N54G

<400> SEQUENCE: 173

```
Phe Ile Arg Asn Lys Ala Gly Gly Tyr Thr Thr Glu
1               5                   10
```

```
<210> SEQ ID NO 174
<211> LENGTH: 12
<212> TYPE: PRT
<213> ORGANISM: Artificial Sequence
<220> FEATURE:
<223> OTHER INFORMATION: Synthetic: 17G8(hyb)VHCDR2 N54A

<400> SEQUENCE: 174

Phe Ile Arg Asn Lys Ala Ala Gly Tyr Thr Thr Glu
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Synthetic: 17G8(hyb)VHCDR2 N54S

<400> SEQUENCE: 175

Phe Ile Arg Asn Lys Ala Ser Gly Tyr Thr Thr Glu
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Synthetic: 17G8(hyb)VHCDR2 N54H

<400> SEQUENCE: 176

Phe Ile Arg Asn Lys Ala His Gly Tyr Thr Thr Glu
1               5                   10

<210> SEQ ID NO 177
<211> LENGTH: 12
<212> TYPE: PRT
<213> ORGANISM: Artificial Sequence
<220> FEATURE:
<223> OTHER INFORMATION: Synthetic: 17G8(hyb)VHCDR2 N54L

<400> SEQUENCE: 177

Phe Ile Arg Asn Lys Ala Leu Gly Tyr Thr Thr Glu
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Synthetic: 17G8(hyb)VHCDR2 N54D

<400> SEQUENCE: 178

Phe Ile Arg Asn Lys Ala Asp Gly Tyr Thr Thr Glu
1               5                   10

<210> SEQ ID NO 179
<211> LENGTH: 10
<212> TYPE: PRT
<213> ORGANISM: Artificial Sequence
<220> FEATURE:
<223> OTHER INFORMATION: Synthetic: 24E3(hyb)VHCDR1

<400> SEQUENCE: 179

Gly Tyr Thr Phe Thr Ser Tyr Asn Met His
1               5                   10

<210> SEQ ID NO 180
```

```
<211> LENGTH: 10
<212> TYPE: PRT
<213> ORGANISM: Artificial Sequence
<220> FEATURE:
<223> OTHER INFORMATION: Synthetic: 24E3(hyb)VHCDR2

<400> SEQUENCE: 180

Ala Ile Tyr Pro Gly Asn Gly Asp Thr Ser
1               5                   10

<210> SEQ ID NO 181
<211> LENGTH: 9
<212> TYPE: PRT
<213> ORGANISM: Artificial Sequence
<220> FEATURE:
<223> OTHER INFORMATION: Synthetic: 24E3(hyb)VHCDR3

<400> SEQUENCE: 181

Trp Asp Trp Gly Gly Tyr Phe Asp Val
1               5

<210> SEQ ID NO 182
<211> LENGTH: 11
<212> TYPE: PRT
<213> ORGANISM: Artificial Sequence
<220> FEATURE:
<223> OTHER INFORMATION: Synthetic: 24E3(hyb)VLCDR1

<400> SEQUENCE: 182

Arg Ala Ser Gln Asp Ile Ser Asn Tyr Leu Asn
1               5                   10

<210> SEQ ID NO 183
<211> LENGTH: 7
<212> TYPE: PRT
<213> ORGANISM: Artificial Sequence
<220> FEATURE:
<223> OTHER INFORMATION: Synthetic: 24E3(hyb)VLCDR2

<400> SEQUENCE: 183

Tyr Thr Ser Arg Leu His Ser
1               5

<210> SEQ ID NO 184
<211> LENGTH: 10
<212> TYPE: PRT
<213> ORGANISM: Artificial Sequence
<220> FEATURE:
<223> OTHER INFORMATION: Synthetic: 24E3(hyb)VLCDR3

<400> SEQUENCE: 184

Gln Gln Gly Asp Thr Leu Pro Trp Thr Phe
1               5                   10

<210> SEQ ID NO 185
<211> LENGTH: 118
<212> TYPE: PRT
<213> ORGANISM: Artificial Sequence
<220> FEATURE:
<223> OTHER INFORMATION: Synthetic: 24E3(hyb)VH

<400> SEQUENCE: 185

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
                20                  25                  30
```

Asn Met His Trp Val Lys Gln Thr Pro Arg Gln Gly Leu Glu Trp Ile
            35                  40                  45

Gly Ala Ile Tyr Pro Gly Asn Gly Asp Thr Ser Tyr Asn Pro Lys Phe
 50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Trp Asp Trp Gly Gly Tyr Phe Asp Val Trp Gly Thr Gly Thr
            100                 105                 110

Thr Val Thr Val Ser Ser
            115

<210> SEQ ID NO 186
<211> LENGTH: 107
<212> TYPE: PRT
<213> ORGANISM: Artificial Sequence
<220> FEATURE:
<223> OTHER INFORMATION: Synthetic: 24E3(hyb) VL

<400> SEQUENCE: 186

Asp Ile Gln Met Thr Gln Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
 50                 55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asp Thr Leu Pro Trp
                85                  90                  95

Thr Phe Gly Gly Gly Thr Lys Leu Gly Ile Lys
            100                 105

<210> SEQ ID NO 187
<211> LENGTH: 572
<212> TYPE: PRT
<213> ORGANISM: Artificial Sequence
<220> FEATURE:
<223> OTHER INFORMATION: Synthetic: 24E3(hyb) heavy chain

<400> SEQUENCE: 187

Gln Ala Tyr Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Arg Gln Gly Leu Glu Trp Ile
            35                  40                  45

Gly Ala Ile Tyr Pro Gly Asn Gly Asp Thr Ser Tyr Asn Pro Lys Phe
 50                  55                  60

Lys Gly Lys Ala Thr Leu Thr Val Asp Lys Ser Ser Thr Ala Tyr
65                  70                  75                  80

Met Gln Leu Ser Ser Leu Thr Ser Glu Asp Ser Ala Val Tyr Phe Cys
                85                  90                  95

Thr Arg Trp Asp Trp Gly Gly Tyr Phe Asp Val Trp Gly Thr Gly Thr
            100                 105                 110

-continued

Thr Val Thr Val Ser Ser Gln Ser Phe Pro Asn Val Phe Pro Leu
        115                 120                 125

Val Ser Cys Glu Ser Pro Leu Ser Asp Lys Asn Leu Val Ala Met Gly
130                 135                 140

Cys Leu Ala Arg Asp Phe Leu Pro Ser Thr Ile Ser Phe Thr Trp Asn
145                 150                 155                 160

Tyr Gln Asn Asn Thr Glu Val Ile Gln Gly Ile Arg Thr Phe Pro Thr
                165                 170                 175

Leu Arg Thr Gly Gly Lys Tyr Leu Ala Thr Ser Gln Val Leu Leu Ser
            180                 185                 190

Pro Lys Ser Ile Leu Glu Gly Ser Asp Glu Tyr Leu Val Cys Lys Ile
        195                 200                 205

His Tyr Gly Gly Lys Asn Arg Asp Leu His Val Pro Ile Pro Ala Val
    210                 215                 220

Ala Glu Met Asn Pro Asn Val Asn Val Phe Val Pro Pro Arg Asp Gly
225                 230                 235                 240

Phe Ser Gly Pro Ala Pro Arg Lys Ser Lys Leu Ile Cys Glu Ala Thr
                245                 250                 255

Asn Phe Thr Pro Lys Pro Ile Thr Val Ser Trp Leu Lys Asp Gly Lys
            260                 265                 270

Leu Val Glu Ser Gly Phe Thr Thr Asp Pro Val Thr Ile Glu Asn Lys
        275                 280                 285

Gly Ser Thr Pro Gln Thr Tyr Lys Val Ile Ser Thr Leu Thr Ile Ser
    290                 295                 300

Glu Ile Asp Trp Leu Asn Leu Asn Val Tyr Thr Cys Arg Val Asp His
305                 310                 315                 320

Arg Gly Leu Thr Phe Leu Lys Asn Val Ser Ser Thr Cys Ala Ala Ser
                325                 330                 335

Pro Ser Thr Asp Ile Leu Thr Phe Thr Ile Pro Pro Ser Phe Ala Asp
            340                 345                 350

Ile Phe Leu Ser Lys Ser Ala Asn Leu Thr Cys Leu Val Ser Asn Leu
        355                 360                 365

Ala Thr Tyr Glu Thr Leu Asn Ile Ser Trp Ala Ser Gln Ser Gly Glu
    370                 375                 380

Pro Leu Glu Thr Lys Ile Lys Ile Met Glu Ser His Pro Asn Gly Thr
385                 390                 395                 400

Phe Ser Ala Lys Gly Val Ala Ser Val Cys Val Glu Asp Trp Asn Asn
                405                 410                 415

Arg Lys Glu Phe Val Cys Thr Val Thr His Arg Asp Leu Pro Ser Pro
            420                 425                 430

Gln Lys Lys Phe Ile Ser Lys Pro Asn Glu Val His Lys His Pro Pro
        435                 440                 445

Ala Val Tyr Leu Leu Pro Pro Ala Arg Glu Gln Leu Asn Leu Arg Glu
    450                 455                 460

Ser Ala Thr Val Thr Cys Leu Val Lys Gly Phe Ser Pro Ala Asp Ile
465                 470                 475                 480

Ser Val Gln Trp Leu Gln Arg Gly Gln Leu Leu Pro Gln Glu Lys Tyr
                485                 490                 495

Val Thr Ser Ala Pro Met Pro Glu Pro Gly Ala Pro Gly Phe Tyr Phe
            500                 505                 510

Thr His Ser Ile Leu Thr Val Thr Glu Glu Trp Asn Ser Gly Glu
        515                 520                 525

```
Thr Tyr Thr Cys Val Val Gly His Glu Ala Leu Pro His Leu Val Thr
            530                 535                 540
Glu Arg Thr Val Asp Lys Ser Thr Gly Lys Pro Thr Leu Tyr Asn Val
545                 550                 555                 560
Ser Leu Ile Met Ser Asp Thr Gly Gly Thr Cys Tyr
                565                 570
```

<210> SEQ ID NO 188
<211> LENGTH: 214
<212> TYPE: PRT
<213> ORGANISM: Artificial Sequence
<220> FEATURE:
<223> OTHER INFORMATION: Synthetic: 24E3(hyb) light chain

<400> SEQUENCE: 188

```
Asp Ile Gln Met Thr Gln Thr Thr Ser Ser Leu Ser Ala Ser Leu Gly
1               5                   10                  15
Asp Arg Val Thr Ile Ser Cys Arg Ala Ser Gln Asp Ile Ser Asn Tyr
            20                  25                  30
Leu Asn Trp Tyr Gln Gln Lys Pro Asp Gly Thr Val Lys Leu Leu Ile
        35                  40                  45
Tyr Tyr Thr Ser Arg Leu His Ser Gly Val Pro Ser Arg Phe Ser Gly
50                  55                  60
Ser Gly Ser Gly Thr Asp Tyr Ser Leu Thr Ile Ser Asn Leu Glu Gln
65                  70                  75                  80
Glu Asp Ile Ala Thr Tyr Phe Cys Gln Gln Gly Asp Thr Leu Pro Trp
                85                  90                  95
Thr Phe Gly Gly Gly Thr Lys Leu Gly Ile Lys Arg Ala Asp Ala Ala
            100                 105                 110
Pro Thr Val Ser Ile Phe Pro Pro Ser Ser Glu Gln Leu Thr Ser Gly
        115                 120                 125
Gly Ala Ser Val Val Cys Phe Leu Asn Asn Phe Tyr Pro Lys Asp Ile
130                 135                 140
Asn Val Lys Trp Lys Ile Asp Gly Ser Glu Arg Gln Asn Gly Val Leu
145                 150                 155                 160
Asn Ser Trp Thr Asp Gln Asp Ser Lys Asp Ser Thr Tyr Ser Met Ser
                165                 170                 175
Ser Thr Leu Thr Leu Thr Lys Asp Glu Tyr Glu Arg His Asn Ser Tyr
            180                 185                 190
Thr Cys Glu Ala Thr His Lys Thr Ser Thr Ser Pro Ile Val Lys Ser
        195                 200                 205
Phe Asn Arg Asn Glu Cys
            210
```

<210> SEQ ID NO 189
<211> LENGTH: 10
<212> TYPE: PRT
<213> ORGANISM: Artificial Sequence
<220> FEATURE:
<223> OTHER INFORMATION: Synthetic: 24E3(hyb)VHCDR2 N54Q

<400> SEQUENCE: 189

```
Ala Ile Tyr Pro Gly Gln Gly Asp Thr Ser
1               5                   10
```

<210> SEQ ID NO 190
<211> LENGTH: 10
<212> TYPE: PRT
<213> ORGANISM: Artificial Sequence

```
<220> FEATURE:
<223> OTHER INFORMATION: Synthetic: 24E3(hyb)VHCDR2 N54G

<400> SEQUENCE: 190

Ala Ile Tyr Pro Gly Gly Gly Asp Thr Ser
1               5                   10

<210> SEQ ID NO 191
<211> LENGTH: 10
<212> TYPE: PRT
<213> ORGANISM: Artificial Sequence
<220> FEATURE:
<223> OTHER INFORMATION: Synthetic: 24E3(hyb)VHCDR2 N54A

<400> SEQUENCE: 191

Ala Ile Tyr Pro Gly Ala Gly Asp Thr Ser
1               5                   10

<210> SEQ ID NO 192
<211> LENGTH: 10
<212> TYPE: PRT
<213> ORGANISM: Artificial Sequence
<220> FEATURE:
<223> OTHER INFORMATION: Synthetic: 24E3(hyb)VHCDR2 N54S

<400> SEQUENCE: 192

Ala Ile Tyr Pro Gly Ser Gly Asp Thr Ser
1               5                   10

<210> SEQ ID NO 193
<211> LENGTH: 10
<212> TYPE: PRT
<213> ORGANISM: Artificial Sequence
<220> FEATURE:
<223> OTHER INFORMATION: Synthetic: 24E3(hyb)VHCDR2 N54H

<400> SEQUENCE: 193

Ala Ile Tyr Pro Gly His Gly Asp Thr Ser
1               5                   10

<210> SEQ ID NO 194
<211> LENGTH: 10
<212> TYPE: PRT
<213> ORGANISM: Artificial Sequence
<220> FEATURE:
<223> OTHER INFORMATION: Synthetic: 24E3(hyb)VHCDR2 N54L

<400> SEQUENCE: 194

Ala Ile Tyr Pro Gly Leu Gly Asp Thr Ser
1               5                   10

<210> SEQ ID NO 195
<211> LENGTH: 10
<212> TYPE: PRT
<213> ORGANISM: Artificial Sequence
<220> FEATURE:
<223> OTHER INFORMATION: Synthetic: 24E3(hyb)VHCDR2 N54D

<400> SEQUENCE: 195

Ala Ile Tyr Pro Gly Asp Gly Asp Thr Ser
1               5                   10

<210> SEQ ID NO 196
<211> LENGTH: 330
<212> TYPE: PRT
<213> ORGANISM: Artificial Sequence
<220> FEATURE:
```

<223> OTHER INFORMATION: Synthetic: Human IgG1 constant region

<400> SEQUENCE: 196

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 197
<211> LENGTH: 327
<212> TYPE: PRT
<213> ORGANISM: Artificial Sequence
<220> FEATURE:
<223> OTHER INFORMATION: Synthetic: Human IgG4 variant constant region
      (also referred to as IgG4mut)

<400> SEQUENCE: 197

Ala Ser Thr Lys Gly Pro Ser Val Phe Pro Leu Ala Pro Cys Ser Arg

```
                1               5                  10                 15
            Ser Thr Ser Glu Ser Thr Ala Ala Leu Gly Cys Leu Val Lys Asp Tyr
                            20                  25                  30

Phe Pro Glu Pro Val Thr Val Ser Trp Asn Ser Gly Ala Leu Thr Ser
                            35                  40                  45

Gly Val His Thr Phe Pro Ala Val Leu Gln Ser Ser Gly Leu Tyr Ser
                            50                  55                  60

Leu Ser Ser Val Val Thr Val Pro Ser Ser Leu Gly Thr Lys Thr
            65                  70                  75                  80

Tyr Thr Cys Asn Val Asp His Lys Pro Ser Asn Thr Lys Val Asp Lys
                            85                  90                  95

Arg Val Glu Ser Lys Tyr Gly Pro Pro Cys Pro Cys Pro Ala Pro
                            100                 105                 110

Glu Ala Ala Gly Gly Pro Ser Val Phe Leu Phe Pro Pro Lys Pro Lys
                            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
            145                 150                 155                 160

Gly Val Glu Val His Asn Ala Lys Thr Lys Pro Arg Glu Glu Gln Phe
                            165                 170                 175

Asn Ser Thr Tyr Arg Val Val Ser Val Leu Thr Val Leu His Gln Asp
                            180                 185                 190

Trp Leu Asn Gly Lys Glu Tyr Lys Cys Lys Val Ser Asn Lys Gly Leu
                            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
            225                 230                 235                 240

Asn Gln Val Ser Leu Thr Cys Leu Val Lys Gly Phe Tyr Pro Ser Asp
                            245                 250                 255

Ile Ala Val Glu Trp Glu Ser Asn Gly Gln Pro Glu Asn Asn Tyr Lys
                            260                 265                 270

Thr Thr Pro Pro Val Leu Asp Ser Asp Gly Ser Phe Phe Leu Tyr Ser
                            275                 280                 285

Arg Leu Thr Val Asp Lys Ser Arg Trp Gln Gln Gly Asn Val Phe Ser
                            290                 295                 300

Cys Ser Val Met His Glu Ala Leu His Asn His Tyr Thr Gln Lys Ser
            305                 310                 315                 320

Leu Ser Leu Ser Leu Gly Lys
                            325

<210> SEQ ID NO 198
<211> LENGTH: 373
<212> TYPE: PRT
<213> ORGANISM: Artificial Sequence
<220> FEATURE:
<223> OTHER INFORMATION: Synthetic: chicken LAP-TGF-beta-1

<400> SEQUENCE: 198

Leu Ser Thr Cys Gln Arg Leu Asp Leu Glu Ala Ala Lys Lys Lys Arg
1               5                   10                  15

Ile Glu Ala Val Arg Gly Gln Ile Leu Ser Lys Leu Arg Leu Thr Ala
                20                  25                  30

Pro Pro Pro Ala Ser Glu Thr Pro Pro Arg Pro Leu Pro Asp Asp Val
```

```
            35                  40                  45
Arg Ala Leu Tyr Asn Ser Thr Gln Glu Leu Leu Lys Gln Arg Ala Arg
 50                  55                  60
Leu Arg Pro Pro Asp Gly Pro Asp Glu Tyr Trp Ala Lys Glu Leu
 65                  70                  75                  80
Arg Arg Ile Pro Met Glu Thr Thr Trp Asp Gly Pro Met Glu His Trp
                 85                  90                  95
Gln Pro Gln Ser His Ser Ile Phe Phe Val Phe Asn Val Ser Arg Val
                100                 105                 110
Arg Ala Glu Val Gly Gly Arg Ala Leu Leu His Arg Ala Glu Leu Arg
                115                 120                 125
Met Leu Arg Gln Lys Ala Ala Ala Asp Ser Ala Gly Thr Glu Gln Arg
130                 135                 140
Leu Glu Leu Tyr Gln Gly Tyr Gly Asn Ala Ser Trp Arg Tyr Leu His
145                 150                 155                 160
Gly Arg Ser Val Arg Ala Thr Ala Asp Asp Glu Trp Leu Ser Phe Asp
                165                 170                 175
Val Thr Asp Ala Val His Gln Trp Leu Ser Gly Ser Glu Leu Leu Gly
                180                 185                 190
Val Phe Lys Leu Ser Val His Cys Pro Cys Glu Met Gly Pro Gly His
                195                 200                 205
Ala Asp Glu Met Arg Ile Ser Ile Glu Gly Phe Glu Gln Gln Arg Gly
210                 215                 220
Asp Met Gln Ser Ile Ala Lys Lys His Arg Arg Val Pro Tyr Val Leu
225                 230                 235                 240
Ala Met Ala Leu Pro Ala Glu Arg Ala Asn Glu Leu His Ser Ala Arg
                245                 250                 255
Arg Arg Arg Asp Leu Asp Thr Asp Tyr Cys Phe Gly Pro Gly Thr Asp
                260                 265                 270
Glu Lys Asn Cys Cys Val Arg Pro Leu Tyr Ile Asp Phe Arg Lys Asp
                275                 280                 285
Leu Gln Trp Lys Trp Ile His Glu Pro Lys Gly Tyr Met Ala Asn Phe
290                 295                 300
Cys Met Gly Pro Cys Pro Tyr Ile Trp Ser Ala Asp Thr Gln Tyr Thr
305                 310                 315                 320
Lys Val Leu Ala Leu Tyr Asn Gln His Asn Pro Gly Ala Ser Ala Ala
                325                 330                 335
Pro Cys Cys Val Pro Gln Thr Leu Asp Pro Leu Pro Ile Ile Tyr Tyr
                340                 345                 350
Val Gly Arg Asn Val Arg Val Glu Gln Leu Ser Asn Met Val Val Arg
                355                 360                 365
Ala Cys Lys Cys Ser
    370

<210> SEQ ID NO 199
<211> LENGTH: 362
<212> TYPE: PRT
<213> ORGANISM: Artificial Sequence
<220> FEATURE:
<223> OTHER INFORMATION: Synthetic: human-chicken LAP-TGF-beta-1 chimera
      #1

<400> SEQUENCE: 199

Leu Ser Thr Cys Gln Arg Leu Asp Leu Glu Ala Ala Lys Lys Lys Arg
 1               5                  10                  15
```

Ile Glu Ala Val Arg Gly Gln Ile Leu Ser Lys Leu Arg Leu Thr Ala
             20                  25                  30

Pro Pro Pro Ala Ser Glu Thr Pro Arg Pro Leu Pro Asp Asp Val
         35                  40                  45

Arg Ala Leu Tyr Asn Ser Thr Gln Glu Leu Leu Lys Gln Arg Ala Arg
     50                  55                  60

Leu Arg Pro Pro Pro Asp Gly Pro Asp Glu Tyr Trp Ala Lys Glu Leu
65                  70                  75                  80

Arg Arg Ile Pro Met Glu Thr Thr Trp Asp Glu Ile Tyr Asp Lys Phe
                 85                  90                  95

Lys Gln Ser Thr His Ser Ile Tyr Met Phe Phe Asn Thr Ser Glu Leu
             100                 105                 110

Arg Glu Ala Val Pro Glu Pro Val Leu Leu Ser Arg Ala Glu Leu Arg
         115                 120                 125

Leu Leu Arg Leu Lys Leu Lys Val Glu Gln His Val Glu Leu Tyr Gln
     130                 135                 140

Lys Tyr Ser Asn Asn Ser Trp Arg Tyr Leu Ser Asn Arg Leu Leu Ala
145                 150                 155                 160

Pro Ser Asp Ser Pro Glu Trp Leu Ser Phe Asp Val Thr Gly Val Val
                 165                 170                 175

Arg Gln Trp Leu Ser Arg Gly Gly Glu Ile Glu Gly Phe Arg Leu Ser
             180                 185                 190

Ala His Cys Ser Cys Asp Ser Arg Asp Asn Thr Leu Gln Val Asp Ile
         195                 200                 205

Asn Gly Phe Thr Thr Gly Arg Arg Gly Asp Leu Ala Thr Ile His Gly
     210                 215                 220

Met Asn Arg Pro Phe Leu Leu Leu Met Ala Thr Pro Leu Glu Arg Ala
225                 230                 235                 240

Gln His Leu Gln Ser Ser Arg His Arg Arg Ala Leu Asp Thr Asn Tyr
                 245                 250                 255

Cys Phe Ser Ser Thr Glu Lys Asn Cys Cys Val Arg Gln Leu Tyr Ile
             260                 265                 270

Asp Phe Arg Lys Asp Leu Gly Trp Lys Trp Ile His Glu Pro Lys Gly
         275                 280                 285

Tyr His Ala Asn Phe Cys Leu Gly Pro Cys Pro Tyr Ile Trp Ser Leu
     290                 295                 300

Asp Thr Gln Tyr Ser Lys Val Leu Ala Leu Tyr Asn Gln His Asn Pro
305                 310                 315                 320

Gly Ala Ser Ala Ala Pro Cys Cys Val Pro Gln Ala Leu Glu Pro Leu
                 325                 330                 335

Pro Ile Val Tyr Tyr Val Gly Arg Lys Pro Lys Val Glu Gln Leu Ser
             340                 345                 350

Asn Met Ile Val Arg Ser Cys Lys Cys Ser
        355                 360

<210> SEQ ID NO 200
<211> LENGTH: 361
<212> TYPE: PRT
<213> ORGANISM: Artificial Sequence
<220> FEATURE:
<223> OTHER INFORMATION: Synthetic: human-chicken LAP-TGF-beta-1 chimera
      #1.2

<400> SEQUENCE: 200

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Thr Ala
            20                  25                  30

Pro Pro Pro Ala Ser Glu Thr Pro Arg Pro Leu Pro Asp Asp Val
        35                  40                  45

Arg Ala Leu Tyr Asn Ser Thr Arg Asp Arg Val Ala Gly Glu Ser Ala
 50                  55                  60

Glu Pro Glu Pro Glu Pro Glu Ala Asp Tyr Tyr Ala Lys Glu Val Thr
 65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
            115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
            195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
            275                 280                 285

His Ala Asn Phe Cys Leu Gly Pro Cys Pro Tyr Ile Trp Ser Leu Asp
290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
            355                 360

<210> SEQ ID NO 201
<211> LENGTH: 362
<212> TYPE: PRT
<213> ORGANISM: Artificial Sequence
<220> FEATURE:
<223> OTHER INFORMATION: Synthetic: human-chicken LAP-TGF-beta-1 chimera
      #1.3

<400> SEQUENCE: 201

Leu Ser Thr Cys Lys Thr Ile Asp Met Glu Leu Val Lys Arg Lys Arg

```
              1               5                  10                 15
            Ile Glu Ala Ile Arg Gly Gln Ile Leu Ser Lys Leu Arg Leu Ala Ser
                             20                 25                 30

Pro Pro Ser Gln Gly Glu Val Pro Gly Pro Leu Pro Glu Ala Val
                             35                 40                 45

Leu Ala Leu Tyr Asn Ser Thr Gln Glu Leu Leu Lys Gln Arg Ala Arg
             50                              55                 60

Leu Arg Pro Pro Asp Gly Pro Asp Glu Tyr Trp Ala Lys Glu Leu
             65                 70                 75                 80

Arg Arg Val Leu Met Val Glu Thr His Asn Glu Ile Tyr Asp Lys Phe
                                 85                 90                 95

Lys Gln Ser Thr His Ser Ile Tyr Met Phe Phe Asn Thr Ser Glu Leu
                            100                105                110

Arg Glu Ala Val Pro Glu Pro Val Leu Leu Ser Arg Ala Glu Leu Arg
                            115                120                125

Leu Leu Arg Leu Lys Leu Lys Val Glu Gln His Val Glu Leu Tyr Gln
             130                135                140

Lys Tyr Ser Asn Asn Ser Trp Arg Tyr Leu Ser Asn Arg Leu Leu Ala
             145                150                155                160

Pro Ser Asp Ser Pro Glu Trp Leu Ser Phe Asp Val Thr Gly Val Val
                            165                170                175

Arg Gln Trp Leu Ser Arg Gly Gly Glu Ile Glu Gly Phe Arg Leu Ser
                            180                185                190

Ala His Cys Ser Cys Asp Ser Arg Asp Asn Thr Leu Gln Val Asp Ile
                            195                200                205

Asn Gly Phe Thr Thr Gly Arg Arg Gly Asp Leu Ala Thr Ile His Gly
             210                215                220

Met Asn Arg Pro Phe Leu Leu Leu Met Ala Thr Pro Leu Glu Arg Ala
             225                230                235                240

Gln His Leu Gln Ser Ser Arg His Arg Arg Ala Leu Asp Thr Asn Tyr
                            245                250                255

Cys Phe Ser Ser Thr Glu Lys Asn Cys Cys Val Arg Gln Leu Tyr Ile
                            260                265                270

Asp Phe Arg Lys Asp Leu Gly Trp Lys Trp Ile His Glu Pro Lys Gly
                            275                280                285

Tyr His Ala Asn Phe Cys Leu Gly Pro Cys Pro Tyr Ile Trp Ser Leu
                            290                295                300

Asp Thr Gln Tyr Ser Lys Val Leu Ala Leu Tyr Asn Gln His Asn Pro
             305                310                315                320

Gly Ala Ser Ala Ala Pro Cys Cys Val Pro Gln Ala Leu Glu Pro Leu
                            325                330                335

Pro Ile Val Tyr Tyr Val Gly Arg Lys Pro Lys Val Glu Gln Leu Ser
                            340                345                350

Asn Met Ile Val Arg Ser Cys Lys Cys Ser
                            355                360
```

<210> SEQ ID NO 202
<211> LENGTH: 366
<212> TYPE: PRT
<213> ORGANISM: Artificial Sequence
<220> FEATURE:
<223> OTHER INFORMATION: Synthetic: human-chicken LAP-TGF-beta-1 chimera
    #2

<400> SEQUENCE: 202

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Gly Pro Met Glu His Trp Gln
                85                  90                  95

Pro Gln Ser His Ser Ile Phe Phe Val Phe Asn Val Ser Arg Val Arg
                100                 105                 110

Ala Glu Val Gly Gly Arg Ala Leu Leu His Arg Ala Glu Leu Arg Met
            115                 120                 125

Leu Arg Gln Lys Ala Ala Ala Asp Ser Ala Gly Thr Glu Gln Arg Leu
130                 135                 140

Glu Leu Tyr Gln Lys Tyr Ser Asn Asn Ser Trp Arg Tyr Leu Ser Asn
145                 150                 155                 160

Arg Leu Leu Ala Pro Ser Asp Ser Pro Glu Trp Leu Ser Phe Asp Val
                165                 170                 175

Thr Gly Val Val Arg Gln Trp Leu Ser Arg Gly Gly Glu Ile Glu Gly
            180                 185                 190

Phe Arg Leu Ser Ala His Cys Ser Cys Asp Ser Arg Asp Asn Thr Leu
    195                 200                 205

Gln Val Asp Ile Asn Gly Phe Thr Thr Gly Arg Arg Gly Asp Leu Ala
210                 215                 220

Thr Ile His Gly Met Asn Arg Pro Phe Leu Leu Leu Met Ala Thr Pro
225                 230                 235                 240

Leu Glu Arg Ala Gln His Leu Gln Ser Ser Arg His Arg Arg Ala Leu
                245                 250                 255

Asp Thr Asn Tyr Cys Phe Ser Ser Thr Glu Lys Asn Cys Cys Val Arg
                260                 265                 270

Gln Leu Tyr Ile Asp Phe Arg Lys Asp Leu Gly Trp Lys Trp Ile His
    275                 280                 285

Glu Pro Lys Gly Tyr His Ala Asn Phe Cys Leu Gly Pro Cys Pro Tyr
    290                 295                 300

Ile Trp Ser Leu Asp Thr Gln Tyr Ser Lys Val Leu Ala Leu Tyr Asn
305                 310                 315                 320

Gln His Asn Pro Gly Ala Ser Ala Ala Pro Cys Cys Val Pro Gln Ala
                325                 330                 335

Leu Glu Pro Leu Pro Ile Val Tyr Tyr Val Gly Arg Lys Pro Lys Val
                340                 345                 350

Glu Gln Leu Ser Asn Met Ile Val Arg Ser Cys Lys Cys Ser
                355                 360                 365

<210> SEQ ID NO 203
<211> LENGTH: 361
<212> TYPE: PRT
<213> ORGANISM: Artificial Sequence
<220> FEATURE:
<223> OTHER INFORMATION: Synthetic: human-chicken LAP-TGF-beta-1 chimera
      #2.1

<400> SEQUENCE: 203
```

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
50                  55                  60

Glu Pro Glu Pro Glu Pro Glu Ala Asp Tyr Tyr Ala Lys Glu Val Thr
65                  70                  75                  80

Arg Ile Pro Met Glu Thr Thr Trp Asp Gly Pro Met Glu His Trp Gln
                85                  90                  95

Pro Gln Ser His Ser Ile Phe Phe Val Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
                195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Ser Ser Thr Glu Lys Asn Cys Cys Val Arg Gln Leu Tyr Ile Asp
            260                 265                 270

Phe Arg Lys Asp Leu Gly Trp Lys Trp Ile His Glu Pro Lys Gly Tyr
        275                 280                 285

His Ala Asn Phe Cys Leu Gly Pro Cys Pro Tyr Ile Trp Ser Leu Asp
290                 295                 300

Thr Gln Tyr Ser Lys Val Leu Ala Leu Tyr Asn Gln His Asn Pro Gly
305                 310                 315                 320

Ala Ser Ala Ala Pro Cys Cys Val Pro Gln Ala Leu Glu Pro Leu Pro
                325                 330                 335

Ile Val Tyr Tyr Val Gly Arg Lys Pro Lys Val Glu Gln Leu Ser Asn
            340                 345                 350

Met Ile Val Arg Ser Cys Lys Cys Ser
                355                 360

<210> SEQ ID NO 204
<211> LENGTH: 364
<212> TYPE: PRT
<213> ORGANISM: Artificial Sequence
<220> FEATURE:
<223> OTHER INFORMATION: Synthetic: human-chicken LAP-TGF-beta-1 chimera
      #2.2
```

```
<400> SEQUENCE: 204

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Val Ser Arg Val Arg
            100                 105                 110

Ala Glu Val Gly Gly Arg Ala Leu Leu His Arg Ala Glu Leu Arg Met
        115                 120                 125

Leu Arg Leu Leu Arg Leu Lys Leu Lys Val Glu Gln His Val Glu Leu
130                 135                 140

Tyr Gln Lys Tyr Ser Asn Asn Ser Trp Arg Tyr Leu Ser Asn Arg Leu
145                 150                 155                 160

Leu Ala Pro Ser Asp Ser Pro Glu Trp Leu Ser Phe Asp Val Thr Gly
                165                 170                 175

Val Val Arg Gln Trp Leu Ser Arg Gly Gly Glu Ile Glu Gly Phe Arg
            180                 185                 190

Leu Ser Ala His Cys Ser Cys Asp Ser Arg Asp Asn Thr Leu Gln Val
        195                 200                 205

Asp Ile Asn Gly Phe Thr Thr Gly Arg Arg Gly Asp Leu Ala Thr Ile
    210                 215                 220

His Gly Met Asn Arg Pro Phe Leu Leu Leu Met Ala Thr Pro Leu Glu
225                 230                 235                 240

Arg Ala Gln His Leu Gln Ser Ser Arg His Arg Arg Ala Leu Asp Thr
                245                 250                 255

Asn Tyr Cys Phe Ser Ser Thr Glu Lys Asn Cys Cys Val Arg Gln Leu
            260                 265                 270

Tyr Ile Asp Phe Arg Lys Asp Leu Gly Trp Lys Trp Ile His Glu Pro
        275                 280                 285

Lys Gly Tyr His Ala Asn Phe Cys Leu Gly Pro Cys Pro Tyr Ile Trp
290                 295                 300

Ser Leu Asp Thr Gln Tyr Ser Lys Val Leu Ala Leu Tyr Asn Gln His
305                 310                 315                 320

Asn Pro Gly Ala Ser Ala Ala Pro Cys Cys Val Pro Gln Ala Leu Glu
                325                 330                 335

Pro Leu Pro Ile Val Tyr Tyr Val Gly Arg Lys Pro Lys Val Glu Gln
            340                 345                 350

Leu Ser Asn Met Ile Val Arg Ser Cys Lys Cys Ser
        355                 360
```

<210> SEQ ID NO 205
<211> LENGTH: 366
<212> TYPE: PRT
<213> ORGANISM: Artificial Sequence
<220> FEATURE:
<223> OTHER INFORMATION: Synthetic: human-chicken LAP-TGF-beta-1 chimera
      #2.3

<400> SEQUENCE: 205

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Met
        115                 120                 125

Leu Arg Gln Lys Ala Ala Ala Asp Ser Ala Gly Thr Glu Gln Arg Leu
    130                 135                 140

Glu Leu Tyr Gln Gly Tyr Gly Asn Ala Ser Trp Arg Tyr Leu His Gly
145                 150                 155                 160

Arg Ser Val Arg Ala Thr Ala Asp Asp Glu Trp Leu Ser Phe Asp Val
                165                 170                 175

Thr Gly Val Val Arg Gln Trp Leu Ser Arg Gly Gly Glu Ile Glu Gly
            180                 185                 190

Phe Arg Leu Ser Ala His Cys Ser Cys Asp Ser Arg Asp Asn Thr Leu
        195                 200                 205

Gln Val Asp Ile Asn Gly Phe Thr Thr Gly Arg Arg Gly Asp Leu Ala
    210                 215                 220

Thr Ile His Gly Met Asn Arg Pro Phe Leu Leu Leu Met Ala Thr Pro
225                 230                 235                 240

Leu Glu Arg Ala Gln His Leu Gln Ser Ser Arg His Arg Arg Ala Leu
                245                 250                 255

Asp Thr Asn Tyr Cys Phe Ser Ser Thr Glu Lys Asn Cys Cys Val Arg
            260                 265                 270

Gln Leu Tyr Ile Asp Phe Arg Lys Asp Leu Gly Trp Lys Trp Ile His
        275                 280                 285

Glu Pro Lys Gly Tyr His Ala Asn Phe Cys Leu Gly Pro Cys Pro Tyr
    290                 295                 300

Ile Trp Ser Leu Asp Thr Gln Tyr Ser Lys Val Leu Ala Leu Tyr Asn
305                 310                 315                 320

Gln His Asn Pro Gly Ala Ser Ala Ala Pro Cys Cys Val Pro Gln Ala
                325                 330                 335

Leu Glu Pro Leu Pro Ile Val Tyr Tyr Val Gly Arg Lys Pro Lys Val
            340                 345                 350

Glu Gln Leu Ser Asn Met Ile Val Arg Ser Cys Lys Cys Ser
        355                 360                 365

<210> SEQ ID NO 206
<211> LENGTH: 360
<212> TYPE: PRT
<213> ORGANISM: Artificial Sequence
<220> FEATURE:
<223> OTHER INFORMATION: Synthetic: human-chicken LAP-TGF-beta-1 chimera

3

<400> SEQUENCE: 206

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Arg Asp Arg Val Ala Gly Glu Ser Ala
50                  55                  60

Glu Pro Glu Pro Glu Pro Glu Ala Asp Tyr Tyr Ala Lys Glu Val Thr
65                  70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Gly
130                 135                 140

Tyr Gly Asn Ala Ser Trp Arg Tyr Leu His Gly Arg Ser Val Arg Ala
145                 150                 155                 160

Thr Ala Asp Asp Glu Trp Leu Ser Phe Asp Val Thr Asp Ala Val His
                165                 170                 175

Gln Trp Leu Ser Gly Gly Glu Ile Glu Gly Phe Arg Leu Ser Ala His
            180                 185                 190

Cys Ser Cys Asp Ser Arg Asp Asn Thr Leu Gln Val Asp Ile Asn Gly
        195                 200                 205

Phe Thr Thr Gly Arg Arg Gly Asp Leu Ala Thr Ile His Gly Met Asn
210                 215                 220

Arg Pro Phe Leu Leu Leu Met Ala Thr Pro Leu Glu Arg Ala Gln His
225                 230                 235                 240

Leu Gln Ser Ser Arg His Arg Arg Ala Leu Asp Thr Asn Tyr Cys Phe
                245                 250                 255

Ser Ser Thr Glu Lys Asn Cys Cys Val Arg Gln Leu Tyr Ile Asp Phe
            260                 265                 270

Arg Lys Asp Leu Gly Trp Lys Trp Ile His Glu Pro Lys Gly Tyr His
        275                 280                 285

Ala Asn Phe Cys Leu Gly Pro Cys Pro Tyr Ile Trp Ser Leu Asp Thr
290                 295                 300

Gln Tyr Ser Lys Val Leu Ala Leu Tyr Asn Gln His Asn Pro Gly Ala
305                 310                 315                 320

Ser Ala Ala Pro Cys Cys Val Pro Gln Ala Leu Glu Pro Leu Pro Ile
                325                 330                 335

Val Tyr Tyr Val Gly Arg Lys Pro Lys Val Glu Gln Leu Ser Asn Met
            340                 345                 350

Ile Val Arg Ser Cys Lys Cys Ser
        355                 360

<210> SEQ ID NO 207
<211> LENGTH: 365
<212> TYPE: PRT
<213> ORGANISM: Artificial Sequence
<220> FEATURE:

<223> OTHER INFORMATION: Synthetic: human-chicken LAP-TGF-beta-1 chimera #4

<400> SEQUENCE: 207

| | | | | | | | | | | | | | | |
|---|---|---|---|---|---|---|---|---|---|---|---|---|---|---|
| Leu | Ser | Thr | Cys | Lys | Thr | Ile | Asp | Met | Glu | Leu | Val | Lys | Arg | Lys | Arg |
| 1 | | | | 5 | | | | | 10 | | | | | 15 | |
| Ile | Glu | Ala | Ile | Arg | Gly | Gln | Ile | Leu | Ser | Lys | Leu | Arg | Leu | Ala | Ser |
| | | | 20 | | | | | 25 | | | | | 30 | | |
| Pro | Pro | Ser | Gln | Gly | Glu | Val | Pro | Pro | Gly | Pro | Leu | Pro | Glu | Ala | Val |
| | | 35 | | | | | 40 | | | | | 45 | | | |
| Leu | Ala | Leu | Tyr | Asn | Ser | Thr | Arg | Asp | Arg | Val | Ala | Gly | Glu | Ser | Ala |
| | 50 | | | | | 55 | | | | | 60 | | | | |
| Glu | Pro | Glu | Pro | Glu | Pro | Glu | Ala | Asp | Tyr | Tyr | Ala | Lys | Glu | Val | Thr |
| 65 | | | | | 70 | | | | | 75 | | | | | 80 |
| Arg | Val | Leu | Met | Val | Glu | Thr | His | Asn | Glu | Ile | Tyr | Asp | Lys | Phe | Lys |
| | | | | 85 | | | | | 90 | | | | | 95 | |
| Gln | Ser | Thr | His | Ser | Ile | Tyr | Met | Phe | Phe | Asn | Thr | Ser | Glu | Leu | Arg |
| | | | 100 | | | | | 105 | | | | | 110 | | |
| Glu | Ala | Val | Pro | Glu | Pro | Val | Leu | Leu | Ser | Arg | Ala | Glu | Leu | Arg | Leu |
| | | 115 | | | | | 120 | | | | | 125 | | | |
| Leu | Arg | Leu | Lys | Leu | Lys | Val | Glu | Gln | His | Val | Glu | Leu | Tyr | Gln | Lys |
| | 130 | | | | | 135 | | | | | 140 | | | | |
| Tyr | Ser | Asn | Asn | Ser | Trp | Arg | Tyr | Leu | Ser | Asn | Arg | Leu | Leu | Ala | Pro |
| 145 | | | | | 150 | | | | | 155 | | | | | 160 |
| Ser | Asp | Ser | Pro | Glu | Trp | Leu | Ser | Phe | Asp | Val | Thr | Gly | Val | Val | Arg |
| | | | | 165 | | | | | 170 | | | | | 175 | |
| Gln | Trp | Leu | Ser | Arg | Gly | Ser | Glu | Leu | Leu | Gly | Val | Phe | Lys | Leu | Ser |
| | | | 180 | | | | | 185 | | | | | 190 | | |
| Val | His | Cys | Pro | Cys | Glu | Met | Gly | Pro | Gly | His | Ala | Asp | Glu | Met | Arg |
| | | 195 | | | | | 200 | | | | | 205 | | | |
| Ile | Ser | Ile | Glu | Gly | Phe | Thr | Thr | Gly | Arg | Arg | Gly | Asp | Leu | Ala | Thr |
| | 210 | | | | | 215 | | | | | 220 | | | | |
| Ile | His | Gly | Met | Asn | Arg | Pro | Phe | Leu | Leu | Leu | Met | Ala | Thr | Pro | Leu |
| 225 | | | | | 230 | | | | | 235 | | | | | 240 |
| Glu | Arg | Ala | Gln | His | Leu | Gln | Ser | Ser | Arg | His | Arg | Arg | Ala | Leu | Asp |
| | | | | 245 | | | | | 250 | | | | | 255 | |
| Thr | Asn | Tyr | Cys | Phe | Ser | Ser | Thr | Glu | Lys | Asn | Cys | Cys | Val | Arg | Gln |
| | | | 260 | | | | | 265 | | | | | 270 | | |
| Leu | Tyr | Ile | Asp | Phe | Arg | Lys | Asp | Leu | Gly | Trp | Lys | Trp | Ile | His | Glu |
| | | 275 | | | | | 280 | | | | | 285 | | | |
| Pro | Lys | Gly | Tyr | His | Ala | Asn | Phe | Cys | Leu | Gly | Pro | Cys | Pro | Tyr | Ile |
| | | 290 | | | | | 295 | | | | | 300 | | | |
| Trp | Ser | Leu | Asp | Thr | Gln | Tyr | Ser | Lys | Val | Leu | Ala | Leu | Tyr | Asn | Gln |
| 305 | | | | | 310 | | | | | 315 | | | | | 320 |
| His | Asn | Pro | Gly | Ala | Ser | Ala | Ala | Pro | Cys | Cys | Val | Pro | Gln | Ala | Leu |
| | | | 325 | | | | | 330 | | | | | 335 | | |
| Glu | Pro | Leu | Pro | Ile | Val | Tyr | Tyr | Val | Gly | Arg | Lys | Pro | Lys | Val | Glu |
| | | 340 | | | | | 345 | | | | | 350 | | | |
| Gln | Leu | Ser | Asn | Met | Ile | Val | Arg | Ser | Cys | Lys | Cys | Ser | | | |
| | 355 | | | | | 360 | | | | | 365 | | | | |

<210> SEQ ID NO 208
<211> LENGTH: 362
<212> TYPE: PRT
<213> ORGANISM: Artificial Sequence
<220> FEATURE:
<223> OTHER INFORMATION: Synthetic: human-chicken LAP-TGF-beta-1 chimera #5

<400> SEQUENCE: 208

```
Leu Ser Thr Cys Lys Thr Ile Asp Met Glu Leu Val Lys Arg Lys Arg
1               5                   10                  15
Ile Glu Ala Ile Arg Gly Gln Ile Leu Ser Lys Leu Arg Leu Ala Ser
            20                  25                  30
Pro Pro Ser Gln Gly Glu Val Pro Pro Gly Pro Leu Pro Glu Ala Val
        35                  40                  45
Leu Ala Leu Tyr Asn Ser Thr Arg Asp Arg Val Ala Gly Glu Ser Ala
    50                  55                  60
Glu Pro Glu Pro Glu Pro Glu Ala Asp Tyr Tyr Ala Lys Glu Val Thr
65                  70                  75                  80
Arg Val Leu Met Val Glu Thr His Asn Glu Ile Tyr Asp Lys Phe Lys
                85                  90                  95
Gln Ser Thr His Ser Ile Tyr Met Phe Phe Asn Thr Ser Glu Leu Arg
            100                 105                 110
Glu Ala Val Pro Glu Pro Val Leu Leu Ser Arg Ala Glu Leu Arg Leu
        115                 120                 125
Leu Arg Leu Lys Leu Lys Val Glu Gln His Val Glu Leu Tyr Gln Lys
    130                 135                 140
Tyr Ser Asn Asn Ser Trp Arg Tyr Leu Ser Asn Arg Leu Leu Ala Pro
145                 150                 155                 160
Ser Asp Ser Pro Glu Trp Leu Ser Phe Asp Val Thr Gly Val Val Arg
                165                 170                 175
Gln Trp Leu Ser Arg Gly Gly Glu Ile Glu Gly Phe Arg Leu Ser Ala
            180                 185                 190
His Cys Ser Cys Asp Ser Arg Asp Asn Thr Leu Gln Val Asp Ile Asn
        195                 200                 205
Gly Phe Glu Gln Gln Arg Gly Asp Met Gln Ser Ile Ala Lys Lys His
    210                 215                 220
Arg Arg Val Pro Tyr Val Leu Ala Met Ala Leu Pro Ala Glu Arg Ala
225                 230                 235                 240
Asn Glu Leu His Ser Ala Arg Arg Arg Asp Leu Asp Thr Asp Tyr
                245                 250                 255
Cys Phe Ser Ser Thr Glu Lys Asn Cys Cys Val Arg Gln Leu Tyr Ile
            260                 265                 270
Asp Phe Arg Lys Asp Leu Gly Trp Lys Trp Ile His Glu Pro Lys Gly
        275                 280                 285
Tyr His Ala Asn Phe Cys Leu Gly Pro Cys Pro Tyr Ile Trp Ser Leu
    290                 295                 300
Asp Thr Gln Tyr Ser Lys Val Leu Ala Leu Tyr Asn Gln His Asn Pro
305                 310                 315                 320
Gly Ala Ser Ala Ala Pro Cys Cys Val Pro Gln Ala Leu Glu Pro Leu
                325                 330                 335
Pro Ile Val Tyr Tyr Val Gly Arg Lys Pro Lys Val Glu Gln Leu Ser
            340                 345                 350
Asn Met Ile Val Arg Ser Cys Lys Cys Ser
        355                 360
```

<210> SEQ ID NO 209
<211> LENGTH: 363
<212> TYPE: PRT

<213> ORGANISM: Artificial Sequence
<220> FEATURE:
<223> OTHER INFORMATION: Synthetic: human-chicken LAP-TGF-beta-1 chimera #6

<400> SEQUENCE: 209

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Gly Pro Leu Pro Glu Ala Val
        35                  40                  45

Leu Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65              70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100                 105                 110

Glu Ala Val Pro Glu Pro Val Leu Leu Ser Arg Ala Glu Leu Arg Leu
        115                 120                 125

Leu Arg Leu Lys Leu Lys Val Glu Gln His Val Glu Leu Tyr Gln Lys
130                 135                 140

Tyr Ser Asn Asn Ser Trp Arg Tyr Leu Ser Asn Arg Leu Leu Ala Pro
145                 150                 155                 160

Ser Asp Ser Pro Glu Trp Leu Ser Phe Asp Val Thr Gly Val Val Arg
                165                 170                 175

Gln Trp Leu Ser Arg Gly Gly Glu Ile Glu Gly Phe Arg Leu Ser Ala
            180                 185                 190

His Cys Ser Cys Asp Ser Arg Asp Asn Thr Leu Gln Val Asp Ile Asn
        195                 200                 205

Gly Phe Thr Thr Gly Arg Arg Gly Asp Leu Ala Thr Ile His Gly Met
210                 215                 220

Asn Arg Pro Phe Leu Leu Leu Met Ala Thr Pro Leu Glu Arg Ala Gln
225                 230                 235                 240

His Leu Gln Ser Ser Arg His Arg Arg Ala Leu Asp Thr Asn Tyr Cys
                245                 250                 255

Phe Gly Pro Gly Thr Asp Glu Lys Asn Cys Cys Val Arg Pro Leu Tyr
            260                 265                 270

Ile Asp Phe Arg Lys Asp Leu Gln Trp Lys Trp Ile His Glu Pro Lys
        275                 280                 285

Gly Tyr Met Ala Asn Phe Cys Met Gly Pro Cys Pro Tyr Ile Trp Ser
290                 295                 300

Ala Asp Thr Gln Tyr Thr Lys Val Leu Ala Leu Tyr Asn Gln His Asn
305                 310                 315                 320

Pro Gly Ala Ser Ala Ala Pro Cys Cys Val Pro Gln Ala Leu Glu Pro
                325                 330                 335

Leu Pro Ile Val Tyr Tyr Val Gly Arg Lys Pro Lys Val Glu Gln Leu
            340                 345                 350

Ser Asn Met Ile Val Arg Ser Cys Lys Cys Ser
        355                 360
```

<210> SEQ ID NO 210
<211> LENGTH: 361

```
<212> TYPE: PRT
<213> ORGANISM: Artificial Sequence
<220> FEATURE:
<223> OTHER INFORMATION: Synthetic: human-chicken LAP-TGF-beta-1 chimera
      #7

<400> SEQUENCE: 210
```

| | | | | | | | | | | | | | |
|---|---|---|---|---|---|---|---|---|---|---|---|---|---|
|Leu|Ser|Thr|Cys|Lys|Thr|Ile|Asp|Met|Glu|Leu|Val|Lys|Arg|Lys|Arg
|1| | | |5| | | | |10| | | | |15

Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu

```
<211> LENGTH: 368
<212> TYPE: PRT
<213> ORGANISM: Artificial Sequence
<220> FEATURE:
<223> OTHER INFORMATION: Synthetic: Chicken-human LAP-TGF-beta-1 chimera
      chB1ex2.1_2.2

<400> SEQUENCE: 211
```

| | | | | | | | | | | | | | | |
|---|---|---|---|---|---|---|---|---|---|---|---|---|---|---|
| Leu | Ser | Thr | Ser | Gln | Arg | Leu | Asp | Leu | Glu | Ala | Ala | Lys | Lys | Arg |
| 1 | | | | 5 | | | | | 10 | | | | | 15 |
| Ile | Glu | Ala | Val | Arg | Gly | Gln | Ile | Leu | Ser | Lys | Leu | Arg | Leu | Thr | Ala |
| | | | 20 | | | | | 25 | | | | | 30 | | |
| Pro | Pro | Pro | Ala | Ser | Glu | Thr | Pro | Pro | Arg | Pro | Leu | Pro | Asp | Asp | Val |
| | | | 35 | | | | | 40 | | | | | 45 | | |
| Arg | Ala | Leu | Tyr | Asn | Ser | Thr | Gln | Glu | Leu | Leu | Lys | Gln | Arg | Ala | Arg |
| | 50 | | | | | 55 | | | | | 60 | | | | |
| Leu | Arg | Pro | Pro | Pro | Asp | Gly | Pro | Asp | Glu | Tyr | Trp | Ala | Lys | Glu | Leu |
| 65 | | | | | 70 | | | | 75 | | | | | 80 | |
| Arg | Arg | Val | Leu | Met | Val | Glu | Thr | His | Asn | Glu | Ile | Tyr | Asp | Lys | Phe |
| | | | | 85 | | | | | 90 | | | | | 95 | |
| Lys | Gln | Ser | Thr | His | Ser | Ile | Tyr | Met | Phe | Phe | Asn | Thr | Ser | Glu | Leu |
| | | | 100 | | | | | 105 | | | | | 110 | | |
| Arg | Glu | Ala | Val | Pro | Glu | Pro | Val | Leu | Leu | Ser | Arg | Ala | Glu | Leu | Arg |
| | | 115 | | | | | 120 | | | | | 125 | | | |
| Leu | Leu | Arg | Leu | Lys | Leu | Lys | Val | Glu | Gln | His | Val | Glu | Leu | Tyr | Gln |
| 130 | | | | | 135 | | | | | 140 | | | | | |
| Lys | Tyr | Gly | Asn | Ala | Ser | Trp | Arg | Tyr | Leu | His | Gly | Arg | Ser | Val | Arg |
| 145 | | | | | 150 | | | | | 155 | | | | | 160 |
| Ala | Thr | Ala | Asp | Asp | Glu | Trp | Leu | Ser | Phe | Asp | Val | Thr | Asp | Ala | Val |
| | | | | 165 | | | | | 170 | | | | | 175 | |
| His | Gln | Trp | Leu | Ser | Gly | Ser | Glu | Leu | Leu | Gly | Val | Phe | Lys | Leu | Ser |
| | | | 180 | | | | | 185 | | | | | 190 | | |
| Val | His | Cys | Pro | Cys | Glu | Met | Gly | Pro | Gly | His | Ala | Asp | Glu | Met | Arg |
| | | 195 | | | | | 200 | | | | | 205 | | | |
| Ile | Ser | Ile | Glu | Gly | Phe | Glu | Gln | Gln | Arg | Gly | Asp | Met | Gln | Ser | Ile |
| 210 | | | | | 215 | | | | | 220 | | | | | |
| Ala | Lys | Lys | His | Arg | Arg | Val | Pro | Tyr | Val | Leu | Ala | Met | Ala | Leu | Pro |
| 225 | | | | | 230 | | | | | 235 | | | | | 240 |
| Ala | Glu | Arg | Ala | Asn | Glu | Leu | His | Ser | Ala | Arg | Arg | Arg | Arg | Asp | Leu |
| | | | | 245 | | | | | 250 | | | | | 255 | |
| Asp | Thr | Asp | Tyr | Cys | Phe | Gly | Pro | Gly | Thr | Asp | Glu | Lys | Asn | Cys | Cys |
| | | | 260 | | | | | 265 | | | | | 270 | | |
| Val | Arg | Pro | Leu | Tyr | Ile | Asp | Phe | Arg | Lys | Asp | Leu | Gln | Trp | Lys | Trp |
| | | 275 | | | | | 280 | | | | | 285 | | | |
| Ile | His | Glu | Pro | Lys | Gly | Tyr | Met | Ala | Asn | Phe | Cys | Met | Gly | Pro | Cys |
| 290 | | | | | 295 | | | | | 300 | | | | | |
| Pro | Tyr | Ile | Trp | Ser | Ala | Asp | Thr | Gln | Tyr | Thr | Lys | Val | Leu | Ala | Leu |
| 305 | | | | | 310 | | | | | 315 | | | | | 320 |
| Tyr | Asn | Gln | His | Asn | Pro | Gly | Ala | Ser | Ala | Ala | Pro | Cys | Cys | Val | Pro |
| | | | | 325 | | | | | 330 | | | | | 335 | |
| Gln | Thr | Leu | Asp | Pro | Leu | Pro | Ile | Ile | Tyr | Tyr | Val | Gly | Arg | Asn | Val |
| | | | 340 | | | | | 345 | | | | | 350 | | |
| Arg | Val | Glu | Gln | Leu | Ser | Asn | Met | Val | Val | Arg | Ala | Cys | Lys | Cys | Ser |
| | | | | 355 | | | | | 360 | | | | | 365 | |

```
<210> SEQ ID NO 212
<211> LENGTH: 372
<212> TYPE: PRT
<213> ORGANISM: Artificial Sequence
<220> FEATURE:
<223> OTHER INFORMATION: Synthetic: Chicken-human LAP-TGF-beta-1 chimera
      chB1ex1.3

<400> SEQUENCE: 212

Leu Ser Thr Ser Gln Arg Leu Asp Leu Glu Ala Ala Lys Lys Lys Arg
1               5                   10                  15

Ile Glu Ala Val Arg Gly Gln Ile Leu Ser Lys Leu Arg Leu Thr Ala
            20                  25                  30

Pro Pro Pro Ala Ser Glu Thr Pro Pro Arg Pro Leu Pro Asp Asp Val
        35                  40                  45

Arg Ala Leu Tyr Asn Ser Thr Arg Asp Arg Val Ala Gly Glu Ser Ala
    50                  55                  60

Glu Pro Glu Pro Glu Pro Glu Ala Asp Tyr Tyr Ala Lys Glu Val Thr
65                  70                  75                  80

Arg Ile Pro Met Glu Thr Thr Trp Asp Gly Pro Met Glu His Trp Gln
                85                  90                  95

Pro Gln Ser His Ser Ile Phe Phe Val Phe Asn Val Ser Arg Val Arg
            100                 105                 110

Ala Glu Val Gly Gly Arg Ala Leu Leu His Arg Ala Glu Leu Arg Met
        115                 120                 125

Leu Arg Gln Lys Ala Ala Ala Asp Ser Ala Gly Thr Glu Gln Arg Leu
130                 135                 140

Glu Leu Tyr Gln Gly Tyr Gly Asn Ala Ser Trp Arg Tyr Leu His Gly
145                 150                 155                 160

Arg Ser Val Arg Ala Thr Ala Asp Asp Glu Trp Leu Ser Phe Asp Val
                165                 170                 175

Thr Asp Ala Val His Gln Trp Leu Ser Gly Ser Glu Leu Leu Gly Val
            180                 185                 190

Phe Lys Leu Ser Val His Cys Pro Cys Glu Met Gly Pro Gly His Ala
        195                 200                 205

Asp Glu Met Arg Ile Ser Ile Glu Gly Phe Glu Gln Gln Arg Gly Asp
    210                 215                 220

Met Gln Ser Ile Ala Lys Lys His Arg Arg Val Pro Tyr Val Leu Ala
225                 230                 235                 240

Met Ala Leu Pro Ala Glu Arg Ala Asn Glu Leu His Ser Ala Arg Arg
                245                 250                 255

Arg Arg Asp Leu Asp Thr Asp Tyr Cys Phe Gly Pro Gly Thr Asp Glu
            260                 265                 270

Lys Asn Cys Cys Val Arg Pro Leu Tyr Ile Asp Phe Arg Lys Asp Leu
        275                 280                 285

Gln Trp Lys Trp Ile His Glu Pro Lys Gly Tyr Met Ala Asn Phe Cys
    290                 295                 300

Met Gly Pro Cys Pro Tyr Ile Trp Ser Ala Asp Thr Gln Tyr Thr Lys
305                 310                 315                 320

Val Leu Ala Leu Tyr Asn Gln His Asn Pro Gly Ala Ser Ala Ala Pro
                325                 330                 335

Cys Cys Val Pro Gln Thr Leu Asp Pro Leu Pro Ile Ile Tyr Tyr Val
            340                 345                 350

Gly Arg Asn Val Arg Val Glu Gln Leu Ser Asn Met Val Val Arg Ala
        355                 360                 365
```

Cys Lys Cys Ser
    370

<210> SEQ ID NO 213
<211> LENGTH: 373
<212> TYPE: PRT
<213> ORGANISM: Artificial Sequence
<220> FEATURE:
<223> OTHER INFORMATION: Synthetic: Chicken-human LAP-TGF-beta-1 chimera
      chB1_ex1.2

<400> SEQUENCE: 213

Leu Ser Thr Ser Gln Arg Leu Asp Leu Glu Ala Ala Lys Lys Lys Arg
1               5                   10                  15

Ile Glu Ala Val Arg Gly Gln Ile Leu Ser Lys Leu Arg Leu Ala Ser
            20                  25                  30

Pro Pro Ser Gln Gly Glu Val Pro Pro Gly Pro Leu Pro Glu Ala Val
        35                  40                  45

Leu Ala Leu Tyr Asn Ser Thr Gln Glu Leu Leu Lys Gln Arg Ala Arg
    50                  55                  60

Leu Arg Pro Pro Asp Gly Pro Asp Glu Tyr Trp Ala Lys Glu Leu
65                  70                  75                  80

Arg Arg Ile Pro Met Glu Thr Thr Trp Asp Gly Pro Met Glu His Trp
                85                  90                  95

Gln Pro Gln Ser His Ser Ile Phe Phe Val Phe Asn Val Ser Arg Val
            100                 105                 110

Arg Ala Glu Val Gly Gly Arg Ala Leu Leu His Arg Ala Glu Leu Arg
        115                 120                 125

Met Leu Arg Gln Lys Ala Ala Asp Ser Ala Gly Thr Glu Gln Arg
    130                 135                 140

Leu Glu Leu Tyr Gln Gly Tyr Gly Asn Ala Ser Trp Arg Tyr Leu His
145                 150                 155                 160

Gly Arg Ser Val Arg Ala Thr Ala Asp Asp Glu Trp Leu Ser Phe Asp
                165                 170                 175

Val Thr Asp Ala Val His Gln Trp Leu Ser Gly Ser Glu Leu Leu Gly
            180                 185                 190

Val Phe Lys Leu Ser Val His Cys Pro Cys Glu Met Gly Pro His
        195                 200                 205

Ala Asp Glu Met Arg Ile Ser Ile Glu Gly Phe Glu Gln Gln Arg Gly
210                 215                 220

Asp Met Gln Ser Ile Ala Lys Lys His Arg Arg Val Pro Tyr Val Leu
225                 230                 235                 240

Ala Met Ala Leu Pro Ala Glu Arg Ala Asn Glu Leu His Ser Ala Arg
                245                 250                 255

Arg Arg Arg Asp Leu Asp Thr Asp Tyr Cys Phe Gly Pro Gly Thr Asp
            260                 265                 270

Glu Lys Asn Cys Cys Val Arg Pro Leu Tyr Ile Asp Phe Arg Lys Asp
        275                 280                 285

Leu Gln Trp Lys Trp Ile His Glu Pro Lys Gly Tyr Met Ala Asn Phe
    290                 295                 300

Cys Met Gly Pro Cys Pro Tyr Ile Trp Ser Ala Asp Thr Gln Tyr Thr
305                 310                 315                 320

Lys Val Leu Ala Leu Tyr Asn Gln His Asn Pro Gly Ala Ser Ala Ala
                325                 330                 335

Pro Cys Cys Val Pro Gln Thr Leu Asp Pro Leu Pro Ile Ile Tyr Tyr
            340                 345                 350

```
Val Gly Arg Asn Val Arg Val Glu Gln Leu Ser Asn Met Val Val Arg
        355                 360                 365

Ala Cys Lys Cys Ser
    370

<210> SEQ ID NO 214
<211> LENGTH: 5
<212> TYPE: PRT
<213> ORGANISM: Artificial Sequence
<220> FEATURE:
<223> OTHER INFORMATION: Synthetic: Linker

<400> SEQUENCE: 214

Pro Val Gly Val Val
1               5

<210> SEQ ID NO 215
<211> LENGTH: 44
<212> TYPE: PRT
<213> ORGANISM: Artificial Sequence
<220> FEATURE:
<223> OTHER INFORMATION: Synthetic: LAP-TGF-beta-1 epitope

<400> SEQUENCE: 215

Val Leu Met Val Glu Thr His Asn Glu Ile Tyr Asp Lys Phe Lys Gln
1               5                   10                  15

Ser Thr His Ser Ile Tyr Met Phe Phe Asn Thr Ser Glu Leu Arg Glu
            20                  25                  30

Ala Val Pro Glu Pro Val Leu Leu Ser Arg Ala Glu
        35                  40

<210> SEQ ID NO 216
<211> LENGTH: 107
<212> TYPE: PRT
<213> ORGANISM: Artificial Sequence
<220> FEATURE:
<223> OTHER INFORMATION: Synthetic: 28G11_L0 VL

<400> SEQUENCE: 216

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Asp Thr Leu Pro Trp
                85                  90                  95

Thr Phe Gly Gln Gly Thr Lys Leu Glu Ile Lys
            100                 105

<210> SEQ ID NO 217
<211> LENGTH: 214
<212> TYPE: PRT
<213> ORGANISM: Artificial Sequence
<220> FEATURE:
<223> OTHER INFORMATION: Synthetic: 28G11_L0

<400> SEQUENCE: 217
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Val Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Asp Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 218
<211> LENGTH: 118
<212> TYPE: PRT
<213> ORGANISM: Artificial Sequence
<220> FEATURE:
<223> OTHER INFORMATION: Synthetic: 20E6_H0.2a VH

<400> SEQUENCE: 218

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Asp Pro Gln Ser Gly Gly Ile Lys Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Arg Leu Arg Ser Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser
        115

<210> SEQ ID NO 219
```

```
<211> LENGTH: 448
<212> TYPE: PRT
<213> ORGANISM: Artificial Sequence
<220> FEATURE:
<223> OTHER INFORMATION: Synthetic: 20E6_H0.2a_IgG1

<400> SEQUENCE: 219
```

| | | | | | | | | | | | | | | | |
|---|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Trp | Met | His | Trp | Val | Arg | Gln | Ala | Pro | Gly | Gln | Gly | Leu | Glu | Trp | Met |
| | | 35 | | | | | 40 | | | | | 45 | | | |
| Gly | Arg | Ile | Asp | Pro | Gln | Ser | Gly | Gly | Ile | Lys | Tyr | Ala | Gln | Lys | Phe |
| | 50 | | | | | 55 | | | | | 60 | | | | |
| Gln | Gly | Arg | Ala | Thr | Leu | Thr | Val | Asp | Thr | Ser | Thr | Ser | Thr | Ala | Tyr |
| 65 | | | | | 70 | | | | | 75 | | | | | 80 |
| Met | Glu | Leu | Ser | Arg | Leu | Arg | Ser | Asp | Asp | Thr | Ala | Val | Tyr | Tyr | Cys |
| | | | | 85 | | | | | 90 | | | | | 95 | |
| Ala | Arg | Trp | Asp | Tyr | Gly | Gly | Tyr | Phe | Asp | Val | Trp | Gly | Gln | Gly | Thr |
| | | | 100 | | | | | 105 | | | | | 110 | | |
| Leu | Val | Thr | Val | Ser | Ser | Ala | Ser | Thr | Lys | Gly | Pro | Ser | Val | Phe | Pro |
| | | 115 | | | | | 120 | | | | | 125 | | | |
| Leu | Ala | Pro | Ser | Ser | Lys | Ser | Thr | Ser | Gly | Gly | Thr | Ala | Ala | Leu | Gly |
| | 130 | | | | | 135 | | | | | 140 | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Val | Val | Thr | Val | Pro | Ser | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | 195 | | | | | 200 | | | | | 205 | | | |
| Asn | Thr | Lys | Val | Asp | Lys | Lys | Val | Glu | Pro | Lys | Ser | Cys | Asp | Lys | Thr |
| | 210 | | | | | 215 | | | | | 220 | | | | |
| His | Thr | Cys | Pro | Pro | Cys | Pro | Ala | Pro | Glu | Leu | Leu | Gly | Gly | Pro | Ser |
| 225 | | | | | 230 | | | | | 235 | | | | | 240 |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | His | Glu | Asp | Pro |
| | | | 260 | | | | | 265 | | | | | 270 | | |
| Glu | Val | Lys | Phe | Asn | Trp | Tyr | Val | Asp | Gly | Val | Glu | Val | His | Asn | Ala |
| | | 275 | | | | | 280 | | | | | 285 | | | |
| Lys | Thr | Lys | Pro | Arg | Glu | Glu | Gln | Tyr | Asn | Ser | Thr | Tyr | Arg | Val | Val |
| | 290 | | | | | 295 | | | | | 300 | | | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Ser | Arg | Asp | Glu | Leu | Thr | Lys | Asn | Gln | Val | Ser | Leu | Thr | Cys |
| | | 355 | | | | | 360 | | | | | 365 | | | |
| Leu | Val | Lys | Gly | Phe | Tyr | Pro | Ser | Asp | Ile | Ala | Val | Glu | Trp | Glu | Ser |
| | 370 | | | | | 375 | | | | | 380 | | | | |

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
        420                 425                 430

Leu His Asn His Tyr Thr Gln Lys Ser Leu Ser Leu Ser Pro Gly Lys
    435                 440                 445

<210> SEQ ID NO 220
<211> LENGTH: 445
<212> TYPE: PRT
<213> ORGANISM: Artificial Sequence
<220> FEATURE:
<223> OTHER INFORMATION: Synthetic: 20E6_H0.2a_IgG4mut

<400> SEQUENCE: 220

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Arg Ile Asp Pro Gln Ser Gly Gly Ile Lys Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Arg Leu Arg Ser Asp Thr Ala Val Tyr Tyr Cys
                85                  90                  95

Ala Arg Trp Asp Tyr Gly Gly Tyr Phe Asp Val Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300
```

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
        340                 345                 350

Gln Glu Glu Met Thr Lys Asn Gln Val Ser Leu Thr Cys Leu Val Lys
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
        420                 425                 430

His Tyr Thr Gln Lys Ser Leu Ser Leu Ser Leu Gly Lys
    435                 440                 445

<210> SEQ ID NO 221
<211> LENGTH: 454
<212> TYPE: PRT
<213> ORGANISM: Artificial Sequence
<220> FEATURE:
<223> OTHER INFORMATION: Synthetic: 7H4_HC (hyb)

<400> SEQUENCE: 221

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Thr Asn Asn Tyr Asn Pro Ser Leu
    50                  55                  60

Lys Asn Arg Ile Ser Ile Thr Arg Asp Thr Ser Lys His Gln Phe Phe
65                  70                  75                  80

Leu Lys Leu Asn Ser Val Thr Thr Glu Asp Thr Ala Thr Tyr Tyr Cys
                85                  90                  95

Ala Arg Ser Phe Tyr Asn Asn Tyr Phe Asp Phe Trp Gly Gln Gly Thr
            100                 105                 110

Thr Leu Thr Val Ser Ser Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160

Ser Gly Ser Leu Ser Ser Ser Val His Thr Phe Pro Ala Leu Leu Gln
                165                 170                 175

Ser Gly Leu Tyr Thr Met Ser Ser Ser Val Thr Val Pro Ser Ser Thr
            180                 185                 190

Trp Pro Ser Gln Thr Val Thr Cys Ser Val Ala His Pro Ala Ser Ser
        195                 200                 205

Thr Thr Val Asp Lys Lys Leu Glu Pro Ser Gly Pro Ile Ser Thr Ile
    210                 215                 220

```
Asn Pro Cys Pro Pro Cys Lys Glu Cys His Lys Cys Pro Ala Pro Asn
225                 230                 235                 240

Leu Glu Gly Gly Pro Ser Val Phe Ile Phe Pro Pro Asn Ile Lys Asp
            245                 250                 255

Val Leu Met Ile Ser Leu Thr Pro Lys Val Thr Cys Val Val Val Asp
        260                 265                 270

Val Ser Glu Asp Asp Pro Asp Val Gln Ile Ser Trp Phe Val Asn Asn
    275                 280                 285

Val Glu Val His Thr Ala Gln Thr Gln Thr His Arg Glu Asp Tyr Asn
290                 295                 300

Ser Thr Ile Arg Val Val Ser Thr Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ser Pro Ile Glu Arg Thr Ile Ser Lys Ile Lys Gly Leu Val Arg Ala
            340                 345                 350

Pro Gln Val Tyr Ile Leu Pro Pro Pro Ala Glu Gln Leu Ser Arg Lys
        355                 360                 365

Asp Val Ser Leu Thr Cys Leu Val Val Gly Phe Asn Pro Gly Asp Ile
    370                 375                 380

Ser Val Glu Trp Thr Ser Asn Gly His Thr Glu Glu Asn Tyr Lys Asp
385                 390                 395                 400

Thr Ala Pro Val Leu Asp Ser Asp Gly Ser Tyr Phe Ile Tyr Ser Lys
                405                 410                 415

Leu Asn Met Lys Thr Ser Lys Trp Glu Lys Thr Asp Ser Phe Ser Cys
            420                 425                 430

Asn Val Arg His Glu Gly Leu Lys Asn Tyr Tyr Leu Lys Lys Thr Ile
        435                 440                 445

Ser Arg Ser Pro Gly Lys
    450

<210> SEQ ID NO 222
<211> LENGTH: 213
<212> TYPE: PRT
<213> ORGANISM: Artificial Sequence
<220> FEATURE:
<223> OTHER INFORMATION: Synthetic: 7H4_LC (hyb)

<400> SEQUENCE: 222

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asp Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Asn Ile Ser Asn Leu Glu Pro
65                  70                  75                  80

Glu Asp Ile Ala Thr Tyr Tyr Cys Leu Gln Tyr Asp Asn Leu Arg Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125
```

```
Ala Ser Val Val Cys Phe Leu Asn Asn Phe Tyr Pro Lys Asp Ile Asn
            130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
        210

<210> SEQ ID NO 223
<211> LENGTH: 118
<212> TYPE: PRT
<213> ORGANISM: Artificial Sequence
<220> FEATURE:
<223> OTHER INFORMATION: Synthetic: 7H4_VH

<400> SEQUENCE: 223

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Asp Gly Thr Asn Asn Tyr Asn Pro Ser Leu
    50                  55                  60

Lys Asn Arg Ile Ser Ile Thr Arg Asp Thr Ser Lys His Gln Phe Phe
65                  70                  75                  80

Leu Lys Leu Asn Ser Val Thr Thr Glu Asp Thr Ala Thr Tyr Tyr Cys
                85                  90                  95

Ala Arg Ser Phe Tyr Asn Asn Tyr Phe Asp Phe Trp Gly Gln Gly Thr
            100                 105                 110

Thr Leu Thr Val Ser Ser
        115

<210> SEQ ID NO 224
<211> LENGTH: 106
<212> TYPE: PRT
<213> ORGANISM: Artificial Sequence
<220> FEATURE:
<223> OTHER INFORMATION: Synthetic: 7H4_VL

<400> SEQUENCE: 224

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asp Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Asn Ile Ser Asn Leu Glu Pro
65                  70                  75                  80

Glu Asp Ile Ala Thr Tyr Tyr Cys Leu Gln Tyr Asp Asn Leu Arg Thr
                85                  90                  95
```

Phe Gly Gly Gly Thr Lys Leu Glu Ile Lys
            100                 105

<210> SEQ ID NO 225
<211> LENGTH: 11
<212> TYPE: PRT
<213> ORGANISM: Artificial Sequence
<220> FEATURE:
<223> OTHER INFORMATION: Synthetic: 7H4_HCDR1

<400> SEQUENCE: 225

Gly Tyr Ser Ile Thr Ser Gly Tyr Tyr Trp Asn
1               5                   10

<210> SEQ ID NO 226
<211> LENGTH: 16
<212> TYPE: PRT
<213> ORGANISM: Artificial Sequence
<220> FEATURE:
<223> OTHER INFORMATION: Synthetic: 7H4_HCDR2

<400> SEQUENCE: 226

Tyr Ile Ser Tyr Asp Gly Thr Asn Asn Tyr Asn Pro Ser Leu Lys Asn
1               5                   10                  15

<210> SEQ ID NO 227
<211> LENGTH: 9
<212> TYPE: PRT
<213> ORGANISM: Artificial Sequence
<220> FEATURE:
<223> OTHER INFORMATION: Synthetic: 7H4_HCDR3

<400> SEQUENCE: 227

Ser Phe Tyr Asn Asn Tyr Phe Asp Phe
1               5

<210> SEQ ID NO 228
<211> LENGTH: 11
<212> TYPE: PRT
<213> ORGANISM: Artificial Sequence
<220> FEATURE:
<223> OTHER INFORMATION: Synthetic: 7H4_LCDR1

<400> SEQUENCE: 228

Lys Ala Ser Gln Asp Ile Asp Lys Tyr Ile Ala
1               5                   10

<210> SEQ ID NO 229
<211> LENGTH: 7
<212> TYPE: PRT
<213> ORGANISM: Artificial Sequence
<220> FEATURE:
<223> OTHER INFORMATION: Synthetic: 7H4_LCDR2

<400> SEQUENCE: 229

Tyr Thr Ser Thr Leu Gln Pro
1               5

<210> SEQ ID NO 230
<211> LENGTH: 8
<212> TYPE: PRT
<213> ORGANISM: Artificial Sequence
<220> FEATURE:
<223> OTHER INFORMATION: Synthetic: 7H4_LCDR3

<400> SEQUENCE: 230

```
Leu Gln Tyr Asp Asn Leu Arg Thr
1               5
```

<210> SEQ ID NO 231
<211> LENGTH: 16
<212> TYPE: PRT
<213> ORGANISM: Artificial Sequence
<220> FEATURE:
<223> OTHER INFORMATION: Synthetic: 7H4_HCDR2 (D55G)

<400> SEQUENCE: 231

```
Tyr Ile Ser Tyr Gly Gly Thr Asn Asn Tyr Asn Pro Ser Leu Lys Asn
1               5                   10                  15
```

<210> SEQ ID NO 232
<211> LENGTH: 16
<212> TYPE: PRT
<213> ORGANISM: Artificial Sequence
<220> FEATURE:
<223> OTHER INFORMATION: Synthetic: 7H4_HCDR2 (D55A)

<400> SEQUENCE: 232

```
Tyr Ile Ser Tyr Ala Gly Thr Asn Asn Tyr Asn Pro Ser Leu Lys Asn
1               5                   10                  15
```

<210> SEQ ID NO 233
<211> LENGTH: 16
<212> TYPE: PRT
<213> ORGANISM: Artificial Sequence
<220> FEATURE:
<223> OTHER INFORMATION: Synthetic: 7H4_HCDR2 (D55E)

<400> SEQUENCE: 233

```
Tyr Ile Ser Tyr Glu Gly Thr Asn Asn Tyr Asn Pro Ser Leu Lys Asn
1               5                   10                  15
```

<210> SEQ ID NO 234
<211> LENGTH: 118
<212> TYPE: PRT
<213> ORGANISM: Artificial Sequence
<220> FEATURE:
<223> OTHER INFORMATION: Synthetic: 7H4_VHmut#1 (D55G)

<400> SEQUENCE: 234

```
Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Gly Thr Asn Asn Tyr Asn Pro Ser Leu
    50                  55                  60

Lys Asn Arg Ile Ser Ile Thr Arg Asp Thr Ser Lys His Gln Phe Phe
65                  70                  75                  80

Leu Lys Leu Asn Ser Val Thr Thr Glu Asp Thr Ala Thr Tyr Tyr Cys
                85                  90                  95

Ala Arg Ser Phe Tyr Asn Asn Tyr Phe Asp Phe Trp Gly Gln Gly Thr
            100                 105                 110

Thr Leu Thr Val Ser Ser
        115
```

<210> SEQ ID NO 235

```
<211> LENGTH: 118
<212> TYPE: PRT
<213> ORGANISM: Artificial Sequence
<220> FEATURE:
<223> OTHER INFORMATION: Synthetic: 7H4_VHmut#2 (D55A)

<400> SEQUENCE: 235

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Ala Gly Thr Asn Asn Tyr Asn Pro Ser Leu
    50                  55                  60

Lys Asn Arg Ile Ser Ile Thr Arg Asp Thr Ser Lys His Gln Phe Phe
65                  70                  75                  80

Leu Lys Leu Asn Ser Val Thr Thr Glu Asp Thr Ala Thr Tyr Tyr Cys
                85                  90                  95

Ala Arg Ser Phe Tyr Asn Asn Tyr Phe Asp Phe Trp Gly Gln Gly Thr
            100                 105                 110

Thr Leu Thr Val Ser Ser
        115

<210> SEQ ID NO 236
<211> LENGTH: 118
<212> TYPE: PRT
<213> ORGANISM: Artificial Sequence
<220> FEATURE:
<223> OTHER INFORMATION: Synthetic: 7H4_VHmut#3 (D55E)

<400> SEQUENCE: 236

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Glu Gly Thr Asn Asn Tyr Asn Pro Ser Leu
    50                  55                  60

Lys Asn Arg Ile Ser Ile Thr Arg Asp Thr Ser Lys His Gln Phe Phe
65                  70                  75                  80

Leu Lys Leu Asn Ser Val Thr Thr Glu Asp Thr Ala Thr Tyr Tyr Cys
                85                  90                  95

Ala Arg Ser Phe Tyr Asn Asn Tyr Phe Asp Phe Trp Gly Gln Gly Thr
            100                 105                 110

Thr Leu Thr Val Ser Ser
        115

<210> SEQ ID NO 237
<211> LENGTH: 454
<212> TYPE: PRT
<213> ORGANISM: Artificial Sequence
<220> FEATURE:
<223> OTHER INFORMATION: Synthetic: 7H4_HCmut#1 (D55G)

<400> SEQUENCE: 237

Asp Val Gln Leu Gln Glu Ser Gly Pro Gly Leu Val Lys Pro Ser Gln
1               5                   10                  15
```

```
Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Gly Thr Asn Asn Tyr Asn Pro Ser Leu
    50                  55                  60

Lys Asn Arg Ile Ser Ile Thr Arg Asp Thr Ser Lys His Gln Phe Phe
65                  70                  75                  80

Leu Lys Leu Asn Ser Val Thr Thr Glu Asp Thr Ala Thr Tyr Tyr Cys
                85                  90                  95

Ala Arg Ser Phe Tyr Asn Asn Tyr Phe Asp Phe Trp Gly Gln Gly Thr
            100                 105                 110

Thr Leu Thr Val Ser Ser Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160

Ser Gly Ser Leu Ser Ser Ser Val His Thr Phe Pro Ala Leu Leu Gln
                165                 170                 175

Ser Gly Leu Tyr Thr Met Ser Ser Ser Val Thr Val Pro Ser Ser Thr
            180                 185                 190

Trp Pro Ser Gln Thr Val Thr Cys Ser Val Ala His Pro Ala Ser Ser
        195                 200                 205

Thr Thr Val Asp Lys Lys Leu Glu Pro Ser Gly Pro Ile Ser Thr Ile
210                 215                 220

Asn Pro Cys Pro Pro Cys Lys Glu Cys His Lys Cys Pro Ala Pro Asn
225                 230                 235                 240

Leu Glu Gly Gly Pro Ser Val Phe Ile Phe Pro Pro Asn Ile Lys Asp
                245                 250                 255

Val Leu Met Ile Ser Leu Thr Pro Lys Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Ile Arg Val Val Ser Thr Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ser Pro Ile Glu Arg Thr Ile Ser Lys Ile Lys Gly Leu Val Arg Ala
            340                 345                 350

Pro Gln Val Tyr Ile Leu Pro Pro Ala Glu Gln Leu Ser Arg Lys
        355                 360                 365

Asp Val Ser Leu Thr Cys Leu Val Val Gly Phe Asn Pro Gly Asp Ile
    370                 375                 380

Ser Val Glu Trp Thr Ser Asn Gly His Thr Glu Glu Asn Tyr Lys Asp
385                 390                 395                 400

Thr Ala Pro Val Leu Asp Ser Asp Gly Ser Tyr Phe Ile Tyr Ser Lys
                405                 410                 415

Leu Asn Met Lys Thr Ser Lys Trp Glu Lys Thr Asp Ser Phe Ser Cys
            420                 425                 430

Asn Val Arg His Glu Gly Leu Lys Asn Tyr Tyr Leu Lys Lys Thr Ile
```

```
              435                 440                 445
Ser Arg Ser Pro Gly Lys
            450

<210> SEQ ID NO 238
<211> LENGTH: 454
<212> TYPE: PRT
<213> ORGANISM: Artificial Sequence
<220> FEATURE:
<223> OTHER INFORMATION: Synthetic: 7H4_HCmut#2 (D55A)

<400> SEQUENCE: 238

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Ala Gly Thr Asn Asn Tyr Asn Pro Ser Leu
    50                  55                  60

Lys Asn Arg Ile Ser Ile Thr Arg Asp Thr Ser Lys His Gln Phe Phe
65                  70                  75                  80

Leu Lys Leu Asn Ser Val Thr Thr Glu Asp Thr Ala Thr Tyr Tyr Cys
                85                  90                  95

Ala Arg Ser Phe Tyr Asn Asn Tyr Phe Asp Phe Trp Gly Gln Gly Thr
            100                 105                 110

Thr Leu Thr Val Ser Ser Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160

Ser Gly Ser Leu Ser Ser Ser Val His Thr Phe Pro Ala Leu Leu Gln
                165                 170                 175

Ser Gly Leu Tyr Thr Met Ser Ser Ser Val Thr Val Pro Ser Ser Thr
            180                 185                 190

Trp Pro Ser Gln Thr Val Thr Cys Ser Val Ala His Pro Ala Ser Ser
        195                 200                 205

Thr Thr Val Asp Lys Lys Leu Glu Pro Ser Gly Pro Ile Ser Thr Ile
    210                 215                 220

Asn Pro Cys Pro Pro Cys Lys Glu Cys His Lys Cys Pro Ala Pro Asn
225                 230                 235                 240

Leu Glu Gly Gly Pro Ser Val Phe Ile Phe Pro Pro Asn Ile Lys Asp
                245                 250                 255

Val Leu Met Ile Ser Leu Thr Pro Lys Val Thr Cys Val Val Val Asp
            260                 265                 270

Val Ser Glu Asp Asp Pro Asp Val Gln Ile Ser Trp Phe Val Asn Asn
        275                 280                 285

Val Glu Val His Thr Ala Gln Thr Gln Thr His Arg Glu Asp Tyr Asn
    290                 295                 300

Ser Thr Ile Arg Val Val Ser Thr Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ser Pro Ile Glu Arg Thr Ile Ser Lys Ile Lys Gly Leu Val Arg Ala
```

```
                340              345              350
Pro Gln Val Tyr Ile Leu Pro Pro Ala Glu Gln Leu Ser Arg Lys
            355              360              365

Asp Val Ser Leu Thr Cys Leu Val Val Gly Phe Asn Pro Gly Asp Ile
    370              375              380

Ser Val Glu Trp Thr Ser Asn Gly His Thr Glu Glu Asn Tyr Lys Asp
385              390              395              400

Thr Ala Pro Val Leu Asp Ser Asp Gly Ser Tyr Phe Ile Tyr Ser Lys
            405              410              415

Leu Asn Met Lys Thr Ser Lys Trp Glu Lys Thr Asp Ser Phe Ser Cys
            420              425              430

Asn Val Arg His Glu Gly Leu Lys Asn Tyr Tyr Leu Lys Lys Thr Ile
            435              440              445

Ser Arg Ser Pro Gly Lys
        450

<210> SEQ ID NO 239
<211> LENGTH: 454
<212> TYPE: PRT
<213> ORGANISM: Artificial Sequence
<220> FEATURE:
<223> OTHER INFORMATION: Synthetic: 7H4_HCmut#3 (D55E)

<400> SEQUENCE: 239

Asp Val Gln Leu Gln Glu Ser Gly Pro Gly Leu Val Lys Pro Ser Gln
1               5                  10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Glu Gly Thr Asn Asn Tyr Asn Pro Ser Leu
    50                  55                  60

Lys Asn Arg Ile Ser Ile Thr Arg Asp Thr Ser Lys His Gln Phe Phe
65                  70                  75                  80

Leu Lys Leu Asn Ser Val Thr Thr Glu Asp Thr Ala Thr Tyr Tyr Cys
            85                  90                  95

Ala Arg Ser Phe Tyr Asn Asn Tyr Phe Asp Phe Trp Gly Gln Gly Thr
            100                 105                 110

Thr Leu Thr Val Ser Ser Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160

Ser Gly Ser Leu Ser Ser Ser Val His Thr Phe Pro Ala Leu Leu Gln
            165                 170                 175

Ser Gly Leu Tyr Thr Met Ser Ser Ser Val Thr Val Pro Ser Ser Thr
        180                 185                 190

Trp Pro Ser Gln Thr Val Thr Cys Ser Val Ala His Pro Ala Ser Ser
    195                 200                 205

Thr Thr Val Asp Lys Lys Leu Glu Pro Ser Gly Pro Ile Ser Thr Ile
    210                 215                 220

Asn Pro Cys Pro Pro Cys Lys Glu Cys His Lys Cys Pro Ala Pro Asn
225                 230                 235                 240

Leu Glu Gly Gly Pro Ser Val Phe Ile Phe Pro Pro Asn Ile Lys Asp
```

```
                    245                 250                 255
Val Leu Met Ile Ser Leu Thr Pro Lys Val Thr Cys Val Val Asp
                260                 265                 270

Val Ser Glu Asp Asp Pro Asp Val Gln Ile Ser Trp Phe Val Asn Asn
            275                 280                 285

Val Glu Val His Thr Ala Gln Thr Gln Thr His Arg Glu Asp Tyr Asn
        290                 295                 300

Ser Thr Ile Arg Val Val Ser Thr Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ser Pro Ile Glu Arg Thr Ile Ser Lys Ile Lys Gly Leu Val Arg Ala
            340                 345                 350

Pro Gln Val Tyr Ile Leu Pro Pro Ala Glu Gln Leu Ser Arg Lys
        355                 360                 365

Asp Val Ser Leu Thr Cys Leu Val Val Gly Phe Asn Pro Gly Asp Ile
    370                 375                 380

Ser Val Glu Trp Thr Ser Asn Gly His Thr Glu Glu Asn Tyr Lys Asp
385                 390                 395                 400

Thr Ala Pro Val Leu Asp Ser Asp Gly Ser Tyr Phe Ile Tyr Ser Lys
                405                 410                 415

Leu Asn Met Lys Thr Ser Lys Trp Glu Lys Thr Asp Ser Phe Ser Cys
            420                 425                 430

Asn Val Arg His Glu Gly Leu Lys Asn Tyr Tyr Leu Lys Lys Thr Ile
        435                 440                 445

Ser Arg Ser Pro Gly Lys
    450

<210> SEQ ID NO 240
<211> LENGTH: 447
<212> TYPE: PRT
<213> ORGANISM: Artificial Sequence
<220> FEATURE:
<223> OTHER INFORMATION: Synthetic: Pembrolizumab heavy chain

<400> SEQUENCE: 240

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
```

```
                145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Lys Thr Tyr Thr Cys Asn Val Asp His Lys
                195                 200                 205
Pro Ser Asn Thr Lys Val Asp Lys Arg Val Glu Ser Lys Tyr Gly Pro
            210                 215                 220
Pro Cys Pro Pro Cys Pro Ala Pro Glu Phe Leu Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser Gln Glu Asp Pro Glu
                260                 265                 270
Val Gln Phe Asn Trp Tyr Val Asp Gly Val Glu Val His Asn Ala Lys
                275                 280                 285
Thr Lys Pro Arg Glu Glu Gln Phe Asn Ser Thr Tyr Arg Val Val Ser
            290                 295                 300
Val Leu Thr Val Leu His Gln Asp Trp Leu Asn Gly Lys Glu Tyr Lys
305                 310                 315                 320
Cys Lys Val Ser Asn Lys Gly Leu Pro Ser Ser Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Gln Glu Glu Met Thr Lys Asn Gln Val Ser Leu Thr Cys Leu
                355                 360                 365
Val Lys Gly Phe Tyr Pro Ser Asp Ile Ala Val Glu Trp Glu Ser Asn
            370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Arg Leu Thr Val Asp Lys Ser Arg
                405                 410                 415
Trp Gln Glu Gly Asn Val Phe Ser Cys Ser Val Met His Glu Ala Leu
                420                 425                 430
His Asn His Tyr Thr Gln Lys Ser Leu Ser Leu Ser Leu Gly Lys
                435                 440                 445

<210> SEQ ID NO 241
<211> LENGTH: 218
<212> TYPE: PRT
<213> ORGANISM: Artificial Sequence
<220> FEATURE:
<223> OTHER INFORMATION: Synthetic: Pembrolizumab light chain

<400> SEQUENCE: 241

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Lys Gly Val Ser Thr Ser
                20                  25                  30
Gly Tyr Ser Tyr Leu His Trp Tyr Gln Gln Lys Pro Gly Gln Ala Pro
                35                  40                  45
Arg Leu Leu Ile Tyr Leu Ala Ser Tyr Leu Glu Ser Gly Val Pro Ala
            50                  55                  60
Arg Phe Ser Gly Ser Gly Ser Gly Thr Asp Phe Thr Leu Thr Ile Ser
```

```
                65                  70                  75                  80
Ser Leu Glu Pro Glu Asp Phe Ala Val Tyr Tyr Cys Gln His Ser Arg
                    85                  90                  95

Asp Leu Pro Leu Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
                115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
        210                 215

<210> SEQ ID NO 242
<211> LENGTH: 9
<212> TYPE: PRT
<213> ORGANISM: Artificial Sequence
<220> FEATURE:
<223> OTHER INFORMATION: Synthetic: 20E6 VHCDR3 consensus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 242

Trp Xaa Tyr Gly Gly Tyr Phe Xaa Xaa
1               5

<210> SEQ ID NO 243
<211> LENGTH: 9
<212> TYPE: PRT
<213> ORGANISM: Artificial Sequence
<220> FEATURE:
<223> OTHER INFORMATION: Synthetic: 20E6 VLCDR3 consensus
<220> FEATURE:
<221> NAME/KEY: misc_feature
<222> LOCATION: (5)..(5)
<223> OTHER INFORMATION: Xaa can be any naturally occurring amino acid

<400> SEQUENCE: 243

Gln Gln Gly Asp Xaa Leu Pro Trp Thr
1               5

<210> SEQ ID NO 244
<211> LENGTH: 330
<212> TYPE: PRT
<213> ORGANISM: Artificial Sequence
<220> FEATURE:
<223> OTHER INFORMATION: Synthetic: Human_IgG1_ P01857_L234A_L235A

<400> SEQUENCE: 244

Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 245
<211> LENGTH: 330
<212> TYPE: PRT
<213> ORGANISM: Artificial Sequence
<220> FEATURE:
<223> OTHER INFORMATION: Synthetic: Human_IgG1_ P01857_L234A_L235A_D265S

<400> SEQUENCE: 245

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

```
Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Ser Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 246
<211> LENGTH: 440
<212> TYPE: PRT
<213> ORGANISM: Artificial Sequence
<220> FEATURE:
<223> OTHER INFORMATION: Synthetic: Nivolumab heavy chain

<400> SEQUENCE: 246

Gln Val Gln Leu Val Glu Ser Gly Gly Val Val Gln Pro Gly Arg
 1               5                  10                  15

Ser Leu Arg Leu Asp Cys Lys Ala Ser Gly Ile Thr Phe Ser Asn Ser
                 20                  25                  30

Gly Met His Trp Val Arg Gln Ala Pro Gly Lys Gly Leu Glu Trp Val
             35                  40                  45

Ala Val Ile Trp Tyr Asp Gly Ser Lys Arg Tyr Tyr Ala Asp Ser Val
         50                  55                  60

Lys Gly Arg Phe Thr Ile Ser Arg Asp Asn Ser Lys Asn Thr Leu Phe
 65                  70                  75                  80
```

```
Leu Gln Met Asn Ser Leu Arg Ala Glu Asp Thr Ala Val Tyr Tyr Cys
                 85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 247
<211> LENGTH: 214
<212> TYPE: PRT
<213> ORGANISM: Artificial Sequence
<220> FEATURE:
<223> OTHER INFORMATION: Synthetic: Nivolumab light chain

<400> SEQUENCE: 247
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 248
<211> LENGTH: 448
<212> TYPE: PRT
<213> ORGANISM: Artificial Sequence
<220> FEATURE:
<223> OTHER INFORMATION: Synthetic: 22F9_N54Q_D102A heavy chain

<400> SEQUENCE: 248

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Gln Ser Gly Ser Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Tyr Tyr Asp Tyr Ala Gly Phe Phe Asp Val Trp Gly Thr Gly Thr
            100                 105                 110

Thr Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

```
Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
            165                 170                 175

Ser Asp Leu Tyr Thr Leu Ser Ser Val Thr Val Thr Ser Ser Thr
        180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Asp Val Ser Glu Asp Asp Pro
        260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys
        355                 360                 365

Met Val Thr Asp Phe Met Pro Glu Asp Ile Tyr Val Glu Trp Thr Asn
370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
                420                 425                 430

Leu His Asn His His Thr Thr Lys Ser Phe Ser Arg Thr Pro Gly Lys
            435                 440                 445

<210> SEQ ID NO 249
<211> LENGTH: 218
<212> TYPE: PRT
<213> ORGANISM: Artificial Sequence
<220> FEATURE:
<223> OTHER INFORMATION: Synthetic: 22F9_N54Q_D102A light chain

<400> SEQUENCE: 249

Asp Ile Val Leu Thr Gln Ser Pro Ala Ser Leu Asp Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Ser Gly Gln Pro Pro
        35                  40                  45

Lys Leu Leu Ile Tyr Leu Ala Ser Asn Leu Glu Ser Gly Val Pro Ala
50                  55                  60
```

```
Arg Phe Ser Gly Ser Gly Ser Gly Thr His Phe Thr Leu Asn Ile His
 65                  70                  75                  80

Pro Val Glu Glu Glu Asp Ala Ala Thr Tyr Tyr Cys Gln His Ser Arg
                 85                  90                  95

Glu Leu Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 250
<211> LENGTH: 12
<212> TYPE: PRT
<213> ORGANISM: Artificial Sequence
<220> FEATURE:
<223> OTHER INFORMATION: Synthetic: Region 1 of LAP-TGF-beta-1

<400> SEQUENCE: 250

Arg Lys Arg Ile Glu Ala Ile Arg Gly Gln Ile Leu
1               5                   10

<210> SEQ ID NO 251
<211> LENGTH: 10
<212> TYPE: PRT
<213> ORGANISM: Artificial Sequence
<220> FEATURE:
<223> OTHER INFORMATION: Synthetic: Region 2 of LAP-TGF-beta-1

<400> SEQUENCE: 251

Leu Ala Ser Pro Pro Ser Gln Gly Glu Val
1               5                   10

<210> SEQ ID NO 252
<211> LENGTH: 9
<212> TYPE: PRT
<213> ORGANISM: Artificial Sequence
<220> FEATURE:
<223> OTHER INFORMATION: Synthetic: Region 3 of LAP-TGF-beta-1

<400> SEQUENCE: 252

Gly Trp Lys Trp Ile His Glu Pro Lys
1               5

<210> SEQ ID NO 253
<211> LENGTH: 7
<212> TYPE: PRT
<213> ORGANISM: Artificial Sequence
<220> FEATURE:
<223> OTHER INFORMATION: Synthetic: Region 4 of LAP-TGF-beta-1

<400> SEQUENCE: 253
```

```
Tyr Val Gly Arg Lys Pro Lys
1               5

<210> SEQ ID NO 254
<211> LENGTH: 21
<212> TYPE: PRT
<213> ORGANISM: Artificial Sequence
<220> FEATURE:
<223> OTHER INFORMATION: Synthetic: 2F8 binding region

<400> SEQUENCE: 254

Val Asp Ile Asn Gly Phe Thr Thr Gly Arg Arg Gly Asp Leu Ala Thr
1               5                   10                  15

Ile His Gly Met Asn
            20

<210> SEQ ID NO 255
<211> LENGTH: 454
<212> TYPE: PRT
<213> ORGANISM: Artificial Sequence
<220> FEATURE:
<223> OTHER INFORMATION: Synthetic: 7H4_HCmut #3 (D55G)

<400> SEQUENCE: 255

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Ser Gly
            20                  25                  30

Tyr Tyr Trp Asn Trp Ile Arg Gln Phe Pro Gly Asn Lys Leu Glu Trp
        35                  40                  45

Met Gly Tyr Ile Ser Tyr Gly Gly Thr Asn Asn Tyr Asn Pro Ser Leu
    50                  55                  60

Lys Asn Arg Ile Ser Ile Thr Arg Asp Thr Ser Lys His Gln Phe Phe
65                  70                  75                  80

Leu Lys Leu Asn Ser Val Thr Thr Glu Asp Thr Ala Thr Tyr Tyr Cys
                85                  90                  95

Ala Arg Ser Phe Tyr Asn Asn Tyr Phe Asp Phe Trp Gly Gln Gly Thr
            100                 105                 110

Thr Leu Thr Val Ser Ser Ala Lys Thr Thr Pro Pro Ser Val Tyr Pro
        115                 120                 125

Leu Ala Pro Gly Cys Gly Asp Thr Thr Gly Ser Ser Val Thr Leu Gly
    130                 135                 140

Cys Leu Val Lys Gly Tyr Phe Pro Glu Ser Val Thr Val Thr Trp Asn
145                 150                 155                 160

Ser Gly Ser Leu Ser Ser Ser Val His Thr Phe Pro Ala Leu Leu Gln
                165                 170                 175

Ser Gly Leu Tyr Thr Met Ser Ser Ser Val Thr Val Pro Ser Ser Thr
            180                 185                 190

Trp Pro Ser Gln Thr Val Thr Cys Ser Val Ala His Pro Ala Ser Ser
        195                 200                 205

Thr Thr Val Asp Lys Lys Leu Glu Pro Ser Gly Pro Ile Ser Thr Ile
    210                 215                 220

Asn Pro Cys Pro Pro Cys Lys Glu Cys His Lys Cys Pro Ala Pro Asn
225                 230                 235                 240

Leu Glu Gly Gly Pro Ser Val Phe Ile Phe Pro Pro Asn Ile Lys Asp
                245                 250                 255

Val Leu Met Ile Ser Leu Thr Pro Lys Val Thr Cys Val Val Val Asp
```

```
                  260                 265                 270
Val Ser Glu Asp Asp Pro Asp Val Gln Ile Ser Trp Phe Val Asn Asn
            275                 280                 285

Val Glu Val His Thr Ala Gln Thr Gln Thr His Arg Glu Asp Tyr Asn
        290                 295                 300

Ser Thr Ile Arg Val Val Ser Thr Leu Pro Ile Gln His Gln Asp Trp
305                 310                 315                 320

Met Ser Gly Lys Glu Phe Lys Cys Lys Val Asn Asn Lys Asp Leu Pro
                325                 330                 335

Ser Pro Ile Glu Arg Thr Ile Ser Lys Ile Lys Gly Leu Val Arg Ala
            340                 345                 350

Pro Gln Val Tyr Ile Leu Pro Pro Pro Ala Glu Gln Leu Ser Arg Lys
        355                 360                 365

Asp Val Ser Leu Thr Cys Leu Val Val Gly Phe Asn Pro Gly Asp Ile
370                 375                 380

Ser Val Glu Trp Thr Ser Asn Gly His Thr Glu Glu Asn Tyr Lys Asp
385                 390                 395                 400

Thr Ala Pro Val Leu Asp Ser Asp Gly Ser Tyr Phe Ile Tyr Ser Lys
                405                 410                 415

Leu Asn Met Lys Thr Ser Lys Trp Glu Lys Thr Asp Ser Phe Ser Cys
                420                 425                 430

Asn Val Arg His Glu Gly Leu Lys Asn Tyr Tyr Leu Lys Lys Thr Ile
            435                 440                 445

Ser Arg Ser Pro Gly Lys
        450

<210> SEQ ID NO 256
<211> LENGTH: 105
<212> TYPE: PRT
<213> ORGANISM: Artificial Sequence
<220> FEATURE:
<223> OTHER INFORMATION: Synthetic: Kappa light chain constant domain

<400> SEQUENCE: 256

Val Ala Ala Pro Ser Val Phe Ile Phe Pro Pro Ser Asp Glu Gln Leu
1               5                   10                  15

Lys Ser Gly Thr Ala Ser Val Val Cys Leu Leu Asn Asn Phe Tyr Pro
                20                  25                  30

Arg Glu Ala Lys Val Gln Trp Lys Val Asp Asn Ala Leu Gln Ser Gly
            35                  40                  45

Asn Ser Gln Glu Ser Val Thr Glu Gln Asp Ser Lys Asp Ser Thr Tyr
50                  55                  60

Ser Leu Ser Ser Thr Leu Thr Leu Ser Lys Ala Asp Tyr Glu Lys His
65                  70                  75                  80

Lys Val Tyr Ala Cys Glu Val Thr His Gln Gly Leu Ser Ser Pro Val
                85                  90                  95

Thr Lys Ser Phe Asn Arg Gly Glu Cys
                100                 105

<210> SEQ ID NO 257
<211> LENGTH: 362
<212> TYPE: PRT
<213> ORGANISM: Artificial Sequence
<220> FEATURE:
<223> OTHER INFORMATION: Synthetic: Human LAP-TGF-beta-1 in Figure 34

<400> SEQUENCE: 257
```

-continued

```
Leu Ser Thr Cys Lys Thr Ile Asp Met Glu Leu Val Lys Arg Lys Arg
1               5                   10                  15

Ile Glu Ala Ile Arg Gly Gln Ile Leu Ser Lys Leu Arg Leu Ala Ser
            20                  25                  30

Pro Pro Ser Gln Gly Glu Val Pro Gly Pro Leu Pro Glu Ala Val
            35              40              45

Leu Ala Leu Tyr Asn Ser Thr Arg Asp Arg Val Ala Gly Glu Ser Ala
            50          55                  60

Glu Pro Glu Pro Glu Pro Glu Ala Asp Tyr Tyr Ala Lys Glu Val Thr
65              70                  75                  80

Arg Val Leu Met Val Glu Thr His Asn Glu Ile Tyr Asp Lys Phe Lys
                85                  90                  95

Gln Ser Thr His Ser Ile Tyr Met Phe Phe Asn Thr Ser Glu Leu Arg
            100             105                 110

Glu Ala Val Pro Glu Pro Val Leu Leu Ser Arg Ala Glu Leu Arg Leu
            115             120                 125

Leu Arg Leu Lys Leu Lys Val Glu Gln His Val Glu Leu Tyr Gln Lys
    130             135                 140

Tyr Ser Asn Asn Ser Trp Arg Tyr Leu Ser Asn Arg Leu Leu Ala Pro
145             150                 155                 160

Ser Asp Ser Pro Glu Trp Leu Ser Phe Asp Val Thr Gly Val Val Arg
                165             170                 175

Gln Trp Leu Ser Arg Gly Gly Glu Ile Glu Gly Phe Arg Leu Ser Ala
            180             185                 190

His Cys Ser Cys Asp Ser Arg Asp Asn Thr Leu Gln Val Asp Ile Asn
            195             200                 205

Ala Gly Phe Thr Thr Gly Arg Arg Gly Asp Leu Ala Thr Ile His Gly
    210             215                 220

Met Asn Arg Pro Phe Leu Leu Leu Met Ala Thr Pro Leu Glu Arg Ala
225             230                 235                 240

Gln His Leu Gln Ser Ser Arg His Arg Arg Ala Leu Asp Thr Asn Tyr
            245             250                 255

Cys Phe Ser Ser Thr Glu Lys Asn Cys Cys Val Arg Gln Leu Tyr Ile
            260             265                 270

Asp Phe Arg Lys Asp Leu Gly Trp Lys Trp Ile His Glu Pro Lys Gly
            275             280             285

Tyr His Ala Asn Phe Cys Leu Gly Pro Cys Pro Tyr Ile Trp Ser Leu
    290             295             300

Asp Thr Gln Tyr Ser Lys Val Leu Ala Leu Tyr Asn Gln His Asn Pro
305             310             315             320

Gly Ala Ser Ala Ala Pro Cys Cys Val Pro Gln Ala Leu Glu Pro Leu
                325             330             335

Pro Ile Val Tyr Tyr Val Gly Arg Lys Pro Lys Val Glu Gln Leu Ser
            340             345             350

Asn Met Ile Val Arg Ser Cys Lys Cys Ser
            355             360
```